United States Patent
Taka et al.

(10) Patent No.: US 8,829,199 B2
(45) Date of Patent: Sep. 9, 2014

(54) AMINOPYRAZOLE DERIVATIVE

(75) Inventors: Naoki Taka, Shizuoka (JP); Masayuki Ohmori, Shizuoka (JP); Kyoko Takami, Shizuoka (JP); Masayuki Matsushita, Kanagawa (JP); Tadakatsu Hayase, Kanagawa (JP); Ikumi Hyodo, Kanagawa (JP); Masami Kochi, Kanagawa (JP); Hiroki Nishii, Kanagawa (JP); Hirosato Ebiike, Kanagawa (JP); Yoshito Nakanishi, Kanagawa (JP); Toshiyuki Mio, Kanagawa (JP); Lisha Wang, Shanghai (CN); Weili Zhao, Shanghai (CN)

(73) Assignees: Chugai Seiyaku Kabushiki Kaisha, Tokyo (JP); F. Hoffmann-La Roche AG, Basel (CH)

( * ) Notice: Subject to any disclaimer, the term of this patent is extended or adjusted under 35 U.S.C. 154(b) by 0 days.

(21) Appl. No.: 13/389,146

(22) PCT Filed: Aug. 5, 2010

(86) PCT No.: PCT/JP2010/063315
§ 371 (c)(1),
(2), (4) Date: Apr. 23, 2012

(87) PCT Pub. No.: WO2011/016528
PCT Pub. Date: Feb. 10, 2011

(65) Prior Publication Data
US 2012/0208811 A1    Aug. 16, 2012

(30) Foreign Application Priority Data

Aug. 7, 2009 (JP) ................................ 2009-184822

(51) Int. Cl.
*A61K 31/4184* (2006.01)
*C07D 401/14* (2006.01)
*C07D 403/14* (2006.01)
*C07D 405/14* (2006.01)
*C07D 413/14* (2006.01)
*C07D 417/14* (2006.01)
*C07D 471/04* (2006.01)

(52) U.S. Cl.
USPC ........ 548/304.4; 544/114; 544/124; 544/139; 544/238; 544/364; 544/370; 546/199; 546/113; 546/273.4; 546/187; 546/168; 546/256; 548/159; 514/233.5; 514/231.5; 514/237.5; 514/252.01; 514/252.05; 514/252.13; 514/255.01; 514/300; 514/314; 514/316; 514/318; 514/322; 514/333; 514/338; 514/367; 514/394

(58) Field of Classification Search
USPC .................................................... 548/304.4
See application file for complete search history.

(56) References Cited

U.S. PATENT DOCUMENTS

| 6,316,466 B1 | 11/2001 | Goldstein et al. |
| 2005/0049288 A1 | 3/2005 | Fryszman et al. |
| 2009/0197866 A1 | 8/2009 | Cherrier et al. |

FOREIGN PATENT DOCUMENTS

| CN | 102099335 | 6/2011 |
| FR | 2831537 | 5/2003 |
| JP | 2002-513784 | 5/2002 |
| JP | 2003-509495 | 3/2003 |
| JP | 2007-521278 | 8/2007 |
| JP | 2011-528686 | 11/2011 |
| WO | WO 94/13643 | 6/1994 |
| WO | WO 99/57101 | 11/1999 |
| WO | WO 01/12600 | 2/2001 |
| WO | WO 01/21591 | 3/2001 |
| WO | WO 03/035065 | 5/2003 |
| WO | WO 2004/096792 | 11/2004 |
| WO | WO 2005/009973 | 2/2005 |
| WO | WO 2006/134318 | 12/2006 |
| WO | WO 2007/077435 | 7/2007 |
| WO | WO 2010/010017 | 1/2010 |
| WO | WO-2010/010017 A1 * | 1/2010 |

OTHER PUBLICATIONS

Golub et al., Science, vol. 286, Oct. 15, 1999, pp. 531-537.*

(Continued)

*Primary Examiner* — Laura L. Stockton
(74) *Attorney, Agent, or Firm* — Fish & Richardson P.C.

(57) ABSTRACT

A compound represented by formula (I) or a pharmacologically acceptable salt thereof, which can inhibit a fibroblast growth factor receptor (FGFR) family kinase in cancer tissues. (In the formula, A represents a 5- to 10-membered heteroaryl group, or a $C_{6-10}$ aryl group; $R_1$ and $R_2$ independently represent H, OH, X, CN, $NO_2$, a $C_{1-4}$ haloalkyl group, a $C_{1-6}$ alkyl group, or the like <$R_1$ and $R_2$ together form a (substituted) 3- to 10-membered heterocyclyl group or a (substituted) 5- to 10-membered heteroaryl group>; $R_3$ represents H, a $C_{1-5}$ alkyl group, a $C_{6-10}$ aryl group, a $C_{1-5}$ alkyl group, or a $C_{1-4}$ haloalkyl group; and $R_4$ represents H, X, a $C_{1-3}$ alkyl group, a $C_{1-4}$ haloalkyl group, OH, CN, $NO_2$, or the like.)

(I)

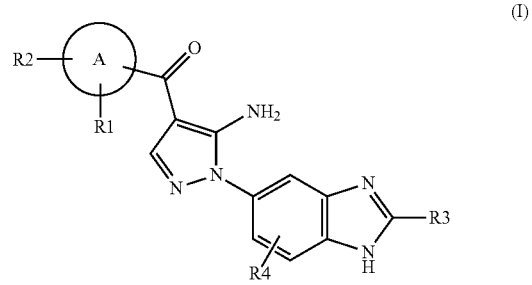

9 Claims, No Drawings

(56) References Cited

OTHER PUBLICATIONS

Cheng et al., Journal of the Pancreas, Jul. 2011, vol. 12, No. 4, pp. 334-338.*
Byron et al., "Inhibition of activated fibroblast growth factor receptor 2 in endometrial cancer cells induces cell death despite PTEN abrogation," *Cancer Res.*, 68(17):6902-7 (2008).
Cappellen et al., "Frequent activating mutations of FGFR3 in human bladder and cervix carcinomas," *Nat. Genet.*, 23(1):18-20 (1999).
Elbauomy Elsheikh et al., "FGFR1 amplification in breast carcinomas: a chromogenic in situ hybridisation analysis," *Breast Cancer Res.*, 9(2):R23 (2007).
Eswarakumar et al., "Cellular signaling by fibroblast growth factor receptors," *Cytokine Growth Factor Rev.*, 16(2):139-49 (2005).
Fonseca et al., "Clinical and biologic implications of recurrent genomic aberrations in myeloma," *Blood.*, 101(11):4569-75 (2003).
Heiskanen et al., "CGH, cDNA and tissue microarray analyses implicate FGFR2 amplification in a small subset of breast tumors," *Anal. Cell Pathol.*, 22(4):229-34 (2001).
MacDonald et al., "The 8p11 myeloproliferative syndrome: a distinct clinical entity caused by constitutive activation of FGFR1," *Acta. Haematol.*, 107(2):101-7 (2002).
Peng et al., "Alterations of chromosomal copy number during progression of diffuse-type gastric carcinomas: metaphase- and array-based comparative genomic hybridization analyses of multiple samples from individual," *J. Pathol.*, 201(3):439-50 (2003).
Rand et al., "Sequence survey of receptor tyrosine kinases reveals mutations in glioblastomas," *Proc. Natl. Acad. Sci. U.S.A.*, 102(40):14344-9 (2005).
Wang et al., "Antisense targeting of basic fibroblast growth factor and fibroblast growth factor receptor-1 in human melanomas blocks intratumoral angiogenesis and tumor growth," *Nat. Med.*, 3(8):887-93 (1997).
Zhao et al., "Homozygous deletions and chromosome amplifications in human lung carcinomas revealed by single nucleotide polymorphism array analysis," *Cancer Res.*, 65(13):5561-70 (2005).
International Search Report for App. Ser. No. PCT/JP2010/063315, mailed Sep. 7, 2010, 8 pages.
Search Report and Written Opinion issued in corresponding Singapore App. Ser. No. 201200851-2, dated Apr. 17, 2013, 19 pages.
International Preliminary Report on Patentability for corresponding International Application. No. PCT/JP2010/063315, dated Mar. 13, 2012, 9 pages.
Supplementary European Search Report for corresponding EP Application No. 10 80 6527, dated Feb. 15, 2013, 3 pages.

* cited by examiner

AMINOPYRAZOLE DERIVATIVE

CROSS-REFERENCE TO RELATED APPLICATIONS

This application is the National Stage of International Application Serial No. PCT/JP2010/063315, filed on Aug. 5, 2010, which claims the benefit of Japanese Application Serial No. 2009-184822, filed on Aug. 7, 2009.

TECHNICAL FIELD

The present invention relates to aminopyrazole derivatives and uses thereof.

BACKGROUND ART

Most of currently promising molecular-targeted drugs against cancer are receptor tyrosine kinase inhibitors such as erlotinib and lapatinib. Many of them are highly effective against cancers with mutation, amplification, or overexpression of target genes. However, such molecular-targeted agents cannot exert efficacy against cancers in which genes that are not their targets are altered. Thus, there is still no established therapeutic method that is effective against such cancers. Inhibitors against novel genes altered in cancer are expected to make a great contribution to treatment of cancer patients on whom conventional drugs have no effect.

Fibroblast growth factor receptors (FGFRs) are kinases belonging to the receptor tyrosine kinase family. FGFR1, FGFR2, FGFR3, and FGFR4 constitute the FGFR family. The ligand is fibroblast growth factor (FGF), and 22 types of structurally similar proteins form a family. It is known that each FGFR is activated upon overexpression, gene amplification, mutation, or translocation, and serves as a cause of cancer. The FGFR signal follows the MAPK pathway or PI3K/AKT pathway. In cancer, the signal is known to be involved in cell growth, angiogenesis, cell migration, invasion, metastasis, and such (Non-patent Document 1).

The FGFR1 gene is known to be amplified in breast cancer and non-small cell lung cancer (Non-patent Documents 2 and 3); mutated in glioblastoma (Non-patent Document 4); translocated to generate a fusion protein in acute myelocytic leukemia (Non-patent Document 5); and overexpressed in pancreatic cancer, bladder cancer, prostatic cancer, and esophageal cancer. Furthermore, FGFR1 is known to be expressed in neovessels and greatly contribute to angiogenesis (Non-patent Document 6). The FGFR2 gene is known to be amplified in stomach cancer and breast cancer (Non-patent Documents 7 and 8); mutated in endometrial cancer (Non-patent Document 9); and overexpressed in prostatic cancer, esophageal cancer, ovarian cancer, pancreatic cancer, brain tumor, and colon cancer. The FGFR3 gene is known to be translocated in multiple myeloma (Non-patent Document 10); mutated in bladder cancer (Non-patent Document 11); and overexpressed in ovarian cancer, non-small cell lung cancer, and hepatocellular carcinoma. Finally, FGFR4 is known to be mutated in lung cancer, ovarian cancer, prostatic cancer, etc.; and overexpressed in thyroid cancer, ovarian cancer, etc.

As described above, all FGFR family kinases have been strongly suggested to be involved in cancer. Thus, the inhibition of the FGFR family kinases in cancer tissues may be a promising therapeutic method for treating the above types of cancer.

PRIOR ART DOCUMENTS

[Non-patent Document 1] Cytokine & Growth Factor Reviews 16 (2005) 139-149
[Non-patent Document 2] Breast Cancer Research 2007, 9:R23
[Non-patent Document 3] Cancer Res 2005; 65(13): 5561-70
[Non-patent Document 4] PNAS (2005), 102(40), 14344-14349.
[Non-patent Document 5] Acta Haematol 2002; 107:101-107
[Non-patent Document 6] Nature Medicine 3, 887-89, 1997
[Non-patent Document 7] J Pathol. 2003 November; 201(3):439-50
[Non-patent Document 8] Anal Cell Pathol. 2001; 22(4):229-34
[Non-patent Document 9] Cancer Res 2008; 68(17):6902-7
[Non-patent Document 10] Blood. 2003; 101: 4569-4575
[Non-patent Document 11] Nat. Genet. 1999 September; 23(1):18-20.

SUMMARY OF THE INVENTION

Problems to be Solved by the Invention

An objective of the present invention is to provide low molecular weight compounds capable of inhibiting fibroblast growth factor receptor (FGFR) family kinases in cancer tissues.

Means for Solving the Problems

Specifically, the present invention includes the following:
[1] A compound represented by following general formula (I), or a pharmaceutically acceptable salt thereof:

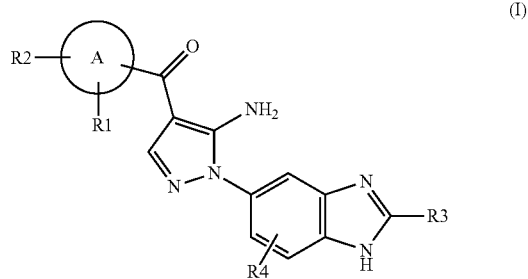

wherein $R_1$, $R_2$, $R_3$, and $R_4$ each independently represents the group listed below:
$R_1$ represents hydrogen, hydroxy, halogen, cyano, nitro, $C_{1-4}$ haloalkyl, $C_{1-6}$ alkyl, $C_{2-6}$ alkenyl, $C_{2-6}$ alkynyl, $C_{3-7}$ cycloalkyl, $C_{6-10}$ aryl $C_{1-4}$ alkyl, $-OR_5$, $-NR_6R_7$, $-(CR_8R_9)_nZ_1$, $-C(O)NR_{12}R_{13}$, $-SR_{14}$, $-SOR_{15}$, $-SO_2R_{16}$, $-NR_{17}SO_2R_{18}$, COOH, $C_{6-10}$ aryl which is optionally substituted by one or more groups independently selected from group P, 5- to 10-membered heteroaryl or 3- to 10-membered heterocyclyl which is optionally substituted by one or more groups independently selected from group Q, $-COR_{19}$, $-COOR_{20}$, $-OC(O)R_{21}$, $-NR_{22}C(O)R_{23}$, $-NR_{24}C(S)R_{25}$, $-C(S)NR_{26}R_{27}$, $-SO_2NR_{28}R_{29}$, $-OSO_2R_{30}$, $-SO_3R_{31}$, or $-Si(R_{32})_3$;
$R_2$ represents hydrogen, hydroxy, halogen, cyano, nitro, $C_{1-4}$ haloalkyl, $C_{1-6}$ alkyl, $C_{2-6}$ alkenyl, $C_{2-6}$ alkynyl, $C_{3-7}$ cycloalkyl, $C_{6-10}$ aryl $C_{1-4}$ alkyl, $-OR_5$, $-NR_6R_7$, $-(CR_8R_9)_nZ_1$, $-C(O)NR_{12}R_{13}$, $-SR_{14}$, $-SOR_{15}$, $-SO_2R_{16}$, $-NR_{17}SO_2R_{18}$, COOH, $C_{6-10}$ aryl which is optionally substituted by one or more groups independently selected from group P, 5- to 10-membered heteroaryl or 3- to 10-membered heterocyclyl which is optionally substituted by one or more groups independently selected from group Q, —$COR_{19}$, —$COOR_{20}$, —$OC(O)R_{21}$, —$NR_{22}C(O)R_{23}$, —$NR_{24}C(S)R_{25}$, —$C(S)NR_{26}R_{27}$, —$SO_2NR_{28}R_{29}$, —$OSO_2R_{30}$, —$SO_3R_{31}$, or —$Si(R_{32})_3$; or $R_1$ and $R_2$, together with an atom linked thereto, form 3- to 10-membered heterocyclyl or 5- to 10-membered heteroaryl, wherein the heterocyclyl or heteroaryl is optionally substituted by halogen;

$R_3$ represents hydrogen, $C_{1-5}$ alkyl, $C_{6-10}$ aryl $C_{1-6}$ alkyl, or $C_{1-4}$ haloalkyl;

$R_4$ represents hydrogen, halogen, $C_{1-3}$ alkyl, $C_{1-4}$ haloalkyl, hydroxy, cyano, nitro, $C_{1-4}$ alkoxy, —$(CH_2)_nZ_1$, —$NR_6R_7$, —$OR_5$, —$C(O)NR_{12}R_{13}$, $SR_{14}$, —$SOR_{15}$, —$SO_2R_{16}$, $NR_{17}SO_2R_{18}$, COOH, —$COR_{19}$, —$COOR_{20}$, —$OC(O)R_{21}$, —$NR_{22}C(O)R_{23}$, —$NR_{24}C(S)R_{25}$, —$C(S)NR_{26}R_{27}$, —$SO_2NR_{28}R_{29}$, —$OSO_2R_{30}$, —$SO_3R_{31}$, or —$Si(R_{32})_3$;

A represents a 5- to 10-membered heteroaryl ring or $C_{6-10}$ aryl ring;

$R_5$ represents $C_{1-5}$ alkyl, $C_{3-7}$ cycloalkyl, $C_{3-7}$ cycloalkyl $C_{1-3}$ alkyl, $C_{2-6}$ alkenyl, $C_{2-6}$ alkynyl, $C_{1-4}$ haloalkyl, $C_{1-3}$ alkoxy $C_{1-4}$ alkyl, $C_{1-3}$ alkoxy $C_{1-4}$ alkoxy $C_{1-4}$ alkyl, $C_{1-4}$ aminoalkyl, $C_{1-4}$ alkylamino $C_{1-4}$ alkyl, di($C_{1-4}$ alkyl)amino $C_{1-4}$ alkyl, $C_{6-10}$ aryl, $C_{6-10}$ aryl $C_{1-3}$ alkyl, or 3- to 10-membered heterocyclyl $C_{1-3}$ alkyl, 3- to 10-membered heterocyclyl, 5- to 10-membered heteroaryl, 5- to 10-membered heteroaryl $C_{1-3}$ alkyl, $C_{1-6}$ monohydroxy alkyl, $C_{1-6}$ dihydroxy alkyl, or $C_{1-6}$ trihydroxy alkyl which is optionally substituted by one or more groups independently selected from group Q;

$R_6$ and $R_7$, which are the same or different, each represents hydrogen, $C_{1-4}$ alkyl, $C_{2-6}$ alkenyl, $C_{2-6}$ alkynyl, $C_{1-4}$ haloalkyl, $C_{1-3}$ alkoxy $C_{1-4}$ alkyl, $C_{6-10}$ aryl $C_{1-3}$ alkyl, 3- to 10-membered heterocyclyl $C_{1-3}$ alkyl, 5- to 10-membered heteroaryl $C_{1-3}$ alkyl, $C_{1-6}$ monohydroxy alkyl, $C_{1-6}$ dihydroxy alkyl, $C_{1-6}$ trihydroxy alkyl, 3- to 10-membered heterocyclyl, $C_{1-4}$ aminoalkyl, $C_{1-4}$ alkylamino $C_{1-4}$ alkyl, di($C_{1-4}$ alkyl)amino $C_{1-4}$ alkyl, or cyano($C_{1-3}$ alkyl); or $R_6$ and $R_7$, together with a nitrogen atom linked thereto, form 3- to 10-membered heterocyclyl or 5- to 10-membered heteroaryl;

n represents 1 to 3;

$R_8$ and $R_9$, which are the same or different, each represents hydrogen, $C_{1-4}$ alkyl, or halogen; or alternatively, $R_8$ and $R_9$, together with a carbon atom linked thereto, form a cycloaliphatic ring;

$Z_1$ represents hydrogen, $NR_{10}R_{11}$, —OH, or 3- to 10-membered heterocyclyl or 5- to 10-membered heteroaryl which is optionally substituted by one or more groups independently selected from group Q;

$R_{10}$ and $R_{11}$, which are the same or different, each represents $C_{1-4}$ alkyl, $C_{2-6}$ alkenyl, $C_{2-6}$ alkynyl, $C_{1-4}$ haloalkyl, $C_{1-3}$ alkoxy $C_{1-4}$ alkyl, cyano($C_{1-3}$ alkyl), or $C_{1-3}$ alkylsulfonyl $C_{1-4}$ alkyl; or alternatively, $R_{10}$ and $R_{11}$, together with a nitrogen atom linked thereto, form 3- to 10-membered heterocyclyl or 5- to 10-membered heteroaryl;

$R_{12}$ and $R_{13}$, which are the same or different, each represents hydrogen, $C_{1-4}$ alkyl, $C_{2-6}$ alkenyl, $C_{2-6}$ alkynyl, $C_{1-4}$ haloalkyl, $C_{1-3}$ alkoxy $C_{1-4}$ alkyl, $C_{6-10}$ aryl, 5- to 10-membered heteroaryl, 3- to 10-membered heterocyclyl, $C_{6-10}$ aryl $C_{1-4}$ alkyl, 3- to 10-membered heterocyclyl $C_{1-3}$ alkyl, 5- to 10-membered heteroaryl $C_{1-3}$ alkyl, cyano($C_{1-3}$ alkyl), $C_{1-3}$ alkylsulfonyl $C_{1-4}$ alkyl, 3- to 10-membered cycloaliphatic ring, 5- to 10-membered heteroaryl, or 3- to 10-membered heterocyclyl; or alternatively, $R_{12}$ and $R_{13}$, together with a nitrogen atom linked thereto, form 3- to 10-membered heterocyclyl or 5- to 10-membered heteroaryl which is optionally substituted by one or more groups independently selected from group Q;

$R_{14}$ represents $C_{1-4}$ alkyl, $C_{2-6}$ alkenyl, $C_{2-6}$ alkynyl, $C_{1-4}$ haloalkyl, $C_{6-10}$ aryl which is optionally substituted by one or more groups independently selected from group P, or 5- to 10-membered heteroaryl or 3- to 10-membered heterocyclyl which is optionally substituted by one or more groups independently selected from group Q;

$R_{15}$ represents $C_{1-4}$ alkyl, $C_{2-6}$ alkenyl, $C_{2-6}$ alkynyl, $C_{1-4}$ haloalkyl, $C_{6-10}$ aryl which is optionally substituted by one or more groups independently selected from group P, or 5- to 10-membered heteroaryl or 3- to 10-membered heterocyclyl which is optionally substituted by one or more groups independently selected from group Q;

$R_{16}$ represents $C_{1-4}$ alkyl, $C_{2-6}$ alkenyl, $C_{2-6}$ alkynyl, $C_{1-4}$ haloalkyl, $C_{6-10}$ aryl which is optionally substituted by one or more groups independently selected from group P, or 5- to 10-membered heteroaryl or 3- to 10-membered heterocyclyl which is optionally substituted by one or more groups independently selected from group Q;

$R_{17}$ represents hydrogen or $C_{1-4}$ alkyl;

$R_{18}$ represents $C_{1-4}$ alkyl, $C_{2-6}$ alkenyl, $C_{2-6}$ alkynyl, $C_{1-4}$ haloalkyl, $C_{6-10}$ aryl which is optionally substituted by one or more groups independently selected from group P, or 5- to 10-membered heteroaryl or 3- to 10-membered heterocyclyl which is optionally substituted by one or more groups independently selected from group Q;

$R_{19}$ represents hydrogen, $C_{1-4}$ alkyl, $C_{3-7}$ cycloalkyl, $C_{1-4}$ haloalkyl, $C_{6-10}$ aryl, or 5- to 10-membered heteroaryl or 3- to 10-membered heterocyclyl which is optionally substituted by one or more groups independently selected from group Q;

$R_{20}$ represents $C_{1-4}$ alkyl, $C_{3-7}$ cycloalkyl, $C_{1-4}$ haloalkyl, $C_{6-10}$ aryl, 5- to 10-membered heteroaryl, or 3- to 10-membered heterocyclyl;

$R_{21}$ represents $C_{1-4}$ alkyl, $C_{3-7}$ cycloalkyl, $C_{1-4}$ haloalkyl, $C_{6-10}$ aryl, 5- to 10-membered heteroaryl, or 3- to 10-membered heterocyclyl;

$R_{22}$ represents hydrogen, $C_{1-4}$ alkyl, or $C_{1-4}$ haloalkyl;

$R_{23}$ represents hydrogen, $C_{1-4}$ alkyl, $C_{3-7}$ cycloalkyl, $C_{1-4}$ haloalkyl, $C_{6-10}$ aryl, 5- to 10-membered heteroaryl, or 3- to 10-membered heterocyclyl;

$R_{24}$ represents hydrogen, $C_{1-4}$ alkyl, or $C_{1-4}$ haloalkyl;

$R_{25}$ represents $C_{1-4}$ alkyl, $C_{3-7}$ cycloalkyl, $C_{1-4}$ haloalkyl, $C_{6-10}$ aryl, 5- to 10-membered heteroaryl, or 3- to 10-membered heterocyclyl;

$R_{26}$ and $R_{27}$, which are the same or different, each represents hydrogen, $C_{1-4}$ alkyl, $C_{2-6}$ alkenyl, $C_{2-6}$ alkynyl, $C_{1-4}$ haloalkyl, $C_{1-3}$ alkoxyl $C_{1-4}$ alkyl, $C_{6-10}$ aryl, 5- to 10-membered heteroaryl, 3- to 10-membered heterocyclyl, $C_{6-10}$ aryl $C_{1-4}$ alkyl, 3- to 10-membered heterocyclyl $C_{1-3}$ alkyl, 5- to 10-membered heteroaryl $C_{1-3}$ alkyl, cyano($C_{1-3}$ alkyl), $C_{1-3}$ alkylsulfonyl $C_{1-4}$ alkyl, or 3- to 10-membered cycloaliphatic ring; or alternatively, $R_{26}$ and $R_{27}$, together with a nitrogen atom linked thereto, form 3- to 10-membered heterocyclyl or 5- to 10-membered heteroaryl;

$R_{28}$ and $R_{29}$, which are the same or different, each represents hydrogen, $C_{1-4}$ alkyl, $C_{2-6}$ alkenyl, $C_{2-6}$ alkynyl, $C_{1-4}$ haloalkyl, $C_{1-3}$ alkoxyl $C_{1-4}$ alkyl, $C_{6-10}$ aryl, 5- to 10-membered heteroaryl, 3- to 10-membered heterocyclyl, $C_{6-10}$ aryl $C_{1-4}$ alkyl, 3- to 10-membered heterocyclyl $C_{1-3}$ alkyl, 5- to 10-membered heteroaryl $C_{1-3}$ alkyl, cyano($C_{1-3}$ alkyl), $C_{1-3}$ alkylsulfonyl $C_{1-4}$ alkyl, or 3- to 10-membered cycloaliphatic ring; or alternatively, $R_{28}$ and $R_{29}$, together with a nitrogen atom linked thereto, form 3- to 10-membered heterocyclyl or 5- to 10-membered heteroaryl;

$R_{30}$ represents $C_{1-4}$ alkyl, $C_{3-7}$ cycloalkyl, $C_{1-4}$ haloalkyl, $C_{6-10}$ aryl, 5- to 10-membered heteroaryl, or 3- to 10-membered heterocyclyl;

R$_{31}$ represents C$_{1-4}$ alkyl, C$_{3-7}$ cycloalkyl, C$_{1-4}$ haloalkyl, C$_{6-10}$ aryl, 5- to 10-membered heteroaryl, or 3- to 10-membered heterocyclyl;

R$_{32}$ represents C$_{1-4}$ alkyl or C$_{6-10}$ aryl;

<Group P> halogen, C$_{1-4}$ alkyl, C$_{1-4}$ haloalkyl, —OH, C$_{1-3}$ alkoxy, C$_{1-3}$ haloalkoxy, 3- to 10-membered heterocyclylamino, —SO$_2$R$_{16}$, —CN, —NO$_2$, and 3- to 10-membered heterocyclyl;

<Group Q> halogen, C$_{1-4}$ alkyl, C$_{1-4}$ haloalkyl, —OH, C$_{1-3}$ alkoxy, C$_{1-6}$ monohydroxy alkyl, C$_{1-6}$ dihydroxy alkyl, C$_{1-6}$ trihydroxy alkyl, 3- to 10 membered heterocyclyl amino, —SO$_2$R$_{16}$, —CN, —NO$_2$, C$_{3-7}$ cycloalkyl, —COR$_{19}$, and 3- to 10-membered heterocyclyl which is optionally substituted by C$_{1-4}$ alkyl.

[2] The compound of [1] or a pharmaceutically acceptable salt thereof, wherein A represents benzene, indole, azaindole, benzofuran, benzothiophene, benzothiazole, quinoline, or pyrrole.

[3] The compound of [1] or [2], or a pharmaceutically acceptable salt thereof, wherein R$_3$ represents hydrogen, C$_{1-4}$ alkyl, C$_{6-10}$ aryl C$_{1-4}$ alkyl, or C$_{1-3}$ perfluoroalkyl.

[4] The compound of any one of [1] to [3], or a pharmaceutically acceptable salt thereof, wherein R$_4$ represents hydrogen, halogen, C$_{1-3}$ alkyl, C$_{1-3}$ perfluoroalkyl, cyano, methanesulfonyl, hydroxyl, alkoxy, or amino.

[5] The compound of [1] or a pharmaceutically acceptable salt thereof, which is selected from the group consisting of:

(1) [5-amino-1-(2-methyl-1H-benzimidazol-5-yl)-1H-pyrazol-4-yl]-(1H-indol-2-yl)-methanone;

(2) [5-amino-1-(2-methyl-1H-benzimidazol-5-yl)-1H-pyrazol-4-yl]-(6-pyrrolidin-1-ylmethyl-1H-indol-2-yl)-methanone;

(3) [5-amino-1-(2-methyl-1H-benzimidazol-5-yl)-1H-pyrazol-4-yl]-[6-(4-hydroxy-piperidin-1-ylmethyl)-1H-indol-2-yl]-methanone;

(4) [5-amino-1-(2-methyl-1H-benzimidazol-5-yl)-1H-pyrazol-4-yl]-(1H-pyrrolo[3,2-c]pyridin-2-yl)-methanone;

(5) [5-amino-1-(2-methyl-1H-benzimidazol-5-yl)-1H-pyrazol-4-yl]-(6-piperazin-1-ylmethyl-1H-indol-2-yl)-methanone;

(6) [5-amino-1-(2-methyl-1H-benzimidazol-5-yl)-1H-pyrazol-4-yl]-[6-(2-morpholin-4-yl-ethoxy)-1H-indol-2-yl]-methanone;

(7) [5-amino-1-(2-methyl-1H-benzimidazol-5-yl)-1H-pyrazol-4-yl]-[6-(tetrahydro-pyran-4-yloxy)-1H-indol-2-yl]-methanone;

(8) [5-amino-1-(2-methyl-1H-benzimidazol-5-yl)-1H-pyrazol-4-yl]-(4-chloro-1H-indol-2-yl)-methanone;

(9) [5-amino-1-(2-methyl-1H-benzimidazol-5-yl)-1H-pyrazol-4-yl]-(5-bromo-1H-indol-2-yl)-methanone;

(10) [5-amino-1-(2-methyl-1H-benzimidazol-5-yl)-1H-pyrazol-4-yl]-(4-iodo-1H-indol-2-yl)-methanone;

(11) 2-[5-amino-1-(2-methyl-1H-benzimidazol-5-yl)-1H-pyrazole-4-carbonyl]-1H-indole-5-carbonitrile;

(12) [5-amino-1-(2-methyl-1H-benzimidazol-5-yl)-1H-pyrazol-4-yl]-(6-bromo-5-fluoro-1H-indol-2-yl)-methanone;

(13) [5-amino-1-(2-methyl-1H-benzimidazol-5-yl)-1H-pyrazol-4-yl]-(5-ethynyl-1H-indol-2-yl)-methanone;

(14) [5-amino-1-(2-methyl-1H-benzimidazol-5-yl)-1H-pyrazol-4-yl]-[6-(2-fluoro-phenyl)-1H-indol-2-yl]-methanone;

(15) [5-amino-1-(2-methyl-1H-benzimidazol-5-yl)-1H-pyrazol-4-yl]-[6-(3-fluoro-phenyl)-1H-indol-2-yl]-methanone;

(16) [5-amino-1-(2-methyl-1H-benzimidazol-5-yl)-1H-pyrazol-4-yl]-[6-(4-fluoro-phenyl)-1H-indol-2-yl]-methanone;

(17) [5-amino-1-(2-methyl-1H-benzimidazol-5-yl)-1H-pyrazol-4-yl]-[6-(2-chloro-phenyl)-1H-indol-2-yl]-methanone;

(18) [5-amino-1-(2-methyl-1H-benzimidazol-5-yl)-1H-pyrazol-4-yl]-[6-(3-chloro-phenyl)-1H-indol-2-yl]-methanone;

(19) [5-amino-1-(2-methyl-1H-benzimidazol-5-yl)-1H-pyrazol-4-yl]-[6-(4-chloro-phenyl)-1H-indol-2-yl]-methanone;

(20) [5-amino-1-(2-methyl-1H-benzimidazol-5-yl)-1H-pyrazol-4-yl]-[6-(2-trifluoromethyl-phenyl)-1H-indol-2-yl]-methanone;

(21) [5-amino-1-(2-methyl-1H-benzimidazol-5-yl)-1H-pyrazol-4-yl]-[6-(3-trifluoromethyl-phenyl)-1H-indol-2-yl]-methanone;

(22) [5-amino-1-(2-methyl-1H-benzimidazol-5-yl)-1H-pyrazol-4-yl]-[6-(4-trifluoromethyl-phenyl)-1H-indol-2-yl]-methanone;

(23) [5-amino-1-(2-methyl-1H-benzimidazol-5-yl)-1H-pyrazol-4-yl]-(4-bromo-1H-indol-2-yl)-methanone;

(24) [5-amino-1-(2-methyl-1H-benzimidazol-5-yl)-1H-pyrazol-4-yl]-[6-(3-fluoro-pyridin-2-yl)-1H-indol-2-yl]-methanone;

(25) [5-amino-1-(2-methyl-1H-benzimidazol-5-yl)-1H-pyrazol-4-yl]-(6-methyl-1H-indol-2-yl)-methanone;

(26) [5-amino-1-(2-methyl-1H-benzimidazol-5-yl)-1H-pyrazol-4-yl]-[5-(4,4-difluoro-piperidine-1-carbonyl)-1H-indol-2-yl]-methanone;

(27) [5-amino-1-(2-methyl-1H-benzimidazol-5-yl)-1H-pyrazol-4-yl]-[5-(3,3-difluoro-piperidine-1-carbonyl)-1H-indol-2-yl]-methanone;

(28) 2-[5-amino-1-(2-methyl-1H-benzimidazol-5-yl)-1H-pyrazole-4-carbonyl]-1H-indole-5-carboxylic acid (2,2,2-trifluoro-ethyl)-amide;

(29) [5-amino-1-(2-methyl-1H-benzimidazol-5-yl)-1H-pyrazol-4-yl]-[6-(5-trifluoromethyl-pyridin-2-yl)-1H-indol-2-yl]-methanone;

(30) [5-amino-1-(2-methyl-1H-benzimidazol-5-yl)-1H-pyrazol-4-yl]-[6-(6-trifluoromethyl-pyridin-2-yl)-1H-indol-2-yl]-methanone;

(31) [5-amino-1-(2-methyl-1H-benzimidazol-5-yl)-1H-pyrazol-4-yl]-[6-(5-chloro-pyridin-2-yl)-1H-indol-2-yl]-methanone;
(32) [5-amino-1-(2-methyl-1H-benzimidazol-5-yl)-1H-pyrazol-4-yl]-[6-(4-methyl-pyridin-2-yl)-1H-indol-2-yl]-methanone;
(33) [5-amino-1-(2-methyl-1H-benzimidazol-5-yl)-1H-pyrazol-4-yl]-[6-(3-chloro-4-fluoro-phenyl)-1H-indol-2-yl]-methanone;
(34) [5-amino-1-(2-methyl-1H-benzimidazol-5-yl)-1H-pyrazol-4-yl]-[6-(3-trifluoromethyl-pyridin-2-yl)-1H-indol-2-yl]-methanone;
(35) [5-amino-1-(2-methyl-1H-benzimidazol-5-yl)-1H-pyrazol-4-yl]-[6-(4-trifluoromethyl-pyridin-2-yl)-1H-indol-2-yl]-methanone;
(36) [5-amino-1-(6-fluoro-2-methyl-1H-benzimidazol-5-yl)-1H-pyrazol-4-yl]-(1H-indol-2-yl)-methanone;
(37) 2-[5-amino-1-(2-methyl-1H-benzimidazol-5-yl)-1H-pyrazole-4-carbonyl]-1H-indole-6-carboxylic acid;
(38) [5-amino-1-(2-methyl-1H-benzimidazol-5-yl)-1H-pyrazol-4-yl]-(6-hydroxymethyl-1H-indol-2-yl)-methanone;
(39) [5-amino-1-(2-methyl-1H-benzimidazol-5-yl)-1H-pyrazol-4-yl]-{6-[2-(4-methyl-piperazin-1-yl)-ethoxy]-1H-indol-2-yl}-methanone;
(40) [5-amino-1-(2-methyl-1H-benzimidazol-5-yl)-1H-pyrazol-4-yl]-[6-(3-methyl-oxetan-3-ylmethoxy)-1H-indol-2-yl]-methanone;
(41) [5-amino-1-(2-methyl-1H-benzimidazol-5-yl)-1H-pyrazol-4-yl]-[6-(3-fluoro-piperidin-1-ylmethyl)-1H-indol-2-yl]-methanone;
(42) [5-amino-1-(2-methyl-1H-benzimidazol-5-yl)-1H-pyrazol-4-yl]-(6-{[bis(2-methoxy-ethyl)amino]-methyl}-1H-indol-2-yl)-methanone;
(43) [5-amino-1-(2-methyl-1H-benzimidazol-5-yl)-1H-pyrazol-4-yl]-{6-[(methyl-prop-2-ynyl-amino)methyl]-1H-indol-2-yl}-methanone;
(44) [5-amino-1-(2-methyl-1H-benzimidazol-5-yl)-1H-pyrazol-4-yl]-[6-(3,3-difluoro-pyrrolidin-1-ylmethyl)-1H-indol-2-yl]-methanone;
(45) [5-amino-1-(2-methyl-1H-benzimidazol-5-yl)-1H-pyrazol-4-yl]-[6-(2,5-dimethyl-pyrrolidin-1-ylmethyl)-1H-indol-2-yl]-methanone;
(46) [5-amino-1-(2-methyl-1H-benzimidazol-5-yl)-1H-pyrazol-4-yl]-[6-(3,3-difluoro-piperidin-1-ylmethyl)-1H-indol-2-yl]-methanone;
(47) [5-amino-1-(2-methyl-1H-benzimidazol-5-yl)-1H-pyrazol-4-yl]-[6-((S)-3-methyl-morpholin-4-ylmethyl)-1H-indol-2-yl]-methanone;
(48) [5-amino-1-(2-methyl-1H-benzimidazol-5-yl)-1H-pyrazol-4-yl]-(6-bromo-1H-indol-2-yl)-methanone;
(49) [5-amino-1-(2-methyl-1H-benzimidazol-5-yl)-1H-pyrazol-4-yl]-(5-iodo-1H-indol-2-yl)-methanone;
(50) [5-amino-1-(2-methyl-1H-benzimidazol-5-yl)-1H-pyrazol-4-yl]-(1H-pyrrolo[3,2-b]pyridin-2-yl)-methanone;
(51) [5-amino-1-(2-methyl-1H-benzimidazol-5-yl)-1H-pyrazol-4-yl]-(5-bromo-6-trifluoromethyl-1H-indol-2-yl)-methanone;
(52) [5-amino-1-(2-methyl-1H-benzimidazol-5-yl)-1H-pyrazol-4-yl]-(6-iodo-1H-indol-2-yl)-methanone;
(53) [5-amino-1-(2-methyl-1H-benzimidazol-5-yl)-1H-pyrazol-4-yl]-(4-methyl-1H-indol-2-yl)-methanone;
(54) [5-amino-1-(2-methyl-1H-benzimidazol-5-yl)-1H-pyrazol-4-yl]-(4-isopropyl-1H-indol-2-yl)-methanone;
(55) [5-amino-1-(2-methyl-1H-benzimidazol-5-yl)-1H-pyrazol-4-yl]-[5-(2-fluoro-phenyl)-1H-indol-2-yl]-methanone;
(56) [5-amino-1-(2-methyl-1H-benzimidazol-5-yl)-1H-pyrazol-4-yl]-(5-benzyl-1H-indol-2-yl)-methanone;
(57) [5-amino-1-(2-methyl-1H-benzimidazol-5-yl)-1H-pyrazol-4-yl]-[5-(2-trifluoromethyl-phenyl)-1H-indol-2-yl]-methanone;
(58) [5-amino-1-(2-methyl-1H-benzimidazol-5-yl)-1H-pyrazol-4-yl]-[5-(3-fluorophenyl)-1H-indol-2-yl]-methanone;
(59) [5-amino-1-(2-methyl-1H-benzimidazol-5-yl)-1H-pyrazol-4-yl]-[5-(3-trifluoromethyl-phenyl)-1H-indol-2-yl]-methanone;
(60) [5-amino-1-(2-methyl-1H-benzimidazol-5-yl)-1H-pyrazol-4-yl]-(4-ethynyl-1H-indol-2-yl)-methanone;
(61) [5-amino-1-(2-methyl-1H-benzimidazol-5-yl)-1H-pyrazol-4-yl]-(5H-[1,3]dioxolo[4,5-f]indol-6-yl)-methanone;
(62) [5-amino-1-(7-fluoro-2-methyl-1H-benzimidazol-5-yl)-1H-pyrazol-4-yl]-(1H-indol-2-yl)-methanone;
(63) [5-amino-1-(2-methyl-1H-benzimidazol-5-yl)-1H-pyrazol-4-yl]-[5-(4-trifluoromethyl-phenyl)-1H-indol-2-yl]-methanone;
(64) [5-amino-1-(2-methyl-1H-benzimidazol-5-yl)-1H-pyrazol-4-yl]-(5-butoxy-1H-indol-2-yl)-methanone;
(65) [5-amino-1-(2-methyl-1H-benzimidazol-5-yl)-1H-pyrazol-4-yl]-[5-(1-methyl-piperidin-4-yl)-1H-indol-2-yl]-methanone;
(66) N-{2-[5-amino-1-(2-methyl-1H-benzimidazol-5-yl)-1H-pyrazole-4-carbonyl]-1H-indol-6-yl}-methanesulfonamide;
(67) [5-amino-1-(2-methyl-1H-benzimidazol-5-yl)-1H-pyrazol-4-yl]-[6-(6-morpholin-4-yl-pyridin-3-yl)-1H-indol-2-yl]-methanone;

(68) [5-amino-1-(2-methyl-1H-benzimidazol-5-yl)-1H-pyrazol-4-yl]-(6-butyl-1H-indol-2-yl)-methanone;
(69) [5-amino-1-(2-methyl-1H-benzimidazol-5-yl)-1H-pyrazol-4-yl]-[6-(1-methyl-1H-pyrazol-4-yl)-1H-indol-2-yl]-methanone;
(70) [5-amino-1-(2-methyl-1H-benzimidazol-5-yl)-1H-pyrazol-4-yl]-[6-(5-methoxy-pyridin-3-yl)-1H-indol-2-yl]-methanone;
(71) [5-amino-1-(2-methyl-1H-benzimidazol-5-yl)-1H-pyrazol-4-yl]-[6-(2-methoxy-pyridin-3-yl)-1H-indol-2-yl]-methanone;
(72) [5-amino-1-(2-methyl-1H-benzimidazol-5-yl)-1H-pyrazol-4-yl]-(6-cyclopropyl-1H-indol-2-yl)-methanone;
(73) [5-amino-1-(2-methyl-1H-benzimidazol-5-yl)-1H-pyrazol-4-yl]-[6-(2-methoxy-phenyl)-1H-indol-2-yl]-methanone;
(74) [5-amino-1-(2-methyl-1H-benzimidazol-5-yl)-1H-pyrazol-4-yl]-(6-phenyl-1H-indol-2-yl)-methanone;
(75) [5-amino-1-(2-methyl-1H-benzimidazol-5-yl)-1H-pyrazol-4-yl]-[6-(5-methanesulfonyl-pyridin-3-yl)-1H-indol-2-yl]-methanone;
(76) [5-amino-1-(2-methyl-1H-benzimidazol-5-yl)-1H-pyrazol-4-yl]-(6-isopropyl-1H-indol-2-yl)-methanone;
(77) [5-amino-1-(2-methyl-1H-benzimidazol-5-yl)-1H-pyrazol-4-yl]-(6-pyridin-2-yl-1H-indol-2-yl)-methanone;
(78) [5-amino-1-(2-methyl-1H-benzimidazol-5-yl)-1H-pyrazol-4-yl]-(5-cyclopropyl-1H-indol-2-yl)-methanone;
(79) [5-amino-1-(2-methyl-1H-benzimidazol-5-yl)-1H-pyrazol-4-yl]-(6-pyridazin-3-yl-1H-indol-2-yl)-methanone;
(80) [5-amino-1-(2-methyl-1H-benzimidazol-5-yl)-1H-pyrazol-4-yl]-(5-isopropoxy-1H-indol-2-yl)-methanone;
(81) [5-amino-1-(2-methyl-1H-benzimidazol-5-yl)-1H-pyrazol-4-yl]-[5-(2-methoxy-ethoxy)-1H-indol-2-yl]-methanone;
(82) [5-amino-1-(2-methyl-1H-benzimidazol-5-yl)-1H-pyrazol-4-yl]-(5-cyclopropylmethoxy-1H-indol-2-yl)-methanone;
(83) [5-amino-1-(2-methyl-1H-benzimidazol-5-yl)-1H-pyrazol-4-yl]-(2,2-difluoro-5H-[1,3]dioxolo[4,5-f]indol-6-yl)-methanone;
(84) [5-amino-1-(2-methyl-1H-benzimidazol-5-yl)-1H-pyrazol-4-yl]-[6-(3-chloro-pyridin-2-yl)-1H-indol-2-yl]-methanone;
(85) [5-amino-1-(2-methyl-1H-benzimidazol-5-yl)-1H-pyrazol-4-yl]-[6-(5-fluoro-pyridin-2-yl)-1H-indol-2-yl]-methanone;
(86) [5-amino-1-(2-methyl-1H-benzimidazol-5-yl)-1H-pyrazol-4-yl]-[6-(6-morpholin-4-yl-pyridazin-3-yl)-1H-indol-2-yl]-methanone;
(87) [5-amino-1-(2-methyl-1H-benzimidazol-5-yl)-1H-pyrazol-4-yl]-(5-chloro-6-cyclopropylmethoxy-1H-indol-2-yl)-methanone;
(88) [5-amino-1-(2-methyl-1H-benzimidazol-5-yl)-1H-pyrazol-4-yl]-[6-(2,4-difluoro-phenyl)-1H-indol-2-yl]-methanone;
(89) [5-amino-1-(2-methyl-1H-benzimidazol-5-yl)-1H-pyrazol-4-yl]-(6-pyridazin-4-yl-1H-indol-2-yl)-methanone;
(90) [5-amino-1-(2-methyl-1H-benzimidazol-5-yl)-1H-pyrazol-4-yl]-(3-fluoro-1H-indol-2-yl)-methanone;
(91) [5-amino-1-(2-methyl-1H-benzimidazol-5-yl)-1H-pyrazol-4-yl]-[5-(1-isopropyl-piperidin-4-yl)-6-trifluoromethyl-1H-indol-2-yl]-methanone;
(92) 2-[5-amino-1-(2-methyl-1H-benzimidazol-5-yl)-1H-pyrazole-4-carbonyl]-1H-indole-6-carbonitrile;
(93) [5-amino-1-(2-methyl-1H-benzimidazol-5-yl)-1H-pyrazol-4-yl]-[5-(1,2,3,6-tetrahydro-pyridin-4-yl)-1H-indol-2-yl]-methanone;
(94) [5-amino-1-(2-methyl-1H-benzimidazol-5-yl)-1H-pyrazol-4-yl]-(5-piperidin-4-yl-1H-indol-2-yl)-methanone;
(95) [5-amino-1-(2-methyl-1H-benzimidazol-5-yl)-1H-pyrazol-4-yl]-[5-((R)-3-fluoro-pyrrolidin-1-ylmethyl)-1H-indol-2-yl]-methanone;
(96) [5-amino-1-(2-methyl-1H-benzimidazol-5-yl)-1H-pyrazol-4-yl]-(6-fluoro-5-piperidin-4-yl-1H-indol-2-yl)-methanone;
(97) [5-amino-1-(2-methyl-1H-benzimidazol-5-yl)-1H-pyrazol-4-yl]-[6-fluoro-5-(1-methyl-piperidin-4-yl)-1H-indol-2-yl]-methanone;
(98) [5-amino-1-(2-methyl-1H-benzimidazol-5-yl)-1H-pyrazol-4-yl]-[5-(1-isopropyl-piperidin-4-yl)-1H-indol-2-yl]-methanone;
(99) [5-amino-1-(2-methyl-1H-benzimidazol-5-yl)-1H-pyrazol-4-yl]-[6-fluoro-5-(1-isopropyl-piperidin-4-yl)-1H-indol-2-yl]-methanone;
(100) [5-amino-1-(2-methyl-1H-benzimidazol-5-yl)-1H-pyrazol-4-yl]-(6-pyridin-3-yl-1H-indol-2-yl)-methanone;
(101) [5-amino-1-(2-methyl-1H-benzimidazol-5-yl)-1H-pyrazol-4-yl]-[5-(6-morpholin-4-ylpyridin-3-yl)-1H-indol-2-yl]-methanone;
(102) [5-amino-1-(2-methyl-1H-benzimidazol-5-yl)-1H-pyrazol-4-yl]-(5-pyridin-3-yl-1H-indol-2-yl)-methanone;
(103) [5-amino-1-(2-methyl-1H-benzimidazol-5-yl)-1H-pyrazol-4-yl]-[5-(6-piperazin-1-yl-pyridin-3-yl)-1H-indol-2-yl]-methanone;
(104) [5-amino-1-(2-methyl-1H-benzimidazol-5-yl)-1H-pyrazol-4-yl]-[5-(6-hydroxy-pyridin-3-yl)-1H-indol-2-yl]-methanone;

(105) [5-amino-1-(2-methyl-1H-benzimidazol-5-yl)-1H-pyrazol-4-yl]-[6-fluoro-5-(4-methyl-piperazin-1-ylmethyl)-1H-indol-2-yl]-methanone;
(106) [5-amino-1-(2-methyl-1H-benzimidazol-5-yl)-1H-pyrazol-4-yl]-(6-fluoro-5-pyrrolidin-1-ylmethyl-1H-indol-2-yl)-methanone;
(107) [5-amino-1-(2-methyl-1H-benzimidazol-5-yl)-1H-pyrazol-4-yl]-[6-(1-methyl-piperidin-4-yl)-1H-indol-2-yl]-methanone;
(108) [5-amino-1-(2-methyl-1H-benzimidazol-5-yl)-1H-pyrazol-4-yl]-[6-(4-morpholin-4-yl-phenyl)-1H-indol-2-yl]-methanone;
(109) [5-amino-1-(2-methyl-1H-benzimidazol-5-yl)-1H-pyrazol-4-yl]-[6-(3,4,5,6-tetrahydro-2H-[1,2']bipyridin-5'-yl)-1H-indol-2-yl]-methanone;
(110) [5-amino-1-(2-methyl-1H-benzimidazol-5-yl)-1H-pyrazol-4-yl]-[6-(6-piperazin-1-yl-pyridin-3-yl)-1H-indol-2-yl]-methanone;
(111) [5-amino-1-(2-methyl-1H-benzimidazol-5-yl)-1H-pyrazol-4-yl]-[5-(6-methoxy-pyridin-3-yl)-1H-indol-2-yl]-methanone;
(112) [5-amino-1-(2-methyl-1H-benzimidazol-5-yl)-1H-pyrazol-4-yl]-[5-((S)-3-methyl-morpholin-4-ylmethyl)-1H-indol-2-yl]-methanone;
(113) [5-amino-1-(2-methyl-1H-benzimidazol-5-yl)-1H-pyrazol-4-yl]-[6-((R)-3-fluoro-pyrrolidin-1-ylmethyl)-1H-indol-2-yl]-methanone;
(114) [5-amino-1-(2-methyl-1H-benzimidazol-5-yl)-1H-pyrazol-4-yl]-[5-(2,5-dimethyl-pyrrolidin-1-ylmethyl)-1H-indol-2-yl]-methanone;
(115) [5-amino-1-(2-methyl-1H-benzimidazol-5-yl)-1H-pyrazol-4-yl]-[5-(3-fluoro-piperidin-1-ylmethyl)-1H-indol-2-yl]-methanone;
(116) [5-amino-1-(2-methyl-1H-benzimidazol-5-yl)-1H-pyrazol-4-yl]-[5-(3,3-difluoro-piperidin-1-ylmethyl)-1H-indol-2-yl]-methanone;
(117) [5-amino-1-(2-methyl-1H-benzimidazol-5-yl)-1H-pyrazol-4-yl]-{6-[2-(4-methyl-piperazin-1-yl)pyridin-4-yl]-1H-indol-2-yl}-methanone;
(118) [5-amino-1-(2-methyl-1H-benzimidazol-5-yl)-1H-pyrazol-4-yl]-(6-pyridin-4-yl-1H-indol-2-yl)-methanone;
(119) [5-amino-1-(2-methyl-1H-benzimidazol-5-yl)-1H-pyrazol-4-yl]-[5-(4-fluoropiperidin-1-ylmethyl)-1H-indol-2-yl]-methanone;
(120) [5-amino-1-(2-methyl-1H-benzimidazol-5-yl)-1H-pyrazol-4-yl]-[5-(4,4-difluoro-piperidin-1-ylmethyl)-1H-indol-2-yl]-methanone;
(121) [5-amino-1-(2-difluoromethyl-1H-benzimidazol-5-yl)-1H-pyrazol-4-yl]-[5-(1-methyl-piperidin-4-yl)-1H-indol-2-yl]-methanone;
(122) [5-amino-1-(2-difluoromethyl-1H-benzimidazol-5-yl)-1H-pyrazol-4-yl]-(1H-indol-2-yl)-methanone;
(123) [5-amino-1-(2-methyl-1H-benzimidazol-5-yl)-1H-pyrazol-4-yl]-[5-(3,3-difluoro-pyrrolidin-1-ylmethyl)-1H-indol-2-yl]-methanone;
(124) [5-amino-1-(2-methyl-1H-benzimidazol-5-yl)-1H-pyrazol-4-yl]-[5-(1-cyclopentyl-piperidin-4-yl)-1H-indol-2-yl]-methanone;
(125) [5-amino-1-(2-methyl-1H-benzimidazol-5-yl)-1H-pyrazol-4-yl]-[5-(1-cyclohexyl-piperidin-4-yl)-1H-indol-2-yl]-methanone;
(126) [5-amino-1-(2-methyl-1H-benzimidazol-5-yl)-1H-pyrazol-4-yl]-(4-bromo-1H-pyrrol-2-yl)-methanone;
(127) [5-amino-1-(2-methyl-1H-benzimidazol-5-yl)-1H-pyrazol-4-yl]-(1H-pyrrol-2-yl)-methanone;
128) [5-amino-1-(2-methyl-1H-benzimidazol-5-yl)-1H-pyrazol-4-yl]-(4-phenyl-1H-pyrrol-2-yl)-methanone;
(129) [5-amino-1-(2-methyl-1H-benzimidazol-5-yl)-1H-pyrazol-4-yl]-[4-(3-chloro-phenyl)-1H-pyrrol-2-yl]-methanone;
(130) [5-amino-1-(2-methyl-1H-benzimidazol-5-yl)-1H-pyrazol-4-yl]-[4-(4-fluoro-phenyl)-1H-pyrrol-2-yl]-methanone;
(131) [5-amino-1-(2-methyl-1H-benzimidazol-5-yl)-1H-pyrazol-4-yl]-[4-(3-fluoro-phenyl)-1H-pyrrol-2-yl]-methanone;
(132) [5-amino-1-(2-methyl-1H-benzimidazol-5-yl)-1H-pyrazol-4-yl]-(6-morpholin-4-ylmethyl-1H-indol-2-yl)-methanone;
(133) [5-amino-1-(2-methyl-1H-benzimidazol-5-yl)-1H-pyrazol-4-yl]-[4-(2-morpholin-4-yl-ethylamino)-1H-indol-2-yl]-methanone;
(134) [5-amino-1-(2-methyl-1H-benzimidazol-5-yl)-1H-pyrazol-4-yl]-[5-(4-methyl-piperazine-1-carbonyl)-1H-indol-2-yl]-methanone;
(135) [5-amino-1-(2-methyl-1H-benzimidazol-5-yl)-1H-pyrazol-4-yl]-[6-(2-morpholin-4-yl-ethylamino)-1H-indol-2-yl]-methanone;
(136) [5-amino-1-(2-methyl-1H-benzimidazol-5-yl)-1H-pyrazol-4-yl]-[5-(piperazine-1-carbonyl)-1H-indol-2-yl]-methanone;
(137) [5-amino-1-(2-methyl-1H-benzimidazol-5-yl)-1H-pyrazol-4-yl]-[4-(2-methoxy-ethylamino)-1H-indol-2-yl]-methanone;
(138) [5-amino-1-(2-methyl-1H-benzimidazol-5-yl)-1H-pyrazol-4-yl]-[4-(2-hydroxy-1-hydroxymethyl-ethylamino)-1H-indol-2-yl]-methanone;
(139) [5-amino-1-(2-methyl-1H-benzimidazol-5-yl)-1H-pyrazol-4-yl]-[4-(2-pyridin-4-yl-ethylamino)-1H-indol-2-yl]-methanone;

(140) [5-amino-1-(2-methyl-1H-benzimidazol-5-yl)-1H-pyrazol-4-yl]-[6-(2-methoxy-ethylamino)-1H-indol-2-yl]-methanone;
(141) [5-amino-1-(2-methyl-1H-benzimidazol-5-yl)-1H-pyrazol-4-yl]-(6-morpholin-4-yl-1H-indol-2-yl)-methanone;
(142) [5-amino-1-(2-methyl-1H-benzimidazol-5-yl)-1H-pyrazol-4-yl]-(4-morpholin-4-yl-1H-indol-2-yl)-methanone;
(143) [5-amino-1-(2-methyl-1H-benzimidazol-5-yl)-1H-pyrazol-4-yl]-(4-morpholin-4-ylmethyl-1H-indol-2-yl)-methanone;
(144) [5-amino-1-(2-methyl-1H-benzimidazol-5-yl)-1H-pyrazol-4-yl]-(5-morpholin-4-ylmethyl-1H-indol-2-yl)-methanone;
(145) [5-amino-1-(2-methyl-1H-benzimidazol-5-yl)-1H-pyrazol-4-yl]-[5-(morpholine-4-carbonyl)-1H-indol-2-yl]-methanone;
(146) [5-amino-1-(2-isopropyl-1H-benzimidazol-5-yl)-1H-pyrazol-4-yl]-(1H-indol-2-yl)-methanone;
(147) [5-amino-1-(2-propyl-1H-benzimidazol-5-yl)-1H-pyrazol-4-yl]-(1H-indol-2-yl)-methanone;
(148) [5-amino-1-(1H-benzimidazol-5-yl)-1H-pyrazol-4-yl]-(1H-indol-2-yl)-methanone;
149) [5-amino-1-(2-trifluoromethyl-1H-benzimidazol-5-yl)-1H-pyrazol-4-yl]-(1H-indol-2-yl)-methanone;
(150) [5-amino-1-(2-ethyl-1H-benzimidazol-5-yl)-1H-pyrazol-4-yl]-(1H-indol-2-yl)-methanone;
(151) [5-amino-1-(2-benzyl-1H-benzimidazol-5-yl)-1H-pyrazol-4-yl]-(1H-indol-2-yl)-methanone;
(152) 1-(4-{2-[5-amino-1-(2-methyl-1H-benzimidazol-5-yl)-1H-pyrazole-4-carbonyl]-1H-indol-5-ylmethyl}-piperazin-1-yl)-ethanone;
(153) [5-amino-1-(2-methyl-1H-benzimidazol-5-yl)-1H-pyrazol-4-yl]-[5-(4-methanesulfonyl-piperazin-1-ylmethyl)-1H-indol-2-yl]-methanone;
(154) [5-amino-1-(2-methyl-1H-benzimidazol-5-yl)-1H-pyrazol-4-yl]-(5-piperazin-1-ylmethyl-1H-indol-2-yl)-methanone;
(155) 1-(4-{2-[5-amino-1-(2-methyl-1H-benzimidazol-5-yl)-1H-pyrazole-4-carbonyl]-1H-indol-6-ylmethyl}piperazin-1-yl)-ethanone;
(156) [5-amino-1-(2-methyl-1H-benzimidazol-5-yl)-1H-pyrazol-4-yl]-[6-(4-methyl-piperazin-1-ylmethyl)-1H-indol-2-yl]-methanone;
(157) [5-amino-1-(2-methyl-1H-benzimidazol-5-yl)-1H-pyrazol-4-yl]-[5-(4-methyl-piperazin-1-ylmethyl)-1H-indol-2-yl]-methanone;
(158) [5-amino-1-(2-methyl-1H-benzimidazol-5-yl)-1H-pyrazol-4-yl]-(5-pyrrolidin-1-ylmethyl-1H-indol-2-yl)-methanone;
(159) [5-amino-1-(2-methyl-1H-benzimidazol-5-yl)-1H-pyrazol-4-yl]-(4-fluoro-1H-indol-2-yl)-methanone;
(160) [5-amino-1-(2-methyl-1H-benzimidazol-5-yl)-1H-pyrazol-4-yl]-(5-fluoro-1H-indol-2-yl)-methanone;
(161) [5-amino-1-(2-methyl-1H-benzimidazol-5-yl)-1H-pyrazol-4-yl]-(6-fluoro-1H-indol-2-yl)-methanone;
(162) [5-amino-1-(2-methyl-1H-benzimidazol-5-yl)-1H-pyrazol-4-yl]-(1H-pyrrolo[2,3-b]pyridin-2-yl)-methanone;
(163) [5-amino-1-(2-methyl-1H-benzimidazol-5-yl)-1H-pyrazol-4-yl]-(5-fluoro-6-morpholin-4-ylmethyl-1H-indol-2-yl)-methanone;
(164) 2-[5-amino-1-(2-methyl-1H-benzimidazol-5-yl)-1H-pyrazole-4-carbonyl]-1H-indole-5-carboxylic acid;
(165) [5-amino-1-(2-methyl-1H-benzimidazol-5-yl)-1H-pyrazol-4-yl]-(5-methoxy-1H-indol-2-yl)-methanone;
(166) [5-amino-1-(2-methyl-1H-benzimidazol-5-yl)-1H-pyrazol-4-yl]-(4,6-dimethoxy-1H-indol-2-yl)-methanone;
(167) [5-amino-1-(2-methyl-1H-benzimidazol-5-yl)-1H-pyrazol-4-yl]-(4-methoxy-1H-indol-2-yl)-methanone;
(168) [5-amino-1-(2-methyl-1H-benzimidazol-5-yl)-1H-pyrazol-4-yl]-(6-methoxy-1H-indol-2-yl)-methanone;
(169) [5-amino-1-(2-methyl-1H-benzimidazol-5-yl)-1H-pyrazol-4-yl]-(4,6-dimethyl-1H-indol-2-yl)-methanone;
(170) [5-amino-1-(2-methyl-1H-benzimidazol-5-yl)-1H-pyrazol-4-yl]-(5-tert-butyl-1H-indol-2-yl)-methanone;
(171) [5-amino-1-(2-methyl-1H-benzimidazol-5-yl)-1H-pyrazol-4-yl]-(5-isopropyl-1H-indol-2-yl)-methanone;
(172) [5-amino-1-(2-methyl-1H-benzimidazol-5-yl)-1H-pyrazol-4-yl]-(5-benzyloxy-1H-indol-2-yl)-methanone;
(173) [5-amino-1-(2-methyl-1H-benzimidazol-5-yl)-1H-pyrazol-4-yl]-(4-benzyloxy-1H-indol-2-yl)-methanone;
(174) [5-amino-1-(2-methyl-1H-benzimidazol-5-yl)-1H-pyrazol-4-yl]-(5,6-dimethoxy-1H-indol-2-yl)-methanone;
(175) [5-amino-1-(2-methyl-1H-benzimidazol-5-yl)-1H-pyrazol-4-yl]-(6-tert-butyl-1H-indol-2-yl)-methanone;
(176) [5-amino-1-(2-methyl-1H-benzimidazol-5-yl)-1H-pyrazol-4-yl]-(5-fluoro-4-trifluoromethyl-1H-indol-2-yl)-methanone;
(177) [5-amino-1-(2-methyl-1H-benzimidazol-5-yl)-1H-pyrazol-4-yl]-(5-phenoxy-1H-indol-2-yl)-methanone;
(178) [5-amino-1-(2-methyl-1H-benzimidazol-5-yl)-1H-pyrazol-4-yl]-(6-methylsulfanyl-1H-indol-2-yl)-methanone;

(179) [5-amino-1-(2-methyl-1H-benzimidazol-5-yl)-1H-pyrazol-4-yl]-(4-tert-butyl-1H-indol-2-yl)-methanone;
(180) [5-amino-1-(2-methyl-1H-benzimidazol-5-yl)-1H-pyrazol-4-yl]-(5-methyl-1H-indol-2-yl)-methanone;
(181) [5-amino-1-(2-methyl-1H-benzimidazol-5-yl)-1H-pyrazol-4-yl]-(5-ethyl-1H-indol-2-yl)-methanone;
(182) [5-amino-1-(2-methyl-1H-benzimidazol-5-yl)-1H-pyrazol-4-yl]-(5-fluoro-6-trifluoromethyl-1H-indol-2-yl)-methanone;
(183) [5-amino-1-(2-methyl-1H-benzimidazol-5-yl)-1H-pyrazol-4-yl]-(6-fluoro-5-methoxy-1H-indol-2-yl)-methanone;
(184) [5-amino-1-(2-methyl-1H-benzimidazol-5-yl)-1H-pyrazol-4-yl]-(6-chloro-5-methoxy-1H-indol-2-yl)-methanone;
(185) [5-amino-1-(2-methyl-1H-benzimidazol-5-yl)-1H-pyrazol-4-yl]-(5-chloro-6-methoxy-1H-indol-2-yl)-methanone;
(186) [5-amino-1-(2-methyl-1H-benzimidazol-5-yl)-1H-pyrazol-4-yl]-(6-isopropoxy-1H-indol-2-yl)-methanone;
(187) [5-amino-1-(2-methyl-1H-benzimidazol-5-yl)-1H-pyrazol-4-yl]-(6-benzyloxy-1H-indol-2-yl)-methanone;
(188) [5-amino-1-(2-methyl-1H-benzimidazol-5-yl)-1H-pyrazol-4-yl]-(4-isopropoxy-1H-indol-2-yl)-methanone;
(189) [5-amino-1-(2-methyl-1H-benzimidazol-5-yl)-1H-pyrazol-4-yl]-(2,3-dihydro-6H-[1,4]dioxino[2,3-f]indol-7-yl)-methanone;
(190) [5-amino-1-(2-methyl-1H-benzimidazol-5-yl)-1H-pyrazol-4-yl]-(4,6-di-tert-butyl-1H-indol-2-yl)-methanone;
(191) 2-[5-amino-1-(2-methyl-1H-benzimidazol-5-yl)-1H-pyrazole-4-carbonyl]-1H-indole-4-carbonitrile;
(192) [5-amino-1-(2-methyl-1H-benzimidazol-5-yl)-1H-pyrazol-4-yl]-(5-imidazol-1-yl-1H-indol-2-yl)-methanone;
(193) [5-amino-1-(2-methyl-1H-benzimidazol-5-yl)-1H-pyrazol-4-yl]-(5-trifluoromethylsulfanyl-1H-indol-2-yl)-methanone;
(194) [5-amino-1-(2-methyl-1H-benzimidazol-5-yl)-1H-pyrazol-4-yl]-(5-methylsulfanyl-1H-indol-2-yl)-methanone;
(195) [5-amino-1-(2-methyl-1H-benzimidazol-5-yl)-1H-pyrazol-4-yl]-(5-methanesulfonyl-1H-indol-2-yl)-methanone;
(196) [5-amino-1-(2-methyl-1H-benzimidazol-5-yl)-1H-pyrazol-4-yl]-[6-(4,4-difluoro-piperidin-1-ylmethyl)-1H-indol-2-yl]-methanone;
(197) [5-amino-1-(2-methyl-1H-benzimidazol-5-yl)-1H-pyrazol-4-yl]-[6-(4-fluoro-piperidin-1-ylmethyl)-1H-indol-2-yl]-methanone;
(198) [5-amino-1-(2-methyl-1H-benzimidazol-5-yl)-1H-pyrazol-4-yl]-[6-(oxetan-3-yloxy)-1H-indol-2-yl]-methanone;
(199) [5-amino-1-(2-methyl-1H-benzimidazol-5-yl)-1H-pyrazol-4-yl]-(6-hydroxy-1H-indol-2-yl)-methanone;
(200) [5-amino-1-(2-methyl-1H-benzimidazol-5-yl)-1H-pyrazol-4-yl]-(6-methanesulfonyl-1H-indol-2-yl)-methanone;
(201) [5-amino-1-(2-methyl-1H-benzimidazol-5-yl)-1H-pyrazol-4-yl]-(4,5-dibromo-1H-pyrrol-2-yl)-methanone;
(202) [5-amino-1-(2-methyl-1H-benzimidazol-5-yl)-1H-pyrazol-4-yl]-(4,5-diphenyl-1H-pyrrol-2-yl)-methanone;
(203) [5-amino-1-(2-methyl-1H-benzimidazol-5-yl)-1H-pyrazol-4-yl]-(4,5-dipyridin-3-yl-1H-pyrrol-2-yl)-methanone;
(204) [5-amino-1-(2-methyl-3H-benzimidazol-5-yl)-1H-pyrazol-4-yl]-(6-chloro-1H-indol-2-yl)-methanone;
(205) [5-amino-1-(2-methyl-1H-benzimidazol-5-yl)-1H-pyrazol-4-yl]-(5-chloro-1H-indol-2-yl)-methanone;
(206) [5-amino-1-(2-methyl-1H-benzimidazol-5-yl)-1H-pyrazol-4-yl]-(1H-indol-3-yl)-methanone;
(207) [5-amino-1-(2-methyl-1H-benzimidazol-5-yl)-1H-pyrazol-4-yl]-(1H-indol-6-yl)-methanone;
(208) [5-amino-1-(2-methyl-1H-benzimidazol-5-yl)-1H-pyrazol-4-yl]-(5-bromo-6-fluoro-1H-indol-2-yl)-methanone;
(209) [5-amino-1-(2-ethyl-1H-benzimidazol-5-yl)-1H-pyrazol-4-yl]-(5-bromo-6-fluoro-1H-indol-2-yl)-methanone;
(210) [5-amino-1-(2-methyl-1H-benzimidazol-5-yl)-1H-pyrazol-4-yl]-(5-trifluoromethyl-1H-indol-2-yl)-methanone;
(211) [5-amino-1-(2-methyl-1H-benzimidazol-5-yl)-1H-pyrazol-4-yl]-(5-trifluoromethoxy-1H-indol-2-yl)-methanone;
(212) [5-amino-1-(2-methyl-1H-benzimidazol-5-yl)-1H-pyrazol-4-yl]-(4,6-dichloro-1H-indol-2-yl)-methanone;
(213) [5-amino-1-(2-methyl-1H-benzimidazol-5-yl)-1H-pyrazol-4-yl]-(6-bromo-4-fluoro-1H-indol-2-yl)-methanone;
(214) [5-amino-1-(2-methyl-1H-benzimidazol-5-yl)-1H-pyrazol-4-yl]-(6-trifluoromethoxy-1H-indol-2-yl)-methanone;
(215) [5-amino-1-(2-ethyl-1H-benzimidazol-5-yl)-1H-pyrazol-4-yl]-(5-trifluoromethoxy-1H-indol-2-yl)-methanone;
(216) [5-amino-1-(2-ethyl-1H-benzimidazol-5-yl)-1H-pyrazol-4-yl]-(5-trifluoromethyl-1H-indol-2-yl)-methanone;
(217) [5-amino-1-(2-methyl-1H-benzimidazol-5-yl)-1H-pyrazol-4-yl]-(5,6-dichloro-1H-indol-2-yl)-methanone;
(218) [5-amino-1-(2-ethyl-1H-benzimidazol-5-yl)-1H-pyrazol-4-yl]-(6-bromo-5-fluoro-1H-indol-2-yl)-methanone;
(219) [5-amino-1-(2-methyl-1H-benzimidazol-5-yl)-1H-pyrazol-4-yl]-(4,5-dichloro-1H-indol-2-yl)-methanone;
(220) [5-amino-1-(2-methyl-1H-benzimidazol-5-yl)-1H-pyrazol-4-yl]-(4,6-difluoro-1H-indol-2-yl)-methanone;

(221) [5-amino-1-(2-methyl-1H-benzimidazol-5-yl)-1H-pyrazol-4-yl]-[6-(3-chloro-pyridin-4-yl)-1H-indol-2-yl]-methanone;
(222) [5-amino-1-(2-methyl-1H-benzimidazol-5-yl)-1H-pyrazol-4-yl]-[6-(6-methyl-pyridine-3-yl)-1H-indol-2-yl]-methanone;
(223) [5-amino-1-(2-methyl-1H-benzimidazol-5-yl)-1H-pyrazol-4-yl]-[6-(5-fluoro-pyridin-3-yl)-1H-indol-2-yl]-methanone;
(224) [5-amino-1-(2-methyl-1H-benzimidazol-5-yl)-1H-pyrazol-4-yl]-[6-(2-trifluoromethyl-pyridin-3-yl)-1H-indol-2-yl]-methanone;
(225) [5-amino-1-(2-methyl-1H-benzimidazol-5-yl)-1H-pyrazol-4-yl]-[6-(5-chloro-2-methoxy-pyridin-3-yl)-1H-indol-2-yl]-methanone;
(226) [5-amino-1-(2-methyl-1H-benzimidazol-5-yl)-1H-pyrazol-4-yl]-[6-(5-chloro-pyridin-3-yl)-1H-indol-2-yl]-methanone;
(227) [5-amino-1-(2-methyl-1H-benzimidazol-5-yl)-1H-pyrazol-4-yl]-(6-thiophen-3-yl-1H-indol-2-yl)-methanone;
(228) [5-amino-1-(2-methyl-1H-benzimidazol-5-yl)-1H-pyrazol-4-yl]-[6-(4-chloropyridin-3-yl)-1H-indol-2-yl]-methanone;
(229) [5-amino-1-(2-methyl-1H-benzimidazol-5-yl)-1H-pyrazol-4-yl]-(6-thiophen-2-yl-1H-indol-2-yl)-methanone;
(230) [5-amino-1-(2-methyl-1H-benzimidazol-5-yl)-1H-pyrazol-4-yl]-[6-(3-fluoro-pyridin-4-yl)-1H-indol-2-yl]-methanone;
(231) [5-amino-1-(2-methyl-1H-benzimidazol-5-yl)-1H-pyrazol-4-yl]-[6-(2-trifluoromethyl-pyridin-4-yl)-1H-indol-2-yl]-methanone;
(232) [5-amino-1-(2-methyl-1H-benzimidazol-5-yl)-1H-pyrazol-4-yl]-[5-(3,3-difluoro-pyrrolidine-1-carbonyl)-1H-indol-2-yl]-methanone;
(233) [5-amino-1-(2-methyl-1H-benzimidazol-5-yl)-1H-pyrazol-4-yl]-[5-(2,6-dimethyl-morpholine-4-carbonyl)-1H-indol-2-yl]-methanone;
(234) [5-amino-1-(2-methyl-1H-benzimidazol-5-yl)-1H-pyrazol-4-yl]-[5-([1,4']bipiperidinyl-1'-carbonyl)-1H-indol-2-yl]-methanone;
(235) [5-amino-1-(2-methyl-1H-benzimidazol-5-yl)-1H-pyrazol-4-yl]-{5-[4-(2,2,2-trifluoro-ethyl)-piperazine-1-carbonyl]-1H-indol-2-yl}-methanone;
(236) [5-amino-1-(2-methyl-1H-benzimidazol-5-yl)-1H-pyrazol-4-yl]-{5-[4-(2-hydroxy-ethyl)-piperazine-1-carbonyl]-1H-indol-2-yl}-methanone;
(237) [5-amino-1-(2-methyl-1H-benzimidazol-5-yl)-1H-pyrazol-4-yl]-[5-(3,3,4,4-tetrafluoro-pyrrolidine-1-carbonyl)-1H-indol-2-yl]-methanone;
(238) [5-amino-1-(2-methyl-1H-benzimidazol-5-yl)-1H-pyrazol-4-yl]-[5-((R)-3-fluoro-pyrrolidine-1-carbonyl)-1H-indol-2-yl]-methanone;
(239) [5-amino-1-(2-methyl-1H-benzimidazol-5-yl)-1H-pyrazol-4-yl]-[5-((S)-3-fluororo-pyrrolidine-1-carbonyl)-1H-indol-2-yl]-methanone;
(240) [5-amino-1-(2-methyl-1H-benzimidazol-5-yl)-1H-pyrazol-4-yl]-[4-(4-methoxy-phenyl)-1H-pyrrol-2-yl]-methanone;
(241) [5-amino-1-(2-methyl-1H-benzimidazol-5-yl)-1H-pyrazol-4-yl]-[4-(3-methoxy-phenyl)-1H-pyrrol-2-yl]-methanone;
(242) [5-amino-1-(2-methyl-1H-benzimidazol-5-yl)-1H-pyrazol-4-yl]-[4,5-bis-(3-fluoro-phenyl)-1H-pyrrol-2-yl]-methanone;
(243) [5-amino-1-(2-methyl-1H-benzimidazol-5-yl)-1H-pyrazol-4-yl]-[4,5-bis-(4-methoxy-phenyl)-1H-pyrrol-2-yl]-methanone;
(244) [5-amino-1-(2-methyl-1H-benzimidazol-5-yl)-1H-pyrazol-4-yl]-[4-(2,4-difluoro-phenyl)-1H-pyrrol-2-yl]-methanone;
(245) [5-amino-1-(2-methyl-1H-benzimidazol-5-yl)-1H-pyrazol-4-yl]-[4-(4-trifluoromethoxy-phenyl)-1H-pyrrol-2-yl]-methanone;
(246) [5-amino-1-(2-methyl-1H-benzimidazol-5-yl)-1H-pyrazol-4-yl]-[4,5-bis-(3-methoxy-phenyl)-1H-pyrrol-2-yl]-methanone;
(247) [5-amino-1-(2-methyl-1H-benzimidazol-5-yl)-1H-pyrazol-4-yl]-benzofuran-2-yl-methanone;
(248) [5-amino-1-(2-methyl-1H-benzimidazol-5-yl)-1H-pyrazol-4-yl]-benzo[b]thiophen-2-yl-methanone;
(249) [5-amino-1-(2-methyl-1H-benzimidazol-5-yl)-1H-pyrazol-4-yl]-benzothiazol-2-yl-methanone;
(250) [5-amino-1-(2-methyl-1H-benzimidazol-5-yl)-1H-pyrazol-4-yl]-(4-fluoro-phenyl)-methanone;
(251) [5-amino-1-(2-methyl-1H-benzimidazol-5-yl)-1H-pyrazol-4-yl]-(3-chloro-phenyl)-methanone;
(252) [5-amino-1-(2-methyl-1H-benzimidazol-5-yl)-1H-pyrazol-4-yl]-quinolin-3-yl-methanone;
(253) [5-amino-1-(2-methyl-1H-benzimidazol-5-yl)-1H-pyrazol-4-yl]-quinolin-7-yl-methanone; and
(254) [5-amino-1-(2-methyl-1H-benzimidazol-5-yl)-1H-pyrazol-4-yl]-quinolin-6-yl-methanone.

[6] A pharmaceutical composition comprising the compound of any one of [1] to [5], or a pharmaceutically acceptable salt thereof; and a carrier.

[7] An agent for inhibiting FGFR activity, which comprises as an active ingredient the compound of any one of [1] to [5], or a pharmaceutically acceptable salt thereof.

[8] An agent for preventing or treating cancer, which comprises as an active ingredient the compound of any one of [1] to [5], or a pharmaceutically acceptable salt thereof.
[9] The agent for preventing or treating cancer of [8], wherein the cancer is at least one selected from the group consisting of:
breast cancer, acute myelocytic leukemia, pancreatic cancer, bladder cancer, prostatic cancer, esophageal cancer, angiogenesis, stomach cancer, uterine body cancer, ovarian cancer, brain tumor, colon cancer, multiple myeloma, hepatocarcinoma, pulmonary cancer, and thyroid cancer.
[10] A method for preventing or treating cancer, comprising administering a pharmaceutically effective amount of a composition comprising the compound of any one of [1] to [5] or a pharmaceutically acceptable salt thereof to a patient in need of prevention or treatment of cancer.
[11] Use of the compound of any one of [1] to [5] or a pharmaceutically acceptable salt thereof in the production of an agent for preventing or treating cancer.
[12] The compound of any one of [1] to [5] or a pharmaceutically acceptable salt thereof, for use in preventing or treating cancer.

The present invention also includes the following.
[101] A compound represented by following general formula (I), or a pharmaceutically acceptable salt thereof:

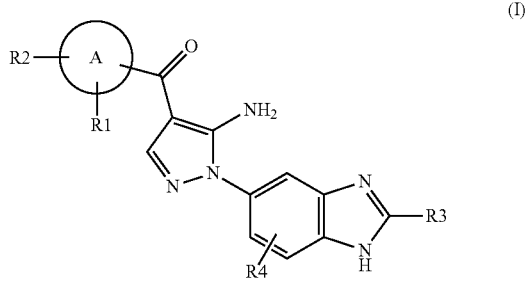

(I)

wherein $R_1$, $R_2$, $R_3$, and $R_4$ each independently represents the group listed below:
$R_1$ represents hydrogen, hydroxy, halogen, cyano, nitro, $C_{1-4}$ haloalkyl, $C_{1-6}$ alkyl, $C_{2-6}$ alkenyl, $C_{2-6}$ alkynyl, $C_{6-10}$ aryl $C_{1-4}$ alkyl, —$OR_5$, —$NR_6R_7$, —$(CR_8R_9)_nZ_1$, —$C(O)NR_{12}R_{13}$, —$SR_{14}$, —$SOR_{15}$, —$SO_2R_{16}$, —$NR_{17}SO_2R_{18}$, COOH, $C_{6-10}$ aryl which is optionally substituted by one or more groups selected from group P, 5- to 10-membered heteroaryl or 3- to 10-membered heterocyclyl which is optionally substituted by one or more groups selected from group Q, —$COR_{19}$, —$COOR_{20}$, —$OC(O)R_{21}$, —$NR_{22}C(O)R_{23}$, —$NR_{24}C(S)R_{25}$, —$C(S)NR_{26}R_{27}$, —$SO_2NR_{28}R_{29}$, —$OSO_2R_{30}$, —$SO_3R_{31}$, or —$Si(R_{32})_3$;
$R_2$ represents hydrogen, hydroxy, halogen, cyano, nitro, $C_{1-4}$ haloalkyl, $C_{1-6}$ alkyl, $C_{2-6}$ alkenyl, $C_{2-6}$ alkynyl, $C_{6-10}$ aryl $C_{1-4}$ alkyl, —$OR_5$, —$NR_6R_7$, —$(CR_8R_9)_nZ_1$, —$C(O)NR_{12}R_{13}$, —$SR_{14}$, —$SOR_{15}$, —$SO_2R_{16}$, —$NR_{17}SO_2R_{18}$, COOH, $C_{6-10}$ aryl which is optionally substituted by one or more groups selected from group P, 5- to 10-membered heteroaryl or 3- to 10-membered heterocyclyl which is optionally substituted by one or more groups selected from group Q, —$COR_{19}$, —$COOR_{20}$, —$OC(O)R_{21}$, —$NR_{22}C(O)R_{23}$, —$NR_{24}C(S)R_{25}$, —$C(S)NR_{26}R_{27}$, —$SO_2NR_{28}R_{29}$, —$OSO_2R_{30}$, —$SO_3R_{31}$, or —$Si(R_{32})_3$; or
$R_1$ and $R_2$, together with an atom linked thereto, form 3- to 10-membered heterocyclyl or 5- to 10-membered heteroaryl, wherein the heterocyclyl or heteroaryl is optionally substituted by halogen;
$R_3$ represents hydrogen, $C_{1-5}$ alkyl, $C_{6-10}$ aryl $C_{1-6}$ alkyl, or $C_{1-4}$ haloalkyl;
$R_4$ represents hydrogen, halogen, $C_{1-3}$ alkyl, $C_{1-4}$ haloalkyl, hydroxy, cyano, nitro, $C_{1-4}$ alkoxy, —$(CH_2)_nZ_1$, —$NR_6R_7$, —$OR_5$, —$C(O)NR_{12}R_{13}$, —$SR_{14}$, —$SOR_{15}$, —$SO_2R_{16}$, $NR_{17}SO_2R_{18}$, COOH, —$COR_{19}$, —$COOR_{20}$, —$OC(O)R_{21}$, —$NR_{22}C(O)R_{23}$, —$NR_{24}C(S)R_{25}$, —$C(S)NR_{26}R_{27}$, —$SO_2NR_{28}R_{29}$, —$OSO_2R_{30}$—$SO_3R_{31}$, or —$Si(R_{32})_3$;
A represents a 5- to 10-membered heteroaryl ring or $C_{6-10}$ aryl ring;
$R_5$ represents $C_{1-5}$ alkyl, $C_{3-7}$ cycloalkyl, $C_{3-7}$ cycloalkyl $C_{1-3}$ alkyl, $C_{2-6}$ alkenyl, $C_{2-6}$ alkynyl, $C_{1-4}$ haloalkyl, $C_{1-3}$ alkoxy $C_{2-4}$ alkyl, $C_{1-3}$ alkoxy $C_{2-4}$ alkoxy $C_{2-4}$ alkyl, $C_{2-4}$ aminoalkyl, $C_{1-4}$ alkylamino $C_{2-4}$ alkyl, di($C_{1-4}$ alkyl)amino $C_{2-4}$ alkyl, $C_{6-10}$ aryl, $C_{6-10}$ aryl $C_{1-3}$ alkyl, or 3- to 10-membered heterocyclyl $C_{1-3}$ alkyl, 3- to 10-membered heterocyclyl, 5- to 10-membered heteroaryl, 5- to 10-membered heteroaryl $C_{1-3}$ alkyl, $C_{1-6}$ monohydroxy alkyl, $C_{1-6}$ dihydroxy alkyl, or $C_{1-6}$ trihydroxy alkyl which is optionally substituted by one or more groups selected from group Q;
$R_6$ and $R_7$, which are the same or different, each represents hydrogen, $C_{1-4}$ alkyl, $C_{2-6}$ alkenyl, $C_{2-6}$ alkynyl, $C_{1-4}$ haloalkyl, $C_{1-3}$ alkoxy $C_{2-4}$ alkyl, $C_{6-10}$ aryl $C_{1-3}$ alkyl, 3- to 10-membered heterocyclyl $C_{1-3}$ alkyl, 5- to 10-membered heteroaryl $C_{1-3}$ alkyl, $C_{2-6}$ monohydroxy alkyl, $C_{2-6}$ dihydroxy alkyl, $C_{2-6}$ trihydroxy alkyl, 3- to 10-membered heterocyclyl, $C_{2-4}$ aminoalkyl, $C_{1-4}$ alkylamino $C_{2-4}$ alkyl, di($C_{1-4}$ alkyl)amino $C_{2-4}$ alkyl, or cyano($C_{1-3}$ alkyl); or $R_6$ and $R_7$, together with a nitrogen atom linked thereto, form 3- to 10-membered heterocyclyl or 5- to 10-membered heteroaryl;
n represents 1 to 3;
$R_8$ and $R_9$, which are the same or different, each represents hydrogen, $C_{1-4}$ alkyl, or halogen; or alternatively, $R_8$ and $R_9$, together with a carbon atom linked thereto, form a cycloaliphatic ring;
$Z_1$ represents hydrogen, $NR_{10}R_{11}$, hydroxyl, or 3- to 10-membered heterocyclyl or 5- to 10-membered heteroaryl which is optionally substituted by one or more groups independently selected from group Q;
$R_{10}$ and $R_{11}$, which are the same or different, each represents $C_{1-4}$ alkyl, $C_{2-6}$ alkenyl, $C_{2-6}$ alkynyl, $C_{1-4}$ haloalkyl, $C_{1-3}$ alkoxy $C_{2-4}$ alkyl, cyano($C_{1-3}$ alkyl), or $C_{1-3}$ alkylsulfonyl $C_{2-4}$ alkyl; or alternatively, $R_{10}$ and $R_{11}$, together with a nitrogen atom linked thereto, form 3- to 10-membered heterocyclyl or 5- to 10-membered heteroaryl;
$R_{12}$ and $R_{13}$, which are the same or different, each represents hydrogen, $C_{1-4}$ alkyl, $C_{2-6}$ alkenyl, $C_{2-6}$ alkynyl, $C_{1-4}$ haloalkyl, $C_{1-3}$ alkoxy $C_{2-4}$ alkyl, $C_{6-10}$ aryl, 5- to 10-membered heteroaryl, 3- to 10-membered heterocyclyl, $C_{6-10}$ aryl $C_{1-4}$ alkyl, 3- to 10-membered heterocyclyl $C_{1-3}$ alkyl, 5- to 10-membered heteroaryl $C_{1-3}$ alkyl, cyano($C_{1-3}$ alkyl), $C_{1-3}$ alkylsulfonyl $C_{2-4}$ alkyl, 3- to 10-membered cycloaliphatic ring, 5- to 10-membered heteroaryl, or 3- to 10-membered heterocyclyl; or alternatively, $R_{12}$ and $R_{13}$, together with a nitrogen atom linked thereto, form 3- to 10-membered heterocyclyl or 5- to 10-membered heteroaryl which is optionally substituted by one or more groups selected from group Q;
$R_{14}$ represents $C_{1-4}$ alkyl, $C_{2-6}$ alkenyl, $C_{2-6}$ alkynyl, $C_{1-4}$ haloalkyl, $C_{6-10}$ aryl which is optionally substituted by one or more groups selected from group P, or 5- to 10-membered heteroaryl or 3- to 10-membered heterocyclyl which is optionally substituted by one or more groups selected from group Q;
$R_{15}$ represents $C_{1-4}$ alkyl, $C_{2-6}$ alkenyl, $C_{2-6}$ alkynyl, $C_{1-4}$ haloalkyl, $C_{6-10}$ aryl which is optionally substituted by one or more groups selected from group P, or 5- to 10-membered heteroaryl or 3- to 10-membered heterocyclyl which is optionally substituted by one or more groups selected from group Q;

$R_{16}$ represents $C_{1-4}$ alkyl, $C_{2-6}$ alkenyl, $C_{2-6}$ alkynyl, $C_{1-4}$ haloalkyl, $C_{6-10}$ aryl which is optionally substituted by one or more groups selected from group P, or 5- to 10-membered heteroaryl or 3- to 10-membered heterocyclyl which is optionally substituted by one or more groups selected from group Q;

$R_{17}$ represents hydrogen or $C_{1-4}$ alkyl;

$R_{18}$ represents $C_{1-4}$ alkyl, $C_{2-6}$ alkenyl, $C_{2-6}$ alkynyl, $C_{1-4}$ haloalkyl, $C_{6-10}$ aryl which is optionally substituted by one or more groups selected from group P, or 5- to 10-membered heteroaryl or 3- to 10-membered heterocyclyl which is optionally substituted by a group(s) selected from group Q;

$R_{19}$ represents hydrogen, $C_{1-4}$ alkyl, $C_{3-7}$ cycloalkyl, $C_{1-4}$ haloalkyl, $C_{6-10}$ aryl, or 5- to 10-membered heteroaryl or 3- to 10-membered heterocyclyl which is optionally substituted by one or more groups selected from group Q;

$R_{20}$ represents $C_{1-4}$ alkyl, $C_{3-7}$ cycloalkyl, $C_{1-4}$ haloalkyl, $C_{6-10}$ aryl, 5- to 10-membered heteroaryl, or 3- to 10-membered heterocyclyl;

$R_{21}$ represents $C_{1-4}$ alkyl, $C_{3-7}$ cycloalkyl, $C_{1-4}$ haloalkyl, $C_{6-10}$ aryl, 5- to 10-membered heteroaryl, or 3- to 10-membered heterocyclyl;

$R_{22}$ represents hydrogen, $C_{1-4}$ alkyl, or $C_{1-4}$ haloalkyl;

$R_{23}$ represents hydrogen, $C_{1-4}$ alkyl, $C_{3-7}$ cycloalkyl, $C_{1-4}$ haloalkyl, $C_{6-10}$ aryl, 5- to 10-membered heteroaryl, or 3- to 10-membered heterocyclyl;

$R_{24}$ represents hydrogen, $C_{1-4}$ alkyl, or $C_{1-4}$ haloalkyl;

$R_{25}$ represents $C_{1-4}$ alkyl, $C_{3-7}$ cycloalkyl, $C_{1-4}$ haloalkyl, $C_{6-10}$ aryl, 5- to 10-membered heteroaryl, or 3- to 10-membered heterocyclyl;

$R_{26}$ and $R_{27}$, which are the same or different, each represents hydrogen, $C_{1-4}$ alkyl, $C_{2-6}$ alkenyl, $C_{2-6}$ alkynyl, $C_{1-4}$ haloalkyl, $C_{1-3}$ alkoxyl $C_{2-4}$ alkyl, $C_{6-10}$ aryl, 5- to 10-membered heteroaryl, 3- to 10-membered heterocyclyl, $C_{6-10}$ aryl $C_{1-4}$ alkyl, 3- to 10-membered heterocyclyl $C_{1-3}$ alkyl, 5- to 10-membered heteroaryl $C_{1-3}$ alkyl, cyano($C_{1-3}$ alkyl), $C_{1-3}$ alkylsulfonyl $C_{2-4}$ alkyl, or 3- to 10-membered cycloaliphatic ring; or alternatively, $R_{26}$ and $R_{27}$, together with a nitrogen atom linked thereto, form 3- to 10-membered heterocyclyl or 5- to 10-membered heteroaryl;

$R_{28}$ and $R_{29}$, which are the same or different, each represents hydrogen, $C_{1-4}$ alkyl, $C_{2-6}$ alkenyl, $C_{2-6}$ alkynyl, $C_{1-4}$ haloalkyl, $C_{1-3}$ alkoxyl $C_{2-4}$ alkyl, $C_{6-10}$ aryl, 5- to 10-membered heteroaryl, 3- to 10-membered heterocyclyl, $C_{6-10}$ aryl $C_{1-4}$ alkyl, 3- to 10-membered heterocyclyl $C_{1-3}$ alkyl, 5- to 10-membered heteroaryl $C_{1-3}$ alkyl, cyano($C_{1-3}$ alkyl), $C_{1-3}$ alkylsulfonyl $C_{2-4}$ alkyl, or 3- to 10-membered cycloaliphatic ring; or alternatively, $R_{28}$ and $R_{29}$, together with a nitrogen atom linked thereto, form 3- to 10-membered heterocyclyl or 5- to 10-membered heteroaryl;

$R_{30}$ represents $C_{1-4}$ alkyl, $C_{3-7}$ cycloalkyl, $C_{1-4}$ haloalkyl, $C_{6-10}$ aryl, 5- to 10-membered heteroaryl, or 3- to 10-membered heterocyclyl;

$R_{31}$ represents $C_{1-4}$ alkyl, $C_{3-7}$ cycloalkyl, $C_{1-4}$ haloalkyl, $C_{6-10}$ aryl, 5- to 10-membered heteroaryl, or 3- to 10-membered heterocyclyl;

$R_{32}$ represents $C_{1-4}$ alkyl or $C_{6-10}$ aryl;

<Group P> hydrogen, halogen, $C_{1-4}$ alkyl, $C_{1-4}$ haloalkyl, —OH, $C_{1-3}$ alkoxy, 3- to 10-membered heterocyclylamino, —$SO_2R_{16}$, —CN, —$NO_2$, and 3- to 10-membered heterocyclyl;

<Group Q> hydrogen, halogen, $C_{1-4}$ alkyl, $C_{1-4}$ haloalkyl, —OH, $C_{1-3}$ alkoxy, 3- to 10-membered heterocyclyl amine, —$SO_2R_{16}$, —CN, —$NO_2$, $C_{3-7}$ cycloalkyl, —$COR_{19}$, and 3- to 10-membered heterocyclyl.

[102] The compound of [101] or a pharmaceutically acceptable salt thereof, wherein A represents indole, azaindole, or pyrrole.

[103] The compound of [101] or [102], or a pharmaceutically acceptable salt thereof, wherein $R_3$ represents hydrogen, $C_{1-4}$ alkyl, $C_{6-10}$ aryl $C_{1-4}$ alkyl, or $C_{1-3}$ perfluoroalkyl.

[104] The compound of any one of [101] to [103], or a pharmaceutically acceptable salt thereof, wherein $R_4$ represents hydrogen, halogen, $C_{1-3}$ alkyl, $C_{1-3}$ perfluoroalkyl, cyano, methanesulfonyl, hydroxyl, alkoxy, or amino.

[105] The compound of [101] or a pharmaceutically acceptable salt thereof, which is selected from the group consisting of:

(1)
[5-amino-1-(2-methyl-1H-benzimidazol-5-yl)-1H-pyrazol-4-yl]-(1H-indol-2-yl)-methanone;

(2)
[5-amino-1-(2-methyl-1H-benzimidazol-5-yl)-1H-pyrazol-4-yl]-(6-pyrrolidin-1-ylmethyl-1H-indol-2-yl)-methanone;

(3)
[5-amino-1-(2-methyl-1H-benzimidazol-5-yl)-1H-pyrazol-4-yl]-[6-(4-hydroxy-piperidin-1-ylmethyl)-1H-indol-2-yl]-methanone;

(4)
[5-amino-1-(2-methyl-1H-benzimidazol-5-yl)-1H-pyrazol-4-yl]-(1H-pyrrolo[3,2-c]pyridin-2-yl)-methanone;

(5)
[5-amino-1-(2-methyl-1H-benzimidazol-5-yl)-1H-pyrazol-4-yl]-(6-piperazin-1-ylmethyl-1H-indol-2-yl)-methanone;

(6)
[5-amino-1-(2-methyl-1H-benzimidazol-5-yl)-1H-pyrazol-4-yl]-[6-(2-morpholin-4-yl-ethoxy)-1H-indol-2-yl]-methanone;

(7)
[5-amino-1-(2-methyl-1H-benzimidazol-5-yl)-1H-pyrazol-4-yl]-[6-(tetrahydro-pyran-4-yloxy)-1H-indol-2-yl]-methanone;

(8)
[5-amino-1-(2-methyl-1H-benzimidazol-5-yl)-1H-pyrazol-4-yl]-(4-chloro-1H-indol-2-yl)-methanone;

(9)
[5-amino-1-(2-methyl-1H-benzimidazol-5-yl)-1H-pyrazol-4-yl]-(5-bromo-1H-indol-2-yl)-methanone;

(10)
[5-amino-1-(2-methyl-1H-benzimidazol-5-yl)-1H-pyrazol-4-yl]-(4-iodo-1H-indol-2-yl)-methanone;

(11)
2-[5-amino-1-(2-methyl-1H-benzimidazol-5-yl)-1H-pyrazole-4-carbonyl]-1H-indole-5-carbonitrile;

(12)
[5-amino-1-(2-methyl-1H-benzimidazol-5-yl)-1H-pyrazol-4-yl]-(6-bromo-5-fluoro-1H-indol-2-yl)-methanone;

(13)
[5-amino-1-(2-methyl-1H-benzimidazol-5-yl)-1H-pyrazol-4-yl]-(5-ethynyl-1H-indol-2-yl)-methanone;

(14)
[5-amino-1-(2-methyl-1H-benzimidazol-5-yl)-1H-pyrazol-4-yl]-[6-(2-fluoro-phenyl)-1H-indol-2-yl]-methanone;

(15) [5-amino-1-(2-methyl-1H-benzimidazol-5-yl)-1H-pyrazol-4-yl]-[6-(3-fluoro-phenyl)-1H-indol-2-yl]-methanone;
(16) [5-amino-1-(2-methyl-1H-benzimidazol-5-yl)-1H-pyrazol-4-yl]-[6-(4-fluoro-phenyl)-1H-indol-2-yl]-methanone;
(17) [5-amino-1-(2-methyl-1H-benzimidazol-5-yl)-1H-pyrazol-4-yl]-[6-(2-chloro-phenyl)-1H-indol-2-yl]-methanone;
(18) [5-amino-1-(2-methyl-1H-benzimidazol-5-yl)-1H-pyrazol-4-yl]-[6-(3-chloro-phenyl)-1H-indol-2-yl]-methanone;
(19) [5-amino-1-(2-methyl-1H-benzimidazol-5-yl)-1H-pyrazol-4-yl]-[6-(4-chloro-phenyl)-1H-indol-2-yl]-methanone;
(20) [5-amino-1-(2-methyl-1H-benzimidazol-5-yl)-1H-pyrazol-4-yl]-[6-(2-trifluoromethyl-phenyl)-1H-indol-2-yl]-methanone;
(21) [5-amino-1-(2-methyl-1H-benzimidazol-5-yl)-1H-pyrazol-4-yl]-[6-(3-trifluoromethyl-phenyl)-1H-indol-2-yl]-methanone;
(22) [5-amino-1-(2-methyl-1H-benzimidazol-5-yl)-1H-pyrazol-4-yl]-[6-(4-trifluoromethyl-phenyl)-1H-indol-2-yl]-methanone;
(23) [5-amino-1-(2-methyl-1H-benzimidazol-5-yl)-1H-pyrazol-4-yl]-(4-bromo-1H-indol-2-yl)-methanone;
(24) [5-amino-1-(2-methyl-1H-benzimidazol-5-yl)-1H-pyrazol-4-yl]-[6-(3-fluoro-pyridin-2-yl)-1H-indol-2-yl]-methanone;
(25) [5-amino-1-(2-methyl-1H-benzimidazol-5-yl)-1H-pyrazol-4-yl]-(6-methyl-1H-indol-2-yl)-methanone;
(26) [5-amino-1-(2-methyl-1H-benzimidazol-5-yl)-1H-pyrazol-4-yl]-[5-(4,4-difluoro-piperidine-1-carbonyl)-1H-indol-2-yl]-methanone;
(27) [5-amino-1-(2-methyl-1H-benzimidazol-5-yl)-1H-pyrazol-4-yl]-[5-(3,3-difluoro-piperidine-1-carbonyl)-1H-indol-2-yl]-methanone;
(28) 2-[5-amino-1-(2-methyl-1H-benzimidazol-5-yl)-1H-pyrazole-4-carbonyl]-1H-indole-5-carboxylic acid (2,2,2-trifluoro-ethyl)-amide;
(29) [5-amino-1-(2-methyl-1H-benzimidazol-5-yl)-1H-pyrazol-4-yl]-[6-(5-trifluoromethyl-pyridin-2-yl)-1H-indol-2-yl]-methanone;
(30) [5-amino-1-(2-methyl-1H-benzimidazol-5-yl)-1H-pyrazol-4-yl]-[6-(6-trifluoromethyl-pyridin-2-yl)-1H-indol-2-yl]-methanone;
(31) [5-amino-1-(2-methyl-1H-benzimidazol-5-yl)-1H-pyrazol-4-yl]-[6-(5-chloro-pyridin-2-yl)-1H-indol-2-yl]-methanone;
(32) [5-amino-1-(2-methyl-1H-benzimidazol-5-yl)-1H-pyrazol-4-yl]-[6-(4-methyl-pyridin-2-yl)-1H-indol-2-yl]-methanone;
(33) [5-amino-1-(2-methyl-1H-benzimidazol-5-yl)-1H-pyrazol-4-yl]-[6-(3-chloro-4-fluoro-phenyl)-1H-indol-2-yl]-methanone;
(34) [5-amino-1-(2-methyl-1H-benzimidazol-5-yl)-1H-pyrazol-4-yl]-[6-(3-trifluoromethyl-pyridin-2-yl)-1H-indol-2-yl]-methanone;
(35) [5-amino-1-(2-methyl-1H-benzimidazol-5-yl)-1H-pyrazol-4-yl]-[6-(4-trifluoromethyl-pyridin-2-yl)-1H-indol-2-yl]-methanone;
(36) [5-amino-1-(6-fluoro-2-methyl-1H-benzimidazol-5-yl)-1H-pyrazol-4-yl]-(1H-indol-2-yl)-methanone;
(37) 2-[5-amino-1-(2-methyl-1H-benzimidazol-5-yl)-1H-pyrazole-4-carbonyl]-1H-indole-6-carboxylic acid;
(38) [5-amino-1-(2-methyl-1H-benzimidazol-5-yl)-1H-pyrazol-4-yl]-(6-hydroxymethyl-1H-indol-2-yl)-methanone;
(39) [5-amino-1-(2-methyl-1H-benzimidazol-5-yl)-1H-pyrazol-4-yl]-{6-[2-(4-methyl-piperazin-1-yl)-ethoxy]-1H-indol-2-yl}-methanone;
(40) [5-amino-1-(2-methyl-1H-benzimidazol-5-yl)-1H-pyrazol-4-yl]-[6-(3-methyl-oxetan-3-ylmethoxy)-1H-indol-2-yl]-methanone;
(41) [5-amino-1-(2-methyl-1H-benzimidazol-5-yl)-1H-pyrazol-4-yl]-[6-(3-fluoro-piperidin-1-ylmethyl)-1H-indol-2-yl]-methanone;
(42) [5-amino-1-(2-methyl-1H-benzimidazol-5-yl)-1H-pyrazol-4-yl]-(6-{[bis(2-methoxy-ethyl)amino]-methyl}-1H-indol-2-yl)-methanone;
(43) [5-amino-1-(2-methyl-1H-benzimidazol-5-yl)-1H-pyrazol-4-yl]-{6-[(methyl-prop-2-ynyl-amino)methyl]-1H-indol-2-yl}-methanone;
(44) [5-amino-1-(2-methyl-1H-benzimidazol-5-yl)-1H-pyrazol-4-yl]-[6-(3,3-difluoro-pyrrolidin-1-ylmethyl)-1H-indol-2-yl]-methanone;
(45) [5-amino-1-(2-methyl-1H-benzimidazol-5-yl)-1H-pyrazol-4-yl]-[6-(2,5-dimethyl-pyrrolidin-1-ylmethyl)-1H-indol-2-yl]-methanone;
(46) [5-amino-1-(2-methyl-1H-benzimidazol-5-yl)-1H-pyrazol-4-yl]-[6-(3,3-difluoro-piperidin-1-ylmethyl)-1H-indol-2-yl]-methanone;
(47) [5-amino-1-(2-methyl-1H-benzimidazol-5-yl)-1H-pyrazol-4-yl]-[6-((S)-3-methyl-morpholin-4-ylmethyl)-1H-indol-2-yl]-methanone;
(48) [5-amino-1-(2-methyl-1H-benzimidazol-5-yl)-1H-pyrazol-4-yl]-(6-bromo-1H-indol-2-yl)-methanone;
(49) [5-amino-1-(2-methyl-1H-benzimidazol-5-yl)-1H-pyrazol-4-yl]-(5-iodo-1H-indol-2-yl)-methanone;
(50) [5-amino-1-(2-methyl-1H-benzimidazol-5-yl)-1H-pyrazol-4-yl]-(1H-pyrrolo[3,2-b]pyridin-2-yl)-methanone;

(51) [5-amino-1-(2-methyl-1H-benzimidazol-5-yl)-1H-pyrazol-4-yl]-(5-bromo-6-trifluoromethyl-1H-indol-2-yl)-methanone;
(52) [5-amino-1-(2-methyl-1H-benzimidazol-5-yl)-1H-pyrazol-4-yl]-(6-iodo-1H-indol-2-yl)-methanone;
(53) [5-amino-1-(2-methyl-1H-benzimidazol-5-yl)-1H-pyrazol-4-yl]-(4-methyl-1H-indol-2-yl)-methanone;
(54) [5-amino-1-(2-methyl-1H-benzimidazol-5-yl)-1H-pyrazol-4-yl]-(4-isopropyl-1H-indol-2-yl)-methanone;
(55) [5-amino-1-(2-methyl-1H-benzimidazol-5-yl)-1H-pyrazol-4-yl]-[5-(2-fluoro-phenyl)-1H-indol-2-yl]-methanone;
(56) [5-amino-1-(2-methyl-1H-benzimidazol-5-yl)-1H-pyrazol-4-yl]-(5-benzyl-1H-indol-2-yl)-methanone;
(57) [5-amino-1-(2-methyl-1H-benzimidazol-5-yl)-1H-pyrazol-4-yl]-[5-(2-trifluoromethyl-phenyl)-1H-indol-2-yl]-methanone;
(58) [5-amino-1-(2-methyl-1H-benzimidazol-5-yl)-1H-pyrazol-4-yl]-[5-(3-fluorophenyl)-1H-indol-2-yl]-methanone;
(59) [5-amino-1-(2-methyl-1H-benzimidazol-5-yl)-1H-pyrazol-4-yl]-[5-(3-trifluoromethyl-phenyl)-1H-indol-2-yl]-methanone;
(60) [5-amino-1-(2-methyl-1H-benzimidazol-5-yl)-1H-pyrazol-4-yl]-(4-ethynyl-1H-indol-2-yl)-methanone;
(61) [5-amino-1-(2-methyl-1H-benzimidazol-5-yl)-1H-pyrazol-4-yl]-(5H-[1,3]dioxolo[4,5-f]indol-6-yl)-methanone;
(62) [5-amino-1-(7-fluoro-2-methyl-1H-benzimidazol-5-yl)-1H-pyrazol-4-yl]-(1H-indol-2-yl)-methanone;
(63) [5-amino-1-(2-methyl-1H-benzimidazol-5-yl)-1H-pyrazol-4-yl]-[5-(4-trifluoromethyl-phenyl)-1H-indol-2-yl]-methanone;
(64) [5-amino-1-(2-methyl-1H-benzimidazol-5-yl)-1H-pyrazol-4-yl]-(5-butoxy-1H-indol-2-yl)-methanone;
(65) [5-amino-1-(2-methyl-1H-benzimidazol-5-yl)-1H-pyrazol-4-yl]-[5-(1-methyl-piperidin-4-yl)-1H-indol-2-yl]-methanone;
(66) N-{2-[5-amino-1-(2-methyl-1H-benzimidazol-5-yl)-1H-pyrazole-4-carbonyl]-1H-indol-6-yl}-methanesulfonamide;
(67) [5-amino-1-(2-methyl-1H-benzimidazol-5-yl)-1H-pyrazol-4-yl]-[6-(6-morpholin-4-yl-pyridin-3-yl)-1H-indol-2-yl]-methanone;
(68) [5-amino-1-(2-methyl-1H-benzimidazol-5-yl)-1H-pyrazol-4-yl]-(6-butyl-1H-indol-2-yl)-methanone;
(69) [5-amino-1-(2-methyl-1H-benzimidazol-5-yl)-1H-pyrazol-4-yl]-[6-(1-methyl-1H-pyrazol-4-yl)-1H-indol-2-yl]-methanone;
(70) [5-amino-1-(2-methyl-1H-benzimidazol-5-yl)-1H-pyrazol-4-yl]-[6-(5-methoxy-pyridin-3-yl)-1H-indol-2-yl]-methanone;
(71) [5-amino-1-(2-methyl-1H-benzimidazol-5-yl)-1H-pyrazol-4-yl]-[6-(2-methoxy-pyridin-3-yl)-1H-indol-2-yl]-methanone;
(72) [5-amino-1-(2-methyl-1H-benzimidazol-5-yl)-1H-pyrazol-4-yl]-(6-cyclopropyl-1H-indol-2-yl)-methanone;
(73) [5-amino-1-(2-methyl-1H-benzimidazol-5-yl)-1H-pyrazol-4-yl]-[6-(2-methoxy-phenyl)-1H-indol-2-yl]-methanone;
(74) [5-amino-1-(2-methyl-1H-benzimidazol-5-yl)-1H-pyrazol-4-yl]-(6-phenyl-1H-indol-2-yl)-methanone;
(75) [5-amino-1-(2-methyl-1H-benzimidazol-5-yl)-1H-pyrazol-4-yl]-[6-(5-methanesulfonyl-pyridin-3-yl)-1H-indol-2-yl]-methanone;
(76) [5-amino-1-(2-methyl-1H-benzimidazol-5-yl)-1H-pyrazol-4-yl]-(6-isopropyl-1H-indol-2-yl)-methanone;
(77) [5-amino-1-(2-methyl-1H-benzimidazol-5-yl)-1H-pyrazol-4-yl]-(6-pyridin-2-yl-1H-indol-2-yl)-methanone;
(78) [5-amino-1-(2-methyl-1H-benzimidazol-5-yl)-1H-pyrazol-4-yl]-(5-cyclopropyl-1H-indol-2-yl)-methanone;
(79) [5-amino-1-(2-methyl-1H-benzimidazol-5-yl)-1H-pyrazol-4-yl]-(6-pyridazin-3-yl-1H-indol-2-yl)-methanone;
(80) [5-amino-1-(2-methyl-1H-benzimidazol-5-yl)-1H-pyrazol-4-yl]-(5-isopropoxy-1H-indol-2-yl)-methanone;
(81) [5-amino-1-(2-methyl-1H-benzimidazol-5-yl)-1H-pyrazol-4-yl]-[5-(2-methoxy-ethoxy)-1H-indol-2-yl]-methanone;
(82) [5-amino-1-(2-methyl-1H-benzimidazol-5-yl)-1H-pyrazol-4-yl]-(5-cyclopropylmethoxy-1H-indol-2-yl)-methanone;
(83) [5-amino-1-(2-methyl-1H-benzimidazol-5-yl)-1H-pyrazol-4-yl]-(2,2-difluoro-5H-[1,3]dioxolo[4,5-f]indol-6-yl)-methanone;
(84) [5-amino-1-(2-methyl-1H-benzimidazol-5-yl)-1H-pyrazol-4-yl]-[6-(3-chloro-pyridin-2-yl)-1H-indol-2-yl]-methanone;
(85) [5-amino-1-(2-methyl-1H-benzimidazol-5-yl)-1H-pyrazol-4-yl]-[6-(5-fluoro-pyridin-2-yl)-1H-indol-2-yl]-methanone;
(86) [5-amino-1-(2-methyl-1H-benzimidazol-5-yl)-1H-pyrazol-4-yl]-[6-(6-morpholin-4-yl-pyridazin-3-yl)-1H-indol-2-yl]-methanone;
(87) [5-amino-1-(2-methyl-1H-benzimidazol-5-yl)-1H-pyrazol-4-yl]-(5-chloro-6-cyclopropylmethoxy-1H-indol-2-yl)-methanone;
(88) [5-amino-1-(2-methyl-1H-benzimidazol-5-yl)-1H-pyrazol-4-yl]-[6-(2,4-difluoro-phenyl)-1H-indol-2-yl]-methanone;

(89) [5-amino-1-(2-methyl-1H-benzimidazol-5-yl)-1H-pyrazol-4-yl]-(6-pyridazin-4-yl-1H-indol-2-yl)-methanone;
(90) [5-amino-1-(2-methyl-1H-benzimidazol-5-yl)-1H-pyrazol-4-yl]-(3-fluoro-1H-indol-2-yl)-methanone;
(91) [5-amino-1-(2-methyl-1H-benzimidazol-5-yl)-1H-pyrazol-4-yl]-[5-(1-isopropyl-piperidin-4-yl)-6-trifluoromethyl-1H-indol-2-yl]-methanone;
(92) 2-[5-amino-1-(2-methyl-1H-benzimidazol-5-yl)-1H-pyrazole-4-carbonyl]-1H-indole-6-carbonitrile;
(93) [5-amino-1-(2-methyl-1H-benzimidazol-5-yl)-1H-pyrazol-4-yl]-[5-(1,2,3,6-tetrahydro-pyridin-4-yl)-1H-indol-2-yl]-methanone;
(94) [5-amino-1-(2-methyl-1H-benzimidazol-5-yl)-1H-pyrazol-4-yl]-(5-piperidin-4-yl-1H-indol-2-yl)-methanone;
(95) [5-amino-1-(2-methyl-1H-benzimidazol-5-yl)-1H-pyrazol-4-yl]-[5-((R)-3-fluoro-pyrrolidin-1-ylmethyl)-1H-indol-2-yl]-methanone;
(96) [5-amino-1-(2-methyl-1H-benzimidazol-5-yl)-1H-pyrazol-4-yl]-(6-fluoro-5-piperidin-4-yl-1H-indol-2-yl)-methanone;
(97) [5-amino-1-(2-methyl-1H-benzimidazol-5-yl)-1H-pyrazol-4-yl]-[6-fluoro-5-(1-methyl-piperidin-4-yl)-1H-indol-2-yl]-methanone;
(98) [5-amino-1-(2-methyl-1H-benzimidazol-5-yl)-1H-pyrazol-4-yl]-[5-(1-isopropyl-piperidin-4-yl)-1H-indol-2-yl]-methanone;
(99) [5-amino-1-(2-methyl-1H-benzimidazol-5-yl)-1H-pyrazol-4-yl]-[6-fluoro-5-(1-isopropyl-piperidin-4-yl)-1H-indol-2-yl]-methanone;
(100) [5-amino-1-(2-methyl-1H-benzimidazol-5-yl)-1H-pyrazol-4-yl]-(6-pyridin-3-yl-1H-indol-2-yl)-methanone;
(101) [5-amino-1-(2-methyl-1H-benzimidazol-5-yl)-1H-pyrazol-4-yl]-[5-(6-morpholin-4-ylpyridin-3-yl)-1H-indol-2-yl]-methanone;
(102) [5-amino-1-(2-methyl-1H-benzimidazol-5-yl)-1H-pyrazol-4-yl]-(5-pyridin-3-yl-1H-indol-2-yl)-methanone;
(103) [5-amino-1-(2-methyl-1H-benzimidazol-5-yl)-1H-pyrazol-4-yl]-[5-(6-piperazin-1-yl-pyridin-3-yl)-1H-indol-2-yl]-methanone;
(104) [5-amino-1-(2-methyl-1H-benzimidazol-5-yl)-1H-pyrazol-4-yl]-[5-(6-hydroxy-pyridin-3-yl)-1H-indol-2-yl]-methanone;
(105) [5-amino-1-(2-methyl-1H-benzimidazol-5-yl)-1H-pyrazol-4-yl]-[6-fluoro-5-(4-methyl-piperazin-1-ylmethyl)-1H-indol-2-yl]-methanone;
(106) [5-amino-1-(2-methyl-1H-benzimidazol-5-yl)-1H-pyrazol-4-yl]-(6-fluoro-5-pyrrolidin-1-ylmethyl-1H-indol-2-yl)-methanone;
(107) [5-amino-1-(2-methyl-1H-benzimidazol-5-yl)-1H-pyrazol-4-yl]-[6-(1-methyl-piperidin-4-yl)-1H-indol-2-yl]-methanone;
(108) [5-amino-1-(2-methyl-1H-benzimidazol-5-yl)-1H-pyrazol-4-yl]-[6-(4-morpholin-4-yl-phenyl)-1H-indol-2-yl]-methanone;
(109) [5-amino-1-(2-methyl-1H-benzimidazol-5-yl)-1H-pyrazol-4-yl]-[6-(3,4,5,6-tetrahydro-2H-[1,2']bipyridin-5'-yl)-1H-indol-2-yl]-methanone;
(110) [5-amino-1-(2-methyl-1H-benzimidazol-5-yl)-1H-pyrazol-4-yl]-[6-(6-piperazin-1-yl-pyridin-3-yl)-1H-indol-2-yl]-methanone;
(111) [5-amino-1-(2-methyl-1H-benzimidazol-5-yl)-1H-pyrazol-4-yl]-[5-(6-methoxy-pyridin-3-yl)-1H-indol-2-yl]-methanone;
(112) [5-amino-1-(2-methyl-1H-benzimidazol-5-yl)-1H-pyrazol-4-yl]-[5-((S)-3-methyl-morpholin-4-ylmethyl)-1H-indol-2-yl]-methanone;
(113) [5-amino-1-(2-methyl-1H-benzimidazol-5-yl)-1H-pyrazol-4-yl]-[6-((R)-3-fluoro-pyrrolidin-1-ylmethyl)-1H-indol-2-yl]-methanone;
(114) [5-amino-1-(2-methyl-1H-benzimidazol-5-yl)-1H-pyrazol-4-yl]-[5-(2,5-dimethyl-pyrrolidin-1-ylmethyl)-1H-indol-2-yl]-methanone;
(115) [5-amino-1-(2-methyl-1H-benzimidazol-5-yl)-1H-pyrazol-4-yl]-[5-(3-fluoro-piperidin-1-ylmethyl)-1H-indol-2-yl]-methanone;
(116) [5-amino-1-(2-methyl-1H-benzimidazol-5-yl)-1H-pyrazol-4-yl]-[5-(3,3-difluoro-piperidin-1-ylmethyl)-1H-indol-2-yl]-methanone;
(117) [5-amino-1-(2-methyl-1H-benzimidazol-5-yl)-1H-pyrazol-4-yl]-{6-[2-(4-methyl-piperazin-1-yl)pyridin-4-yl]-1H-indol-2-yl}-methanone;
(118) [5-amino-1-(2-methyl-1H-benzimidazol-5-yl)-1H-pyrazol-4-yl]-(6-pyridin-4-yl-1H-indol-2-yl)-methanone;
(119) [5-amino-1-(2-methyl-1H-benzimidazol-5-yl)-1H-pyrazol-4-yl]-[5-(4-fluoropiperidin-1-ylmethyl)-1H-indol-2-yl]-methanone;
(120) [5-amino-1-(2-methyl-1H-benzimidazol-5-yl)-1H-pyrazol-4-yl]-[5-(4,4-difluoro-piperidin-1-ylmethyl)-1H-indol-2-yl]-methanone;
(121) [5-amino-1-(2-difluoromethyl-1H-benzimidazol-5-yl)-1H-pyrazol-4-yl]-[5-(1-methyl-piperidin-4-yl)-1H-indol-2-yl]-methanone;
(122) [5-amino-1-(2-difluoromethyl-1H-benzimidazol-5-yl)-1H-pyrazol-4-yl]-(1H-indol-2-yl)-methanone;
(123) [5-amino-1-(2-methyl-1H-benzimidazol-5-yl)-1H-pyrazol-4-yl]-[5-(3,3-difluoro-pyrrolidin-1-ylmethyl)-1H-indol-2-yl]-methanone;

(124) [5-amino-1-(2-methyl-1H-benzimidazol-5-yl)-1H-pyrazol-4-yl]-[5-(1-cyclopentyl-piperidin-4-yl)-1H-indol-2-yl]-methanone;
(125) [5-amino-1-(2-methyl-1H-benzimidazol-5-yl)-1H-pyrazol-4-yl]-[5-(1-cyclohexyl-piperidin-4-yl)-1H-indol-2-yl]-methanone;
(126) [5-amino-1-(2-methyl-1H-benzimidazol-5-yl)-1H-pyrazol-4-yl]-(4-bromo-1H-pyrrol-2-yl)-methanone;
(127) [5-amino-1-(2-methyl-1H-benzimidazol-5-yl)-1H-pyrazol-4-yl]-(1H-pyrrol-2-yl)-methanone;
(128) [5-amino-1-(2-methyl-1H-benzimidazol-5-yl)-1H-pyrazol-4-yl]-(4-phenyl-1H-pyrrol-2-yl)-methanone;
(129) [5-amino-1-(2-methyl-1H-benzimidazol-5-yl)-1H-pyrazol-4-yl]-[4-(3-chloro-phenyl)-1H-pyrrol-2-yl]-methanone;
(130) [5-amino-1-(2-methyl-1H-benzimidazol-5-yl)-1H-pyrazol-4-yl]-[4-(4-fluoro-phenyl)-1H-pyrrol-2-yl]-methanone;
(131) [5-amino-1-(2-methyl-1H-benzimidazol-5-yl)-1H-pyrazol-4-yl]-[4-(3-fluoro-phenyl)-1H-pyrrol-2-yl]-methanone;
(132) [5-amino-1-(2-methyl-1H-benzimidazol-5-yl)-1H-pyrazol-4-yl]-(6-morpholin-4-ylmethyl-1H-indol-2-yl)-methanone;
(133) [5-amino-1-(2-methyl-1H-benzimidazol-5-yl)-1H-pyrazol-4-yl]-[4-(2-morpholin-4-yl-ethylamino)-1H-indol-2-yl]-methanone;
(134) [5-amino-1-(2-methyl-1H-benzimidazol-5-yl)-1H-pyrazol-4-yl]-[5-(4-methyl-piperazine-1-carbonyl)-1H-indol-2-yl]-methanone;
(135) [5-amino-1-(2-methyl-1H-benzimidazol-5-yl)-1H-pyrazol-4-yl]-[6-(2-morpholin-4-yl-ethylamino)-1H-indol-2-yl]-methanone;
(136) [5-amino-1-(2-methyl-1H-benzimidazol-5-yl)-1H-pyrazol-4-yl]-[5-(piperazine-1-carbonyl)-1H-indol-2-yl]-methanone;
(137) [5-amino-1-(2-methyl-1H-benzimidazol-5-yl)-1H-pyrazol-4-yl]-[4-(2-methoxy-ethylamino)-1H-indol-2-yl]-methanone;
(138) [5-amino-1-(2-methyl-1H-benzimidazol-5-yl)-1H-pyrazol-4-yl]-[4-(2-hydroxy-1-hydroxymethyl-ethylamino)-1H-indol-2-yl]-methanone;
(139) [5-amino-1-(2-methyl-1H-benzimidazol-5-yl)-1H-pyrazol-4-yl]-[4-(2-pyridin-4-yl-ethylamino)-1H-indol-2-yl]-methanone;
(140) [5-amino-1-(2-methyl-1H-benzimidazol-5-yl)-1H-pyrazol-4-yl]-[6-(2-methoxy-ethylamino)-1H-indol-2-yl]-methanone;
(141) [5-amino-1-(2-methyl-1H-benzimidazol-5-yl)-1H-pyrazol-4-yl]-(6-morpholin-4-yl-1H-indol-2-yl)-methanone;
(142) [5-amino-1-(2-methyl-1H-benzimidazol-5-yl)-1H-pyrazol-4-yl]-(4-morpholin-4-yl-1H-indol-2-yl)-methanone;
(143) [5-amino-1-(2-methyl-1H-benzimidazol-5-yl)-1H-pyrazol-4-yl]-(4-morpholin-4-ylmethyl-1H-indol-2-yl)-methanone;
(144) [5-amino-1-(2-methyl-1H-benzimidazol-5-yl)-1H-pyrazol-4-yl]-(5-morpholin-4-ylmethyl-1H-indol-2-yl)-methanone;
(145) [5-amino-1-(2-methyl-1H-benzimidazol-5-yl)-1H-pyrazol-4-yl]-[5-(morpholine-4-carbonyl)-1H-indol-2-yl]-methanone;
(146) [5-amino-1-(2-isopropyl-1H-benzimidazol-5-yl)-1H-pyrazol-4-yl]-(1H-indol-2-yl)-methanone;
(147) [5-amino-1-(2-propyl-1H-benzimidazol-5-yl)-1H-pyrazol-4-yl]-(1H-indol-2-yl)-methanone;
(148) [5-amino-1-(1H-benzimidazol-5-yl)-1H-pyrazol-4-yl]-(1H-indol-2-yl)-methanone;
149) [5-amino-1-(2-trifluoromethyl-1H-benzimidazol-5-yl)-1H-pyrazol-4-yl]-(1H-indol-2-yl)-methanone;
(150) [5-amino-1-(2-ethyl-1H-benzimidazol-5-yl)-1H-pyrazol-4-yl]-(1H-indol-2-yl)-methanone;
(151) [5-amino-1-(2-benzyl-1H-benzimidazol-5-yl)-1H-pyrazol-4-yl]-(1H-indol-2-yl)-methanone;
152) 1-(4-{2-[5-amino-1-(2-methyl-1H-benzimidazol-5-yl)-1H-pyrazole-4-carbonyl]-1H-indol-5-ylmethyl}-piperazin-1-yl)-ethanone;
(153) [5-amino-1-(2-methyl-1H-benzimidazol-5-yl)-1H-pyrazol-4-yl]-[5-(4-methanesulfonyl-piperazin-1-ylmethyl)-1H-indol-2-yl]-methanone;
(154) [5-amino-1-(2-methyl-1H-benzimidazol-5-yl)-1H-pyrazol-4-yl]-(5-piperazin-1-ylmethyl-1H-indol-2-yl)-methanone;
(155) 1-(4-{2-[5-amino-1-(2-methyl-1H-benzimidazol-5-yl)-1H-pyrazole-4-carbonyl]-1H-indol-6-ylmethyl}piperazin-1-yl)-ethanone;
(156) [5-amino-1-(2-methyl-1H-benzimidazol-5-yl)-1H-pyrazol-4-yl]-[6-(4-methyl-piperazin-1-ylmethyl)-1H-indol-2-yl]-methanone;
(157) [5-amino-1-(2-methyl-1H-benzimidazol-5-yl)-1H-pyrazol-4-yl]-[5-(4-methyl-piperazin-1-ylmethyl)-1H-indol-2-yl]-methanone;
(158) [5-amino-1-(2-methyl-1H-benzimidazol-5-yl)-1H-pyrazol-4-yl]-(5-pyrrolidin-1-ylmethyl-1H-indol-2-yl)-methanone;
(159) [5-amino-1-(2-methyl-1H-benzimidazol-5-yl)-1H-pyrazol-4-yl]-(4-fluoro-1H-indol-2-yl)-methanone;
(160) [5-amino-1-(2-methyl-1H-benzimidazol-5-yl)-1H-pyrazol-4-yl]-(5-fluoro-1H-indol-2-yl)-methanone;

(161) [5-amino-1-(2-methyl-1H-benzimidazol-5-yl)-1H-pyrazol-4-yl]-(6-fluoro-1H-indol-2-yl)-methanone;
(162) [5-amino-1-(2-methyl-1H-benzimidazol-5-yl)-1H-pyrazol-4-yl]-(1H-pyrrolo[2,3-b]pyridin-2-yl)-methanone;
(163) [5-amino-1-(2-methyl-1H-benzimidazol-5-yl)-1H-pyrazol-4-yl]-(5-fluoro-6-morpholin-4-ylmethyl-1H-indol-2-yl)-methanone;
(164) 2-[5-amino-1-(2-methyl-1H-benzimidazol-5-yl)-1H-pyrazole-4-carbonyl]-1H-indole-5-carboxylic acid;
(165) [5-amino-1-(2-methyl-1H-benzimidazol-5-yl)-1H-pyrazol-4-yl]-(5-methoxy-1H-indol-2-yl)-methanone;
(166) [5-amino-1-(2-methyl-1H-benzimidazol-5-yl)-1H-pyrazol-4-yl]-(4,6-dimethoxy-1H-indol-2-yl)-methanone;
(167) [5-amino-1-(2-methyl-1H-benzimidazol-5-yl)-1H-pyrazol-4-yl]-(4-methoxy-1H-indol-2-yl)-methanone;
(168) [5-amino-1-(2-methyl-1H-benzimidazol-5-yl)-1H-pyrazol-4-yl]-(6-methoxy-1H-indol-2-yl)-methanone;
(169) [5-amino-1-(2-methyl-1H-benzimidazol-5-yl)-1H-pyrazol-4-yl]-(4,6-dimethyl-1H-indol-2-yl)-methanone;
(170) [5-amino-1-(2-methyl-1H-benzimidazol-5-yl)-1H-pyrazol-4-yl]-(5-tert-butyl-1H-indol-2-yl)-methanone;
(171) [5-amino-1-(2-methyl-1H-benzimidazol-5-yl)-1H-pyrazol-4-yl]-(5-isopropyl-1H-indol-2-yl)-methanone;
(172) [5-amino-1-(2-methyl-1H-benzimidazol-5-yl)-1H-pyrazol-4-yl]-(5-benzyloxy-1H-indol-2-yl)-methanone;
(173) [5-amino-1-(2-methyl-1H-benzimidazol-5-yl)-1H-pyrazol-4-yl]-(4-benzyloxy-1H-indol-2-yl)-methanone;
(174) [5-amino-1-(2-methyl-1H-benzimidazol-5-yl)-1H-pyrazol-4-yl]-(5,6-dimethoxy-1H-indol-2-yl)-methanone;
(175) [5-amino-1-(2-methyl-1H-benzimidazol-5-yl)-1H-pyrazol-4-yl]-(6-tert-butyl-1H-indol-2-yl)-methanone;
(176) [5-amino-1-(2-methyl-1H-benzimidazol-5-yl)-1H-pyrazol-4-yl]-(5-fluoro-4-trifluoromethyl-1H-indol-2-yl)-methanone;
(177) [5-amino-1-(2-methyl-1H-benzimidazol-5-yl)-1H-pyrazol-4-yl]-(5-phenoxy-1H-indol-2-yl)-methanone;
(178) [5-amino-1-(2-methyl-1H-benzimidazol-5-yl)-1H-pyrazol-4-yl]-(6-methylsulfanyl-1H-indol-2-yl)-methanone;
(179) [5-amino-1-(2-methyl-1H-benzimidazol-5-yl)-1H-pyrazol-4-yl]-(4-tert-butyl-1H-indol-2-yl)-methanone;
(180) [5-amino-1-(2-methyl-1H-benzimidazol-5-yl)-1H-pyrazol-4-yl]-(5-methyl-1H-indol-2-yl)-methanone;
(181) [5-amino-1-(2-methyl-1H-benzimidazol-5-yl)-1H-pyrazol-4-yl]-(5-ethyl-1H-indol-2-yl)-methanone;
(182) [5-amino-1-(2-methyl-1H-benzimidazol-5-yl)-1H-pyrazol-4-yl]-(5-fluoro-6-trifluoromethyl-1H-indol-2-yl)-methanone;
(183) [5-amino-1-(2-methyl-1H-benzimidazol-5-yl)-1H-pyrazol-4-yl]-(6-fluoro-5-methoxy-1H-indol-2-yl)-methanone;
(184) [5-amino-1-(2-methyl-1H-benzimidazol-5-yl)-1H-pyrazol-4-yl]-(6-chloro-5-methoxy-1H-indol-2-yl)-methanone;
(185) [5-amino-1-(2-methyl-1H-benzimidazol-5-yl)-1H-pyrazol-4-yl]-(5-chloro-6-methoxy-1H-indol-2-yl)-methanone;
(186) [5-amino-1-(2-methyl-1H-benzimidazol-5-yl)-1H-pyrazol-4-yl]-(6-isopropoxy-1H-indol-2-yl)-methanone;
(187) [5-amino-1-(2-methyl-1H-benzimidazol-5-yl)-1H-pyrazol-4-yl]-(6-benzyloxy-1H-indol-2-yl)-methanone;
(188) [5-amino-1-(2-methyl-1H-benzimidazol-5-yl)-1H-pyrazol-4-yl]-(4-isopropoxy-1H-indol-2-yl)-methanone;
(189) [5-amino-1-(2-methyl-1H-benzimidazol-5-yl)-1H-pyrazol-4-yl]-(2,3-dihydro-6H-[1,4]dioxino[2,3-f]indol-7-yl)-methanone;
(190) [5-amino-1-(2-methyl-1H-benzimidazol-5-yl)-1H-pyrazol-4-yl]-(4,6-di-tert-butyl-1H-indol-2-yl)-methanone;
(191) 2-[5-amino-1-(2-methyl-1H-benzimidazol-5-yl)-1H-pyrazole-4-carbonyl]-1H-indole-4-carbonitrile;
(192) [5-amino-1-(2-methyl-1H-benzimidazol-5-yl)-1H-pyrazol-4-yl]-(5-imidazol-1-yl-1H-indol-2-yl)-methanone;
(193) [5-amino-1-(2-methyl-1H-benzimidazol-5-yl)-1H-pyrazol-4-yl]-(5-trifluoromethylsulfanyl-1H-indol-2-yl)-methanone;
(194) [5-amino-1-(2-methyl-1H-benzimidazol-5-yl)-1H-pyrazol-4-yl]-(5-methylsulfanyl-1H-indol-2-yl)-methanone;
(195) [5-amino-1-(2-methyl-1H-benzimidazol-5-yl)-1H-pyrazol-4-yl]-(5-methanesulfonyl-1H-indol-2-yl)-methanone;
(196) [5-amino-1-(2-methyl-1H-benzimidazol-5-yl)-1H-pyrazol-4-yl]-[6-(4,4-difluoro-piperidin-1-ylmethyl)-1H-indol-2-yl]-methanone;
(197) [5-amino-1-(2-methyl-1H-benzimidazol-5-yl)-1H-pyrazol-4-yl]-[6-(4-fluoro-piperidin-1-ylmethyl)-1H-indol-2-yl]-methanone;
(198) [5-amino-1-(2-methyl-1H-benzimidazol-5-yl)-1H-pyrazol-4-yl]-[6-(oxetan-3-yloxy)-1H-indol-2-yl]-methanone;
(199) [5-amino-1-(2-methyl-1H-benzimidazol-5-yl)-1H-pyrazol-4-yl]-(6-hydroxy-1H-indol-2-yl)-methanone;
(200) [5-amino-1-(2-methyl-1H-benzimidazol-5-yl)-1H-pyrazol-4-yl]-(6-methanesulfonyl-1H-indol-2-yl)-methanone;
(201) [5-amino-1-(2-methyl-1H-benzimidazol-5-yl)-1H-pyrazol-4-yl]-(4,5-dibromo-1H-pyrrol-2-yl)-methanone;

(202)
[5-amino-1-(2-methyl-1H-benzimidazol-5-yl)-1H-pyrazol-4-yl]-(4,5-diphenyl-1H-pyrrol-2-yl)-methanone; and
(203)
[5-amino-1-(2-methyl-1H-benzimidazol-5-yl)-1H-pyrazol-4-yl]-(4,5-dipyridin-3-yl-1H-pyrrol-2-yl)-methanone.

[106] A pharmaceutical composition comprising the compound of any one of [101] to [105], or a pharmaceutically acceptable salt thereof; and a carrier.

[107] An agent for inhibiting FGFR activity, which comprises as an active ingredient the compound of any one of [101] to [105], or a pharmaceutically acceptable salt thereof.

[108] An agent for preventing or treating cancer, which comprises as an active ingredient the compound of any one of [101] to [105], or a pharmaceutically acceptable salt thereof.

[109] The agent for preventing or treating cancer of [108], wherein the cancer is at least one selected from the group consisting of:
breast cancer, acute myelocytic leukemia, pancreatic cancer, bladder cancer, prostatic cancer, esophageal cancer, angiogenesis, stomach cancer, uterine body cancer, ovarian cancer, brain tumor, colon cancer, multiple myeloma, hepatocarcinoma, pulmonary cancer, and thyroid cancer.

[110] A method for preventing or treating cancer, comprising administering a pharmaceutically effective amount of a composition comprising the compound of any one of [101] to [105] or a pharmaceutically acceptable salt thereof to a patient in need of prevention or treatment of cancer.

[111] Use of the compound of any one of [101] to [105] or a pharmaceutically acceptable salt thereof in the production of an agent for preventing or treating cancer.

[112] The compound of any one of [101] to [105] or a pharmaceutically acceptable salt thereof, for preventing or treating cancer.

Effects of the Invention

The compounds of the present invention and pharmaceutically acceptable salts thereof have the activity of inhibiting FGFR family kinases in cancer tissues. Furthermore, the compounds of the present invention can exert efficacy on novel genes (non-target genes) altered in cancer, and thus can prevent and/or treat cancers against which no effective therapy has been available.

MODE FOR CARRYING OUT THE INVENTION

The present invention relates to aminopyrazole derivatives and uses thereof. The present inventors for the first time synthesized compounds represented by formula (I) shown above or pharmaceutically acceptable salts thereof and discovered that the compounds or salts thereof had the activity of inhibiting the FGFR family kinases.

Herein, the "alkyl" refers to a monovalent group derived from an aliphatic hydrocarbon by removing an arbitrary hydrogen atom. It contains no heteroatom nor unsaturated carbon-carbon bond in the backbone, and has a subset of hydrocarbyl or hydrocarbon group structures which contain hydrogen and carbon atoms. The alkyl group includes linear and branched structures. Preferred alkyl groups include alkyl groups with one to six carbon atoms ($C_{1-6}$; hereinafter, "$C_{p-q}$" means that the number of carbon atoms is p to q), $C_{1-5}$ alkyl groups, $C_{1-4}$ alkyl groups, and $C_{1-3}$ alkyl groups.

Specifically, the alkyl includes, for example, methyl group, ethyl group, n-propyl group, isopropyl group, n-butyl group, isobutyl group, s-butyl group, t-butyl group, pentyl group, isopentyl group, 2,3-dimethylpropyl group, 3,3-dimethylbutyl group, and hexyl group.

Herein, "alkenyl" refers to a monovalent hydrocarbon group having at least one double bond (two adjacent SP2 carbon atoms), and includes those of linear and branched forms. Depending on the configuration of the double bond and substituents (if any), the geometry of the double bond can be of entgegen (E) or zusammen (Z), or cis or trans configuration. Preferred alkenyl groups include $C_{2-6}$ alkenyl groups.

Specifically, the alkenyl includes, for example, vinyl group, allyl group, 1-propenyl group, 2-propenyl group, 1-butenyl group, 2-butenyl group (including cis and trans), 3-butenyl group, pentenyl group, and hexenyl group.

Herein, "alkynyl" refers to a monovalent hydrocarbon group having at least one triple bond (two adjacent SP carbon atoms), and includes those of linear and branched forms. Preferred alkynyl groups include $C_{2-6}$ alkynyl groups.

Specifically, the alkynyl includes, for example, ethynyl group, 1-propynyl group, propargyl group, 3-butynyl group, pentynyl group, and hexynyl group.

The alkenyl and alkynyl may each have one or more double bonds or triple bonds.

Herein, "cycloalkyl" refers to a saturated or partially saturated cyclic monovalent aliphatic hydrocarbon group, and includes monocyclic groups, bicyclo rings, and spiro rings. Preferred cycloalkyl includes $C_{3-7}$ cycloalkyl groups. Specifically, the cycloalkyl group includes, for example, cyclopropyl group, cyclobutyl group, cyclopentyl group, cyclohexyl group, and cycloheptyl group.

Herein, "cycloalkylalkyl" refers to a group in which an arbitrary hydrogen atom of an "alkyl" defined above is substituted with a "cycloalkyl" defined above. Preferred cycloalkylalkyl groups include $C_{3-7}$ cycloalkyl$C_{1-3}$ alkyl, and specifically includes, for example, cyclopropylmethyl group and cyclopropylethyl group.

Herein, "hetero atom" refers to a nitrogen atom (N), oxygen atom (O), or sulfur atom (S).

Herein, "halogen atom" refers to a fluorine atom, chlorine atom, bromine atom, or iodine atom.

Herein, "haloalkyl" refers to a group in which preferably one to nine, more preferably one to five identical or different "halogen atoms" defined above are linked to an "alkyl" defined above.

Specifically, the haloalkyl includes, for example, chloromethyl group, dichloromethyl group, trichloromethyl group, fluoromethyl group, difluoromethyl group, perfluoroalkyl group (such as trifluoromethyl group and —$CF_2CF_3$), and 2,2,2-trifluoroethyl group.

Herein, "alkoxy" refers to an oxy group linked with an "alkyl" defined above. Preferred alkoxy includes $C_{1-4}$ alkoxy groups and $C_{1-3}$ alkoxy groups. Specifically, alkoxy includes, for example, methoxy group, ethoxy group, 1-propoxy group, 2-propoxy group, n-butoxy group, i-butoxy group, sec-butoxy group, and tert-butoxy group.

Herein, "haloalkoxy" refers to a group in which preferably one to nine, more preferably one to five identical or different halogen atoms defined above are linked to an "alkoxy" defined above.

Specifically, the haloalkoxy includes, for example, chloromethoxy group, trichloromethoxy group, and trifluoromethoxy group.

Herein, "aryl" refers to a monovalent aromatic hydrocarbon ring. The aryl preferably includes $C_{6-10}$ aryl. Specifically, the aryl includes, for example, phenyl group and naphthyl groups (for example, 1-naphthyl group and 2-naphthyl group).

Herein, "alicyclic ring" refers to a monovalent non-aromatic hydrocarbon ring. The alicyclic ring may have unsaturated bonds within its ring, and may be a multicyclic group having two or more rings. The carbon atoms constituting the ring may be oxidized to form a carbonyl. The number of atoms constituting an alicyclic ring preferably ranges from three to ten (3- to 10-membered aliphatic ring). The alicyclic ring includes, for example, cycloalkyl rings, cycloalkenyl rings, and cycloalkynyl rings.

Herein, "heteroaryl" refers to a monovalent aromatic heterocyclic group in which the ring-constituting atoms include preferably one to five hetero atoms. The heteroaryl may be partially saturated, and may be a monocyclic or condensed ring (for example, a bicyclic heteroaryl condensed with a benzene ring or monocyclic heteroaryl ring). The number of ring-constituting atoms preferably ranges from five to ten (5- to 10-membered heteroaryl).

Specifically, the heteroaryl includes, for example, furyl group, thienyl group, pyrrolyl group, imidazolyl group, pyrazolyl group, thiazolyl group, isothiazolyl group, oxazolyl group, isooxazolyl group, oxadiazolyl group, thiadiazolyl group, triazolyl group, tetrazolyl group, pyridyl group, pyrimidyl group, pyridazinyl group, pyrazinyl group, triazinyl group, benzofuranyl group, benzothienyl group, benzothiadiazolyl group, benzothiazolyl group, benzoxazolyl group, benzoxadiazolyl group, benzoimidazolyl group, indolyl group, isoindolyl group, azaindolyl group, indazolyl group, quinolyl group, isoquinolyl group, cinnolinyl group, quinazolinyl group, quinoxalinyl group, benzodioxolyl group, indolidinyl group, and imidazopyridyl group.

Herein, "heterocyclyl" refers to a non-aromatic monovalent heterocyclic group in which the ring-constituting atoms include preferably one to five hetero atoms. The heterocyclyl may contain double or triple bonds in its ring. The carbon atoms may be oxidized to form carbonyl. The ring may be a monocyclic or condensed ring. The number of the ring-constituting atoms preferably ranges from three to ten (3- to 10-membered heterocyclyl).

Specifically, the heterocyclyl includes, for example, oxetanyl group, dihydrofuryl group, tetrahydrofuryl group, dihydropyranyl group, tetrahydropyranyl group, tetrahydropyridyl group, morpholinyl group, thiomorpholinyl group, pyrrolidinyl group, piperidinyl group, piperazinyl group, pyrazolidinyl group, imidazolinyl group, imidazolidinyl group, oxazolidinyl group, isooxazolidinyl group, thiazolidinyl group, isothiazolidinyl group, thiadiazolidinyl group, azetidinyl group, oxazolidone group, benzodioxanyl group, benzoxazolyl group, dioxolanyl group, and dioxanyl group.

Herein, "arylalkyl" refers to a group in which an arbitrary hydrogen atom in an "alkyl" defined above is substituted with an "aryl" defined above. The arylalkyl preferably includes $C_{6-10}$ aryl $C_{1-4}$ alkyl and $C_{6-10}$ aryl $C_{1-3}$ alkyl. Specifically, the arylalkyl includes, for example, benzyl group, phenethyl group, and naphthylmethyl group.

Herein, "heteroarylalkyl" refers to a group in which an arbitrary hydrogen atom in an alkyl defined above is substituted with a "heteroaryl" defined above. The heteroarylalkyl preferably includes 5- to 10-membered heteroaryl $C_{1-3}$ alkyl. Specifically, the heteroarylalkyl includes, for example, pyrrolylmethyl group, imidazolylmethyl group, thienylmethyl group, pyridylmethyl group, pyrimidylmethyl group, quinolylmethyl group, and pyridylethyl group.

Herein, "heterocyclylalkyl" refers to a group in which an arbitrary hydrogen atom in an "alkyl" defined above is substituted with a "heterocyclyl" defined above. The heterocyclylalkyl preferably includes 3- to 10-membered heterocyclyl $C_{1-3}$ alkyl. Specifically, the heterocyclylalkyl includes, for example, morpholinylmethyl group, morpholinylethyl group, thiomorpholinylmethyl group, pyrrolidinylmethyl group, piperidinylmethyl group, piperazinylmethyl group, piperazinylethyl group, and oxetanylmethyl group.

Herein, "monohydroxyalkyl" refers to a group in which an arbitrary hydrogen atom in an "alkyl" defined above is substituted with a hydroxyl group. The monohydroxyalkyl preferably includes $C_{1-6}$ monohydroxyalkyl and $C_{2-6}$ monohydroxyalkyl. Specifically, the monohydroxyalkyl includes, for example, hydroxymethyl group, 1-hydroxyethyl group, and 2-hydroxyethyl group.

Herein, "dihydroxyalkyl" refers to a group in which two arbitrary hydrogen atoms in an "alkyl" defined above are substituted with two hydroxyl groups. The dihydroxyalkyl preferably includes $C_{1-6}$ dihydroxyalkyl and $C_{2-6}$ dihydroxyalkyl. Specifically, the dihydroxyalkyl includes, for example, 1,2-dihydroxyethyl group, 1,2-dihydroxypropyl group, and 1,3-dihydroxypropyl group.

Herein, "trihydroxyalkyl" refers to a group in which three arbitrary hydrogen atoms in an "alkyl" defined above are substituted with three hydroxyl groups. The trihydroxyalkyl preferably includes $C_{1-6}$ trihydroxyalkyl and $C_{2-6}$ trihydroxyalkyl.

Herein, "alkoxyalkyl" refers to a group in which an arbitrary hydrogen atom in an "alkyl" defined above is substituted with an "alkoxy" defined above. The alkoxyalkyl preferably includes $C_{1-3}$ alkoxy $C_{1-4}$ alkyl and $C_{1-3}$ alkoxy $C_{2-4}$ alkyl. Specifically, the alkoxyalkyl includes, for example, methoxyethyl.

Herein, "alkoxyalkoxyalkyl" refers to a group in which an arbitrary hydrogen atom in the terminal alkyl of an "alkoxyalkyl" defined above is substituted with an "alkoxy" defined above. The alkoxyalkoxyalkyl preferably includes $C_{1-3}$ alkoxy $C_{1-4}$ alkoxy $C_{1-4}$ alkyl and $C_{1-3}$ alkoxy $C_{2-4}$ alkoxy $C_{2-4}$ alkyl.

Herein, "aminoalkyl" refers to a group in which an arbitrary hydrogen atom in an "alkyl" defined above is substituted with an amino group. The aminoalkyl group preferably includes $C_{1-4}$ aminoalkyl and $C_{2-4}$ aminoalkyl.

Herein, "alkylamino" refers to an amino group linked with an "alkyl" defined above. The alkylamino preferably includes $C_{1-4}$ alkylamino.

Herein, "dialkylamino" refers to an amino group linked with two "alkyls" defined above. The two alkyl groups may be same or different. The dialkylamino preferably includes di($C_{1-4}$ alkyl)amino.

Herein, "alkylaminoalkyl" refers to a group in which an arbitrary hydrogen atom in an "alkyl" defined above is substituted with an "alkylamino" defined above. The alkylaminoalkyl preferably includes $C_{1-4}$ alkylamino $C_{1-4}$ alkyl and $C_{1-4}$ alkylamino $C_{2-4}$ alkyl.

Herein, "dialkylaminoalkyl" refers to a group in which an arbitrary hydrogen atom in an "alkyl" defined above is substituted with a "dialkylamino" defined above. The dialkylaminoalkyl preferably includes di($C_{1-4}$ alkyl)amino $C_{1-4}$ alkyl and di($C_{1-4}$ alkyl)amino $C_{2-4}$ alkyl.

Herein, "heterocyclylamino" refers to an amino group linked with a "heterocyclyl" defined above. The heterocyclylamino preferably includes 3- to 10-membered heterocyclylamino.

Herein, "cyanoalkyl" refers to a group in which an arbitrary hydrogen atom in an "alkyl" defined above is substituted with a cyano group. The cyanoalkyl preferably includes cyano ($C_{1-3}$ alkyl).

Herein, "alkylsulfonyl" refers to a sulfonyl group linked with an "alkyl" defined above (i.e. alkyl-$SO_2$—). The alkylsulfonyl preferably includes $C_{1-3}$ alkylsulfonyl. Specifically, the alkylsulfonyl includes methylsulfonyl, ethylsulfonyl, n-propylsulfonyl, and i-propylsulfonyl.

Herein, "alkylsulfonylalkyl" refers to a group in which an arbitrary hydrogen atom in an "alkyl" defined above is substituted with an "alkylsulfonyl" defined above. The alkylsulfonylalkyl preferably includes $C_{1-3}$ alkylsulfonyl $C_{1-4}$ alkyl and $C_{1-3}$ alkylsulfonyl $C_{2-4}$ alkyl.

The compounds of the present invention include free forms and pharmaceutically acceptable salts thereof. Such "salts" include, for example, inorganic acid salts, organic acid salts, inorganic base salts, organic base salts, and acidic or basic amino acid salts.

Preferred inorganic acid salts include, for example, hydrochloride, hydrobromide, sulfate, nitrate, and phosphate. Preferred organic salts include, for example, acetate, succinate, fumarate, maleate, tartrate, citrate, lactate, malate, stearate, benzoate, methanesulfonate, and p-toluenesulfonate. A particularly preferred salt in the present invention is malate.

Preferred inorganic base salts include, for example, alkali metal salts such as sodium salts and potassium salts; alkali earth metal salts such as calcium salts and magnesium salts; aluminum salts; and ammonium salts. Preferred organic base salts include, for example, diethylamine salts, diethanolamine salts, meglumine salts, and N,N-dibenzylethylenediamine salts.

Preferred acidic amino acid salts include, for example, aspartate and glutamate. Preferred basic amino acid salts include, for example, arginine salts, lysine salts, and ornithine salts.

When the compounds of the present invention are left standing in the atmosphere, they may absorb moisture to adsorb water or form hydrates. Such hydrates are also included in the salts of the present invention.

Furthermore, the compounds of the present invention may absorb other solvents to form solvates. Such solvates are also included in the salts of the present invention.

All structurally possible isomers (geometric isomers, optical isomers, stereoisomers, tautomers, etc.) of the compounds of the present invention and mixtures of such isomers are included in the present invention.

The compounds of the present invention may have polymorphic crystalline forms. Such polymorphs are all included in the present invention.

The compounds of the present invention include prodrugs thereof. The prodrugs refer to derivatives of the compounds of the present invention which have a chemically or metabolically degradable group, and upon administration to the living body, revert to the original compounds and exhibit the original drug efficacy. The prodrugs include non-covalent complexes and salts.

The compounds of the present invention include those in which one or more atoms within the molecule have been replaced with isotopes. Herein, the isotope refers to an atom which has the same atomic number (proton number) but is different in mass number (sum of protons and neutrons). The target atoms to be replaced with an isotope in the compounds of the present invention, include, for example, hydrogen atom, carbon atom, nitrogen atom, oxygen atom, phosphorus atom, sulfur atom, fluorine atom, and chlorine atom. Their isotopes include $^2H$, $^3H$, $^{13}C$, $^{14}C$, $^{15}N$, $^{17}O$, $^{18}O$, $^{31}P$, $^{32}P$, $^{35}S$, $^{18}F$ and $^{36}Cl$. In particular, radioisotopes such as $^3H$ and $^{14}C$, which decay emitting radiation, are useful in in vivo tissue distribution study etc. of pharmaceuticals or compounds. Stable isotopes do not decay, are almost constant in abundance, and emit no radiation. For this reason, stable isotopes can be used safely. The compounds of the present invention can be converted into isotope-substituted compounds according to conventional methods by replacing reagents used in synthesis with reagents containing corresponding isotopes.

Preferably, the compounds of the present invention represented by formula (I) shown above are as follows:

$R_1$ shown above preferably represents hydrogen, hydroxy, halogen, cyano, nitro, $C_{1-4}$ haloalkyl, $C_{1-6}$ alkyl, $C_{2-6}$ alkenyl, $C_{2-6}$ alkynyl, $C_{3-7}$ cycloalkyl, $C_{6-10}$ aryl $C_{1-4}$ alkyl, —$OR_5$, —$NR_6R_2$, —$(CR_8R_9)_nZ_1$, —$C(O)NR_{12}R_{13}$, —$SR_{14}$, —$SOR_{15}$, —$SO_2R_{16}$, —$NR_{17}SO_2R_{18}$, COOH, $C_{6-10}$ aryl which is optionally substituted with one or more groups independently selected from group P, 5- to 10-membered heteroaryl or 3- to 10-membered heterocyclyl each of which is optionally substituted with one or more groups independently selected from group Q, —$COR_{19}$, —$COOR_{20}$, —$OC(O)R_{21}$, —$NR_{22}C(O)R_{23}$, —$NR_{24}C(S)R_{25}$, —$C(S)NR_{26}R_{27}$, —$SO_2NR_{28}R_{29}$, —$OSO_2R_{30}$, —$SO_3R_{31}$, or —$Si(R_{32})_3$.

$R_1$ shown above more preferably represents hydrogen, hydroxy, halogen, cyano, $C_{1-4}$ haloalkyl, $C_{1-6}$ alkyl, $C_{2-6}$ alkynyl, $C_{3-7}$ cycloalkyl, $C_{6-10}$ aryl $C_{1-4}$ alkyl, —$OR_5$, —$NR_6R_7$, —$(CR_8R_9)_nZ_1$, —$C(O)NR_{12}R_{13}$, —$SR_{14}$, —$SO_2R_{16}$, —$NR_{17}SO_2R_{18}$, COOH, $C_{6-10}$ aryl which is optionally substituted with one or more groups independently selected from group P, or 5- to 10-membered heteroaryl or 3- to 10-membered heterocyclyl each of which is optionally substituted with one or more groups independently selected from group Q. Specifically, the above 5- to 10-membered heteroaryl is particularly preferably an imidazolyl group, thienyl group, pyridyl group, pyridazinyl group, or pyrazolyl group. The above 3- to 10-membered heterocyclyl is particularly preferably a morpholinyl group, tetrahydropyridyl group, or piperidinyl group.

$R_2$ shown above preferably represents hydrogen, hydroxy, halogen, cyano, nitro, $C_{1-4}$ haloalkyl, $C_{1-6}$ alkyl, $C_{2-6}$ alkenyl, $C_{2-6}$ alkynyl, $C_{3-7}$ cycloalkyl, $C_{6-10}$ aryl $C_{1-4}$ alkyl, —$OR_5$, —$NR_6R_2$, —$(CR_8R_9)_nZ_1$, —$C(O)NR_{12}R_{13}$, —$SR_{14}$, —$SOR_{15}$, —$SO_2R_{16}$, —$NR_{17}SO_2R_{18}$, COOH, $C_{6-10}$ aryl which is optionally substituted with one or more groups independently selected from group P, 5- to 10-membered heteroaryl or 3- to 10-membered heterocyclyl each of which is optionally substituted with one or more groups independently selected from group Q, —$COR_{19}$, —$COOR_{20}$, —$OC(O)R_{21}$, —$NR_{22}C(O)R_{23}$, —$NR_{24}C(S)R_{25}$, —$C(S)NR_{26}R_{27}$, —$SO_2NR_{28}R_{29}$, —$OSO_2R_{30}$, —$SO_3R_{31}$, or —$Si(R_{32})_3$.

$R_2$ shown above more preferably represents hydrogen, halogen, $C_{1-4}$ haloalkyl, $C_{1-6}$ alkyl, —$OR_5$, $C_{6-10}$ aryl which is optionally substituted with one or more groups independently selected from group P, or 5- to 10-membered heteroaryl which is optionally substituted with one or more groups independently selected from group Q. Specifically, this 5- to 10-membered heteroaryl is particularly preferably a pyridyl group.

$R_1$ and $R_2$ shown above can preferably be taken together with the atoms to which they are attached to form 3- to 10-membered heterocyclyl or 5- to 10-membered heteroaryl. The heterocyclyl or heteroaryl may have a halogen atom as a substituent. Specifically, the 3- to 10-membered heterocyclyl formed together with the atoms to which $R_1$ and $R_2$ are attached, is particularly preferably a dioxolanyl group or dioxanyl group.

$R_3$ shown above preferably represents hydrogen, $C_{1-5}$ alkyl, $C_{6-10}$ aryl $C_{1-6}$ alkyl, or $C_{1-4}$ haloalkyl, more preferably hydrogen, $C_{1-4}$ alkyl, $C_{6-10}$ aryl $C_{1-4}$ alkyl, or $C_{1-3}$ perfluoroalkyl, and particularly preferably $C_1$ alkyl.

$R_4$ shown above preferably represents hydrogen, halogen, $C_{1-3}$ alkyl, $C_{1-4}$ haloalkyl, hydroxy, cyano, nitro, $C_{1-4}$ alkoxy, —$(CH_2)_nZ_1$, —$NR_6R_7$, —$OR_5$, —$C(O)NR_{12}R_{13}$, —$SR_{14}$, —$SOR_{15}$, —$SO_2R_{16}$, $NR_{17}SO_2R_{18}$, COOH, —$COR_{19}$, —COOR$_{20}$, —OC(O)R$_{21}$, —NR$_{22}$C(O)R$_{23}$, —NR$_{24}$C(S)R$_{25}$, —C(S)NR$_{26}$R$_{27}$, —SO$_2$NR$_{28}$R$_{29}$, —OSO$_2$R$_{30}$—SO$_3$R$_{31}$, or —Si(R$_{32}$)$_3$.

R$_4$ shown above more preferably represents hydrogen, halogen, C$_{1-3}$ alkyl, C$_{1-3}$ perfluoroalkyl, cyano, methanesulfonyl, hydroxyl, alkoxy, or amino, and particularly preferably hydrogen or halogen.

Ring A shown above is represented by the following formula:

(herein, it may be simply referred to as "A"). Ring A is preferably a 5- to 10-membered heteroaryl ring or C$_{6-10}$ aryl ring, more preferably benzene, indole, azaindole, benzofuran, benzothiophene, benzothiazole, quinoline, or pyrrole, and particularly preferably indole or pyrrole.

R$_5$ shown above preferably represents C$_{1-5}$ alkyl, C$_{3-7}$ cycloalkyl, C$_{3-7}$ cycloalkyl C$_{1-3}$ alkyl, C$_{2-6}$ alkenyl, C$_{2-6}$ alkynyl, C$_{1-4}$ haloalkyl, C$_{1-3}$ alkoxy C$_{1-4}$ alkyl, C$_{1-3}$ alkoxy C$_{1-4}$ alkoxy C$_{1-4}$ alkyl, C$_{1-4}$ amino alkyl, C$_{1-4}$ alkylamino C$_{1-4}$ alkyl, di(C$_{1-4}$ alkyl)amino C$_{1-4}$ alkyl, C$_{6-10}$ aryl, C$_{6-10}$ aryl C$_{1-3}$ alkyl, or 3- to 10-membered heterocyclyl C$_{1-3}$ alkyl, 3- to 10-membered heterocyclyl, 5- to 10-membered heteroaryl, or 5- to 10-membered heteroaryl C$_{1-3}$ alkyl, each of which is optionally substituted with one or more groups independently selected from group Q, C$_{1-6}$ monohydroxyalkyl, C$_{1-6}$ dihydroxyalkyl, or C$_{1-6}$ trihydroxyalkyl.

R$_5$ shown above more preferably represents C$_{1-5}$ alkyl, C$_{3-7}$ cycloalkyl C$_{1-3}$ alkyl, C$_{1-4}$ haloalkyl, C$_{1-3}$ alkoxy C$_{1-4}$ alkyl, C$_{6-10}$ aryl, C$_{6-10}$ aryl C$_{1-3}$ alkyl, or 3- to 10-membered heterocyclyl C$_{1-3}$ alkyl or 3- to 10-membered heterocyclyl each of which is optionally substituted with one or more groups independently selected from group Q. Specifically, the above 3- to 10-membered heterocyclylalkyl is particularly preferably a piperazinylethyl group, oxetanylmethyl group, or morpholinylethyl group. The above 3- to 10-membered heterocyclyl is particularly preferably an oxetanyl group or tetrahydropyranyl group.

R$_6$ and R$_7$ shown above may be the same or different, and each preferably represents hydrogen, C$_{1-4}$ alkyl, C$_{2-6}$ alkenyl, C$_{2-6}$ alkynyl, C$_{1-4}$ haloalkyl, C$_{1-3}$ alkoxy C$_{2-4}$ alkyl, C$_{6-10}$ aryl C$_{1-3}$ alkyl, 3- to 10-membered heterocyclyl C$_{1-3}$ alkyl, 5- to 10-membered heteroaryl C$_{1-3}$ alkyl, C$_{1-6}$ monohydroxyalkyl, C$_{1-6}$ dihydroxyalkyl, C$_{1-6}$ trihydroxyalkyl, 3- to 10-membered heterocyclyl, C$_{1-4}$ aminoalkyl, C$_{1-4}$ alkylamino C$_{1-4}$ alkyl, di(C$_{1-4}$ alkyl)amino C$_{1-4}$ alkyl, or cyano(C$_{1-3}$ alkyl).

R$_6$ and R$_7$ shown above more preferably each independently represent hydrogen, C$_{1-3}$ alkoxy C$_{1-4}$ alkyl, 3- to 10-membered heterocyclyl C$_{1-3}$ alkyl, 5- to 10-membered heteroaryl C$_{1-3}$ alkyl, or C$_{1-6}$ dihydroxyalkyl. Specifically, the 3- to 10-membered heterocyclylalkyl is particularly preferably a morpholinylethyl group, and the 5- to 10-membered heteroarylalkyl is particularly preferably a pyridylethyl group.

Alternatively, R$_6$ and R$_7$ shown above can preferably be taken together with the nitrogen atoms to which they are attached to form 3- to 10-membered heterocyclyl or 5- to 10-membered heteroaryl.

"n" shown above represents an integer from 1 to 3. Preferably, n is 1.

R$_8$ and R$_9$ shown above preferably may be the same or different, and each represents hydrogen, C$_{1-4}$ alkyl, or halogen, and more preferably hydrogen.

Alternatively, R$_8$ and R$_9$ shown above can preferably be taken together with the carbon atoms to which they are attached to form an alicyclic ring.

Z$_1$ shown above preferably represents hydrogen, NR$_{10}$R$_{11}$, —OH, or 3- to 10-membered heterocyclyl or 5- to 10-membered heteroaryl each of which is optionally substituted with one or more groups independently selected from group Q, more preferably NR$_{10}$R$_{11}$ or —OH, or 3- to 10-membered heterocyclyl which is optionally substituted with one or more groups independently selected from group Q. Specifically, the above 3- to 10-membered heterocyclyl is particularly preferably a pyrrolidinyl group, piperazinyl group, piperidinyl group, or morpholinyl group.

R$_{10}$ and R$_{11}$ shown above preferably may be the same or different, and each preferably represents C$_{1-4}$ alkyl, C$_{2-6}$ alkenyl, C$_{2-6}$ alkynyl, C$_{1-4}$ haloalkyl, C$_{1-3}$ alkoxy C$_{1-4}$ alkyl, cyano(C$_{1-3}$ alkyl), or C$_{1-3}$ alkylsulfonyl C$_{1-4}$ alkyl, more preferably C$_{1-4}$ alkyl, C$_{2-6}$ alkenyl, or C$_{1-3}$ alkoxy C$_{2-4}$ alkyl.

Alternatively, R$_{10}$ and R$_{11}$ shown above can preferably be taken together with the nitrogen atoms to which they are attached to form 3- to 10-membered heterocyclyl or 5- to 10-membered heteroaryl.

R$_{12}$ and R$_{13}$ shown above preferably may be the same or different, and each represents hydrogen, C$_{1-4}$ alkyl, C$_{2-6}$ alkenyl, C$_{2-6}$ alkynyl, C$_{1-4}$ haloalkyl, C$_{1-3}$ alkoxy C$_{1-4}$ alkyl, C$_{6-10}$ aryl, 5- to 10-membered heteroaryl, 3- to 10-membered heterocyclyl, C$_{6-10}$ aryl C$_{1-4}$ alkyl, 3- to 10-membered heterocyclyl C$_{1-3}$ alkyl, 5- to 10-membered heteroaryl C$_{1-3}$ alkyl, cyano(C$_{1-3}$ alkyl), C$_{1-3}$ alkylsulfonyl C$_{1-4}$ alkyl, or 3- to 10-membered alicyclic ring, more preferably hydrogen, C$_{1-4}$ alkyl, or C$_{1-4}$ haloalkyl.

Alternatively, R$_{12}$ and R$_{13}$ shown above preferably can be taken together with the nitrogen atoms to which they are attached to form 3- to 10-membered heterocyclyl or 5- to 10-membered heteroaryl each of which is optionally substituted with one or more groups independently selected from group Q, and particularly preferably 3- to 10-membered heterocyclylalkyl. Specifically, piperazinyl group, morpholinyl group, pyrrolidinyl group, and piperidinyl group are more preferred.

R$_{14}$ shown above preferably represents C$_{1-4}$ alkyl, C$_{2-6}$ alkenyl, C$_{2-6}$ alkynyl, C$_{1-4}$ haloalkyl, C$_{6-10}$ aryl which is optionally substituted with one or more groups independently selected from group P, or 5- to 10-membered heteroaryl or 3- to 10-membered heterocyclyl each of which is optionally substituted with one or more groups independently selected from group Q, and more preferably represents C$_{1-4}$ alkyl or C$_{1-4}$ haloalkyl.

R$_{15}$ shown above preferably represents C$_{1-4}$ alkyl, C$_{2-6}$ alkenyl, C$_{2-6}$ alkynyl, C$_{1-4}$ haloalkyl, C$_{6-10}$ aryl which is optionally substituted with one or more groups independently selected from group P, or 5- to 10-membered heteroaryl or 3- to 10-membered heterocyclyl each of which is optionally substituted with one or more groups independently selected from group Q.

R$_{16}$ shown above preferably represents C$_{1-4}$ alkyl, C$_{2-6}$ alkenyl, C$_{2-6}$ alkynyl, C$_{1-4}$ haloalkyl, C$_{6-10}$ aryl which is optionally substituted with one or more groups independently selected from group P, or 5- to 10-membered heteroaryl or 3- to 10-membered heterocyclyl each of which is optionally substituted with one or more groups independently selected from group Q, and more preferably represents C$_{1-4}$ alkyl.

R$_{17}$ shown above preferably represents hydrogen or C$_{1-4}$ alkyl, and more preferably hydrogen.

$R_{18}$ shown above preferably represents $C_{1-4}$ alkyl, $C_{2-6}$ alkenyl, $C_{2-6}$ alkynyl, $C_{1-4}$ haloalkyl, $C_{6-10}$ aryl which is optionally substituted with one or more groups independently selected from group P, or 5- to 10-membered heteroaryl or 3- to 10-membered heterocyclyl each of which is optionally substituted with one or more groups independently selected from group Q, and more preferably represents $C_{1-4}$ alkyl.

$R_{19}$ shown above preferably represents hydrogen, $C_{1-4}$ alkyl, $C_{3-7}$ cycloalkyl, $C_{1-4}$ haloalkyl, $C_{6-10}$ aryl, or 5- to 10-membered heteroaryl or 3- to 10-membered heterocyclyl each of which is optionally substituted with one or more groups independently selected from group Q, and more preferably represents hydrogen, or 5- to 10-membered heteroaryl or 3- to 10-membered heterocyclyl each of which is optionally substituted with one or more groups independently selected from group Q. Specifically, this 3- to 10-membered heterocyclyl is more preferably a piperazinyl group, morpholinyl group, pyrrolidinyl group, or piperidinyl group.

$R_{20}$ shown above preferably represents $C_{1-4}$ alkyl, $C_{3-7}$ cycloalkyl, $C_{1-4}$ haloalkyl, $C_{6-10}$ aryl, 5- to 10-membered heteroaryl, or 3- to 10-membered heterocyclyl.

$R_{21}$ shown above preferably represents $C_{1-4}$ alkyl, $C_{3-7}$ cycloalkyl, $C_{1-4}$ haloalkyl, $C_{6-10}$ aryl, 5- to 10-membered heteroaryl, or 3- to 10-membered heterocyclyl.

$R_{22}$ shown above preferably represents hydrogen, $C_{1-4}$ alkyl, or $C_{1-4}$ haloalkyl.

$R_{23}$ shown above preferably represents hydrogen, $C_{1-4}$ alkyl, $C_{3-7}$ cycloalkyl, $C_{1-4}$ haloalkyl, $C_{6-10}$ aryl, 5- to 10-membered heteroaryl, or 3- to 10-membered heterocyclyl.

$R_{24}$ shown above preferably represents hydrogen, $C_{1-4}$ alkyl, or $C_{1-4}$ haloalkyl.

$R_{25}$ shown above preferably represents $C_{1-4}$ alkyl, $C_{3-7}$ cycloalkyl, $C_{1-4}$ haloalkyl, $C_{6-10}$ aryl, 5- to 10-membered heteroaryl, or 3- to 10-membered heterocyclyl.

$R_{26}$ and $R_{27}$ shown above preferably may be the same or different, and each represents hydrogen, $C_{1-4}$ alkyl, $C_{2-6}$ alkenyl, $C_{2-6}$ alkynyl, $C_{1-4}$ haloalkyl, $C_{1-3}$ alkoxy $C_{1-4}$ alkyl, $C_{6-10}$ aryl, 5- to 10-membered heteroaryl, 3- to 10-membered heterocyclyl, $C_{6-10}$ aryl $C_{1-4}$ alkyl, 3- to 10-membered heterocyclyl $C_{1-3}$ alkyl, 5- to 10-membered heteroaryl $C_{1-3}$ alkyl, cyano($C_{1-3}$ alkyl), $C_{1-3}$ alkylsulfonyl $C_{1-4}$ alkyl, or 3- to 10-membered alicyclic ring.

Alternatively, $R_{26}$ and $R_{27}$ shown above can preferably be taken together with the nitrogen atoms to which they are attached to form 3- to 10-membered heterocyclyl or 5- to 10-membered heteroaryl.

$R_{28}$ and $R_{29}$ shown above preferably may be the same or different, and each represents hydrogen, $C_{1-4}$ alkyl, $C_{2-6}$ alkenyl, $C_{2-6}$ alkynyl, $C_{1-4}$ haloalkyl, $C_{1-3}$ alkoxy $C_{1-4}$ alkyl, $C_{6-10}$ aryl, 5- to 10-membered heteroaryl, 3- to 10-membered heterocyclyl, $C_{6-10}$ aryl $C_{1-4}$ alkyl, 3- to 10-membered heterocyclyl $C_{1-3}$ alkyl, 5- to 10-membered heteroaryl $C_{1-3}$ alkyl, cyano($C_{1-3}$ alkyl), $C_{1-3}$ alkylsulfonyl $C_{1-4}$ alkyl, or 3- to 10-membered alicyclic ring.

Alternatively, $R_{28}$ and $R_{29}$ shown above preferably can be taken together with the nitrogen atoms to which they are attached to form 3- to 10-membered heterocyclyl or 5- to 10-membered heteroaryl.

$R_{30}$ shown above preferably represents $C_{1-4}$ alkyl, $C_{3-7}$ cycloalkyl, $C_{1-4}$ haloalkyl, $C_{6-10}$ aryl, 5- to 10-membered heteroaryl, or 3- to 10-membered heterocyclyl.

$R_{31}$ shown above preferably represents $C_{1-4}$ alkyl, $C_{3-7}$ cycloalkyl, $C_{1-4}$ haloalkyl, $C_{6-10}$ aryl, 5- to 10-membered heteroaryl, or 3- to 10-membered heterocyclyl.

$R_{32}$ shown above preferably represents $C_{1-4}$ alkyl, or $C_{6-10}$ aryl. Preferred substituents included in group P defined above are halogen, $C_{1-4}$ alkyl, $C_{1-4}$ haloalkyl, —OH, $C_{1-3}$ alkoxy, $C_{1-3}$ haloalkoxy, 3- to 10-membered heterocyclylamino, —SO$_2$R, —CN, —NO$_2$, and 3- to 10-membered heterocyclyl; and more preferably halogen, $C_{1-4}$ haloalkyl, $C_{1-3}$ alkoxy, $C_{1-3}$ haloalkoxy, and 3- to 10-membered heterocyclyl. Specifically, this 3- to 10-membered heterocyclyl is particularly preferably a morpholinyl group.

Preferred substituents included in group Q defined above are halogen, $C_{1-4}$ alkyl, $C_{1-4}$ haloalkyl, —OH, $C_{1-3}$ alkoxy, $C_{1-6}$ monohydroxyalkyl, $C_{1-6}$ dihydroxyalkyl, $C_{1-6}$ trihydroxyalkyl, 3- to 10-membered heterocyclylamino, —SO$_2$, —CN, —NO$_2$, $C_{3-7}$ cycloalkyl, —COR$_{19}$, and 3- to 10-membered heterocyclyl which is optionally substituted with $C_{1-4}$ alkyl; and more preferably halogen, $C_{1-4}$ alkyl, $C_{1-4}$ haloalkyl, —OH, $C_{1-3}$ alkoxy, $C_{1-6}$ monohydroxyalkyl, —SO$_2$R$_{16}$, $C_{3-7}$ cycloalkyl, —COR$_{19}$, and 3- to 10-membered heterocyclyl which is optionally substituted with $C_{1-4}$ alkyl. Specifically, this 3- to 10-membered heterocyclyl is more preferably a piperazinyl group, piperidinyl group, or morpholinyl group.

Specifically, the compounds of the present invention include, for example:

(1) [5-amino-1-(2-methyl-1H-benzimidazol-5-yl)-1H-pyrazol-4-yl]-(1H-indol-2-yl)-methanone;

(2) [5-amino-1-(2-methyl-1H-benzimidazol-5-yl)-1H-pyrazol-4-yl]-(6-pyrrolidin-1-ylmethyl-1H-indol-2-yl)-methanone;

(3) [5-amino-1-(2-methyl-1H-benzimidazol-5-yl)-1H-pyrazol-4-yl]-[6-(4-hydroxy-piperidin-1-ylmethyl)-1H-indol-2-yl]-methanone;

(4) [5-amino-1-(2-methyl-1H-benzimidazol-5-yl)-1H-pyrazol-4-yl]-(1H-pyrrolo[3,2-c]pyridin-2-yl)-methanone;

(5) [5-amino-1-(2-methyl-1H-benzimidazol-5-yl)-1H-pyrazol-4-yl]-(6-piperazin-1-ylmethyl-1H-indol-2-yl)-methanone;

(6) [5-amino-1-(2-methyl-1H-benzimidazol-5-yl)-1H-pyrazol-4-yl]-[6-(2-morpholin-4-yl-ethoxy)-1H-indol-2-yl]-methanone;

(7) [5-amino-1-(2-methyl-1H-benzimidazol-5-yl)-1H-pyrazol-4-yl]-[6-(tetrahydro-pyran-4-yloxy)-1H-indol-2-yl]-methanone;

(8) [5-amino-1-(2-methyl-1H-benzimidazol-5-yl)-1H-pyrazol-4-yl]-(4-chloro-1H-indol-2-yl)-methanone;

(9) [5-amino-1-(2-methyl-1H-benzimidazol-5-yl)-1H-pyrazol-4-yl]-(5-bromo-1H-indol-2-yl)-methanone;

(10) [5-amino-1-(2-methyl-1H-benzimidazol-5-yl)-1H-pyrazol-4-yl]-(4-iodo-1H-indol-2-yl)-methanone;

(11) 2-[5-amino-1-(2-methyl-1H-benzimidazol-5-yl)-1H-pyrazole-4-carbonyl]-1H-indole-5-carbonitrile;

(12) [5-amino-1-(2-methyl-1H-benzimidazol-5-yl)-1H-pyrazol-4-yl]-(6-bromo-5-fluoro-1H-indol-2-yl)-methanone;

(13) [5-amino-1-(2-methyl-1H-benzimidazol-5-yl)-1H-pyrazol-4-yl]-(5-ethynyl-1H-indol-2-yl)-methanone;

(14) [5-amino-1-(2-methyl-1H-benzimidazol-5-yl)-1H-pyrazol-4-yl]-[6-(2-fluoro-phenyl)-1H-indol-2-yl]-methanone;
(15) [5-amino-1-(2-methyl-1H-benzimidazol-5-yl)-1H-pyrazol-4-yl]-[6-(3-fluoro-phenyl)-1H-indol-2-yl]-methanone;
(16) [5-amino-1-(2-methyl-1H-benzimidazol-5-yl)-1H-pyrazol-4-yl]-[6-(4-fluoro-phenyl)-1H-indol-2-yl]-methanone;
(17) [5-amino-1-(2-methyl-1H-benzimidazol-5-yl)-1H-pyrazol-4-yl]-[6-(2-chloro-phenyl)-1H-indol-2-yl]-methanone;
(18) [5-amino-1-(2-methyl-1H-benzimidazol-5-yl)-1H-pyrazol-4-yl]-[6-(3-chloro-phenyl)-1H-indol-2-yl]-methanone;
(19) [5-amino-1-(2-methyl-1H-benzimidazol-5-yl)-1H-pyrazol-4-yl]-[6-(4-chloro-phenyl)-1H-indol-2-yl]-methanone;
(20) [5-amino-1-(2-methyl-1H-benzimidazol-5-yl)-1H-pyrazol-4-yl]-[6-(2-trifluoromethyl-phenyl)-1H-indol-2-yl]-methanone;
(21) [5-amino-1-(2-methyl-1H-benzimidazol-5-yl)-1H-pyrazol-4-yl]-[6-(3-trifluoromethyl-phenyl)-1H-indol-2-yl]-methanone;
(22) [5-amino-1-(2-methyl-1H-benzimidazol-5-yl)-1H-pyrazol-4-yl]-[6-(4-trifluoromethyl-phenyl)-1H-indol-2-yl]-methanone;
(23) [5-amino-1-(2-methyl-1H-benzimidazol-5-yl)-1H-pyrazol-4-yl]-(4-bromo-1H-indol-2-yl)-methanone;
(24) [5-amino-1-(2-methyl-1H-benzimidazol-5-yl)-1H-pyrazol-4-yl]-[6-(3-fluoro-pyridin-2-yl)-1H-indol-2-yl]-methanone;
(25) [5-amino-1-(2-methyl-1H-benzimidazol-5-yl)-1H-pyrazol-4-yl]-(6-methyl-1H-indol-2-yl)-methanone;
(26) [5-amino-1-(2-methyl-1H-benzimidazol-5-yl)-1H-pyrazol-4-yl]-[5-(4,4-difluoro-piperidine-1-carbonyl)-1H-indol-2-yl]-methanone;
(27) [5-amino-1-(2-methyl-1H-benzimidazol-5-yl)-1H-pyrazol-4-yl]-[5-(3,3-difluoro-piperidine-1-carbonyl)-1H-indol-2-yl]-methanone;
(28) 2-[5-amino-1-(2-methyl-1H-benzimidazol-5-yl)-1H-pyrazole-4-carbonyl]-1H-indole-5-carboxylic acid (2,2,2-trifluoro-ethyl)-amide;
(29) [5-amino-1-(2-methyl-1H-benzimidazol-5-yl)-1H-pyrazol-4-yl]-[6-(5-trifluoromethyl-pyridin-2-yl)-1H-indol-2-yl]-methanone;
(30) [5-amino-1-(2-methyl-1H-benzimidazol-5-yl)-1H-pyrazol-4-yl]-[6-(6-trifluoromethyl-pyridin-2-yl)-1H-indol-2-yl]-methanone;
(31) [5-amino-1-(2-methyl-1H-benzimidazol-5-yl)-1H-pyrazol-4-yl]-[6-(5-chloro-pyridin-2-yl)-1H-indol-2-yl]-methanone;
(32) [5-amino-1-(2-methyl-1H-benzimidazol-5-yl)-1H-pyrazol-4-yl]-[6-(4-methyl-pyridin-2-yl)-1H-indol-2-yl]methanone;
(33) [5-amino-1-(2-methyl-1H-benzimidazol-5-yl)-1H-pyrazol-4-yl]-[6-(3-chloro-4-fluoro-phenyl)-1H-indol-2-yl]-methanone;
(34) [5-amino-1-(2-methyl-1H-benzimidazol-5-yl)-1H-pyrazol-4-yl]-[6-(3-trifluoromethyl-pyridin-2-yl)-1H-indol-2-yl]-methanone;
(35) [5-amino-1-(2-methyl-1H-benzimidazol-5-yl)-1H-pyrazol-4-yl]-[6-(4-trifluoromethyl-pyridin-2-yl)-1H-indol-2-yl]methanone;
(36) [5-amino-1-(6-fluoro-2-methyl-1H-benzimidazol-5-yl)-1H-pyrazol-4-yl]-(1H-indol-2-yl)-methanone;
(37) 2-[5-amino-1-(2-methyl-1H-benzimidazol-5-yl)-1H-pyrazole-4-carbonyl]-1H-indole-6-carboxylic acid;
(38) [5-amino-1-(2-methyl-1H-benzimidazol-5-yl)-1H-pyrazol-4-yl]-(6-hydroxymethyl-1H-indol-2-yl)-methanone;
(39) [5-amino-1-(2-methyl-1H-benzimidazol-5-yl)-1H-pyrazol-4-yl]-{6-[2-(4-methyl-piperazin-1-yl)-ethoxy]-1H-indol-2-yl}-methanone;
(40) [5-amino-1-(2-methyl-1H-benzimidazol-5-yl)-1H-pyrazol-4-yl]-[6-(3-methyl-oxetan-3-ylmethoxy)-1H-indol-2-yl]-methanone;
(41) [5-amino-1-(2-methyl-1H-benzimidazol-5-yl)-1H-pyrazol-4-yl]-[6-(3-fluoro-piperidin-1-ylmethyl)-1H-indol-2-yl]-methanone;
(42) [5-amino-1-(2-methyl-1H-benzimidazol-5-yl)-1H-pyrazol-4-yl]-(6-{[bis(2-methoxy-ethyl)-amino]-methyl}-1H-indol-2-yl)-methanone;
(43) [5-amino-1-(2-methyl-1H-benzimidazol-5-yl)-1H-pyrazol-4-yl]-{6-[(methyl-prop-2-ynyl-amino)-methyl]-1H-indol-2-yl}-methanone;
(44) [5-amino-1-(2-methyl-1H-benzimidazol-5-yl)-1H-pyrazol-4-yl]-[6-(3,3-difluoro-pyrrolidin-1-ylmethyl)-1H-indol-2-yl]-methanone;
(45) [5-amino-1-(2-methyl-1H-benzimidazol-5-yl)-1H-pyrazol-4-yl]-[6-(2,5-dimethyl-pyrrolidin-1-ylmethyl)-1H-indol-2-yl]-methanone;
(46) [5-amino-1-(2-methyl-1H-benzimidazol-5-yl)-1H-pyrazol-4-yl]-[6-(3,3-difluoro-piperidin-1-ylmethyl)-1H-indol-2-yl]-methanone;
(47) [5-amino-1-(2-methyl-1H-benzimidazol-5-yl)-1H-pyrazol-4-yl]-[6-((S)-3-methyl-morpholin-4-ylmethyl)-1H-indol-2-yl]-methanone;
(48) [5-amino-1-(2-methyl-1H-benzimidazol-5-yl)-1H-pyrazol-4-yl]-(6-bromo-1H-indol-2-yl)-methanone;
(49) [5-amino-1-(2-methyl-1H-benzimidazol-5-yl)-1H-pyrazol-4-yl]-(5-iodo-1H-indol-2-yl)-methanone;

(50) [5-amino-1-(2-methyl-1H-benzimidazol-5-yl)-1H-pyrazol-4-yl]-(1H-pyrrolo[3,2-b]pyridin-2-yl)-methanone;
(51) [5-amino-1-(2-methyl-1H-benzimidazol-5-yl)-1H-pyrazol-4-yl]-(5-bromo-6-trifluoromethyl-1H-indol-2-yl)-methanone;
(52) [5-amino-1-(2-methyl-1H-benzimidazol-5-yl)-1H-pyrazol-4-yl]-(6-iodo-1H-indol-2-yl)-methanone;
(53) [5-amino-1-(2-methyl-1H-benzimidazol-5-yl)-1H-pyrazol-4-yl]-(4-methyl-1H-indol-2-yl)-methanone;
(54) [5-amino-1-(2-methyl-1H-benzimidazol-5-yl)-1H-pyrazol-4-yl]-(4-isopropyl-1H-indol-2-yl)-methanone;
(55) [5-amino-1-(2-methyl-1H-benzimidazol-5-yl)-1H-pyrazol-4-yl]-[5-(2-fluoro-phenyl)-1H-indol-2-yl]-methanone;
(56) [5-amino-1-(2-methyl-1H-benzimidazol-5-yl)-1H-pyrazol-4-yl]-(5-benzyl-1H-indol-2-yl)-methanone;
(57) [5-amino-1-(2-methyl-1H-benzimidazol-5-yl)-1H-pyrazol-4-yl]-[5-(2-trifluoromethyl-phenyl)-1H-indol-2-yl]-methanone;
(58) [5-amino-1-(2-methyl-1H-benzimidazol-5-yl)-1H-pyrazol-4-yl]-[5-(3-fluorophenyl)-1H-indol-2-yl]-methanone;
(59) [5-amino-1-(2-methyl-1H-benzimidazol-5-yl)-1H-pyrazol-4-yl]-[5-(3-trifluoromethyl-phenyl)-1H-indol-2-yl]-methanone;
(60) [5-amino-1-(2-methyl-1H-benzimidazol-5-yl)-1H-pyrazol-4-yl]-(4-ethynyl-1H-indol-2-yl)-methanone;
(61) [5-amino-1-(2-methyl-1H-benzimidazol-5-yl)-1H-pyrazol-4-yl]-(5H-[1,3]dioxolo[4,5-f]indol-6-yl)-methanone;
(62) [5-amino-1-(7-fluoro-2-methyl-1H-benzimidazol-5-yl)-1H-pyrazol-4-yl]-(1H-indol-2-yl)-methanone;
(63) [5-amino-1-(2-methyl-1H-benzimidazol-5-yl)-1H-pyrazol-4-yl]-[5-(4-trifluoromethyl-phenyl)-1H-indol-2-yl]-methanone;
(64) [5-amino-1-(2-methyl-1H-benzimidazol-5-yl)-1H-pyrazol-4-yl]-(5-butoxy-1H-indol-2-yl)-methanone;
(65) [5-amino-1-(2-methyl-1H-benzimidazol-5-yl)-1H-pyrazol-4-yl]-[5-(1-methyl-piperidin-4-yl)-1H-indol-2-yl]methanone;
(66) N-{2-[5-amino-1-(2-methyl-1H-benzimidazol-5-yl)-1H-pyrazole-4-carbonyl]-1H-indol-6-yl}-methanesulfonamide;
(67) [5-amino-1-(2-methyl-1H-benzimidazol-5-yl)-1H-pyrazol-4-yl]-[6-(6-morpholin-4-yl-pyridin-3-yl)-1H-indol-2-yl]-methanone;
(68) [5-amino-1-(2-methyl-1H-benzimidazol-5-yl)-1H-pyrazol-4-yl]-(6-butyl-1H-indol-2-yl)-methanone;
(69) [5-amino-1-(2-methyl-1H-benzimidazol-5-yl)-1H-pyrazol-4-yl]-[6-(1-methyl-1H-pyrazol-4-yl)-1H-indol-2-yl]-methanone;
(70) [5-amino-1-(2-methyl-1H-benzimidazol-5-yl)-1H-pyrazol-4-yl]-[6-(5-methoxy-pyridin-3-yl)-1H-indol-2-yl]-methanone;
(71) [5-amino-1-(2-methyl-1H-benzimidazol-5-yl)-1H-pyrazol-4-yl]-[6-(2-methoxy-pyridin-3-yl)-1H-indol-2-yl]-methanone;
(72) [5-amino-1-(2-methyl-1H-benzimidazol-5-yl)-1H-pyrazol-4-yl]-(6-cyclopropyl-1H-indol-2-yl)-methanone;
(73) [5-amino-1-(2-methyl-1H-benzimidazol-5-yl)-1H-pyrazol-4-yl]-[6-(2-methoxy-phenyl)-1H-indol-2-yl]-methanone;
(74) [5-amino-1-(2-methyl-1H-benzimidazol-5-yl)-1H-pyrazol-4-yl]-(6-phenyl-1H-indol-2-yl)-methanone;
(75) [5-amino-1-(2-methyl-1H-benzimidazol-5-yl)-1H-pyrazol-4-yl]-[6-(5-methanesulfonyl-pyridin-3-yl)-1H-indol-2-yl]-methanone;
(76) [5-amino-1-(2-methyl-1H-benzimidazol-5-yl)-1H-pyrazol-4-yl]-(6-isopropyl-1H-indol-2-yl)-methanone;
(77) [5-amino-1-(2-methyl-1H-benzimidazol-5-yl)-1H-pyrazol-4-yl]-(6-pyridin-2-yl-1H-indol-2-yl)-methanone;
(78) [5-amino-1-(2-methyl-1H-benzimidazol-5-yl)-1H-pyrazol-4-yl]-(5-cyclopropyl-1H-indol-2-yl)-methanone;
(79) [5-amino-1-(2-methyl-1H-benzimidazol-5-yl)-1H-pyrazol-4-yl]-(6-pyridazin-3-yl-1H-indol-2-yl)-methanone;
(80) [5-amino-1-(2-methyl-1H-benzimidazol-5-yl)-1H-pyrazol-4-yl]-(5-isopropoxy-1H-indol-2-yl)-methanone;
(81) [5-amino-1-(2-methyl-1H-benzimidazol-5-yl)-1H-pyrazol-4-yl]-[5-(2-methoxy-ethoxy)-1H-indol-2-yl]-methanone;
(82) [5-amino-1-(2-methyl-1H-benzimidazol-5-yl)-1H-pyrazol-4-yl]-(5-cyclopropylmethoxy-1H-indol-2-yl)-methanone;
(83) [5-amino-1-(2-methyl-1H-benzimidazol-5-yl)-1H-pyrazol-4-yl]-(2,2-difluoro-5H-[1,3]dioxolo[4,5-f]indol-6-yl)-methanone;
(84) [5-amino-1-(2-methyl-1H-benzimidazol-5-yl)-1H-pyrazol-4-yl]-[6-(3-chloro-pyridin-2-yl)-1H-indol-2-yl]-methanone;
(85) [5-amino-1-(2-methyl-1H-benzimidazol-5-yl)-1H-pyrazol-4-yl]-[6-(5-fluoro-pyridin-2-yl)-1H-indol-2-yl]-methanone;
(86) [5-amino-1-(2-methyl-1H-benzimidazol-5-yl)-1H-pyrazol-4-yl]-[6-(6-morpholin-4-yl-pyridazin-3-yl)-1H-indol-2-yl]-methanone;
(87) [5-amino-1-(2-methyl-1H-benzimidazol-5-yl)-1H-pyrazol-4-yl]-(5-chloro-6-cyclopropylmethoxy-1H-indol-2-yl)-methanone;

(88) [5-amino-1-(2-methyl-1H-benzimidazol-5-yl)-1H-pyrazol-4-yl]-[6-(2,4-difluoro-phenyl)-1H-indol-2-yl]-methanone;
(89) [5-amino-1-(2-methyl-1H-benzimidazol-5-yl)-1H-pyrazol-4-yl]-(6-pyridazin-4-yl-1H-indol-2-yl)-methanone;
(90) [5-amino-1-(2-methyl-1H-benzimidazol-5-yl)-1H-pyrazol-4-yl]-(3-fluoro-1H-indol-2-yl)-methanone;
(91) [5-amino-1-(2-methyl-1H-benzimidazol-5-yl)-1H-pyrazol-4-yl]-[5-(1-isopropyl-piperidin-4-yl)-6-trifluoromethyl-1H-indol-2-yl]-methanone;
(92) 2-[5-amino-1-(2-methyl-1H-benzimidazol-5-yl)-1H-pyrazole-4-carbonyl]-1H-indole-6-carbonitrile;
(93) [5-amino-1-(2-methyl-1H-benzimidazol-5-yl)-1H-pyrazol-4-yl]-[5-(1,2,3,6-tetrahydro-pyridin-4-yl)-1H-indol-2-yl]-methanone;
(94) [5-amino-1-(2-methyl-1H-benzimidazol-5-yl)-1H-pyrazol-4-yl]-(5-piperidin-4-yl-1H-indol-2-yl)-methanone;
(95) [5-amino-1-(2-methyl-1H-benzimidazol-5-yl)-1H-pyrazol-4-yl]-[5-((R)-3-fluoro-pyrrolidin-1-ylmethyl)-1H-indol-2-yl]-methanone;
(96) [5-amino-1-(2-methyl-1H-benzimidazol-5-yl)-1H-pyrazol-4-yl]-(6-fluoro-5-piperidin-4-yl-1H-indol-2-yl)-methanone;
(97) [5-amino-1-(2-methyl-1H-benzimidazol-5-yl)-1H-pyrazol-4-yl]-[6-fluoro-5-(1-methyl-piperidin-4-yl)-1H-indol-2-yl]-methanone;
(98) [5-amino-1-(2-methyl-1H-benzimidazol-5-yl)-1H-pyrazol-4-yl]-[5-(1-isopropyl-piperidin-4-yl)-1H-indol-2-yl]-methanone;
(99) [5-amino-1-(2-methyl-1H-benzimidazol-5-yl)-1H-pyrazol-4-yl]-[6-fluoro-5-(1-isopropyl-piperidin-4-yl)-1H-indol-2-yl]-methanone;
(100) [5-amino-1-(2-methyl-1H-benzimidazol-5-yl)-1H-pyrazol-4-yl]-(6-pyridin-3-yl-1H-indol-2-yl)-methanone;
(101) [5-amino-1-(2-methyl-1H-benzimidazol-5-yl)-1H-pyrazol-4-yl]-[5-(6-morpholin-4-yl-pyridin-3-yl)-1H-indol-2-yl]-methanone;
(102) [5-amino-1-(2-methyl-1H-benzimidazol-5-yl)-1H-pyrazol-4-yl]-(5-pyridin-3-yl-1H-indol-2-yl)-methanone;
(103) [5-amino-1-(2-methyl-1H-benzimidazol-5-yl)-1H-pyrazol-4-yl]-[5-(6-piperazin-1-yl-pyridin-3-yl)-1H-indol-2-yl]-methanone;
(104) [5-amino-1-(2-methyl-1H-benzimidazol-5-yl)-1H-pyrazol-4-yl]-[5-(6-hydroxy-pyridin-3-yl)-1H-indol-2-yl]-methanone;
(105) [5-amino-1-(2-methyl-1H-benzimidazol-5-yl)-1H-pyrazol-4-yl]-[6-fluoro-5-(4-methyl-piperazin-1-ylmethyl)-1H-indol-2-yl]-methanone;
(106) [5-amino-1-(2-methyl-1H-benzimidazol-5-yl)-1H-pyrazol-4-yl]-(6-fluoro-5-pyrrolidin-1-ylmethyl-1H-indol-2-yl)-methanone;
(107) [5-amino-1-(2-methyl-1H-benzimidazol-5-yl)-1H-pyrazol-4-yl]-[6-(1-methyl-piperidin-4-yl)-1H-indol-2-yl]-methanone;
(108) [5-amino-1-(2-methyl-1H-benzimidazol-5-yl)-1H-pyrazol-4-yl]-[6-(4-morpholin-4-yl-phenyl)-1H-indol-2-yl]-methanone;
(109) [5-amino-1-(2-methyl-1H-benzimidazol-5-yl)-1H-pyrazol-4-yl]-[6-(3,4,5,6-tetrahydro-2H-[1,2']bipyridin-5'-yl)-1H-indol-2-yl]-methanone;
(110) [5-amino-1-(2-methyl-1H-benzimidazol-5-yl)-1H-pyrazol-4-yl]-[6-(6-piperazin-1-yl-pyridin-3-yl)-1H-indol-2-yl]-methanone;
(111) [5-amino-1-(2-methyl-1H-benzimidazol-5-yl)-1H-pyrazol-4-yl]-[5-(6-methoxy-pyridin-3-yl)-1H-indol-2-yl]-methanone;
(112) [5-amino-1-(2-methyl-1H-benzimidazol-5-yl)-1H-pyrazol-4-yl]-[5-((S)-3-methyl-morpholin-4-yl methyl)-1H-indol-2-yl]-methanone;
(113) [5-amino-1-(2-methyl-1H-benzimidazol-5-yl)-1H-pyrazol-4-yl]-[6-((R)-3-fluoro-pyrrolidin-1-ylmethyl)-1H-indol-2-yl]-methanone;
(114) [5-amino-1-(2-methyl-1H-benzimidazol-5-yl)-1H-pyrazol-4-yl]-[5-(2,5-dimethyl-pyrrolidin-1-ylmethyl)-1H-indol-2-yl]-methanone;
(115) [5-amino-1-(2-methyl-1H-benzimidazol-5-yl)-1H-pyrazol-4-yl]-[5-(3-fluoro-piperidin-1-ylmethyl)-1H-indol-2-yl]-methanone;
(116) [5-amino-1-(2-methyl-1H-benzimidazol-5-yl)-1H-pyrazol-4-yl]-[5-(3,3-difluoro-piperidin-1-ylmethyl)-1H-indol-2-yl]-methanone;
(117) [5-amino-1-(2-methyl-1H-benzimidazol-5-yl)-1H-pyrazol-4-yl]-{6-[2-(4-methyl-piperazin-1-yl)pyridin-4-yl]-1H-indol-2-yl}-methanone;
(118) [5-amino-1-(2-methyl-1H-benzimidazol-5-yl)-1H-pyrazol-4-yl]-(6-pyridin-4-yl-1H-indol-2-yl)-methanone;
(119) [5-amino-1-(2-methyl-1H-benzimidazol-5-yl)-1H-pyrazol-4-yl]-[5-(4-fluoropiperidin-1-ylmethyl)-1H-indol-2-yl]-methanone;
(120) [5-amino-1-(2-methyl-1H-benzimidazol-5-yl)-1H-pyrazol-4-yl]-[5-(4,4-difluoro-piperidin-1-ylmethyl)-1H-indol-2-yl]-methanone;
(121) [5-amino-1-(2-difluoromethyl-1H-benzimidazol-5-yl)-1H-pyrazol-4-yl]-[5-(1-methyl-piperidin-4-yl)-1H-indol-2-yl]-methanone;
(122) [5-amino-1-(2-difluoromethyl-1H-benzimidazol-5-yl)-1H-pyrazol-4-yl]-(1H-indol-2-yl)-methanone;

(123)
[5-amino-1-(2-methyl-1H-benzimidazol-5-yl)-1H-pyrazol-4-yl]-[5-(3,3-difluoro-pyrrolidin-1-ylmethyl)-1H-indol-2-yl]-methanone;
(124)
[5-amino-1-(2-methyl-1H-benzimidazol-5-yl)-1H-pyrazol-4-yl]-[5-(1-cyclopentyl-piperidin-4-yl)-1H-indol-2-yl]-methanone;
(125)
[5-amino-1-(2-methyl-1H-benzimidazol-5-yl)-1H-pyrazol-4-yl]-[5-(1-cyclohexyl-piperidin-4-yl)-1H-indol-2-yl]-methanone;
(126)
[5-amino-1-(2-methyl-1H-benzimidazol-5-yl)-1H-pyrazol-4-yl]-(4-bromo-1H-pyrrol-2-yl)-methanone;
(127)
[5-amino-1-(2-methyl-1H-benzimidazol-5-yl)-1H-pyrazol-4-yl]-(1H-pyrrol-2-yl)-methanone;
(128)
[5-amino-1-(2-methyl-1H-benzimidazol-5-yl)-1H-pyrazol-4-yl]-(4-phenyl-1H-pyrrol-2-yl)-methanone;
(129)
[5-amino-1-(2-methyl-1H-benzimidazol-5-yl)-1H-pyrazol-4-yl]-[4-(3-chloro-phenyl)-1H-pyrrol-2-yl]-methanone;
(130)
[5-amino-1-(2-methyl-1H-benzimidazol-5-yl)-1H-pyrazol-4-yl]-[4-(4-fluoro-phenyl)-1H-pyrrol-2-yl]-methanone;
(131)
[5-amino-1-(2-methyl-1H-benzimidazol-5-yl)-1H-pyrazol-4-yl]-[4-(3-fluoro-phenyl)-1H-pyrrol-2-yl]-methanone;
(132)
[5-amino-1-(2-methyl-1H-benzimidazol-5-yl)-1H-pyrazol-4-yl]-(6-morpholin-4-ylmethyl-1H-indol-2-yl)-methanone;
(133)
[5-amino-1-(2-methyl-1H-benzimidazol-5-yl)-1H-pyrazol-4-yl]-[4-(2-morpholin-4-yl-ethylamino)-1H-indol-2-yl]-methanone;
(134)
[5-amino-1-(2-methyl-1H-benzimidazol-5-yl)-1H-pyrazol-4-yl]-[5-(4-methyl-piperazine-1-carbonyl)-1H-indol-2-yl]-methanone;
(135)
[5-amino-1-(2-methyl-1H-benzimidazol-5-yl)-1H-pyrazol-4-yl]-[6-(2-morpholin-4-yl-ethylamino)-1H-indol-2-yl]-methanone;
(136)
[5-amino-1-(2-methyl-1H-benzimidazol-5-yl)-1H-pyrazol-4-yl]-[5-(piperazine-1-carbonyl)-1H-indol-2-yl]-methanone;
(137)
[5-amino-1-(2-methyl-1H-benzimidazol-5-yl)-1H-pyrazol-4-yl]-[4-(2-methoxy-ethylamino)-1H-indol-2-yl]-methanone;
(138)
[5-amino-1-(2-methyl-1H-benzimidazol-5-yl)-1H-pyrazol-4-yl]-[4-(2-hydroxy-1-hydroxymethyl-ethylamino)-1H-indol-2-yl]-methanone;
(139)
[5-amino-1-(2-methyl-1H-benzimidazol-5-yl)-1H-pyrazol-4-yl]-[4-(2-pyridin-4-yl-ethylamino)-1H-indol-2-yl]-methanone;
(140)
[5-amino-1-(2-methyl-1H-benzimidazol-5-yl)-1H-pyrazol-4-yl]-[6-(2-methoxy-ethylamino)-1H-indol-2-yl]-methanone;
(141)
[5-amino-1-(2-methyl-1H-benzimidazol-5-yl)-1H-pyrazol-4-yl]-(6-morpholin-4-yl-1H-indol-2-yl)-methanone;
(142)
[5-amino-1-(2-methyl-1H-benzimidazol-5-yl)-1H-pyrazol-4-yl]-(4-morpholin-4-yl-1H-indol-2-yl)-methanone;
(143)
[5-amino-1-(2-methyl-1H-benzimidazol-5-yl)-1H-pyrazol-4-yl]-(4-morpholin-4-ylmethyl-1H-indol-2-yl)-methanone;
(144)
[5-amino-1-(2-methyl-1H-benzimidazol-5-yl)-1H-pyrazol-4-yl]-(5-morpholin-4-ylmethyl-1H-indol-2-yl)-methanone;
(145)
[5-amino-1-(2-methyl-1H-benzimidazol-5-yl)-1H-pyrazol-4-yl]-[5-(morpholine-4-carbonyl)-1H-indol-2-yl]-methanone;
(146)
[5-amino-1-(2-isopropyl-1H-benzimidazol-5-yl)-1H-pyrazol-4-yl]-(1H-indol-2-yl)-methanone;
(147)
[5-amino-1-(2-propyl-1H-benzimidazol-5-yl)-1H-pyrazol-4-yl]-(1H-indol-2-yl)-methanone;
(148)
[5-amino-1-(1H-benzimidazol-5-yl)-1H-pyrazol-4-yl]-(1H-indol-2-yl)-methanone;
(149)
[5-amino-1-(2-trifluoromethyl-1H-benzimidazol-5-yl)-1H-pyrazol-4-yl]-(1H-indol-2-yl)-methanone;
(150)
[5-amino-1-(2-ethyl-1H-benzimidazol-5-yl)-1H-pyrazol-4-yl]-(1H-indol-2-yl)-methanone;
(151)
[5-amino-1-(2-benzyl-1H-benzimidazol-5-yl)-1H-pyrazol-4-yl]-(1H-indol-2-yl)methanone;
(152)
1-(4-{2-[5-amino-1-(2-methyl-1H-benzimidazol-5-yl)-1H-pyrazole-4-carbonyl]-1H-indol-5-ylmethyl}-piperazin-1-yl)-ethanone;
(153)
[5-amino-1-(2-methyl-1H-benzimidazol-5-yl)-1H-pyrazol-4-yl]-[5-(4-methanesulfonyl-piperazin-1-ylmethyl)-1H-indol-2-yl]-methanone;
(154)
[5-amino-1-(2-methyl-1H-benzimidazol-5-yl)-1H-pyrazol-4-yl]-(5-piperazin-1-ylmethyl-1H-indol-2-yl)-methanone;
(155)
1-(4-{2-[5-amino-1-(2-methyl-1H-benzimidazol-5-yl)-1H-pyrazole-4-carbonyl]-1H-indol-6-ylmethyl}-piperazin-1-yl)-ethanone;
(156)
[5-amino-1-(2-methyl-1H-benzimidazol-5-yl)-1H-pyrazol-4-yl]-[6-(4-methyl-piperazin-1-ylmethyl)-1H-indol-2-yl]-methanone;
(157)
[5-amino-1-(2-methyl-1H-benzimidazol-5-yl)-1H-pyrazol-4-yl]-[5-(4-methyl-piperazin-1-ylmethyl)-1H-indol-2-yl]-methanone;
(158)
[5-amino-1-(2-methyl-1H-benzimidazol-5-yl)-1H-pyrazol-4-yl]-(5-pyrrolidin-1-ylmethyl-1H-indol-2-yl)-methanone;
(159)
[5-amino-1-(2-methyl-1H-benzimidazol-5-yl)-1H-pyrazol-4-yl]-(4-fluoro-1H-indol-2-yl)-methanone;

(160) [5-amino-1-(2-methyl-1H-benzimidazol-5-yl)-1H-pyrazol-4-yl]-(5-fluoro-1H-indol-2-yl)-methanone;
(161) [5-amino-1-(2-methyl-1H-benzimidazol-5-yl)-1H-pyrazol-4-yl]-(6-fluoro-1H-indol-2-yl)-methanone;
(162) [5-amino-1-(2-methyl-1H-benzimidazol-5-yl)-1H-pyrazol-4-yl]-(1H-pyrrolo[2,3-b]pyridin-2-yl)-methanone;
(163) [5-amino-1-(2-methyl-1H-benzimidazol-5-yl)-1H-pyrazol-4-yl]-(5-fluoro-6-morpholin-4-ylmethyl-1H-indol-2-yl)-methanone;
(164) 2-[5-amino-1-(2-methyl-1H-benzimidazol-5-yl)-1H-pyrazole-4-carbonyl]-1H-indole-5-carboxylic acid;
(165) [5-amino-1-(2-methyl-1H-benzimidazol-5-yl)-1H-pyrazol-4-yl]-(5-methoxy-1H-indol-2-yl)-methanone;
(166) [5-amino-1-(2-methyl-1H-benzimidazol-5-yl)-1H-pyrazol-4-yl]-(4,6-dimethoxy-1H-indol-2-yl)-methanone;
(167) [5-amino-1-(2-methyl-1H-benzimidazol-5-yl)-1H-pyrazol-4-yl]-(4-methoxy-1H-indol-2-yl)-methanone;
(168) [5-amino-1-(2-methyl-1H-benzimidazol-5-yl)-1H-pyrazol-4-yl]-(6-methoxy-1H-indol-2-yl)-methanone;
(169) [5-amino-1-(2-methyl-1H-benzimidazol-5-yl)-1H-pyrazol-4-yl]-(4,6-dimethyl-1H-indol-2-yl)-methanone;
(170) [5-amino-1-(2-methyl-1H-benzimidazol-5-yl)-1H-pyrazol-4-yl]-(5-tert-butyl-1H-indol-2-yl)-methanone;
(171) [5-amino-1-(2-methyl-1H-benzimidazol-5-yl)-1H-pyrazol-4-yl]-(5-isopropyl-1H-indol-2-yl)-methanone;
(172) [5-amino-1-(2-methyl-1H-benzimidazol-5-yl)-1H-pyrazol-4-yl]-(5-benzyloxy-1H-indol-2-yl)-methanone;
(173) [5-amino-1-(2-methyl-1H-benzimidazol-5-yl)-1H-pyrazol-4-yl]-(4-benzyloxy-1H-indol-2-yl)-methanone;
(174) [5-amino-1-(2-methyl-1H-benzimidazol-5-yl)-1H-pyrazol-4-yl]-(5,6-dimethoxy-1H-indol-2-yl)-methanone;
(175) [5-amino-1-(2-methyl-1H-benzimidazol-5-yl)-1H-pyrazol-4-yl]-(6-tert-butyl-1H-indol-2-yl)-methanone;
(176) [5-amino-1-(2-methyl-1H-benzimidazol-5-yl)-1H-pyrazol-4-yl]-(5-fluoro-4-trifluoromethyl-1H-indol-2-yl)-methanone;
(177) [5-amino-1-(2-methyl-1H-benzimidazol-5-yl)-1H-pyrazol-4-yl]-(5-phenoxy-1H-indol-2-yl)-methanone;
(178) [5-amino-1-(2-methyl-1H-benzimidazol-5-yl)-1H-pyrazol-4-yl]-(6-methylsulfanyl-1H-indol-2-yl)-methanone;
(179) [5-amino-1-(2-methyl-1H-benzimidazol-5-yl)-1H-pyrazol-4-yl]-(4-tert-butyl-1H-indol-2-yl)-methanone;
(180) [5-amino-1-(2-methyl-1H-benzimidazol-5-yl)-1H-pyrazol-4-yl]-(5-methyl-1H-indol-2-yl)-methanone;
(181) [5-amino-1-(2-methyl-1H-benzimidazol-5-yl)-1H-pyrazol-4-yl]-(5-ethyl-1H-indol-2-yl)-methanone;
(182) [5-amino-1-(2-methyl-1H-benzimidazol-5-yl)-1H-pyrazol-4-yl]-(5-fluoro-6-trifluoromethyl-1H-indol-2-yl)-methanone;
(183) [5-amino-1-(2-methyl-1H-benzimidazol-5-yl)-1H-pyrazol-4-yl]-(6-fluoro-5-methoxy-1H-indol-2-yl)-methanone;
(184) [5-amino-1-(2-methyl-1H-benzimidazol-5-yl)-1H-pyrazol-4-yl]-(6-chloro-5-methoxy-1H-indol-2-yl)-methanone;
(185) [5-amino-1-(2-methyl-1H-benzimidazol-5-yl)-1H-pyrazol-4-yl]-(5-chloro-6-methoxy-1H-indol-2-yl)-methanone;
(186) [5-amino-1-(2-methyl-1H-benzimidazol-5-yl)-1H-pyrazol-4-yl]-(6-isopropoxy-1H-indol-2-yl)-methanone;
(187) [5-amino-1-(2-methyl-1H-benzimidazol-5-yl)-1H-pyrazol-4-yl]-(6-benzyloxy-1H-indol-2-yl)-methanone;
(188) [5-amino-1-(2-methyl-1H-benzimidazol-5-yl)-1H-pyrazol-4-yl]-(4-isopropoxy-1H-indol-2-yl)-methanone;
(189) [5-amino-1-(2-methyl-1H-benzimidazol-5-yl)-1H-pyrazol-4-yl]-(2,3-dihydro-6H-[1,4]dioxino[2,3-f]indol-7-yl)-methanone;
(190) [5-amino-1-(2-methyl-1H-benzimidazol-5-yl)-1H-pyrazol-4-yl]-(4,6-di-tert-butyl-1H-indol-2-yl)-methanone;
(191) 2-[5-amino-1-(2-methyl-1H-benzimidazol-5-yl)-1H-pyrazole-4-carbonyl]-1H-indole-4-carbonitrile;
(192) [5-amino-1-(2-methyl-1H-benzimidazol-5-yl)-1H-pyrazol-4-yl]-(5-imidazol-1-yl-1H-indol-2-yl)-methanone;
(193) [5-amino-1-(2-methyl-1H-benzimidazol-5-yl)-1H-pyrazol-4-yl]-(5-trifluoromethylsulfanyl-1H-indol-2-yl)-methanone;
(194) [5-amino-1-(2-methyl-1H-benzimidazol-5-yl)-1H-pyrazol-4-yl]-(5-methylsulfanyl-1H-indol-2-yl)-methanone;
(195) [5-amino-1-(2-methyl-1H-benzimidazol-5-yl)-1H-pyrazol-4-yl]-(5-methanesulfonyl-1H-indol-2-yl)-methanone;
(196) [5-amino-1-(2-methyl-1H-benzimidazol-5-yl)-1H-pyrazol-4-yl]-[6-(4,4-difluoro-piperidin-1-ylmethyl)-1H-indol-2-yl]-methanone;
(197) [5-amino-1-(2-methyl-1H-benzimidazol-5-yl)-1H-pyrazol-4-yl]-[6-(4-fluoro-piperidin-1-ylmethyl)-1H-indol-2-yl]-methanone;
(198) [5-amino-1-(2-methyl-1H-benzimidazol-5-yl)-1H-pyrazol-4-yl]-[6-(oxetan-3-yloxy)-1H-indol-2-yl]-methanone;
(199) [5-amino-1-(2-methyl-1H-benzimidazol-5-yl)-1H-pyrazol-4-yl]-(6-hydroxy-1H-indol-2-yl)-methanone;
(200) [5-amino-1-(2-methyl-1H-benzimidazol-5-yl)-1H-pyrazol-4-yl]-(6-methanesulfonyl-1H-indol-2-yl)-methanone;

(201) [5-amino-1-(2-methyl-1H-benzimidazol-5-yl)-1H-pyrazol-4-yl]-(4,5-dibromo-1H-pyrrol-2-yl)-methanone;
(202) [5-amino-1-(2-methyl-1H-benzimidazol-5-yl)-1H-pyrazol-4-yl]-(4,5-diphenyl-1H-pyrrol-2-yl)-methanone; and
(203) [5-amino-1-(2-methyl-1H-benzimidazol-5-yl)-1H-pyrazol-4-yl]-(4,5-dipyridin-3-yl-1H-pyrrol-2-yl)-methanone.
(204) [5-amino-1-(2-methyl-3H-benzimidazol-5-yl)-1H-pyrazol-4-yl]-(6-chloro-1H-indol-2-yl)-methanone;
(205) [5-amino-1-(2-methyl-1H-benzimidazol-5-yl)-1H-pyrazol-4-yl]-(5-chloro-1H-indol-2-yl)-methanone;
(206) [5-amino-1-(2-methyl-1H-benzimidazol-5-yl)-1H-pyrazol-4-yl]-(1H-indol-3-yl)-methanone;
(207) [5-amino-1-(2-methyl-1H-benzimidazol-5-yl)-1H-pyrazol-4-yl]-(1H-indol-6-yl)-methanone;
(208) [5-amino-1-(2-methyl-1H-benzimidazol-5-yl)-1H-pyrazol-4-yl]-(5-bromo-6-fluoro-1H-indol-2-yl)-methanone;
(209) [5-amino-1-(2-ethyl-1H-benzimidazol-5-yl)-1H-pyrazol-4-yl]-(5-bromo-6-fluoro-1H-indol-2-yl)-methanone;
(210) [5-amino-1-(2-methyl-1H-benzimidazol-5-yl)-1H-pyrazol-4-yl]-(5-trifluoromethyl-1H-indol-2-yl)-methanone;
(211) [5-amino-1-(2-methyl-1H-benzimidazol-5-yl)-1H-pyrazol-4-yl]-(5-trifluoromethoxy-1H-indol-2-yl)-methanone;
(212) [5-amino-1-(2-methyl-1H-benzimidazol-5-yl)-1H-pyrazol-4-yl]-(4,6-dichloro-1H-indol-2-yl)-methanone;
(213) [5-amino-1-(2-methyl-1H-benzimidazol-5-yl)-1H-pyrazol-4-yl]-(6-bromo-4-fluoro-1H-indol-2-yl)-methanone;
(214) [5-amino-1-(2-methyl-1H-benzimidazol-5-yl)-1H-pyrazol-4-yl]-(6-trifluoromethoxy-1H-indol-2-yl)-methanone;
(215) [5-amino-1-(2-ethyl-1H-benzimidazol-5-yl)-1H-pyrazol-4-yl]-(5-trifluoromethoxy-1H-indol-2-yl)-methanone;
(216) [5-amino-1-(2-ethyl-1H-benzimidazol-5-yl)-1H-pyrazol-4-yl]-(5-trifluoromethyl-1H-indol-2-yl)-methanone;
(217) [5-amino-1-(2-methyl-1H-benzimidazol-5-yl)-1H-pyrazol-4-yl]-(5,6-dichloro-1H-indol-2-yl)-methanone;
(218) [5-amino-1-(2-ethyl-1H-benzimidazol-5-yl)-1H-pyrazol-4-yl]-(6-bromo-5-fluoro-1H-indol-2-yl)-methanone;
(219) [5-amino-1-(2-methyl-1H-benzimidazol-5-yl)-1H-pyrazol-4-yl]-(4,5-dichloro-1H-indol-2-yl)-methanone;
(220) [5-amino-1-(2-methyl-1H-benzimidazol-5-yl)-1H-pyrazol-4-yl]-(4,6-difluoro-1H-indol-2-yl)-methanone;
(221) [5-amino-1-(2-methyl-1H-benzimidazol-5-yl)-1H-pyrazol-4-yl]-[6-(3-chloro-pyridin-4-yl)-1H-indol-2-yl]-methanone;
(222) [5-amino-1-(2-methyl-1H-benzimidazol-5-yl)-1H-pyrazol-4-yl]-[6-(6-methyl-pyridine-3-yl)-1H-indol-2-yl]-methanone;
(223) [5-amino-1-(2-methyl-1H-benzimidazol-5-yl)-1H-pyrazol-4-yl]-[6-(5-fluoro-pyridin-3-yl)-1H-indol-2-yl]-methanone;
(224) [5-amino-1-(2-methyl-1H-benzimidazol-5-yl)-1H-pyrazol-4-yl]-[6-(2-trifluoromethyl-pyridin-3-yl)-1H-indol-2-yl]-methanone;
(225) [5-amino-1-(2-methyl-1H-benzimidazol-5-yl)-1H-pyrazol-4-yl]-[6-(5-chloro-2-methoxy-pyridin-3-yl)-1H-indol-2-yl]-methanone;
(226) [5-amino-1-(2-methyl-1H-benzimidazol-5-yl)-1H-pyrazol-4-yl]-[6-(5-chloro-pyridin-3-yl)-1H-indol-2-yl]-methanone;
(227) [5-amino-1-(2-methyl-1H-benzimidazol-5-yl)-1H-pyrazol-4-yl]-(6-thiophen-3-yl-1H-indol-2-yl)-methanone;
(228) [5-amino-1-(2-methyl-1H-benzimidazol-5-yl)-1H-pyrazol-4-yl]-[6-(4-chloropyridin-3-yl)-1H-indol-2-yl]-methanone;
(229) [5-amino-1-(2-methyl-1H-benzimidazol-5-yl)-1H-pyrazol-4-yl]-(6-thiophen-2-yl-1H-indol-2-yl)-methanone;
(230) [5-amino-1-(2-methyl-1H-benzimidazol-5-yl)-1H-pyrazol-4-yl]-[6-(3-fluoro-pyridin-4-yl)-1H-indol-2-yl]-methanone;
(231) [5-amino-1-(2-methyl-1H-benzimidazol-5-yl)-1H-pyrazol-4-yl]-[6-(2-trifluoromethyl-pyridin-4-yl)-1H-indol-2-yl]-methanone;
(232) [5-amino-1-(2-methyl-1H-benzimidazol-5-yl)-1H-pyrazol-4-yl]-[5-(3,3-difluoro-pyrrolidine-1-carbonyl)-1H-indol-2-yl]-methanone;
(233) [5-amino-1-(2-methyl-1H-benzimidazol-5-yl)-1H-pyrazol-4-yl]-[5-(2,6-dimethyl-morpholine-4-carbonyl)-1H-indol-2-yl]-methanone;
(234) [5-amino-1-(2-methyl-1H-benzimidazol-5-yl)-1H-pyrazol-4-yl]-[5-([1,4']bipiperidinyl-1'-carbonyl)-1H-indol-2-yl]-methanone;
(235) [5-amino-1-(2-methyl-1H-benzimidazol-5-yl)-1H-pyrazol-4-yl]-{5-[4-(2,2,2-trifluoro-ethyl)-piperazine-1-carbonyl]-1H-indol-2-yl}-methanone;
(236) [5-amino-1-(2-methyl-1H-benzimidazol-5-yl)-1H-pyrazol-4-yl]-{5-[4-(2-hydroxy-ethyl)-piperazine-1-carbonyl]-1H-indol-2-yl}-methanone;
(237) [5-amino-1-(2-methyl-1H-benzimidazol-5-yl)-1H-pyrazol-4-yl]-[5-(3,3,4,4-tetrafluoro-pyrrolidine-1-carbonyl)-1H-indol-2-yl]-methanone;
(238) [5-amino-1-(2-methyl-1H-benzimidazol-5-yl)-1H-pyrazol-4-yl]-[5-((R)-3-fluoro-pyrrolidine-1-carbonyl)-1H-indol-2-yl]-methanone;

(239)
[5-amino-1-(2-methyl-1H-benzimidazol-5-yl)-1H-pyrazol-4-yl]-[5-((S)-3-fluororo-pyrrolidine-1-carbonyl)-1H-indol-2-yl]-methanone;
(240)
[5-amino-1-(2-methyl-1H-benzimidazol-5-yl)-1H-pyrazol-4-yl]-[4-(4-methoxy-phenyl)-1H-pyrrol-2-yl]-methanone;
(241)
[5-amino-1-(2-methyl-1H-benzimidazol-5-yl)-1H-pyrazol-4-yl]-[4-(3-methoxy-phenyl)-1H-pyrrol-2-yl]-methanone;
(242)
[5-amino-1-(2-methyl-1H-benzimidazol-5-yl)-1H-pyrazol-4-yl]-[4,5-bis-(3-fluoro-phenyl)-1H-pyrrol-2-yl]-methanone;
(243)
[5-amino-1-(2-methyl-1H-benzimidazol-5-yl)-1H-pyrazol-4-yl]-[4,5-bis-(4-methoxy-phenyl)-1H-pyrrol-2-yl]-methanone;
(244)
[5-amino-1-(2-methyl-1H-benzimidazol-5-yl)-1H-pyrazol-4-yl]-[4-(2,4-difluoro-phenyl)-1H-pyrrol-2-yl]-methanone;
(245)
[5-amino-1-(2-methyl-1H-benzimidazol-5-yl)-1H-pyrazol-4-yl]-[4-(4-trifluoromethoxy-phenyl)-1H-pyrrol-2-yl]-methanone;
(246)
[5-amino-1-(2-methyl-1H-benzimidazol-5-yl)-1H-pyrazol-4-yl]-[4,5-bis-(3-methoxy-phenyl)-1H-pyrrol-2-yl]-methanone;
(247)
[5-amino-1-(2-methyl-1H-benzimidazol-5-yl)-1H-pyrazol-4-yl]-benzofuran-2-yl-methanone;
(248)
[5-amino-1-(2-methyl-1H-benzimidazol-5-yl)-1H-pyrazol-4-yl]-benzo[b]thiophen-2-yl-methanone;
(249)
[5-amino-1-(2-methyl-1H-benzimidazol-5-yl)-1H-pyrazol-4-yl]-benzothiazol-2-yl-methanone;
(250)
[5-amino-1-(2-methyl-1H-benzimidazol-5-yl)-1H-pyrazol-4-yl]-(4-fluoro-phenyl)-methanone;
(251)
[5-amino-1-(2-methyl-1H-benzimidazol-5-yl)-1H-pyrazol-4-yl]-(3-chloro-phenyl)-methanone;
(252)
[5-amino-1-(2-methyl-1H-benzimidazol-5-yl)-1H-pyrazol-4-yl]-quinolin-3-yl-methanone;
(253)
[5-amino-1-(2-methyl-1H-benzimidazol-5-yl)-1H-pyrazol-4-yl]-quinolin-7-yl-methanone; and
(254)
[5-amino-1-(2-methyl-1H-benzimidazol-5-yl)-1H-pyrazol-4-yl]-quinolin-6-yl-methanone.

The above compounds represented by formula (I) of the present invention and pharmaceutically acceptable salts thereof are useful as compounds that have an activity of inhibiting kinases of the fibroblast growth factor receptor (FGFR) family. Thus, the compounds are useful in preventing and/or treating cancer (for example, breast cancer, acute myelocytic leukemia, pancreatic cancer, bladder cancer, prostatic cancer, esophageal cancer, angiogenesis, stomach cancer, uterine body cancer, ovarian cancer, brain tumor (including glioblastoma), colon cancer, multiple myeloma, hepatocarcinoma, pulmonary cancer (including small cell and non-small cell lung cancers), and thyroid cancer.

The compounds of the present invention and salts thereof can be formulated into tablets, powders, fine granules, granules, coated tablets capsules, syrups, troches, inhalants, suppositories, injections, ointments, eye ointments, eye drops, nasal drops, ear drops, cataplasms, lotions, and the like by conventional methods. For the formulation, conventional excipients, binders, lubricants, colorants, flavoring agents, and if needed, stabilizers, emulsifiers, absorbefacients, surfactants, pH adjusting agents, preservatives, antioxidants, and the like can be used. The compounds of the present invention are formulated by combining ingredients that are generally used as materials for pharmaceutical preparations, using conventional methods.

For example, to produce oral formulations, the compounds of the present invention or pharmaceutically acceptable salts thereof are combined with excipients, and if needed, binders, disintegrating agents, lubricants, colorants, flavoring agents, and the like; and then formulated into powders, fine granules, granules, tablets, coated tablets, capsules, and the like by conventional methods.

The ingredients include, for example, animal and vegetable oils such as soybean oils, beef tallow, and synthetic glycerides; hydrocarbons such as liquid paraffin, squalane, and solid paraffin; ester oils such as octyldodecyl myristate and isopropyl myristate; higher alcohols such as cetostearyl alcohol and behenyl alcohol; silicon resins; silicon oils; surfactants such as polyoxyethylene fatty acid esters, sorbitan fatty acid esters, glycerin fatty acid esters, polyoxyethylene sorbitan fatty acid esters, polyoxyethylene hydrogenated castor oils, and polyoxyethylene/polyoxypropylene block copolymers; water-soluble polymers such as hydroxyethyl cellulose, polyacrylic acids, carboxyvinyl polymers, polyethylene glycol, polyvinylpyrrolidone, and methyl cellulose; lower alcohols such as ethanol and isopropanol; polyalcohols such as glycerin, propylene glycol, dipropylene glycol, and sorbitol; saccharides such as glucose and sucrose; inorganic powders such as silicic anhydride, magnesium aluminum silicate, and aluminum silicate; and purified water.

Excipients include, for example, lactose, cornstarch, sucrose, glucose, mannitol, sorbit, crystalline cellulose, and silicon dioxide.

Binders include, for example, polyvinyl alcohol, polyvinyl ether, methyl cellulose, ethyl cellulose, Arabic gum, tragacanth, gelatin, shellac, hydroxypropyl methyl cellulose, hydroxypropyl cellulose, polyvinylpyrrolidone, polypropylene glycol/polyoxyethylene block polymer, and meglumine.

Disintegrating agents include, for example, starch, agar, gelatin powder, crystalline cellulose, calcium carbonate, sodium bicarbonate, calcium citrate, dextran, pectin, and calcium carboxymethyl cellulose.

Lubricants include, for example, magnesium stearate, talc, polyethylene glycol, silica, and hardened vegetable oil.

Colorants approved for use as additives for pharmaceuticals are used. Flavoring agents used include, for example, cacao powder, menthol, aromatic powder, peppermint oil, borneol, and cinnamon powder.

Of course, these tablets and granules may be coated with sugar, or if needed, other appropriate coatings. Alternatively, when liquid preparations such as syrups and injections are produced, the compounds of the present invention or pharmaceutically acceptable salts thereof are combined with pH adjusting agents, solubilizers, isotonizing agents, or such, and if needed, solubilizing agents, stabilizers, and such, and then formulated using conventional methods.

Methods for producing external preparations are not limited, and they can be produced by conventional methods. Various conventional materials for pharmaceuticals, quasi-drugs, cosmetics, and the like can be used as base materials in the production. Specifically, the base materials used include, for example, animal and vegetable oils, mineral oils, ester oils, waxes, higher alcohols, fatty acids, silicon oils, surfactants, phospholipids, alcohols, polyalcohols, water-soluble polymers, clay minerals, and purified water. Furthermore, as necessary, it is possible to add pH adjusting agents, antioxidants, chelating agents, preservatives, colorants, flavoring agents, and such. However, the base materials for external preparations of the present invention are not limited thereto.

Furthermore, if needed, the preparations may be combined with components that have an activity of inducing differentiation, or components such as blood flow-enhancing agents, antimicrobial agents, antiphlogistic agents, cell-activating agents, vitamins, amino acids, humectants, and keratolytic agents. The above-described base materials can be added at an amount that provides a concentration typically selected in the production of external preparations.

When the compounds of the present invention, salts, or hydrates thereof are administered, their dosage forms are not particularly limited, and they may be administered orally or parenterally by conventionally used methods. They can be formulated and administered as tablets, powders, granules, capsules, syrups, troches, inhalants, suppositories, injections, ointments, eye ointments, eye drops, nasal drops, ear drops, cataplasms, lotions, and the like.

The dosage of pharmaceuticals of the present invention can be appropriately selected depending on the severity of symptom, age, sex, weight, administration method, type of salt, specific type of disease, and such.

The dosage considerably varies depending on the type of disease, severity of symptom, age, sex, sensitivity to the agent, and such of the patient. Typically, the agent is administered to an adult once or several times a day at a daily dose of about 0.03 to 1000 mg, preferably 0.1 to 500 mg, and more preferably 0.1 to 100 mg. When an injection is used, the daily dose is typically about 1 to 3000 μg/kg, preferably about 3 to 1000 μg/kg.

When the compounds of the present invention are produced, material compounds and various reagents may form salts, hydrates, or solvates. The type varies depending on the starting material, solvent used, and such, and is not particularly limited as long as the reactions are not inhibited.

The solvents to be used vary depending on the starting material, reagent, and such, and as a matter of course, they are not particularly limited as long as they can dissolve starting materials to some extent without inhibiting the reactions.

Various isomers (for example, geometric isomers, optical isomers based on asymmetric carbons, rotational isomers, stereoisomers, and tautomers) can be purified and isolated by conventional separation methods such as recrystallization, diastereomer salt methods, enzyme-based resolution methods, various chromatographic methods (for example, thin-layer chromatography, column chromatography, high performance liquid chromatography, and gas chromatography).

When a compound of the present invention is obtained in a free form, it can be converted by conventional methods into a salt or hydrate thereof that may be formed from the compound of the present invention. When a compound of the present invention is obtained as a salt or hydrate thereof, it can be converted by conventional methods into a free form of the compound of the present invention.

The compounds of the present invention can be purified and isolated using conventional chemical methods such as extraction, concentration, distilling off, crystallization, filtration, re-crystallization, and various chromatographic methods.

All the prior art documents cited in this specification are incorporated herein by reference.

The general methods for producing the compounds of the present invention and working examples are described below.

The compounds of the present invention can be synthesized by various methods. Some of them are illustrated with reference to the schemes shown below. The schemes are for illustrative purposes, and the present invention is not limited to the chemical reactions and conditions shown therein. In the schemes shown below, some substituents may be omitted for clarity, but this is not intended to limit the disclosure of the schemes. Representative compounds of the present invention can be synthesized using appropriate intermediates, known compounds, and reagents.

Production of the Compound Represented by Formula (I)

Scheme A shows a method for producing the compound represented by formula (I).

In the schemes and general production methods below, the definitions of $R_1$ and others are shown in each scheme or general production method. $R_{33}$ to $R_{37}$ are defined as follows:

$R_{33}$ represents an alkyl group.

$R_{34}$ and $R_{35}$ each represent an alkyl group. Alternatively, a plurality of $R_{34}$ or a plurality of $R_{35}$ together form a ring.

$R_{36}$ represents an alkyl group. Alternatively, a plurality of $R_{36}$ together form a ring.

$R_{37}$ represents an alkyl or aryl group.

The compound of formula (I) in which $R_1$, $R_2$, $R_3$, and $R_4$ are defined as in the compound represented by general formula (I) shown above can be produced by the method described below.

Scheme A

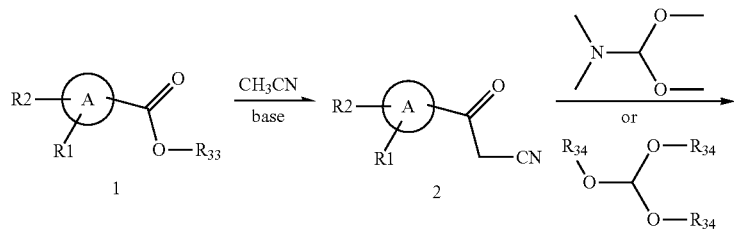

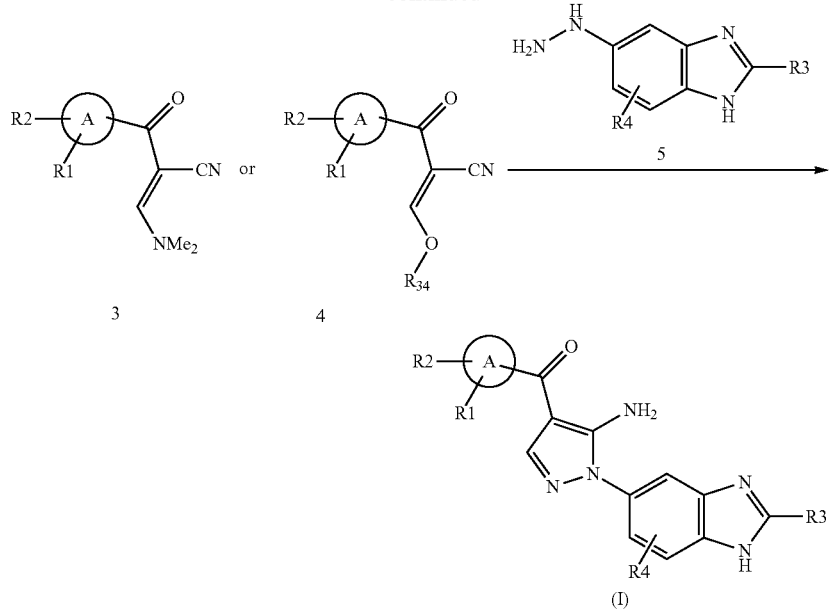

2-Ketoacetonitrile of formula (2) is obtained through a reaction between the carboxylic acid ester represented by formula (1) and acetonitrile anion which is generated by allowing a base to act on acetonitrile.

The compound represented by formula (1) is commercially available or can be prepared by methods known in the art. For example, aryl/heteroaryl carboxylic acid esters of formula (1) such as indole-2-carboxylic acid ethyl ester, benzofuran-2-carboxylic acid ethyl ester, benzothiophene-2-carboxylic acid methyl ester, pyrrole-2-carboxylic acid methyl ester, and quinoline-6-carboxylic acid methyl ester, are commercially available. Other compounds can be prepared by heating corresponding carboxylic acids in alcohol ($R_{33}OH$) in the presence of an acid (for example, sulfuric acid). Alternatively, the methyl ester of formula (1), in which $R_{33}$ is a methyl group, can be prepared through a reaction with trimethylsilyldiazomethane or diazomethane in a solvent (for example, dichloromethane or methanol).

The compound of formula (2) can be prepared by methods known in the art. It can be prepared by treating acetonitrile with a base (for example, lithium diisopropylamide or n-butyl lithium) and then reacting the resultant acetonitrile anion with aryl/heteroaryl carboxylic acid ester.

The compound of formula (3) can be prepared by methods known in the art. 2-Keto-3-dimethylamino-acrylonitrile of formula (3) can be prepared by reacting 2-ketoacetonitrile of formula (2) with N,N-dimethylformamide dimethyl acetal in a solvent (for example, toluene or tetrahydrofuran).

The compound of formula (4) can be prepared by methods known in the art. 2-Keto-3-alkoxy-acrylonitrile of formula (4) can be prepared by reacting 2-ketoacetonitrile of formula (2) and trialkyl orthoformate in a solvent (for example, acetonitrile, chloroform, or acetic anhydride) under heat.

The compound of formula (I) can be prepared by methods known in the art. 5-Amino-ketopyrazole of formula (I) can be prepared by reacting 2-keto-3-dimethylamino-acrylonitrile of formula (3) with benzimidazol-5-yl hydrazine of formula (5) in the presence or absence of a base (for example, triethylamine or pyridine) in a solvent (for example, ethanol or N,N-dimethylacetamide); or reacting 2-keto-3-alkoxy-acrylonitrile of formula (4) with benzimidazol-5-yl hydrazine of formula (5) or a compound in which the hydrazine in formula (5) has been protected (for example, N-benzhydrylidene-N'-(2-methyl-1H-benzimidazol-5-yl)-hydrazine, N'-(2-methyl-1H-benzimidazol-5-yl)-hydrazine carboxylic acid tert-butyl ester, or N-tert-butoxycarbonyl-N'-(2-methyl-1H-benzimidazol-5-yl)-hydrazine carboxylic acid tert-butyl ester), in the presence or absence of a base (for example, triethylamine or pyridine) in a solvent (for example, ethanol or N,N-dimethylacetamide).

When compounds with ring A having an NH group such as indole or pyrrole are synthesized, in some cases, an ester of formula (1) is used to form an aminopyrazole ring through the reactions of formula (3) or (4) and formula (5), and then deprotection is carried out to give formula (I) with ring A having an NH group.

Protecting groups for indole include arylsulfonyl groups (for example, benzenesulfonyl group and toluenesulfonyl group).

Formula (1) in which ring A is an indole ring protected by an arylsulfonyl group can be obtained by reacting formula (I) in which ring A is an unprotected indol with arylsulfonyl chloride (for example, benzyl halide or p-methoxybenzyl halide) in a solvent (for example, tetrahydrofuran or dimethylformamide) in the presence of a base (for example, sodium hydride or diisopropylethylamine).

Protecting groups for pyrrole include benzyl groups (for example, benzyl group and p-methoxybenzyl group). Formula (1) in which A is a pyrrole ring protected by a benzyl group can be obtained by reacting formula (I) in which A is an unprotected pyrrole with benzyl halide (for example, benzyl chloride, benzyl bromide, or 4-methoxybenzyl bromide) in a solvent (for example, tetrahydrofuran or dimethylformamide).

If the compound of formula (1) with desired $R_1$ or $R_2$ is not commercially available, it is possible to synthesize an ester of formula (1) having desired $R_1$ or $R_2$ by any one of methods (a) to (y) described below, and then synthesize formula (I) by the same method as in scheme A. Alternatively, the compound of formula (I) with a convertible substituent at $R_1$ or $R_2$ can be synthesized and then converted into the compound with desired substitutent $R_1$ or $R_2$.

The conversion of substituent $R_1$ or $R_2$ can be achieved by any one of methods (a) to (y) described below.

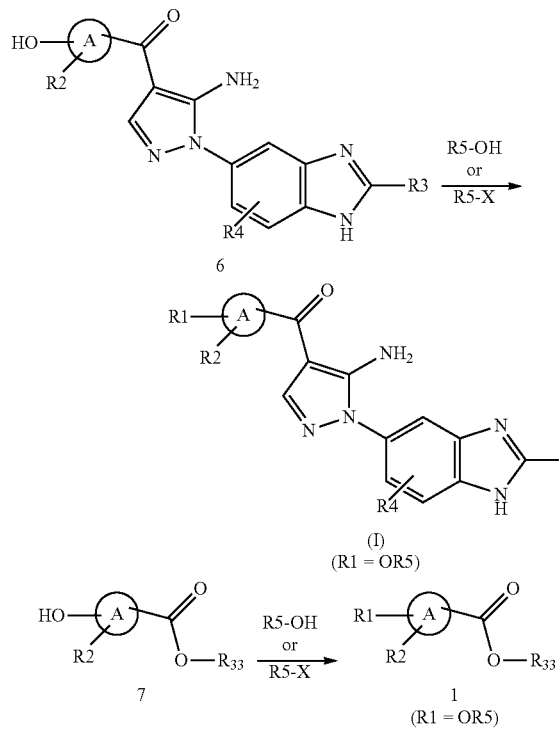

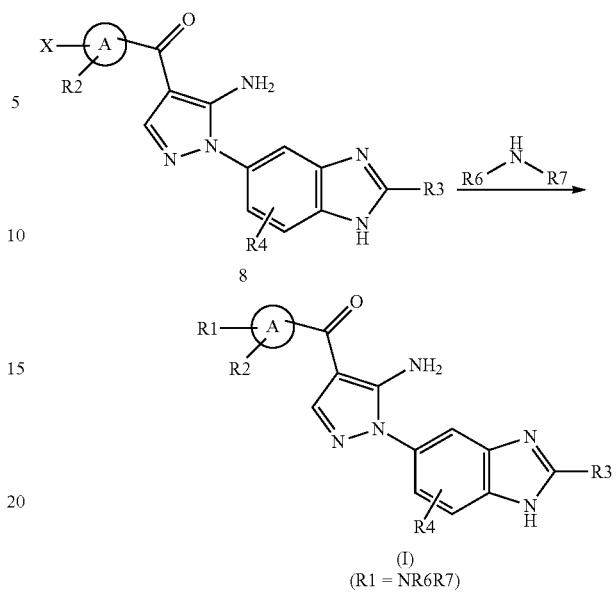

Method (a)

When $R_1$ is an ether (—$OR_5$), the compound of formula (I) can be prepared through Mitsunobu reaction between alcohol ($R_5$OH) and the compound of formula (6) in which $R_1$ is a hydroxyl group, or through etherification in the presence of a base between the compound of formula (6) in which $R_1$ is a hydroxyl group and $R_5$X having leaving group X, such as halogen or alkylsulfonyloxy group.

Alternatively, an ester of formula (1) in which $R_1$ is ether (—$OR_5$) can be prepared through Mitsunobu reaction between alcohol ($R_5$OH) and an ester of formula (7) in which $R_1$ has a hydroxyl group, or through etherification in the presence of a base between the ester of formula (7) and $R_5$X having leaving group X, such as halogen or alkylsulfonyloxy group.

The ester of formula (1) in which $R_1$ is ether (—$OR_5$) can be used to prepare the compound of formula (I) in which $R_1$ is ether (—$OR_5$) by the same method as in scheme A.

In general, Mitsunobu reaction can be carried out using alcohol ($R_5$OH) and a compound having a hydroxyl group, in a solvent (for example, tetrahydrofuran or dioxane) in the presence of an azo compound (for example, diethyl azodicarboxylate or diisopropyl azodicarboxylate), phosphine (for example, triphenylphosphine or tri-n-butylphosphine).

In general, etherification can be carried out by heating a compound having a hydroxyl group and $R_5$X having leaving group X such as halogen or alkylsulfonyloxy group, in a solvent (for example, dimethylformamide or tetrahydrofuran) in the presence of a base (for example, sodium hydride or potassium carbonate).

Method (b)

The compound of formula (I) in which $R_1$ is an amino group ($NR_6R_7$) can be prepared by reacting the compound of formula (8) having halogen with an amine ($NR_6R_7$) at room temperature or under heat in the presence of a base (for example, cesium carbonate, sodium tert-butoxide, or potassium phosphate) and a ligand (for example, N,N-dimethylglycine, 1,10-phenanthroline, or tri-tert-butylphosphine) in a solvent (for example, dimethylsulfoxide, dimethylformamide, toluene, or dioxane) using a copper catalyst (for example, copper iodide) or palladium catalyst (for example, palladium acetate).

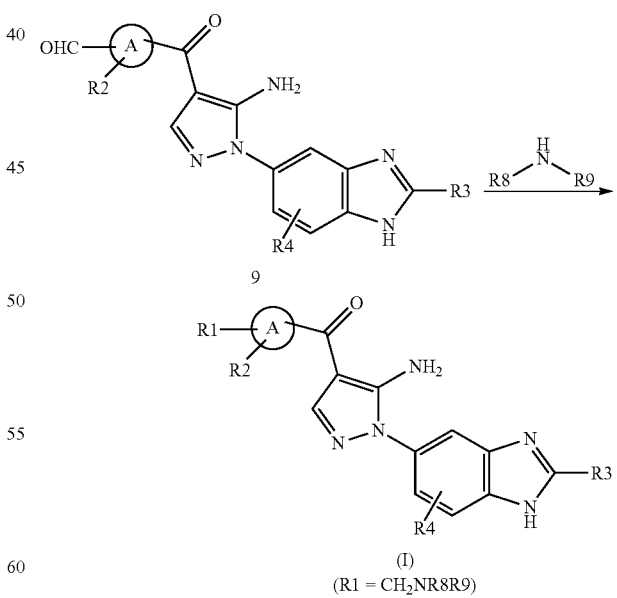

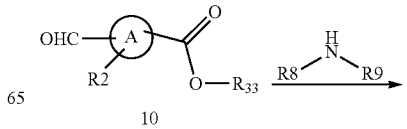

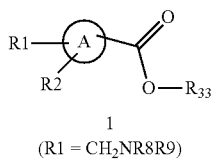

(R1 = CH$_2$NR8R9)

Method (c)

The compound of formula (I) in which R$_1$ is an aminomethyl group (—(CR$_8$R$_9$)$_n$Z$_1$, R$_8$=R$_9$=H) can be prepared through reductive amination between amine (NHR$_8$R$_9$) and the compound of formula (9) having an aldehyde group. Alternatively, an ester of formula (1) in which R$_1$ is an aminomethyl group (—(CR$_8$R$_9$)$_n$Z$_1$, R$_8$=R$_9$=H) can be prepared through reductive amination between amine (NHR$_8$R$_9$) and an ester of formula (10) having an aldehyde group. The compound of formula (I) in which R$_1$ is an aminomethyl group (—(CR$_8$R$_9$)$_n$Z$_1$, R$_8$=R$_9$=H) can be obtained by the same method as in scheme A using the ester of formula (1) in which R$_1$ is an aminomethyl group (—(CR$_8$R$_9$)$_n$Z$_1$, R$_8$=R$_9$=H).

In general, reductive amination can be carried out with aldehyde and amine (NHR$_8$R$_9$) using a reducing agent (for example, sodium triacetoxyborohydride, sodium cyanoborohydride, or sodium borohydride) in a solvent (for example, dichloromethane, 1,2-dichloroethane, or methanol), in the presence of an acid (for example, acetic acid) in some cases, at from 0° C. to room temperature.

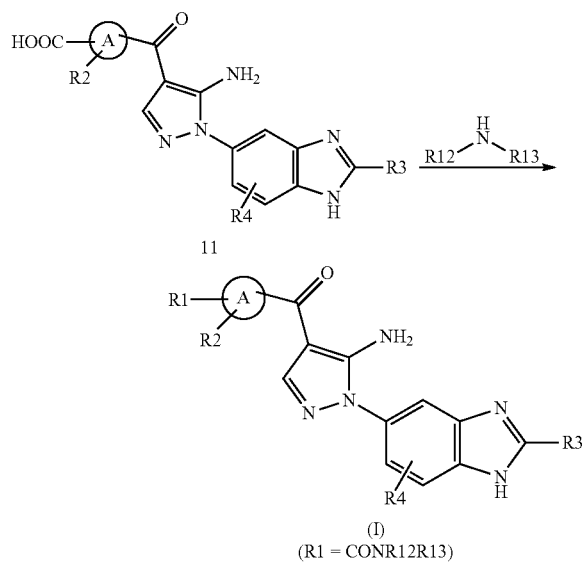

Method (d)

The compound of formula (I) in which R$_1$ is an amide (CONR$_{12}$R$_{13}$) can be prepared by reacting the carboxylic acid of formula (11) with an amine (NHR$_{12}$R$_{13}$) in the presence of a condensation agent.

In general, amide synthesis is be achieved by converting carboxylic acid into acyl halide or activated ester using a halogenating agent (for example, thionyl chloride or oxalyl chloride) or an activator (for example, ethyl chloroformate), respectively, and then reacting it with an amine (NHR$_{12}$R$_{13}$) in a solvent (for example, tetrahydrofuran, dimethylformamide, or dichloromethane).

Alternatively, amide synthesis is achieved by synthesizing an active ester from carboxylic acid using a condensation agent (for example, dicyclohexylcarbodiimide) in the presence of a base (for example, triethylamine) in a solvent (for example, tetrahydrofuran, dimethylformamide, or dichloromethane), and then treating the resulting active ester with an amine (NHR$_{12}$R$_{13}$).

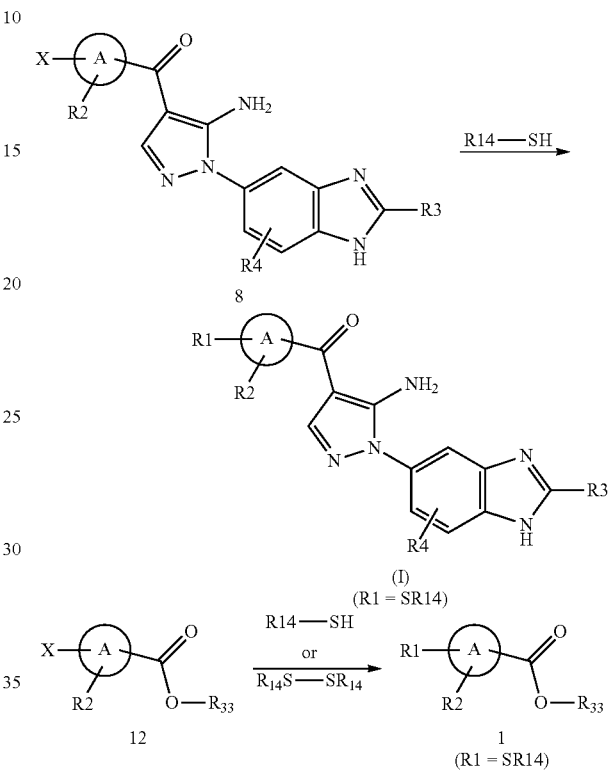

Method (e)

The compound of formula (I) in which R$_1$ is sulfide (—SR$_{14}$) can be prepared by reacting thiol with the compound of formula (8) having halogen in the presence of a base (for example, cesium carbonate, lithium hexamethyldisilazide or potassium phosphate) and a catalyst (for example, copper iodide, or palladium acetate) in a solvent (for example, dimethylsulfoxide or 1,2-dimethoxyethane) under heat.

The ester of formula (1) in which R$_1$ is sulfide (—SR$_{14}$) can be prepared by reacting thiol with the ester of formula (12) having halogen in the presence of a base (for example, cesium carbonate, lithium hexamethyldisilazide or potassium phosphate) and a catalyst (for example, copper iodide, or palladium acetate) in a solvent (for example, dimethylsulfoxide or 1,2-dimethoxyethane) with heating.

Alternatively, the ester of formula (1) can be prepared by reacting the ester of formula (12) with a base (for example, n-butyl lithium) at a low temperature (−80 to 0° C.) in a solvent (for example, diethyl ether or tetrahydrofuran), and then reacting it with alkylsulfide or dialkyldisulfide. The ester of formula (1) in which R$_1$ is sulfide (—SR$_{14}$) can be used to prepare the compound of formula (I) in which R$_1$ is sulfide (—SR$_{14}$) by the same method as in scheme A.

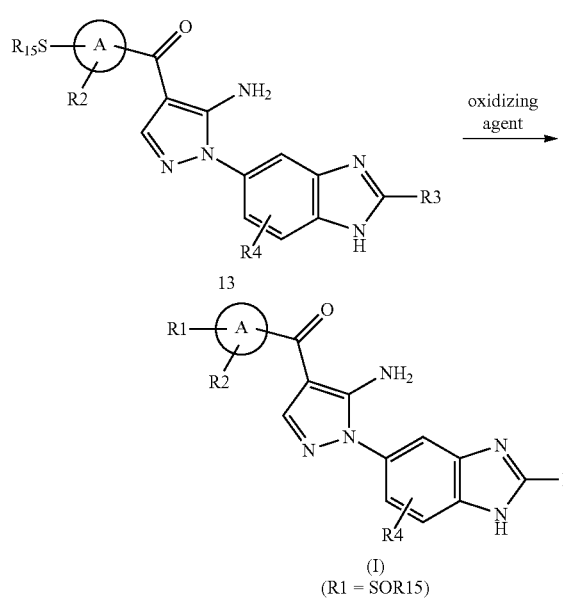

Method (f)

The compound of formula (I) in which $R_1$ is sulfoxide (—$SO_2R_{15}$) can be prepared by treating the compound of formula (13) having a sulfide group (—$SR_{15}$) with an oxidizing agent (for example, m-chloroperbenzoic acid, oxon, or hydrogen peroxide) in a solvent (for example, dichloromethane, methanol, or water).

Method (g)

The compound of formula (I) in which $R_1$ is sulfone (—$SO_2R_{16}$) can be prepared by treating the compound of formula (14) having sulfide (—$SR_{16}$) with an oxidizing agent (for example, m-chloroperbenzoic acid, oxon, or hydrogen peroxide) in a solvent (for example, dichloromethane, methanol, or water).

The ester of formula (1) in which $R_1$ is sulfone (—$SO_2R_{16}$) can be prepared by treating the sulfide of formula (15) with an oxidizing agent (for example, m-chloroperbenzoic acid, oxon, or hydrogen peroxide) in a solvent (for example, dichloromethane, methanol, or water). The ester of formula (1) in which as $R_1$ is sulfone (—$SO_2R_{16}$) can be used to prepare the compound of formula (I) in which $R_1$ is sulfone (—$SO_2R_{16}$) by the same method as in scheme A.

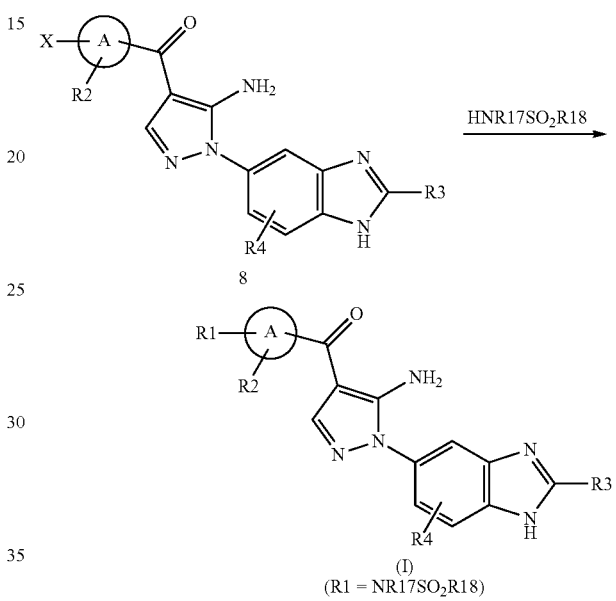

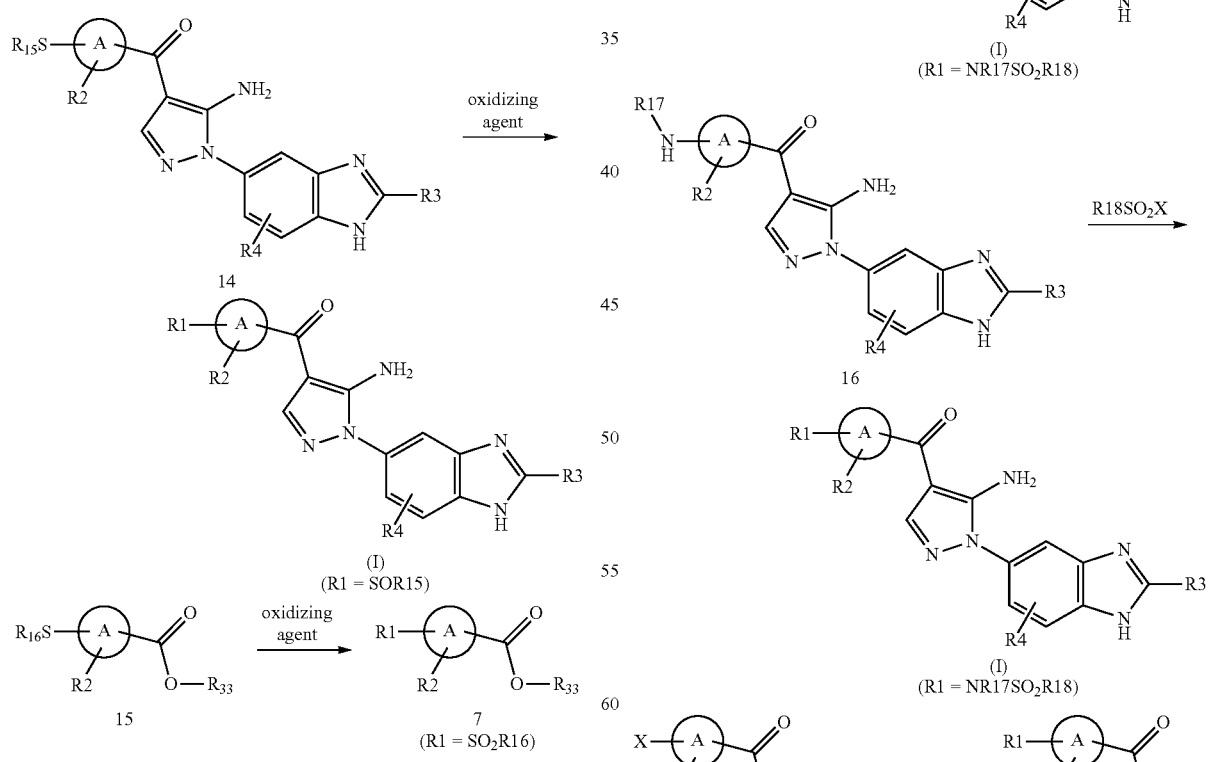

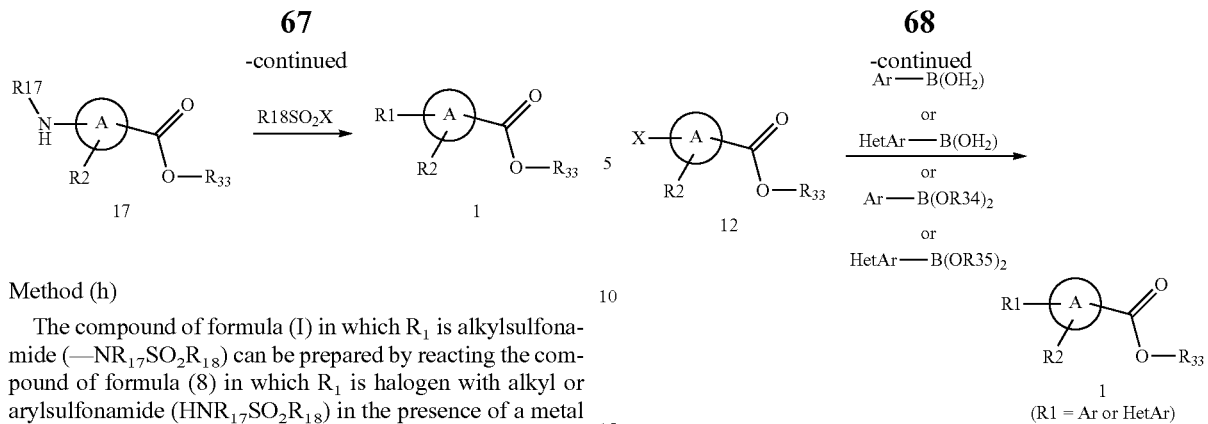

Method (h)

The compound of formula (I) in which $R_1$ is alkylsulfonamide (—$NR_{17}SO_2R_{18}$) can be prepared by reacting the compound of formula (8) in which $R_1$ is halogen with alkyl or arylsulfonamide ($HNR_{17}SO_2R_{18}$) in the presence of a metal such as copper. Alternatively, it can be prepared by reacting the compound of formula (16) having an amino group (—$NHR_{17}$) with an alkyl or arylsulfonyl halide.

Alternatively, the ester of formula (1) in which $R_1$ is alkylsulfonamide (—$NR_{17}SO_2R_{18}$) can be prepared by reacting the ester of formula (12) having halogen with alkyl or arylsulfonamide ($HNR_{17}SO_2R_{18}$) in the presence of a metal such as copper. Alternatively, it can be prepared by reacting the ester of formula (17) having an amino group (—$NHR_{17}$) with alkyl, arylsulfonyl halide, or such. The ester of formula (1) in which $R_1$ is alkylsulfonamide (—$NR_{17}SO_2R_{18}$) can be used to prepare the compound of formula (I) in which $R_1$ is alkylsulfonamide (—$NR_{17}SO_2R_{18}$) by the same method as in scheme A.

In general, the synthesis from a halogen compound is achieved by reacting a halogen compound with alkyl or arylsulfonamide in the presence of a base (for example, cesium carbonate or potassium phosphate), a catalyst (for example, palladium acetate or copper iodide), and, in some cases, a ligand (for example, tri-t-butylphosphine or N,N-dimethylglycine) in a solvent (for example, dioxane, toluene, or dimethylformamide) with heating.

In general, the synthesis from an amine compound is achieved by reacting an amine compound with alkyl or arylsulfonyl halide in the presence of a base (for example, triethylamine) in a solvent (for example, dichloromethane).

Method (i)

The compound of formula (I) in which $R_1$ is aryl or heteroaryl can be prepared through Suzuki coupling reaction between the compound of formula (8) having halogen and aryl boronic acid, heteroaryl boronic acid, aryl boronic acid ester, or heteroaryl boronic acid ester.

Alternatively, the ester of formula (1) in which $R_1$ is aryl or heteroaryl can be prepared through Suzuki coupling reaction between the ester of formula (12) having halogen and aryl boronic acid, heteroaryl boronic acid, aryl boronic acid ester, or heteroaryl boronic acid ester. The ester of formula (1) in which $R_1$ is aryl or heteroaryl can be used to prepare the compound of formula (I) in which $R_1$ is aryl or heteroaryl by the same method as in scheme A.

In general, Suzuki coupling reaction is conducted by heating aryl halide or heteroaryl halide together with aryl boronic acid, heteroaryl boronic acid, aryl boronic acid ester, or heteroaryl boronic acid ester in the presence of a base (for example, potassium phosphate or cesium carbonate) and a catalyst (for example, palladium acetate or tetrakistriphenylphosphine) in a solvent (for example, dioxane or toluene).

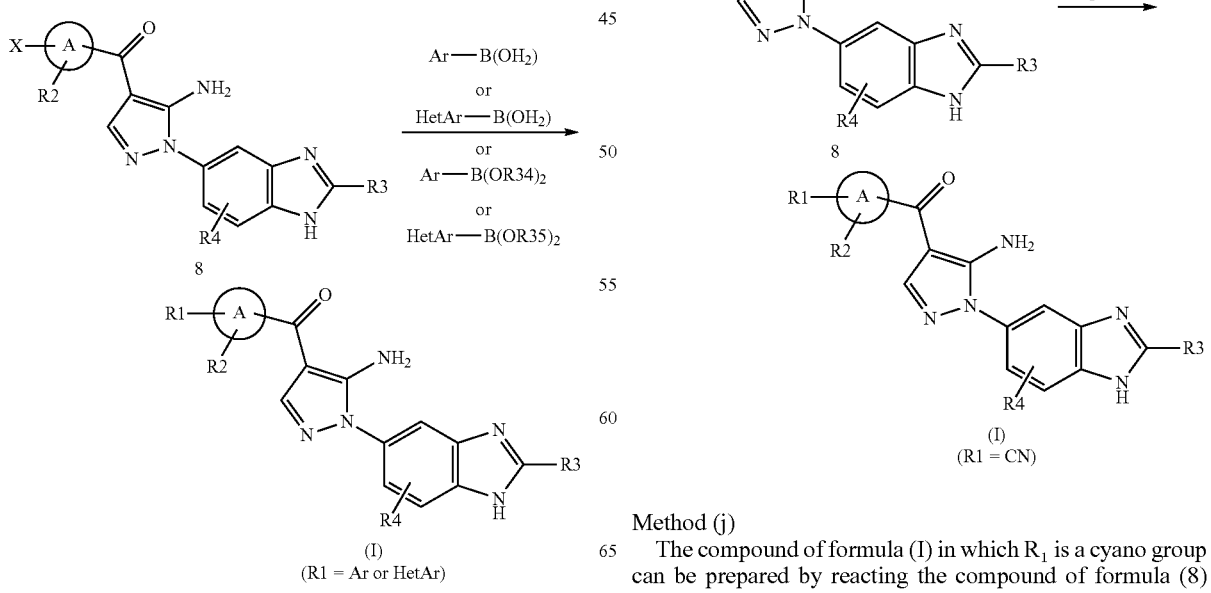

Method (j)

The compound of formula (I) in which $R_1$ is a cyano group can be prepared by reacting the compound of formula (8) having halogen (X) with a cyanide such as copper cyanide.

In general, cyanidation is carried out by heating a halogen compound, alkylsulfonyloxy compound, or arylsulfonyloxy compound together with a cyanidating agent (for example, copper (I) cyanide or potassium cyanide) in a solvent (for example, dimethylformamide or N-methylpyrrolidone).

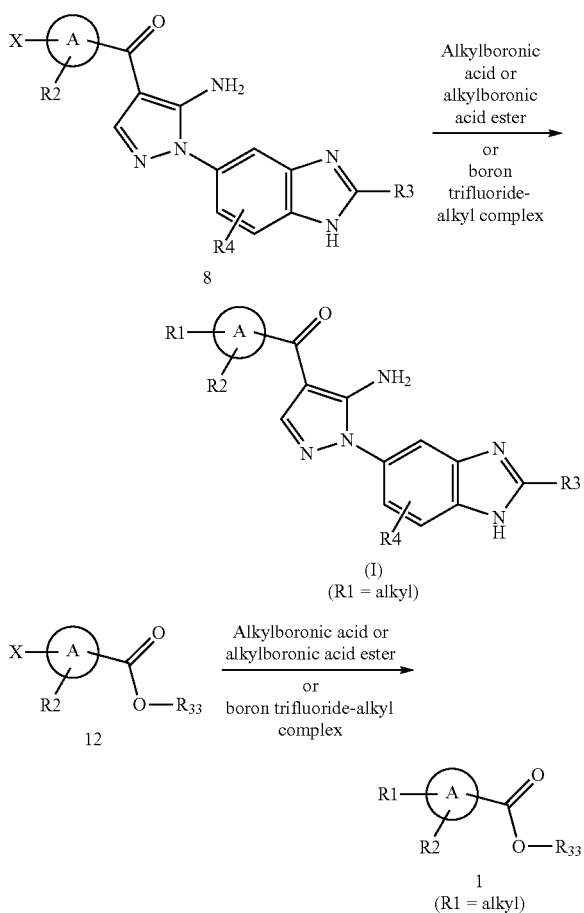

Method (k)

The compound of formula (I) in which $R_1$ is an alkyl group can be prepared through Suzuki reaction between the compound of formula (8) having halogen and alkylboronic acid, alkylboronic acid ester, or a boron trifluoride-alkyl complex.

The ester of formula (1) in which $R_1$ is an alkyl group can be prepared through Suzuki reaction between the ester of formula (12) having halogen and alkylboronic acid, alkylboronic acid ester, or a boron trifluoride-alkyl complex. The ester of formula (1) in which $R_1$ is an alkyl group can be used to prepare the compound of formula (I) in which $R_1$ is an alkyl group by the same method as in scheme A.

In general, Suzuki reaction is conducted by heating a mixture of a halogen compound, a boron derivative (for example, alkylboronic acid, alkyl boronic acid ester, or boron trifluoride-alkyl complex), and a base (for example, potassium carbonate or potassium phosphate) in a solvent (for example, xylene, toluene, dimethylformamide, dioxane, or tetrahydrofuran) in the presence of a palladium catalyst (for example, palladium acetate) and, in some cases, a ligand (for example, triphenylphosphine).

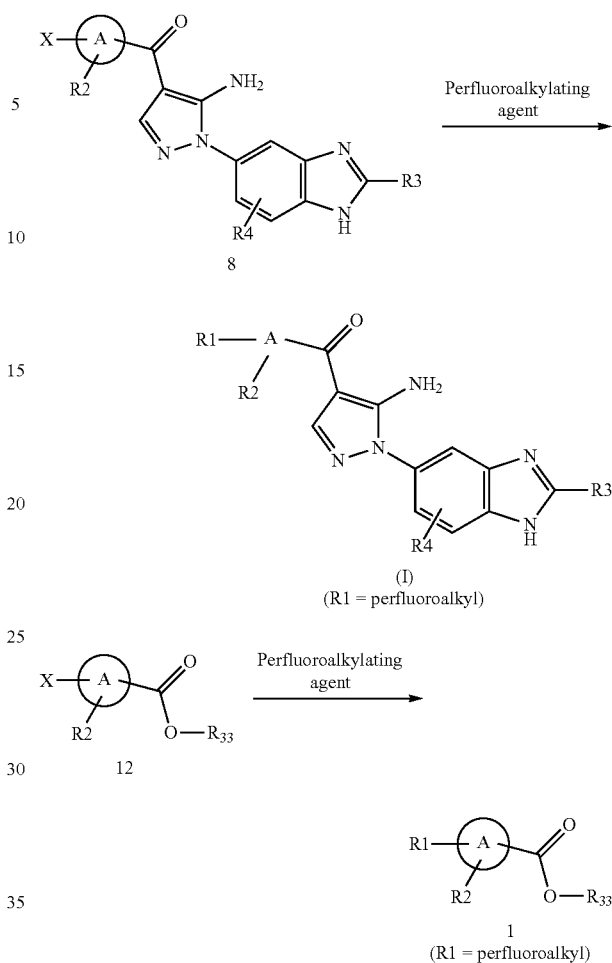

Method (l)

The compound of formula (I) in which $R_1$ is a perfluoroalkyl group can be prepared by reacting the compound of formula (8) having halogen with a perfluoroalkylating agent.

The ester of formula (12) in which $R_1$ is a perfluoroalkyl group can be prepared by reacting the ester of formula (11) having halogen with a perfluoroalkylating agent. The ester of formula (1) in which $R_1$ is a perfluoroalkyl group can be used to prepare the compound of formula (I) in which $R_1$ is a perfluoroalkyl group by the same method as in scheme A.

In general, perfluoroalkylation is achieved by reacting a halogen compound, copper (for example, copper or copper (I) iodide), a perfluoroalkylating agent (such as potassium perfluoroalkyl carboxylate, triethylsilyl perfluoroalkyl, or perfluoroalkyl iodide) in a solvent (for example, dimethylsulfoxide or dimethylformamide) under heat.

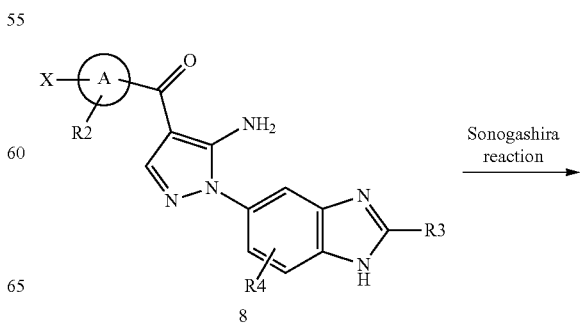

-continued

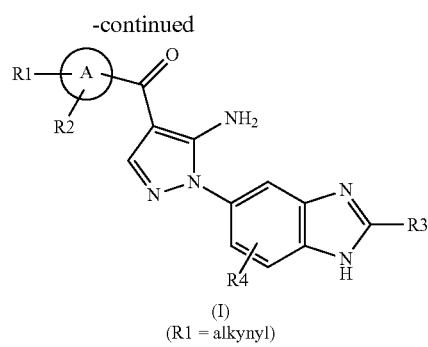

(I)
(R1 = alkynyl)

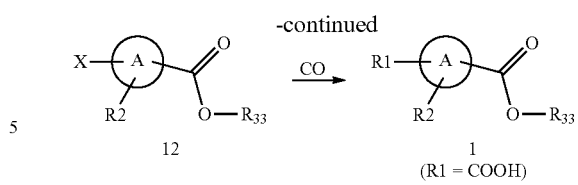

Method (m)

The compound of formula (I) in which $R_1$ is an alkynyl group can be prepared through Sonogashira reaction of the compound of formula (8) having halogen.

The ester of formula (1) in which $R_1$ is an alkynyl group can be prepared through Sonogashira reaction of the ester of formula (12) having halogen. The ester of formula (1) in which $R_1$ is an alkynyl group can be used to prepare the compound of formula (I) in which $R_1$ is an alkynyl group by the same method as in scheme A.

In general, Sonogashira reaction is conducted by reacting aryl halide or heteroaryl halide with an alkynylating agent (for example, trimethylsilylacetylene) in the presence of a base (for example, triethylamine or potassium carbonate), a copper catalyst (for example, copper (I) iodide), and a palladium catalyst (for example, bis(triphenylphosphine)palladium dichloride) in a solvent (for example, tetrahydrofuran or toluene) under heat.

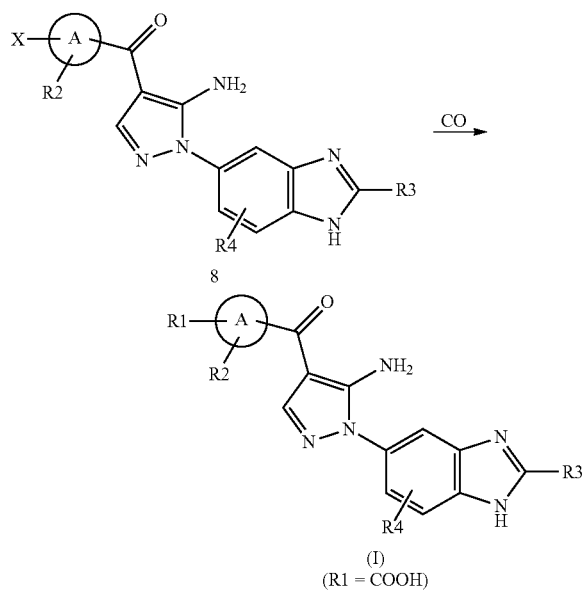

Method (n)

The compound of formula (I) in which $R_1$ is a carboxyl group can be prepared through a reaction for introducing carbon monoxide into the compound of formula (8) having halogen.

The ester of formula (1) in which $R_1$ is a carboxyl group can be prepared through a reaction for introducing carbon monoxide into the ester of formula (12) having halogen. The ester of formula (1) in which $R_1$ is a carboxyl group can be protected at the carboxyl group (for example, tert-butyl ester) and then used to prepare the compound of formula (I) in which $R_1$ is a carboxyl group by the same method as in scheme A.

In general, the introduction of carbon monoxide is achieved by reacting aryl halide or heteroaryl halide in the presence of a base (for example, triethylamine or sodium carbonate), a palladium catalyst (for example, palladium acetate), and a ligand (for example, triphenylphosphine) in a solvent (for example, dimethylsulfoxide or water) under a carbon monoxide atmosphere. Alternatively, the introduction is achieved by reacting aryl halide or heteroaryl halide with a base (for example, n-butyl lithium) in a solvent (for example, diethyl ether or tetrahydrofuran) at a low temperature (−80 to 0° C.), and then reacting carbon monoxide therewith.

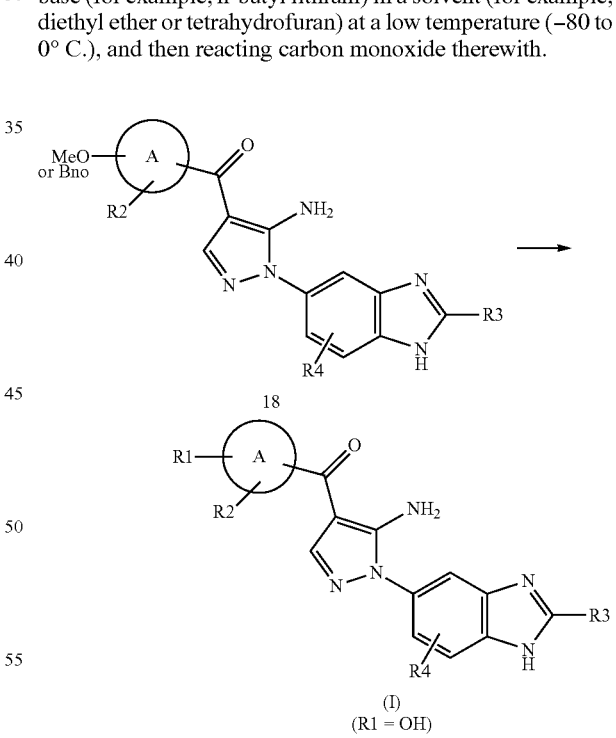

Method (o)

The compound of formula (I) in which $R_1$ is a hydroxyl group can be prepared through dealkylation of the compound of formula (18) having a methoxy group or benzyloxy group.

In general, demethylation of methoxy group is achieved by reacting a mixture of a methoxy compound and a solvent (for example, dichloromethane) with a Lewis acid (for example, boron trifluoride or aluminum chloride). Alternatively, the demethylation is achieved by reacting the methoxy compound in the presence of pyridine hydrochloride with heating.

In general, debenzylation of benzyloxy group is achieved through a reaction in the presence of a catalyst (for example, palladium carbon or palladium hydroxide) in a solvent (for example, methanol) under a hydrogen atmosphere.

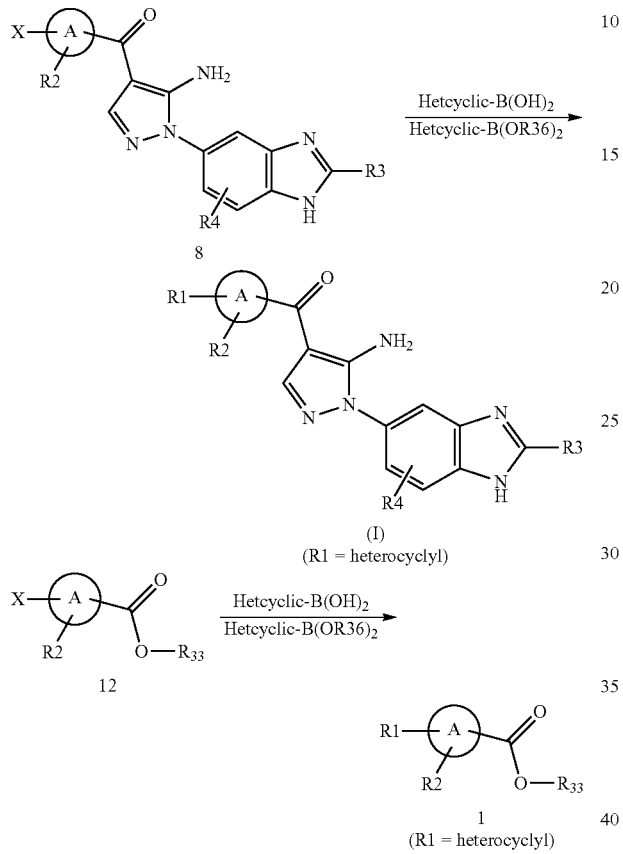

Method (p)

The compound of formula (I) in which $R_1$ is an aliphatic heterocyclyl can be prepared through Suzuki coupling reaction of the compound of formula (8) having halogen with aliphatic heterocyclyl boronic acid or aliphatic heterocyclyl boronic acid ester.

The ester of formula (1) in which $R_1$ is an aliphatic heterocyclyl can be prepared through Suzuki coupling reaction of the ester of formula (12) having halogen with aliphatic heterocyclyl boronic acid or aliphatic heterocyclyl boronic acid ester. The resulting ester of formula (1) in which $R_1$ is an aliphatic heterocyclyl can be used to prepare the compound of formula (I) in which $R_1$ is an aliphatic heterocyclyl by the same method as in scheme A.

In general, Suzuki coupling reaction of aliphatic heterocyclyl is achieved by reacting aryl halide or heteroaryl halide with aliphatic heterocyclyl boronic acid or aliphatic heterocyclyl boronic acid ester in the presence of a base (for example, potassium phosphate) and a palladium catalyst (for example, tetrakistriphenylphosphine) in a solvent (for example, dioxane or water) under heat.

Method (q)

The compound of formula (I) in which $R_1$ is acyloxy (—OC(O)$R_{21}$) can be prepared through acylation between the compound of formula (6) in which $R_1$ is a hydroxy group and acyl halide or carboxylic anhydride.

In general, acylation of hydroxyl group is achieved by reacting a hydroxy compound and acyl halide or anhydrous carboxylic acid in the presence of a base (for example, triethylamine) in a solvent (for example, dichloromethane or pyridine).

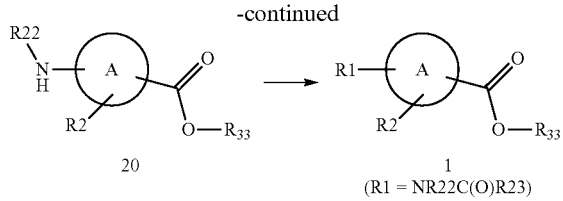

Method (r)

The compound of formula (I) having carbamide (—NR$_{22}$C(O)R$_{23}$) as R$_1$ can be prepared by acylation of the compound of formula (19) having an amino group (—NHR$_{22}$).

The ester of formula (1) having carbamide (—NR$_{22}$C(O)R$_{23}$) as R$_1$ can be prepared by acylation of the ester of formula (20) having an amino group (—NHR$_{22}$).

In general, acylation of an amino group is achieved by reacting an amine compound with acyl halide or carboxylic anhydride in the presence of a base (for example, triethylamine) in a solvent (for example, dichloromethane or pyridine). Alternatively, acylation is achieved by reacting an amine compound with carboxylic acid in the presence of a base (for example, triethylamine) and a condensation agent (for example, dicyclohexylcarbodiimide) in a solvent (for example, tetrahydrofuran or dichloromethane).

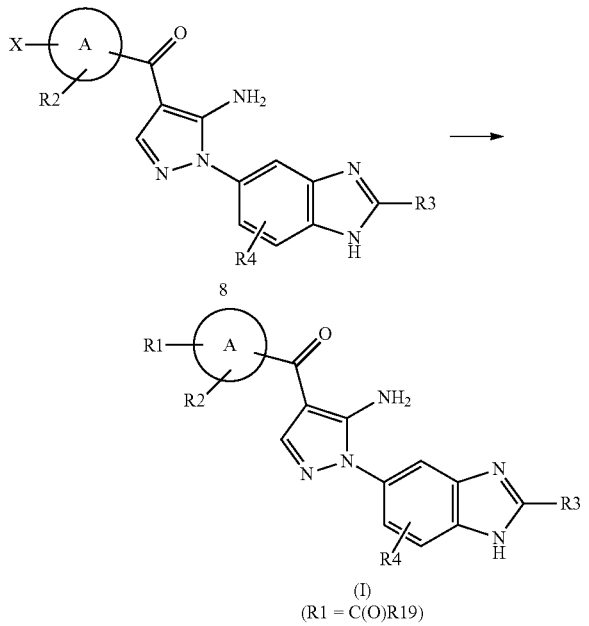

Method (s)

The compound of formula (I) having aldehyde (C(O)R$_{19}$; R$_{19}$=H) or ketone (C(O)R$_{19}$; R$_{19}$ is other than H) as R$_1$ can be prepared by a reaction for introducing a carbonyl source into the compound of formula (8) having halogen.

In general, in aldehyde synthesis, the reaction for introducing a carbonyl source is achieved by heating a halogen compound in the presence of a catalyst (for example, palladium acetate or tetrakis(triphenylphosphine) palladium), a base (for example, sodium carbonate or triethylamine), and a reducing agent (for example, triethylsilane) in a solvent (for example, tetrahydrofuran or N,N-dimethylformamide), in a carbon monoxide atmosphere under ambient or elevated pressure. Meanwhile, in ketone synthesis, the reaction for introducing a carbonyl source is achieved using aldehyde, enol ether derivative, hydrazone derivative, or the like, instead of carbon monoxide, as a carbonyl source.

Alternatively, the reaction is achieved by halogen/metal exchange of a halogen compound using a base (for example, tert-butyl lithium), followed by reaction with a carbonyl source (for example, N,N-dimethylformamide, N,N-dimethylalkylamide, or carboxylic acid ester).

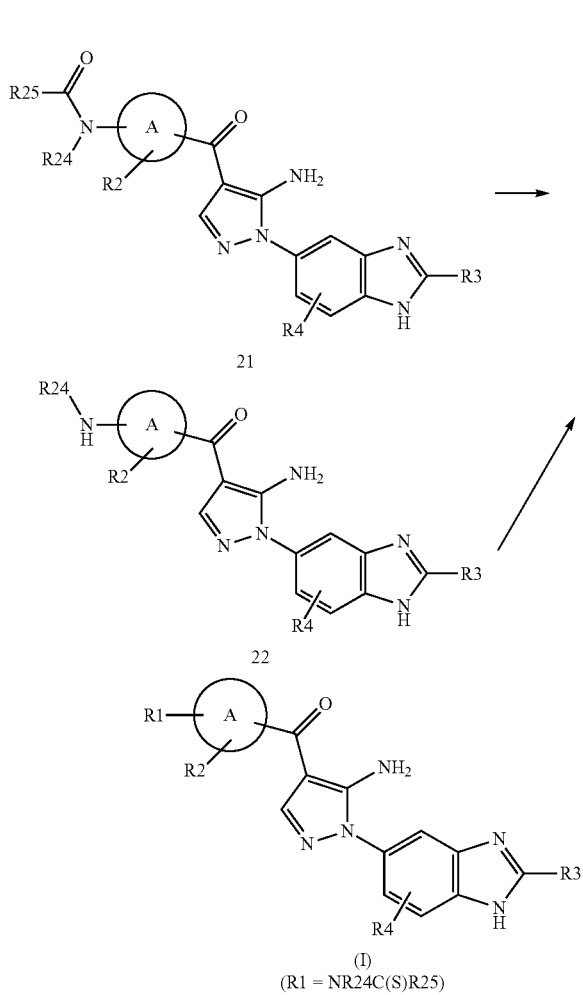

Method (t)

The compound of formula (I) having thioamide (—NR$_{24}$C(S)R$_{25}$) as R$_1$ can be prepared by treating the compound of formula (21) having amide (—NR$_{24}$C(O)R$_{25}$) with a sulfurizing agent (for example, Lawesson's reagent). Alternatively, the compound of formula (I) can be prepared by a reaction between the compound of formula (22) having an amino group (NHR$_{24}$) and thiocarboxylic acid ester.

In general, thiocarbonylation is achieved by reacting, with heating, a carbamide compound with a sulfurizing agent (for example, Lawesson's reagent) in a solvent (for example, toluene).

The reaction between the compound of formula (22) having an amino group (NHR$_{24}$) and thiocarboxylic acid ester is achieved by reacting, with heating, an amine compound with thiocarboxylic acid ester in a solvent (for example, methanol).

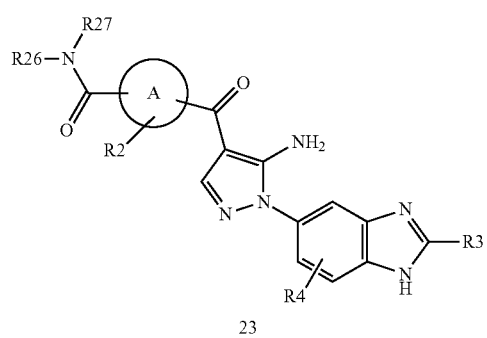

23

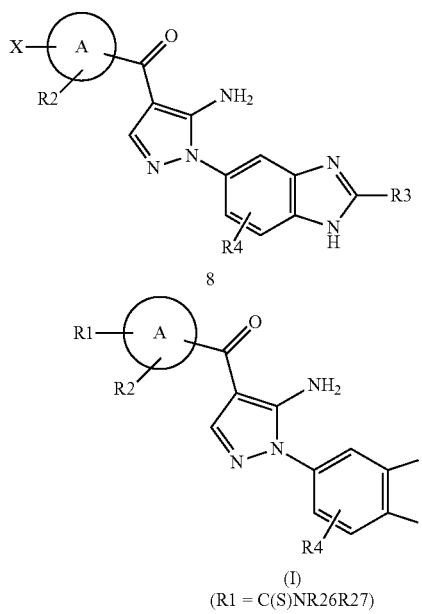

8

(I)
(R1 = C(S)NR26R27)

Method (u)

The compound of formula (I) having thioamide (—C(S)NR$_{26}$R$_{27}$) as R$_1$ can be prepared by treating the compound of formula (23) having amide (—C(O)NR$_{26}$R$_{27}$) with a sulfurizing agent (for example, Lawesson's reagent). Alternatively, the compound of formula (I) can be prepared by a reaction between a thioisocyanate derivative and the compound of formula (8) having halogen.

In general, thiocarbonylation is achieved by reacting, with heating, a carbamide compound with a sulfurizing agent (for example, Lawesson's reagent) in a solvent (for example, toluene).

In general, the reaction with a thioisocyanate derivative is carried out by treatment of a halogen compound with a base (for example, t-butyl lithium) in a solvent (for example, tetrahydrofuran or diethyl ether) at a low temperature (for example, −80 to 0° C.), and then reaction with a thioisocyanate derivative.

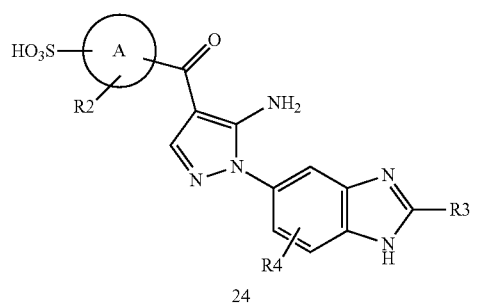

24

-continued

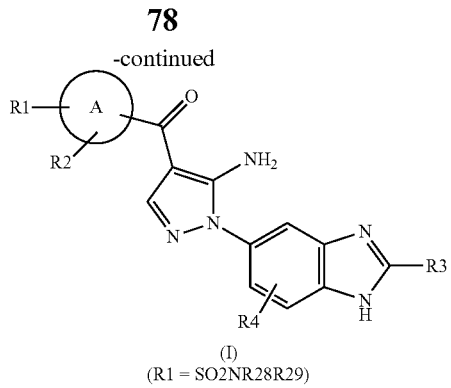

(I)
(R1 = SO2NR28R29)

Method (v)

The compound of formula (I) having sulfonamide (—SO$_2$NR$_{28}$R$_{29}$) as R$_1$ can be prepared by conversion of the compound of formula (24) having sulfonic acid into sulfonyl halide using a halogenating agent (for example, thionyl chloride or phosphorus oxychloride), followed by reaction with amine (NHR$_{28}$R$_{29}$) in the presence of a base (for example, triethylamine) in a solvent (for example, dichloromethane or pyridine).

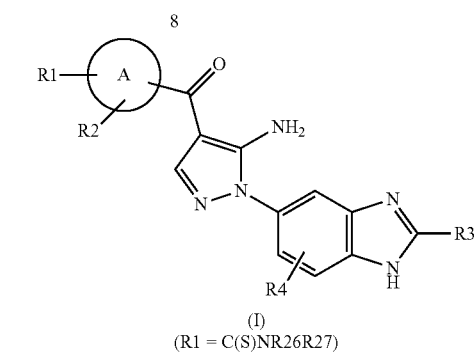

6

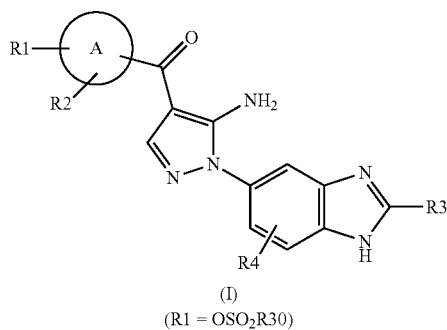

(I)
(R1 = OSO2R30)

Method (w)

The compound of formula (I) having sulfonic acid ester (—OSO$_2$R$_{30}$) as R$_1$ can be prepared by reacting the compound of formula (6) having a hydroxyl group with sulfonyl halide (R$_{30}$SO$_2$X) or sulfonic acid anhydride ((R$_{30}$SO$_2$)O) in the presence of a base (for example, triethylamine, pyridine, or sodium hydride) in a solvent (for example, dichloromethane or dimethylformamide).

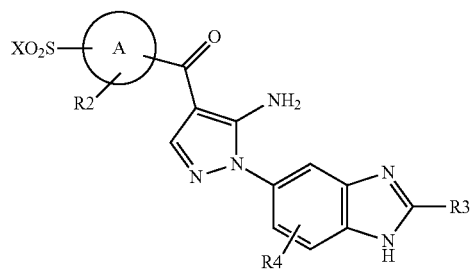

25

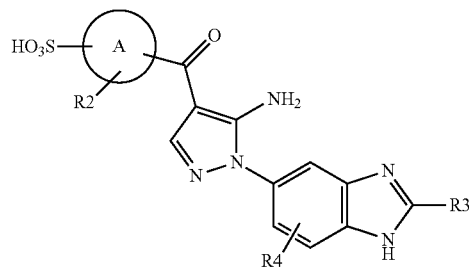

24

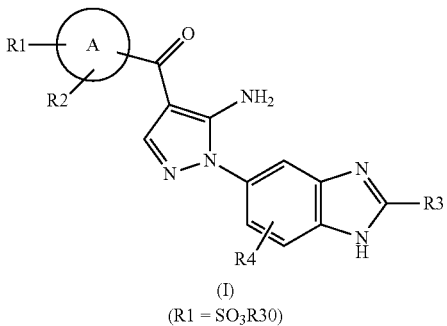

(I)
(R1 = SO₃R30)

Method (x)

The compound of formula (I) having sulfonic acid ester (—SO₃R₃₁) as R₁ can be prepared by reacting the compound of formula (25) having sulfonyl halide as R₁ with alcohol (R₃₁OH) in the presence of a base (for example, triethylamine or 4-dimethylaminopyridine) in a solvent (for example, dichloromethane or diethyl ether).

Alternatively, the compound of formula (I) can be prepared by reacting the compound of formula (24) having sulfonic acid as R₁ with alcohol (R₃₁OH) in the presence of a base (for example, triethylamine, 4-dimethylaminopyridine, or sodium hydride) or a catalyst (for example, cobalt chloride), in a solvent (for example, dichloromethane or diethyl ether). Alternatively, the compound of formula (I) can be prepared by reacting the compound of formula (24) having sulfonic acid as R₁ with a halogen compound (R₃₁X) in a solvent (for example, acetonitrile).

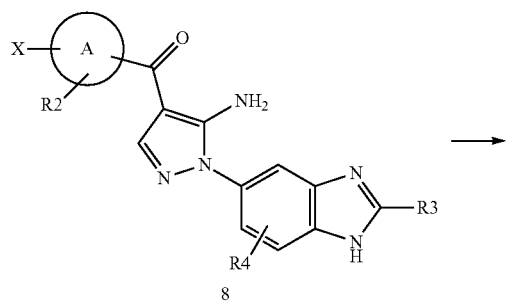

8

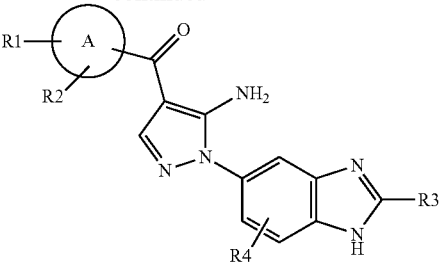

(I)
(R1 = Si(R32)₃)

Method (y)

The compound of formula (I) having a trialkylsilyl group (—Si(R₃₂)₃) as R₁ can be prepared by treatment of the compound of formula (8) having halogen with a base (for example, n-butyl lithium) in a solvent (for example, tetrahydrofuran) at a low temperature (−80 to 0° C.), followed by treatment with trialkyl halide (XSi(R₃₂)₃).

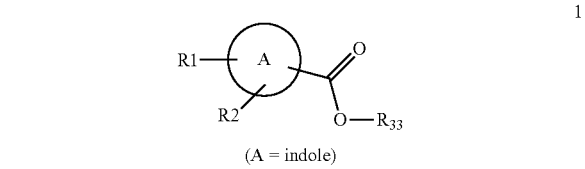

1

(A = indole)

The ester of formula (1) having indole as ring A is commercially available, or can be prepared by methods well-known in the art, for example, methods (1) to (3) described below.

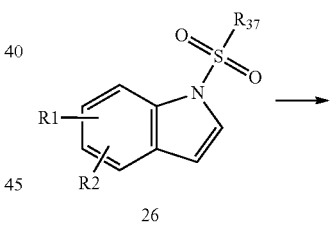

26

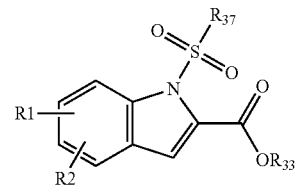

27

Method (1)

The indole of formula (27) having an alkoxycarbonyl group (C(O)OR₃₃) can be prepared by alkoxycarbonylation of the indole compound of formula (26) which is protected by an alkylsulfonyl or aryl sulfonyl group.

In general, alkoxycarbonylation is achieved by reacting a base (for example, lithium diisopropyl amide) with the indole compound of formula (26) which is protected by an alkylsulfonyl or aryl sulfonyl group, in a solvent (for example, tetrahydrofuran), and then reacting this with a carbonyl source (for example, ethyl chloroformate).

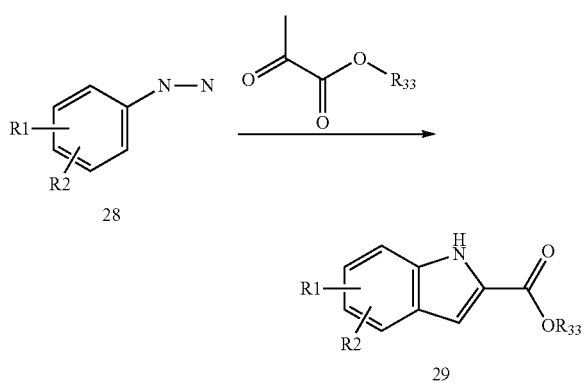

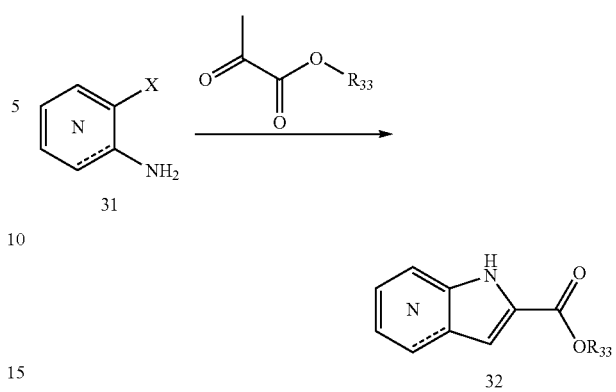

Method (2)

The indole of formula of (29) having an alkoxycarbonyl group ($C(O)OR_{33}$) can be prepared as follows: pyruvate ester is reacted with the hydrazine derivative of formula (28) in a solvent (for example, methanol or ethanol) under an acidic condition (for example, in hydrochloric acid or acetic acid) to produce a hydrazone derivative; and this hydrazone derivative is reacted in a solvent (for example, ethanol, dichloromethane, or toluene) under an acidic condition (for example, in hydrochloric acid or methanesulfonic acid).

Method (4)

The azaindole of formula of (32) having an alkoxycarbonyl group ($C(O)OR_{33}$) can be prepared as follows: pyruvate ester is reacted with the aminohalopyridine of formula (31) in a solvent (for example, pyridine) as described in Lachance, N. et al., Synthesis, 15, 2571, (2005); and the resulting enamine is heated in the presence of a palladium catalyst (for example, tetrakis(triphenylphosphine)palladium) and a base (for example, dicyclohexylmethylamine)

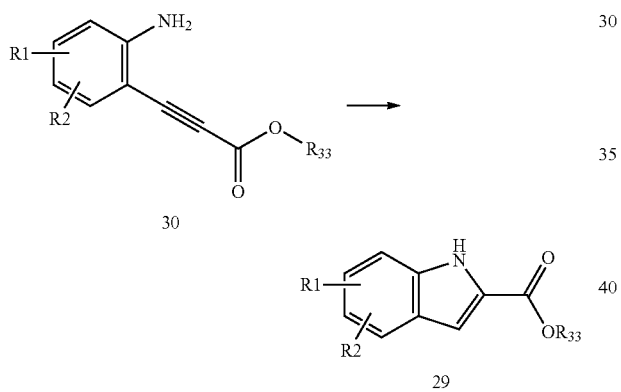

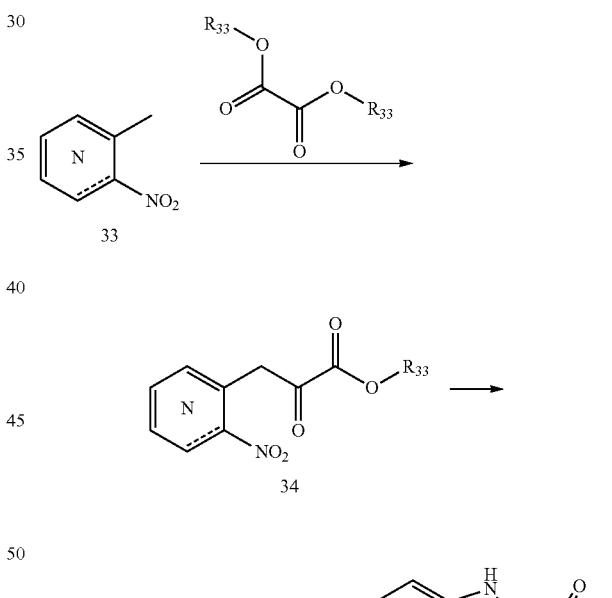

Method (3)

The indole of formula (29) having an alkoxycarbonyl group ($C(O)OR_{33}$) can be prepared by heating the o-ethynyl aniline derivative of formula (30) in the presence of a catalyst (for example, copper acetate) in a solvent (for example, dichloroethane) as described in Hiroya, K. et al. (J. Org. Chem., 69, 1126, (2004)) or Hiroya, K. et al. (Tetrahedron Letters, 43, 1277, (2002)).

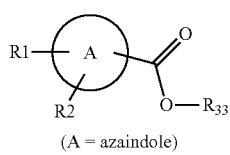

(A = azaindole)

The ester of formula (1) having azaindole as ring A is commercially available, or can be prepared by methods well-known in the art, for example, by methods (4) to (7) described below.

Method (5)

The azaindole of formula (32) having an alkoxycarbonyl group ($C(O)OR_{33}$) can be prepared as described in Romanelli, M. N. et al., Arkivoc, 286, (2004) by synthesis of the intermediate of formula (34) by reacting oxalic acid ester with the methylnitropyridine of formula (33) in the presence of a base (sodium ethoxide or such) in a solvent (for example, ethanol); followed by catalytic reduction under a hydrogen atmosphere.

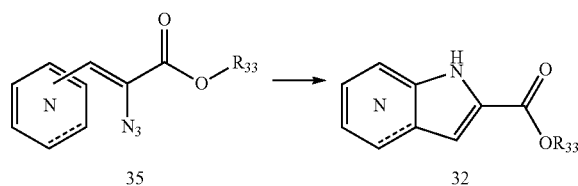

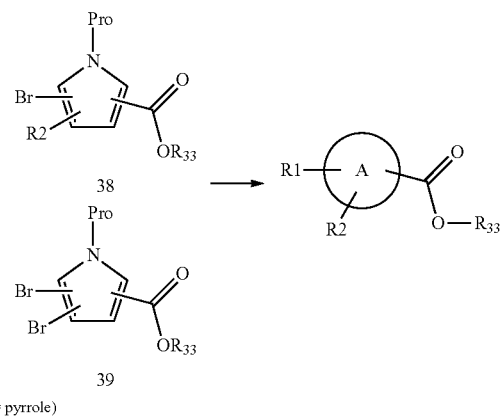

Method (6)

The azaindole of formula (32) having an alkoxycarbonyl group ($C(O)OR_{33}$) can be prepared by thermal decomposition of the 2-azido-3-pyridine acrylic acid ester of formula (35) in a solvent (for example, mesitylene) by heating as described in Roy, P. J. et al., Synthesis, 16, 2751, (2005).

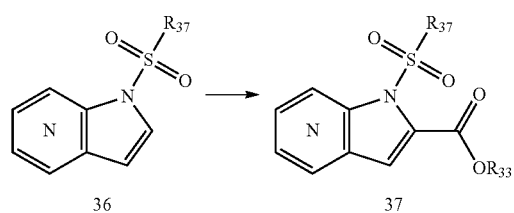

(A = pyrrole)

The ester of formula (1) in which A is a pyrrole ring, and either one or both of $R_1$ and $R_2$ are aryl or heteroaryl group(s) can be prepared by Suzuki coupling reaction between the monobromopyrrole of formula (38) or dibromopyrrole of formula (39), and aryl boronic acid, heteroaryl boronic acid, aryl boronic acid ester, or heteroaryl boronic acid ester.

Method (7)

The azaindole of formula (37) having an alkoxycarbonyl group ($C(O)OR_{33}$) can be prepared by alkoxycarbonylation of the azaindole compound of formula (36) which is protected by an alkylsulfonyl group or aryl sulfonyl group.

In general, alkoxycarbonylation of azaindole at position 2 is achieved as follows: a base (for example, lithium diisopropyl amide) is reacted with the azaindole compound of formula (36) which is protected by an alkylsulfonyl group or aryl sulfonyl group, in a solvent (for example, tetrahydrofuran); and then this is reacted with a carbonyl source (for example, ethyl chloroformate).

The benzimidazolyl-5-hydrazine of formula (5) is commercially available, or can be prepared by methods well-known in the art, for example, by methods (8) to (11) described below.

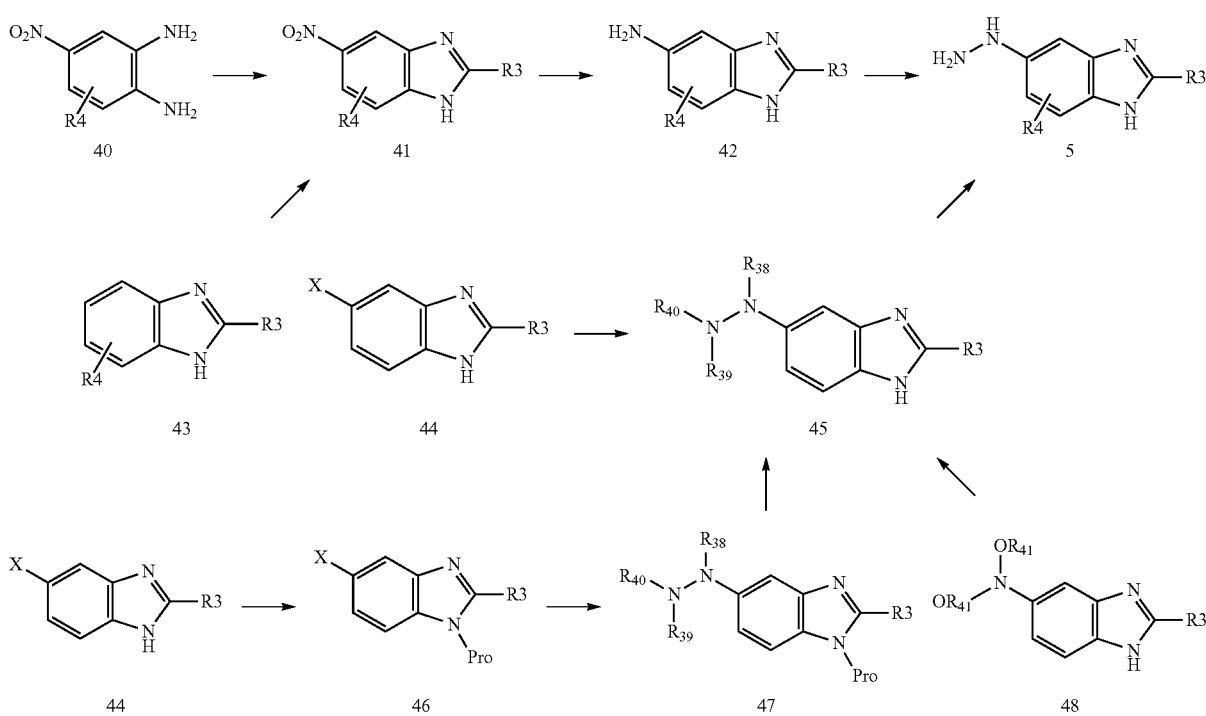

The benzimidazolyl-5-hydrazine of formula (5) can be prepared by methods well-known in the art.

Method (8)

The 5-nitrobenzimidazole of formula (41) is prepared by reacting the 4-nitro-1,2-phenylenediamine of formula (40) with carboxylic acid ($R_3COOH$), aldehyde ($R_3CHO$), ortho-carboxylic acid triester ($R_3C(OR)_3$), or acyl halide ($R_3COX$) under an acidic condition (for example, in hydrochloric acid or sulfuric acid), or in the presence of Lewis acid (for example, boron trifluoride/diethyl ether complex or dichlorooxozirconium (IV)), in a solvent (for example, methanol or xylene).

The aniline derivative of formula (42) is prepared by catalytic reduction of the prepared compound of formula (41) under a hydrogen atmosphere in the presence of a catalyst (for example, palladium carbon or palladium hydroxide) in a solvent (for example, methanol or ethanol).

The 5-benzimidazolyl-5-hydrazine of formula (5) is prepared by subsequent diazotization under an acidic condition (for example, in hydrochloric acid) and reduction using tin (II) chloride or such (for example, tin (II) chloride). Meanwhile, the 5-nitrobenzimidazole of formula (41) can also be prepared by nitration of the benzimidazole of formula (43).

Functional groups can be modified, for example, by methods described in "Smith and March, March's Advanced Organic Chemistry (Fifth ed., John Wiley & Sons, 2001)" or "Richard C. Larock, Comprehensive Organic Transformations (VCH Publishers, Inc., 1989)". Compounds used as a material for the production may be those commercially available, or as necessary, may be produced by conventional methods.

(Method 9)

Alternatively, the compound of formula (46) was prepared by introducing a protecting group into the benzimidazole moiety of the 5-halobenzimidazole of formula (44) in the reaction system. The protecting group used is preferably a group that can be readily and selectively removed for deprotection in subsequent steps. Methods of selection of protecting groups and deprotection are described, for example, in Greene and Wuts, Protective Groups in Organic Synthesis (third ed., John Wiley & Sons, 1999). The methods are appropriately used depending on the reaction condition. For example, a dimethoxymethyl group, trimethylsilyl group, p-methoxybenzyl group, tetrahydropyranyl group, formyl group, benzenesulfonyl group or such can be introduced as a protecting group under acidic or basic conditions. When a protecting group is introduced, acids are preferably used in a range of about 1% to about 1 equivalent. The acids include inorganic acids such as hydrochloric acid; sulfuric acid or sulfonic acids such as toluenesulfonic acid; carboxylic acids such as acetic acid, propionic acid, and benzoic acid; salts of strong acids such as pyridinium toluenesulfonate; and substances that generate hydrochloric acid in the reaction system, such as trimethylsilyl chloride. In addition to the above Brönsted acids, Lewis acids such as metal halides including zinc chloride, magnesium chloride, and lithium chloride are also effectively used in the reaction for introducing protecting groups. When a protecting group is introduced, bases are preferably used at one equivalent or more; or in some cases, at an excess amount such as about three equivalents. The bases preferably used include metal hydrides such as sodium hydride and potassium hydride; metal carbonates such as potassium carbonate and cesium carbonate; and metal alcoholates such as potassium t-butoxide and sodium t-butoxide.

Then, a base was added for halogen/metal exchange reaction to produce an intermediate in which the halogen group of formula (46) is replaced with a metal. Alkyl lithium or alkyl magnesium halide is preferably used as the base. More preferred bases include lower alkyl magnesium halides such as isopropyl magnesium chloride, isopropyl magnesium bromide, sec-butyl magnesium chloride, and cyclohexyl magnesium chloride. Solvents that ensure the stability of metal reagents in the reaction system are preferably used in the halogen/metal exchange reaction. The solvents include, for example, ether solvents such as diethyl ether, dimethoxyethane, and tetrahydrofuran. A reaction temperature that ensures the stability of metal reagents in the reaction system is preferred. Considering known halogen/metal exchange reactions described in documents, the preferred temperature ranges from about −80° C. to room temperature, more preferably from about −78° C. to 15° C. The bases used herein are in solutions commercially available, or prepared using alkyl halides and metal lithium or metal magnesium. An intermediate resulting from replacement of the halogen group of formula (46) with a metal is treated with an azodicarboxylic acid derivative (for example, azodicarboxylic acid di-tert-butyl ester or azodicarboxylic acid diethyl ester) to obtain the compound of formula (47). Then, the benzimidazole-protecting group is removed for deprotection to provide the protected hydrazine of formula (45). The protected hydrazine of formula (45) can be purified and isolated from the reaction solution as a free form or a salt with an appropriate acid. The appropriate acids include not only inorganic acids such as hydrochloric acid, hydrobromic acid, and sulfuric acid, but also any acids that are effective in the crystallization and purification. The acids include, for example, sulfonic acids such as methanesulfonic acid and toluenesulfonic acid, and carboxylic acids such as acetic acid, benzoic acid, malic acid, maleic acid, and fumaric acid. Finally, the hydrazine-protecting group is removed for deprotection to provide the benzimidazolyl hydrazine of formula (5). The deprotection may be carried out under known acidic or basic conditions described in documents. Acids used in the deprotection include not only inorganic acids such as hydrochloric acid, hydrobromic acid, and sulfuric acid, but also strong acids including carboxylic acids such as trifluoroacetic acid and pentafluoropropionic acid, and sulfonic acids such as methanesulfonic acid and toluenesulfonic acid. As necessary, the reaction solution can be diluted with an appropriate solvent, and the deprotection can be carried out. The solvents preferably used herein include amide solvents such as DMF, DMA, and NMP. The benzoimidazolyl hydrazine of formula (5) of interest can be produced by treatment in such a solvent at a temperature ranging from about ice-cold temperature to the boiling point of the solvent. Meanwhile, bases suitably used in the deprotection include alkyl metal hydroxides such as sodium hydroxide and potassium hydroxide, alkyl metal carbonates such as sodium carbonate and potassium carbonate. The benzoimidazolyl hydrazine of formula (5) of interest can be produced by treatment in the presence of such a base in alcohol such as methanol or ethanol at a temperature ranging from about ice-cold temperature to the boiling point of the solvent.

(Method 10)

Alternatively, the benzimidazole moiety of the 5-halobenzimidazole of formula (44) is protected with an above-described protecting group in the reaction system to provide the compound of formula (46). This is then heated in the presence of a hydrazine derivative (for example, di-tert-butyloxycarbonyl hydrazine), a base (for example, cesium carbonate or potassium carbonate), a transition metal catalyst (for example, palladium acetate, copper iodide, or copper bromide), a ligand (for example, triphenylphosphine, N,N-dimethyl glycine, or N,N'-dimethyl ethylene diamine), in a solvent (for example, N,N-dimethylacetamide). Thus, the compound of formula (47) is obtained. Then, the benzimidazole-protecting group is removed for deprotection to provide the protected hydrazine of formula (45). Finally, the hydrazine-protecting group is removed for deprotection by the method as described above to provide the benzimidazolyl hydrazine of formula (5).

Method (11)

Alternatively, the boronic acid derivative of formula (48) and a hydrazine derivative (for example, di-tert-butyloxycarbonyl hydrazine or azodicarboxylic acid di-tert-butyl ester) is stirred in the presence of a base (for example, tetramethyl ethylene diamine), a copper catalyst (for example, copper iodide, copper fluoride, or copper acetate) in a solvent (for example, methanol, tetrahydrofuran, or 1,2-dimethoxyethane) under a nitrogen atmosphere or in the air, at a temperature ranging from about room temperature to the boiling point of the solvent. Thus, the protected hydrazine of formula (45) is obtained. Finally, the hydrazine-protecting group is removed for deprotection by the method as described above to provide the benzimidazolyl hydrazine of formula (5).

EXAMPLES

The present invention is more specifically described below with reference to the Examples and test examples, but it is not to be construed as being limited thereto. All the starting materials and reagents were obtained from commercial suppliers or synthesized by known methods. Typically, $^1$H-NMR spectra were obtained by measurement, with or without Me$_4$Si as an internal reference, using EX270 (JEOL), Mercury300 (Varian), ECP-400 (JEOL), or 400-MR (Varian) (s=singlet; d=doublet; t=triplet; brs=broad singlet; m=multiple). Mass spectrometric measurements were carried out using the mass spectrometer LCQ Classic (Thermo Electron), ZQ2000 (Waters), or ZMD4000 (Waters). Microwaves were generated using Initiator™ (Biotage).

Example 1

Synthesis of [5-amino-1-(2-methyl-1H-benzimidazol-5-yl)-1H-pyrazol-4-yl]-(1H-indol-2-yl)-methanone

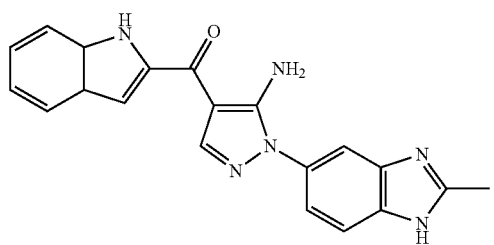 [SMILES: Cc1nc2cc(-n3ncc(C(=O)C4=CC5C=CC=CC5N4)c3N)ccc2[nH]1]

An aqueous solution (1.67 ml) of 4 M sodium hydroxide was added to an ethanol solution (17 ml) of [5-amino-1-(2-methyl-1H-benzimidazol-5-yl)-1H-pyrazol-4-yl]-(1-benzenesulfonyl-1H-indol-2-yl)methanone (87 mg). The resulting mixture was stirred at room temperature for 2 hours. The reaction mixture was poured into water. The resulting solid was collected by filtration, washed with water, and dried to give [5-amino-1-(2-methyl-1H-benzimidazol-5-yl)-1H-pyrazol-4-yl]-(1H-indol-2-yl)methanone (40 mg, 63%).

$^1$H-NMR (DMSO-D$_6$) δ: 12.47 (1H, s), 11.70 (1H, s), 8.32 (1H, s), 7.70 (1H, d, J=8.0 Hz), 7.66-7.55 (2H, m), 7.50-7.45 (2H, m), 7.31-7.23 (2H, m), 7.10-7.06 (1H, m), 7.01 (2H, brs), 2.53 (3H, s)

ESI (LC-MS positive mode) m/z 357 [(M+H)$^+$]

Example 1A

Synthesis of [5-amino-1-(2-methyl-3H-benzimidazol-5-yl)-1H-pyrazol-4-yl]-(1H-indol-2-yl)-methanone L-malate

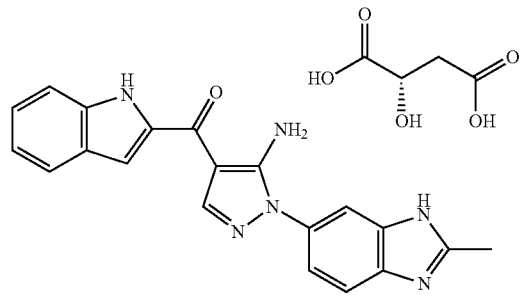 [SMILES: Cc1nc2ccc(-n3ncc(C(=O)c4cc5ccccc5[nH]4)c3N)cc2[nH]1 ; O=C(O)C[C@H](O)C(=O)O]

Predetermined amounts of L-malic acid (68 g, 0.507 mol) and [5-amino-1-(2-methyl-3H-benzimidazol-5-yl)-1H-pyrazol-4-yl]-(1H-indol-2-yl)-methanone hydrate (190 g, 0.507 mol) were dissolved in dimethyl sulfoxide (0.418 l, 2.2 v/w) and acetone (0.418 l, 2.2 v/w). Then, the resulting solution was filtered using a Kiriyama rohto (No. 4 paper filter), and placed into a 10-1 separable flask with a jacket. The reaction solution was heated at 50° C. for dissolution.

A predetermined amount of L-malic acid (544.4 g, 4.06 mol) was dissolved in acetone (1.25 l, 6.6 v/w) and acetic acid (0.418 l, 2.2 v/w). Then, the resulting solution was filtered using a Kiriyama rohto (No. 4 paper filter), and placed into a 10-1 separable flask with a jacket while keeping the inner temperature at 45° C. or higher. The seed crystal (0.95 g, 0.5%) was suspended in acetone (7.5 ml), and then this was placed into a 10-1 separable flask with a jacket.

After seven hours, the suspension was cooled to 25° C. The crystals were collected by filtration using a Kiriyama rohto, and washed twice with acetone (0.85 l, 5 v/w). The resulting wet powder was placed into a 10-1 separable flask with a jacket.

Acetone (2.85 l, 15 v/w) was added into the flask, and the suspension was stirred for three hours at 50° C. The resulting crystals were collected by filtration using a Kiriyama rohto, and washed twice with acetone (0.85 l, 5 v/w).

The resulting wet powder was dried for three hours under reduced pressure at an outer temperature of 40° C. to provide [5-amino-1-(2-methyl-3H-benzimidazol-5-yl)-1H-pyrazol-4-yl]-(1H-indol-2-yl)-methanone L-malate (556.9 g, 73%).

$^1$H-NMR (DMSO-D$_6$) δ: 11.69 (1H, s), 8.31 (1H, s), 8.25-7.00 (10H, m), 4.25-4.22 (1H, m), 3.33 (2H, brs), 2.69-2.32 (9H, m)

FAB positive mode m/z 157.1, 232.1, 289.2, 357.2 [(M+H)$^+$]

Example 1B

Synthesis of [5-amino-1-(2-methyl-1H-benzimidazol-5-yl)-1H-pyrazol-4-yl]-(1H-indol-2-yl)-methanone hydrochloride

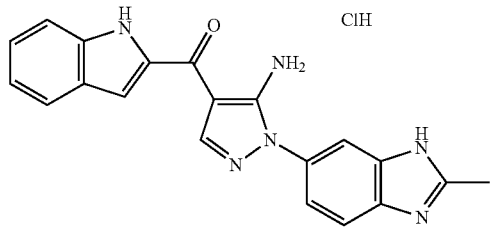 [SMILES: Cl ; Cc1nc2ccc(-n3ncc(C(=O)c4cc5ccccc5[nH]4)c3N)cc2[nH]1]

[5-Amino-1-(2-methyl-1H-benzimidazol-5-yl)-1H-pyrazol-4-yl]-(1H-indol-2-yl)-methanone (194 mg) was dissolved in dimethylformamide (1.94 ml). An aqueous solution of 2 M hydrochloric acid (300 μl) was divided into five portions and separately added dropwise thereto at 25° C. 2-Propanol (4 ml) was divided into three portions and separately added to the reaction solution at five-minute intervals. The resulting precipitate was collected by filtration, and washed with 2-propanol (1 ml). Then, the powder was dried under reduced pressure at 40° C. This yielded an opalescent powder (188 mg, 88%).

11.72 (1H, s), 8.39 (1H, s), 7.96 (1H, d, J=2.1 Hz), 7.92 (1H, d, J=8.7 Hz), 7.71 (1H, t, J=2.1 Hz), 7.68 (1H, t, J=2.1 Hz), 7.51 (1H, s), 7.48 (1H, d, J=2.1 Hz), 7.28 (1H, d, J=7.6 Hz), 7.23 (3H, s), 7.09 (1H, t, J=7.6 Hz), 2.82 (3H, s).

ESI (LC-MS positive mode) m/z 357 [(M+H)$^+$]

Example 1C

Synthesis of [5-amino-1-(2-methyl-1H-benzimidazol-5-yl)-1H-pyrazol-4-yl]-(1H-indol-2-yl)-methanone1-methanesulfonate monohydrate

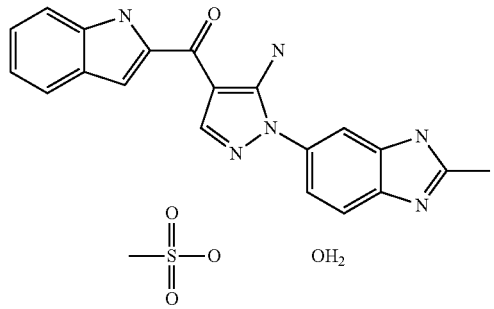

An aqueous solution (64.9 ml) of 2 M methanesulfonic acid was added to a dimethylformamide solution (420 ml) of [5-amino-1-(2-methyl-1H-benzimidazol-5-yl)-1H-pyrazol-4-yl]-(1H-indol-2-yl)-methanone (42 g). This was stirred at room temperature for 20 minutes. Then, methyl-t-butyl ether (105 ml) was added to the reaction solution. 3.0 mg of a seed crystal was added thereto, and this was stirred at room temperature. After confirmation of crystal precipitation, methyl-t-butyl ether (105 ml) was divided into four portions and separately added to the reaction solution at 15-minute intervals. The reaction solution was stirred at room temperature for 1.5 hours. The resulting crystals were collected by filtration using a Kiriyama rohto. The solid collected by filtration was washed three times with methyl-t-butyl ether (210 ml), and dried to provide [5-amino-1-(2-methyl-1H-benzimidazol-5-yl)-1H-pyrazol-4-yl]-(1H-indol-2-yl)-methanone1-methanesulfonate monohydrate (42.68 g, 84%).

$^1$H-NMR (DMSO-D$_6$) δ: 11.70 (1H, s), 8.39 (1H, s), 7.99 (1H, d, J=1.6 Hz), 7.94 (1H, d, J=8.8 Hz), 7.74-7.68 (2H, m), 7.51-7.46 (2H, m), 7.29-7.18 (3H, m), 7.11-7.06 (1H, m), 2.84 (3H, s), 2.37 (3H, s)

ESI (LC-MS positive mode) m/z 357 [(M+H)$^+$]

The compounds of Examples 2 to 35 listed in Table 1 were synthesized by the same method as in Example 1.

TABLE 1

| Example | Structure | Compound name | m/z | 1H-NMR |
|---|---|---|---|---|
| 2 | 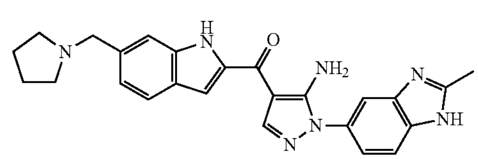 [SMILES: Cc1nc2cc(-n3ncc(C(=O)c4cc5ccc(CN6CCCC6)cc5[nH]4)c3N)ccc2[nH]1] | [5-amino-1-(2-methyl-1H-benzimidazol-5-yl)-1H-pyrazol-4-yl]-(6-pyrrolidin-1-ylmethyl-1H-indol-2-yl-methanone | 440 | 1H-NMR (DMSO-D6) δ: 12.46 (1.0H, d, J = 3.9 Hz), 11.62 (1.0H, s), 8.30 (1.0H, d, J = 4.9 Hz), 7.61 (3.0H, m), 7.41 (2.0H, m), 7.29 (1.0H, t, J = 7.3 Hz), 7.10-6.90 (3.0H, m), 3.66 (2.0H, s), 2.54 (3H, s), 2.48-2.42 (2.0H, m), 1.71 (4.0H, m). |

TABLE 1-continued

| Example | Structure | Compound name | m/z | 1H-NMR |
|---|---|---|---|---|
| 3 | 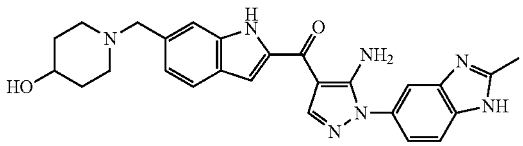 [SMILES: Cc1nc2cc(-n3ncc(C(=O)c4cc5ccc(CN6CCC(O)CC6)cc5[nH]4)c3N)ccc2[nH]1] | [5-amino-1-(2-methyl-1H-benzimidazol-5-yl)-1H-pyrazol-4-yl]-[6-(4-hydroxy-piperidin-1-ylmethyl)-1H-indol-2-yl]-methanone | 470 | 1H-NMR (CD3OD) δ: 8.27 (1.0H, s), 7.70-7.60 (3.0H, m), 7.44 (1.0H, s), 7.40-7.30 (2.0H, m), 7.11 (1.0H, dd, J = 8.1, 1.2 Hz), 3.64 (3.0H, m), 2.90-2.80 (2H, m), 2.61 (3.0H, s), 2.30-2.20 (2.0H, m), 1.90-1.80 (2.0H, m), 1.65-1.50 (2.0H, m). |
| 4 | 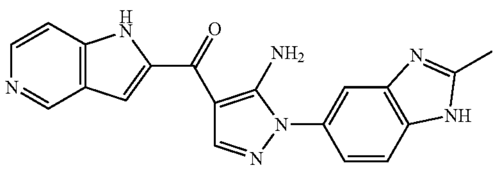 [SMILES: Cc1nc2cc(-n3ncc(C(=O)c4cc5cnccc5[nH]4)c3N)ccc2[nH]1] | [5-amino-1-(2-methyl-1H-benzimidazol-5-yl)-1H-pyrazol-4-yl]-(1H-pyrrolo[3,2-c]-pyridin-2-yl)-methanone | 358 | $^1$H-NMR(CD$_3$OD) δ: 9.02-8.98 (1H, m), 8.31 (1H, s), 8.25 (1H, d, J = 5.9 Hz), 7.70-7.65 (2H, m), 7.59-7.56 (1H, m), 7.51 (1H, d, J = 5.9 Hz), 7.39 (1H, dd, J = 8.8, 2.0 Hz), 2.62 (3H, s). |
| 5 | 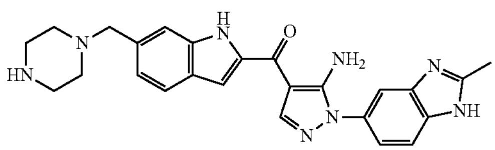 [SMILES: Cc1nc2cc(-n3ncc(C(=O)c4cc5ccc(CN6CCNCC6)cc5[nH]4)c3N)ccc2[nH]1] | [5-amino-1-(2-methyl-1H-benzimidazol-5-yl)-1H-pyrazol-4-yl]-(6-piperazin-1-ylmethyl)-1H-indol-2-yl)-methanone | 455 | 1H-NMR (CD3OD) δ: 8.27 (1.0H, s), 7.74-7.68 (3.0H, m), 7.48-7.20 (2.0H, m), 7.36 (1.0H, d, J = 1.0 Hz), 7.13 (1.0H, m), 3.74 (2.0H m), 3.25-3.20 (4.0H, m), 2.77-2.70 (4.0H, m), 2.66 (3.0H, s). |
| 6 | 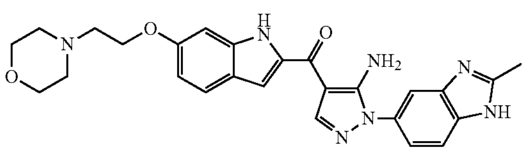 [SMILES: Cc1nc2cc(-n3ncc(C(=O)c4cc5ccc(OCCN6CCOCC6)cc5[nH]4)c3N)ccc2[nH]1] | [5-amino-1-(2-methyl-1H-benzimidazol-5-yl)-1H-pyrazol-4-yl]-[6-(2-morpholin-4-yl-ethoxy)-1H-indol-2-yl]-methanone | 486 | 1H-NMR (DMSO-D6) δ: 12.45 (1.0H, br s), 11.50 (1.0H br s), 8.27 (1.0H, s), 7.60-7.55 (3.0H, m), 7.40 (1.0H, br s), 7.32-7.28 (1.0H, m), 6.93 (3.0H, br s), 6.75 (1.0H, dd, J = 8.8, 2.4 Hz), 4.11 (2.0H, t, J = 5.9 Hz), 3.60 (4.0H, t, J = 4.6 Hz), 3.34-3.28 (4.0H, m), 2.73 (2.0H, t, J = 5.9 Hz), 2.53 (3.0H, s). |
| 7 | 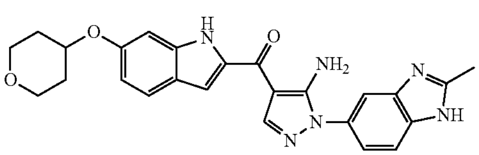 [SMILES: Cc1nc2cc(-n3ncc(C(=O)c4cc5ccc(OC6CCOCC6)cc5[nH]4)c3N)ccc2[nH]1] | [5-amino-1-(2-methyl-1H-benzimidazol-5-yl)-1H-pyrazol-4-yl]-[6-(tetrahydro-pyran-4-yloxy)-1H-indol-2-yl]-methanone | 457 | 1H-NMR (DMSO-D6) δ: 12.46 (1.0H, br s), 11.44 (1.0H, br s), 8.27 (1.0H, s), 7.61-7.57 (3.0H, m), 7.39 (1.0H, br s), 7.29 (1.0H, d, J = 8.3 Hz), 6.98-6.95 (3.0H, m), 6.79 (1.0H, d, J = 8.8 Hz), 4.59-4.53 (1.0H, m), 3.90-3.85 (2.0H, m), 3.53-3.43 (2.0H, m), 2.53 (3.0H, s), 2.02-1.99 (2.0H, m), 1.68-1.69 (2.0H, m). |
| 8 | 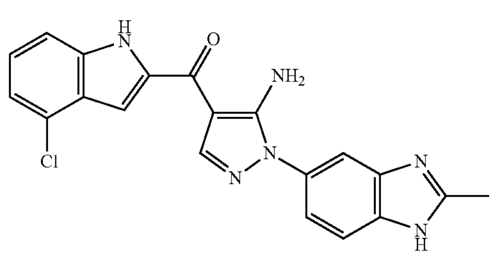 [SMILES: Cc1nc2cc(-n3ncc(C(=O)c4cc5c(Cl)cccc5[nH]4)c3N)ccc2[nH]1] | [5-amino-1-(2-methyl-1H-benzimidazol-5-yl)-1H-pyrazol-4-yl]-(4-chloro-1H-indol-2-yl)-methanone | 391, 393 | 1H-NMR (DMSO-D6) δ: 12.49 (1H, s), 12.10 (1H, s), 8.32 (1H, d, J = 3.6 Hz), 7.66 (1H, dd, J = 4.9, 3.3 Hz), 7.58 (1H, t, J = 4.0 Hz), 7.47 (1H, d, J = 7.9 Hz), 7.32-7.31 (3H, m), 7.26 (1H, t, J = 7.7 Hz), 7.19 (1H, s), 7.16 (1H, s), 2.54 (3H, s). |

TABLE 1-continued

| Example | Structure | Compound name | m/z | 1H-NMR |
|---|---|---|---|---|
| 9 | 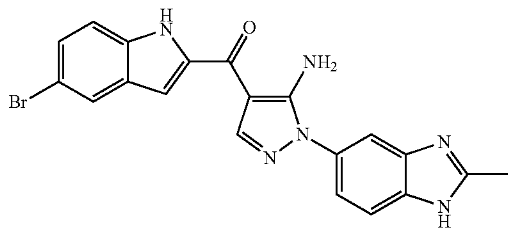 [SMILES: Cc1nc2cc(-n3ncc(C(=O)c4cc5cc(Br)ccc5[nH]4)c3N)ccc2[nH]1] | [5-amino-1-(2-methyl-1H-benzimidazol-5-yl)-1H-pyrazol-4-yl]-(5-bromo-1H-indol-2-yl)-methanone | 435, 437 | 1H-NMR (DMSO-D6) δ: 12.48 (1H, s), 11.93 (1H, s), 8.28 (1H, s), 7.88 (1H, d, J = 1.5 Hz), 7.63-7.59 (2H, m), 7.47-7.44 (2H, m), 7.37 (1H, dd, J = 8.6, 1.9 Hz), 7.29 (1H, dd, J = 8.6, 1.9 Hz), 7.04 (2H, s), 2.54 (3H, s). |
| 10 | 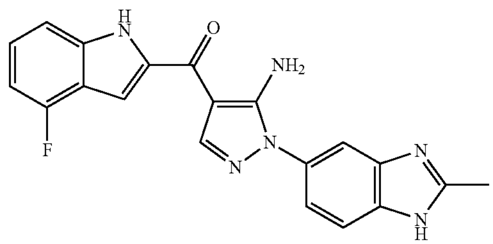 [SMILES: Cc1nc2cc(-n3ncc(C(=O)c4cc5c(F)cccc5[nH]4)c3N)ccc2[nH]1] | [5-amino-1-(2-methyl-1H-benzimidazol-5-yl)-1H-pyrazol-4-yl]-(4-iodo-1H-indol-2-yl)-methanone | 483 | 1H-NMR (DMSO-D6) δ: 12.23 (1.0H, s), 8.22 (1.0H, s), 7.64-7.57 (2.0H, m), 7.54-7.48 (2.0H, m), 7.29 (1.0H, dd, J = 8.3, 1.9 Hz), 7.10-6.95 (3.0H, m), 3.16 (2H, s), 2.53 (3H, s). |
| 11 | 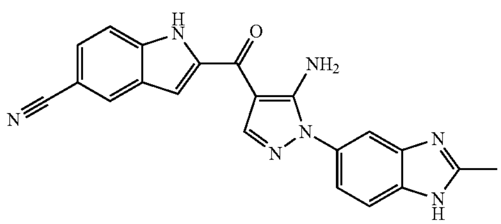 [SMILES: Cc1nc2cc(-n3ncc(C(=O)c4cc5cc(C#N)ccc5[nH]4)c3N)ccc2[nH]1] | 2-[5-amino-1-(2-methyl-1H-benzimidazol-5-yl)-1H-pyrazole-4-carbonyl]-1H-indole-5-carbonitrile | 382 | 1H-NMR (DMSO-D6) δ: 12.46 (1.0H, s), 12.26 (1.0H, s), 8.30-8.23 (2.0H, m), 7.60 (5.0H, m), 7.28 (1.0H, d, J = 8.4 Hz), 7.05 (2.0H, m), 2.52 (3.0H, s). |
| 12 | 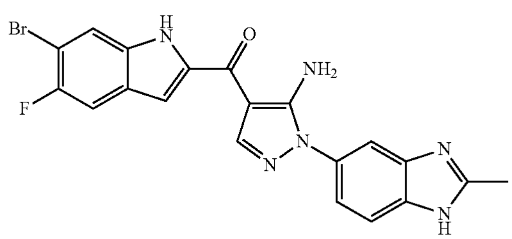 [SMILES: Cc1nc2cc(-n3ncc(C(=O)c4cc5cc(F)c(Br)cc5[nH]4)c3N)ccc2[nH]1] | [5-amino-1-(2-methyl-1H-benzimidazol-5-yl)-1H-pyrazol-4-yl]-(6-bromo-5-fluoro-1H-indol-2-yl)-methanone | 453, 455 | 1H-NMR (DMSO-D6) δ: 12.16 (1.0H, s), 8.28 (1.0H, s), 7.73 (1.0H, m), 7.63-7.60 (3H, m), 7.44 (1.0H, s), 7.27 (1.0H, m), 7.05 (2.0H, br s), 2.53 (3H, s). |
| 13 | 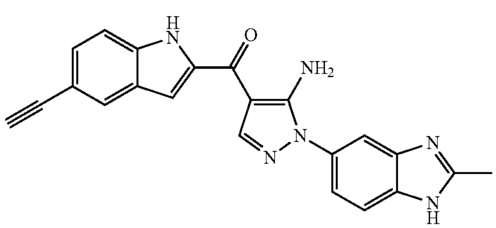 [SMILES: C#Cc1ccc2[nH]c(C(=O)c3cnn(-c4ccc5[nH]c(C)nc5c4)c3N)cc2c1] | [5-amino-1-(2-methyl-1H-benzimidazol-5-yl)-1H-pyrazol-4-yl]-(5-ethynyl-1H-indol-2-yl)-methanone | 381 | 1H-NMR (DMSO-D6) δ: 12.45 (1.0H, s), 11.91 (1.0H, s), 8.29 (1.1H, s), 7.85 (1.0H, s), 7.61 (2.0H, m), 7.48 (2.0H, m), 7.34-7.28 (2.0H, m), 7.01-6.90 (2H, m), 3.99 (1.0H, s), 2.54 (3.0H, s). |
| 14 | 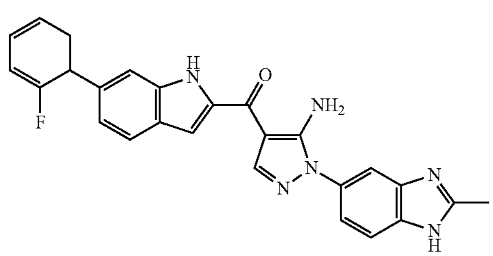 [SMILES: Cc1nc2cc(-n3ncc(C(=O)c4cc5ccc(C6CC=CC=C6F)cc5[nH]4)c3N)ccc2[nH]1] | [5-amino-1-(2-methyl-1H-benzimidazol-5-yl)-1H-pyrazol-4-yl]-[6-(2-fluoro-phenyl)-1H-indol-2-yl]-methanone | 451 | 1H-NMR (DMSO-D6) δ: 8.35 (1H, s), 7.79 (1H, d, J = 8.6 Hz), 7.63-7.58 (6H, m), 7.52 (1H, s), 7.42-7.26 (3H, m), 7.05 (2H, br s), 2.54 (3H, s). |

TABLE 1-continued

| Example | Structure | Compound name | m/z | 1H-NMR |
|---|---|---|---|---|
| 15 | 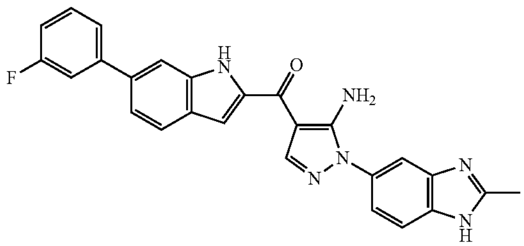 [SMILES: Cc1nc2cc(-n3ncc(C(=O)c4cc5ccc(-c6cccc(F)c6)cc5[nH]4)c3N)ccc2[nH]1] | [5-amino-1-(2-methyl-1H-benzimidazol-5-yl)-1H-pyrazol-4-yl]-[6-(3-fluoro-phenyl)-1H-indol-2-yl]-methanone | 451 | 1H-NMR (DMSO-D6) δ: 12.48 (1H, s), 11.86 (1H, s), 8.34 (1H, s), 7.80 (1H, d, J = 8.6 Hz), 7.73 (2H, br s), 7.65-7.42 (25H, m), 7.30 (1H, d, J = 6.9 Hz), 7.02 (2H, br s), 2.54 (3H, s). |
| 16 | 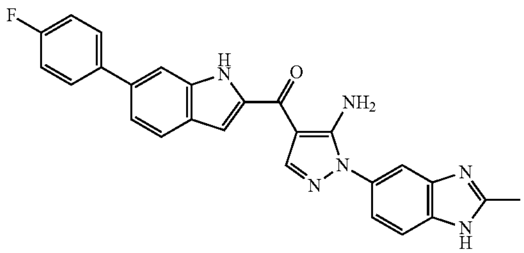 [SMILES: Cc1nc2cc(-n3ncc(C(=O)c4cc5ccc(-c6ccc(F)cc6)cc5[nH]4)c3N)ccc2[nH]1] | [5-amino-1-(2-methyl-1H-benzimidazol-5-yl)-1H-pyrazol-4-yl]-[6-(4-fluoro-phenyl)-1H-indol-2-yl]-methanone | 451 | 1H-NMR (DMSO-D6) δ: 12.50 (1H, s), 11.82 (1H, s), 8.34 (1H, s), 7.81-7.65 (5H, m), 7.50 (1H, br s), 7.43-7.27 (5H, m), 7.03 (2H, br s), 2.54 (3H, s). |
| 17 | 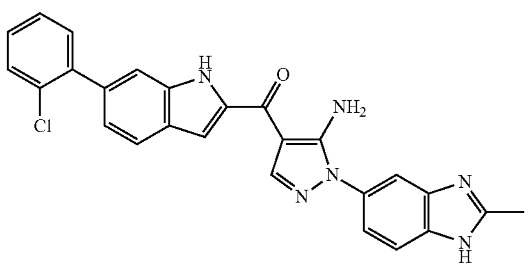 [SMILES: Cc1nc2cc(-n3ncc(C(=O)c4cc5ccc(-c6ccccc6Cl)cc5[nH]4)c3N)ccc2[nH]1] | [5-amino-1-(2-methyl-1H-benzimidazol-5-yl)-1H-pyrazol-4-yl]-[6-(2-chloro-phenyl)-1H-indol-2-yl]-methanone | 467, 469 | 1H-NMR (DMSO-D6) δ: 12.49 (1H, s), 11.84 (1H, s), 8.35 (1H, d, J = 3.1 Hz), 7.77 (1H, d, J = 8.2 Hz), 7.66 (1H, t, J = 4.2 Hz), 7.59-7.57 (3H, m), 7.53-7.50 (2H, brs), 7.49-7.39 (2H, m), 7.30 (1H, d, J = 6.8 Hz), 7.14 (1H, dd, J = 8.1, 1.3 Hz), 7.04 (2H, d, J = 14.5 Hz), 2.54 (3H, s). |
| 18 | 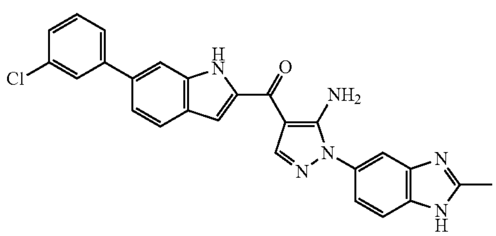 [SMILES: Cc1nc2cc(-n3ncc(C(=O)c4cc5ccc(-c6cccc(Cl)c6)cc5[nH]4)c3N)ccc2[nH]1] | [5-amino-1-(2-methyl-1H-benzimidazol-5-yl)-1H-pyrazol-4-yl]-[6-(3-chloro-phenyl)-1H-indol-2-yl]-methanone | 467, 469 | 1H-NMR (DMSO-D6) δ: 12.49 (1H, s), 11.86 (1H, s), 8.34 (1H, d, J = 3.0 Hz), 7.80 (1H, d, J = 8.4 Hz), 7.72 (3H, m), 7.68-7.66 (3H, m), 7.58 (1H, d, J = 8.4 Hz), 7.51 (1H, d, J = 7.6 Hz), 7.43 (1H, d, J = 7.9 Hz), 7.30 (1H, ddd, J = 8.6, 4.1, 1.8 Hz), 7.05 (2H, d, J = 14.0 Hz), 2.54 (3H, s). |
| 19 | 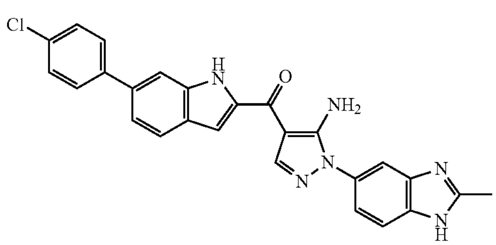 [SMILES: Cc1nc2cc(-n3ncc(C(=O)c4cc5ccc(-c6ccc(Cl)cc6)cc5[nH]4)c3N)ccc2[nH]1] | [5-amino-1-(2-methyl-1H-benzimidazol-5-yl)-1H-pyrazol-4-yl]-[6-(4-chloro-phenyl)-1H-indol-2-yl]-methanone | 467, 469 | 1H-NMR (DMSO-D6) δ: 12.49 (1H, s), 11.85 (1H, s), 8.34 (1H, s), 7.79 (2H, d, J = 8.1 Hz), 7.75-7.71 (2H, m), 7.72-7.68 (1H, m), 7.64-7.60 (1H, m), 7.54 (2H, d, J = 8.1 Hz), 7.51 (1H, d, J = 2.0 Hz) 7.41 (1H, dd, J = 8.4, 1.6 Hz), 7.30 (1H, dd, J = 8.7, 1.5 Hz), 7.05 (2H, br s), 2.54 (3H, s). |
| 20 | 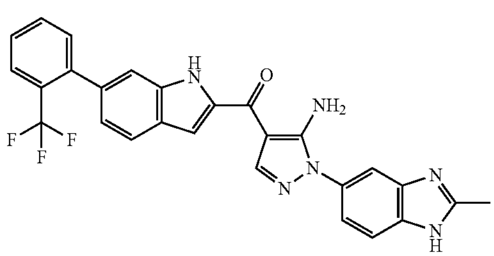 [SMILES: Cc1nc2cc(-n3ncc(C(=O)c4cc5ccc(-c6ccccc6C(F)(F)F)cc5[nH]4)c3N)ccc2[nH]1] | [5-amino-1-(2-methyl-1H-benzimidazol-5-yl)-1H-pyrazol-4-yl]-[6-(2-trifluoromethyl-phenyl)-1H-indol-2-yl]-methanone | 501 | 1H-NMR (CD3OD) δ: 8.32 (1H, s), 7.96 (1H, s), 7.85 (1H, d, J = 8.7 Hz), 7.77 (1H, t, J = 8.6 Hz), 7.68-7.62 (5H, m), 7.42 (1H, dt, J = 13.3, 5.4 Hz), 7.06 (2H, d, J = 8.7 Hz), 2.65 (3H, s). |

TABLE 1-continued

| Example | Structure | Compound name | m/z | 1H-NMR |
|---|---|---|---|---|
| 21 | 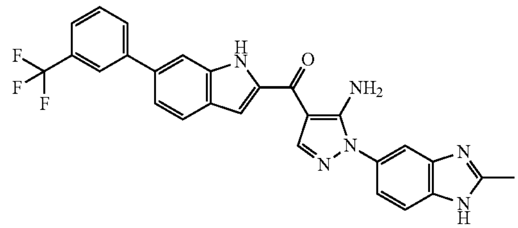 [SMILES: Cc1nc2cc(-n3ncc(C(=O)c4cc5ccc(-c6cccc(C(F)(F)F)c6)cc5[nH]4)c3N)ccc2[nH]1] | [5-amino-1-(2-methyl-1H-benzimidazol-5-yl)-1H-pyrazol-4-yl]-[6-(3-trifluoromethyl-phenyl)-1H-indol-2-yl]-methanone | 501 | 1H-NMR (CD3OD) δ: 8.29 (1H, s), 7.94 (2H, br s), 7.83 (1H, dd, J = 8.4, 0.7 Hz), 7.76-7.75 (1H, m), 7.67 (1H, br s), 7.65-7.62 (2H, m), 7.43 (1H, d, J = 1.5 Hz), 7.40-7.39 (2H, m), 7.36 (1H, d, J = 2.0 Hz), 2.61 (3H, s). |
| 22 | 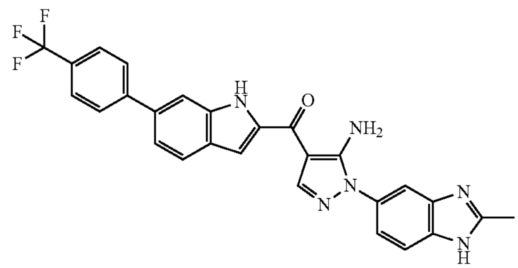 [SMILES: Cc1nc2cc(-n3ncc(C(=O)c4cc5ccc(-c6ccc(C(F)(F)F)cc6)cc5[nH]4)c3N)ccc2[nH]1] | [5-amino-1-(2-methyl-1H-benzimidazol-5-yl)-1H-pyrazol-4-yl]-[6-(4-trifluoromethyl-phenyl)-1H-indol-2-yl]-methanone | 501 | 1H-NMR (CD3OD) δ: 8.31 (1H, s), 7.89 (2H, d, J = 8.1 Hz), 7.85 (1H, dd, J = 8.3, 0.7 Hz), 7.81-7.80 (1H, m), 7.75 (2H, d, J = 8.1 Hz), 7.69-7.65 (2H, m), 7.46 (1H, dd, J = 8.4, 1.6 Hz), 7.43 (2H, d, J = 0.8 Hz), 7.39 (2H, dd, J = 8.5, 2.1 Hz), 2.62 (3H, s). |
| 23 | 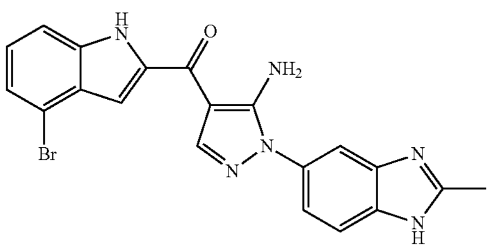 [SMILES: Cc1nc2cc(-n3ncc(C(=O)c4cc5c(Br)cccc5[nH]4)c3N)ccc2[nH]1] | [5-amino-1-(2-methyl-1H-benzimidazol-5-yl)-1H-pyrazol-4-yl]-(4-bromo-1H-indol-2-yl)-methanone | 435, 437 | 1H-NMR (DMSO-D6) δ: 13.0-11.5 (1H, s), 11.2-10.5 (1H, s), 8.28 (1H, s), 7.60 (2H, t, J = 4.3 Hz), 7.49 (1H, d, J = 8.4 Hz), 7.29-7.25 (2H, m), 7.14 (2H, t, J = 9.1 Hz), 3.17 (2H, s), 2.53 (3H, s). |
| 24 | 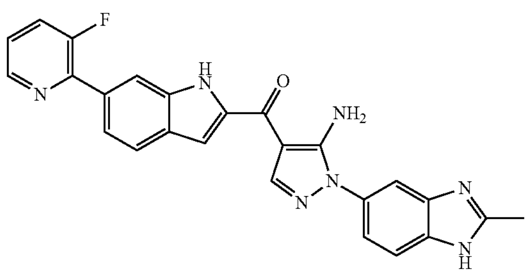 [SMILES: Cc1nc2cc(-n3ncc(C(=O)c4cc5ccc(-c6ncccc6F)cc5[nH]4)c3N)ccc2[nH]1] | [5-amino-1-(2-methyl-1H-benzimidazol-5-yl)-1H-pyrazol-4-yl]-[6-(3-fluoro-pridin-2-yl)-1H-indol-2-yl]-methanone | 452 | 1H-NMR (DMSO-D6) δ: 12.49 (1H, s), 11.94 (1H, d, J = 2.2 Hz), 8.57 (1H, td, J = 3.0, 1.5 Hz), 8.36 (1H, s), 8.13 (1H, s), 7.87-7.81 (2H, m), 7.73 (1H, dt, J = 8.6, 1.5 Hz), 7.64-7.62 (2H, m), 7.52 (1H, d, J = 1.5 Hz), 7.49-7.45 (1H, m), 7.31 (1H, dd, J = 8.6, 1.9 Hz), 7.06 (2H, s), 2.54 (3H, s). |
| 25 | 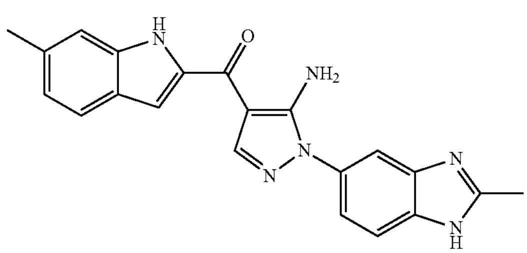 | [5-amino-1-(2-methyl-1H-benzimidazol-5-yl)-1H-pyrazol-4-yl]-(6-methyl-1H-indol-2-yl)-methanone | 371 | 1H-NMR (DMSO-D6) δ: 12.44 (1.0H, d, J = 3.7 Hz), 11.63 (1.0H, d, J = 1.6 Hz), 8.28 (1.0H, d, J = 4.7 Hz), 7.67-7.62 (1.0H, m), 7.59-7.54 (2.0H, m), 7.39 (1.1H, s), 7.32-7.24 (2.0H, m), 7.03-6.84 (3.0H, m), 2.53 (3.0H, s), 2.41 (3.0H, s). |
| 26 | 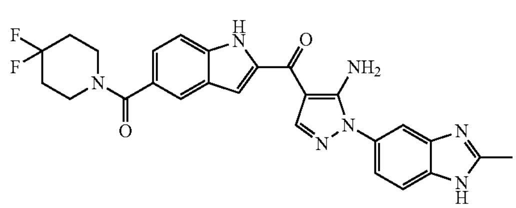 [SMILES: Cc1nc2cc(-n3ncc(C(=O)c4cc5cc(C(=O)N6CCC(F)(F)CC6)ccc5[nH]4)c3N)ccc2[nH]1] | [5-amino-1-(2-methyl-1H-benzimidazol-5-yl)-1H-pyrazol-4-yl]-(5-(4,4-difluoro-piperidine-1-carbonyl)-1H-indol-2-yl]-methanone | 504 | 1H-NMR (DMSO-D6) δ: 12.42 (1.0H, s), 11.88 (1.0H, s), 8.28 (1.0H, s), 7.80 (1.0H, d, J = 1.2 Hz), 7.65-7.45 (4.0H, m), 7.32 (1.0H, dd, J = 8.4, 1.6 Hz), 7.26 (1.0H, m), 7.05-6.90 (2.0H, m), 3.70-3.55 (4.0H, m), 2.51 (3H, s), 2.10-1.95 (4.0H, m). |

TABLE 1-continued

| Example | Structure | Compound name | m/z | 1H-NMR |
|---|---|---|---|---|
| 27 | 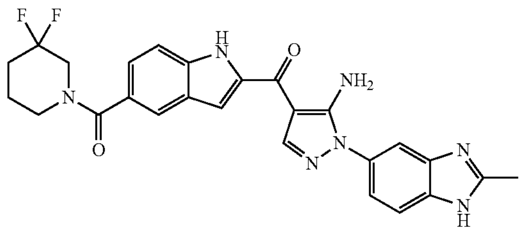 [SMILES: Cc1nc2cc(-n3ncc(C(=O)c4cc5cc(C(=O)N6CCCC(F)(F)C6)ccc5[nH]4)c3N)ccc2[nH]1] | [5-amino-1-(2-methyl-1H-benzimidazol-5-yl)-1H-pyrazol-4-yl]-(5-(3,3-difluoro-piperidine-1-carbonyl)-1H-indol-2-yl]-methanone | 504 | 1H-NMR (DMSO-D6) δ: 12.42 (1.0H, s), 11.90 (1.0H, s), 8.28 (1.0H, s), 7.74 (1..0H, d, J = 0.8 Hz), 7.65-7.45 (4.0H, m), 7.30-7.23 (2.0H, m), 6.99 (2.0H, m), 3.84 (2.0H, m), 3.51 (2.0H, m), 2.51 (3.0H, s), 2.20-2.00 (2.0, m), 1.74-1.60 (2.0H, s). |
| 28 | 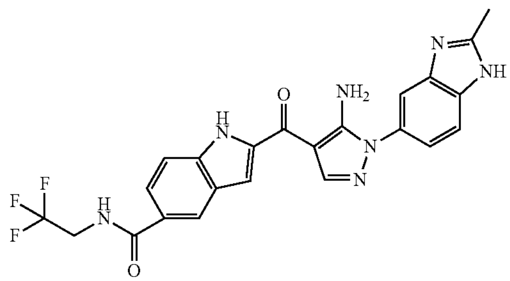 [SMILES: Cc1nc2cc(-n3ncc(C(=O)c4cc5cc(C(=O)NCC(F)(F)F)ccc5[nH]4)c3N)ccc2[nH]1] | 2-[5-amino-1-(2-methyl-1H-benzimidazol-5-yl)-1H-pyrazole-4-carbonyl]-1H-indole-5-carboxylic acid (2,2,2-trifluoro-ethyl)-amide | 482 | 1H-NMR (DMSO-D6) δ:12.43 (1.0H, s), 11.96 (1.0H, s), 8.98 (1.0H, d, J = 6.5 Hz), 8.31 (2.0H, m), 7.79 (1.0H, dd, J = 8.7, 1.7 Hz), 7.70-7.50 (40H, m), 7.28 (1.0H, m), 7.05-6.90 (2.0H, m), 4.15-4.00 (2.0H, m), 2.52 (3.0H, s). |
| 29 | 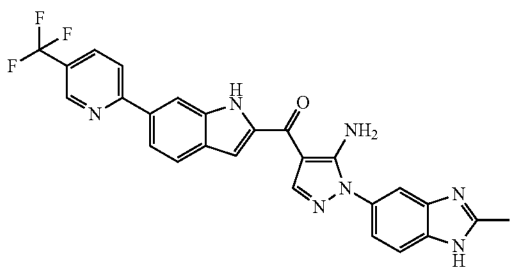 [SMILES: Cc1nc2cc(-n3ncc(C(=O)c4cc5ccc(-c6ccc(C(F)(F)F)cn6)cc5[nH]4)c3N)ccc2[nH]1] | [5-amino-1-(2-methyl-1H-benzimidazol-5-yl)-1H-pyrazol-4-yl]-[6-(5-trifluoromethyl-pyridin-2-yl)-1H-indol-2-yl]-methanone | 502 | 1H-NMR(DMSO-D6) δ: 12.49 (1H, s), 12.02 (1H, d, J = 1.6 Hz), 9.06 (1H, d, J = 1.1 Hz), 8.35 (2H, s), 8.28 (1H, dd, J = 8.8, 2.2 Hz), 8.21 (1H, d, J = 8.2 Hz), 7.91 (1H, dd, J = 8.2, 1.6 Hz), 7.84 (1H, d, J = 8.2 Hz), 7.64-7.62 (2H, m), 7.53 (1H, d, J = 1.1 Hz), 7.31 (1H, dd, J = 8.2, 2.2 Hz), 7.07 (2H, s), 2.54 (3H, s). |
| 30 | 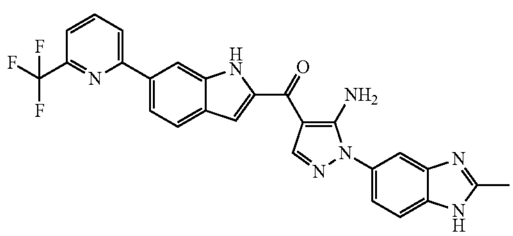 [SMILES: Cc1nc2cc(-n3ncc(C(=O)c4cc5ccc(-c6cccc(C(F)(F)F)n6)cc5[nH]4)c3N)ccc2[nH]1] | 5-amino-1-(2-methyl-1H-benzimidazol-5-yl)-1H-pyrazol-4-yl]-[6-(6-trifluoromethyl-pyridin-2-yl)-1H-indol-2-yl]-methanone | 502 | 1H-NMR (DMSO-D6) δ: 12.48 (1H, s), 11.94 (1H, d, J = 2.2 Hz), 8.34-8.31 (3H, m), 8.18 (1H, t, J = 7.7 Hz), 7.88-7.84 (3H, m), 7.65-7.58 (2H, m), 7.52 (1H, d, J = 1.6 Hz), 7.31-7.30 (1H, m), 7.06 (2H, d, J = 22.0 Hz), 2.54 (3H, s). |
| 31 | 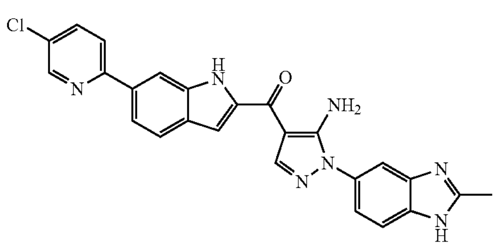 | 5-amino-1-(2-methyl-1H-benzimidazol-5-yl)-1H-pyrazol-4-yl]-[6-(5-chloro-pyridin-2-yl)-1H-indol-2-yl]-methanone | 468, 470 | 1H-NMR (DMSO-D6) δ: 12.48 (1H, s), 11.95 (1H, s), 8.72 (1H, dd, J = 2.2, 1.1 Hz), 8.34 (1H, s), 8.25 (1H, s), 8.04-7.99 (2H, m), 7.82-7.80 (2H, m), 7.63 (2H, s), 7.51 (1H, s), 7.30 (1H, dd, J = 8.5, 1.9 Hz), 7.05 (2H, d, J = 6.6 Hz), 2.54 (3H, s). |
| 32 | 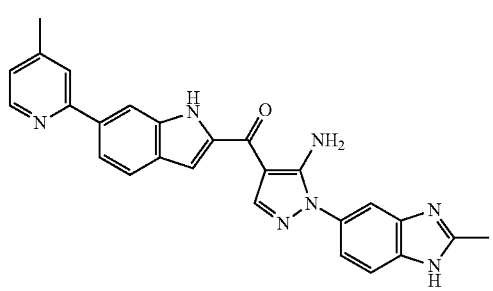 [SMILES: Cc1ccnc(-c2ccc3cc(C(=O)c4cnn(-c5ccc6[nH]c(C)nc6c5)c4N)[nH]c3c2)c1] | 5-amino-1-(2-methyl-1H-benzimidazol-5-yl)-1H-pyrazol-4-yl]-[6-(4-methyl-pyridin-2-yl)-1H-indol-2-yl]-methanone | 448 | 1H-NMR (CD3OD) δ: 8.46 (1H, dd, J = 5.2, 0.4 Hz), 8.31 (1H, s), 8.05-8.04 (1H, m), 7.93 (1H, dd, J = 8.0, 1.7 Hz), 7.84 (1H, dd, J = 8.4, 0.7 Hz), 7.77-7.76 (1H, m), 7.69-7.67 (2H, m), 7.43 (1H, d, J = 0.8 Hz), 7.39 (1H, dd, J = 8.6, 2.0 Hz), 7.22-7.13 (1H, m), 2.62 (3H, s), 2.48 (3H, s). |

TABLE 1-continued

| Example | Structure | Compound name | m/z | 1H-NMR |
|---|---|---|---|---|
| 33 | 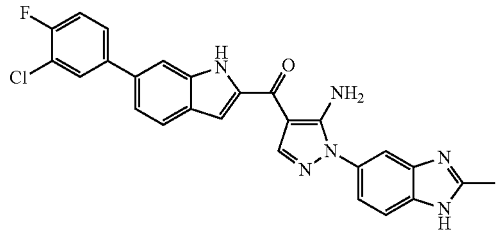 [SMILES: Cc1nc2cc(-n3ncc(C(=O)c4cc5ccc(-c6ccc(F)c(Cl)c6)cc5[nH]4)c3N)ccc2[nH]1] | 5-amino-1-(2-methyl-1H-benzimidazol-5-yl)-1H-pyrazol-4-yl]-[6-(3-chloro-4-fluoro-phenyl)-1H-indol-2-yl]-methanone | 484, 486 | 1H-NMR (DMSO-D6) δ: 12.48 (1H, s), 11.85 (1H, s), 8.34 (1H, s), 7.87 (1H, dd, J = 7.1, 2.2 Hz), 7.79 (1H, d, J = 8.2 Hz), 7.74-7.66 (2H, m), 7.65-7.58 (2H, m), 7.57-7.49 (2H, m), 7.41 (1H, d, J = 8.2 Hz), 7.30 (1H, d, J = 8.2 Hz), 7.04 (2H, s), 2.54 (3H, s). |
| 34 | 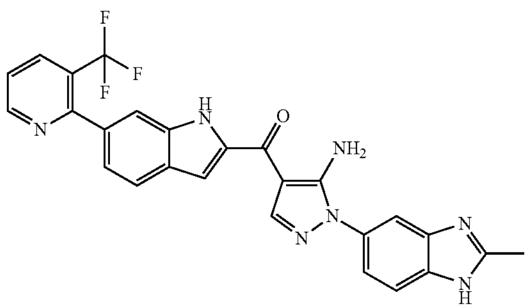 [SMILES: Cc1nc2cc(-n3ncc(C(=O)c4cc5ccc(-c6ncccc6C(F)(F)F)cc5[nH]4)c3N)ccc2[nH]1] | 5-amino-1-(2-methyl-1H-benzimidazol-5-yl)-1H-pyrazol-4-yl]-[6-(3-trifluoromethyl-pyridin-2-yl)-1H-indol-2-yl]-methanone | 502 | 1H-NMR (DMSO-D6) δ: 12.48 (1H, s), 11.96 (1H, s), 8.95 (1H, d, J = 4.9 Hz), 8.35-8.34 (2H, m), 8.26 (1H, s), 7.93 (1H, dd, J = 8.5, 1.4 Hz), 7.82 (1H, d, J = 8.2 Hz), 7.70 (1H, d, J = 5.5 Hz), 7.62-7.60 (2H, m), 7.52 (1H, s), 7.30 (1H, dd, J = 8.5, 1.9 Hz), 7.06 (2H, s), 2.54 (3H, s). |
| 35 | 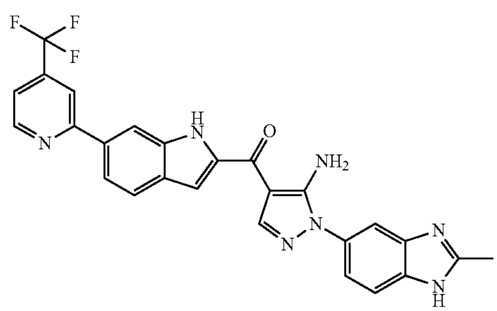 [SMILES: Cc1nc2cc(-n3ncc(C(=O)c4cc5ccc(-c6cc(C(F)(F)F)ccn6)cc5[nH]4)c3N)ccc2[nH]1] | 5-amino-1-(2-methyl-1H-benzimidazol-5-yl)-1H-pyrazol-4-yl]-[6-(4-trifluoromethyl-pyridin-2-yl)-1H-indol-2-yl]-methanone | 502 | 1H-NMR (DMSO-D6) δ: 12.47 (1H, s), 11.90 (1H, d, J = 1.6 Hz), 8.92 (1H, d, J = 3.8 Hz), 8.35-8.31 (2H, m), 7.78 (1H, d, J = 8.2 Hz), 7.67-7.60 (4H, m), 7.53 (1H, d, J = 1.6 Hz), 7.30 (1H, d, J = 8.2 Hz), 7.19 (1H, d, J = 8.2 Hz), 7.04 (2H, d, J = 10.4 Hz), 2.54 (3H, s). |

Example 36

Synthesis of [5-amino-1-(6-fluoro-2-methyl-1H-benzimidazol-5-yl)-1H-pyrazol-4-yl]-(1H-indol-2-yl)-methanone

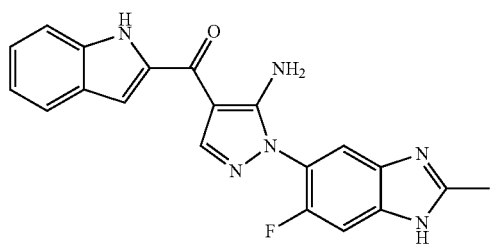 [SMILES: Cc1nc2cc(-n3ncc(C(=O)c4cc5ccccc5[nH]4)c3N)c(F)cc2[nH]1]

[5-Amino-1-(6-fluoro-2-methyl-1H-benzimidazol-5-yl)-1H-pyrazol-4-yl]-(1-benzenesulfonyl-1H-indol-2-yl)methanone (114 mg, 0.22 mmol) was dissolved in isopropanol (2.2 ml), and an aqueous solution of 1 M sodium hydroxide (2.2 ml) was added thereto. The resulting mixture was heated at 90° C. with stirring under a nitrogen atmosphere for two hours. After the reaction mixture was cooled to room temperature, water and a saturated aqueous solution of sodium dihydrogen phosphate were added thereto. The product was extracted with ethyl acetate. The organic layer was isolated, washed with an saturated aqueous solution of sodium chloride, and dried over magnesium sulfate. The desiccant was removed by filtration. The filtrate was concentrated under reduced pressure, and the resulting residue was purified by silica gel column chromatography (amino silica gel; dichloromethane/methanol=100/5) to give [5-amino-1-(6-fluoro-2-methyl-1H-benzimidazol-5-yl)-1H-pyrazol-4-yl]-(1H-indol-2-yl)methanone as a yellow solid (75 mg, 89.8%).

$^1$H-NMR (DMSO-D$_6$) δ: 12.60 (1.0H, brs), 11.70 (1.0H, brs), 8.31 (1.0H, s), 7.69 (1.0H, d, J=7.6 Hz), 7.62 (1.0H, d, J=6.8 Hz), 7.55 (1.0H, d, J=10.7 Hz), 7.50-7.45 (2.0H, m), 7.25 (1.0H, dd, J=7.6, 7.6 Hz), 7.08 (1.0H, dd, J=7.6, 7.6 Hz), 7.02 (2.0H, brs), 2.53 (3.0H, s)

ESI (LC-MS positive mode) m/z 375 [(M+H)$^+$]

The compounds of Examples 37 to 63 listed in Table 2 were synthesized by the same method as in Examples 36.

TABLE 2

| Example | Structure | Compound name |
|---|---|---|
| 37 | 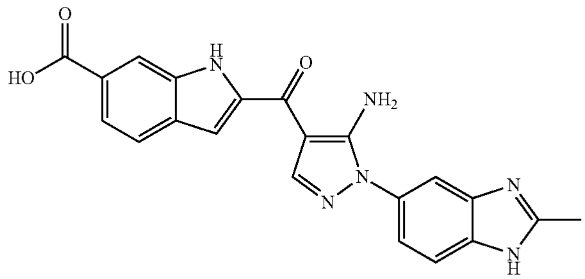 [SMILES: Cc1nc2cc(-n3ncc(C(=O)c4cc5ccc(C(=O)O)cc5[nH]4)c3N)ccc2[nH]1] | 2-[5-amino-1-(2-methyl-1H-benzimidazol-5-yl)-1H-pyrazole-4-carbonyl]-1H-indole-6-carboxylic acid |
| 38 | 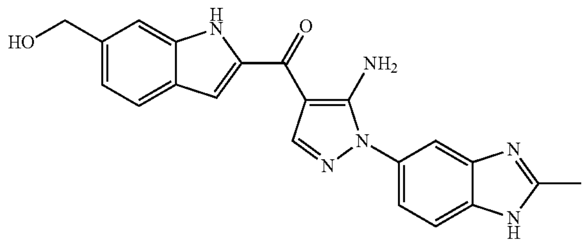 [SMILES: Cc1nc2cc(-n3ncc(C(=O)c4cc5ccc(CO)cc5[nH]4)c3N)ccc2[nH]1] | [5-amino-1-(2-methyl-1H-benzimidazol-5-yl)-1H-pyrazol-4-yl]-(6-hydroxymethyl-1H-indol-2-yl)-methanone |
| 39 | 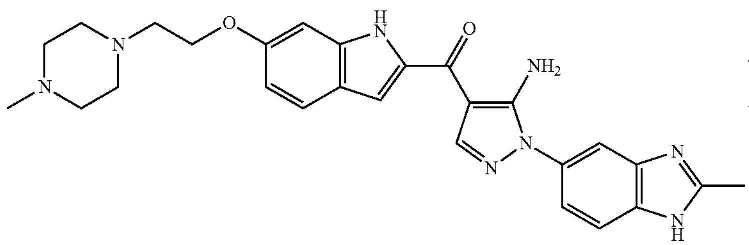 | [5-amino-1-(2-methyl-1H-benzimidazol-5-yl)-1H-pyrazol-4-yl]-{6-[2-(4-methyl-piperazin-1-yl)-ethoxy]-1H-indol-2-yl}-methanone |
| 40 | 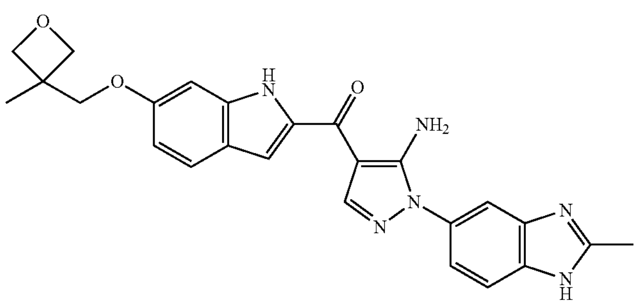 | [5-amino-1-(2-methyl-1H-benzimidazol-5-yl)-1H-pyrazol-4-yl]-[6-(3-methyl-oxetan-3-ylmethoxy)-1H-indol-2-yl]-methanone |
| 41 | 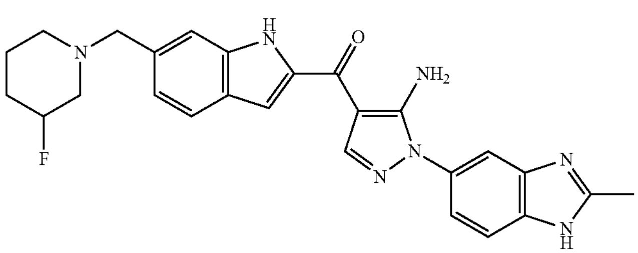 [SMILES: Cc1nc2cc(-n3ncc(C(=O)c4cc5ccc(CN6CCCC(F)C6)cc5[nH]4)c3N)ccc2[nH]1] | [5-amino-1-(2-methyl-1H-benzimidazol-5-yl)-1H-pyrazol-4-yl]-[6-(3-fluoro-piperidin-1-ylmethyl)-1H-indol-2-yl]-methanone |
| 42 | 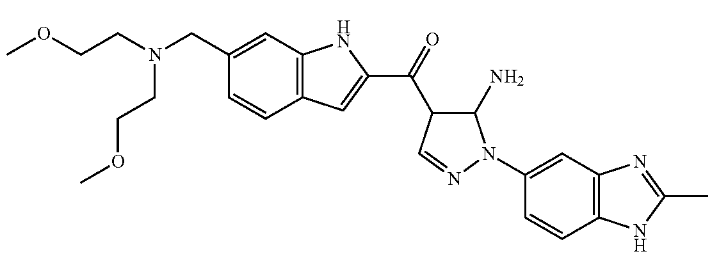 | [5-amino-1-(2-methyl-1H-benzimidazol-5-yl)-1H-pyrazol-4-yl]-(6-[bis(2-methoxy-ethyl)-amino]-methyl}-1H-indol-2-yl)-methanone |

TABLE 2-continued

| | | |
|---|---|---|
| 43 | | [5-amino-1-(2-methyl-1H-benzimidazol-5-yl)-1H-pyrazol-4-yl]-{6-[(methyl-prop-2-ynyl-amino)-methyl]-1H-indol-2-yl}-methanone |
| 44 | | [5-amino-1-(2-methyl-1H-benzimidazol-5-yl)-1H-pyrazol-4-yl]-[6-(3,3-difluoro-pyrrolidin-1-ylmethyl)-1H-indol-2-yl]-methanone |
| 45 | | [5-amino-1-(2-methyl-1H-benzimidazol-5-yl)-1H-pyrazol-4-yl]-[6-(2,5-dimethyl-pyrrolidin-1-ylmethyl)-1H-indol-2-yl]-methanone |
| 46 | | [5-amino-1-(2-methyl-1H-benzimidazol-5-yl)-1H-pyrazol-4-yl]-[6-(3,3-difluoro-piperidin-1-ylmethyl)-1H-indol-2-yl]-methanone |
| 47 | | [5-amino-1-(2-methyl-1H-benzimidazol-5-yl)-1H-pyrazol-4-yl]-[6-((S)-3-methyl-morpholin-4-ylmethyl)-1H-indol-2-yl]-methanone |
| 48 | | [5-amino-1-(2-methyl-1H-benzimidazol-5-yl)-1H-pyrazol-4-yl]-(6-bromo-1H-indol-2-yl)-methanone |

TABLE 2-continued

| 49 | 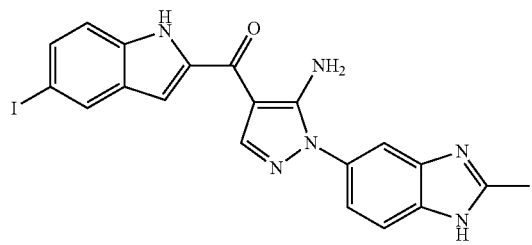 [SMILES: Cc1nc2cc(-n3ncc(C(=O)c4cc5cc(I)ccc5[nH]4)c3N)ccc2[nH]1] | [5-amino-1-(2-methyl-1H-benzimidazol-5-yl)-1H-pyrazol-4-yl]-(5-iodo-1H-indol-2-yl)-methanone |
| 50 | 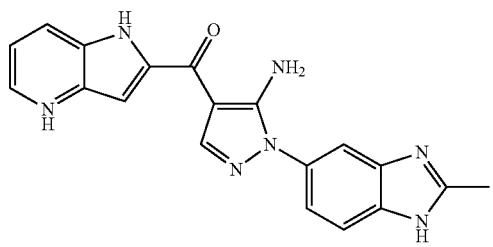 [SMILES: Cc1nc2cc(-n3ncc(C(=O)c4cc5ncccc5[nH]4)c3N)ccc2[nH]1] | [5-amino-1-(2-methyl-1H-benzimidazol-5-yl)-1H-pyrazol-4-yl]-(1H-pyrrolo[3,2-b]pyridin-2-yl)-methanone |
| 51 | 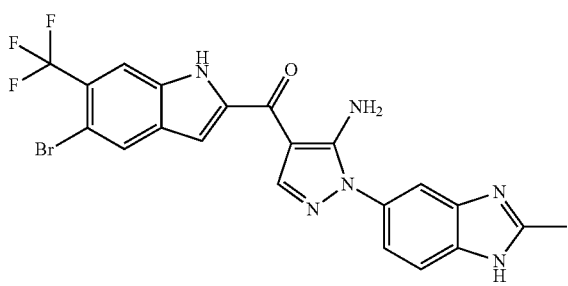 [SMILES: Cc1nc2cc(-n3ncc(C(=O)c4cc5cc(Br)c(C(F)(F)F)cc5[nH]4)c3N)ccc2[nH]1] | [5-amino-1-(2-methyl-1H-benzimidazol-5-yl)-1H-pyrazol-4-yl]-(5-bromo-6-trifluoromethyl-1H-indol-2-yl)-methanone |
| 52 | 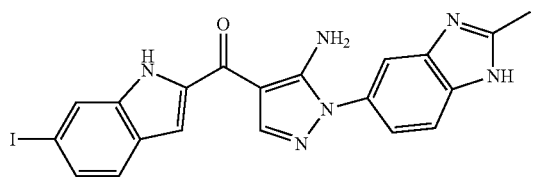 [SMILES: Cc1nc2cc(-n3ncc(C(=O)c4cc5ccc(I)cc5[nH]4)c3N)ccc2[nH]1] | [5-amino-1-(2-methyl-1H-benzimidazol-5-yl)-1H-pyrazol-4-yl]-(6-iodo-1H-indol-2-yl)-methanone |
| 53 | 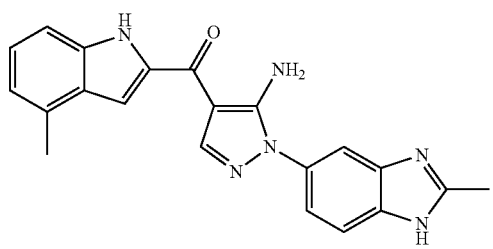 | [5-amino-1-(2-methyl-1H-benzimidazol-5-yl)-1H-pyrazol-4-yl]-(4-methyl-1H-indol-2-yl)-methanone |
| 54 | 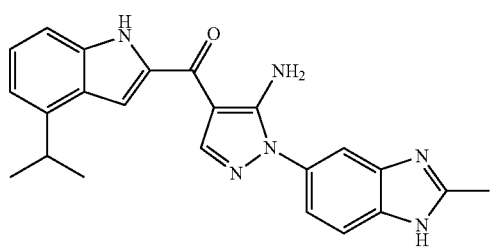 [SMILES: Cc1nc2cc(-n3ncc(C(=O)c4cc5c(C(C)C)cccc5[nH]4)c3N)ccc2[nH]1] | [5-amino-1-(2-methyl-1H-benzimidazol-5-yl)-1H-pyrazol-4-yl]-(4-isopropyl-1H-indol-2-yl)-methanone |

TABLE 2-continued

| # | Structure | Name |
|---|---|---|
| 55 | | [5-amino-1-(2-methyl-1H-benzimidazol-5-yl)-1H-pyrazol-4-yl]-[5-(2-fluoro-phenyl)-1H-indol-2-yl]-methanone |
| 56 | | [5-amino-1-(2-methyl-1H-benzimidazol-5-yl)-1H-pyrazol-4-yl]-(5-benzyl-1H-indol-2-yl)-methanone |
| 57 | | [5-amino-1-(2-methyl-1H-benzimidazol-5-yl)-1H-pyrazol-4-yl]-[5-(2-trifluoromethyl-phenyl)-1H-indol-2-yl]-methanone |
| 58 | | [5-amino-1-(2-methyl-1H-benzimidazol-5-yl)-1H-pyrazol-4-yl]-[5-(3-fluorophenyl)-1H-indol-2-yl]-methanone |
| 59 | | [5-amino-1-(2-methyl-1H-benzimidazol-5-yl)-1H-pyrazol-4-yl]-[5-(3-trifluoromethyl-phenyl)-1H-indol-2-yl]-methanone |
| 60 | | [5-amino-1-(2-methyl-1H-benzimidazol-5-yl)-1H-pyrazol-4-yl]-(4-ethynyl-1H-indol-2-yl)-methanone |

TABLE 2-continued

| | | | |
|---|---|---|---|
| 61 | (structure) | | [5-amino-1-(2-methyl-1H-benzimidazol-5-yl)-1H-pyrazol-4-yl]-(5H-[1,3]dioxolo[4,5-f]indol-6-yl)-methanone |
| 62 | (structure) | | [5-amino-1-(7-fluoro-2-methyl-1H-benzimidazol-5-yl)-1H-pyrazol-4-yl]-(1H-indol-2-yl)-methanone |
| 63 | (structure) | | [5-amino-1-(2-methyl-1H-benzimidazol-5-yl)-1H-pyrazol-4-yl]-[5-(4-trifluoromethyl-phenyl)-1H-indol-2-yl]-methanone |

| Example | m/z | 1H-NMR |
|---|---|---|
| 37 | 401 | 1H-NMR (DMSO-D6) δ: 12.74 (1H, br s), 12.06 (1H, s), 8.36 (1H, s), 8.15 (1H, s), 7.78-7.76 (3H, m), 7.65 (1H, dd, J = 8.4, 1.4 Hz), 7.52 (1H, dd, J = 2.2, 0.8 Hz), 7.49 (1H, br s), 7.17 (2H, br s), 2.67 (3H, s). |
| 38 | 387 | 1H-NMR (CD3OD) δ: 8.32 (1H, s), 7.89 (1H, d, J = 2.2 Hz), 7.85 (1H, d, J = 8.8 Hz), 7.70-7.69 (2H, m), 7.49 (1H, s), 7.36 (1H, s), 7.11 (1H, dd, J = 8.2, 1.1Hz), 4.72 (2H, s), 2.83 (3H, s). |
| 39 | 499 | 1H-NMR (DMSO-D6) δ: 12.51 (1.0H, br s), 11.49 (1.0H, br s), 8.27 (1.0H, s), 7.61-7.55 (3.0H, m), 7.40 (1.0H br s), 7.29 (1.0H, dd, J = 8.3, 2.0 Hz), 6.94-6.93 (3.0H, m), 6.74 (1.0H, dd, J = 8.8, 2.0 Hz), 4.09 (2.0H, t, J = 6.8 Hz), 3.32-3.30 (4.0H, m), 2.72 (2.0H, t, J = 5.8 Hz), 2.53 (3.0H, s), 2.34-2.32 (4.0H, br m), 2.15 (3.0H, s). |
| 40 | 457 | 1H-NMR (DMSO-D6) δ: 12.54 (1.0H, br s), 11.56 (1.0H, br s), 8.28 (1.0H, s), 7.61-7.57 (3.0H, m), 7.41 (1.0H, br s), 7.28 (1.0H, dd, J = 8.3, 2.0 Hz), 6.97-6.95 (3.0H, m), 6.79 (1.0H, dd, J = 8.8, 2.4 Hz), 4.55 (2.0H, d, J = 5.9 Hz), 4.33 (2.0H, d, J = 5.9 Hz), 4.08 (2.0H, s), 2.53 (3.0H, s), 1.40 (3.0H, s). |
| 41 | 472 | 1H-NMR (DMSO-D6) δ: 12.48 (1.0H, br s), 11.65 (1.0H, br s), 8.30 (1.0H, s), 7.64-7.62 (3.0H, m), 7.43 (1.0H, br s), 7.40 (1.0H, br s), 7.29 (10H, dd, J = 8.3, 1.0 Hz), 7.04-7.02 (3.0H, m), 4.69-4.57 (1.0H, m), 3.59 (2.0H, s), 2.74-2.67 (1.0H, m), 2.53 (3.0H, s), 2.61-2.49 (1.0H, m), 2.46-2.33 (1.0H, m), 2.28-2.23 (1.0H, m), 1.83-1.72 (2.0H, m), 1.55-1.43 (2.0H, m). |
| 42 | 502 | 1H-NMR (DMSO-D6) δ: 12.49 (1.0H, br s), 11.62 (1.0H, br s), 8.30 (1.0H, s), 7.62-7.60 (3.0H, m), 7.41 (1.0H, br s), 7.41 (1.0H, br s), 7.29 (1.0H, d, J = 8.3 Hz), 7.05 (1.0H, d, J = 7.8 Hz), 6.99 (1.0H, br s), 6.97 (1.0H, br s), 3.73 (1.0H, s), 3.42 (4.0H, t, J = 6.1Hz), 3.22 (3.0H, s), 3.22 (3.0H, s), 2.66 (4.0H, t, J = 6.1Hz), 2.53 (3.0H, s). |
| 43 | 438 | 1H-NMR (CD3OD) δ: 8.27 (1.0H, s), 7.71-7.65 (3.0H, m), 7.47 (1.0H, s), 7.40-7.36 (2.0H, m), 7.13 (1.0H, dd, J = 8.1, 1.2 Hz), 3.73 (2.0H, s), 3.32-3.30 (2.0H, m), 2.73 (1.0H, t, J = 2.4 Hz), 2.62 (3.0H, s), 2.38 (3.0H, s). |
| 44 | 476 | 1H-NMR (DMSO-D6) δ: 12.47 (1.0H, br s), 11.67 (1.0H, br s), 8.30 (1.0H, s), 7.65-7.63 (3.0H, m), 7.43 (1.0H, br s), 7.42 (1.0H, br s), 7.29 (1.0H, dd, J = 8.5, 1.7 Hz), 7,06-6.99 (3.0H, m), 3.71 (2.0H, s), 2.87 (2.0H, t, J = 13.4 Hz), 2.71 (2.0H, t, J = 7.1Hz), 2.53 (3.0H, s), 2.33-2.20 (2.0H, m). |

TABLE 2-continued

| | | |
|---|---|---|
| 45 | 468 | 1H-NMR (DMSO-D6) δ: 12.47 (1.0H, br s), 11.56 (1.0H, br s), 8.29 (1.0H, s), 7.67-7.59 (3.0H, m), 7.46-7.41 (2.0H, m), 7.30 (1.0H, d, J = 8.8 Hz), 7.11-6.97 (3.0H, m), 3.93-3.51 (2.0H, m), 3.02-2.94 (1.0H, m), 2.63-2.57 (1.0H, m), 2.53 (3.0H, s), 2.00-1.93 (1.0H, m), 1.81-1.76 (1.0H, m), 1.36-1.28 (2.0H, m), 0.97 (3.0H, d, J = 6.1 Hz), 0.96 (3.0H, d, J = 6.1 Hz). |
| 46 | 490 | 1H-NMR (DMSO-D6) δ: 12.47 (1.0H, br s), 11.67 (1.0H, br s), 8.30 (1.0H, s), 7.65-7.62 (3.0H, m), 7.43 (1.0H, br s), 7.41 (1.0H, br s), 7.29 (1.0H, dd, J = 8.8, 2.0 Hz), 7.05-7.00 (3.0H, m), 3.66 (2.0H, s), 2.64 (2.0H, t, J = 12.2 Hz), 2.53 (3.0H, s), 2.44-2.42 (2.0H, m), 1.93-1.83 (2.0H, m), 1.69-1.63 (2.0H, m). |
| 47 | 470 | 1H-NMR (DMSO-D6) δ: 12.47 (1.0H, br s), 11.62 (1.0H, br s), 8.30 (1.0H, s), 7.64-7.58 (3.0H, m), 7.42 (1.0H, br s), 7.42 (1.0H, br s), (1.0H, d, J = 8.8 Hz), 7.07-6.98 (3.0H, m), 4.12-4.09 (1.0H, br m), 3.66-3.60 (2.0H, m), 3.46-3.40 (1.0H, m), 3.20-3.14 (3.0H, m), 2.53 (3.0H, s), 2.44-2.40 (1.0H, m), 2.14-2.07 (1.0H, m), 1.05-1.04 (3.0H, br m). |
| 48 | 435, 437 | 1H-NMR (DMSO-D6) δ: 12.48 (1H, s), 11.86 (1H, s), 8.32 (1H, d, J = 3.1 Hz), 7.68 (1H, d, J = 3.6 Hz), 7.65 (2H, br s), 7.58-7.56 (1H, m), 7.50 (1H, br s), 7.30-7.28 (1H, m), 7.22 (1H, dd, J = 8.6, 1.6 Hz), 7.05 (2H, d, J = 14.2 Hz), 2.53 (3H, s). |
| 49 | 483 | 1H-NMR (DMSO-D6) δ: 12.45 (1.0H, s), 11.87 (1.0H, s), 8.26 (1.1H, d, J = 4.7 Hz), 8.06 (1.0H, d, J = 1.8 Hz), 7.65 (1.0H, d, J = 8.4 Hz), 7.56 (1.0H, t, J = 4.1 Hz), 7.50 (1.0H, dd, J = 8.6, 1.6 Hz), 7.39 (1.0H, s), 7.33 (1.0H, d, J = 8.6 Hz), 7.28 (1.0H, m), 7.01 (2.0H, m), 2.53 (3.0H, d, J = 1.0 Hz). |
| 50 | 358 | 1H-HMR (CD3OD) δ: 9.02-8.98 (1H, m), 8.31 (1H, s), 8.25 (1H, d, J = 5.9 Hz), 7.70-7.65 (2H, m), 7.59-7.56 (1H, m), 7.51 (1H, d, J = 5.9 Hz), 7.39 (1H, dd, J = 8.8, 2.0 Hz), 2.62 (3H, s). |
| 51 | 503, 505 | 1H-NMR (DMSO-D6) δ: 12.49 (1.0H, br s), 12.33 (1.0H, br s), 8.30 (1.0H, s), 8.17 (1.0H, s), 7.94 (1.0H, s), 7.62-7.52 (3.0H, m), 7.29 (1.0H, dd, J = 8.5, 1.7 Hz), 7.12 (2.0H, s), 2.53 (3.0H, s). |
| 52 | 483 | 1H-NMR (DMSO-D6) δ: 12.43 (1.0H, s), 11.77 (1.0H, s), 8.30 (1.0H, s), 7.86 (1.0H, s), 7.58 (3.0H, m), 7.46 (1.0H, s), 7.36 (1.0H, dd, J = 8.4, 1.6 Hz), 7.29 (1.0H, m), 7.05-6.90 (2.0H, m), 2.53 (3.0H, s). |
| 53 | 371 | 1H-NMR (DMSO-D6) δ: 12.47 (1.0H, br s), 11.66 (1.0H, br s), 8.40 (1.0H, s), 7.62-7.60 (2.0H, m), 7.46 (1.0H, s), 7.30-7.28 (2.0H, m), 7.14 (1.0H, dd, J = 7.3, 7.3 Hz), 6.99 (2.0H, br s), 6.86 (1.0H, d, J = 7.3 Hz), 2.57 (3.0H, s), 2.53 (3.0H, s). |
| 54 | 399 | 1H-NMR (DMSO-D6) δ: 12.47 (1.0H, br s), 11.69 (1.0H, br s), 8.23 (1.0H, s), 7.64-7.59 (2.0H, m), 7.29 (1.0H, dd, J = 8.3, 1.5 Hz), 7.25 (1.0H, br s), 7.15 (1.0H, dd, J = 8.0, 8.0 Hz), 7.04-6.97 (3.0H, m), 6.55 (1.0H, d, J = 8.0 Hz), 4.79-4.73 (1.0H, m), 2.53 (3.0H, s), 1.38 (6.0H, d, J = 5.9 Hz), |
| 55 | 451 | 1H-NMR (DMSO-D6) δ: 12.45 (1H, br s), 11.82 (1H, s), 8.32 (1H, d, J = 4.9 Hz], 7.85 (1H, s), 7.65-7.63 (1H, m), 7.58-7.52 (4H, m), 7.44-7.42 (1H, m), 7.39-7.35 (1H, m), 7.31-7.28 (3H, m), 7.04 (1H, br s), 6.99 (1H, br s), 2.52 (3H, s). |
| 56 | 447 | 1H-NMR (DMSO-D6) δ: 12.47 (1H, br s), 11.62 (1H, br s), 8.29 (1H, s), 7.69-7.53 (2H, m), 7.52-7.48 (1H, m), 7.42-7.36 (2H, m), 7.32-7.23 (5H, m), 7.20-7.12 (2H, m), 7.06-6.93 (2H, m), 4.02 (2H, s), 2.53 (3H, s). |
| 57 | 501 | 1H-NMR (DMSO-D6) δ: 12.48 (1H, br s), 11.82 (1H, s), 8.31 (1H, s), 7.83-7.81 (1H, m), 7.72-7.70 (1H, m), 7.60-7.57 (4H, m), 7.52-7.50 (2H, m), 7.45 (1H, d, J = 7.2 Hz), 7.28 (1H, dd, J = 8.4, 2.0 Hz), 7.19-7.17 (1H, m), 7.01 (2H, br s), 2.52 (3H, s). |
| 58 | 451 | 1H-NMR (DMSO-D6) δ: 12.47 (1H, s), 11.81 (1H, s), 8.30 (1H, s), 7.99 (1H, s), 7.61-7.46 (8H, m), 7.28 (1H, dd, J = 8.4, 1.8 Hz), 7.15-7.12 (1H, m), 7.01 (2H, br s), 2.52 (3H, s). |
| 59 | 501 | 1H-NMR (DMSO-D6) δ: 12.48 (1H, br s), 11.84 (1H, s), 8.29 (1H, s), 8.05 (1H, d, J = 1.3 Hz), 8.02-8.00 (1H, m), 7.97 (1H, s), 7.72-7.58 (5H, m), 7.51 (1H, s), 7.28 (1H, dd, J = 8.4, 2.2 Hz), 7.02 (2H, s), 2.62 (3H, s). |
| 60 | 381 | 1H-NMR (DMSO-D6) δ: 12.47 (1.0H, br s), 12.01 (1.0H, br s), 8.24 (1.0H, s), 7.62-7.60 (2.0H, m), 7.57-7.53 (1.0H, m), 7.31-7.24 (4.0H, m), 7.03 (2.0H, br s), 4.44 (1.0H, s), 2.53 (3.0H, s). |
| 61 | 401 | 1H-NMR (DMSO-D6) δ: 12.46 (1H, s), 11.52 (1H, s), 8.23 (1H, s), 7.59-7.68 (2H, m), 732 (1H, s), 7.27 (1H, dd, J = 8.6, 2.0 Hz), 7.07 (1H, s), 8.92 (2H, br s), 8.90 (1H, s), 5.99 (2H, s), 2.52 (3H, s). |
| 62 | 375 | 1H-NMR (DMSO-D6) δ: 12.81 (1.0H, s), 11.68 (1.0H, s), 8.33 (1.0H, s), 7 .70 (1.0H, d, J = 8.0 Hz), 7.50-7.40 (3.0H, m), 7.30-7.22 (1.0H, m), 7.18 (1.0H, d, J = 11.2 Hz), 7.09 (3.0H, m), 2.55 (3.0H, s). |
| 63 | 501 | 1H-NMR (DMSO-D6) δ: 12.46 (1H, d, J = 5.3 Hz), 11.86 (1H, s), 8.31 (1H, d, J = 5.3 Hz), 8.05 (1H, s), 7.92 (2H, d, J = 9.4 Hz), 7.80 (2H, d, J = 8.4 Hz), 7.63-7.57 (4H, m), 7.53 (1H, s), 7.30-7.27 (1H, m), 7.06 (1H, s), 7.00 (1H, s), 2.52 (3H, s). |

Example 64

Synthesis of [5-amino-1-(2-methyl-1H-benzimidazol-5-yl)-1H-pyrazol-4-yl]-(5-butoxy-1H-indol-2-yl)-methanone

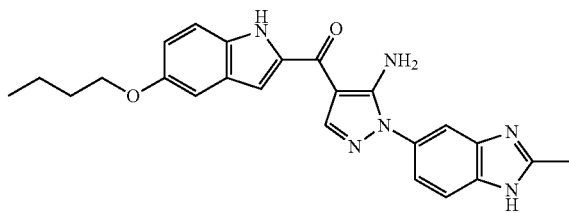 [SMILES: CCCCOc1ccc2[nH]c(C(=O)c3cnn(-c4ccc5[nH]c(C)nc5c4)c3N)cc2c1]

A mixture consisting of [5-amino-1-(2-methyl-1H-benzimidazol-5-yl)-1H-pyrazol-4-yl]-[5-butoxy-1-(toluene-4-sulfonyl)-1H-indol-2-yl]-methanone (70 mg), dioxane (3 ml), and an aqueous solution of 5 M sodium hydroxide (300 μl) was stirred under reflux for two hours. The reaction mixture was cooled in an ice bath, and acidified with an aqueous solution of 5 M hydrochloric acid. The solvent was distilled off under reduced pressure. Water was added to the residue obtained by concentration under reduced pressure. The solid was collected by filtration, washed with water, and dried to give [5-amino-1-(2-methyl-1H-benzimidazol-5-yl)-1H-pyrazol-4-yl]-(5-butoxy-1H-indol-2-yl)-methanone (35 mg, 65%).

$^1$H-NMR (DMSO-$D_6$) δ: 12.45 (1H, s), 11.54 (1H, d, J=1.8 Hz), 8.25 (1H, s), 7.65-7.63 (1H, brm), 7.57-7.55 (1H, brm), 7.36 (1H, d, J=8.8 Hz), 7.32 (1H, d, J=1.8 Hz), 7.30-7.28 (1H, brm), 7.12 (1H, d, J=2.4 Hz), 7.01 (1H, brs), 6.95 (1H, brs), 6.90 (1H, dd, J=8.8, 2.4 Hz), 3.98 (2H, t, J=6.4 Hz), 2.53 (3H, s), 1.76-1.69 (2H, m), 1.51-1.44 (2H, m), 0.95 (3H, t, J=7.3 Hz)

ESI (LC-MS positive mode) m/z 429 [(M+H)$^+$]

The compounds of Examples 65 to 89, and 204 to 239 listed in Table 3 were synthesized by the same method as in Example 64.

TABLE 3

| Example | Structure | Compound name |
|---|---|---|
| 65 | 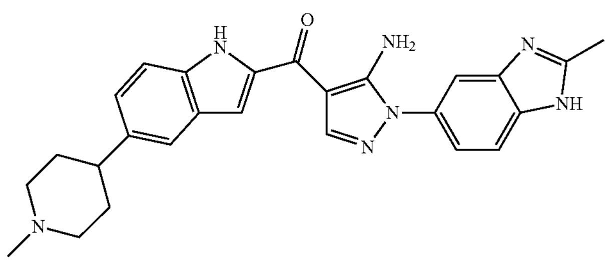 | [5-amino-1-(2-methyl-1H-benzimidazol-5-yl)-1H-pyrazol-4-yl]-[5-(1-methyl-piperidin-4-yl)-1H-indol-2-yl] methanone |
| 66 | 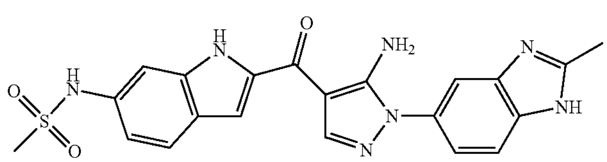 | N-{2-[5-amino-1-(2-methyl-1H-benzimidazol-5-yl)-1H-pyrazole-4-carbonyl]-1H-indol-6-yl}-methanesulfonamide |
| 67 | 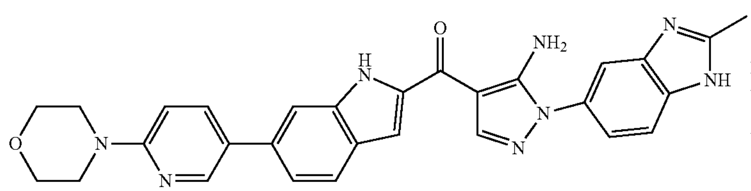 [SMILES: Cc1nc2cc(-n3ncc(C(=O)c4cc5ccc(-c6ccc(N7CCOCC7)nc6)cc5[nH]4)c3N)ccc2[nH]1] | [5-amino-1-(2-methyl-1H-benzimidazol-5-yl)-1H-pyrazol-4-yl]-[6-(6-morpholin-4-yl-pyridin-3-yl)-1H-indol-2-yl]-methanone |
| 68 | 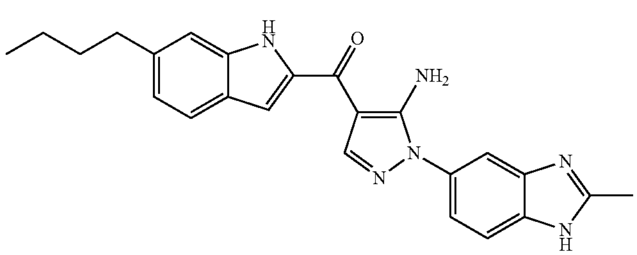 [SMILES: CCCCc1ccc2cc(C(=O)c3cnn(-c4ccc5[nH]c(C)nc5c4)c3N)[nH]c2c1] | [5-amino-1-(2-methyl-1H-benzimidazol-5-yl)-1H-pyrazol-4-yl]-(6-butyl-1H-indol-2-yl)-methanone |

TABLE 3-continued

| | | |
|---|---|---|
| 69 | 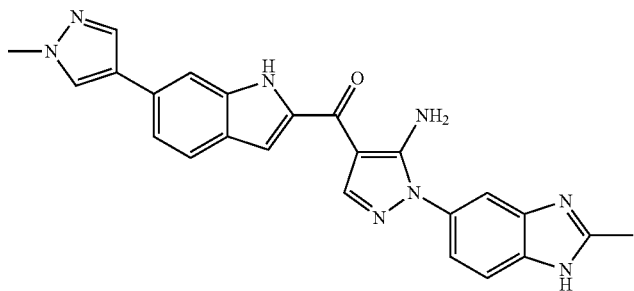 | [5-amino-1-(2-methyl-1H-benzimidazol-5-yl)-1H-pyrazol-4-yl]-[6-(1-methyl-1H-pyrazol-4-yl)-1H-indol-2-yl]-methanone |
| 70 | 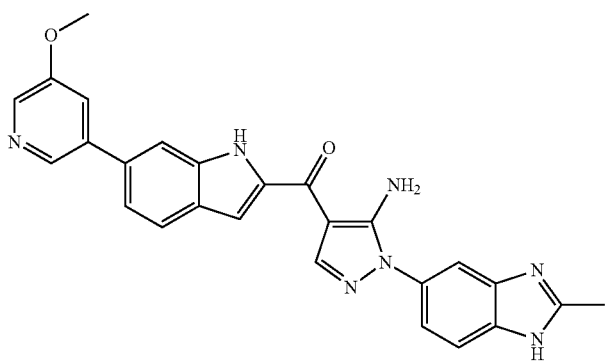 [SMILES: COc1cncc(-c2ccc3cc(C(=O)c4cnn(-c5ccc6[nH]c(C)nc6c5)c4N)[nH]c3c2)c1] | [5-amino-1-(2-methyl-1H-benzimidazol-5-yl)-1H-pyrazol-4-yl]-[6-(5-methoxy-pyridin-3-yl)-1H-indol-2-yl]-methanone |
| 71 | 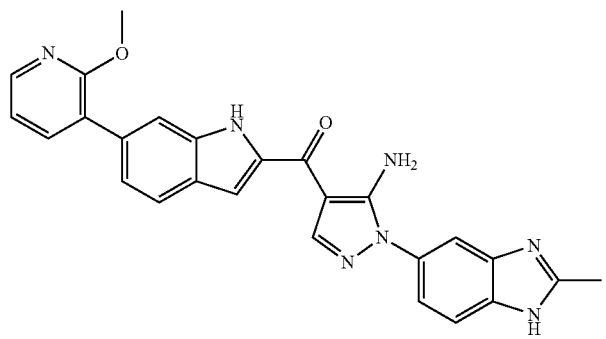 [SMILES: COc1ncccc1-c1ccc2cc(C(=O)c3cnn(-c4ccc5[nH]c(C)nc5c4)c3N)[nH]c2c1] | [5-amino-1-(2-methyl-1H-benzimidazol-5-yl)-1H-pyrazol-4-yl]-[6-(2-methoxy-pyridin-3-yl)-1H-indol-2-yl]-methanone |
| 72 | 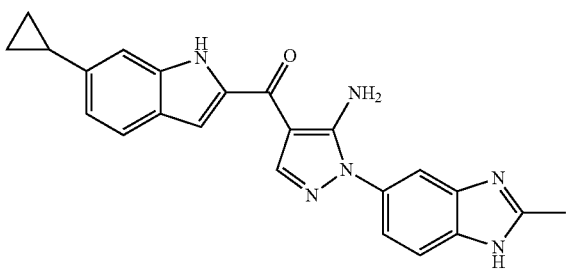 [SMILES: Cc1nc2cc(-n3ncc(C(=O)c4cc5ccc(C6CC6)cc5[nH]4)c3N)ccc2[nH]1] | [5-amino-1-(2-methyl-1H-benzimidazol-5-yl)-1H-pyrazol-4-yl]-(6-cyclopropyl-1H-indol-2-yl)-methanone |
| 73 | 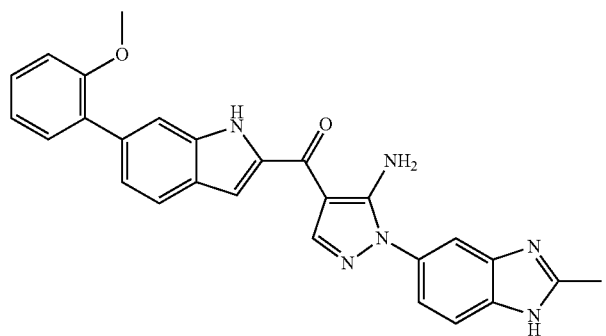 [SMILES: COc1ccccc1-c1ccc2cc(C(=O)c3cnn(-c4ccc5[nH]c(C)nc5c4)c3N)[nH]c2c1] | [5-amino-1-(2-methyl-1H-benzimidazol-5-yl)-1H-pyrazol-4-yl]-[6-(2-methoxy-phenyl)-1H-indol-2-yl]-methanone |

TABLE 3-continued

| 74 | 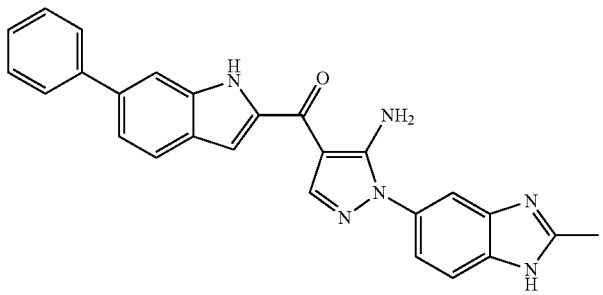 [SMILES: Cc1nc2cc(-n3ncc(C(=O)c4cc5ccc(-c6ccccc6)cc5[nH]4)c3N)ccc2[nH]1] | [5-amino-1-(2-methyl-1H-benzimidazol-5-yl)-1H-pyrazol-4-yl]-(6-phenyl-1H-indol-2-yl)-methanone |
| 75 | 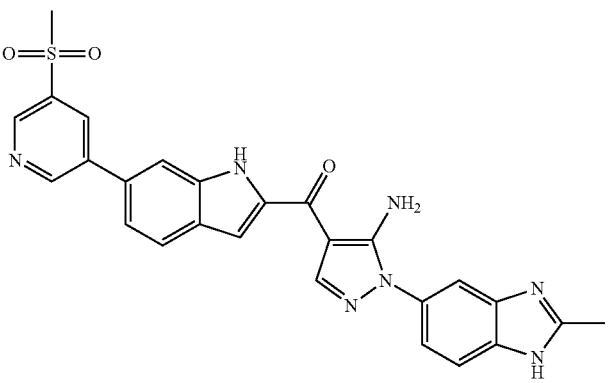 [SMILES: Cc1nc2cc(-n3ncc(C(=O)c4cc5ccc(-c6cncc(S(C)(=O)=O)c6)cc5[nH]4)c3N)ccc2[nH]1] | [5-amino-1-(2-methyl-1H-benzimidazol-5-yl)-1H-pyrazol-4-yl]-[6-(5-methanesulfonyl-pyridin-3-yl)-1H-indol-2-yl]-methanone |
| 76 | 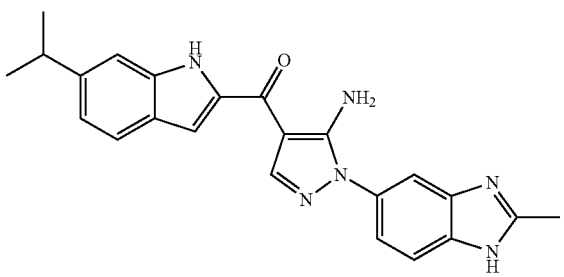 [SMILES: Cc1nc2cc(-n3ncc(C(=O)c4cc5ccc(C(C)C)cc5[nH]4)c3N)ccc2[nH]1] | [5-amino-1-(2-methy)-1H-benzimidazol-5-yl)-1H-pyrazol-4-yl]-(6-isopropyl-1H-indol-2-yl)-methanone |
| 77 | 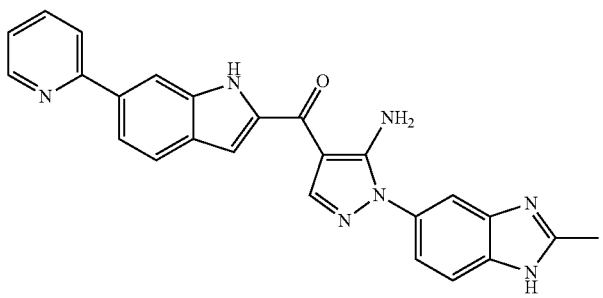 [SMILES: Cc1nc2cc(-n3ncc(C(=O)c4cc5ccc(-c6ccccn6)cc5[nH]4)c3N)ccc2[nH]1] | [5-amino-1-(2-methyl-1H-benzimidazol-5-yl)-1H-pyrazol-4-yl]-(6-pyridin-2-yl-1H-indol-2-yl)-methanone |
| 78 | 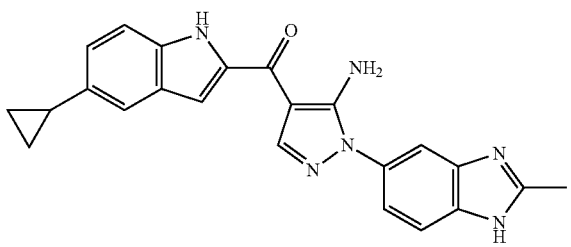 [SMILES: Cc1nc2cc(-n3ncc(C(=O)c4cc5cc(C6CC6)ccc5[nH]4)c3N)ccc2[nH]1] | [5-amino-1-(2-methyl-1H-benzimidazol-5-yl)-1H-parazol-4-yl]-(5-cyclopropyl-1H-indol-2-yl)-methanone |

TABLE 3-continued

| # | Structure | Name |
|---|---|---|
| 79 | 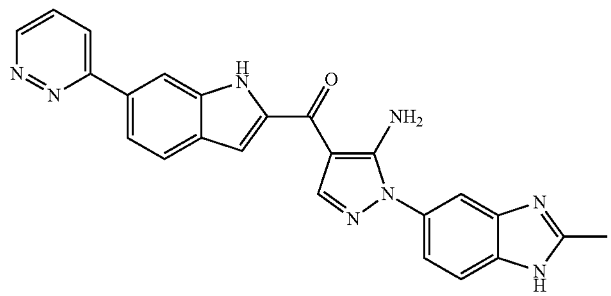 [SMILES: Cc1nc2cc(-n3ncc(C(=O)c4cc5ccc(-c6cccnn6)cc5[nH]4)c3N)ccc2[nH]1] | [5-amino-1-(2-methyl-1H-benzimidazol-5-yl)-1H-pyrazol-4-yl]-(6-pyridazin-3-yl-1H-indol-2-yl)-methanone |
| 80 | 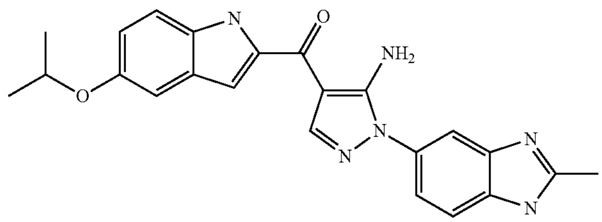 [SMILES: Cc1nc2cc(-n3ncc(C(=O)c4cc5cc(OC(C)C)ccc5[nH]4)c3N)ccc2[nH]1] | [5-amino-1-(2-methyl-1H-benzimidazol-5-yl)-1H-pyrazol-4-yl]-(5-isopropoxy-1H-indol-2-yl)-methanone |
| 81 | 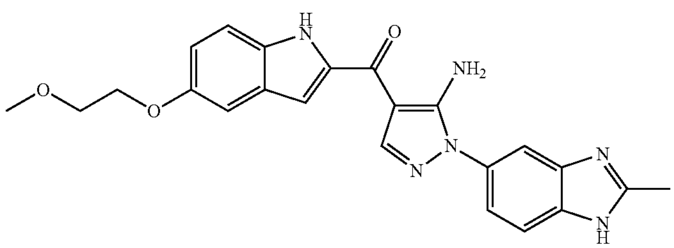 | [5-amino-1-(2-methyl-1H-benzimidazol-5-yl)-1H-pyrazol-4-yl]-[5-(2-methoxy-ethoxy)-1H-indol-2-yl]-methanone |
| 82 | 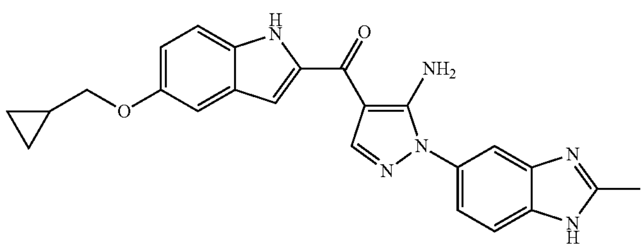 [SMILES: Cc1nc2cc(-n3ncc(C(=O)c4cc5cc(OCC6CC6)ccc5[nH]4)c3N)ccc2[nH]1] | [5-amino-1-(2-methyl-1H-benzimidazol-5-yl)-1H-pyrazol-4-yl]-(5-cyclopropylmethoxy-1H-indol-2-yl)-methanone |
| 83 | 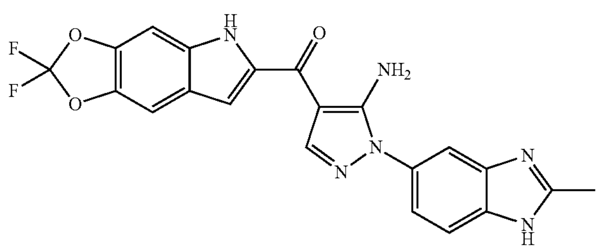 [SMILES: Cc1nc2cc(-n3ncc(C(=O)c4cc5cc6c(cc5[nH]4)OC(F)(F)O6)c3N)ccc2[nH]1] | [5-amino-1-(2-methyl-1H-benzimidazol-5-yl)-1H-pyrazol-4-yl]-(2,2-difluoro-5H-[1,3]dioxolo[4,5-f]indol-6-yl)-methanone |
| 84 | 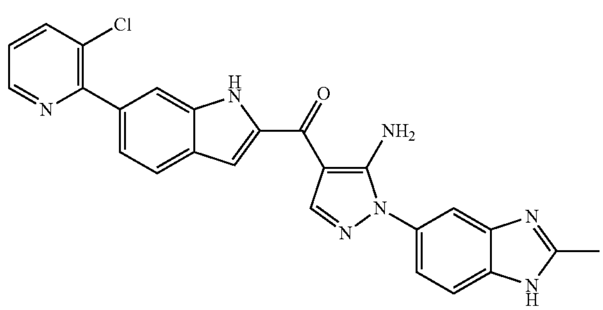 [SMILES: Cc1nc2cc(-n3ncc(C(=O)c4cc5ccc(-c6ncccc6Cl)cc5[nH]4)c3N)ccc2[nH]1] | [5-amino-1-(2-methyl-1H-benzimidazol-5-yl)-1H-pyrazol-4-yl]-[6-(3-chloro-pyridin-2-yl)-1H-indol-2-yl]-methanone |

TABLE 3-continued

| | | |
|---|---|---|
| 85 | | [5-amino-1-(2-methyl-1H-benzimidazol-5-yl)-1H-pyrazol-4-yl]-[6-(5-fluoro-pyridin-2-yl)-1H-indol-2-yl]-methanone |
| 86 | | [5-amino-1-(2-methyl-1H-benzimidazol-5-yl)-1H-pyrazol-4-yl]-[6-(6-morpholin-4-yl-pyridazin-3-yl)-1H-indol-2-yl]-methanone |
| 87 | | [5-amino-1-(2-methyl-1H-benzimidazol-5-yl)-1H-pyrazol-4-yl]-(5-chloro-6-cyclopropylmethoxy-1H-indol-2-yl)-methanone |
| 88 | | [5-amino-1-(2-methyl-1H-benzimidazol-5-yl)-1H-pyrazol-4-yl]-[6-(2,4-difluoro-phenyl)-1H-indol-2-yl]-methanone |
| 89 | | [5-amino-1-(2-methyl-1H-benzimidazol-5-yl)-1H-pyrazol-4-yl]-(6-pyridazin-4-yl-1H-indol-2-yl)-methanone |

TABLE 3-continued

| 204 | 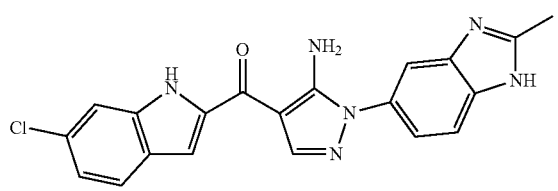 [SMILES: Cc1nc2cc(-n3ncc(C(=O)c4cc5ccc(Cl)cc5[nH]4)c3N)ccc2[nH]1] | [5-amino-1-(2-methyl-3H-benzimidazol-5-yl)-1H-pyrazol-4-yl]-(6-chloro-1H-indol-2-yl)-methanone |
| 205 | 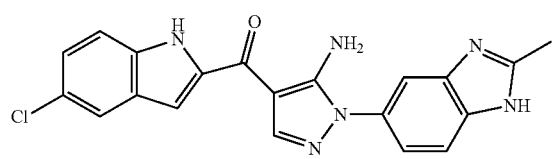 [SMILES: Cc1nc2cc(-n3ncc(C(=O)c4cc5cc(Cl)ccc5[nH]4)c3N)ccc2[nH]1] | [5-amino-1-(2-methyl-1H-benzimidazol-5-yl)-1H-pyrazol-4-yl]-(5-chloro-1H-indol-2-yl)-methanone |
| 206 | 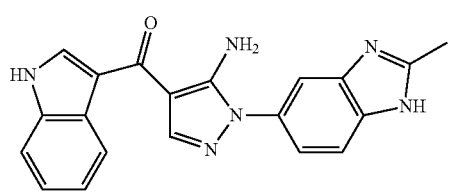 [SMILES: Cc1nc2cc(-n3ncc(C(=O)c4c[nH]c5ccccc45)c3N)ccc2[nH]1] | [5-amino-1-(2-methyl-1H-benzimidazol-5-yl)-1H-pyrazol-4-yl]-(1H-indol-3-yl)-methanone |
| 207 | 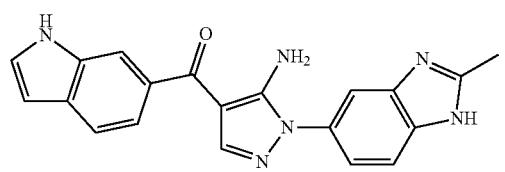 [SMILES: Cc1nc2cc(-n3ncc(C(=O)c4ccc5cc[nH]c5c4)c3N)ccc2[nH]1] | [5-amino-1-(2-methyl-1H-benzimidazol-5-yl)-1H-pyrazol-4-yl]-(1H-indol-6-yl)-methanone |
| 208 | 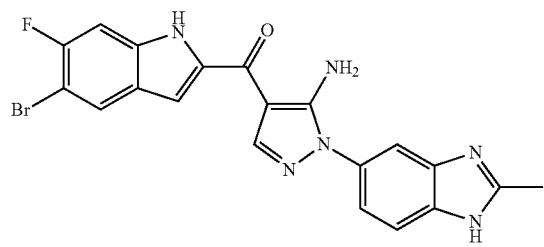 [SMILES: Cc1nc2cc(-n3ncc(C(=O)c4cc5cc(Br)c(F)cc5[nH]4)c3N)ccc2[nH]1] | [5-amino-1-(2-methyl-1H-benzimidazol-5-yl)-1H-pyrazol-4-yl]-(5-bromo-6-fluoro-1H-indol-2-yl)-methanone |
| 209 | 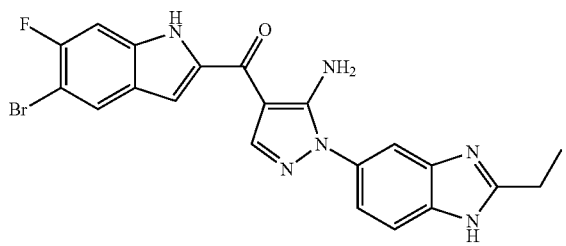 [SMILES: CCc1nc2cc(-n3ncc(C(=O)c4cc5cc(Br)c(F)cc5[nH]4)c3N)ccc2[nH]1] | [5-amino-1-(2-ethyl-1H-benzimidazol-5-yl)-1H-pyrazol-4-yl]-(5-bromo-6-fluoro-1H-indol-2-yl)-methanone |
| 210 | 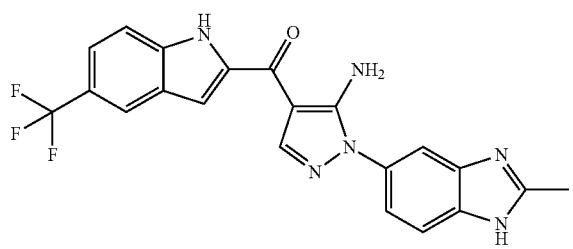 [SMILES: Cc1nc2cc(-n3ncc(C(=O)c4cc5cc(C(F)(F)F)ccc5[nH]4)c3N)ccc2[nH]1] | [5-amino-1-(2-methyl-1H-benzimidazol-5-yl)-1H-pyrazol-4-yl]-(5-trifluoromethyl-1H-indol-2-yl)-methanone |

TABLE 3-continued

| | | |
|---|---|---|
| 211 | 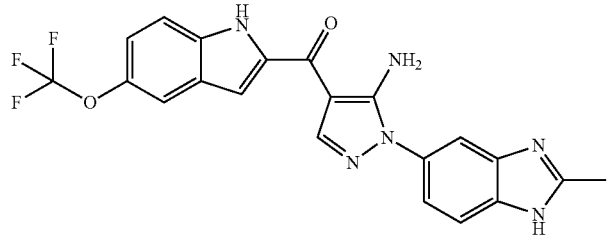 [SMILES: Cc1nc2cc(-n3ncc(C(=O)c4cc5cc(OC(F)(F)F)ccc5[nH]4)c3N)ccc2[nH]1] | [5-amino-1-(2-methyl-1H-benzimidazol-5-yl)-1H-pyrazol-4-yl]-(5-trifluoromethoxy-1H-indol-2-yl)-methanone |
| 212 | 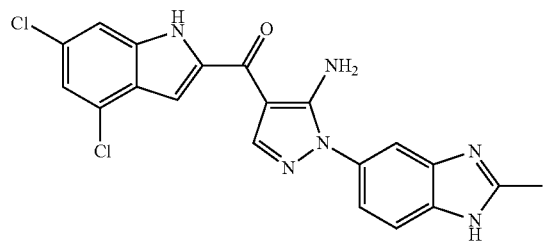 [SMILES: Cc1nc2cc(-n3ncc(C(=O)c4cc5c(Cl)cc(Cl)cc5[nH]4)c3N)ccc2[nH]1] | [5-amino-1-(2-methyl-1H-benzimidazol-5-yl)-1H-pyrazol-4-yl]-(4,6-dichloro-1H-indol-2-yl)-methanone |
| 213 | 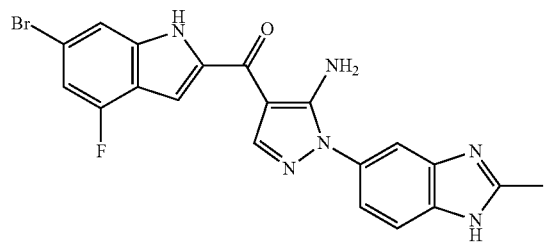 | [5-amino-1-(2-methyl-1H-benzimidazol-5-yl)-1H-pyrazol-4-yl]-(6-bromo-4-fluoro-1H-indol-2-yl)-methanone |
| 214 | 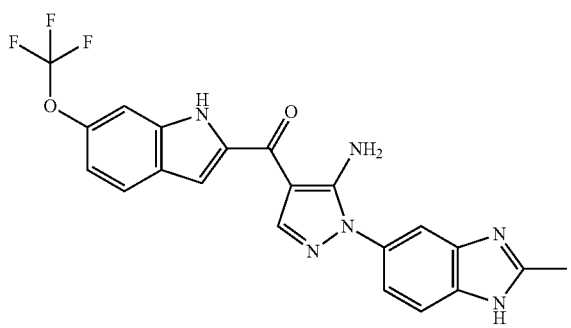 [SMILES: Cc1nc2cc(-n3ncc(C(=O)c4cc5ccc(OC(F)(F)F)cc5[nH]4)c3N)ccc2[nH]1] | [5-amino-1-(2-methyl-1H-benzimidazol-5-yl)-1H-pyrazol-4-yl]-(6-trifluoromethoxy-1H-indol-2-yl)-methanone |
| 215 | 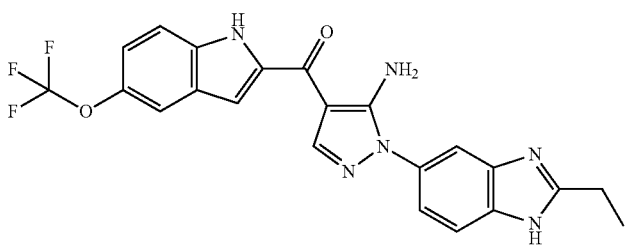 [SMILES: CCc1nc2cc(-n3ncc(C(=O)c4cc5cc(OC(F)(F)F)ccc5[nH]4)c3N)ccc2[nH]1] | [5-amino-1-(2-ethyl-1H-benzimidazol-5-yl)-1H-pyrazol-4-yl]-(5-trifluoromethoxy-1H-indol-2-yl)-methanone |
| 216 | 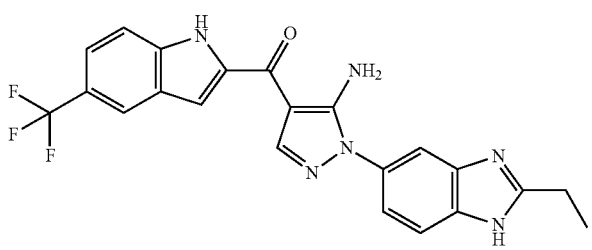 [SMILES: CCc1nc2cc(-n3ncc(C(=O)c4cc5cc(C(F)(F)F)ccc5[nH]4)c3N)ccc2[nH]1] | [5-amino-1-(2-ethyl-1H-benzimidazol-5-yl)-1H-pyrazol-4-yl]-(5-trifluoromethyl-1H-indol-2-yl)-methanone |

TABLE 3-continued

| | | |
|---|---|---|
| 217 | 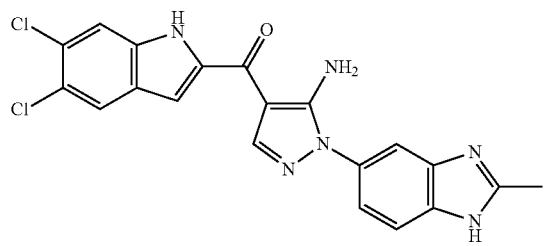 [SMILES: Cc1nc2cc(-n3ncc(C(=O)c4cc5cc(Cl)c(Cl)cc5[nH]4)c3N)ccc2[nH]1] | [5-amino-1-(2-methyl-1H-benzimidazol-5-yl)-1H-pyrazol-4-yl]-(5,6-dichloro-1H-indol-2-yl)-methanone |
| 218 | 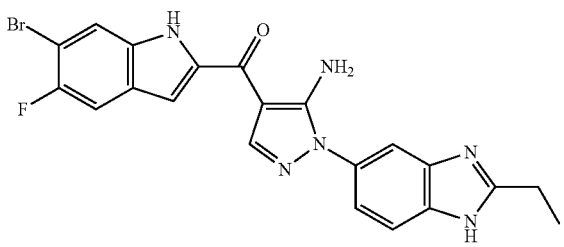 [SMILES: CCc1nc2cc(-n3ncc(C(=O)c4cc5cc(F)c(Br)cc5[nH]4)c3N)ccc2[nH]1] | [5-amino-1-(2-ethyl-1H-benzimidazol-5-yl)-1H-pyrazol-4-yl]-(6-bromo-5-fluoro-1H-indol-2-yl)-methanone |
| 219 | 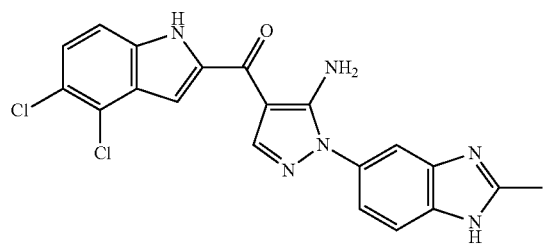 [SMILES: Cc1nc2cc(-n3ncc(C(=O)c4cc5c(Cl)c(Cl)ccc5[nH]4)c3N)ccc2[nH]1] | [5-amino-1-(2-methyl-1H-benzimidazol-5-yl)-1H-pyrazol-4-yl]-(4,5-dichloro-1H-indol-2-yl)-methanone |
| 220 | 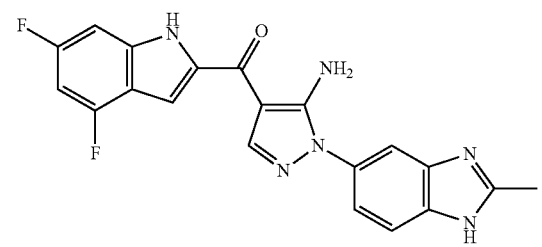 [SMILES: Cc1nc2cc(-n3ncc(C(=O)c4cc5c(F)cc(F)cc5[nH]4)c3N)ccc2[nH]1] | [5-amino-1-(2-methyl-1H-benzimidazol-5-yl)-1H-pyrazol-4-yl]-(4,6-difluoro-1H-indol-2-yl)-methanone |
| 221 | 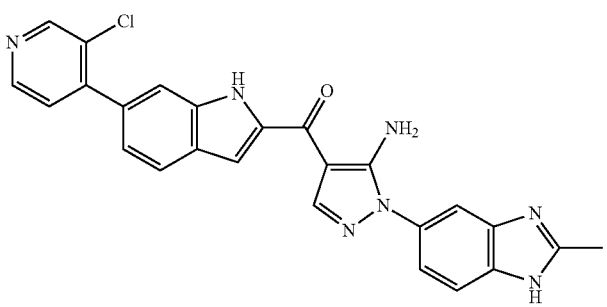 [SMILES: Cc1nc2cc(-n3ncc(C(=O)c4cc5ccc(-c6ccncc6Cl)cc5[nH]4)c3N)ccc2[nH]1] | [5-amino-1-(2-methyl-1H-benzimidazol-5-yl)-1H-pyrazol-4-yl]-[6-(3-chloro-pyridin-4-yl)-1H-indol-2-yl]-methanone |
| 222 | 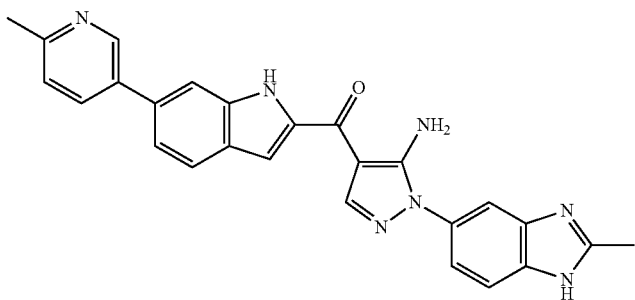 | [5-amino-1-(2-methyl-1H-benzimidazol-5-yl)-1H-pyrazol-4-yl]-[6-(6-methyl-pyridine-3-yl)-1H-indol-2-yl]-methanone |

TABLE 3-continued

| 223 | 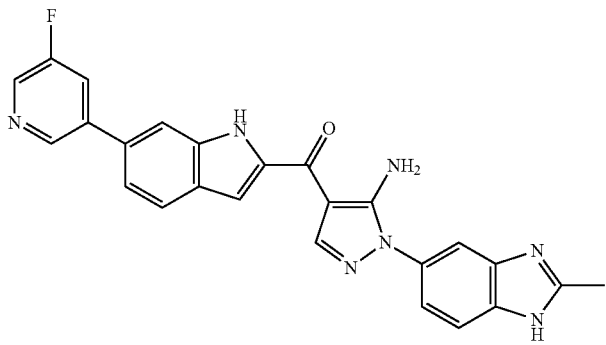 [SMILES: Cc1nc2cc(-n3ncc(C(=O)c4cc5ccc(-c6cncc(F)c6)cc5[nH]4)c3N)ccc2[nH]1] | [5-amino-1-(2-methyl-1H-benzimidazol-5-yl)-1H-pyrazol-4-yl]-[6-(5-fluoro-pyridin-3-yl)-1H-indol-2-yl]-methanone |
| --- | --- | --- |
| 224 | 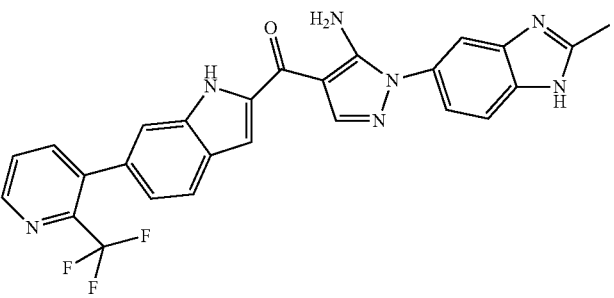 [SMILES: Cc1nc2cc(-n3ncc(C(=O)c4cc5ccc(-c6cccnc6C(F)(F)F)cc5[nH]4)c3N)ccc2[nH]1] | [5-amino-1-(2-methyl-1H-benzimidazol-5-yl)-1H-pyrazol-4-yl]-[6-(2-trifluoromethyl-pyridin-3-yl)-1H-indol-2-yl]-methanone |
| 225 | 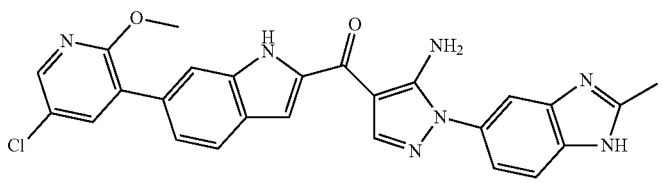 [SMILES: COc1ncc(Cl)cc1-c1ccc2cc(C(=O)c3cnn(-c4ccc5[nH]c(C)nc5c4)c3N)[nH]c2c1] | [5-amino-1-(2-methyl-1H-benzimidazol-5-yl)-1H-pyrazol-4-yl]-[6-(5-chloro-2-methoxy-pyridin-3-yl)-1H-indol-2-yl]-methanone |
| 226 | 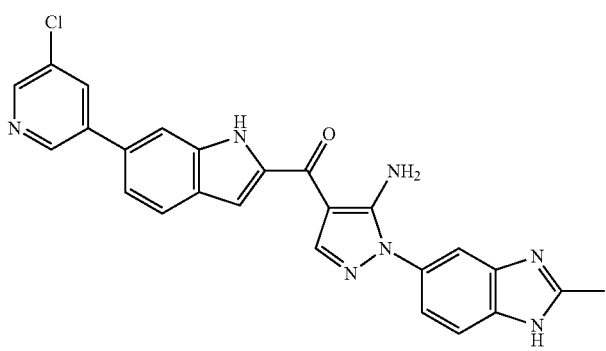 [SMILES: Cc1nc2cc(-n3ncc(C(=O)c4cc5ccc(-c6cncc(Cl)c6)cc5[nH]4)c3N)ccc2[nH]1] | [5-amino-1-(2-methyl-1H-benzimidazol-5-yl)-1H-pyrazol-4-yl]-[6-(5-chloro-pyridin-3-yl)-1H-indol-2-yl]-methanone |
| 227 | 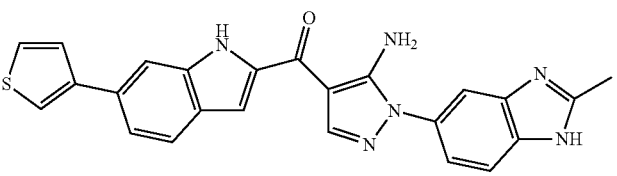 [SMILES: Cc1nc2cc(-n3ncc(C(=O)c4cc5ccc(-c6ccsc6)cc5[nH]4)c3N)ccc2[nH]1] | [5-amino-1-(2-methyl-1H-benzimidazol-5-yl)-1H-pyrazol-4-yl]-(6-thiophen-3-yl-1H-indol-2-yl)-methanone |
| 228 | 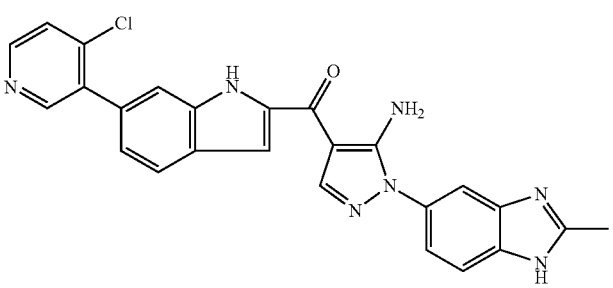 [SMILES: Cc1nc2cc(-n3ncc(C(=O)c4cc5ccc(-c6cnccc6Cl)cc5[nH]4)c3N)ccc2[nH]1] | [5-amino-1-(2-methyl-1H-benzimidazol-5-yl)-1H-pyrazol-4-yl]-[6-(4-chloropyridin-3-yl)-1H-indol-2-yl]-methanone |

TABLE 3-continued

| 229 | 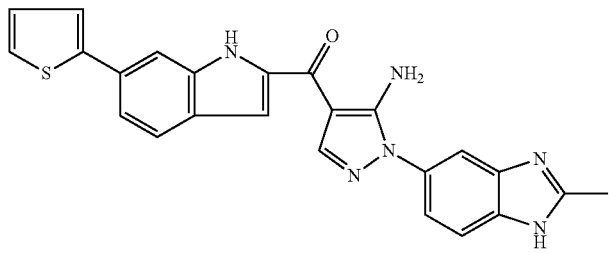 [SMILES: Cc1nc2cc(-n3ncc(C(=O)c4cc5ccc(-c6cccs6)cc5[nH]4)c3N)ccc2[nH]1] | [5-amino-1-(2-methyl-1H-benzimidazol-5-yl)-1H-pyrazol-4-yl]-(6-thiophen-2-yl-1H-indol-2-yl)-methanone |
| 230 | 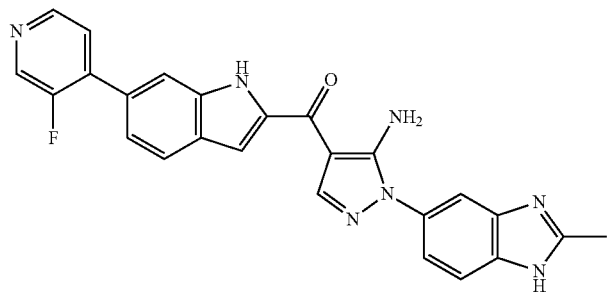 [SMILES: Cc1nc2cc(-n3ncc(C(=O)c4cc5ccc(-c6ccncc6F)cc5[nH]4)c3N)ccc2[nH]1] | [5-amino-1-(2-methyl-1H-benzimidazol-5-yl)-1H-pyrazol-4-yl]-[6-(3-fluoro-pyridin-4-yl)-1H-indol-2-yl]-methanone |
| 231 | 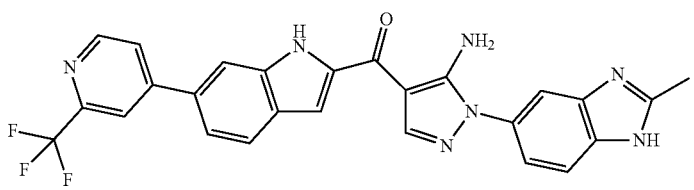 [SMILES: Cc1nc2cc(-n3ncc(C(=O)c4cc5ccc(-c6ccnc(C(F)(F)F)c6)cc5[nH]4)c3N)ccc2[nH]1] | [5-amino-1-(2-methyl-1H-benzimidazol-5-yl)-1H-pyrazol-4-yl]-[6-(2-trifluoromethyl-pyridin-4-yl)-1H-indol-2-yl]-methanone |
| 232 | 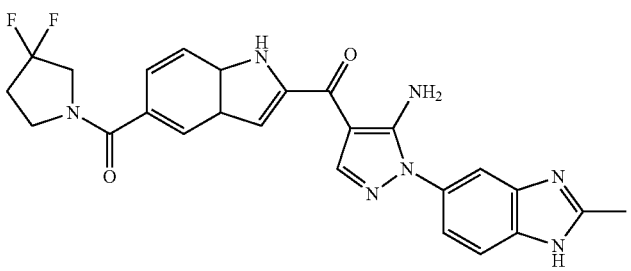 [SMILES: Cc1nc2cc(-n3ncc(C(=O)C4=CC5C=C(C(=O)N6CCC(F)(F)C6)C=CC5N4)c3N)ccc2[nH]1] | [5-amino-1-(2-methyl-1H-benzimidazol-5-yl)-1H-pyrazol-4-yl]-[5-(3,3-difluoro-pyrrolidine-1-carbonyl)-1H-indol-2-yl]-methanone |
| 233 | 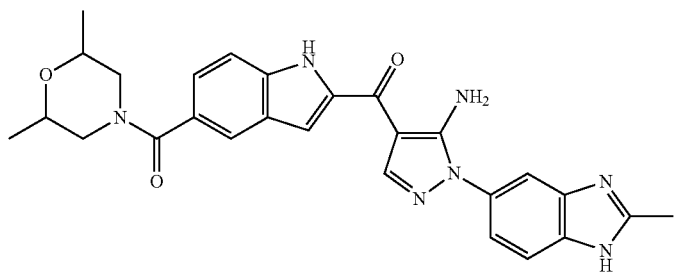 | [5-amino-1-(2-methyl-1H-benzimidazol-5-yl)-1H-pyrazol-4-yl]-[5-(2,6-dimethyl-morpholine-4-carbonyl)-1H-indol-2-yl]-methanone |
| 234 | 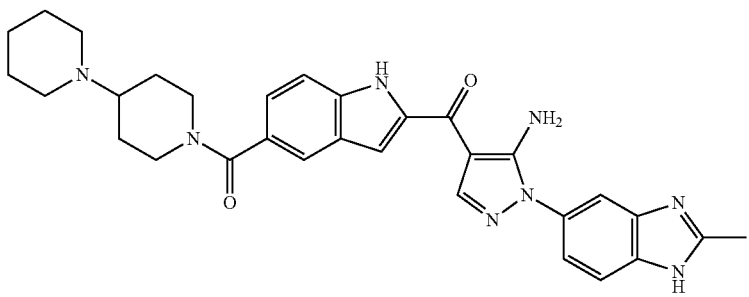 [SMILES: Cc1nc2cc(-n3ncc(C(=O)c4cc5cc(C(=O)N6CCC(N7CCCCC7)CC6)ccc5[nH]4)c3N)ccc2[nH]1] | [5-amino-1-(2-methyl-1H-benzimidazol-5-yl)-1H-pyrazol-4-yl]-[5-([1,4']bipiperidinyl-1'-carbonyl)-1H-indol-2-yl]-methanone |

| | | |
|---|---|---|
| 235 | 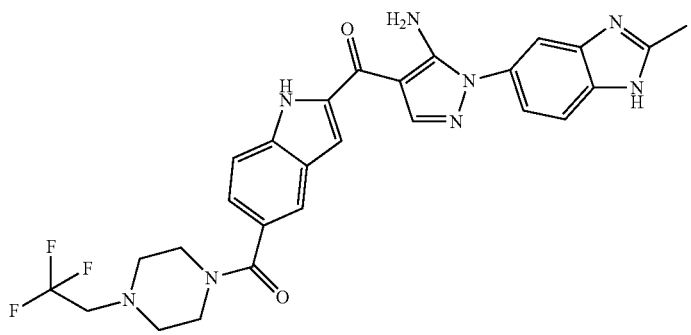 [SMILES: Cc1nc2cc(-n3ncc(C(=O)c4cc5cc(C(=O)N6CCN(CC(F)(F)F)CC6)ccc5[nH]4)c3N)ccc2[nH]1] | [5-amino-1-(2-methyl-1H-benzimidazo)-5-yl)-1H-pyrazol-4-yl]-{5-[4-(2,2,2-trifluoro-ethyl)-piperazine-1-carbonyl]-1H-indol-2-yl}-methanone |
| 236 | 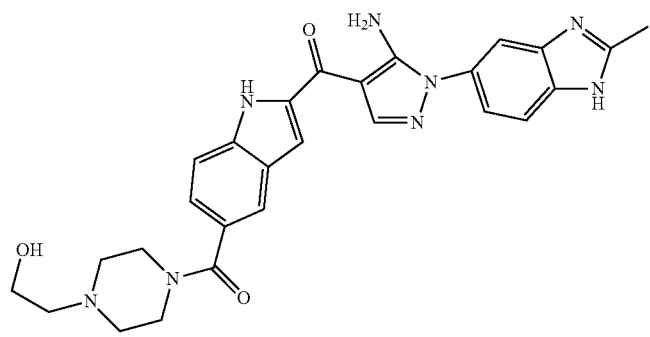 [SMILES: Cc1nc2cc(-n3ncc(C(=O)c4cc5cc(C(=O)N6CCN(CCO)CC6)ccc5[nH]4)c3N)ccc2[nH]1] | [5-amino-1-(2-methyl-1H-benzimidazol-5-yl)-1H-pyrazol-4-yl]-{5-[4-(2-hydroxy-ethyl)-piperazine-1-carbonyl]-1H-indol-2-yl}-methanone |
| 237 | 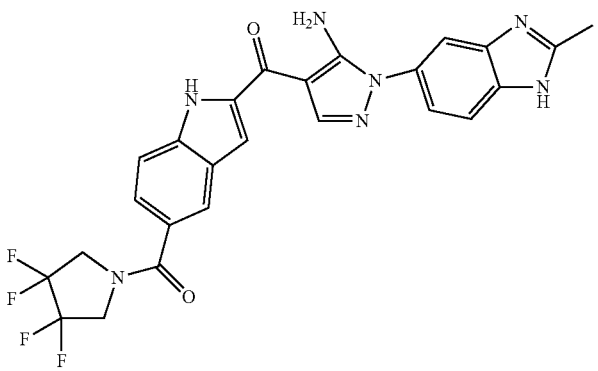 [SMILES: Cc1nc2cc(-n3ncc(C(=O)c4cc5cc(C(=O)N6CC(F)(F)C(F)(F)C6)ccc5[nH]4)c3N)ccc2[nH]1] | [5-amino-1-(2-methyl-1H-benzimidazol-5-yl)-1H-pyrazol-4-yl]-[5-(3,3,4,4-tetrafluoro-pyrrolidine-1-carbonyl)-1H-indol-2-yl]-methanone |
| 238 | 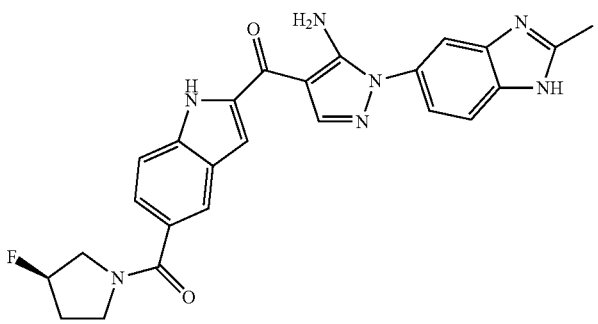 [SMILES: Cc1nc2cc(-n3ncc(C(=O)c4cc5cc(C(=O)N6CC[C@@H](F)C6)ccc5[nH]4)c3N)ccc2[nH]1] | [5-amino-1-(2-methyl-1H-benzimidazol-5-yl)-1H-pyrazol-4-yl]-[5-((R)-3-fluoro-pyrrolidine-1-carbonyl)-1H-indol-2-yl]-methanone |

TABLE 3-continued

| 239 | | [5-amino-1-(2-methyl-1H-benzimidazol-5-yl)-1H-pyrazol-4-yl]-[5-((S)-3-fluroro-pyrrolidine-1-carbonyl)-1H-indol-2-yl]-methanone |

| Example | m/z | 1H-NMR |
|---|---|---|
| 65 | 454 | 1H-NMR (DMSO-D6) δ: 12.45 (1H, s), 11.56 (1H, d, J = 1.8 Hz), 8.28 (1H, s), 7.66-7.62 (1H, br m), 7.60-7.55 (1H, br m), 7.50 (1H, d, J = 1.8 Hz), 7.40 (1H, d, J = 8.5 Hz), 7.37 (1H, d, J = 1.8 Hz), 7.29 (1H, d, J = 6.5 Hz), 7.16 (1H, dd, J = 8.5, 1.8 Hz), 7.00 (1H, br s), 6.95 (1H, br s), 2.89-2.87 (2H, m), 2.65-2.51 (1H, br m), 2.53 (3H, s), 2.20 (3H, s), 2.01-1.95 (2H, m), 1.82-1.65 (4H, m). |
| 66 | 450 | 1H-NMR (DMSO-D6) δ: 12.45 (1H, s), 11.65 (1H, s), 9.67 (1H, s), 8.28 (1H, s), 7.67-7.54 (3H, m), 7.42 (2H, s), 7.29 (1H, s), 7.02-6.93 (3H, m), 2.95 (3H, s), 2.53 (3H, s). |
| 67 | 519 | 1H-NMR (DMSO-D6) δ: 12.48 (1H, s), 11.73 (1H, s), 8.49 (1H, d, J = 2.4 Hz), 8.33 (1H, s), 7.90 (1H, dd, J = 9.2, 2.4 Hz), 7.76 (1H, d, J = 7.9 Hz), 7.66-7.58 (3H, m), 7.48 (1H, s), 7.37 (1H, dd, J = 8.5, 1.2 Hz), 7.30 (1H, dd, J = 8.5, 1.8 Hz), 7.01 (2H, s), 6.96 (1H, d, J = 8.5 Hz), 3.78-3.70 (4H, m), 3.54-3.47 (4H, m), 2.54 (3H, s). |
| 68 | 413 | 1H-NMR (DMSO-D6) δ: 12.46 (1H, s), 11.54 (1H, s), 8.28 (1H, s), 7.59-7.57 (3H, m), 7.38 (1H, d, J = 1.4 Hz), 7.28 (1H, dd, J = 8.4, 2.0 Hz), 7.25 (1H, s), 6.96 (2H, s), 6.93 (1H, dd, J = 8.3, 1.5 Hz), 2.68-2.65 (2H, m), 2.52 (3H, s), 1.62-1.55 (2H, m), 1.34-1.30 (2H, m), 0.90 (3H, t, J = 7.3 Hz). |
| 69 | 437 | 1H-NMR (DMSO-D6) δ: 12.49 (1H, s), 11.68 (1H, s), 8.31 (1H, s), 8.14 (1H, s), 7.84 (1H, s), 7.67 (1H, d, J = 8.5 Hz), 7.62-7.56 (3H, m), 7.43 (1H, s), 7.32 (1H, dd, J = 8.5, 1.2 Hz), 7.28 (1H, dd, J = 8.5, 1.8 Hz), 6.99 (2H, s), 3.89 (3H, s), 2.54 (3H, s). |
| 70 | 464 | 1H-NMR (DMSO-D6) δ: 11.87 (1H, s), 8.51 (1H, d, J = 1.8 Hz), 8.38 (1H, s), 8.31 (1H, d, J = 3.1 Hz), 7.83 (1H, d, J = 8.5 Hz), 7.79-7.72 (3H, m), 7.64 (1H, t, J = 2.9 Hz), 7.53 (1H, d, J = 1.8 Hz), 7.49-7.45 (2H, m), 7.14 (2H, s), 3.94 (3H, s), 2.65 (3H, s). |
| 71 | 464 | 1H-NMR (DMSO-D6) δ: 11.87 (1H, s), 8.51 (1H, d. J = 1.8 Hz), 8.38 (1H, s), 8.31 (1H, d, J = 3.1 Hz), 7.83 (1H, d, J = 8.5 Hz), 7.79-7.72 (3H, m), 7.64 (1H, t, J = 2.1 Hz), 7.53 (1H, d, J = 1.8 Hz), 7.49-7.45 (2H, m), 7.14 (2H, s), 3.94 (3H, s), 2.65 (3H, s). |
| 72 | 397 | 1H-NMR (DMSO-D6) δ: 12.46 (1H, s), 11.49 (1H, s), 8.27 (1H, s), 7.59 (1H, br s), 7.56 (1H, s), 7.54 (1H, s), 7.37 (1H, d, J = 1.4 Hz), 7.27 (1H, dd, J = 8.5, 2.1 Hz), 7.16 (1H, s), 6.95 (2H, br s), 6.80 (1H, dd, J = 8.4, 1.6 Hz), 2.52 (3H, s), 2.04-1.97 (1H, m), 0.96 (2H, ddd, J = 9.5, 5.2, 3.0 Hz), 0.69-0.65 (2H, m). |
| 73 | 463 | 1H-NMR (DMSO-D6) δ: 12.49 (1H, s), 11.71 (1H, s), 8.34 (1H, s), 7.75-7.55 (4H, m), 7.48 (1H, s), 7.40-7.28 (3H, m), 7.20 (1H, d, J = 8.5 Hz), 7.13 (1H, d, J = 8.5 Hz), 7.09-6.98 (3H, m), 3.78 (3H, s), 2.4 (3H, s), |
| 74 | 433 | 1H-NMR (DMSO-D6) δ: 12.49 (1H, s), 11.80 (1H, s), 8.34 (1H, s), 7.79 (1H, d, J = 8.5 Hz), 7.73-7.60 (5H, s), 7.52-7.47 (3H, m), 7.41 (1H, dd, J = 8.5, 1.2 Hz), 7.37 (1H, t, J = 7.3 Hz), 7.30 (1H, dd, J = 8.2, 2.1 Hz), 7.04 (2H, s), 2.54 (3H, s). |
| 75 | 512 | 1H-NMR (DMSO-D6) δ: 12.48 (1H, s), 11.97 (1H, s), 9.26 (1H, s), 9.06 (1H, s), 8.55 (1H, s), 8.35 (1H, d, J = 3.7 Hz), 7.93-7.84 (2H, m), 7.79-7.51 (4H, m), 7.31 (1H, t, J = 7.0 Hz), 7.09 (1H, s), 7.03 (1H, s), 3.44 (3H, s), 2.54 (3H, s). |
| 76 | 399 | 1H-NMR (DMSO-D6) δ: 12.46 (1H, s), 11.54 (1H, s), 8.27 (1H, s), 7.60-7.58 (3H, m), 7.38 (1H, d, J = 1.6 Hz), 7.29-7.26 (2H, m), 7.00 (1H, dd, J = 8.5, 1.5 Hz), 6.96 (2H, br s), 3.01-2.94 (1H, m), 2.52 (3H, s), 1.26 (3H, s), 1.24 (3H, s). |
| 77 | 434 | 1H-NMR (DMSO-D6) δ: 12.49 (1H, s), 11.91 (1H, s), 8.68 (1H, d, J = 4.9 Hz), 8.34 (1H, s), 8.26 (1H, s), 7.97 (1H, d, J = 7.9 Hz), 7.91-7.87 (1H, m), 7.81 (2H, q, J = 8.5 Hz), 7.63 (2H, s), 7.50 (1H, s), 7.36-7.28 (2H, m), 7.04 (2H, s), 2.54 (3H, s). |
| 78 | 397 | 1H-NMR (DMSO-D6) δ: 12.46 (1H, s), 11.56 (1H, s), 8.27 (1H, s), 7.64-7.57 (2H, br m), 7.37 (1H, s), 7.36 (1H, d, J = 8.6 Hz), 7.33 (1H, d, J = 1.5 Hz), 7.28 (1H, dd, J = 8.2. 2.1 Hz), 7.00 (1H, dd, J = 8.5, 1.5 Hz), 6.99 (2H, br s), 2.53 (3H, s), 2.03-1.97 (1H, m), 0.95-0.90 (2H, m), 0.68-0.64 (2H, m). |

TABLE 3-continued

| | | |
|---|---|---|
| 79 | 435 | 1H-NMR (DMSO-D6) δ: 12.49 (1H, s), 12.03 (1H, s), 9.20 (1H, dd, J = 4.9, 1.5 Hz), 8.35 (2H, d, J = 8.0 Hz), 8.24 (1H, d, J = 8.5 Hz), 7.87 (2H, s), 7.78 (1H, dd, J = 8.5, 4.9 Hz), 7.63 (1H, s), 7.54 (2H, s), 7.31 (1H, dd, J = 8.0, 1.6 Hz), 7.06 (2H, s), 2.54 (3H, s). |
| 80 | 415 | 1H-NMR (DMSO-D6) δ: 12.46 (1H, s), 11.62 (1H, d, J = 1.8 Hz), 8.26 (1H, s), 7.65-7.55 (2H, br m), 7.36 (1H, d, J = 8.9 Hz), 7.32 (1H, d, J = 1.8 Hz), 7.29 (1H, dd, J = 8.5, 1.8 Hz), 7.13 (1H, d, J = 2.2 Hz), 6.98 (2H, br s), 6.89 (1H, dd, J = 8.9, 2.2 Hz), 4.58-4.52 (1H, m), 2.53 (3H, s), 1.29 (6H, d, J = 6.1 Hz). |
| 81 | 431 | 1H-NMR (DMSO-D6) δ: 12.46 (1H, s), 11.56 (1H, d, J = 1.2 Hz), 8.27 (1H, s), 7.64-7.57 (2H, br m), 7.37 (1H, d, J = 9.1 Hz), 7.33 (1H, d, J = 1.2 Hz), 7.29 (1H, d, J = 8.5, 1.8 Hz), 7.13 (1H, d, J = 2.4 Hz), 6.99 (2H, br s), 6.92 (1H, dd, J = 9.1, 2.4 Hz), 4.11-4.08 (2H, m), 3.70-3.68 (2H, m), 3.33 (3H, s), 2.53 (3H, s). |
| 82 | 427 | 1H-NMR (DMSO-D6) δ: 12.46 (1H, s), 11.54 (1H, s), 8.26 (1H, s), 7.65-7.55 (2H, br m), 7.36 (1H, d, J = 8.8 Hz), 7.31 (1H, s), 7.28 (1H, dd, J = 8.2, 2.2 Hz), 7.09 (1H, d, J = 2.5 Hz), 6.98 (2H, s), 6.92 (1H, dd, J = 8.8, 2.5 Hz), 3.82 (2H, d, J = 7.1 Hz), 2.53 (3H, s), 1.28-1.20 (1H, m), 0.60-0.56 (2H, m), 0.37-0.31 (2H, m). |
| 83 | 437 | 1H-NMR (DMSO-D6) δ: 12.46 (1H, s), 11.96 (1H, s), 8.26 (1H, s), 7.66-7.55 (2H, br m), 7.60 (1H, s), 7.60 (1H, d, J = 1.9 Hz), 7.36 (1H, s), 7.28 (1H, dd, J = 8.5, 1.9 Hz), 7.01 (2H, br s), 2.53 (3H, s). |
| 84 | 468, 470 | 1H-NMR (DMSO-D6) δ: 12.48 (1H, s), 11.90 (1H, s), 8.66 (1H, dd, J = 4.7, 1.4 Hz), 8.38 (1H, s), 9.07 (1H, dd, J = 8.0, 1.4 Hz), 7.84 (1H, s), 7.79 (1H, d, J = 8.2 Hz), 7.64 (2H, s), 7.53 (1H, s), 7.46-7.41 (2H, m), 7.31 (1H, dd, J = 8.5, 1.9 Hz), 7.05 (2H, s), 2.53 (3H, t, J = 5.5 Hz). |
| 85 | 452 | 1H-NMR (DMSO-D6) δ: 12.48 (1H, s), 11.92 (1H, s), 8.68 (1H, d, J = 2.7 Hz), 6.35 (1H, s), 8.21 (1H, d, J = 1.1 Hz), 8.05 (1H, dd, J = 8.8, 4.4 Hz), 7.85-7.79 (3H, m), 7.63 (2H, s), 7.50 (1H, s), 7.31 (1H, dd, J = 8.5, 1.9 Hz), 7.05 (2H, s), 2.56 (3H, s). |
| 86 | 520 | 1H-NMR (DMSO-D6) δ: 12.47 (1H, d, J = 6.5 Hz), 11.90 (1H, d, J = 2.2 Hz), 8.34 (1H, d, J = 4.9 Hz), 6.17 (1H, s), 7.98 (1H, d, J = 9.3 Hz), 7.82-7.74 (2H, m), 7.68-7.64 (1H, m), 7.60-7.56 (1H, m), 7.50 (1H, s), 7.38 (1H, d, J = 9.3 Hz), 7.33-7.28 (1H, m), 7.07 (1H, s), 7.01 (1H, s), 3.80-3.74 (4H, m), 3.65-3.60 (4H, m), 2.53 (3H, s). |
| 87 | 461, 463 | 1H-NMR (DMSO-D6) δ: 12.45 (1H, s), 11.66 (1H s), 8.25 (1H, s), 7.72 (1H, s), 7.62-7.68 (2H, m), 7.37 (1H, d, J = 1.3 Hz), 7.28 (1H, dd, J = 8.2, 1.3 Hz), 7.02 (1H, s), 6.97 (2H, s), 3.92 (2H, d, J = 7.1 Hz), 2.53 (3H, s), 1.35-1.25 (1H, m), 0.64-0.59 (2H, m), 0.44-0.39 (2H, m). |
| 88 | 469 | 1H-NMR (DMSO-D6) δ: 12.51 (1H, s), 11.86 (1H, s), 8.35 (1H, s), 7.79 (1H, d, J = 7.7 Hz), 7.62 (4H, s), 7.62 (1H, s), 7.46-7.16 (4H, m), 7.05 (2H, s), 2.54 (3H, s). |
| 89 | 435 | 1H-NMR (DMSO-D6) δ: 12.48 (1H, s), 12.04 (1H, s), 9.67-9.64 (1H, m), 9.27 (1H, d, J = 5.5 Hz), 8.35 (1H, d, J = 4.4 Hz), 8.02 (1H, dd, J = 5.5, 2.7 Hz), 7.95 (1H, s), 7.89 (1H, d, J = 8.8 Hz), 7.67-7.56 (4H, m), 7.30 (1H, t, J = 6.3 Hz), 7.10 (1H, s), 7.04 (1H, s), 2.54 (3H, s). |
| 204 | 391 | 11.8 (1H, br s), 8.28 (1H, m), 7.70-7.68 (1H, m), 7.60 (2H, m), 7.46 (2H, m), 7.29-7.27 (1H, m), 7.01 (2H, m), 2.52 (3H, s) |
| 205 | 391 | 11.91 (s, 1H), 8.30 (s, 1H), 7.71 (m, 1H), 7.45 (m, 4H), 7.26 (m, 1H), 7.09 (s, 2H), 2.62 (s, 3H). |
| 206 | 357 | 11.92 (s, 1H), 8.32 (m, 1H), 8.25 (d, J = 7.6 Hz, 1H), 8.20 (s, 1H), 7.77 (m, 2H), 7.51 (m, 2H), 7.18 (m, 2H), 6.97 (s, 2H), 2.67 (s, 3H). |
| 207 | 357 | 12.42 (s, 1H), 11.36 (s, 1H), 7.91 (s, 1H), 7.85 (m, 1H), 7.66 (d, J = 8.3 Hz, 1H), 7.58 (m, 3H), 7.48 (d, J = 8 Hz, 1H), 7.29 (d, J = 8.7 Hz, 1H), 6.95 (br s, 2H), 6.54 (s, 1H), 2.53 (s, 3H). |
| 208 | 453 | 12.48 9 (s, 1H), 11.97 (s, 1H), 8.27 (s, 1H), 8.01 (d, J = 7 Hz, 1H), 7.62 (m, 2H), 7.36 (d, J = 9.6 Hz, 1H), 7.29 (d, J = 7.6 Hz, 1H), 7.02 (br s, 2H), 2.54 (s, 3H) |
| 209 | 467 | 12.48 (s, 1H), 11.98 (s, 1H), 8.27 (d, J = 4.5 Hz, 1H), 8.01 (d, J = 6.8 Hz, 1H), 7.67 (m, 1H), 7.57 (s, 1H), 7.46 (s, 1H), 7.37 (d, J = 9.4 Hz, 1H), 7.29 (t, J = 7.7 Hz, 1H), 7.03 (m, 2H), 2.86 (m, 2H), 1.34 (m, 3H) |
| 210 | 425 | 12.15 (s, 1H), 8.33 (s, 1H), 8.10 (s, 1H), 7.74 (m, 2H), 7.67 (d, J = 8.5 Hz, 1H), 7.62 (s, 1H), 7.54 (d, J = 8.5 Hz, 1H), 7.45 (d, J = 8.6 Hz, 1H), 7.13 (m, 2H), 2.65 (s, 3H) |
| 211 | 441 | 12.48 (s, 1H), 11.99 (s, 1H), 8.29 (d, J = 4.8 Hz, 1H), 7.66 (d, J = 8.6 Hz, 2H), 7.56 (d, J = 9.3 Hz, 1H), 7.52 (s, 2H), 7.27 (m, 2H), 7.16 (m, 1H), 7.05 (m, 2H), 2.53 (s, 3H) |
| 212 | 425 | 12.47 (s, 1H), 12.21 (s, 1H), 8.33 (d, J = 5.6 Hz, 1H), 7.95 (br s, 1H), 7.65 (d, J = 7.8 Hz, 1H), 7.56 (d, J = 6.9 Hz, 1H), 7.48 (s, 1H), 7.37 (s, 1H), 7.28 (m, 1H), 7.22 (m, 1H), 7.09 (s, 1H), 7.03 (s, 1H), 2.53 (s, 3H) |

TABLE 3-continued

| | | |
|---|---|---|
| 213 | 453 | 12.16 (s, 1H), 8.38 (s, 1H), 7.65 (m, 2H), 7.50 (d, J = 5.3 Hz, 2H), 7.34 (m, 1H), 7.13 (m, 1H), 7.09 (m, 2H), 2.57 (s, 3H) |
| 214 | 441 | 12.5 (s, 1H), 11.93 (s, 1H), 8.31 (s, 1H), 7.80 (d, J = 8.7 Hz, 1H), 7.62 (s, 2H), 7.53 (s, 1H), 7.41 (s, 1H), 7.29 (d, J = 8.5 Hz, 1H), 7.20 (m, 1H), 7.06 (m, 3H), 2.53 (s, 3H). |
| 215 | 455 | 12.50 (s, 1H), 11.98 (s, 1H), 8.29 (s, 1H), 7.67 (s, 1H), 7.63 (br s, 1H), 7.57 (d, J = 8.9 Hz, 1H), 7.51 (m, 1H), 7.29 (d, J = 8.3 Hz, 1H), 7.23 (d, J = 8.4 Hz, 1H), 7.04 (s, 1H), 2.87 (m, 2H), 1.48 (m, 3H) |
| 216 | 439 | 12.16 (s, 1H), 8.33 (br s, 1H), 8.10 (br s, 1H), 7.73 (m, 2H), 7.67 (d, J = 8.2 Hz, 1H), 7.62 (s, 1H), 7.54 (d, J = 8.3 Hz, 1H), 7.43 (m, 1H), 7.12 (br s, 3H), 2.96 (m, 2H), 1.37 (m, 3H) |
| 217 | 425 | 11.98 (s, 1H), 8.30 (s, 1H), 7.96 (s, 1H), 7.70 (m, 3H), 7.46 (s, 1H), 7.42 (d, J = 8.8 Hz, 1H), 7.11 (s, 2H), 2.67 (s, 3H) |
| 218 | 467 | 11.91 (s, 1H), 8.28 (s, 1H), 7.74 (d, J = 6 Hz, 1H), 7.64 (d, J = 9 Hz, 3H), 7.46 (s, 1H), 7.31 (d, J = 7.8 Hz, 1H), 7.06 (br s, 2H), 2.89 (q, J = 7.2 Hz, 2H), 1.35 (t, J = 7.2 Hz, 3H). |
| 219 | 425 | 12.46 (s, 2H), 7.66 (m, 1H), 7.57 (d, J = 7.6 Hz, 1H), 7.49 (m, 1H), 7.43 (d, J = 8.7 Hz, 1H), 7.30 (t, J = 6.6 Hz, 1H), 7.05 (m, 2H), 2.53 (s, 3H) |
| 220 | 393 | 12.40 (m, 1H), 12.12 (s, 1H), 8.37 (s, 1H), 7.62 (s, 2H), 7.49 (s, 1H), 7.29 (m, 1H), 7.07 (m, 3H), 6.94 (m, 1H), 2.54 (s, 3H). |
| 221 | 468 | 11.95 (bs, 1H), 8.75 (s, 1H), 8.59 (d, 1H, J = 4 Hz), 8.41 (bs, 1H), 7.95 (m, 1H), 7.89 (m, □), 7.82 (d, 1H, J = 12 Hz), 7.66 (m, 1H), 7.64 (m, 1H), 7.54 (m, 2H), 7.22 (m, 2H), 6.86 (s, 1H), 6.63 (s, 1H), 2.8 (s, 3H), 2.18 (s, 3H) |
| 222 | 448 | 8.73 (1H, m), 8.30 (1H, m), 8.07-8.04 (1H, m), 7.86-7.84 (2H, m), 7.75 (1H, m), 7.68 (2H, m), 7.42-7.39 (4H, m), 2.62 (3H, s), 2.59 (3H, s) |
| 223 | 452 | 11.95 (s, 1H), 8.009 (m, 1H), 7.80 (m, 2H), 7.70 (m, 1H), 7.54 (m, 2H), 7.38 (d, 1H, J = 12 Hz), 7.17 (bs, 1H), 2.85 (s, 1H), 2.65 (m, 1H), 2.55 (s, 3H) |
| 224 | 502 | 8.30 (s, 2H), 8.17 (m, 1H), 8.06 (t, 1H, J = 8 Hz), 7.86 (q, 2H, J = 12 Hz), 7.67 (d, 3H, J = 8 Hz), 7.40 (m, 2H), 2.61 (m, 3H), |
| 225 | 498 | 8.30 (1H, s), 8.09 (1H, d, J = 2.8 Hz), 7.78 (2H, m), 7.69 (3H, m), 7.42 (2H, m), 7.28 (1H, m), 5.78 (2H, m), 3.96 (3H, s), 2.63 (3H, s), 2.02 (3H, m) |
| 226 | 468 | 12.55 (bs, 1H), 11.95 (bs, 1H), 8.87 (s, 1H), 8.62 (d, 1H, J = 2.4 Hz), 8.34 (s, 1H), 8.23 (t, 1H, J = 2 Hz), 7.82 (d, 1H, J = 8 Hz), 7.78 (s, 1H), 7.60 (m, 3H), 7.52 (m, 1H), 7.47 (d, 1H, J = 8 Hz), 7.28 (m, 1H), 7.05 (m, 1H), 2.54 (s, 3H) |
| 227 | 439 | 12.55 (bs, 1H), 11.74 (s, 1H), 8.32 (s, 1H), 7.82 (m, 1H), 7.71 (m, 2H), 7.66 (m, 1H), 7.60 (m, 2H), 7.54 (d, 1H, J = 4 Hz), 7.3 (m, 1H), 2.54 (s, 3H) |
| 228 | 468 | 11.87 (s, 1H), 8.61 (m, 2H), 8.51 (m, 2H), 8.36 (bs, 1H), 7.78 (m, 3H), 7.66 (m, 1H), 7.51 (m, 3H), 7.15 (m, 3H), 3.04 (s, 2H), 2.68 (s, 3H), 1.47 (bs, 1H), 1.16 (m, 6H) |
| 229 | 439 | 11.75 (s, 1H), 8.35 (s, 1H), 7.75 (m, 4H), 7.48 (m, 5H), 7.14 (m, 3H), 3.08 (s, 1H), 2.65 (s, 3H), |
| 230 | 452 | 12.59 (s, 1H), 11.96 (s, 1H), 8.66 (d, 1H, J = 8 Hz), 8.51 (d, 1H, J = 4 Hz), 8.34 (m, 1H), 7.84 (d, 2H), 7.81 (s, 1H), 7.67 (m, 2H), 7.56 (m, 2H), 7.29 (m, 1H), 7.02 (m, 2H), 2.67 (3, 3H) |
| 231 | 502 | 12.69 (bs, 1H), 11.98 (s, 1H), 8.83 (d, 1H, J = 4 Hz), 8.31 (m, 1H), 8.16 (m, 1H), 8.05 (d, 1H, J = 4 Hz), 7.94 (s, 1H), 7.86 (d, 1H, J = 8 Hz), 7.62 (m, 3H), 7.54 (m, 1H), 7.31 (d, 1H, J = 8 Hz), 7.07 (bs, 2H), 2.55 (s, 3H) |
| 232 | 490 | 8.33 (bs, 1H), 8.03 (bs, 1H), 7.81 (m, 2H), 7.56 (m, 2H), 7.50 (m, 2H), 4.24 (t, 4H, J = 12 Hz), 2.66 (s, 3H), 1.49 (m, 1H), 1.39 (m, 3H), 1.28 (m, 4H) |
| 233 | 498 | 12.46 (d, 1H, J = 4 Hz), 11.91 (s, 1H), 8.32 (m, 1H), 7.77 (m, 1H), 7.65 (m, 1H), 7.56 (m, 1H), 7.51 (m, 1H), 7.27 (m, 2H), 7.05 (m, 1H), 7.0 (s, 1H), 3.55 (bs, 2H), 2.62 (s, 3H), 1.23 (m, 5H), 1.07 (bs, 3H |
| 234 | 551 | 8.28 (s, 1H), 7.83 (s, 1H), 7.63 (m, 2H), 7.55 (m, 1H), 7.45 (s, 1H), 7.32 (d, 2H, 7.05 (s, 1H, J = 8 Hz), 2.60 (m, 8H), 1.88 (m, 2H), 1.62 (m, 4H) |

TABLE 3-continued

| 235 | 551 | 8.28 (s, 1H), 7.84 (s, 1H), 7.64 (d, 2H, J = 8 Hz), 7.55 (d, 1H, J = 8.68 Hz), 7.45 (s, 1H), 7.35 (t, 1H, J = 8 Hz), 3.67 (bs, 4H), 3.17 (t, 2H, J = 8 Hz), 2.74 (m, 4H), 2.36 (s, 3H), |
| --- | --- | --- |
| 236 | 513 | 8.28 (s, 1H), 7.84 (s, 1H), 7.65 (m, 2H), 7.55 (d, 1H, J = 8 Hz), 7.46 (s, 1H), 7.35 (m, 2H), 3.69 (m, 6H), 6.82 (m, 3H), 3.33 (s, 1H), 2.64 (s, 3H), 2.56 (m, 6H) |
| 237 | 526 | 8.289 (s, 1H), 7.99 (m, 1H), 7.65 (m, 2H), 7.55 (m, 1H), 7.47 (m, 2H), 7.39 (d, 1H, J = 8 Hz), 3.95 (t, 2H, J = 12 Hz), 3.87 (t, 2H, J = 8 Hz), 2.61 (s, 3H), 2.45 (bs, 2H) |
| 238 | 472 | 8.29 (s, 1H), 7.97 (d, 1H, J = 12 Hz), 7.67 (m, 2H), 7.55 (m, 1H), 7.47 (m, 2H), 7.37 (d, 2H, J = 8 Hz), 5.3 (m, 1H), 3.84 (m, 6H), 2.61 (s, 3H) |
| 239 | 472 | 8.29 (s, 1H), 7.97 (d, 1H), 7.65 (m, 2H), 7.55 (m, 1H,), 7.47 (m, 2H), 7.35 (d, 1H, J = 8 Hz), 5.3 (m, 1H), 3.77 (m, 4H), 2.61 (s, 3H), 2.2 (bs, 2H) |

Example 90

Synthesis of [5-amino-1-(2-methyl-1H-benzimidazol-5-yl)-1H-pyrazol-4-yl]-(3-fluoro-1H-indol-2-yl)-methanone

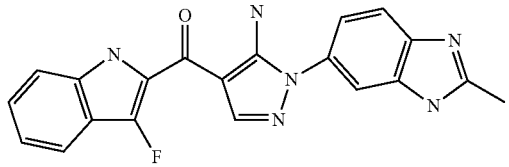 [SMILES: Cc1nc2ccc(-n3ncc(C(=O)c4[nH]c5ccccc5c4F)c3N)cc2[nH]1]

[5-Amino-1-(2-methyl-1H-benzimidazol-5-yl)-1H-pyrazol-4-yl]-[3-fluoro-1-(toluene-4-sulfonyl)-1H-indol-2-yl]-methanone (25.0 mg, 0.041 mmol) was dissolved in methane sulfonic acid (0.25 ml), and stirred at room temperature for one hour. The pH of the reaction mixture was adjusted to 6 using an aqueous solution of 1 M sodium hydroxide. After extraction with ethyl acetate, the extract was dried over anhydrous sodium sulfate. The desiccant was removed by filtration. The filtrate was concentrated under reduced pressure, and the resulting residue was purified by silica gel column chromatography (dichloromethane/methanol=60/1 to 40/1) to give [5-amino-1-(2-methyl-1H-benzimidazol-5-yl)-1H-pyrazol-4-yl]-(3-fluoro-1H-indol-2-yl)-methanone was obtained as a pale yellow solid (8.7 g, with a yield of 55%).

$^1$H-NMR (DMSO-$D_6$) δ 12.48 (1H, s), 11.50 (1H, s), 8.03 (1H, d, J=3.1 Hz), 7.69 (1H, d, J=8.5 Hz), 7.62 (2H, s), 7.45 (1H, d, J=8.5 Hz), 7.25-7.35 (2H, m), 7.15 (1H, t, J=7.3 Hz), 7.05 (2H, s), 2.53 (3H, s)

ESI (LC-MS positive mode) m/z 375 [(M+H)$^+$]

The compounds of Examples 91 to 131 listed in Table 4 were synthesized by the same method as in Example 90.

TABLE 4

| Example | Structure | Compound name |
| --- | --- | --- |
| 91 | 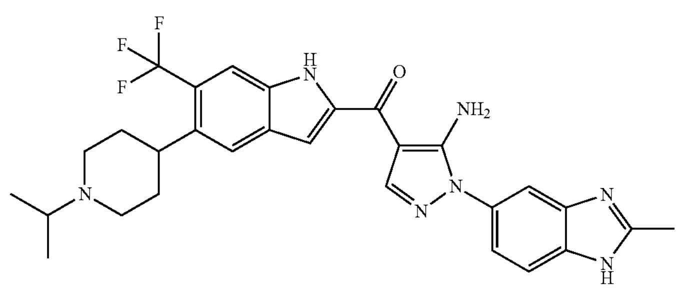 [SMILES: Cc1nc2cc(-n3ncc(C(=O)c4cc5cc(C6CCN(C(C)C)CC6)c(C(F)(F)F)cc5[nH]4)c3N)ccc2[nH]1] | [5-amino-1-(2-methyl-1H-benzimidazol-5-yl)-1H-pyrazol-4-yl]-[5-(1-isopropyl-piperidin-4-yl)-6-trifluoromethyl-1H-indol-2-yl]-methanone |
| 92 | 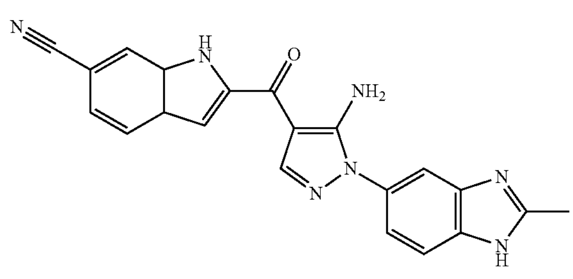 [SMILES: Cc1nc2cc(-n3ncc(C(=O)C4=CC5C=CC(C#N)=CC5N4)c3N)ccc2[nH]1] | 2-[5-amino-1-(2-methyl-1H-benzimidazol-5-yl)-1H-pyrazole-4-carbonyl]-1H-indole-6-carbonitrile |

TABLE 4-continued

| 93 | 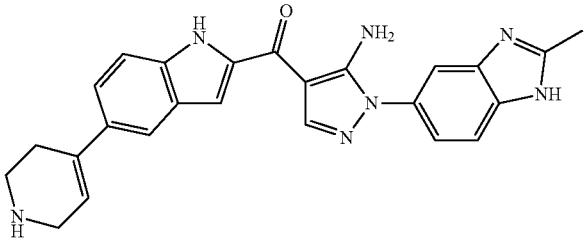 [SMILES: Cc1nc2cc(-n3ncc(C(=O)c4cc5cc(C6=CCNCC6)ccc5[nH]4)c3N)ccc2[nH]1] | [5-amino-1-(2-methyl-1H-benzimidazol-5-yl)-1H-pyrazol-4-yl]-[5-(1,2,3,6-tetrahydro-pyridin-4-yl)-1H-indol-2-yl]-methanone |
| --- | --- | --- |
| 94 | 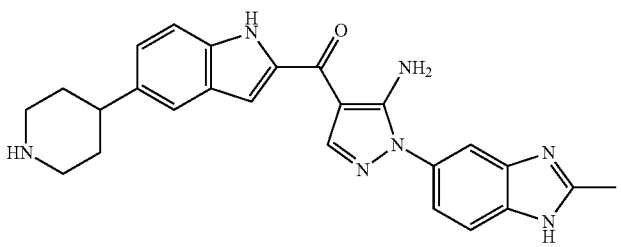 [SMILES: Cc1nc2cc(-n3ncc(C(=O)c4cc5cc(C6CCNCC6)ccc5[nH]4)c3N)ccc2[nH]1] | [5-amino-1-(2-methyl-1H-benzimidazol-5-yl)-1H-pyrazol-4-yl]-(5-piperidin-4-yl-1H-indol-2-yl)-methanone |
| 95 | 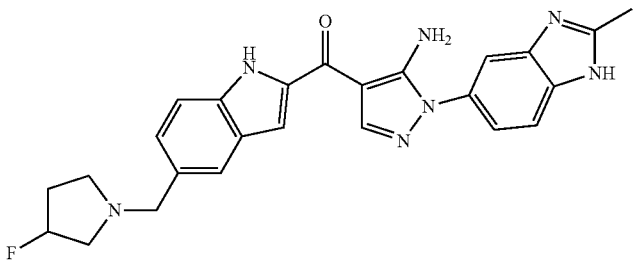 [SMILES: Cc1nc2cc(-n3ncc(C(=O)c4cc5cc(CN6CCC(F)C6)ccc5[nH]4)c3N)ccc2[nH]1] | [5-amino-1-(2-methyl-1H-benzimidazol-5-yl)-1H-pyrazol-4-yl]-[5-((R)-3-fluoro-pyrrolidin-1-ylmethyl)-1H-indol-2-yl]-methanone |
| 96 | 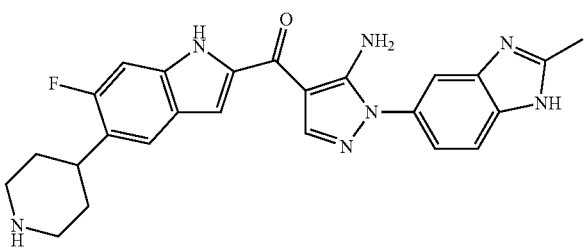 [SMILES: Cc1nc2cc(-n3ncc(C(=O)c4cc5cc(C6CCNCC6)c(F)cc5[nH]4)c3N)ccc2[nH]1] | [5-amino-1-(2-methyl-1H-benzimidazol-5-yl)-1H-pyrazol-4-yl]-(6-fluoro-5-piperidin-4-yl-1H-indol-2-yl)-methanone |
| 97 | 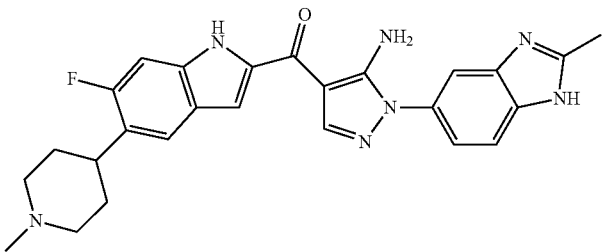 | [5-amino-1-(2-methyl-1H-benzimidazol-5-yl)-1H-pyrazol-4-yl]-[6-fluoro-5-(1-methyl-piperidin-4-yl)-1H-indol-2-yl]-methanone |
| 98 | 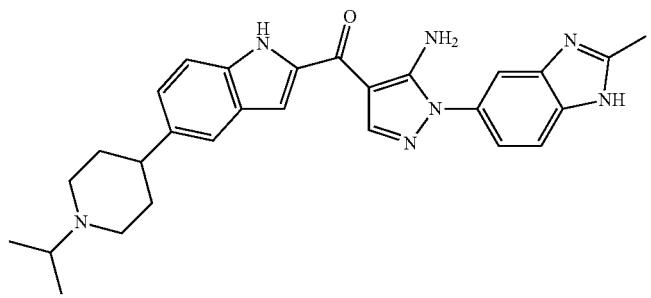 [SMILES: Cc1nc2cc(-n3ncc(C(=O)c4cc5cc(C6CCN(C(C)C)CC6)ccc5[nH]4)c3N)ccc2[nH]1] | [5-amino-1-(2-methyl-1H-benzimidazol-5-yl)-1H-pyrazol-4-yl]-[5-(1-isopropyl-piperidin-4-yl)-1H-indol-2-yl]-methanone |

TABLE 4-continued

| | | |
|---|---|---|
| 99 | 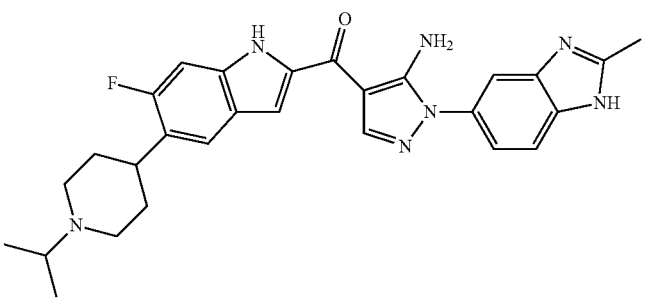 [SMILES: Cc1nc2cc(-n3ncc(C(=O)c4cc5cc(C6CCN(C(C)C)CC6)c(F)cc5[nH]4)c3N)ccc2[nH]1] | [5-amino-1-(2-methyl-1H-benzimidazol-5-yl)-1H-pyrazol-4-yl]-[6-fluoro-5-(1-isopropyl-piperidin-4-yl)-1H-indol-2-yl]-methanone |
| 100 |  | [5-amino-1-(2-methyl-1H-benzimidazol-5-yl)-1H-pyrazol-4-yl]-(6-pyridin-3-yl-1H-indol-2-yl)-methanone |
| 101 | 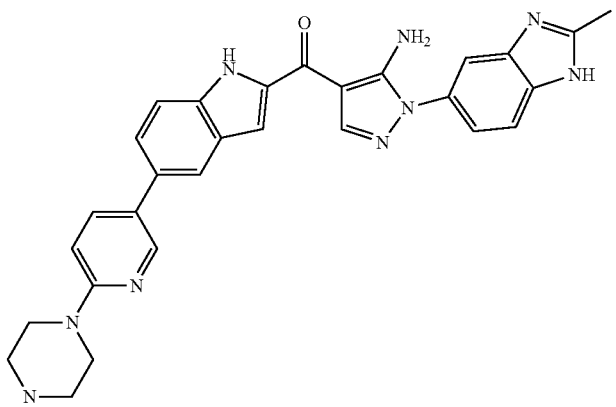 [SMILES: Cc1nc2cc(-n3ncc(C(=O)c4cc5cc(-c6ccc(N7CCNCC7)nc6)ccc5[nH]4)c3N)ccc2[nH]1] | [5-amino-1-(2-methyl-1H-benzimidazol-5-yl)-1H-pyrazol-4-yl]-[5-(6-morpholin-4-yl-pyridin-3-yl)-1H-indol-2-yl]-methanone |
| 102 | 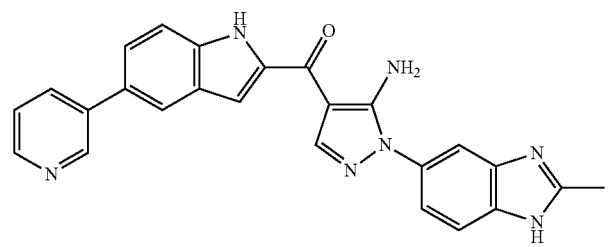 [SMILES: Cc1nc2cc(-n3ncc(C(=O)c4cc5cc(-c6cccnc6)ccc5[nH]4)c3N)ccc2[nH]1] | [5-amino-1-(2-methyl-1H-benzimidazol-5-yl)-1H-pyrazol-4-yl]-(5-pyridin-3-yl-1H-indol-2-yl)-methanone |
| 103 | 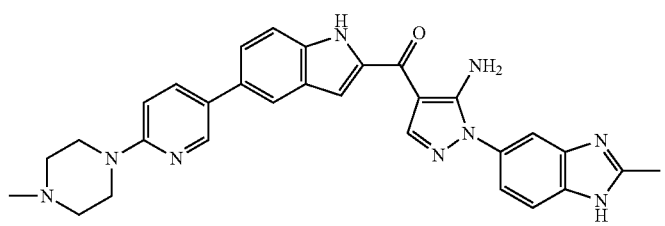 | [5-amino-1-(2-methyl-1H-benzimidazol-5-yl)-1H-pyrazol-4-yl]-[5-(6-piperazin-1-yl-pyridin-3-yl)-1H-indol-2-yl]-methanone |
| 104 | 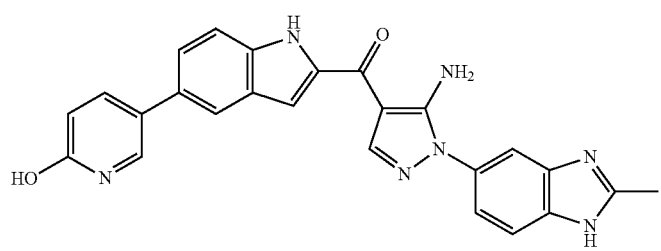 [SMILES: Cc1nc2cc(-n3ncc(C(=O)c4cc5cc(-c6ccc(O)nc6)ccc5[nH]4)c3N)ccc2[nH]1] | [5-amino-1-(2-methyl-1H-benzimidazol-5-yl)-1H-pyrazol-4-yl]-[5-(6-hydroxy-pyridin-3-yl)-1H-indol-2-yl]-methanone |

TABLE 4-continued

| | | |
|---|---|---|
| 105 | 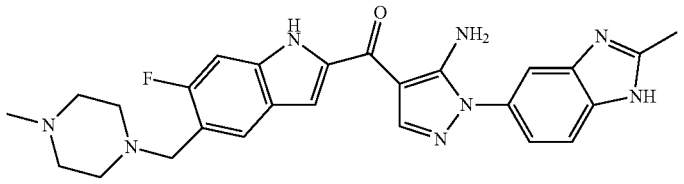 | [5-amino-1-(2-methyl-1H-benzimidazol-5-yl)-1H-pyrazol-4-yl]-[6-fluoro-5-(4-methyl-piperazin-1-yl-methyl)-1H-indol-2-yl]-methanone |
| 106 | 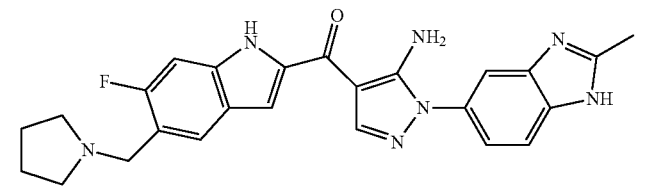 [SMILES: Cc1nc2cc(-n3ncc(C(=O)c4cc5cc(CN6CCCC6)c(F)cc5[nH]4)c3N)ccc2[nH]1] | [5-amino-1-(2-methyl-1H-benzimidazol-5-yl)-1H-pyrazol-4-yl]-(6-fluoro-5-pyrrolidin-1-ylmethyl-1H-indol-2-yl)-methanone |
| 107 | 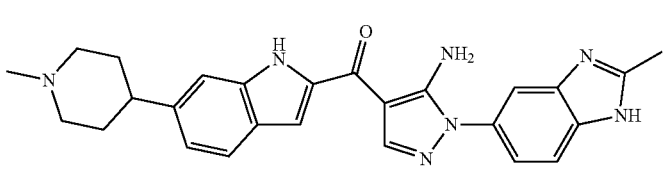 | [5-amino-1-(2-methyl-1H-benzimidazol-5-yl)-1H-pyrazol-4-yl]-[6-(1-methyl-piperidin-4-yl)-1H-indol-2-yl]-methanone |
| 108 | 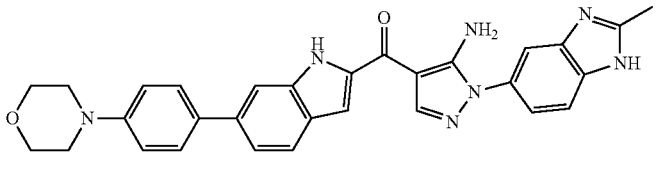 [SMILES: Cc1nc2cc(-n3ncc(C(=O)c4cc5ccc(-c6ccc(N7CCOCC7)cc6)cc5[nH]4)c3N)ccc2[nH]1] | [5-amino-1-(2-methyl-1H-benzimidazol-5-yl)-1H-pyrazol-4-yl]-[6-(4-morpholin-4-yl-phenyl)-1H-indol-2-yl]-methanone |
| 109 | 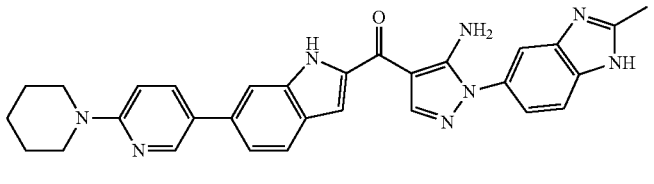 [SMILES: Cc1nc2cc(-n3ncc(C(=O)c4cc5ccc(-c6ccc(N7CCCCC7)nc6)cc5[nH]4)c3N)ccc2[nH]1] | [5-amino-1-(2-methyl-1H-benzimidazol-5-yl)-1H-pyrazol-4-yl]-[6-(3,4,5,6-tetrahydro-2H-[1,2']bipyridin-5'-yl)-1H-indol-2-yl]-methanone |
| 110 | 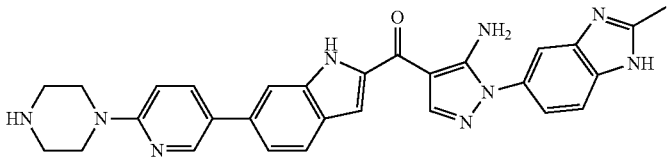 [SMILES: Cc1nc2cc(-n3ncc(C(=O)c4cc5ccc(-c6ccc(N7CCNCC7)nc6)cc5[nH]4)c3N)ccc2[nH]1] | [5-amino-1-(2-methyl-1H-benzimidazol-5-yl)-1H-pyrazol-4-yl]-[6-(6-piperazin-1-yl-pyridin-3-yl)-1H-indol-2-yl]-methanone |
| 111 | 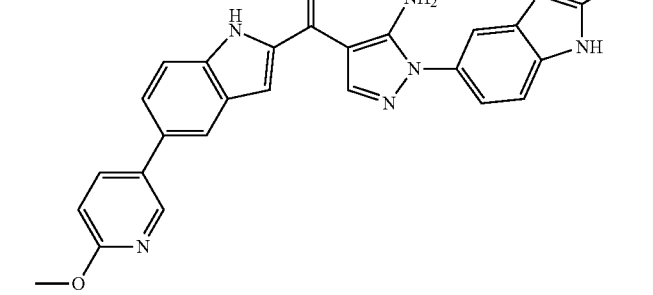 | [5-amino-1-(2-methyl-1H-benzimidazol-5-yl)-1H-pyrazol-4-yl]-[5-(6-methoxy-pyridin-3-yl)-1H-indol-2-yl]-methanone |
| 112 | 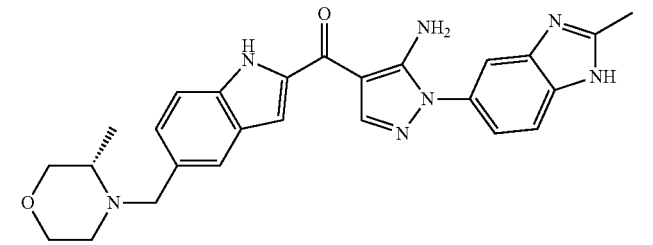 [SMILES: Cc1nc2cc(-n3ncc(C(=O)c4cc5cc(CN6CCOC[C@@H]6C)ccc5[nH]4)c3N)ccc2[nH]1] | [5-amino-1-(2-methyl-1H-benzimidazol-5-yl)-1H-pyrazol-4-yl]-[5-((S)-3-methyl-morpholin-4-ylmethyl)-1H-indol-2-yl-methanone |

US 8,829,199 B2

151 152

TABLE 4-continued

| 113 | 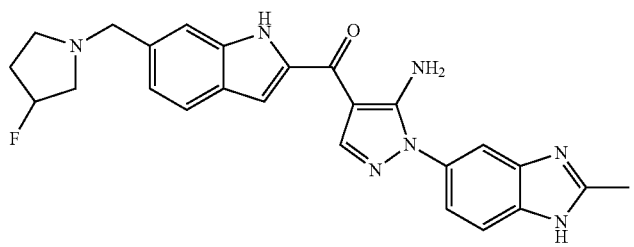 [SMILES: Cc1nc2cc(-n3ncc(C(=O)c4cc5ccc(CN6CCC(F)C6)cc5[nH]4)c3N)ccc2[nH]1] | [5-amino-1-(2-methyl-1H-benzimidazol-5-yl)-1H-pyrazol-4-yl]-[6-((R)-3-fluoro-pyrrolidin-1-ylmethyl)-1H-indol-2-yl]-methanone |
| --- | --- | --- |
| 114 | 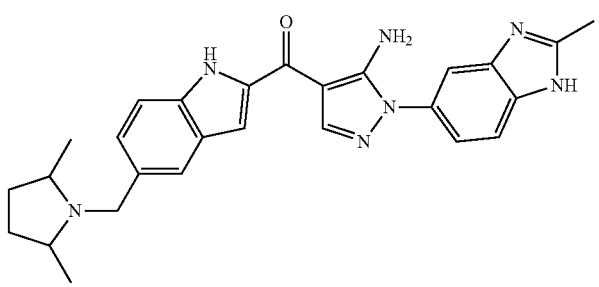 [SMILES: Cc1nc2cc(-n3ncc(C(=O)c4cc5cc(CN6C(C)CCC6C)ccc5[nH]4)c3N)ccc2[nH]1] | [5-amino-1-(2-methyl-1H-benzimidazol-5-yl)-1H-pyrazol-4-yl]-[5-(2,5-dimethyl-pyrrolidin-1-ylmethyl)-1H-indol-2-yl]-methanone |
| 115 | 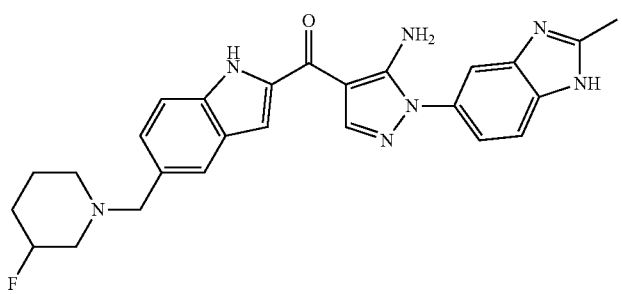 [SMILES: Cc1nc2cc(-n3ncc(C(=O)c4cc5cc(CN6CCCC(F)C6)ccc5[nH]4)c3N)ccc2[nH]1] | [5-amino-1-(2-methyl-1H-benzimidazol-5-yl)-1H-pyrazol-4-yl]-[5-(3-fluoro-piperidin-1-ylmethyl)-1H-indol-2-yl]-methanone |
| 116 | 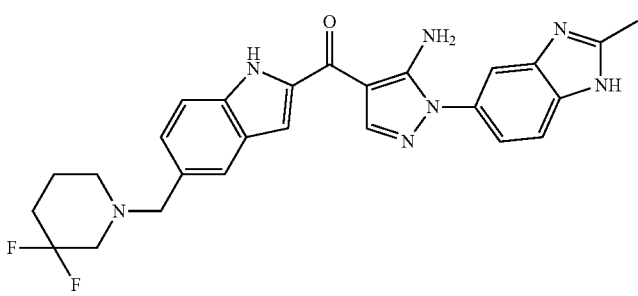 [SMILES: Cc1nc2cc(-n3ncc(C(=O)c4cc5cc(CN6CCCC(F)(F)C6)ccc5[nH]4)c3N)ccc2[nH]1] | [5-amino-1-(2-methyl-1H-benzimidazol-5-yl)-1H-pyrazol-4-yl]-[5-(3,3-difluoro-piperidin-1-ylmethyl)-1H-indol-2-yl]-methanone |
| 117 | 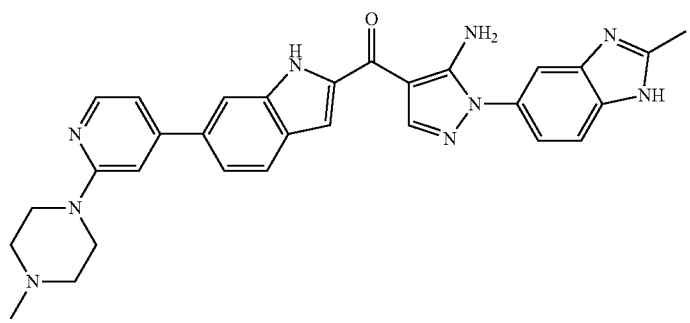 [SMILES: Cc1nc2cc(-n3ncc(C(=O)c4cc5ccc(-c6ccnc(N7CCN(C)CC7)c6)cc5[nH]4)c3N)ccc2[nH]1] | [5-amino-1-(2-methyl-1H-benzimidazol-5-yl)-1H-pyrazol-4-yl]-{6-[2-(4-methyl-piperazin-1-yl)pyridin-4-yl]-1H-indol-2-yl}-methanone |
| 118 | 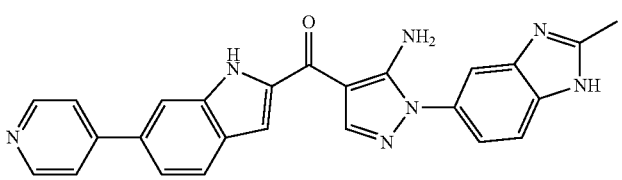 [SMILES: Cc1nc2cc(-n3ncc(C(=O)c4cc5ccc(-c6ccncc6)cc5[nH]4)c3N)ccc2[nH]1] | [5-amino-1-(2-methyl-1H-benzimidazol-5-yl)-1H-pyrazol-4-yl]-(6-pyridin-4-yl-1H-indol-2-yl)-methanone |

TABLE 4-continued

| 119 | 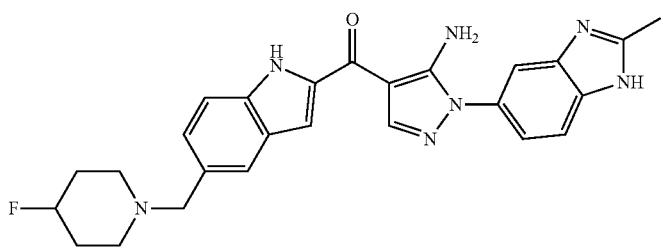 [SMILES: Cc1nc2cc(-n3ncc(C(=O)c4cc5cc(CN6CCC(F)CC6)ccc5[nH]4)c3N)ccc2[nH]1] | [5-amino-1-(2-methyl-1H-benzimidazol-5-yl)-1H-pyrazol-4-yl]-[5-(4-fluoropiperidin-1-ylmethyl)-1H-indol-2-yl]-methanone |
| 120 | 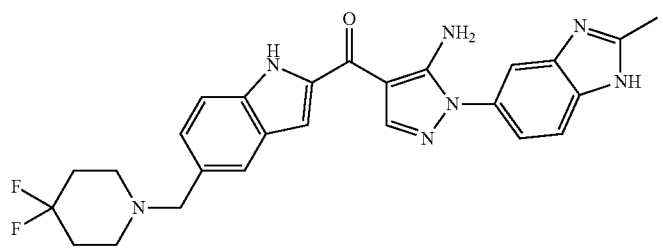 [SMILES: Cc1nc2cc(-n3ncc(C(=O)c4cc5cc(CN6CCC(F)(F)CC6)ccc5[nH]4)c3N)ccc2[nH]1] | [5-amino-1-(2-methyl-1H-benzimidazol-5-yl)-1H-pyrazol-4-yl]-[5-(4,4-difluoro-piperidin-1-ylmethyl)-1H-indol-2-yl]-methanone |
| 121 | 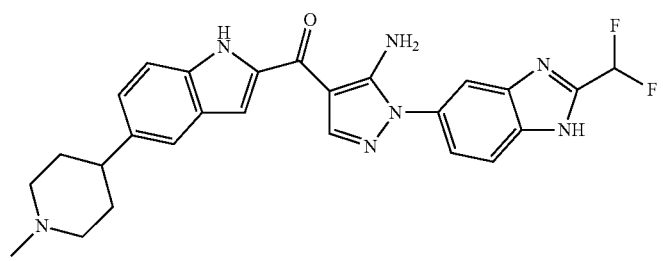 [SMILES: CN1CCC(c2ccc3[nH]c(C(=O)c4cnn(-c5ccc6[nH]c(C(F)F)nc6c5)c4N)cc3c2)CC1] | [5-amino-1-(2-difluoromethyl-1H-benzimidazol-5-yl)-1H-pyrazol-4-yl]-[5-(1-methyl-piperidin-4-yl)-1H-indol-2-yl]-methanone |
| 122 | 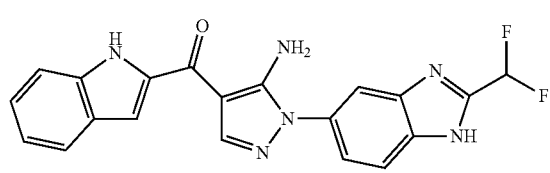 [SMILES: Nc1c(C(=O)c2cc3ccccc3[nH]2)cnn1-c1ccc2[nH]c(C(F)F)nc2c1] | [5-amino-1-(2-difluoromethyl-1H-benzimidazol-5-yl)-1H-pyrazol-4-yl]-(1H-indol-2-yl)-methanone |
| 123 | 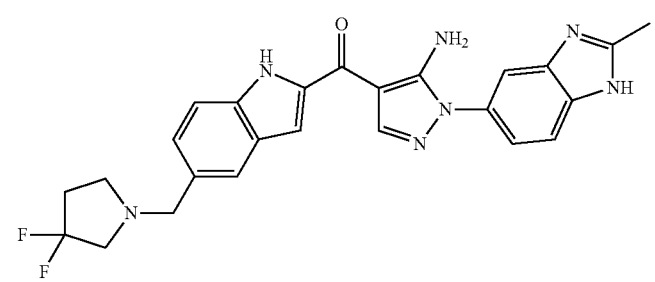 [SMILES: Cc1nc2cc(-n3ncc(C(=O)c4cc5cc(CN6CCC(F)(F)C6)ccc5[nH]4)c3N)ccc2[nH]1] | [5-amino-1-(2-methyl-1H-benzimidazol-5-yl)-1H-pyrazol-4-yl]-[5-(3,3-difluoro-pyrrolidin-1-ylmethyl)-1H-indol-2-yl]-methanone |
| 124 | 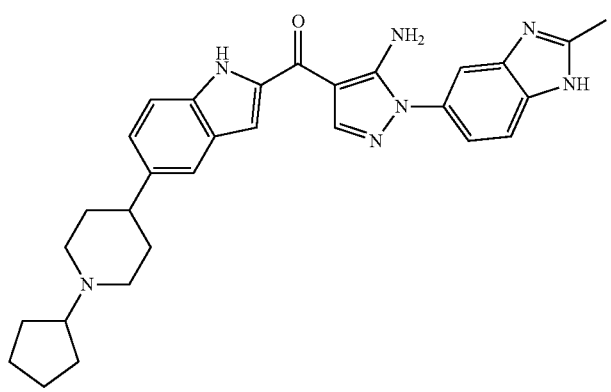 [SMILES: Cc1nc2cc(-n3ncc(C(=O)c4cc5cc(C6CCN(C7CCCC7)CC6)ccc5[nH]4)c3N)ccc2[nH]1] | [5-amino-1-(2-methyl-1H-benzimidazol-5-yl)-1H-pyrazol-4-yl]-[5-(1-cyclopentyl-piperidin-4-yl)-1H-indol-2-yl]-methanone |

TABLE 4-continued

| 125 | 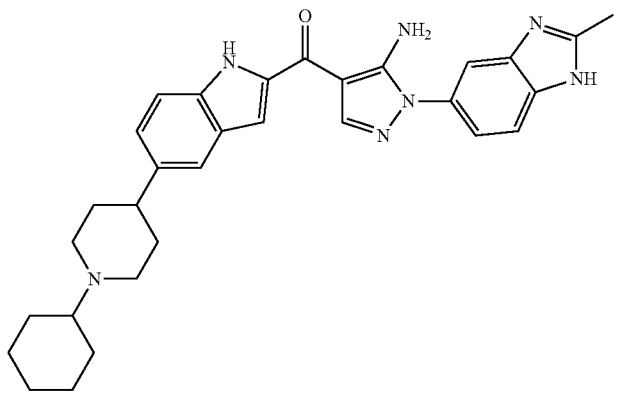 [SMILES: Cc1nc2cc(-n3ncc(C(=O)c4cc5cc(C6CCN(C7CCCCC7)CC6)ccc5[nH]4)c3N)ccc2[nH]1] | [5-amino-1-(2-methyl-1H-benzimidazol-5-yl)-1H-pyrazol-4-yl]-[5-(1-cyclohexyl-piperidin-4-yl)-1H-indol-2-yl]-methanone |
| 126 | 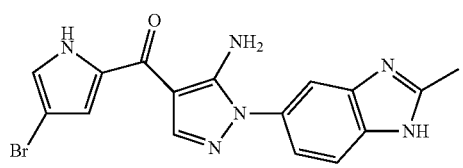 [SMILES: Cc1nc2cc(-n3ncc(C(=O)c4cc(Br)c[nH]4)c3N)ccc2[nH]1] | [5-amino-1-(2-methyl-1H-benzimidazol-5-yl)-1H-pyrazol-4-yl]-(4-bromo-1H-pyrrol-2-yl)-methanone |
| 127 | 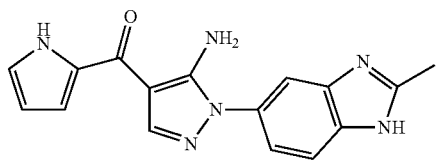 [SMILES: Cc1nc2cc(-n3ncc(C(=O)c4ccc[nH]4)c3N)ccc2[nH]1] | [5-amino-1-(2-methyl-1H-benzimidazol-5-yl)-1H-pyrazol-4-yl]-(1H-pyrrol-2-yl)-methanone |
| 128 | 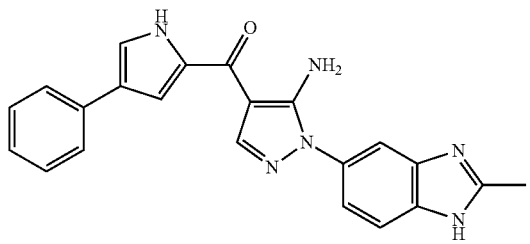 [SMILES: Cc1nc2cc(-n3ncc(C(=O)c4cc(-c5ccccc5)c[nH]4)c3N)ccc2[nH]1] | [5-amino-1-(2-methyl-1H-benzimidazol-5-yl)-1H-pyrazol-4-yl]-(4-phenyl-1H-pyrrol-2-yl)-methanone |
| 129 | 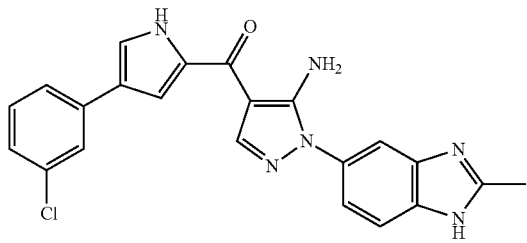 [SMILES: Cc1nc2cc(-n3ncc(C(=O)c4cc(-c5cccc(Cl)c5)c[nH]4)c3N)ccc2[nH]1] | [5-amino-1-(2-methyl-1H-benzimidazol-5-yl)-1H-pyrazol-4-yl]-[4-(3-chloro-phenyl)-1H-pyrrol-2-yl]-methanone |
| 130 | 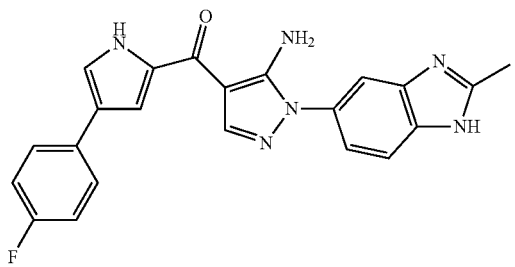 [SMILES: Cc1nc2cc(-n3ncc(C(=O)c4cc(-c5ccc(F)cc5)c[nH]4)c3N)ccc2[nH]1] | [5-amino-1-(2-methyl-1H-benzimidazol-5-yl)-1H-pyrazol-4-yl]-[4-(4-fluoro-phenyl)-1H-pyrrol-2-yl]-methanone |

TABLE 4-continued

| | | |
|---|---|---|
| 131 |  | [5-amino-1-(2-methyl-1H-benzimidazol-5-yl)-1H-pyrazol-4-yl]-[4-(3-fluoro-phenyl)-1H-pyrrol-2-yl]-methanone |

| Example | m/z | 1H-NMR |
|---|---|---|
| 91 | 550 | 1H-NMR (DMSO-D6) δ: 12.48 (1H, s), 11.99 (1H, s), 8.30 (1H, s), 7.87 (1H, s), 7.79 (1H, s), 7.66-7.55 (2H, br m), 7.45 (1H, s), 7.29 (1H, d, J = 8.5 Hz), 7.06 (2H, br s), 2.96-2.89 (2H, m), 2.84-2.70 (2H, m), 2.53 (3H, s), 2.26-2.18 (2H, m), 1.81-1.71 (4H, m), 1.01 (6H, d, J = 6.7 Hz). |
| 92 | 382 | 1H-NMR (DMSO-D6) δ: 12.47 (1H, s), 12.24 (1H, s), 8.33 (1H, s), 7.93-7.86 (2H, m), 7.67-7.55 (3H, m), 7.42 (1H, dd, J = 8.5, 1.2 Hz), 7.29 (1H, dd, J = 8.5, 1.8 Hz), 7.10 (2H, s), 2.54 (3H, s). |
| 93 | 438 | 1H-NMR (DMSO-D6) δ: 12.45 (1H, s), 11.65 (1H, s), 8.28 (1H, s), 7.67-7.54 (3H, m), 7.44-7.39 (3H, m), 7.29 (1H, d, J = 8.5 Hz), 6.99 (2H, br s), 6.16 (1H, s), 3.41-3.38 (2H, m), 2.95 (2H, t, J = 5.5 Hz), 2.53 (1H, s), 2.43-2.41 (2H, m). |
| 94 | 440 | 1H-NMR (DMSO-D6) δ: 12.44 (1H, s), 11.55 (1H, s), 8.28 (1H, s), 7.66-7.55 (2H, br m), 7.48 (1H, s), 7.40 (1H, d, J = 8.5 Hz), 7.37 (1H, d, J = 1.2 Hz), 7.29 (1H, d, J = 8.5 Hz), 7.15 (1H, dd, J = 8.5, 1.2 Hz), 6.97 (2H, br s), 3.05-3.02 (2H, m), 2.67-2.58 (3H, m), 2.53 (3H, s), 1.75-1.72 (2H, m), 1.61-1.50 (2H, m). |
| 95 | 458 | 1H-NMR (DMSO-D6) δ: 12.46 (1H, d, J = 4.9 Hz), 11.65 (1H, d, J = 1.2 Hz), 8.30 (1H, d, J = 4.9 Hz), 7.65 (1H, dd, J = 5.2, 3.4 Hz), 7.59-7.57 (2H, m), 7.44-7.42 (2H, m), 7.32-7.27 (1H, m), 7.23 (1H, dd, J = 8.2, 1.5 Hz), 6.99 (2H, d, J = 22.0 Hz), 5.20 (1H, dt, J = 55.9, 6.6 Hz), 3.67 (2H, s), 2.81-2.76 (2H, m), 2.66-2.68 (1H, m), 2.54 (3H, s), 2.34-2.32 (1H, m), 2.18-2.13 (1H, m), 1.90-1.84 (1H, m). |
| 96 | 458 | 1H-NMR (DMSO-D6) δ: 12.45 (1H, s), 11.63 (1H, s), 8.27 (1H, s), 7.62-7.59 (2H, br m), 7.55 (1H, d, J = 7.3 Hz), 7.43 (1H, s), 7.28 (1H, dd, J = 8.5, 2.4 Hz), 7.14 (1H, d, J = 11.0 Hz), 6.97 (2H, br s), 3.06-3.03 (2H, m), 2.91-2.85 (1H, m), 2.66-2.59 (2H, m), 2.53 (3H, s), 1.75-1.72 (2H, m), 1.63-1.53 (2H, m). |
| 97 | 472 | 1H-NMR (DMSO-D6) δ: 12.45 (1H, s), 11.64 (1H, d, J = 1.5 Hz), 8.27 (1H, s), 7.66-7.62 (1H, br m), 7.59-7.53 (1H, br m), 7.57 (1H, d, J = 7.3 Hz), 7.42 (1H, d, J = 1.5 Hz), 7.28 (1H, d, J = 9.8 Hz), 7.14 (1H, d, J = 11.6 Hz), 6.97 (2H, br s), 2.92-2.87 (2H, m), 2.79-2.72 (1H, m), 2.53 (3H, s), 2.21 (3H, s), 2.04-1.07 (2H, m), 1.78-1.69 (4H, m). |
| 98 | 482 | 1H-NMR (DMSO-D6) δ: 12.45 (1H, s), 11.55 (1H, d, J = 1.8 Hz), 8.28 (1H, s), 7.65-7.63 (1H, br m), 7.59-7.56 (1H, br m), 7.49 (1H, s), 7.39 (1H, d, J = 8.5 Hz), 7.36 (1H, d, J = 1.5 Hz), 7.29 (1H, d, J = 9.1 Hz), 7.16 (1H, dd, J = 8.5, 1.5 Hz), 7.00 (1H, br s), 6.95 (1H, br s), 2.92-2.87 (2H, m), 2.76-2.68 (1H, m), 2.55-2.52 (1H, m), 2.53 (3H, s), 2.27-2.20 (2H, m), 1.83-1.77 (2H, m), 1.71-1.60 (2H, m), 1.00 (6H, d, J = 6.7 Hz). |
| 99 | 500 | 1H-NMR (DMSO-D6) δ: 12.45 (1H, s), 11.64 (1H, d, J = 1.5 Hz), 8.27 (1H, s), 7.66-7.61 (1H, br m), 7.59-7.55 (1H, br m), 7.57 (1H, d, J = 7.3 Hz), 7.41 (1H, d, J = 1.6 Hz), 7.28 (1H, d, J = 7.9 Hz), 7.14 (1H, d, J = 11.6 Hz), 7.00 (1H br s), 6.95 (1H, br s), 2.93-2.88 (2H, m), 2.77-2.69 (2H, m), 2.53 (3H, s), 2.30-2.22 (2H, m), 1.84-1.78 (2H, m), 1.75-1.65 (2H, m), 1.01 (6H, d, J = 6.7 Hz). |
| 100 | 434 | 1H-NMR (DMSO-D6) δ: 12.47 (1H, s), 11.86 (1H, s), 8.90 (1H, d, J = 2.4 Hz), 8.56 (1H, d, J = 4.9 Hz), 8.34 (1H, s), 8.08 (1H, d, J = 7.9 Hz), 7.83 (1H, d, J = 7.9 Hz), 7.73 (1H, s), 7.62 (2H, s), 7.53-7.43 (3H, m), 7.30 (2H, dd, J = 8.2, 1.5 Hz), 7.03 (3H, s), 2.54 (3H, s). |
| 101 | 519 | 1H-NMR (DMSO-D6) δ: 12.47 (1H, s), 11.74 (1H, d, J = 1.2 Hz), 8.49 (1H, d, J = 2.4 Hz), 8.32 (1H, s), 7.91-7.90 (2H, m), 7.66-7.47 (5H, m), 7.30 (1H, d, J = 8.5 Hz), 7.02 (2H, d, J = 19.5 Hz), 8.94 (1H, d, J = 9.2 Hz), 3.73 (4H, dd, J = 4.6, 2.3 Hz), 3.49 (4H, dd, J = 4.9, 2.4 Hz), 2.54 (3H, s). |
| 102 | 434 | 1H-NMR (DMSO-D6) δ: 12.47 (1H, s), 11.86 (1H, d, J = 1.8 Hz), 8.93 (1H, d, J = 2.4 Hz), 8.64 (1H, dd, J = 4.9, 1.2 Hz), 8.33 (1H, s), 8.10 (1H, dt, J = 8.1, 1.8 Hz), 8.03 (1H, s), 7.64-7.69 (4H, m), 7.52 (1H, d, J = 1.8 Hz), 7.49 (1H, dd, J = 7.6, 4.6 Hz), 7.31 (1H, d, J = 8.5 Hz), 7.03 (2H, d, J = 20.1 Hz), 2.54 (3H, s). |

TABLE 4-continued

| | | |
|---|---|---|
| 103 | 518 | 1H-NMR (DMSO-D6) δ: 12.48 (1H, s), 11.74 (1H, s), 8.45 (1H, d, J = 3.1 Hz), 8.32 (1H, s), 7.87-7.85 (2H, m), 7.69-7.49 (5H, m), 7.47 (1H, s), 7.30 (1H, dd, J = 8.5, 1.8 Hz), 7.02 (2H, s), 6.89 (1H, d, J = 9.2 Hz), 3.44 (4H, t, J = 5.1 Hz), 2.80 (4H, t, J = 5.1 Hz), 2.54 (3H, s). |
| 104 | 450 | 1H-NMR (DMSO-D6) δ: 12.89 (1H, s), 11.76 (1H, s), 8.38 (1H, s), 8.00 (1H, d, J = 1.8 Hz), 7.95 (1H, d, J = 9.2 Hz), 7.88 (1H, dd, J = 9.7, 2.5 Hz), 7.82 (1H, s), 7.73 (1H, dd, J = 8.5 1.8 Hz), 7.67 (1H, d, J = 2.5 Hz), 7.52-7.48 (4H, m), 7.25 (2H, s), 6.47 (1H, d, J = 9.7 Hz), 2.84 (3H, s). |
| 105 | 487 | 1H-NMR (DMSO-D6) δ: 12.47 (1H, s), 11.71 (1H, s), 8.29 (1H, s), 7.65 (1H, d, J = 7.3 Hz), 7.62-7.57 (2H, br m), 7.46 (1H, s), 7.28 (1H, dd, J = 8.5, 1.8 Hz), 7.15 (1H, d, J = 11.0 Hz), 6.99 (2H, br s), 3.56 (2H, s), 2.53 (3H, s), 2.47-2.38 (4H, br m), 2.35-2.28 (4H, br m), 2.14 (3H, s). |
| 106 | 458 | 1H-NMR (DMSO-D6) δ: 12.48 (1H, s), 11.69 (1H, s), 8.29 (1H, s), 7.67 (1H, d, J = 7.3 Hz), 7.62-7.58 (2H, br m), 7.45 (1H, s), 7.28 (1H, dd, J = 8.5, 1.8 Hz), 7.14 (1H, d, J = 11.0 Hz), 6.99 (2H, br s), 3.68 (2H, s), 2.53 (3H, s), 2.52-2.45 (4H, m), 1.72-1.67 (4H, m). |
| 107 | 454 | 1H-NMR (DMSO-D6) δ: 12.47 (1H, s), 11.56 (1H, s), 8.28 (1H, s), 7.63-7.57 (2H, br m), 7.60 (1H, d, J = 8.5 Hz), 7.39 (1H, d, J = 1.8 Hz), 7.30 (1H, s), 7.28 (1H, dd, J = 8.5, 1.8 Hz), 6.99 (1H, dd, J = 8.5, 1.8 Hz), 6.98 (2H, br s), 2.91-2.86 (2H, br m), 2.55-2.51 (1H, br m), 2.53 (3H, s), 2.20 (3H, s), 2.02-1.96 (2H, m), 1.79-1.64 (4H, m). |
| 108 | 518 | 1H-NMR (DMSO-D6) δ: 12.47 (1H, s), 11.69 (1H, s), 8.32 (1H, d, J = 1.8 Hz), 7.73 (1H, d, J = 6.7 Hz), 7.64-7.56 (5H, m), 7.46 (1H, s), 7.37 (1H, d, J = 8.5 Hz), 7.30 (1H, d, J = 8.5 Hz), 7.09-6.97 (4H, m), 3.80-3.73 (4H, m), 3.19-3.14 (4H, m), 2.53 (3H, s). |
| 109 | 517 | 1H-NMR (DMSO-D6) δ: 11.70 (1H, s), 8.45 (1H, d, J = 2.4 Hz), 8.33 (1H, s), 7.83 (1H, dd, J = 8.9, 2.7 Hz), 7.74 (1H, d, J = 8.5 Hz), 7.64-7.59 (4H, d, J = 8.5 Hz), 7.47 (1H, s), 7.36 (1H, d, J = 8.5 Hz), 7.30 (1H, dd, J = 8.5, 1.8 Hz), 7.01 (2H, s), 6.92 (1H, d, J = 9.2 Hz), 3.58 (4H, t, J = 5.2 Hz), 2.54 (3H, s), 1.64-1.57 (6H, m). |
| 110 | 518 | 1H-NMR (DMSO-D6) δ: 12.47 (1H, s), 11.71 (1H, s), 8.46 (1H, d, J = 2.4 Hz), 8.33 (1H, s), 7.85 (1H, dd, J = 8.5, 2.4 Hz), 7.75 (1H, d, J = 8.5 Hz), 7.65-7.58 (3H, m), 7.47 (1H, s), 7.36 (1H, d, J = 7.9 Hz), 7.30 (1H, dd, J = 8.5, 1.8 Hz), 7.01 (2H, s), 6.91 (1H, d, J = 9.2 Hz), 3.46 (4H, t, J = 4.9 Hz), 2.80 (1H, t, J = 4.9 Hz), 2.54 (3H, s). |
| 111 | 464 | 1H-NMR (DMSO-D6) δ: 12.47 (1H, s), 11.79 (1H, s), 8.49 (1H, d, J = 2.4 Hz), 8.32 (1H, s), 8.03 (1H, dd, J = 8.9, 2.7 Hz), 7.93 (1H, s), 7.62-7.54 (4H, m), 7.49 (1H, s), 7.30 (1H, dd, J = 8.2, 2.1 Hz), 7.02 (2H, s), 6.92 (1H, d, J = 9.2 Hz), 3.91 (3H, s), 2.54 (3H, s). |
| 112 | 470 | 1H-NMR (DMSO-D6) δ: 12.46 (1H, s), 11.65 (1H, s), 8.30 (1H, s), 7.60-7.58 (3H, m), 7.44-7.42 (2H, m), 7.30 (1H, d, J = 8.5 Hz), 7.22 (1H, d, J = 8.5 Hz), 6.99 (2H, s), 4.08 (1H, d, J = 12.8 Hz), 3.64-3.61 (2H, m), 3.43-3.40 (2H, m), 3.17-3.14 (2H, m), 2.63 (3H, s), 2.42-2.40 (1H, m), 2.12-2.08 (1H, m), 1.06 (3H, d, J = 6.7 Hz). |
| 113 | 458 | 1H-NMR (DMSO-D6) δ: 12.48 (1H, s), 11.64 (1H, s), 8.29 (1H, s), 7.61-7.58 (3H, m), 7.42-7.40 (2H, m), 7.28 (1H, dd, J = 8.5, 2.1 Hz), 7.04 (1H, dd, J = 8.2, 1.2 Hz), 6.98 (2H, br s), 5.28-5.11 (1H, m), 3.68 (2H, s), 2.82-2.75 (2H, m), 2.67-2.65 (1H, m), 2.52 (3H, s), 2.32-2.30 (1H, m), 2.20-2.08 (1H, m), 1.94-1.78 (1H, m). |
| 114 | 468 | 1H-NMR (DMSO-D6) δ: 12.44 (1H, d, J = 4.3 Hz), 11.60 (1H, s), 8.30 (1H, d, J = 4.3 Hz), 7.65-7.55 (3H, m), 7.41-7.40 (2H, m), 7.28-7.21 (2H, m), 6.98 (2H, d, J = 22.0 Hz), 3.90-3.52 (2H, m), 2.97-2.95 (1H, m), 2.61 (1H, dd, J = 11.0, 5.5 Hz), 2.53 (3H, s), 1.99-1.93 (1H, m), 1.80-1.74 (1H, m), 1.32-1.27 (2H, m), 0.97 (6H, t, J = 6.1 Hz). |
| 115 | 472 | 1H-NMR (DMSO-D6) δ: 12.45 (1H, s), 11.64 (1H, s), 8.29 (1H, s), 7.63-7.56 (3H, m), 7.44-7.41 (2H, m), 7.29 (1H, d, J = 8.5 Hz), 7.20 (1H, d, J = 8.5 Hz), 6.98 (2H, s), 4.62 (1H, d, J = 48.2 Hz), 3.57 (2H, s), 2.75-2.21 (4H, m), 2.53 (3H, s), 1.80-1.74 (2H, m), 1.52-1.43 (2H, m). |
| 116 | 490 | 1H-NMR (DMSO-D6) δ: 12.46 (1H, s), 11.66 (1H, s), 8.30 (1H, s), 7.61-7.58 (3H, m), 7.45-7.42 (2H, m), 7.29 (1H, dd, J = 8.5, 1.8 Hz), 7.20 (1H, d, J = 8.5 Hz), 6.99 (2H, s), 3.64 (2H, s), 2.59-2.51 (4H, m), 2.53 (3H, s), 1.88-1.86 (2H, m), 1.66-1.64 (2H, m). |
| 117 | 532 | 1H-NMR (DMSO-D6) δ: 12.47 (1H, s), 11.72 (1H, d, J = 1.2 Hz), 8.46 (1H, d, J = 3.1 Hz), 8.33 (1H, s), 7.86 (1H, dd, J = 8.9, 2.7 Hz), 7.75 (1H, d, J = 8.5 Hz), 7.68-7.55 (3H, m), 7.48 (1H, d, J = 1.2 Hz), 7.36 (1H, dd, J = 8.2, 1.5 Hz) 7.30 (1H, d, J = 7.9 Hz), 7.07-6.93 (3H, dd, m), 3.57-3.52 (4H, m), 2.53 (3H, s), 2.44-2.39 (4H, m), 2.23 (3H, s). |
| 118 | 434 | 1H-NMR (DMSO-D6) δ: 8.65 (2H, dd, J = 4.6, 1.5 Hz), 8.34 (1H, s), 7.84 (2H, d, J = 9.2 Hz), 7.72 (2H, dd, J = 4.6, 1.5 Hz), 7.61 (2H, t, J = 4.6 Hz), 7.55-7.50 (2H, m), 7.29 (1H, dd, J = 8.2, 2.1 Hz), 7.06 (2H, s), 2.55 (3H, s). |

TABLE 4-continued

| | | |
|---|---|---|
| 119 | 472 | 1H-NMR (DMSO-D6) δ: 12.46 (1H, d, J = 4.9 Hz), 11.66 (1H, d, J = 1.8 Hz), 8.30 (1H, d, J = 4.9 Hz), 7.65 (1H, dd, J = 5.2, 3.4 Hz), 7.58-7.56 (2H, m), 7.44-7.42 (2H, m), 7.32-7.27 (1H, m), 7.21 (1H, d, J = 4.9 Hz), 7.00 (2H, d, J = 22.6 Hz), 4.72-4.65 (1H, m), 3.54 (2H, s), 2.53 (3H, s), 2.51-2.48 (2H, m), 2.32-2.31 (2H, m), 1.89-1.83 (2H, m), 1.73-1.71 (2H, m). |
| 120 | 490 | 1H-NMR (DMSO-D6) δ: 12.45 (1H, s), 11.66 (1H, s), 8.29 (1H, s), 7.61-7.58 (3H, m), 7.43-7.42 (2H, m), 7.29 (1H, dd, J = 8.4, 2.1 Hz), 7.22 (1H, dd, J = 8.4, 1.8 Hz), 6.99 (2H, s), 3.61 (2H, s), 3.34-3.30 (4H, m), 2.53 (3H, s), 1.99-1.90 (4H, m). |
| 121 | 490 | 1H-NMR (DMSO-D6) δ: 13.60 (1H, br s), 11.58 (1H, d, J = 1.8 Hz), 8.31 (1H, s), 7.83-7.80 (2H, m), 7.51-7.46 (2H, m), 7.45-7.38 (2H, m), 7.32-7.14 (2H, br m), 7.08 (2H, br s), 2.93-2.85 (2H, m), 2.56-2.50 (1H, m), 2.21 (3H, s), 2.04-1.96 (2H, m), 1.81-1.65 (4H, br m). |
| 122 | 393 | 1H-NMR (DMSO-D6) δ: 13.60 (1H, br s), 11.69 (1H, s), 8.34 (1H, s), 7.84-7.80 (2H, m), 7.70 (1H, d, J = 7.4 Hz), 7.51-7.45 (3H, m), 7.32-7.19 (2H, m), 7.12-7.06 (3H, m). |
| 123 | 476 | 1H-NMR (DMSO-D6) δ: 12.47 (1H, s), 11.68 (1H, s), 8.30 (1H, d, J = 4.9 Hz), 7.65 (1H, dd, J = 5.0, 3.4 Hz), 7.61-7.55 (2H, m), 7.47-7.41 (2H, m), 7.30 (1H, t, J = 6.4 Hz), 7.22 (1H, d, J = 8.5 Hz), 7.00 (2H, d, J = 21.4 Hz), 3.69 (2H, s), 2.86 (2H, t, J = 13.5 Hz), 2.66-2.42 (2H, m), 2.61 (3H, s), 2.29-2.22 (2H, m). |
| 124 | 508 | 1H-NMR (DMSO-D6) δ: 12.47 (1H, s), 11.57 (1H, d, J = 1.2 Hz), 8.29 (1H, d, J = 3.7 Hz), 7.66-7.56 (2H, m), 7.50 (1H, s), 7.43-7.37 (2H, m), 7.29 (1H, t, J = 6.1 Hz), 7.17 (1H, dd, J = 8.5, 1.2 Hz), 6.99 (2H, d, J = 22.0 Hz), 3.06 (2H, d, J = 11.0 Hz), 2.54 (3H, s), 2.02 (2H, t, J = 10.7 Hz), 1.64-1.48 (14H, m). |
| 125 | 522 | 1H-NMR (DMSO-D6) δ: 12.46 (1H, s), 11.57 (1H, d, J = 1.8 Hz), 8.29 (1H, s), 7.62-7.58 (2H, m), 7.49 (1H, s), 7.40-7.37 (2H, m), 7.29 (1H, d, J = 7.9 Hz), 7.16 (1H, dd, J = 8.5, 1.2 Hz), 6.98 (2H, d, J = 20.8 Hz), 2.93 (2H, d, J = 11.6 Hz), 2.53 (3H, s), 2.36-2.31 (3H, m), 1.80-1.57 (9H, m), 1.22-1.14 (6H, m). |
| 126 | 385, 387 | 1H-NMR (DMSO-D6) δ: 12.47 (1H, s), 12.04 (1H, s), 8.20 (1H, s), 7.61-7.57 (1H, m), 7.27 (1H, dd, J = 8.5, 1.7 Hz), 7.19-7.18 (2H, m), 6.93-6.90 (3H, m), 2.53 (3H, s). |
| 127 | 307 | 1H-NMR (DMSO-D6) δ: 12.46 (1H, s), 11.71 (1H, s), 8.16 (1H, d, J = 3.0 Hz), 7.59 (2H, dd, J = 23.6, 7.1 Hz), 7.29 (1H, d, J = 10.0 Hz), 7.08 (1H, d, J = 15.4 Hz), 6.85 (2H, d, J = 14.8 Hz), 6.24-6.22 (2H, m), 2.53 (3H, s). |
| 128 | 383 | 1H-NMR (CD3OD) δ: 8.54 (1H, s), 8.25 (1H, s), 7.94 (1H, d, J = 1.5 Hz), 7.91 (1H, d, J = 1.8 Hz), 7.67-7.63 (2H, m), 7.44-7.31 (5H, m), 2.61 (3H, s). |
| 129 | 417 | 1H-NMR (CD3OD) δ: 8.30-8.26 (1H, m), 7.66 (2H, dt, J = 5.4, 2.4 Hz), 7.58 (1H, dq, J = 7.8, 0.9 Hz), 7.48 (1H, d, J = 1.6 Hz), 7.42 (1H, d, J = 1.5 Hz), 7.39 (1H, d, J = 2.0 Hz), 7.36 (1H, d, J = 1.8 Hz), 7.31 (1H, d, J = 7.9 Hz), 7.17 (1H, dq, J = 8.0, 1.0 Hz), 2.61 (3H, s). |
| 130 | 401 | 1H-NMR (CD3OD) δ: 8.26 (1H, s), 7.66-7.63 (3H, m), 7.40 (1H, dd, J = 3.7, 1.7 Hz), 7.36 (1H, dd, J = 3.0, 1.8 Hz), 7.11 (1H, d, J = 2.1 Hz), 7.08 (2H, t, J = 2.1 Hz), 7.05 (1H, d, J = 2.1 Hz), 2.61 (3H, s). |
| 131 | 401 | 1H-NMR (CD3OD) δ: 8.27 (1H, s), 7.66-7.65 (2H, m), 7.47 (1H, d, J = 1.5 Hz), 7.45 (1H, t, J = 1.2 Hz), 7.42 (1H, d, J = 1.6 Hz), 7.39-7.35 (2H, m), 7.33-7.31 (1H, m), 6.94-6.86 (1H, m), 2.61 (3H, s). |

Example 132

Synthesis of [5-amino-1-(2-methyl-1H-benzimidazol-5-yl)-1H-pyrazol-4-yl]-(6-morpholin-4-ylmethyl-1H-indol-2-yl)-methanone

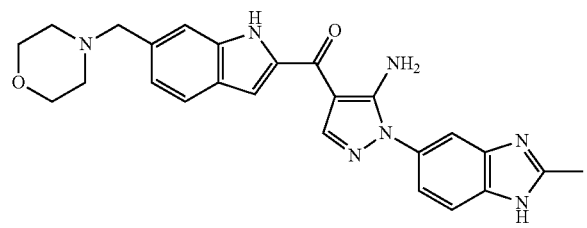 [SMILES: Cc1nc2cc(-n3ncc(C(=O)c4cc5ccc(CN6CCOCC6)cc5[nH]4)c3N)ccc2[nH]1]

[5-Amino-1-(2-methyl-1H-benzimidazol-5-yl)-1H-pyrazol-4-yl]-(1-benzenesulfonyl-6-morpholin-4-ylmethyl-1H-indol-2-yl)-methanone (132 mg, 0.22 mmol) was dissolved in tetrahydrofuran (THF) (1.0 ml), and then a tetrahydrofuran (THF) solution of 1 M tetrabutylammonium fluoride (0.46 ml, 0.46 mmol) was added thereto. The mixture was heated at 65° C. with stirring for 22 hours. The reaction mixture was then cooled to room temperature, and concentrated under reduced pressure. The resulting residue was purified by silica gel column chromatography (dichloromethane/methanol=100/10) to give [5-amino-1-(2-methyl-1H-benzimidazol-5-yl)-1H-pyrazol-4-yl]-(6-morpholin-4-ylmethyl-1H-indol-2-yl)-methanone as a yellow solid (74 mg, 75%).

$^1$H-NMR (DMSO-D$_6$) δ: 12.48 (1.0H, brs), 11.64 (1.0H, brs), 8.30 (1.0H, s), 7.64-7.60 (3.0H, m), 7.42-7.41 (2.0H, m), 7.29 (1.0H, dd, J=8.5, 2.2 Hz), 7.06 (1.0H, dd, J=8.3, 1.0 Hz), 6.99 (2.0H, brs), 3.58 (4.0H, t, J=4.4 Hz), 3.55 (2.0H, s), 2.53 (3.0H, s), 2.39-2.37 (4.0H, brm)

ESI (LC-MS positive mode) m/z 456 [(M+H)$^+$]

The compounds of Examples 133 to 143 listed in Table 5 were synthesized by the same method as in Example 132.

TABLE 5

| Example | Structure | Compound name |
|---|---|---|
| 133 | 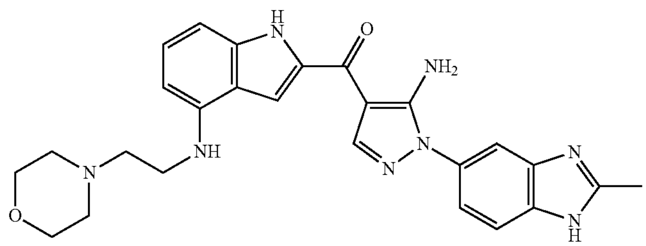 [SMILES: Cc1nc2cc(-n3ncc(C(=O)c4cc5c(NCCN6CCOCC6)cccc5[nH]4)c3N)ccc2[nH]1] | [5-amino-1-(2-methyl-1H-benzimidazol-5-yl)-1H-pyrazol-4-yl]-[4-(2-morpholin-4-yl-ethylamino)-1H-indol-2-yl]-methanone |
| 134 | 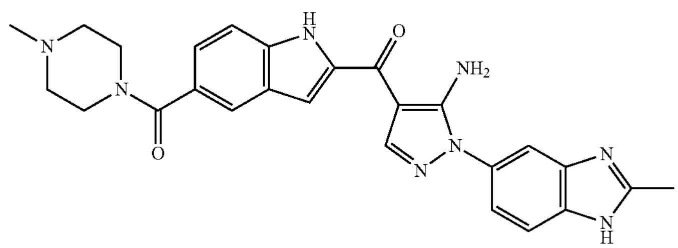 | [5-amino-1-(2-methyl-1H-benzimidazol-5-yl)-1H-pyrazol-4-yl]-[5-(4-methyl-piperazine-1-carbonyl)-1H-indol-2-yl]-methanone |
| 135 | 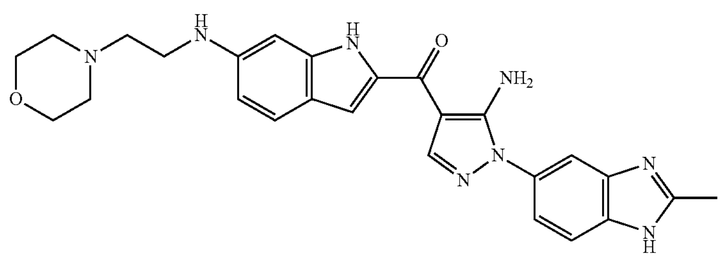 [SMILES: Cc1nc2cc(-n3ncc(C(=O)c4cc5ccc(NCCN6CCOCC6)cc5[nH]4)c3N)ccc2[nH]1] | [5-amino-1-(2-methyl-1H-benzimidazol-5-yl)-1H-pyrazol-4-yl]-[6-(2-morpholin-4-yl-ethylamino)-1H-indol-2-yl]-methanone |
| 136 | 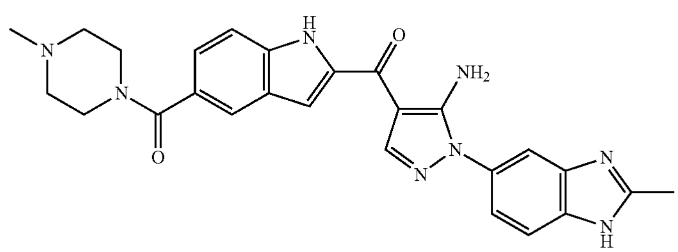 | [5-amino-1-(2-methyl-1H-benzimidazol-5-yl)-1H-pyrazol-4-yl]-[5-(piperazine-1-carbonyl)-1H-indol-2-yl]-methanone |
| 137 | 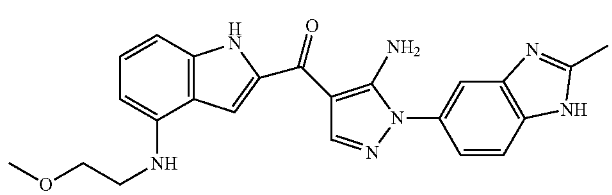 | [5-amino-1-(2-methyl-1H-benzimidazol-5-yl)-1H-pyrazol-4-yl]-[4-(2-methoxy-ethylamino)-1H-indol-2-yl]-methanone |
| 138 | 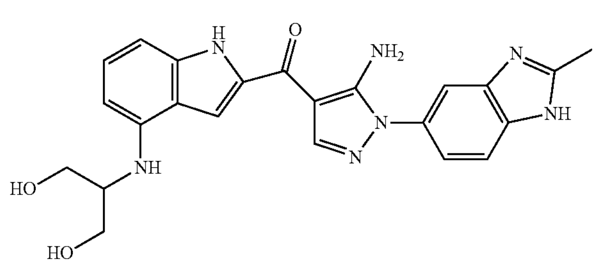 [SMILES: Cc1nc2cc(-n3ncc(C(=O)c4cc5c(NC(CO)CO)cccc5[nH]4)c3N)ccc2[nH]1] | [5-amino-1-(2-methyl-1H-benzimidazol-5-yl)-1H-pyrazol-4-yl]-[4-(2-hydroxy-1-hydroxymethyl-ethylamino)-1H-indol-2-yl]-methanone |

TABLE 5-continued

| | | |
|---|---|---|
| 139 | 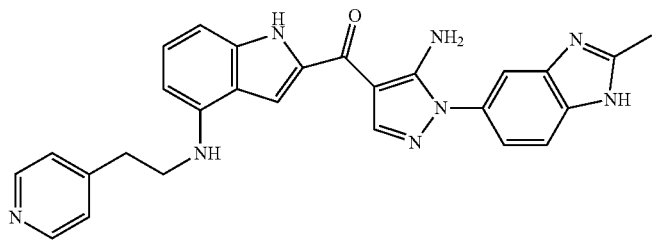 [SMILES: Cc1nc2cc(-n3ncc(C(=O)c4cc5c(NCCc6ccncc6)cccc5[nH]4)c3N)ccc2[nH]1] | [5-amino-1-(2-methyl-1H-benzimidazol-5-yl)-1H-pyrazol-4-yl]-[4-(2-pyridin-4-yl-ethylamino)-1H-indol-2-yl]-methanone |
| 140 | 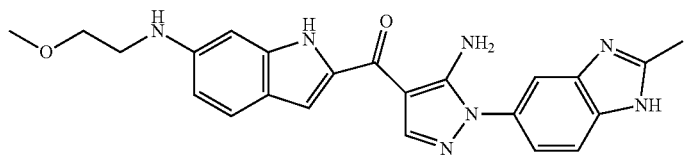 | [5-amino-1-(2-methyl-1H-benzimidazol-5-yl)-1H-pyrazol-4-yl]-[6-(2-methoxy-ethylamino)-1H-indol-2-yl]-methanone |
| 141 | 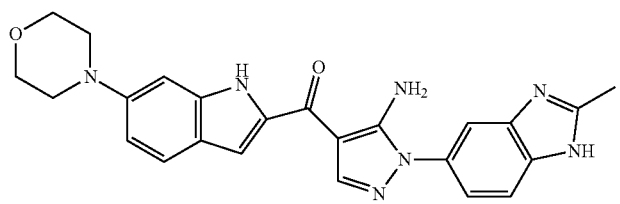 [SMILES: Cc1nc2cc(-n3ncc(C(=O)c4cc5ccc(N6CCOCC6)cc5[nH]4)c3N)ccc2[nH]1] | [5-amino-1-(2-methyl-1H-benzimidazol-5-yl)-1H-pyrazol-4-yl]-(6-morpholin-4-yl-1H-indol-2-yl)-methanone |
| 142 | 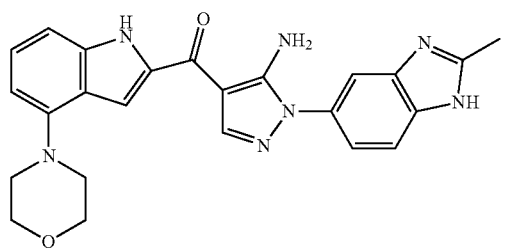 [SMILES: Cc1nc2cc(-n3ncc(C(=O)c4cc5c(N6CCOCC6)cccc5[nH]4)c3N)ccc2[nH]1] | [5-amino-1-(2-methyl-1H-benzimidazol-5-yl)-1H-pyrazol-4-yl]-(4-morpholin-4-yl-1H-indol-2-yl)-methanone |
| 143 | 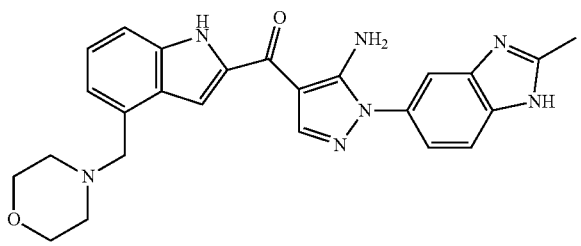 [SMILES: Cc1nc2cc(-n3ncc(C(=O)c4cc5c(CN6CCOCC6)cccc5[nH]4)c3N)ccc2[nH]1] | [5-amino-1-(2-methyl-1H-benzimidazol-5-yl)-1H-pyrazol-4-yl]-(4-morpholin-4-ylmethyl-1H-indol-2-yl)-methanone |

| Example | m/z | 1H-NMR |
|---|---|---|
| 133 | 485 | 1H-NMR (CD3OD) δ: 8.32 (1.0H, s), 7.73-7.61 (2.0H, s), 7.58 (1.0H, d, J = 1.0 Hz), 7.38 (1H, dd, J = 8.8, 2.0 Hz), 7.11 (1H, t, J = 7.8 Hz), 6.79 (1H, d, J = 8.3 Hz), 6.21 (1H, d, J = 7.3 Hz), 3.77-3.72 (4H, m), 3.45 (2H, q, J = 6.0 Hz), 2.76 (2H, t, J = 6.0 Hz), 2.61 (3H, s), 2.55-2.63 (4H, m). |
| 134 | 483 | 1H-NMR (DMSO-D6) δ: 12.47 (1.0H, s), 11.91 (1.0H, s), 8.31 (1.0H, d, J = 4.4 Hz), 7.75 (1.0H, s), 7.66 (1.0H, m), 7.67 (1.0H, m), 7.52 (2.0H, m), 7.29 (2.0H, m), 7.10-7.00 (2.0H, m), 3.56-3.51 (4.0H, m), 2.53 (3.0H, s), 2.40-2.25 (4.0H, m), 2.21 (3.0H, s). |
| 135 | 485 | 1H-NMR (DMSO-D6) δ: 12.45 (10H, br s), 11.55 (1.0H br s), 8.27 (1.0H, s), 7.60-7.55 (3.0H, m), 7.40 (1.0H, br s), 7.32-7.28 (1.0H, m), 6.93 (3.0H, br s), 6.75 (1.0H, dd, J = 8.8, 2.4 Hz), 4.11 (2.0H, t, J = 5.9 Hz), 3.60 (4.0H, t, J = 4.6 Hz), 3.34-3.28 (4.0H, m), 2.73 (2.0H, t, J = 5.9 Hz), 2.53 (3.0H, s). |
| 136 | 469 | 1H-NMR (CD3OD) δ: 8.28 (1.0H, s), 7.88 (1.0H, s), 7.68-7.64 (2.0H, m), 7.58 (1.0H, d, J = 8.3 Hz), 7.46 (1.0H, m), 7.40-7.36 (2.0H, m), 3.75 (4.0H, m), 3.01 (4.0H, m), 2.61 (3.0H, s). |
| 137 | 430 | $^1$H-NMR (CD$_3$OD) δ: 8.33 (1H, s), 7.66-7.59 (3H, m), 7.37 (1H, dd, J = 8.8, 2.0 Hz), 7.10 (1H, t, J = 7.8 Hz), 6.78 (1H, d, J = 8.3 Hz), 6.21 (1H, d, J = 7.3 Hz), 3.70 (2H, t, J = 5.8 Hz), 3.46 (2H, t, J = 5.8 Hz), 2.60 (3.0H, s). |
| 138 | 446 | $^1$H-NMR (CD$_3$OD) δ: 8.35(1H, s), 7.72-7.61 (3H, m), 7.37 (1H, dd, J = 8.8, 2.0 Hz), 7.10 (1H, t, J = 8.1 Hz), 6.78 (1H, d, J = 8.3 Hz), 6.29 (1H, d, J = 7.8 Hz), 3.85-3.71 (5H, m), 2.61 (3H, s). |

TABLE 5-continued

| 139 | 477 | ¹H-NMR (CD₃OD) δ: 8.43 (2H, dd, J = 4.4, 1.5 Hz), 8.30 (1H, s), 7.74-7.61 (2H, s), 7.57 (1H, s), 7.40-7.35 (3H, m), 7.13 (1H, t, J = 8.1 Hz), 6.79 (1H, d, J = 8.3 Hz), 6.26 (1H, d, J = 7.8 Hz), 3.61 (2H, t, J = 7.1 Hz), 3.09 (2H, t, J = 7.1 Hz), 2.62 (3H, s). |
|---|---|---|
| 140 | 430 | 1H-NMR (CD3OD) δ: 8.23 (1.0H, s), 7.67 (2.0H, br s), 7.46-7.44 (1.0H, m), 7.38 (1.0H, dd, J = 8.8, 2.0 Hz), 7.27 (1.0H, s), 6.63-6.60 (2.0H, m), 3.65 (2.0H, t, J = 6.4 Hz), 3.41 (3.0H, s), 3.34 (2.0H, t, J = 5.4 Hz), 2.62 (3.0H, s). |
| 141 | 442 | 1H-NMR (DMSO-D6) δ: 12.48 (1.0H, br s), 11.39 (1.0H, br s), 8.27 (1.0H, s), 7.61 (2.0H, br s), 7.64 (1.0H, d, J = 8.8 Hz), 7.35 (1.0H, d, J = 2.0 Hz), 7.29 (1.0H, dd, J = 8.3, 2.0 Hz), 6.93-6.91 (3.0H, m), 6.84 (1.0H, br s), 3.78 (4.0H, t, J = 4.8 Hz), 3.12 (4.0H, t, J = 4.8 Hz), 2.53 (3.0H, s). |
| 142 | 442 | ¹H-NMR (CD₃OD) δ: 8.23 (1H, s), 7.67 (2H, s), 7.38 (1H, dd, J = 8.8, 2.0 Hz), 7.29 (1H, s), 7.23-7.14 (2H, m), 6.63-6.60 (1H, m), 3.99-3.94 (4H, m), 3.27-3.22 (4H, m), 2.61 (3H, s). |
| 143 | 456 | ¹H-NMR (CD₃OD) δ: 8.31 (1H, s), 7.75-7.62 (2H, m), 7.59 (1H, s), 7.45-7.37 (2H, m), 7.25 (1H, t, J = 7.8 Hz), 7.10-7.06 (1H, m), 3.88 (2H, s), 3.75-3.69 (4H, m), 2.62 (3H, s), 2.60-2.53 (4H, m). |

Example 144

Synthesis of [5-amino-1-(2-methyl-1H-benzimidazol-5-yl)-1H-pyrazol-4-yl]-(5-morpholin-4-ylmethyl-1H-indol-2-yl)-methanone

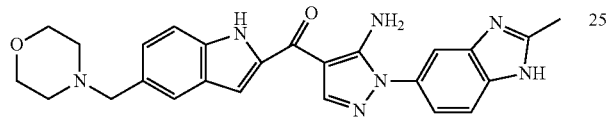

Cesium carbonate (1.29 g) was added to a methanol solution (20 ml) of [5-amino-1-(2-methyl-1H-benzimidazol-5-yl)-1H-pyrazol-4-yl]-(1-benzenesulfonyl-5-morpholin-4-ylmethyl-1H-indol-2-yl)-methanone (110 mg), and stirred at room temperature for 16 hours. Then, water (5 ml) and ammonia water (3 ml) were added to the reaction mixture and stirred for three hours. The reaction mixture was concentrated under reduced pressure. Water was added to the resulting residue. After ethyl acetate extraction, the extract was washed with a saturated aqueous solution of sodium chloride, and then dried over anhydrous sodium sulfate. The desiccant was removed by filtration. The filtrate was concentrated under reduced pressure. The resulting residue was purified by silica gel column chromatography (methanol/dichloromethane=0/100 to 20/100) to give [5-amino-1-(2-methyl-1H-benzimidazol-5-yl)-1H-pyrazol-4-yl]-(5-morpholin-4-ylmethyl-1H-indol-2-yl)-methanone (33 mg).

¹H-NMR (DMSO-D₆) δ: 12.47 (1.0H, s), 11.67 (1.0H, s), 8.30 (1.0H, s), 7.60 (3.0H, m), 7.44 (2.0H, m), 7.30 (1.0H, dd, J=8.4, 2.1 Hz), 7.23 (1.0H, dd, J=8.4, 1.5 Hz), 7.01 (2.0H, m), 3.58 (4.0H, t, J=4.4 Hz), 3.54 (2.0H, s), 2.55 (3.0H, s), 2.38 (4.0H, m)

ESI (LC-MS positive mode) m/z 456 [(M+H)⁺]

The compounds of Examples 145 to 164 listed in Table 6 were synthesized by the same method as in Example 144.

TABLE 6

| Example | Structure | Compound name |
|---|---|---|
| 145 | (structure) | [5-amino-1-(2-methyl-1H-benzimidazol-5-yl)-1H-pyrazol-4-yl]-[5-(morpholine-4-carbonyl)-1H-indol-2-yl]-methanone |
| 146 | (structure) | [5-amino-1-(2-isopropyl-1H-benzimidazol-5-yl)-1H-pyrazol-4-yl]-(1H-indol-2-yl)-methanone |
| 147 | (structure) | [5-amino-1-(2-propyl-1H-benzimidazol-5-yl)-1H-pyrazol-4-yl]-(1H-indol-2-yl)-methanone |

TABLE 6-continued

| | | |
|---|---|---|
| 148 | 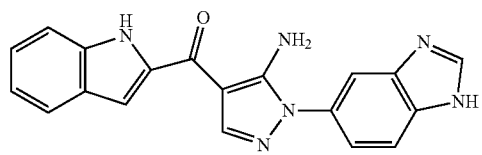 [SMILES: Nc1c(C(=O)c2cc3ccccc3[nH]2)cnn1-c1ccc2[nH]cnc2c1] | [5-amino-1-(1H-benzimidazol-5-yl)-1H-pyrazol-4-yl]-(1H-indol-2-yl)-methanone |
| 149 | 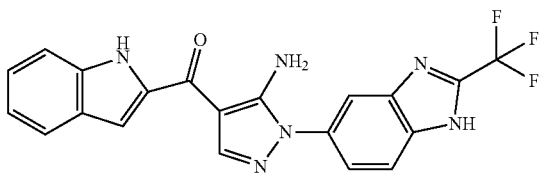 [SMILES: Nc1c(C(=O)c2cc3ccccc3[nH]2)cnn1-c1ccc2[nH]c(C(F)(F)F)nc2c1] | [5-amino-1-(2-trifluoromethyl-1H-benzimidazol-5-yl)-1H-pyrazol-4-yl]-(1H-indol-2-yl)-methanone |
| 150 | 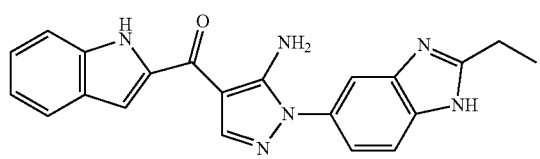 [SMILES: CCc1nc2cc(-n3ncc(C(=O)c4cc5ccccc5[nH]4)c3N)ccc2[nH]1] | [5-amino-1-(2-ethyl-1H-benzimidazol-5-yl)-1H-pyrazol-4-yl]-(1H-indol-2-yl)-methanone |
| 151 | 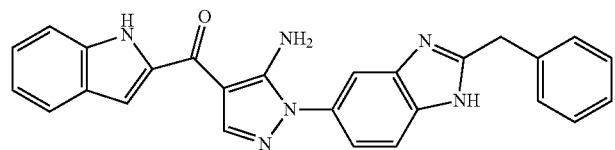 [SMILES: Nc1c(C(=O)c2cc3ccccc3[nH]2)cnn1-c1ccc2[nH]c(Cc3ccccc3)nc2c1] | [5-amino-1-(2-benzyl-1H-benzimidazol-5-yl)-1H-pyrazol-4-yl]-(1H-indol-2-yl)methanone |
| 152 | 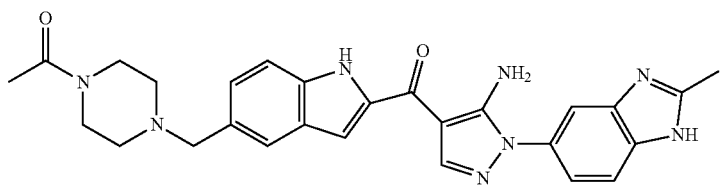 [SMILES: CC(=O)N1CCN(Cc2ccc3[nH]c(C(=O)c4cnn(-c5ccc6[nH]c(C)nc6c5)c4N)cc3c2)CC1] | 1-(4-{2-[5-amino-1-(2-methyl-1H-benzimidazol-5-yl)-1H-pyrazole-4-carbonyl]-1H-indol-5-ylmethyl}-piperazin-1-yl)-ethanone |
| 153 | 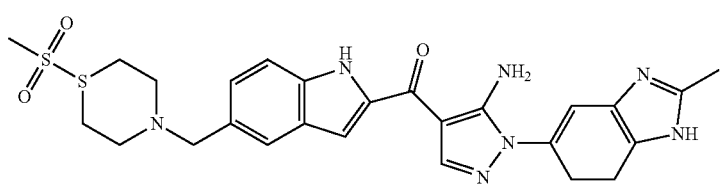 | [5-amino-1-(2-methyl-1H-benzimidazol-5-yl)-1H-pyrazol-4-yl]-[5-(4-methanesulfonyl-piperazin-1-ylmethyl)-1H-indol-2-yl]-methanone |
| 154 | 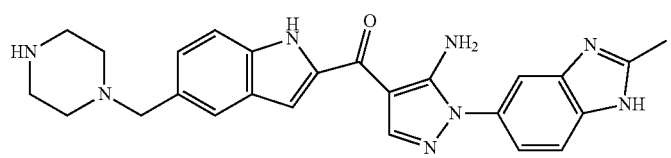 [SMILES: Cc1nc2cc(-n3ncc(C(=O)c4cc5cc(CN6CCNCC6)ccc5[nH]4)c3N)ccc2[nH]1] | [5-amino-1-(2-methyl-1H-benzimidazol-5-yl)-1H-pyrazol-4-yl]-(5-piperazin-1-ylmethyl-1H-indol-2-yl)-methanone |
| 155 | 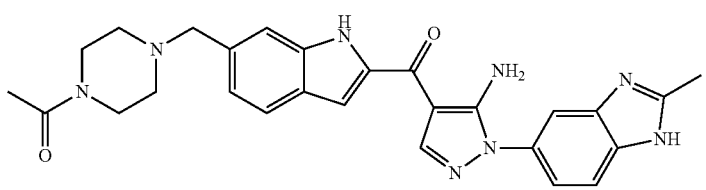 [SMILES: CC(=O)N1CCN(Cc2ccc3cc(C(=O)c4cnn(-c5ccc6[nH]c(C)nc6c5)c4N)[nH]c3c2)CC1] | 1-(4-{2-[5-amino-1-(2-methyl-1H-benzimidazol-5-yl)-1H-pyrazole-4-carbonyl]-1H-indol-6-ylmethyl}-piperazin-1-yl)-ethanone |
| 156 | 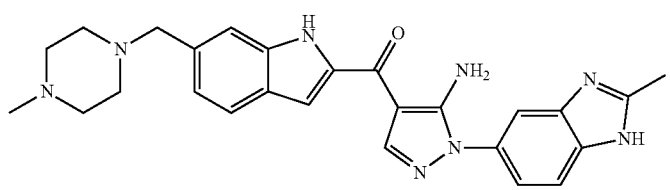 | [5-amino-1-(2-methyl-1H-benzimidazol-5-yl)-1H-pyrazol-4-yl]-[6-(4-methyl-piperazin-1-ylmethyl)-1H-indol-2-yl]-methanone |

TABLE 6-continued

| # | Structure | Name |
|---|---|---|
| 157 | 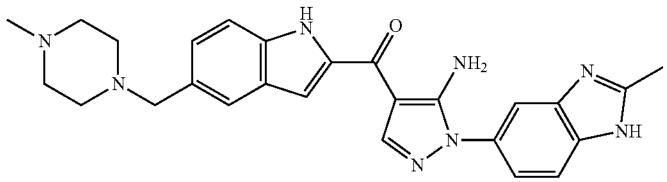 | [5-amino-1-(2-methyl-1H-benzimidazol-5-yl)-1H-pyrazol-4-yl]-[5-(4-methyl-piperazin-1-ylmethyl)-1H-indol-2-yl]-methanone |
| 158 | 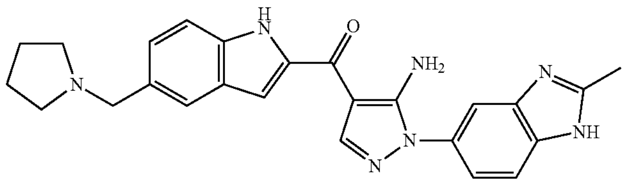 [SMILES: Cc1nc2cc(-n3ncc(C(=O)c4cc5cc(CN6CCCC6)ccc5[nH]4)c3N)ccc2[nH]1] | [5-amino-1-(2-methyl-1H-benzimidazol-5-yl)-1H-pyrazol-4-yl]-(5-pyrrolidin-1-ylmethyl-1H-indol-2-yl)-methanone |
| 159 | 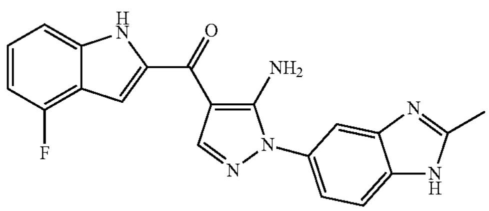 [SMILES: Cc1nc2cc(-n3ncc(C(=O)c4cc5c(F)cccc5[nH]4)c3N)ccc2[nH]1] | [5-amino-1-(2-methyl-1H-benzimidazol-5-yl)-1H-pyrazol-4-yl]-(4-fluoro-1H-indol-2-yl)-methanone |
| 160 | 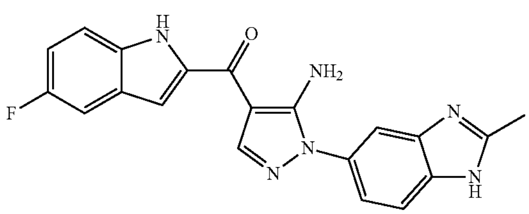 [SMILES: Cc1nc2cc(-n3ncc(C(=O)c4cc5cc(F)ccc5[nH]4)c3N)ccc2[nH]1] | [5-amino-1-(2-methyl-1H-benzimidazol-5-yl)-1H-pyrazol-4-yl]-(5-fluoro-1H-indol-2-yl)-methanone |
| 161 | 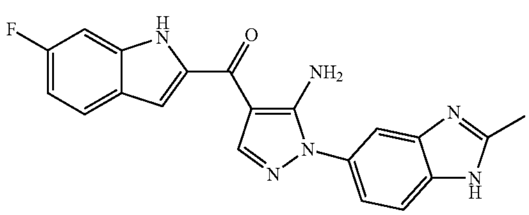 [SMILES: Cc1nc2cc(-n3ncc(C(=O)c4cc5ccc(F)cc5[nH]4)c3N)ccc2[nH]1] | [5-amino-1-(2-methyl-1H-benzimidazol-5-yl)-1H-pyrazol-4-yl]-(6-fluoro-1H-indol-2-yl)-methanone |
| 162 | 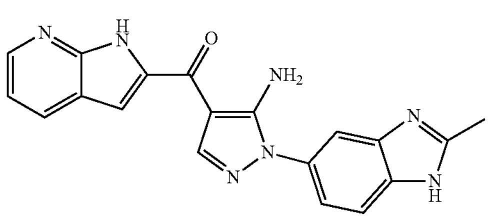 [SMILES: Cc1nc2cc(-n3ncc(C(=O)c4cc5cccnc5[nH]4)c3N)ccc2[nH]1] | [5-amino-1-(2-methyl-1H-benzimidazol-5-yl)-1H-pyrazol-4-yl]-(1H-pyrrolo[2,3-b]pyridin-2-yl)-methanone |

TABLE 6-continued

| 163 | [chemical structure] | [5-amino-1-(2-methyl-1H-benzimidazol-5-yl)-1H-pyrazol-4-yl]-(5-fluoro-6-morpholin-4-ylmethyl-1H-indol-2-yl)-methanone |
| 164 | [chemical structure] | 2-[5-amino-1-(2-methyl-1H-benzimidazol-5-yl)-1H-pyrazole-4-carbonyl]-1H-indole-5-carboxylic acid |

| Example | m/z | 1H-NMR |
|---|---|---|
| 145 | 470 | 1H-NMR (DMSO-D6) δ: 12.47 (1.0H, s), 11.92 (1.0H, s), 8.31 (1.0H, s), 7.79 (1.0H, s), 7.61 (2.0H, m), 7.53 (2.0H, m), 7.32-7.29 (1.0H, m), 7.32 (1.0H, dd, J = 8.8, 1.5 Hz), 7.10-6.95 (2.0H, m), 3.62-3.51 (8.0H, m), 2.54 (3.0H, s). |
| 146 | 385 | $^1$H-NMR (CD3OD) δ: 8.28 (1H, s), 7.73-7.67 (3H, m), 7.50-7.47 (1H, m), 7.40-7.37 (2H, m), 7.29-7.24 (1H, m), 7.12-7.07 (1H, m), 3.30-3.247 (2H, m), 1.45 (6H, d, J = 7.5 Hz). |
| 147 | 385 | $^1$H-NMR (DMSO-D$_6$) δ: 12.46 (1H, s), 11.70 (1H, s), 8.31 (1H, s), 7.71-7.66 (2H, m), 7.59-7.57 (1H, m), 7.50-7.45 (2H, m), 7.32-7.23 (2H, m), 7.10-6.98 (3H, m), 2.83 (2H, t, J = 7.4 Hz), 1.85-1.79 (2H, m), 0.96 (3H, t, J = 7.3 Hz). |
| 148 | 343 | $^1$H-NMR (CD3OD) δ: 8.32 (1H, s), 8.29 (1H, s), 7.83-7.80 (2H, m), 7.72 (1H, d, d = 8.1 Hz), 7.50-7.46 (2H, m), 7.38 (1H, s), 7.27 (1H, t, J = 7.2 Hz), 7.09 (1H, t, J = 7.2 Hz). |
| 149 | 411 | $^1$H-NMR (DMSO-D$_6$) δ: 12.58 (1H, s), 11.71 (1H, s), 8.36 (1H, s), 7.89-7.81 (2H, m), 7.70 (1H, d, J = 7.4 Hz), 7.50-7.46 (3H, m), 7.27-7.23 (1H, m), 7.10-7.06 (3H, m). |
| 150 | 371 | $^1$H-NMR (DMSO-D$_6$) δ: 12.40 (1H, s), 11.68 (1H, s), 8.26 (1H, s), 7.66-7.64 (1H, m), 7.61-7.52 (2H, m), 7.45-7.40 (2H, m), 7.26-7.18 (2H, m), 7.05-7.01 (1H, m), 6.90 (1.1H, s), 2.83 (2H, d, J = 7.6 Hz), 1.29 (3H, t, J = 7.5 Hz). |
| 151 | 433 | $^1$H-NMR (DMSO-D$_6$) δ: 12.60 (1H, s), 11.70 (1H, s), 8.31 (1H, s), 7.69 (1H, d, J = 8.2 Hz), 7.67-7.59 (2H, m), 7.49-7.45 (2H, m), 7.37-7.23 (7H, m), 7.10-7.06 (1H, m), 7.03-6.97 (2H, m), 4.22 (2H, s). |
| 152 | 497 | 1H-NMR (CD3OD) δ: 8.27 (1.0H, s), 7.66 (3.0H, m), 7.46 (1.0H, d, J = 8.3 Hz), 7.38 (1.0H, dd, J = 8.8, 2.0 Hz), (1.0H, s), 7.30 (1.0H, dd, J = 8.5, 1.7 Hz), 3.64 (2.0H, s), 3.56 (4.2H, dt, J = 21.6, 4.9 Hz), 2.61 (3.0H, s), 2.49 (4.0H, td, J = 10.5, 5.5 Hz), 2.07 (3.0H, s). |
| 153 | 533 | 1H-NMR (CD3OD) δ: 8.27 (1.0H, s), 7.67 (3.0H, m), 7.46 (1.0H, d, J = 8.3 Hz), 7.38 (1.0H, dd, J = 8.3, 2.0 Hz), 7.35 (1.0H, s), 7.30 (1.0H, dd, J = 8.3, 1.5 Hz), 3.67 (2.0H, s), 3.23 (4.0H, s), 2.83 (3.0H, s), 2.65-2.55 (4.0H, m), 2.61 (3.0H, s). |
| 154 | 455 | 1H-NMR (CD3OD) δ: 8.28 (1H, s), 7.70-7.62 (3.0H, m), 7.47 (1.1H, d, J = 8.8 Hz), 7.39 (1.0H, dd, J = 8.3, 2.0 Hz), 7.36 (1.0H, d, J = 1.0 Hz), 7.30 (1.0H, dd, J = 8.8, 1.5 Hz), 3.67-3.60 (2.0H, m), 2.95-2.85 (4.0H, m), 2.62 (3.0H, s), 2.60-2.50 (2.0H, s). |
| 155 | 497 | 1H-NMR (DMSO-D6) δ: 12.49 (1.0H, br s), 11.66 (1.0H, br s), 8.30 (1.0H, s), 7.65-7.60 (3.0H, m), 7.43-7.41 (2.0H, m), 7.29 (1.0H, dd, J = 8.3, 2.0 Hz), 7.06 (1.0H, dd, J = 8.3, 1.0 Hz), 5.99 (2.0H, br s), 3.58 (2.0H, s), 3.45-3.41 (4.0H, m), 2.53 (3.0H, s), 2.39 (2.0H, t, J = 4.6 Hz), 2.33 (2.0H, t, J = 4.9 Hz), 1.98 (3.0H, s). |
| 156 | 469 | 1H-NMR (DMSO-D6) δ: 12.47 (1.0H, br s), 11.63 (1.0H, br s), 8.30 (1.0H, s), 7.65-7.56 (3.0H, m), 7.42-7.40 (2.0H, m), 7.30-7.28 (1.0H, m), 7.04-6.97 (3.0H, m), 3.53 (2.0H, s), 3.36-3.30 (4.0H, m), 2.53 (3.0H, s), 2.46-2.33 (4.0H, m), 2.15 (3.0H, s). |
| 157 | 469 | 1H-NMR (CD3OD) δ: 8.27 (1.0H, s), 7.66 (3.0H, m), 7.45 (1.0H, d, J = 8.3 Hz), 7.40-7.33 (2.0H, m), 7.31-7.25 (1.0H, m), 3.64 (2.0H, s), 2.70-2.40 (8H, m), 2.61 (3.0H, s), 2.28 (3.0H, s). |
| 158 | 440 | 1H-HMR (CD3OD) δ: 8.27 (1.0H, s), 7.66 (3.0H, m), 7.46 (1.0H, d, J = 8.3 Hz), 7.38 (1.0H, dd, J = 8.3, 2.0 Hz), 7.35 (1.0H, s), 7.30 (1.0H, dd, J = 8.5, 1.7 Hz), 3.75 (2.0H, s), 2.65-2.55 (4.0H, m), 2.61 (3.0H, s), 1.82 (4.0H, s). |
| 159 | 375 | $^1$H-NMR (DMSO-D$_6$) δ: 12.46 (1H, s), 12.04 (1H, s), 8.36 (1H, s), 7.68-7.55 (2H, m), 7.45 (1H, s), 7.34-7.20 (3H, m), 7.09-6.97 (2H, m), 6.88-6.84 (1H, m), 2.53 (3H, s). |
| 160 | 375 | $^1$H-NMR (DMSO-D$_6$) δ: 12.48(1H, s), 11.81 (1H, s) 8.29 (1H, s), 7.69-7.53 (2H, m), 7.50-7.47 (1H, m), 7.44-7.41 (2H, m), 7.29 (1H, dd, J = 8.4, 2.0 Hz), 7.15-7.10 (1H, m), 7.07-6.97 (2H, s), 2.53 (3H, s). |
| 161 | 375 | $^1$H-NMR (DMSO-D$_6$) δ: 12.48 (1H, s), 11.78 (1H, s), 8.30 (1H, s), 7.73-7.70 (1H, m), 7.64-7.56 (2H, m), 7.49 (1H, s), 7.30-7.27 (1H, m), 7.20-7.17 (1H, m), 7.00-6.94 (3H, m), 2.53 (3H, s). |
| 162 | 358 | $^1$H-NMR (DMSO-D$_8$) δ: 12.48 (1H, s), 12.23 (1H, s), 8.40 (1H, dd, J = 4.6, 1.7 Hz), 8.27 (1H, s), 8.13 (1H, dd, J = 8.0, 1.6 Hz), 7.61 (2H, m), 7.41 (1H, s), 7.29 (1H, dd, J = 8.5, 2.1 Hz), 7.16-7.15 (1H, m), 7.04 (2H, s), 2.53 (3.6H, s). |
| 163 | 474 | $^1$H-NMR (DMSO-D$_6$) δ: 12.46 (1H, m), 11.74 (1H, s), 8.28 (1H, d, J = 5.1 Hz), 7.67-7.63 (1H, m), 7.58-7.56 (1H, m), 7.49 (1H, d, J = 6.3 Hz), 7.42-7.39 (2H, m), 7.31-7.27 (1H, m), 7.05-6.99 (2H, m), 3.62-3.55 (6H, m), 2.53 (3H, s), 2.47-2.39 (4H, m). |

TABLE 6-continued

| 164 | 401 | 1H-NMR (DMSO-D6) δ: 12.57 (1.0H, s), 12.47 (1.0H, d, J = 5.4 Hz), 12.04 (1.0H, s), 8.40 (1.0H, s), 8.34 (1.0H, t, J = 4.6 Hz), 7.84 (1.0H, dd, J = 8.5, 1.7 Hz), 7.68-7.62 (2.0H, m), 7.57 (1.0H, d, J = 8.3 Hz), 7.53 (1.0H, d, J = 8.3 Hz), 7.29 (1.0H, m), 7.10-6.95 (2.0H, m), 2.54 (3.0H, s). |
|---|---|---|

Step 1: Synthesis of [5-amino-1-(2-methyl-1H-benzimidazol-5-yl)-1H-pyrazol-4-yl]-(1-benzenesulfonyl-1H-indol-2-yl)-methanone (1001)

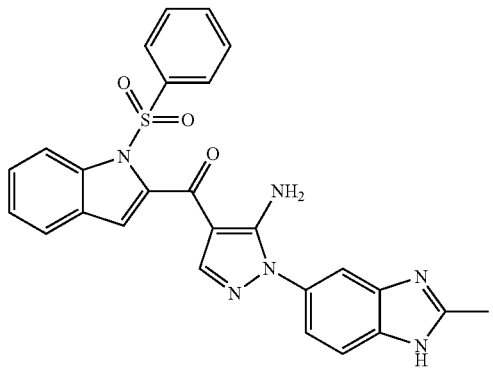 [SMILES: Cc1nc2cc(-n3ncc(C(=O)c4cc5ccccc5n4S(=O)(=O)c4ccccc4)c3N)ccc2[nH]1]

(2-Methyl-1H-benzimidazol-5-yl)-hydrazine dihydrochloride (830 mg) was added to an ethanol solution (15 ml) of crude 2-(1-benzenesulfonyl-1H-indole-2-carbonyl)-3-dimethylamino acrylonitrile (1.17 g). The reaction mixture was heated with stirring under reflux for four hours. After cooling to room temperature, the mixture was allowed to stand at room temperature. The precipitated solid was collected by filtration, and washed with ethanol to give [5-amino-1-(2-methyl-1H-benzimidazol-5-yl)-1H-pyrazol-4-yl]-(1-benzenesulfonyl-1H-indol-2-yl)-methanone was obtained as a yellow solid (1.5 g, with a two-step yield of 91%).

$^1$H-NMR (DMSO-D$_6$) δ: 8.15-8.13 (2H, m), 8.02 (1H, dd, J=8.4, 0.8 Hz), 7.97 (1H, d, J=2.0 Hz), 7.92 (1H, d, J=8.8 Hz), 7.87 (1H, s), 7.76-7.62 (5H, m), 7.49-7.45 (1H, m), 7.36-7.26 (4H, m), 2.82 (3H, m)

ESI (LC-MS positive mode) m/z 497 [(M+H)$^+$]

The compounds of numbers 1002 to 1082, and 1511 to 1527 listed in Table 7 were synthesized by the same method as in Step 1.

TABLE 7

| Compound No. | Structure | Compound name | m/z |
|---|---|---|---|
| 1002 | 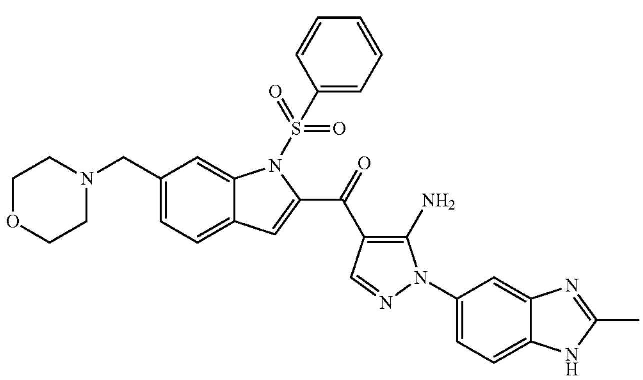 | [5-amino-1-(2-methyl-1H-benzimidazol-5-yl)-1H-pyrazol-4-yl]-(1-benzenesulfonyl-6-morpholin-4-ylmethyl-1H-indol-2-yl)-methanone | 596 |
| 1003 | 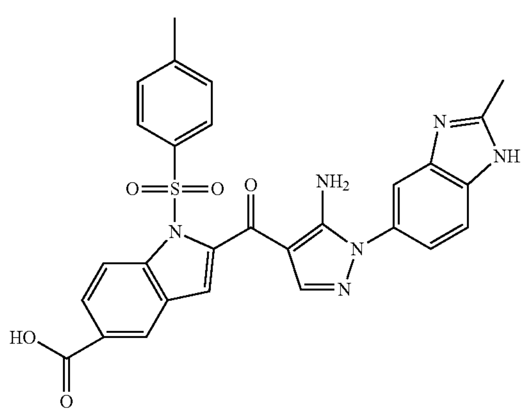 [SMILES: Cc1ccc(S(=O)(=O)n2c(C(=O)c3cnn(-c4ccc5[nH]c(C)nc5c4)c3N)cc3cc(C(=O)O)ccc32)cc1] | 2-[5-amino-1-(2-methyl-1H-benzimidazol-5-yl)-1H-pyrazol-4-carbonyl]-1-(toluene-4-sulfonyl)-1H-indole-5-carboxylic acid | 555 |

TABLE 7-continued

| Compound No. | Structure | Compound name | m/z |
|---|---|---|---|
| 1004 | 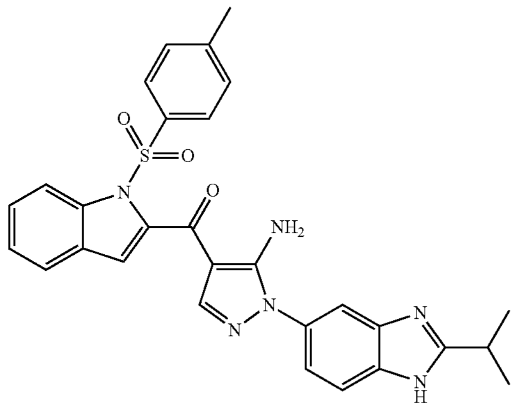 [SMILES: Cc1ccc(S(=O)(=O)n2c(C(=O)c3cnn(-c4ccc5[nH]c(C(C)C)nc5c4)c3N)cc3ccccc32)cc1] | [5-amino-1-(2-isopropyl-1H-benzimidazol-5-yl)-1H-pyrazol-4-yl]-[1-(toluene-4-sulfonyl)-1H-indol-2-yl]-methanone | 539 |
| 1005 | 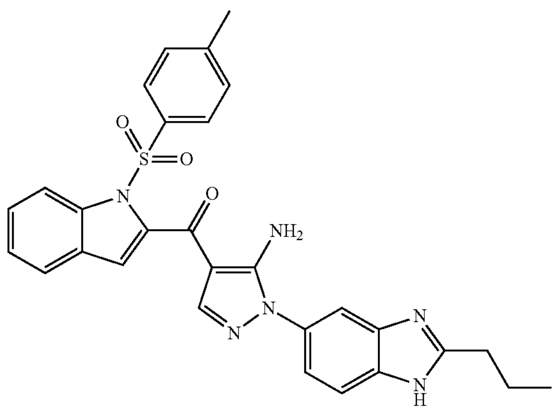 [SMILES: CCCc1nc2cc(-n3ncc(C(=O)c4cc5ccccc5n4S(=O)(=O)c4ccc(C)cc4)c3N)ccc2[nH]1] | [5-amino-1-(2-propyl-1H-benzimidazol-5-yl)-1H-pyrazol-4-yl]-[1-(toluene-4-sulfonyl)-1H-indol-2-yl]-methanone | 539 |
| 1006 | 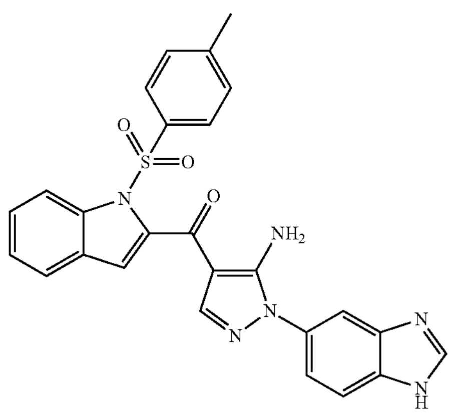 [SMILES: Cc1ccc(S(=O)(=O)n2c(C(=O)c3cnn(-c4ccc5[nH]cnc5c4)c3N)cc3ccccc32)cc1] | [5-amino-1-(1H-benzimidazol-5-yl)-1H-pyrazol-4-yl]-[1-(toluene-4-sulfonyl)-1H-indol-2-yl]-methanone | 497 |
| 1007 | 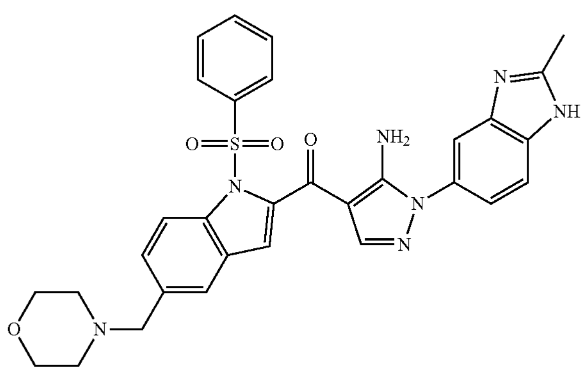 [SMILES: Cc1nc2cc(-n3ncc(C(=O)c4cc5cc(CN6CCOCC6)ccc5n4S(=O)(=O)c4ccccc4)c3N)ccc2[nH]1] | [5-amino-1-(2-methyl-1H-benzimidazol-5-yl)-1H-pyrazol-4-yl]-(1-benzenesulfonyl-5-morpholin-4-ylmethyl-1H-indol-2-yl)-methanone | 596 |

TABLE 7-continued

| Compound No. | Structure | Compound name | m/z |
|---|---|---|---|
| 1008 | 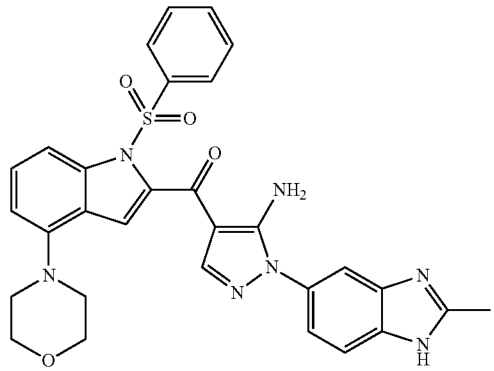 [SMILES: Cc1nc2cc(-n3ncc(C(=O)c4cc5c(N6CCOCC6)cccc5n4S(=O)(=O)c4ccccc4)c3N)ccc2[nH]1] | [5-amino-1-(2-methyl-1H-benzimidazol-5-yl)-1H-pyrazol-4-yl]-(1-benzenesulfonyl-4-morpholin-4-yl-1H-indol-2-yl)-methanone | 582 |
| 1009 | 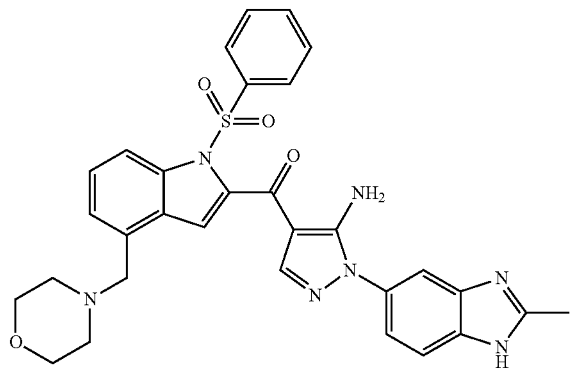 [SMILES: Cc1nc2cc(-n3ncc(C(=O)c4cc5c(CN6CCOCC6)cccc5n4S(=O)(=O)c4ccccc4)c3N)ccc2[nH]1] | [5-amino-1-(2-methyl-1H-benzimidazol-5-yl)-1H-pyrazol-4-yl]-(1-benzenesulfonyl-4-morpholin-4-ylmethyl-1H-indol-2-yl)-methanone | 596 |
| 1010 | 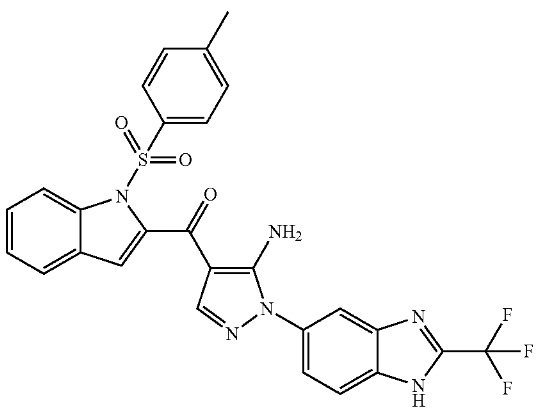 [SMILES: Cc1ccc(S(=O)(=O)n2c(C(=O)c3cnn(-c4ccc5[nH]c(C(F)(F)F)nc5c4)c3N)cc3ccccc32)cc1] | [5-amino-1-(2-trifluoromethyl-1H-benzimidazol-5-yl)-1H-pyrazol-4-yl]-[1-(toluene-4-sulfonyl)-1H-indol-2-yl]-methanone | 565 |
| 1011 | 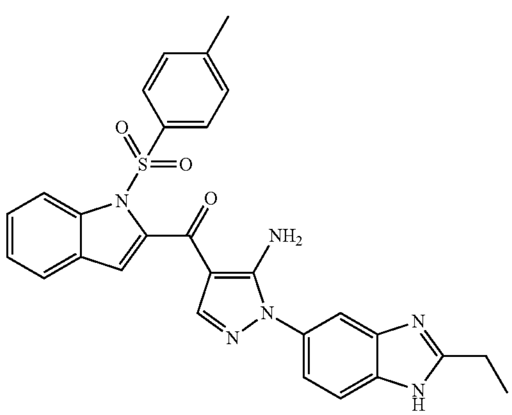 [SMILES: CCc1nc2cc(-n3ncc(C(=O)c4cc5ccccc5n4S(=O)(=O)c4ccc(C)cc4)c3N)ccc2[nH]1] | [5-amino-1-(2-ethyl-1H-benzimidazol-5-yl)-1H-pyrazol-4-yl]-[1-(toluene-4-sulfonyl)-1H-indol-2-yl]-methanone | 525 |

TABLE 7-continued

| Compound No. | Structure | Compound name | m/z |
|---|---|---|---|
| 1012 | 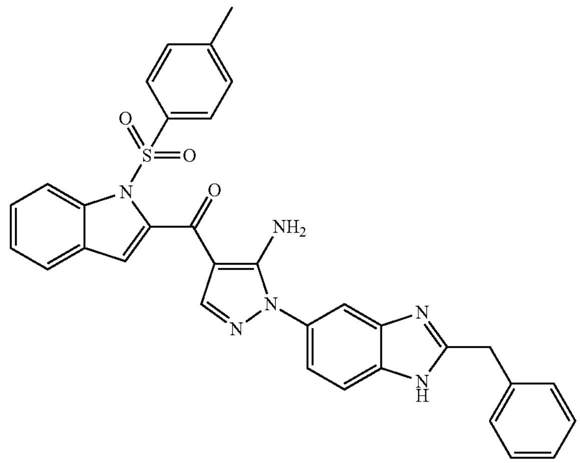 [SMILES: Cc1ccc(S(=O)(=O)n2c(C(=O)c3cnn(-c4ccc5[nH]c(Cc6ccccc6)nc5c4)c3N)cc3ccccc32)cc1] | [5-amino-1-(2-benzyl-1H-benzimidazol-5-yl)-1H-pyrazol-4-yl]-[1-(toluene-4-sulfonyl)-1H-indol-2-yl]-methanone | 587 |
| 1013 | 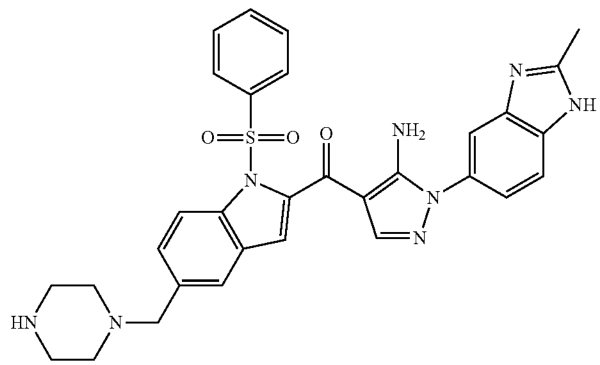 [SMILES: Cc1nc2cc(-n3ncc(C(=O)c4cc5cc(CN6CCNCC6)ccc5n4S(=O)(=O)c4ccccc4)c3N)ccc2[nH]1] | [5-amino-1-(2-methyl-1H-benzimidazol-5-yl)-1H-pyrazol-4-yl]-(1-benzene-sulfonyl-5-piperazin-1-ylmethyl-1H-indol-2-yl)-methanone | 595 |
| 1014 | 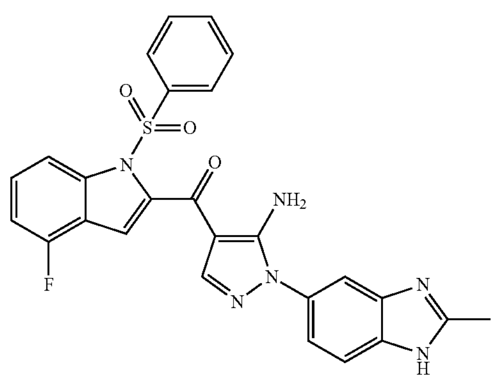 [SMILES: Cc1nc2cc(-n3ncc(C(=O)c4cc5c(F)cccc5n4S(=O)(=O)c4ccccc4)c3N)ccc2[nH]1] | [5-amino-1-(2-methyl-1H-benzimidazol-5-yl)-1H-pyrazol-4-yl]-(1-benzene-sulfonyl-4-fluoro-1H-indol-2-yl)-methanone | 515 |
| 1015 | 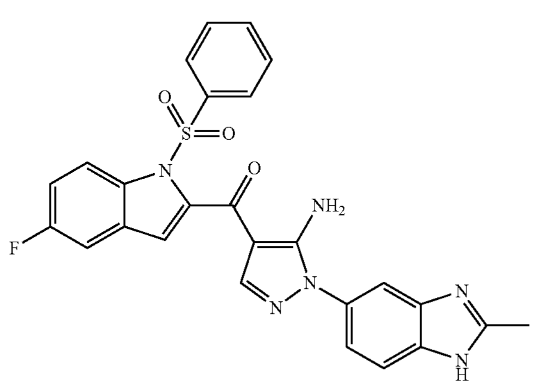 [SMILES: Cc1nc2cc(-n3ncc(C(=O)c4cc5cc(F)ccc5n4S(=O)(=O)c4ccccc4)c3N)ccc2[nH]1] | [5-amino-1-(2-methyl-1H-benzimidazol-5-yl)-1H-pyrazol-4-yl]-(1-benzene-sulfonyl-5-fluoro-1H-indol-2-yl)-methanone | 515 |

TABLE 7-continued

| Compound No. | Structure | Compound name | m/z |
|---|---|---|---|
| 1016 | 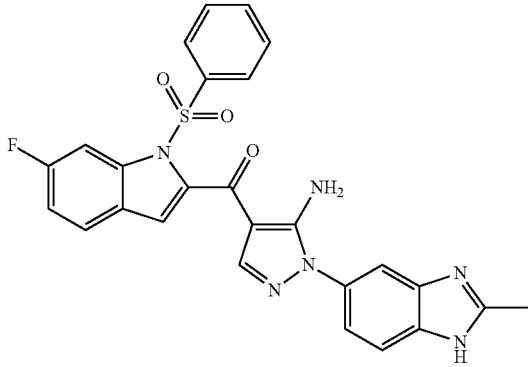 [SMILES: Cc1nc2cc(-n3ncc(C(=O)c4cc5ccc(F)cc5n4S(=O)(=O)c4ccccc4)c3N)ccc2[nH]1] | [5-amino-1-(2-methyl-1H-benzimidazol-5-yl)-1H-pyrazol-4-yl]-(1-benzene-sulfonyl-6-fluoro-1H-indol-2-yl)-methanone | 515 |
| 1017 | 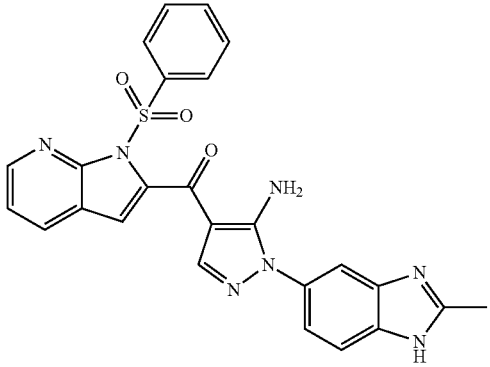 [SMILES: Cc1nc2cc(-n3ncc(C(=O)c4cc5cccnc5n4S(=O)(=O)c4ccccc4)c3N)ccc2[nH]1] | [5-amino-1-(2-methyl-1H-benzimidazol-5-yl)-1H-pyrazol-4-yl]-(1-benzene-sulfonyl-1H-pyrrolo[2,3-6]pyridin-2-yl)-methanone | 498 |
| 1018 | 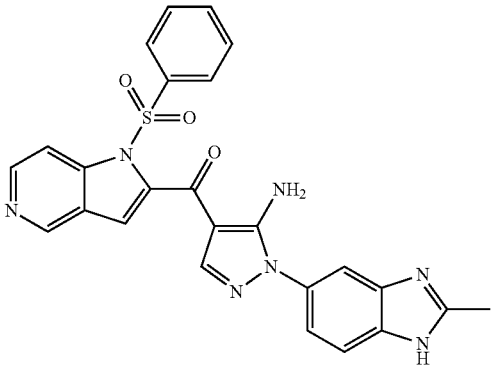 [SMILES: Cc1nc2cc(-n3ncc(C(=O)c4cc5cnccc5n4S(=O)(=O)c4ccccc4)c3N)ccc2[nH]1] | [5-amino-1-(2-methyl-1H-benzimidazol-5-yl)-1H-pyrazol-4-yl]-(1-benzene-sulfonyl-1H-pyrrolo[3,2-c]pyridin-2-yl)-methanone | 498 |
| 1019 | 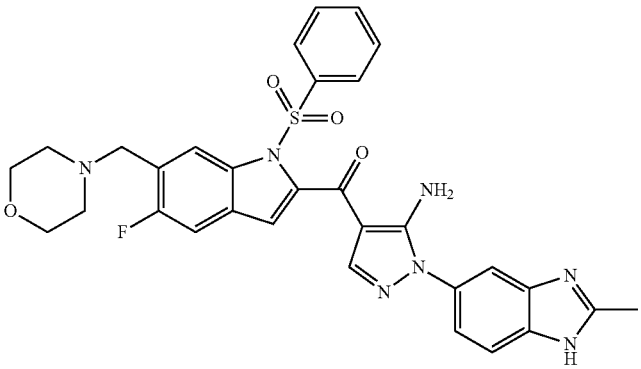 [SMILES: Cc1nc2cc(-n3ncc(C(=O)c4cc5cc(F)c(CN6CCOCC6)cc5n4S(=O)(=O)c4ccccc4)c3N)ccc2[nH]1] | [5-amino-1-(2-methyl-1H-benzimidazol-5-yl)-1H-pyrazol-4-yl]-(1-benzene-sulfonyl-5-fluoro-6-morpholin-4-ylmethly-1H-indol-2-yl)-methanone | 614 |

TABLE 7-continued

| Compound No. | Structure | Compound name | m/z |
|---|---|---|---|
| 1020 | 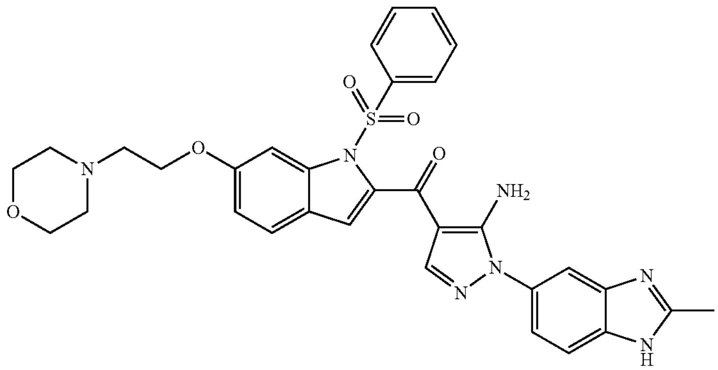 [SMILES: Cc1nc2cc(-n3ncc(C(=O)c4cc5ccc(OCCN6CCOCC6)cc5n4S(=O)(=O)c4ccccc4)c3N)ccc2[nH]1] | [5-amino-1-(2-methyl-1H-benzimidazol-5-yl)-1H-pyrazol-4-yl]-[1-benzenesulfonyl-6-(2-morpholin-4-yl-ethoxy)-1H-indol-2-yl]-methanone | 626 |
| 1021 | 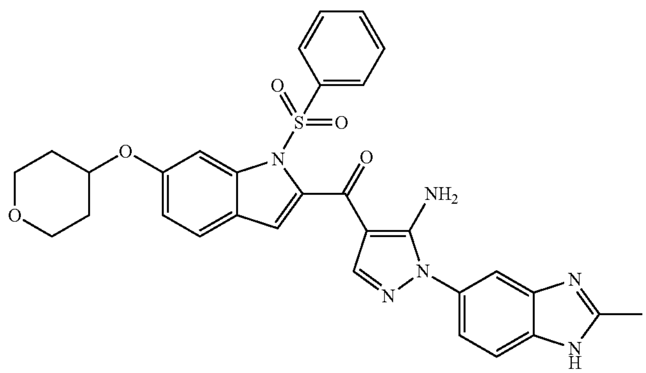 [SMILES: Cc1nc2cc(-n3ncc(C(=O)c4cc5ccc(OC6CCOCC6)cc5n4S(=O)(=O)c4ccccc4)c3N)ccc2[nH]1] | [5-amino-1-(2-methyl-1H-benzimidazol-5-yl)-1H-pyrazol-4-yl]-[1-benzenesulfonyl-6-tetrahydropyran-4-yloxy)-1H-indol-2-yl]-methanone | 597 |
| 1022 | 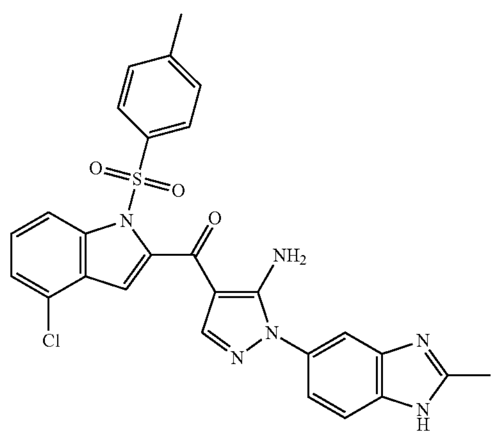 [SMILES: Cc1ccc(S(=O)(=O)n2c(C(=O)c3cnn(-c4ccc5[nH]c(C)nc5c4)c3N)cc3c(Cl)cccc32)cc1] | [5-amino-1-(2-methyl-1H-benzimidazol-5-yl)-1H-pyrazol-4-yl]-[4-chloro-1-(toluene-4-sulfonyl)-1H-indol-2-yl]-methanone | 545, 547 |
| 1023 | 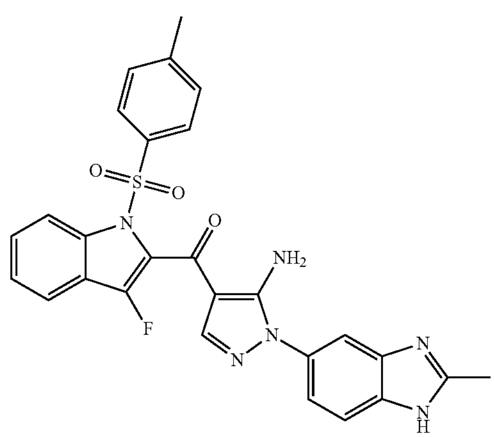 [SMILES: Cc1ccc(S(=O)(=O)n2c(C(=O)c3cnn(-c4ccc5[nH]c(C)nc5c4)c3N)c(F)c3ccccc32)cc1] | [5-amino-1-(2-methyl-1H-benzimidazol-5-yl)-1H-pyrazol-4-yl]-[3-fluoro-1-(toluene-4-sulfonyl)-1H-indol-2-yl]-methanone | 529 |

TABLE 7-continued

| Compound No. | Structure | Compound name | m/z |
|---|---|---|---|
| 1024 | 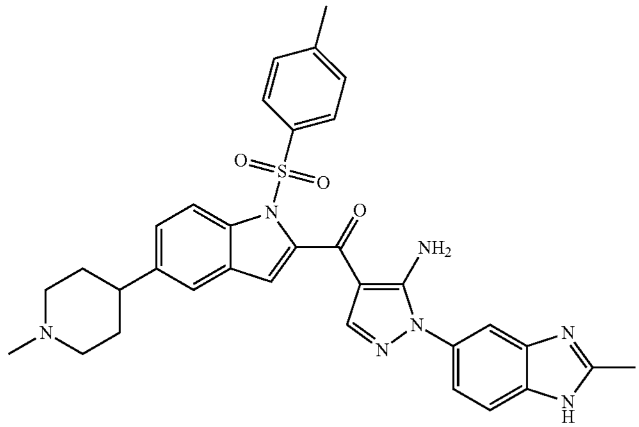 | [5-amino-1-(2-methyl-1H-benzimidazol-5-yl)-1H-pyrazol-4-yl]-[5-(1-methyl-piperidin-4-yl)-1-(toluene-4-sulfonyl)-1H-indol-2-yl]-methanone | 608 |
| 1025 | 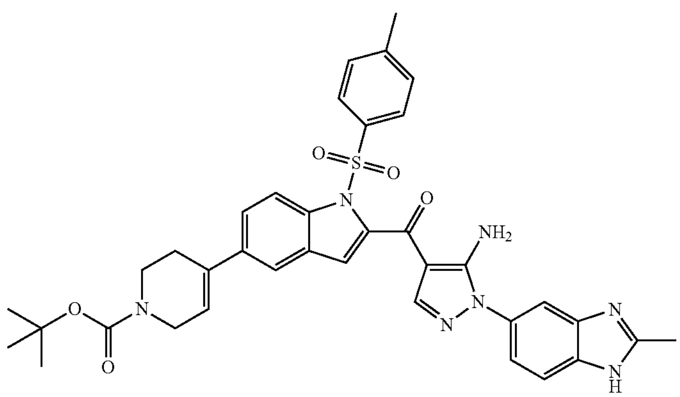 [SMILES: Cc1ccc(S(=O)(=O)n2c(C(=O)c3cnn(-c4ccc5[nH]c(C)nc5c4)c3N)cc3cc(C4=CCN(C(=O)OC(C)(C)C)CC4)ccc32)cc1] | 4-[2-[5-amino-1-(2-methyl-1H-benzimidazol-5-yl)-1H-pyrazole-4-carbonyl]-1-(toluene-4-sulfonyl)-1H-indol-5-yl]-3,6-dihydro-2H-pyridine-1-carboxylic acid tert-butyl ester | 692 |
| 1026 | 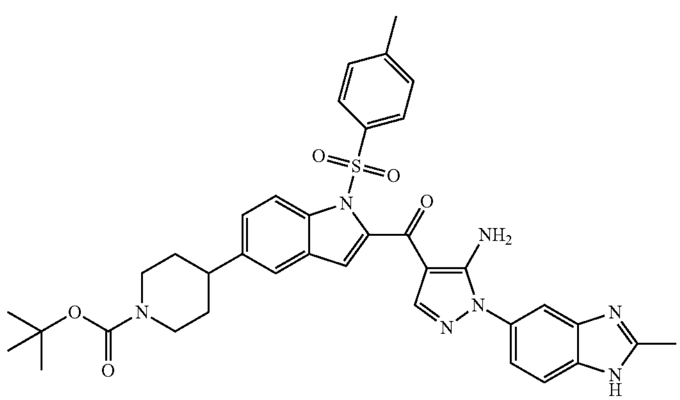 [SMILES: Cc1ccc(S(=O)(=O)n2c(C(=O)c3cnn(-c4ccc5[nH]c(C)nc5c4)c3N)cc3cc(C4CCN(C(=O)OC(C)(C)C)CC4)ccc32)cc1] | 4-[2-[5-amino-1-(2-methyl-1H-benzimidazol-5-yl)-1H-pyrazole-4-carbonyl]-1-(toluene-4-sulfonyl)-1H-indol-5-yl]-piperidine-1-carboxylic acid tert-butyl ester | 694 |

TABLE 7-continued

| Compound No. | Structure | Compound name | m/z |
|---|---|---|---|
| 1027 | 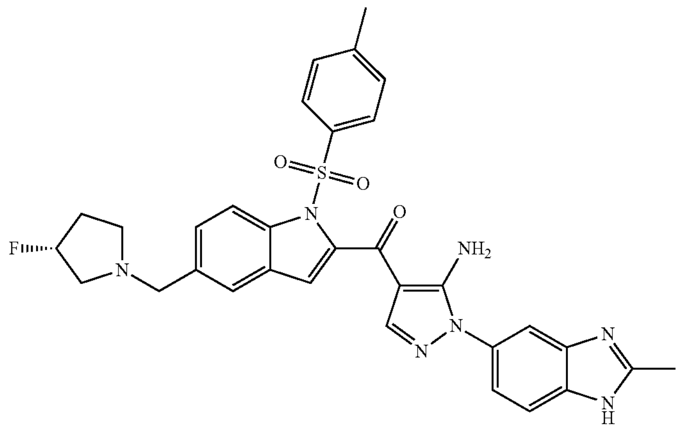 [SMILES: Cc1ccc(S(=O)(=O)n2c(C(=O)c3cnn(-c4ccc5[nH]c(C)nc5c4)c3N)cc3cc(CN4CC[C@@H](F)C4)ccc32)cc1] | [5-amino-1-(2-methyl-1H-benzimidazol-5-yl)-1H-pyrazol-4-yl]-[5-((R)-3-fluoro-pyrrolidin-1-ylmethyl)-1-(toluene-4-sulfonyl)-1H-indol-2-yl]-methanone | 612 |
| 1028 | 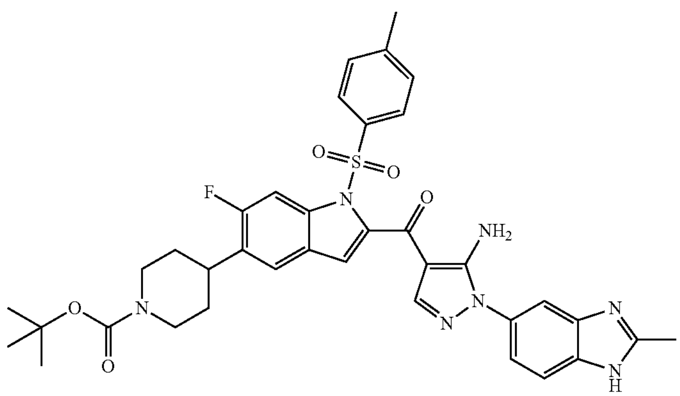 [SMILES: Cc1ccc(S(=O)(=O)n2c(C(=O)c3cnn(-c4ccc5[nH]c(C)nc5c4)c3N)cc3cc(C4CCN(C(=O)OC(C)(C)C)CC4)c(F)cc32)cc1] | 4-[2-[5-amino-1-(2-methyl-1H-benzimidazol-5-yl)-1H-pyrazole-4-carbonyl]-6-fluoro-1-(toluene-4-sulfonyl)-1H-indol-5-yl]-piperidine-1-carboxylic acid tert-butyl ester | 712 |
| 1029 | 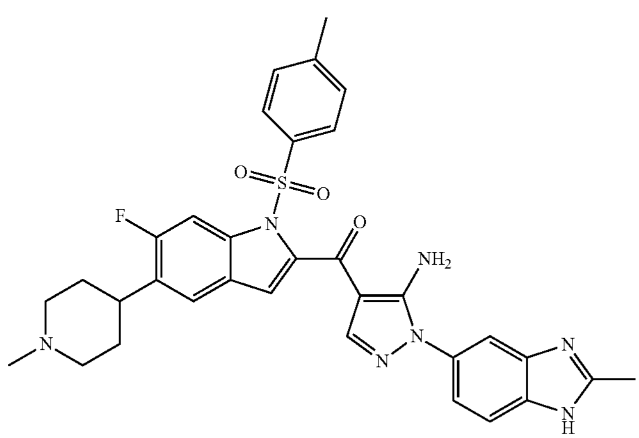 | [5-amino-1-(2-methyl-1H-benzimidazol-5-yl)-1H-pyrazol-4-yl]-[6-fluoro-5-(1-methyl-piperidin-4-yl)-1-(toluene-4-sulfonyl)-1H-indol-2-yl]-methanone | 626 |

TABLE 7-continued

| Compound No. | Structure | Compound name | m/z |
|---|---|---|---|
| 1030 | 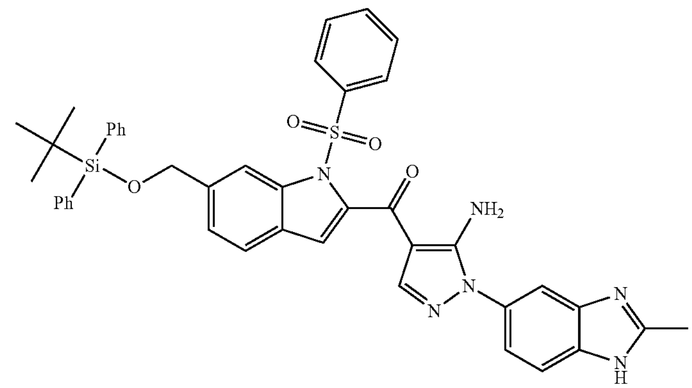 [SMILES: Cc1nc2cc(-n3ncc(C(=O)c4cc5ccc(CO[Si](c6ccccc6)(c6ccccc6)C(C)(C)C)cc5n4S(=O)(=O)c4ccccc4)c3N)ccc2[nH]1] | [5-amino-1-(2-methyl-1H-benzimidazol-5-yl)-1H-pyrazol-4-yl]-[1-benzene-sulfonyl-6-(tert-butyl-dipheyl-silanyloxymethyl)-1H-indol-2-yl] methanone | 765 |
| 1031 | 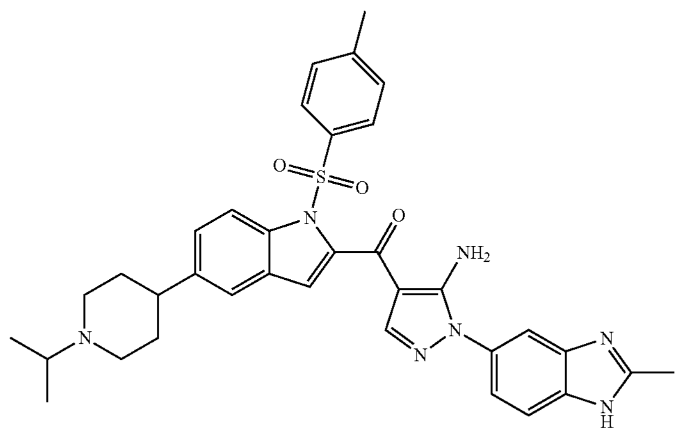 [SMILES: Cc1ccc(S(=O)(=O)n2c(C(=O)c3cnn(-c4ccc5[nH]c(C)nc5c4)c3N)cc3cc(C4CCN(C(C)C)CC4)ccc32)cc1] | [5-amino-1-(2-methyl-1H-benzimidazol-5-yl)-1H-pyrazol-4-yl]-[5-(1-isopropyl-piperidin-4-yl)-1-(toluene-4-sulfonyl)-1H-indol-2-yl]-methanone | 636 |
| 1032 | 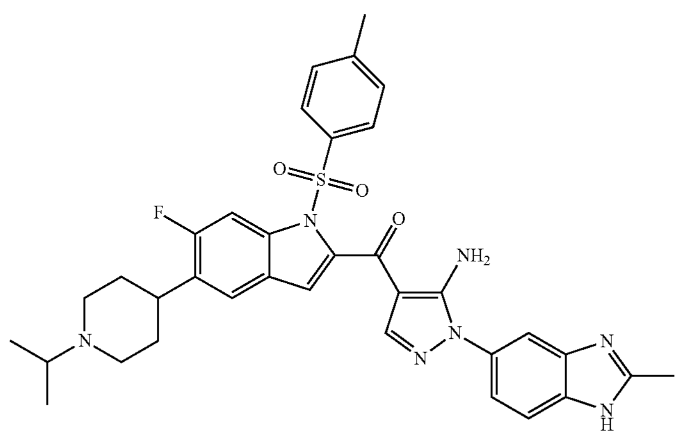 [SMILES: Cc1ccc(S(=O)(=O)n2c(C(=O)c3cnn(-c4ccc5[nH]c(C)nc5c4)c3N)cc3cc(C4CCN(C(C)C)CC4)c(F)cc32)cc1] | [5-amino-1-(2-methyl-1H-benzimidazol-5-yl)-1H-pyrazol-4-yl]-[6-fuloro-5-(1-isopropyl-piperidin-4-yl)-1-(toluene-4-sulfonyl)-1H-indol-2-yl]-methanone | 654 |
| 1033 | 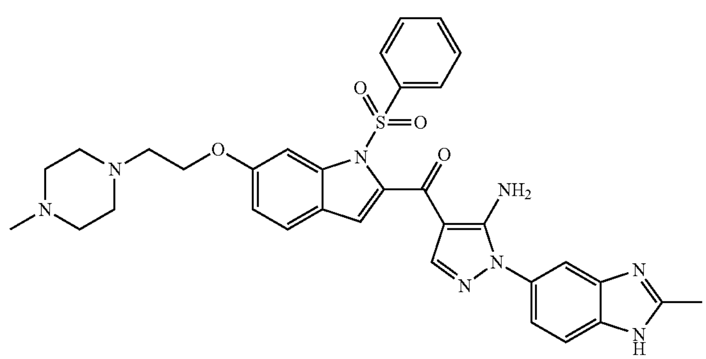 | [5-amino-1-(2-methyl-1H-benzimidazol-5-yl)-1H-pyrazol-4-yl]-{1-benzene-sulfonyl-6-[2-(4-methyl-piperidin-1-yl)-ethoxy]-1H-indol-2-yl}-methanone | 639 |

TABLE 7-continued

| Compound No. | Structure | Compound name | m/z |
|---|---|---|---|
| 1034 | 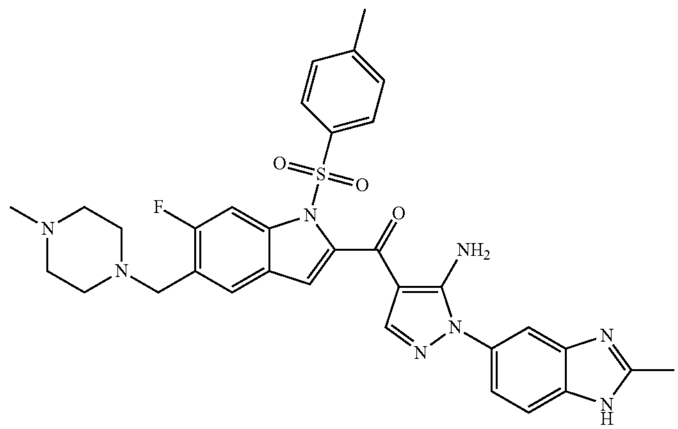 | [5-amino-1-(2-methyl-1H-benzimidazol-5-yl)-1H-pyrazol 4-yl]-[6-fluoro-5-(4-methyl-piperadin-1-ylmethy)-1-(toluene-4-sulfonyl)-1H-indol-2-yl]-methanone | 641 |
| 1035 | 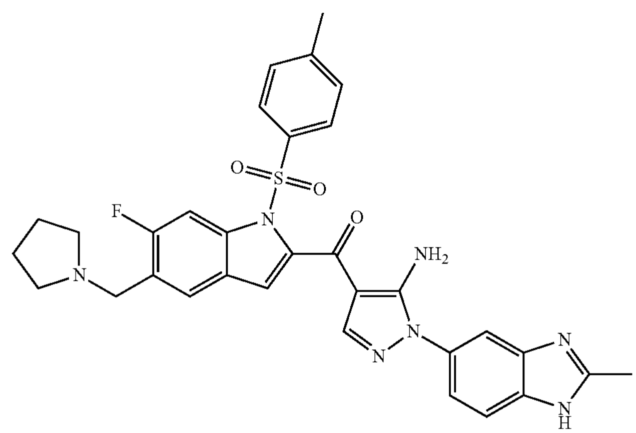 [SMILES: Cc1ccc(S(=O)(=O)n2c(C(=O)c3cnn(-c4ccc5[nH]c(C)nc5c4)c3N)cc3cc(CN4CCCC4)c(F)cc32)cc1] | [5-amino-1-(2-methyl-1H-benzimidazol-5-yl)-1H-pyrazol-4-yl]-[6-fluoro-5-pyrrolidin-1-ylmethyl-1-(toluene-4-sulfonyl)-1H-indol-2-yl]-methanone | 612 |
| 1036 | 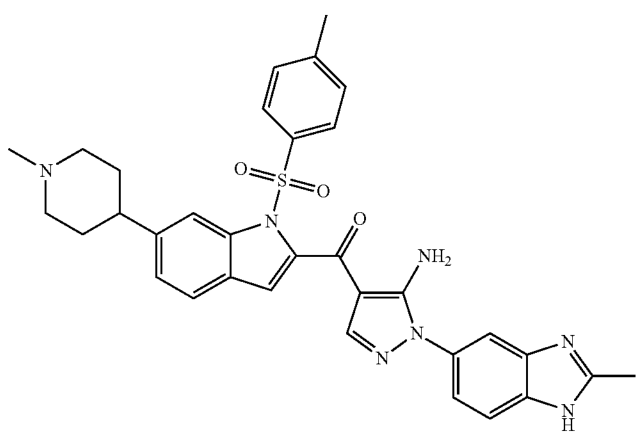 | [5-amino-1-(2-methyl-1H-benzimidazol-5-yl)-1H-pyrazol-4-yl]-[6-(1-methyl-piperidin-4-yl)-1-(toluene-4-sulfonyl)-1H-indol-2-yl]-methanone | 608 |

TABLE 7-continued

| Compound No. | Structure | Compound name | m/z |
|---|---|---|---|
| 1037 | 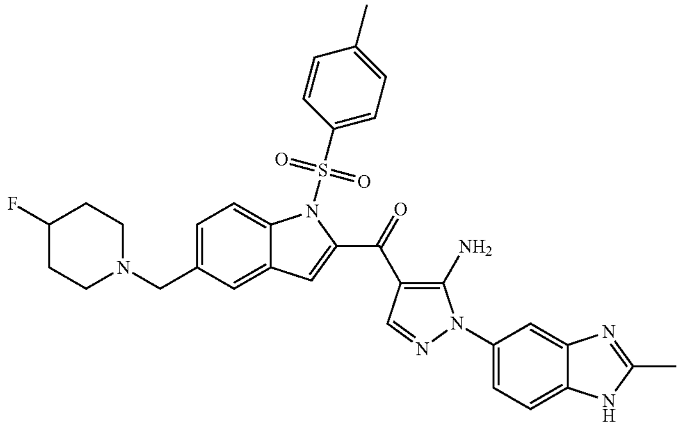 [SMILES: Cc1ccc(S(=O)(=O)n2c(C(=O)c3cnn(-c4ccc5[nH]c(C)nc5c4)c3N)cc3cc(CN4CCC(F)CC4)ccc32)cc1] | [5-amino-1-(2-methyl-1H-benzimidazol-5-yl)-1H-pyrazol-4-yl]-[5-(4-fluoro-piperidin-1-ylmethyl)-1-(toluene-4-sulfonyl)-1H-indol-2-yl]-methanone | 626 |
| 1038 | 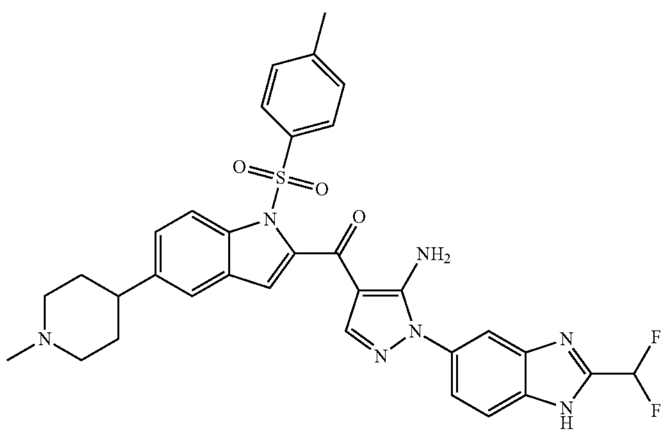 [SMILES: Cc1ccc(S(=O)(=O)n2c(C(=O)c3cnn(-c4ccc5[nH]c(C(F)F)nc5c4)c3N)cc3cc(C4CCN(C)CC4)ccc32)cc1] | [5-amino-1-(2-difluoro-methyl-1H-benzimidazol-5-yl)-1H-pyrazol-4-yl]-[5-(1-methyl-piperidin-4-yl)-1-(toluene-4-sulfonyl)-1H-indol-2-yl]-methanone | 644 |
| 1039 | 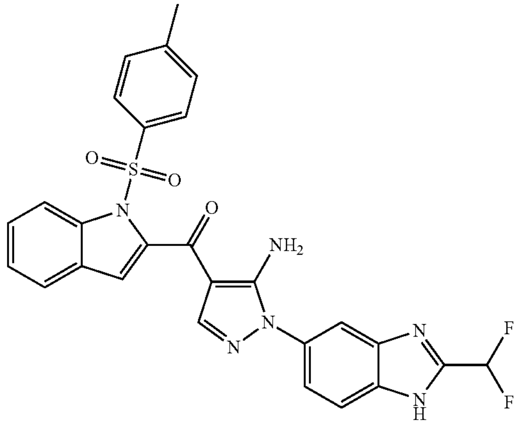 [SMILES: Cc1ccc(S(=O)(=O)n2c(C(=O)c3cnn(-c4ccc5[nH]c(C(F)F)nc5c4)c3N)cc3ccccc32)cc1] | [5-amino-1-(2-difluoro-methyl-1H-benzimidazol-5-yl)-1H-pyrazol-4-yl]-[1-(toluene-4-sulfonyl)-1H-indol-2-yl]-methanone | 547 |

TABLE 7-continued

| Compound No. | Structure | Compound name | m/z |
|---|---|---|---|
| 1040 | 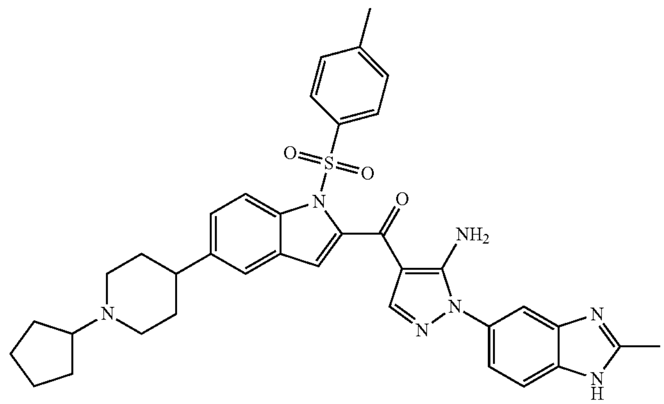 [SMILES: Cc1ccc(S(=O)(=O)n2c(C(=O)c3cnn(-c4ccc5[nH]c(C)nc5c4)c3N)cc3cc(C4CCN(C5CCCC5)CC4)ccc32)cc1] | [5-amino-1-(2-methyl-1H-benzimidazol-5-yl)-1H-pyrazol-4-yl]-[5-(1-cyclopentyl-piperidin-4-yl)-1-(toluene-4-sulfonyl)-1H-indol-2-yl]-methanone | 662 |
| 1041 | 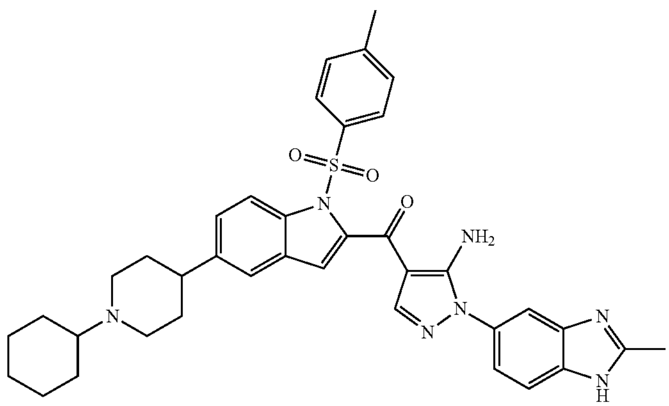 [SMILES: Cc1ccc(S(=O)(=O)n2c(C(=O)c3cnn(-c4ccc5[nH]c(C)nc5c4)c3N)cc3cc(C4CCN(C5CCCCC5)CC4)ccc32)cc1] | [5-amino-1-(2-methyl-1H-benzimidazol-5-yl)-1H-pyrazol-4-yl]-[5-(1-cyclohexyl-piperidin-4-yl)-1-(toluene-4-sulfonyl)-1H-indol-2-yl]-methanone | 676 |
| 1042 | 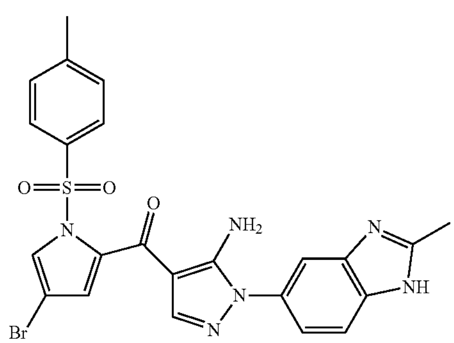 [SMILES: Cc1ccc(S(=O)(=O)n2cc(Br)cc2C(=O)c2cnn(-c3ccc4[nH]c(C)nc4c3)c2N)cc1] | [5-amino-1-(2-methyl-1H-benzimidazol-5-yl)-1H-pyrazol-4-yl]-[4-bromo-1-(toluene-4-sulfonyl)-1H-pyrrol-2-yl]-methanone | 539, 541 |
| 1043 | 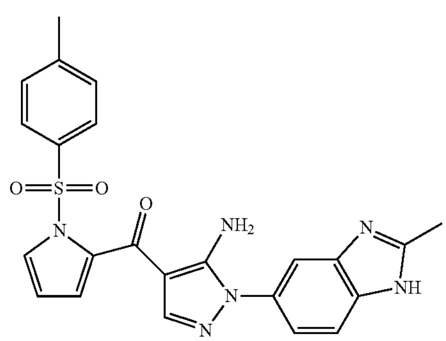 [SMILES: Cc1ccc(S(=O)(=O)n2cccc2C(=O)c2cnn(-c3ccc4[nH]c(C)nc4c3)c2N)cc1] | [5-amino-1-(2-methyl-1H-benzimidazol-5-yl)-1H-pyrazol-4-yl]-[1-(toluene-4-sulfonyl)-1H-pyrrol-2-yl]-methanone | 461 |

TABLE 7-continued

| Compound No. | Structure | Compound name | m/z |
|---|---|---|---|
| 1044 | 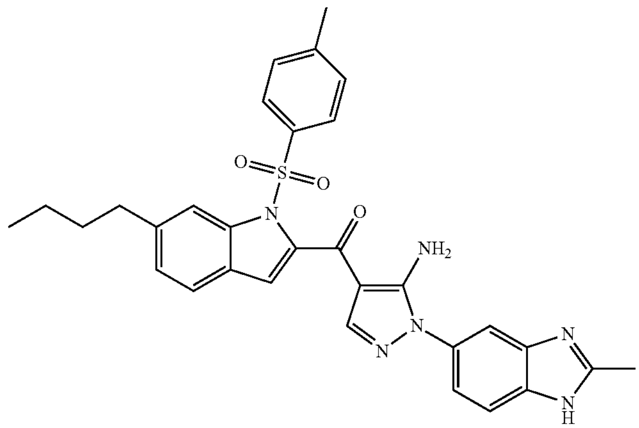 [SMILES: CCCCc1ccc2cc(C(=O)c3cnn(-c4ccc5[nH]c(C)nc5c4)c3N)n(S(=O)(=O)c3ccc(C)cc3)c2c1] | [5-amino-1-(2-methyl-1H-benzimidazol-5-yl)-1H-pyrazol-4-yl]-[6-butyl-1-(toluene-4-sulfonyl)-1H-indol-2-yl]-methanone | 567 |
| 1045 | 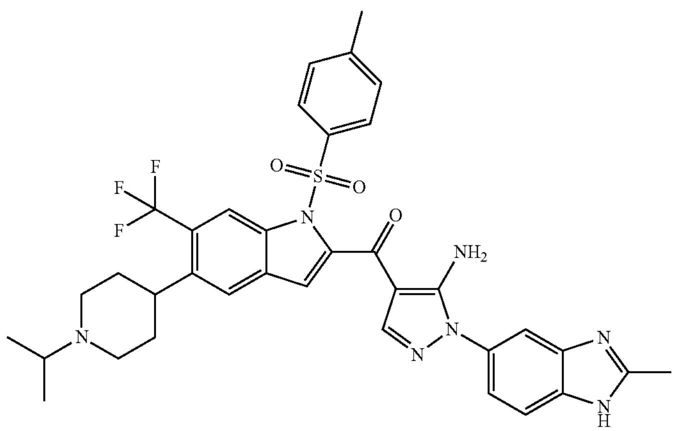 [SMILES: Cc1ccc(S(=O)(=O)n2c(C(=O)c3cnn(-c4ccc5[nH]c(C)nc5c4)c3N)cc3cc(C4CCN(C(C)C)CC4)c(C(F)(F)F)cc32)cc1] | [5-amino-1-(2-methyl-1H-benzimidazol-5-yl)-1H-pyrazol-4-yl]-[5-(1-isopropyl-piperidin-4-yl)-1-(toluene-4-sulfonyl)-6-trifluoro-methyl-1H-indol-2-yl]-methanone | 704 |
| 1046 | 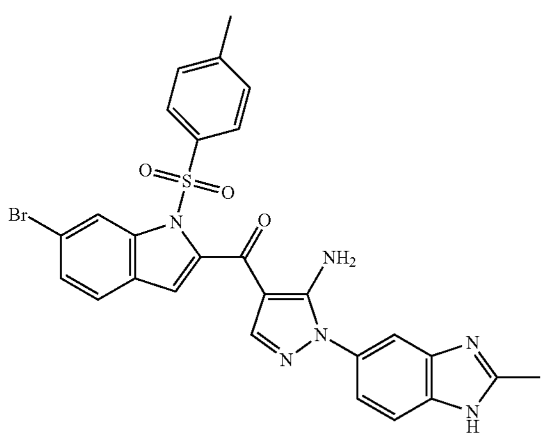 [SMILES: Cc1ccc(S(=O)(=O)n2c(C(=O)c3cnn(-c4ccc5[nH]c(C)nc5c4)c3N)cc3ccc(Br)cc32)cc1] | [5-amino-1-(2-methyl-1H-benzimidazol-5-yl)-1H-pyrazol-4-yl]-6-bromo-1-(toluene-4-sulfonyl)-1H-indol-2-yl]-methanone | 589, 591 |

TABLE 7-continued

| Compound No. | Structure | Compound name | m/z |
|---|---|---|---|
| 1047 | 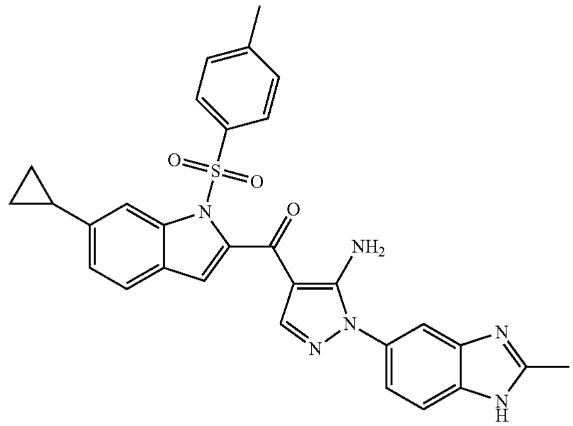 [SMILES: Cc1ccc(S(=O)(=O)n2c(C(=O)c3cnn(-c4ccc5[nH]c(C)nc5c4)c3N)cc3ccc(C4CC4)cc32)cc1] | [5-amino-1-(2-methyl-1H-benzimidazol-5-yl)-1H-pyrazol-4-yl]-[6-cyclopropyl-1-(toluene-4-sulfonyl)-1H-indol-2-yl]-methanone | 551 |
| 1048 | 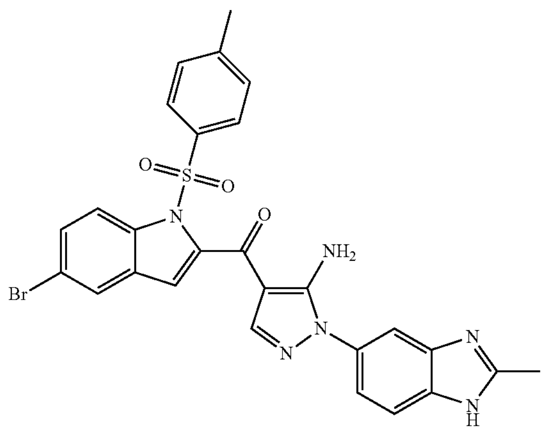 [SMILES: Cc1ccc(S(=O)(=O)n2c(C(=O)c3cnn(-c4ccc5[nH]c(C)nc5c4)c3N)cc3cc(Br)ccc32)cc1] | [5-amino-1-(2-methyl-1H-benzimidazol-5-yl)-1H-pyrazol-4-yl]-[5-bromo-1-(toluene-4-sulfonyl)-1H-indol-2-yl]-methanone | 589, 591 |
| 1049 | 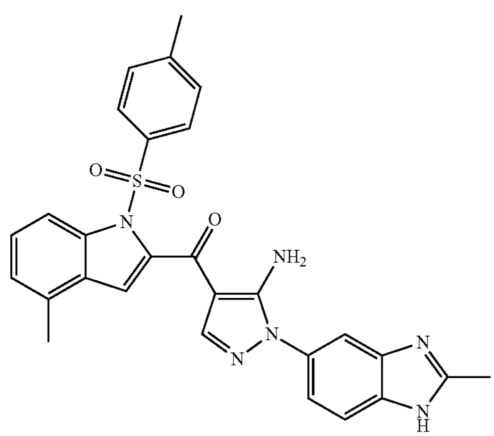 [SMILES: Cc1ccc(S(=O)(=O)n2c(C(=O)c3cnn(-c4ccc5[nH]c(C)nc5c4)c3N)cc3c(C)cccc32)cc1] | [5-amino-1-(2-methyl-1H-benzimidazol-5-yl)-1H-pyrazol-4-yl]-[4-iodo-1-(toluene-4-sulfonyl)-1H-indol-2-yl]-methanone | 637 |

| Compound No. | Structure | Compound name | m/z |
|---|---|---|---|
| 1050 | 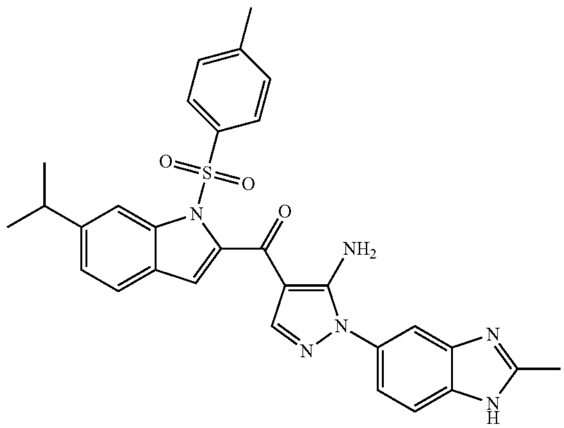 [SMILES: Cc1ccc(S(=O)(=O)n2c(C(=O)c3cnn(-c4ccc5[nH]c(C)nc5c4)c3N)cc3ccc(C(C)C)cc32)cc1] | [5-amino-1-(2-methyl-1H-benzimidazol-5-yl)-1H-pyrazol-4-yl]-[6-isopropyl-1-(toluene-4-sulfonyl)-1H-indol-2-yl]-methanone | 553 |
| 1051 | 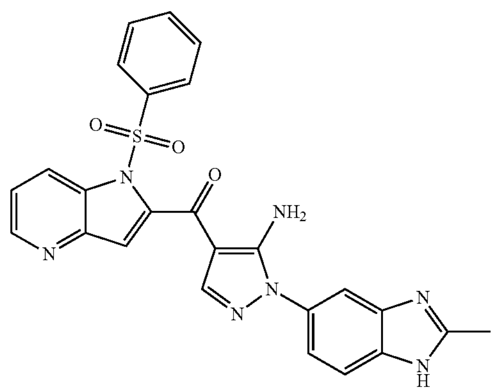 [SMILES: Cc1nc2cc(-n3ncc(C(=O)c4cc5ncccc5n4S(=O)(=O)c4ccccc4)c3N)ccc2[nH]1] | [5-amino-1-(2-methyl-1H-benzimidazol-5-yl)-1H-pyrazol-4-yl]-(1-benzenesulfonyl-1H-pyrrolo[3,2-b]pyridin-2-yl)-methanone | 498 |
| 1052 | 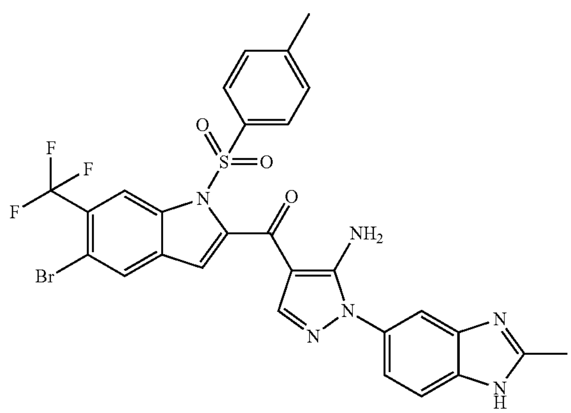 [SMILES: Cc1ccc(S(=O)(=O)n2c(C(=O)c3cnn(-c4ccc5[nH]c(C)nc5c4)c3N)cc3cc(Br)c(C(F)(F)F)cc32)cc1] | [5-amino-1-(2-methyl-1H-benzimidazol-5-yl)-1H-pyrazol-4-yl]-[5-bromo-1-(toluene-4-sulfonyl)-6-trifluoromethyl-1H-indol-2-yl]-methanone | 657, 659 |
| 1053 | 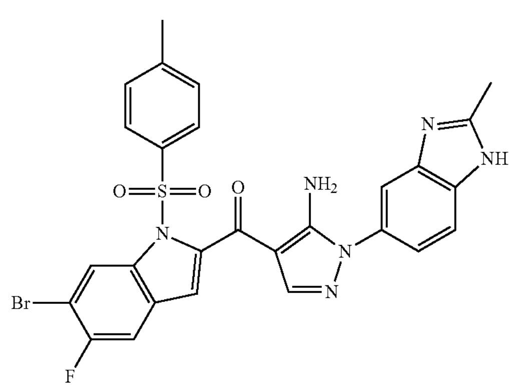 [SMILES: Cc1ccc(S(=O)(=O)n2c(C(=O)c3cnn(-c4ccc5[nH]c(C)nc5c4)c3N)cc3cc(F)c(Br)cc32)cc1] | [5-amino-1-(2-methyl-1H-benzimidazol-5-yl)-1H-pyrazol-4-yl]-[6-bromo-5-fluoro-1-(toluene-4-sulfonyl)-1H-indol-2-yl]-methanone | 607, 609 |

TABLE 7-continued

| Compound No. | Structure | Compound name | m/z |
|---|---|---|---|
| 1054 | 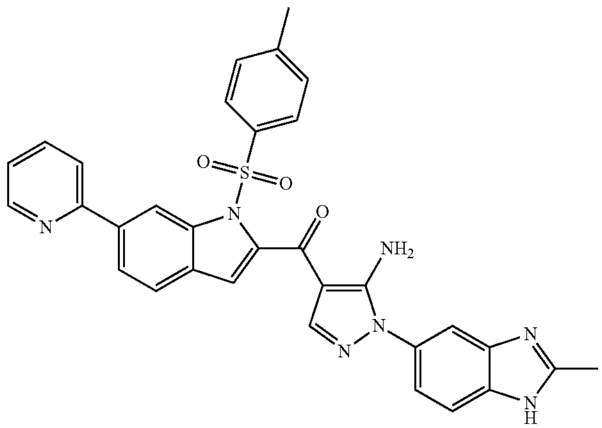 [SMILES: Cc1ccc(S(=O)(=O)n2c(C(=O)c3cnn(-c4ccc5[nH]c(C)nc5c4)c3N)cc3ccc(-c4ccccn4)cc32)cc1] | [5-amino-1-(2-methyl-1H-benzimidazol-5-yl)-1H-pyrazol-4-yl]-[6-pyridin-2-yl-1-(toluene-4-sulfonyl)-1H-indol-2-yl]-methanone | 588 |
| 1055 | 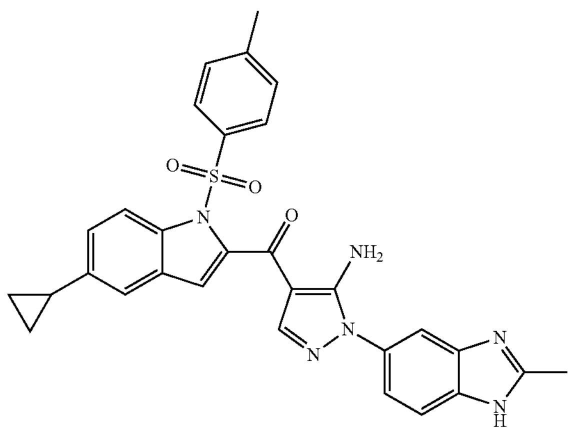 [SMILES: Cc1ccc(S(=O)(=O)n2c(C(=O)c3cnn(-c4ccc5[nH]c(C)nc5c4)c3N)cc3cc(C4CC4)ccc32)cc1] | [5-amino-1-(2-methyl-1H-benzimidazol-5-yl)-1H-pyrazol-4-yl]-[5-cyclopropyl-1-(toluene-4-sulfonyl)-1H-indol-2-yl]-methanone | 551 |
| 1056 | 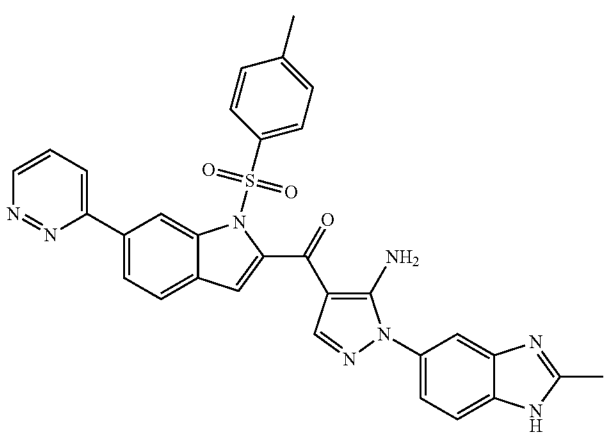 [SMILES: Cc1ccc(S(=O)(=O)n2c(C(=O)c3cnn(-c4ccc5[nH]c(C)nc5c4)c3N)cc3ccc(-c4cccnn4)cc32)cc1] | [5-amino-1-(2-methyl-1H-benzimidazol-5-yl)-1H-pyrazol-4-yl]-[6-pyridazin-3-yl-1-(toluene-4-sulfonyl)-1H-indol-2-yl]-methanone | 589 |

TABLE 7-continued

| Compound No. | Structure | Compound name | m/z |
|---|---|---|---|
| 1057 | 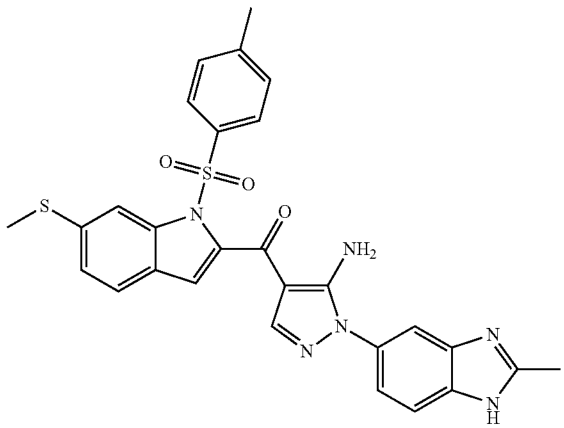 | [5-amino-1-(2-methyl-1H-benzimidazol-5-yl)-1H-pyrazol-4-yl]-[6-methyl-sulfanyl-1-(toluene-4-sulfonyl)-1H-indol-2-yl]-methanone | 557 |
| 1058 | 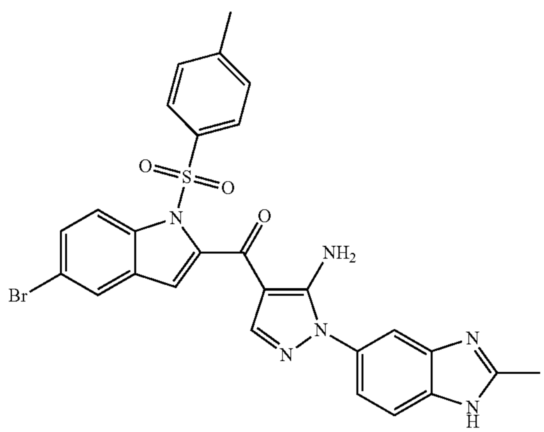 [SMILES: Cc1ccc(S(=O)(=O)n2c(C(=O)c3cnn(-c4ccc5[nH]c(C)nc5c4)c3N)cc3cc(Br)ccc32)cc1] | [5-amino-1-(2-methyl-1H-benzimidazol-5-yl)-1H-pyrazol-4-yl]-[5-bromo-1-(toluene-4-sulfonyl)-1H-indol-2-yl]-methanone | 589, 591 |
| 1059 | 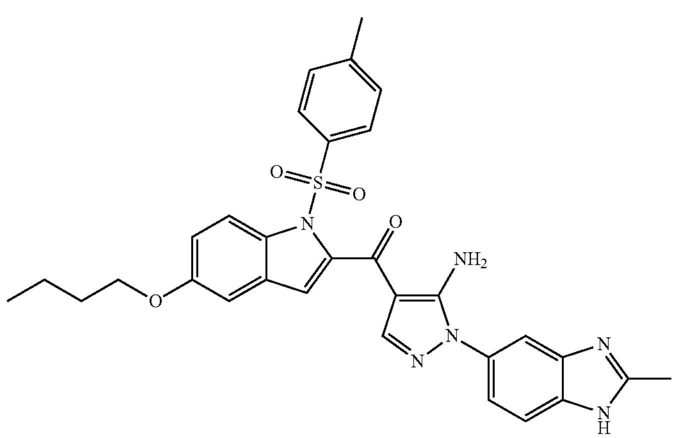 [SMILES: CCCCOc1ccc2c(c1)cc(C(=O)c1cnn(-c3ccc4[nH]c(C)nc4c3)c1N)n2S(=O)(=O)c1ccc(C)cc1] | [5-amino-1-(2-methyl-1H-benzimidazol-5-yl)-1H-pyrazol-4-yl]-[5-butoxy-1-(toluene-4-sulfonyl)-1H-indol-2-yl]-methanone | 583 |

TABLE 7-continued

| Compound No. | Structure | Compound name | m/z |
|---|---|---|---|
| 1060 | 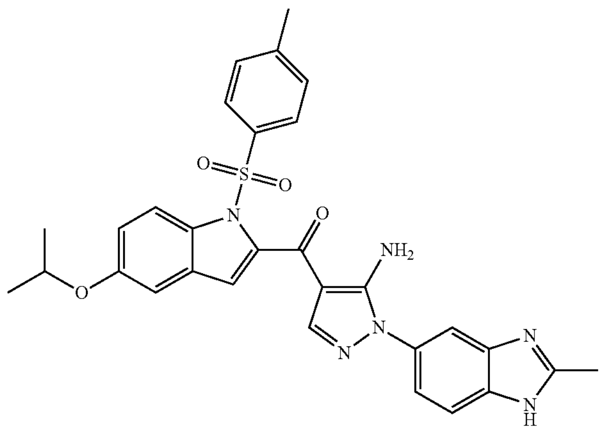 [SMILES: Cc1ccc(S(=O)(=O)n2c(C(=O)c3cnn(-c4ccc5[nH]c(C)nc5c4)c3N)cc3cc(OC(C)C)ccc32)cc1] | [5-amino-1-(2-methyl-1H-benzimidazol-5-yl)-1H-pyrazol-4-yl]-[5-isopropoxy-1-(toluene-4-sulfonyl)-1H-indol-2-yl]-methanone | 569 |
| 1061 | 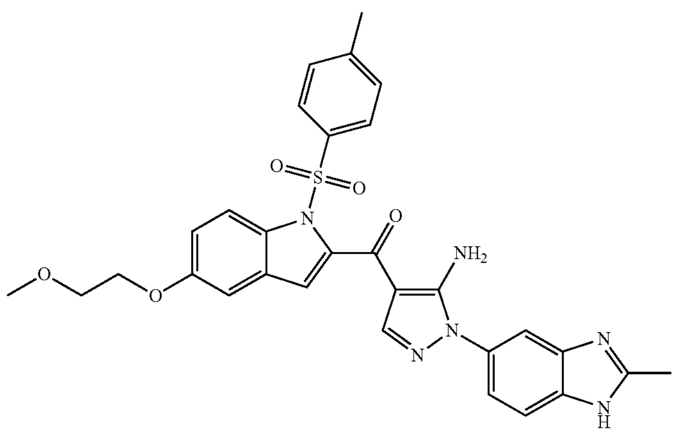 | [5-amino-1-(2-methyl-1H-benzimidazol-5-yl)-1H-pyrazol-4-yl]-[5-(2-methoxy-ethoxy)-1-(toluene-4-sulfonyl)-1H-indol-2-yl]-methanone | 585 |
| 1062 | 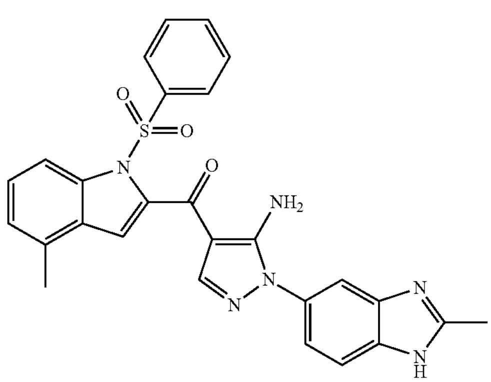 | [5-amino-1-(2-methyl-1H-benzimidazol-5-yl)-1H-pyrazol-4-yl]-(1-benzenesulfonyl-4-methyl-1H-indol-2-yl)-methanone | 511 |

TABLE 7-continued

| Compound No. | Structure | Compound name | m/z |
|---|---|---|---|
| 1063 | 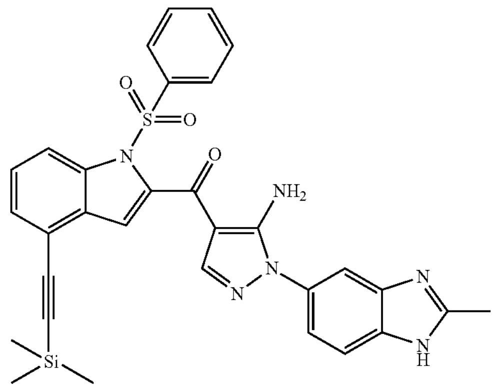 [SMILES: Cc1nc2cc(-n3ncc(C(=O)c4cc5c(C#C[Si](C)(C)C)cccc5n4S(=O)(=O)c4ccccc4)c3N)ccc2[nH]1] | [5-amino-1-(2-methyl-1H-benzimidazol-5-yl)-1H-pyrazol-4-yl]-(1-benzene-sulfonyl-4-trimethyl-silanylethynyl-1H-indol-2-yl]-methanone | 593 |
| 1064 | 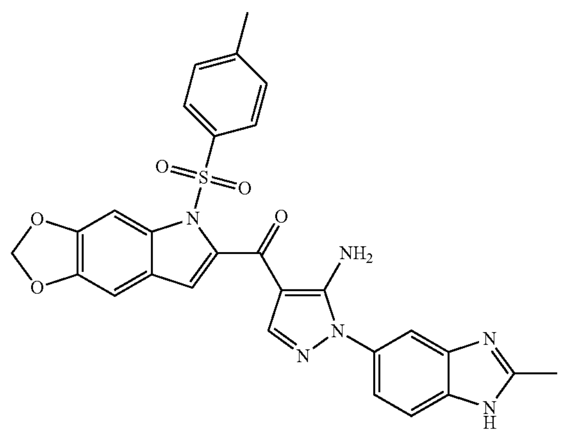 [SMILES: Cc1ccc(S(=O)(=O)n2c(C(=O)c3cnn(-c4ccc5[nH]c(C)nc5c4)c3N)cc3cc4c(cc32)OCO4)cc1] | [5-amino-1-(2-methyl-1H-benzimidazol-5-yl)-1H-pyrazol-4-yl]-[5-(toluene-4-sulfonyl)-5H-[1,3]dioxolo[4,5-f]indol-6-yl]-methanone | 555 |
| 1065 | 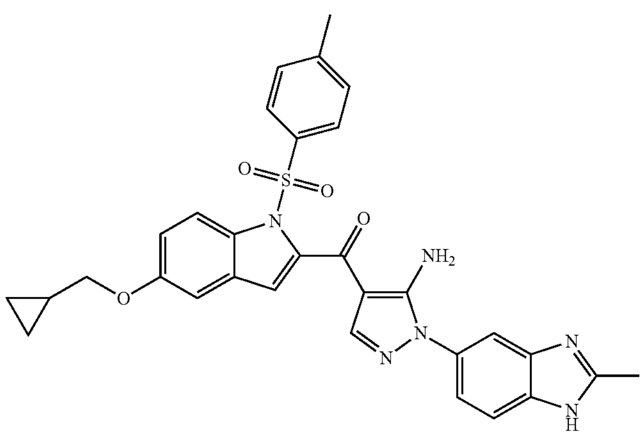 [SMILES: Cc1ccc(S(=O)(=O)n2c(C(=O)c3cnn(-c4ccc5[nH]c(C)nc5c4)c3N)cc3cc(OCC4CC4)ccc32)cc1] | [5-amino-1-(2-methyl-1H-benzimidazol-5-yl)-1H-pyrazol-4-yl]-[5-cyclopropyl-methoxy-1-(toluene-4-sulfonyl)-1H-indol-2-yl]-methanone | 581 |
| 1066 | 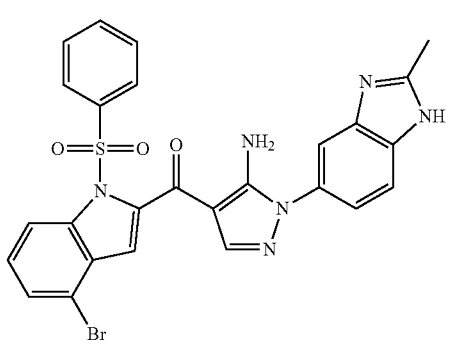 [SMILES: Cc1nc2cc(-n3ncc(C(=O)c4cc5c(Br)cccc5n4S(=O)(=O)c4ccccc4)c3N)ccc2[nH]1] | [5-amino-1-(2-methyl-1H-benzimidazol-5-yl)-1H-pyrazol-4-yl]-(1-benzene-sulfonyl-4-bromo-1H-indol-2-yl]-methanone | 575, 577 |

TABLE 7-continued

| Compound No. | Structure | Compound name | m/z |
|---|---|---|---|
| 1067 | 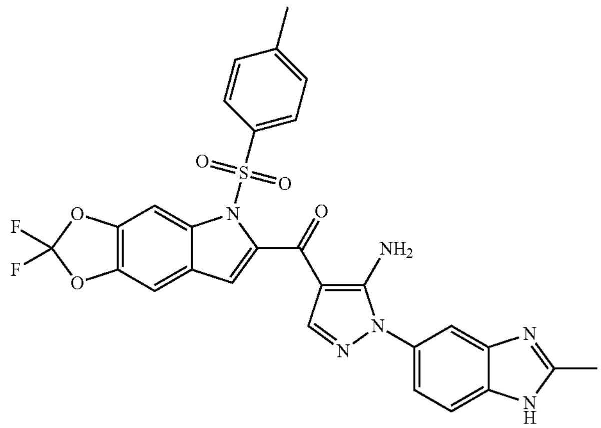 [SMILES: Cc1ccc(S(=O)(=O)n2c(C(=O)c3cnn(-c4ccc5[nH]c(C)nc5c4)c3N)cc3cc4c(cc32)OC(F)(F)O4)cc1] | [5-amino-1-(2-methyl-1H-benzimidazol-5-yl)-1H-pyrazol-4-yl]-[2,2-difluoro-5-(toluene-4-sulfonyl)-5H-[1,3]dioxolo[4,5-f]indol-6-yl]-methanone | 591 |
| 1068 | 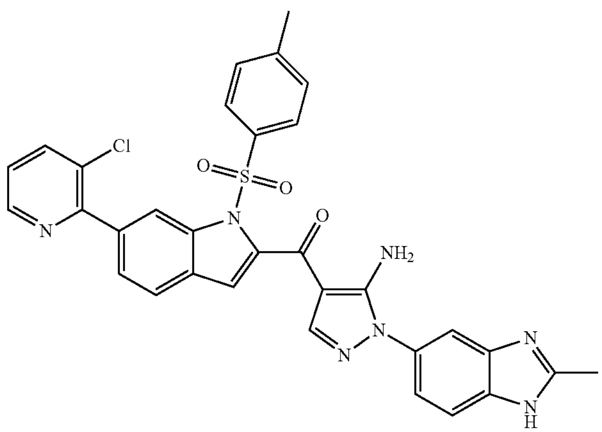 [SMILES: Cc1ccc(S(=O)(=O)n2c(C(=O)c3cnn(-c4ccc5[nH]c(C)nc5c4)c3N)cc3ccc(-c4ncccc4Cl)cc32)cc1] | [5-amino-1-(2-methyl-1H-benzimidazol-5-yl)-1H-pyrazol-4-yl]-[6-(3-chloro-pyridin-2-yl)-1-(toluene-4-sulfonyl)-1H-indol-2-yl]-methanone | 622 |
| 1069 | 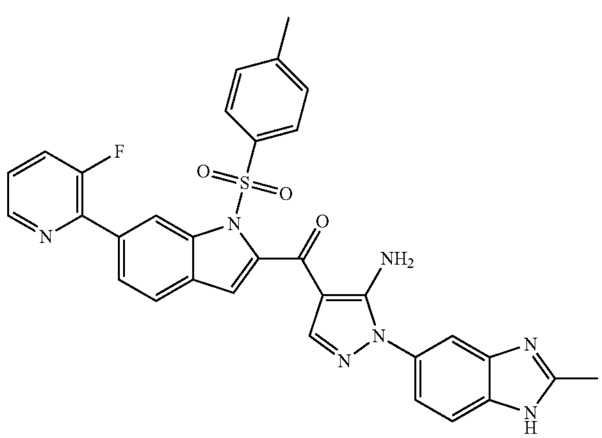 | [5-amino-1-(2-methyl-1H-benzimidazol-5-yl)-1H-pyrazol-4-yl]-[6-(3-fluoro-pyridin-2-yl)-1-(toluene-4-sulfonyl)-1H-indol-2-yl]-methanone | 606 |

TABLE 7-continued

| Compound No. | Structure | Compound name | m/z |
|---|---|---|---|
| 1070 | 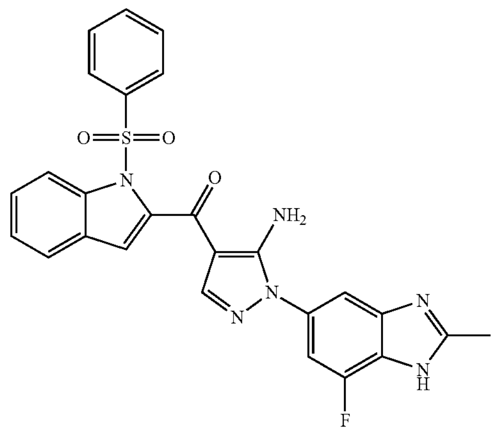 [SMILES: Cc1nc2cc(-n3ncc(C(=O)c4cc5ccccc5n4S(=O)(=O)c4ccccc4)c3N)cc(F)c2[nH]1] | [5-amino-1-(7-fluoro-2-methyl-1H-benzimidazol-5-yl)-1H-pyrazol-4-yl]-(1-benzenesulfonyl-1H-indol-2-yl)-methanone | 515 |
| 1071 | 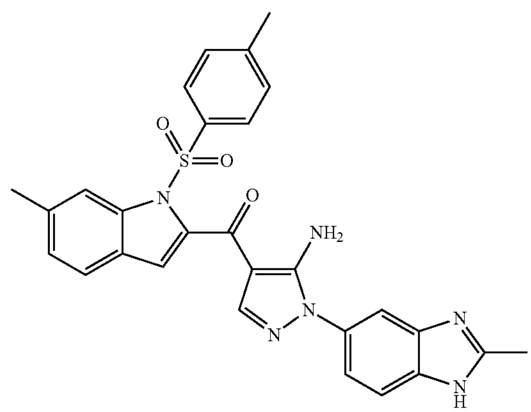 | [5-amino-1-(2-methyl-1H-benzimidazol-5-yl)-1H-pyrazol-4-yl]-[6-methyl-1-(toluene-4-sulfonyl)-1H-indol-2-yl]-methanone | 525 |
| 1072 | 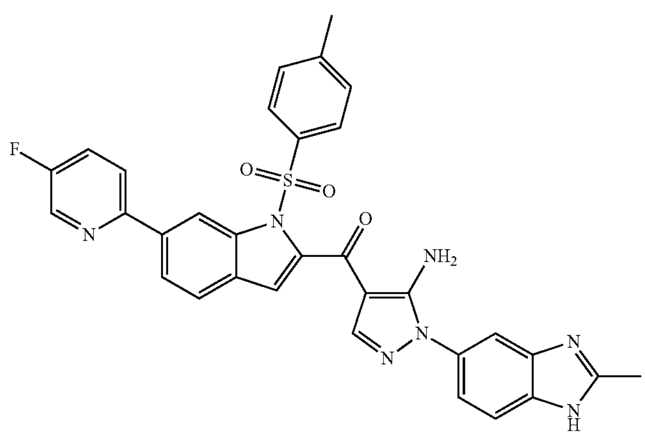 [SMILES: Cc1ccc(S(=O)(=O)n2c(C(=O)c3cnn(-c4ccc5[nH]c(C)nc5c4)c3N)cc3ccc(-c4ccc(F)cn4)cc32)cc1] | [5-amino-1-(2-methyl-1H-benzimidazol-5-yl)-1H-pyrazol-4-yl]-[6-(5-fluoro-pyridin-2-yl)-1-(toluene-4-sulfonyl)-1H-indol-2-yl]-methanone | 606 |

TABLE 7-continued

| Compound No. | Structure | Compound name | m/z |
|---|---|---|---|
| 1073 | 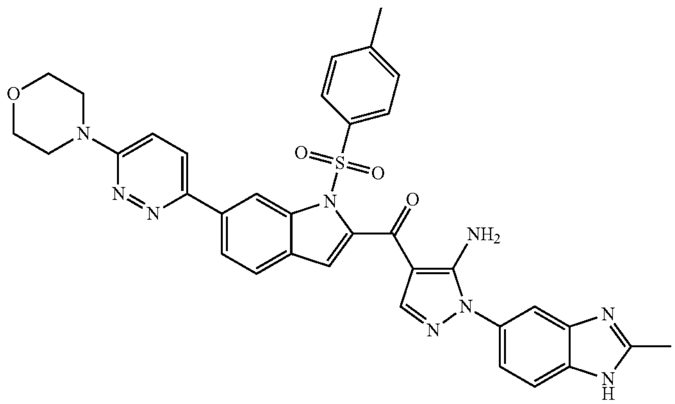 [SMILES: Cc1ccc(S(=O)(=O)n2c(C(=O)c3cnn(-c4ccc5[nH]c(C)nc5c4)c3N)cc3ccc(-c4ccc(N5CCOCC5)nn4)cc32)cc1] | [5-amino-1-(2-methyl-1H-benzimidazol-5-yl)-1H-pyrazol-4-yl]-[6-(6-morpholin-4-yl-pyridazin-3-yl)-1-(toluene-4-sulfonyl)-1H-indol-2-yl]-methanone | 674 |
| 1074 | 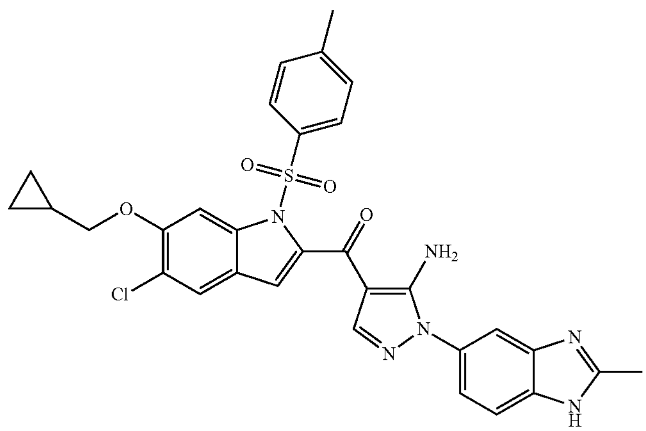 [SMILES: Cc1ccc(S(=O)(=O)n2c(C(=O)c3cnn(-c4ccc5[nH]c(C)nc5c4)c3N)cc3cc(Cl)c(OCC4CC4)cc32)cc1] | [5-amino-1-(2-methyl-1H-benzimidazol-5-yl)-1H-pyrazol-4-yl]-[5-chloro-6-cyclopropyl-methoxy-1-(toluene-4-sulfonyl)-1H-indol-2-yl]-methanone | 615, 617 |
| 1075 | 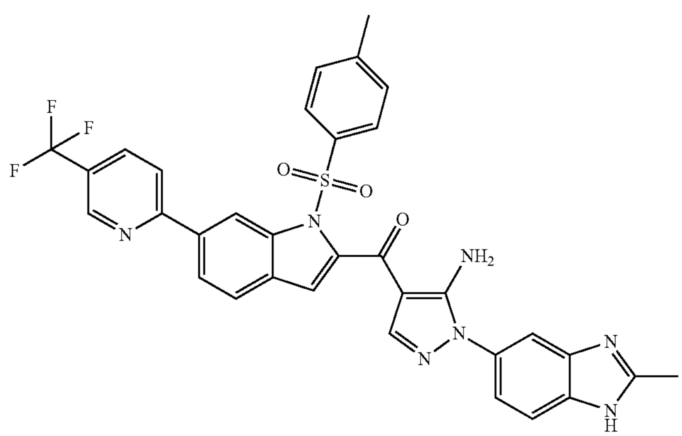 [SMILES: Cc1ccc(S(=O)(=O)n2c(C(=O)c3cnn(-c4ccc5[nH]c(C)nc5c4)c3N)cc3ccc(-c4ccc(C(F)(F)F)cn4)cc32)cc1] | [5-amino-1-(2-methyl-1H-benzimidazol-5-yl)-1H-pyrazol-4-yl]-[1-(toluene-4-sulfonyl)-6-(5-trifluoromethyl-pyridin-2-yl)-1H-indol-2-yl]-methanone | 656 |

TABLE 7-continued

| Compound No. | Structure | Compound name | m/z |
|---|---|---|---|
| 1076 | 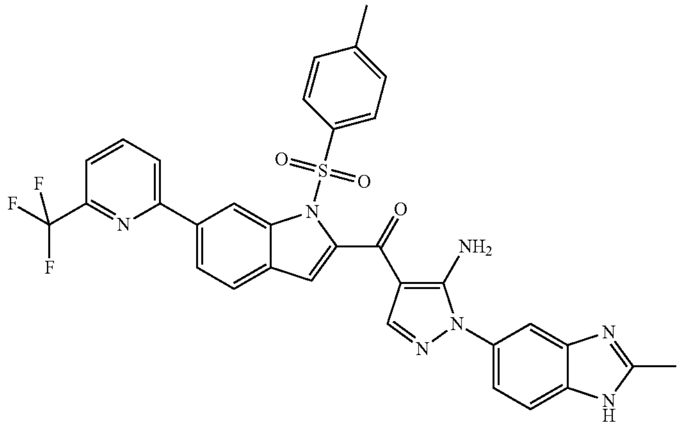 [SMILES: Cc1ccc(S(=O)(=O)n2c(C(=O)c3cnn(-c4ccc5[nH]c(C)nc5c4)c3N)cc3ccc(-c4cccc(C(F)(F)F)n4)cc32)cc1] | [5-amino-1-(2-methyl-1H-benzimidazol-5-yl)-1H-pyrazol-4-yl]-[1-(toluene-4-sulfonyl)-6-(6-trifluoromethyl-pyridin-2-yl)-1H-indol-2-yl]-methanone | 656 |
| 1077 | 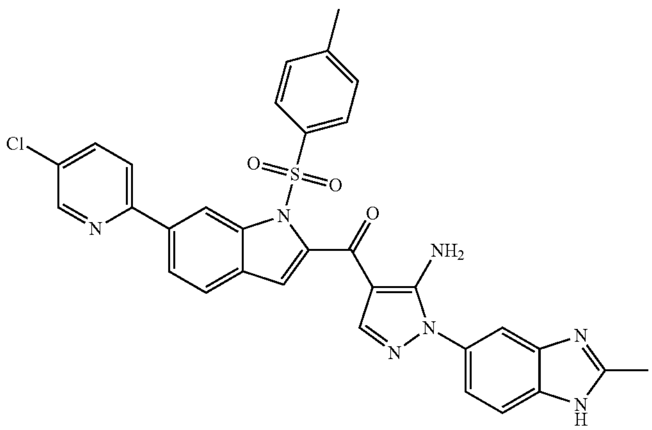 [SMILES: Cc1ccc(S(=O)(=O)n2c(C(=O)c3cnn(-c4ccc5[nH]c(C)nc5c4)c3N)cc3ccc(-c4ccc(Cl)cn4)cc32)cc1] | [5-amino-1-(2-methyl-1H-benzimidazol-5-yl)-1H-pyrazol-4-yl]-[6-(5-chloro-pyridin-2-yl)-1-(toluene-4-sulfonyl)-1H-indol-2-yl]-methanone | 621, 623 |
| 1078 | 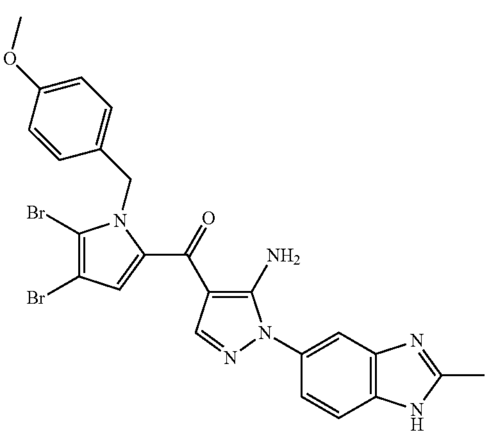 [SMILES: COc1ccc(Cn2c(C(=O)c3cnn(-c4ccc5[nH]c(C)nc5c4)c3N)cc(Br)c2Br)cc1] | [5-amino-1-(2-methyl-1H-benzimidazol-5-yl)-1H-pyrazol-4-yl]-[4,5-dibromo-1-(4-methoxy-benzyl)-1H-pyrrol-2-yl]-methanone | 583, 585, 587 |

TABLE 7-continued

| Compound No. | Structure | Compound name | m/z |
|---|---|---|---|
| 1079 | 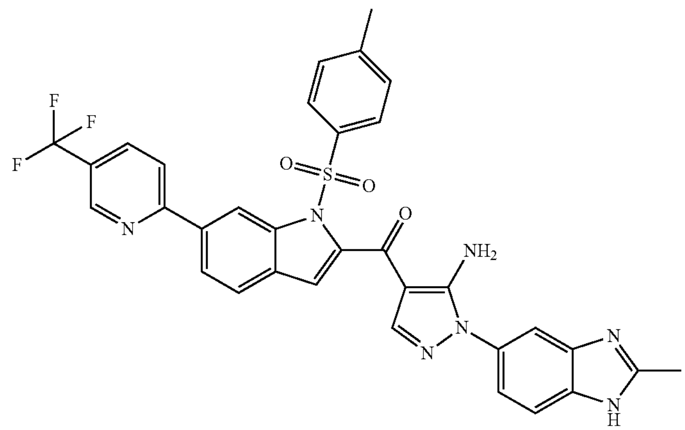 [SMILES: Cc1ccc(S(=O)(=O)n2c(C(=O)c3cnn(-c4ccc5[nH]c(C)nc5c4)c3N)cc3ccc(-c4ccc(C(F)(F)F)cn4)cc32)cc1] | [5-amino-1-(2-methyl-1H-benzimidazol-5-yl)-1H-pyrazol-4-yl]-[1-(toluene-4-sulfonyl)-6-(5-trifluoromethyl-pyridin-2-yl)-1H-indol-2-yl]-methanone | 656 |
| 1080 | 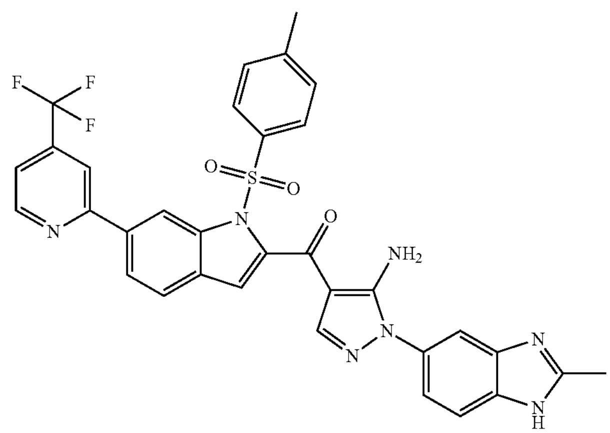 [SMILES: Cc1ccc(S(=O)(=O)n2c(C(=O)c3cnn(-c4ccc5[nH]c(C)nc5c4)c3N)cc3ccc(-c4cc(C(F)(F)F)ccn4)cc32)cc1] | [5-amino-1-(2-methyl-1H-benzimidazol-5-yl)-1H-pyrazol-4-yl]-[1-(toluene-4-sulfonyl)-6-(4-trifluoromethyl-pyridin-2-yl)-1H-indol-2-yl]-methanone | 656 |
| 1081 | 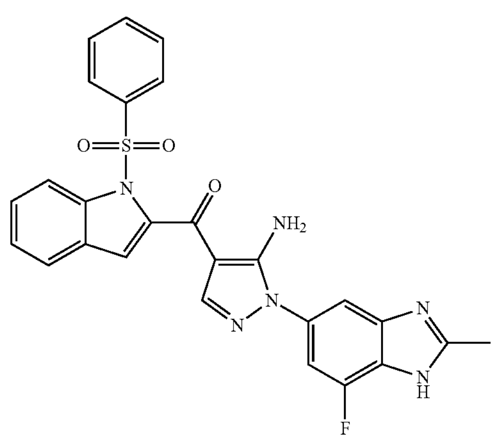 [SMILES: Cc1nc2cc(-n3ncc(C(=O)c4cc5ccccc5n4S(=O)(=O)c4ccccc4)c3N)cc(F)c2[nH]1] | [5-amino-1-(7-fluoro-2-methyl-1H-benzimidazol-5-yl)-1H-pyrazol-4-yl]-(1-benzenesulfonyl-1H-indol-2-yl)-methanone | 515 |

TABLE 7-continued

| Compound No. | Structure | Compound name | m/z |
|---|---|---|---|
| 1082 | 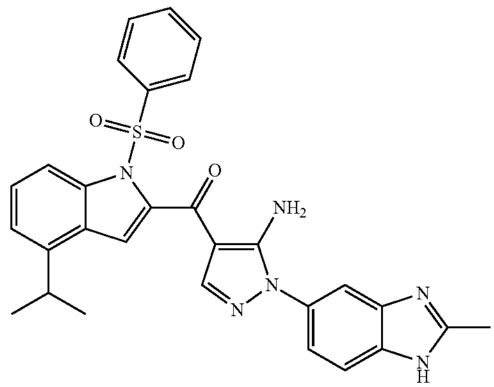 [SMILES: Cc1nc2cc(-n3ncc(C(=O)c4cc5c(C(C)C)cccc5n4S(=O)(=O)c4ccccc4)c3N)ccc2[nH]1] | [5-amino-1-(2-methyl-1H-benzimidazol-5-yl)-1H-pyrazol-4-yl]-(1-benzenesulfonyl-4-isopropyl-1H-indol-2-yl]-methanone | 539 |
| 1511 | 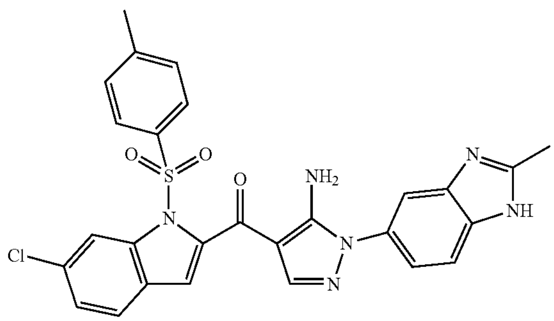 [SMILES: Cc1ccc(S(=O)(=O)n2c(C(=O)c3cnn(-c4ccc5[nH]c(C)nc5c4)c3N)cc3ccc(Cl)cc32)cc1] | [5-amino-1-(2-methyl-1H-benzimidazol-5-yl)-1H-pyrazol-4-yl]-[6-chloro-1-(toluene-4-sulfonyl)-1H-indol-2-yl]-methanone | 545 |
| 1512 | 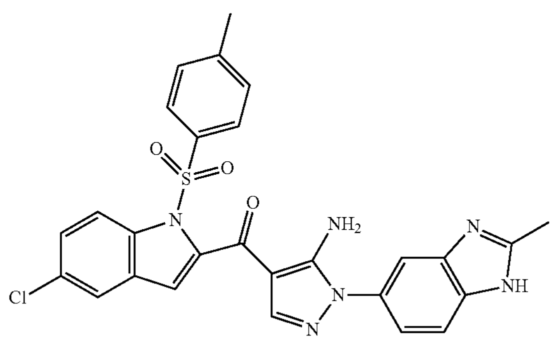 [SMILES: Cc1ccc(S(=O)(=O)n2c(C(=O)c3cnn(-c4ccc5[nH]c(C)nc5c4)c3N)cc3cc(Cl)ccc32)cc1] | [5-amino-1-(2-methyl-1H-benzimidazol-5-yl)-1H-pyrazol-4-yl]-[6-chloro-1-(toluene-4-sulfonyl)-1H-indol-2-yl]-methanone | 545 |
| 1513 | 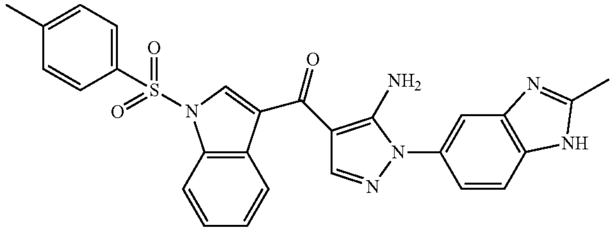 | [5-amino-1-(2-methyl-1H-benzimidazol-5-yl)-1H-pyrazol-4-yl]-[1-(toluene-4-sulfonyl)-1H-indol-3-yl]-methanone | 511 |

TABLE 7-continued

| Compound No. | Structure | Compound name | m/z |
|---|---|---|---|
| 1514 | 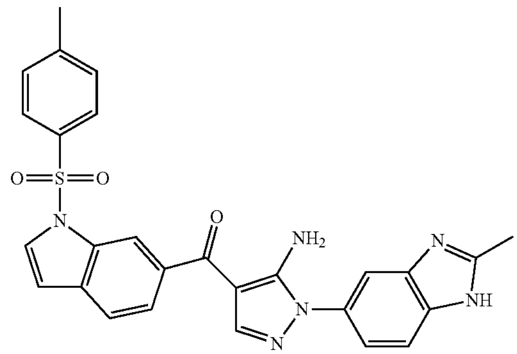 [SMILES: Cc1ccc(S(=O)(=O)n2ccc3ccc(C(=O)c4cnn(-c5ccc6[nH]c(C)nc6c5)c4N)cc32)cc1] | [5-amino-1-(2-methyl-1H-benzimidazol-5-yl)-1H-pyrazol-4-yl]-[1-(toluene-4-sulfonyl)-1H-indol-6-yl]-methanone | 511 |
| 1515 | 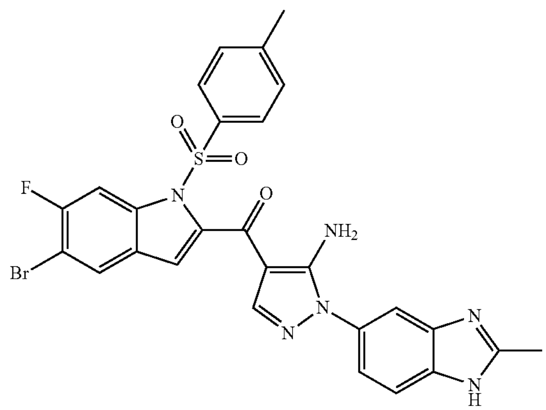 [SMILES: Cc1ccc(S(=O)(=O)n2c(C(=O)c3cnn(-c4ccc5[nH]c(C)nc5c4)c3N)cc3cc(Br)c(F)cc32)cc1] | [5-amino-1-(2-methyl-1H-benzimidazol-5-yl)-1H-pyrazol-4-yl]-[5-bromo-6-fluoro-1-(toluene-4-sulfonyl)-1H-indol-2-yl]-methanone | 607 |
| 1516 | 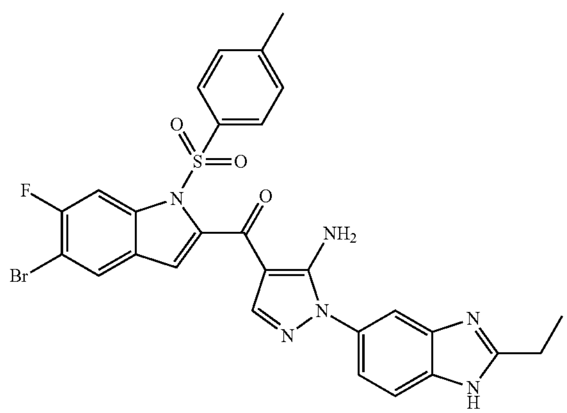 [SMILES: CCc1nc2cc(-n3ncc(C(=O)c4cc5cc(Br)c(F)cc5n4S(=O)(=O)c4ccc(C)cc4)c3N)ccc2[nH]1] | [5-amino-1-(2-ethyl-1H-benzimidazol-5-yl)-1H-pyrazol-4-yl]-[5-bromo-6-fluoro-1-(toluene-4-sulfonyl)-1H-indol-2-yl]-methanone | 621 |
| 1517 | 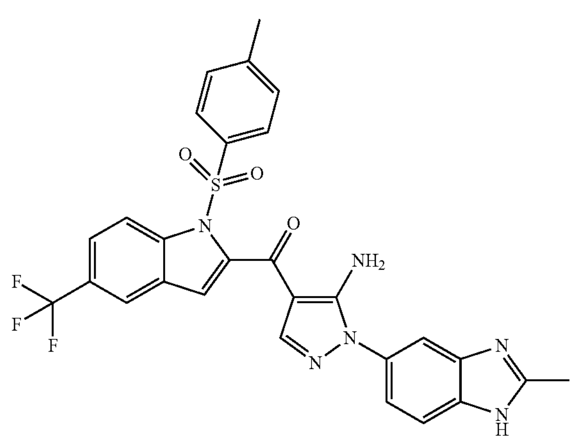 [SMILES: Cc1ccc(S(=O)(=O)n2c(C(=O)c3cnn(-c4ccc5[nH]c(C)nc5c4)c3N)cc3cc(C(F)(F)F)ccc32)cc1] | [5-amino-1-(2-methyl-1H-benzimidazol-5-yl)-1H-pyrazol-4-yl]-[1-(toluene-4-sulfonyl)-5-trifluoromethyl-1H-indol-2-yl]-methanone | 579 |

TABLE 7-continued

| Compound No. | Structure | Compound name | m/z |
|---|---|---|---|
| 1518 | 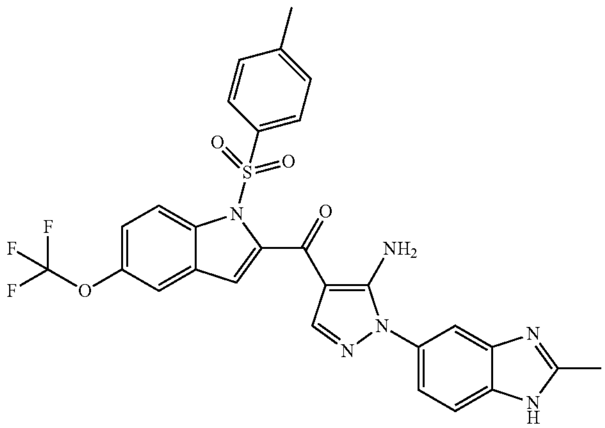 [SMILES: Cc1ccc(S(=O)(=O)n2c(C(=O)c3cnn(-c4ccc5[nH]c(C)nc5c4)c3N)cc3cc(OC(F)(F)F)ccc32)cc1] | [5-amino-1-(2-methyl-1H-benzimidazol-5-yl)-1H-pyrazol-4-yl]-[1-(toluene-4-sulfonyl)-5-trifluoromethoxy-1H-indol-2-yl]-methanone | 595 |
| 1519 | 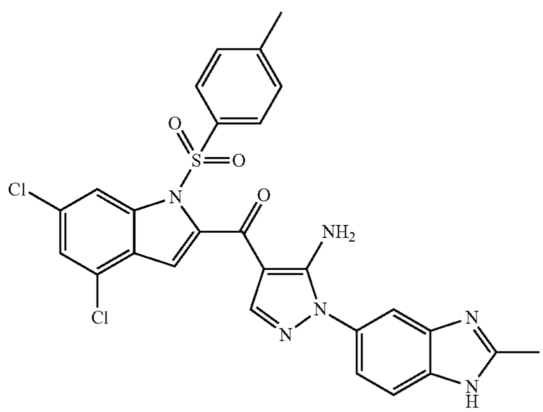 [SMILES: Cc1ccc(S(=O)(=O)n2c(C(=O)c3cnn(-c4ccc5[nH]c(C)nc5c4)c3N)cc3c(Cl)cc(Cl)cc32)cc1] | [5-amino-1-(2-methyl-1H-benzimidazol-5-yl)-1H-pyrazol-4-yl]-[4,6-dichloro-1-(toluene-4-sulfonyl)-1H-indol-2-yl]-methanone | 579 |
| 1520 | 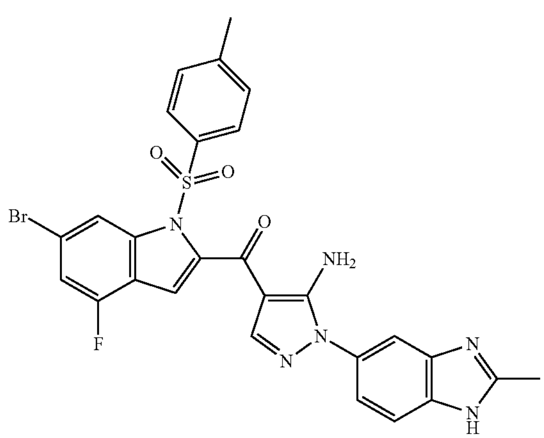 [SMILES: Cc1ccc(S(=O)(=O)n2c(C(=O)c3cnn(-c4ccc5[nH]c(C)nc5c4)c3N)cc3c(F)cc(Br)cc32)cc1] | [5-amino-1-(2-methyl-1H-benzimidazol-5-yl)-1H-pyrazol-4-yl]-[6-bromo-4-fluoro-1-(toluene-4-sulfonyl)-1H-indol-2-yl]-methanone | 607 |

TABLE 7-continued

| Compound No. | Structure | Compound name | m/z |
|---|---|---|---|
| 1521 | 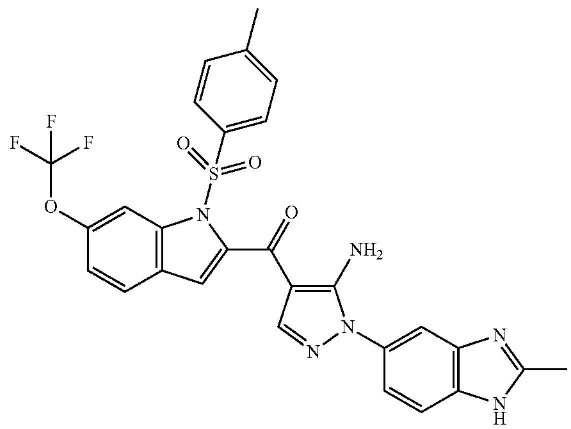 [SMILES: Cc1ccc(S(=O)(=O)n2c(C(=O)c3cnn(-c4ccc5[nH]c(C)nc5c4)c3N)cc3ccc(OC(F)(F)F)cc32)cc1] | [5-amino-1-(2-methyl-1H-benzimidazol-5-yl)-1H-pyrazol-4-yl]-[1-(toluene-4-sulfonyl)-6-trifluoromethoxy-1H-indol-2-yl]-methanone | 595 |
| 1522 | 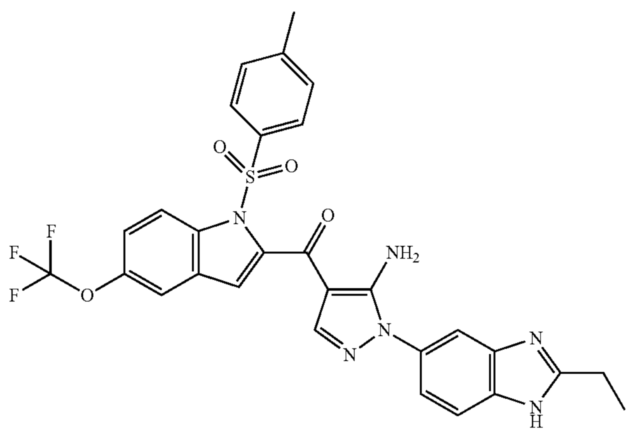 [SMILES: CCc1nc2cc(-n3ncc(C(=O)c4cc5cc(OC(F)(F)F)ccc5n4S(=O)(=O)c4ccc(C)cc4)c3N)ccc2[nH]1] | [5-amino-1-(2-ethyl-1H-benzimidazol-5-yl)-1H-pyrazol-4-yl]-[1-(toluene-4-sulfonyl)-5-trifluoromethoxy-1H-indol-2-yl]-methanone | 609 |
| 1523 | 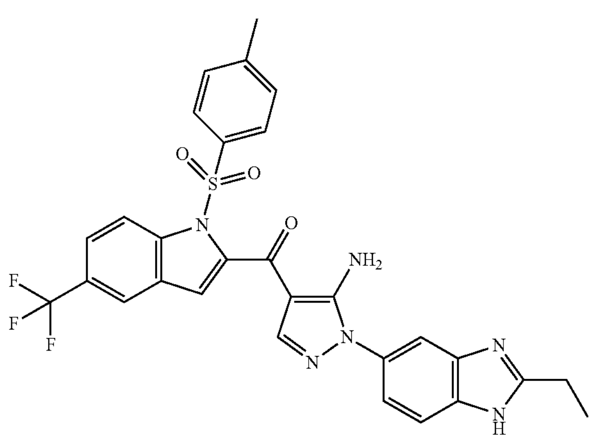 [SMILES: CCc1nc2cc(-n3ncc(C(=O)c4cc5cc(C(F)(F)F)ccc5n4S(=O)(=O)c4ccc(C)cc4)c3N)ccc2[nH]1] | [5-amino-1-(2-ethyl-1H-benzimidazol-5-yl)-1H-pyrazol-4-yl]-[1-(toluene-4-sulfonyl)-5-trifluoromethyl-1H-indol-2-yl]-methanone | 593 |

TABLE 7-continued

| Compound No. | Structure | Compound name | m/z |
|---|---|---|---|
| 1524 | 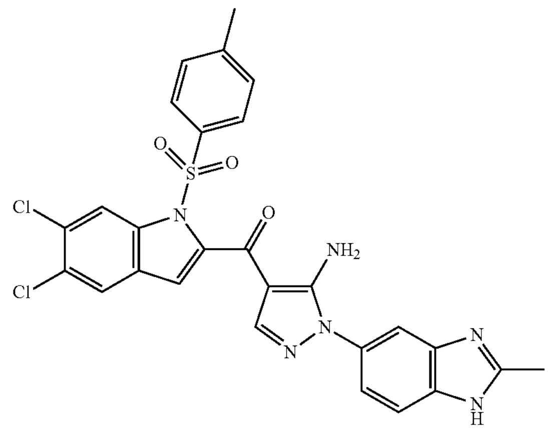 [SMILES: Cc1ccc(S(=O)(=O)n2c(C(=O)c3cnn(-c4ccc5[nH]c(C)nc5c4)c3N)cc3cc(Cl)c(Cl)cc32)cc1] | [5-amino-1-(2-methyl-1H-benzimidazol-5-yl)-1H-pyrazol-4-yl]-[5,6-dichloro-1-(toluene-4-sulfonyl)-1H-indol-2-yl]-methanone | 579 |
| 1525 | 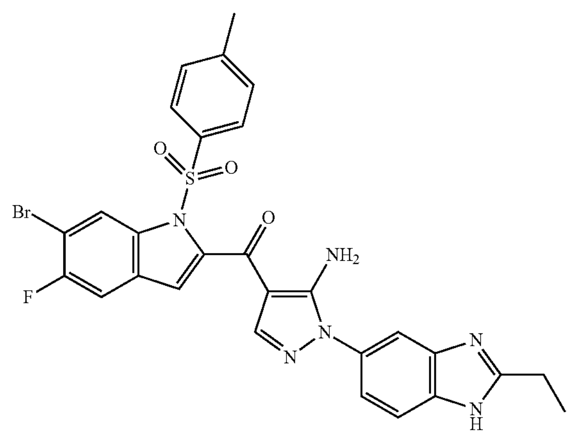 [SMILES: CCc1nc2cc(-n3ncc(C(=O)c4cc5cc(F)c(Br)cc5n4S(=O)(=O)c4ccc(C)cc4)c3N)ccc2[nH]1] | [5-amino-1-(2-ethyl-1H-benzimidazol-5-yl)-1H-pyrazol-4-yl]-[6-bromo-5-fluoro-1-(toluene-4-sulfonyl)-1H-indol-2-yl]-methanone | 621 |
| 1526 | 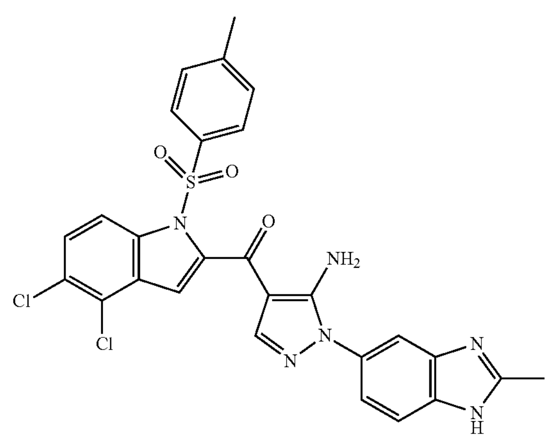 [SMILES: Cc1ccc(S(=O)(=O)n2c(C(=O)c3cnn(-c4ccc5[nH]c(C)nc5c4)c3N)cc3c(Cl)c(Cl)ccc32)cc1] | [5-amino-1-(2-methyl-1H-benzimidazol-5-yl)-1H-pyrazol-4-yl]-[4,5-dichloro-1-(toluene-4-sulfonyl)-1H-indol-2-yl]-methanone | 579 |

TABLE 7-continued

| Compound No. | Structure | Compound name | m/z |
|---|---|---|---|
| 1527 | 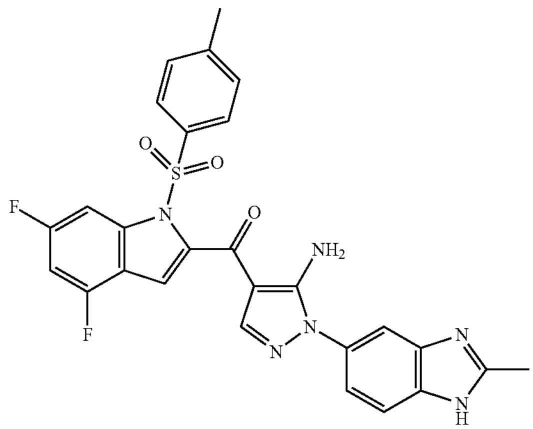 [SMILES: Cc1ccc(S(=O)(=O)n2c(C(=O)c3cnn(-c4ccc5[nH]c(C)nc5c4)c3N)cc3c(F)cc(F)cc32)cc1] | [5-amino-1-(2-methyl-1H-benzimidazol-5-yl)-1H-pyrazol-4-yl]-[4,6-difluoro-1-(toluene-4-sulfonyl)-1H-indol-2-yl]-methanone | 547 |

Examples 165 to 195, and 247 to 254

The compounds of Examples 165 to 195, and 247 to 254 listed in Table 8 were synthesized using compounds having indole ring with unprotected nitrogen atoms by the same method as in Step 1.

TABLE 8

| Example | Structure | Compound name | m/z | 1H-NMR |
|---|---|---|---|---|
| 165 | 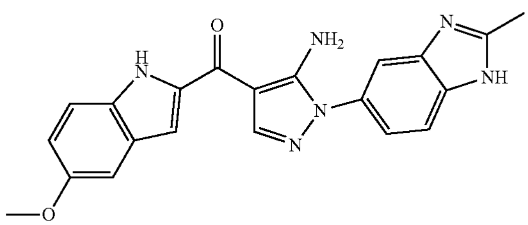 | [5-amino-1-(2-methyl-1H-benzimidazol-5-yl)-1H-pyrazol-4-yl]-(5-methoxy-1H-indol-2-yl)-methanone | 387 | 1H-NMR (DMSO-D6) δ: 12.47 (1H, s), 11.56 (1H, s), 8.27 (1H, s), 7.62 (2H, s), 7.39-7.35 (2H, m), 7.29 (1H, dd, J = 8.5, 1.8 Hz), 7.13 (1H, d, J = 2.4 Hz), 6.99 (2H, s), 6.91 (1H, dd, J = 8.5, 2.4 Hz), 3.78 (3H, s), 2.53 (3H, s). |
| 166 | 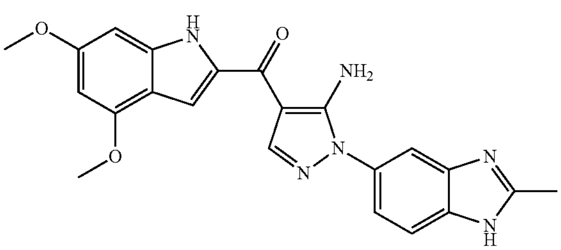 | [5-amino-1-(2-methyl-1H-benzimidazol-5-yl)-1H-pyrazol-4-yl]-(4,6-dimethoxy-1H-indol-2-yl)-methanone | 417 | 1H-NMR (DMSO-D6) δ: 12.46 (1H, s), 11.56 (1H, d, J = 1.8 Hz), 8.22 (1H, s), 7.62-7.57 (2H, m), 7.31-7.28 (1H, m), 7.25 (1H, d, J = 1.8 Hz), 6.92 (2H, d, J = 22.0 Hz), 6.53 (1H, s), 6.21 (1H, d, J = 1.8 Hz), 3.88 (3H, s), 3.79 (3H, s), 2.53 (3H, s). |
| 167 | 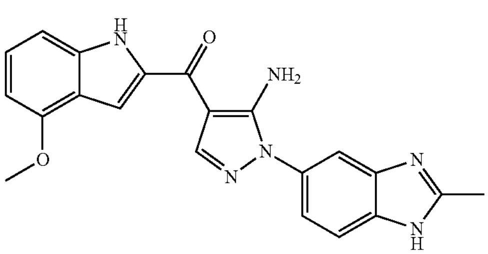 [SMILES: COc1cccc2[nH]c(C(=O)c3cnn(-c4ccc5[nH]c(C)nc5c4)c3N)cc12] | [5-amino-1-(2-methyl-1H-benzimidazol-5-yl)-1H-pyrazol-4-yl]-(4-methoxy-1H-indol-2-yl)-methanone | 387 | 1H-NMR (DMSO-D6) δ: 12.47 (1H, s), 11.73 (1H, s). 8.25 (1H, s), 7.62-7.60 (2H, m), 7.32-7.28 (2H, m), 7.18 (1H, dd, J = 7.9, 4.0 Hz), 7.07 (1H, d, J = 8.5 Hz), 6.98 (2H, s), 6.55 (1H, d, J = 7.3 Hz), 3.92 (3H, s), 2.53 (3H, s). |

TABLE 8-continued

| Example | Structure | Compound name | m/z | 1H-NMR |
|---|---|---|---|---|
| 168 | 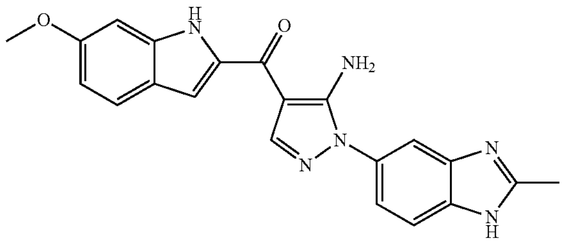 | [5-amino-1-(2-methyl-1H-benzimidazol-5-yl)-1H-pyrazol-4-yl]-(6-methoxy-1H-indol-2-yl)-methanone | 387 | 1H-NMR (DMSO-D6) δ: 12.46 (1H, s), 11.53 (1H, s), 8.28 (1H, s), 7.60-7.57 (3H, m), 7.41 (1H, d, J = 1.8 Hz), 7.29 (1H, dd, J = 8.5, 1.8 Hz), 6.95-6.93 (3H, m), 6.75 (1H, dd, J = 8.9, 2.1 Hz), 3.80 (3H, s), 2.53 (3H, s). |
| 169 | 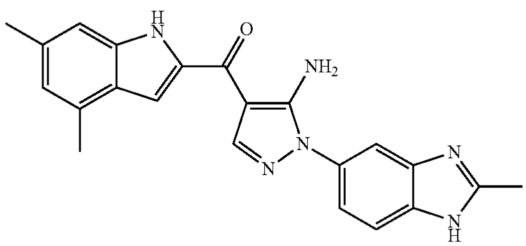 | [5-amino-1-(2-methyl-1H-benzimidazol-5-yl)-1H-pyrazol-4-yl]-(4,6-dimethyl-1H-indol-2-yl)-methanone | 385 | 1H-NMR (DMSO-D6) δ: 12.46 (1H, s), 11.51 (1H, s), 8.37 (1H, s), 7.65-7.57 (2H, br m), 7.40 (1H, br s), 7.29 (1H, d, J = 8.5 Hz), 7.07 (1H, br s), 6.96 (2H, br s), 6.70 (1H, br s), 2.53 (3H, s), 2.53 (3H, s), 2.37 (3H, s). |
| 170 | 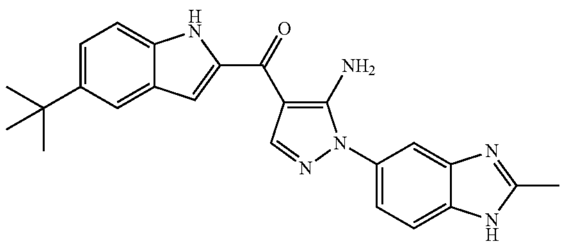 [SMILES: Cc1nc2cc(-n3ncc(C(=O)c4cc5cc(C(C)(C)C)ccc5[nH]4)c3N)ccc2[nH]1] | [5-amino-1-(2-methyl-1H-benzimidazol-5-yl)-1H-pyrazol-4-yl]-(5-tert-butyl-1H-indol-2-yl)-methanone | 413 | 1H-NMR (DMSO-D6) δ: 12.46 (1H, s), 11.55 (1H, s), 8.27 (1H, s), 7.64-7.68 (2H, br m), 7.63 (1H, d, J = 1.5Hz), 7.41 (1H, d, J = 8.5 Hz), 7.40 (1H, s), 7.36 (1H, dd, J = 8.5, 1.5 Hz), 7.29 (1H, dd, J = 8.5, 1.8 Hz), 6.99 (2H, br s), 2.53 (3H, d, J = 4.3 Hz), 1.35 (9H, s). |
| 171 | 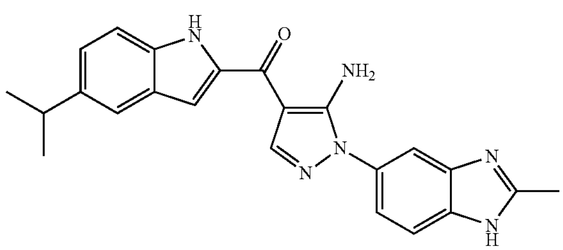 [SMILES: Cc1nc2cc(-n3ncc(C(=O)c4cc5cc(C(C)C)ccc5[nH]4)c3N)ccc2[nH]1] | [5-amino-1-(2-methyl-1H-benzimidazol-5-yl)-1H-pyrazol-4-yl]-(5-isopropyl-1H-indol-2-yl)-methanone | 399 | 1H-NMR (DMSO-D6) δ: 12.46 (1H, s), 11.56 (1H, s), 8.28 (1H, s), 7.64-7.56 (2H, br m), 7.50 (1H, s), 7.40 (1H, d, J = 8.5 Hz), 7.37 (1H, d, J = 1.5 Hz), 7.29 (1H, dd, J = 8.5, 1.8 Hz), 7.17 (1H, dd, J = 8.5, 1.5 Hz), 6.98 (2H, br s), 3.01-2.94 (1H, m), 2.53 (3H, s), 1.26 (6H, d, J = 6.7 Hz). |
| 172 | 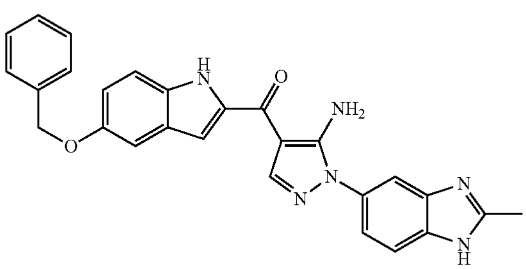 [SMILES: Cc1nc2cc(-n3ncc(C(=O)c4cc5cc(OCc6ccccc6)ccc5[nH]4)c3N)ccc2[nH]1] | [5-amino-1-(2-methyl-1H-benzimidazol-5-yl)-1H-pyrazol-4-yl]-(5-benzyloxy-1H-indol-2-yl)-methanone | 463 | 1H-NMR (DMSO-D6) δ: 12.46 (1H, s), 11.58 (1H, d, J = 1.8 Hz), 8.27 (1H, d, J = 3.0 Hz), 7.65-7.55 (2H, m), 7.49-7.47 (2H, m), 7.42-7.38 (3H, m), 7.33-7.29 (3H, m), 7.21 (1H, d, J = 2.4 Hz), 7.01-6.98 (3H, m), 5.12 (2H, s), 2.53 (3H, s). |
| 173 | 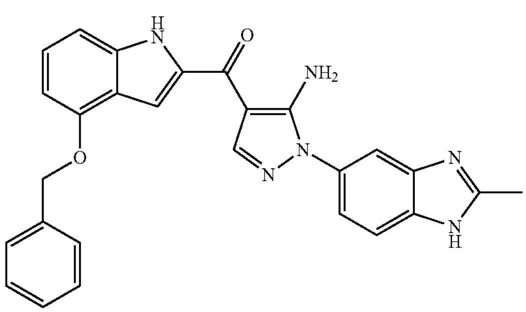 [SMILES: Cc1nc2cc(-n3ncc(C(=O)c4cc5c(OCc6ccccc6)cccc5[nH]4)c3N)ccc2[nH]1] | [5-amino-1-(2-methyl-1H-benzimidazol-5-yl)-1H-pyrazol-4-yl]-(4-benzyloxy-1H-indol-2-yl)-methanone | 463 | 1H-NMR (DMSO-D6) δ: 12.46 (1H, s), 11.75 (1H, d, J = 1.8 Hz), 8.27 (1H, s), 7.62-7.58 (4H, m), 7.42 (2H, t, J = 10.4 Hz), 7.35-7.30 (3H, m), 7.15 (1H, dd, J = 7.9, 4.0 Hz), 7.08 (1H, d, J = 8.5 Hz), 6.97 (2H, d, J = 19.5 Hz), 6.64 (1H, d, J = 7.9 Hz), 5.29 (2H, s), 2.53 (3H, s). |

TABLE 8-continued

| Example | Structure | Compound name | m/z | 1H-NMR |
|---|---|---|---|---|
| 174 | 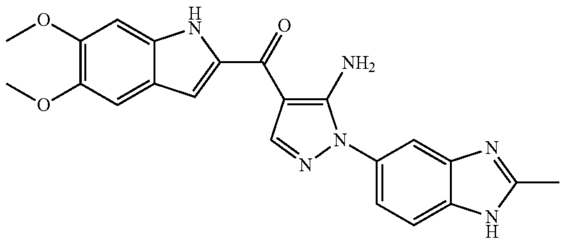 | [5-amino-1-(2-methyl-1H-benzimidazol-5-yl)-1H-pyrazol-4-yl]-(5,6-dimethoxy-1H-indol-2-yl)-methanone | 417 | 1H-NMR (DMSO-D6) δ: 12.45 (1H, s), 11.43 (1H, d, J = 1.6 Hz), 8.24 (1H, d, J = 4.4 Hz), 7.66-7.55 (2H, m), 7.32-7.27 (2H, m), 7.12 (1H, s), 6.94-6.91 (3H, m), 3.81 (3H, s), 3.79 (3H, s), 2.53 (3H, s). |
| 175 | 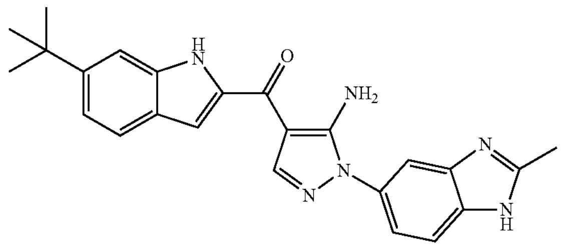 [SMILES: Cc1nc2cc(-n3ncc(C(=O)c4cc5ccc(C(C)(C)C)cc5[nH]4)c3N)ccc2[nH]1] | [5-amino-1-(2-methyl-1H-benzimidazol-5-yl)-1H-pyrazol-4-yl]-(6-tert-butyl-1H-indol-2-yl)-methanone | 413 | 1H-NMR (DMSO-D6) δ: 12.45 (1H, s), 11.63 (1H, s), 8.28 (1H, s), 7.62-7.58 (2H, br m), 7.61 (1H, d, J = 8.5 Hz), 7.44 (1H, s), 7.38 (1H, d, J = 1.2 Hz), 7.28 (1H, dd, J = 8.5, 1.8 Hz), 7.19 (1H, dd, J = 8.5, 1.2 Hz), 6.98 (2H, br s), 2.53 (3H, s), 1.35 (9H, s). |
| 176 | 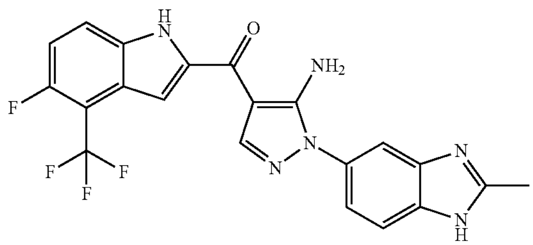 [SMILES: Cc1nc2cc(-n3ncc(C(=O)c4cc5c(C(F)(F)F)c(F)ccc5[nH]4)c3N)ccc2[nH]1] | [5-amino-1-(2-methyl-1H-benzimidazol-5-yl)-1H-pyrazol-4-yl]-(5-fluoro-4-trifluoromethyl-1H-indol-2-yl)-methanone | 443 | 1H-NMR (DMSO-D6) δ: 12.48 (1.0H, br s), 12.38 (1.0H, br s), 8.22 (1.0H, s), 7.82 (1.0H, dd, J = 9.0, 4.2 Hz), 7.64-7.59 (2.0H, m), 7.38-7.28 (3.0H, m), 7.10-7.07 (2.0H, br m), 2.54 (3.0H, s). |
| 177 | 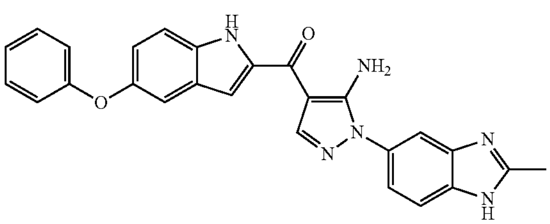 [SMILES: Cc1nc2cc(-n3ncc(C(=O)c4cc5cc(Oc6ccccc6)ccc5[nH]4)c3N)ccc2[nH]1] | [5-amino-1-(2-methyl-1H-benzimidazol-5-yl)-1H-pyrazol-4-yl]-(5-phenoxy-1H-indol-2-yl)-methanone | 449 | 1H-NMR (DMSO-D6) δ: 12.46 (1H, s), 11.77 (1H, s), 8.27 (1H, s), 7.68-7.55 (2H, br m), 7.51 (1H, d, J = 8.8 Hz), 7.41 (1H, s), 7.37-7.33 (2H, m), 7.30-7.27 (2H, m), 7.08 (1H, d, J = 7.5 Hz), 7.06-7.00 (2H, m), 7.03 (1H, dd, J = 8.8, 2.4 Hz), 6.96 (2H, d, J = 7.5 Hz), 2.53 (3H, s). |
| 178 | 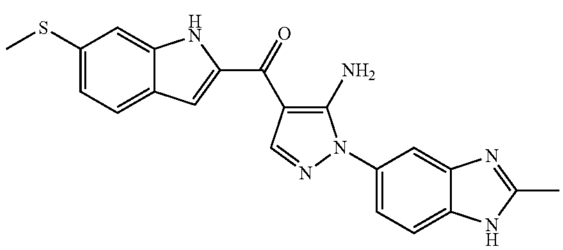 | [5-amino-1-(2-methyl-1H-benzimidazol-5-yl)-1H-pyrazol-4-yl]-(6-methylsulfanyl-1H-indol-2-yl)-methanone | 403 | 1H-NMR (DMSO-D6) δ: 12.45 (1H, s), 11.62 (1H, d, J = 1.8 Hz), 8.29 (1H, d, J = 5.5 Hz), 7.65-7.61 (2H, m), 7.56 (1H, d, J = 8.5 Hz), 7.43 (1H, s), 7.33 (1H, s), 7.30-7.26 (1H, m), 7.02-7.00 (2H, m), 6.97 (1H, s), 2.53 (3H, d, J = 1.8 Hz), 2.52 (3H, s). |
| 179 | 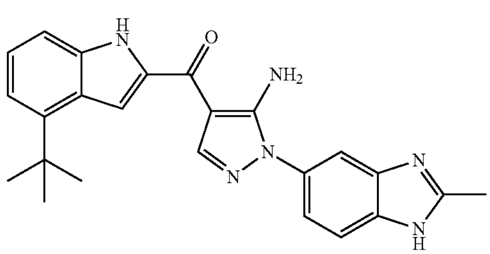 [SMILES: Cc1nc2cc(-n3ncc(C(=O)c4cc5c(C(C)(C)C)cccc5[nH]4)c3N)ccc2[nH]1] | [5-amino-1-(2-methyl-1H-benzimidazol-5-yl)-1H-pyrazol-4-yl]-(4-tert-butyl-1H-indol-2-yl)-methanone | 413 | 1H-NMR (DMSO-D6) δ: 12.46 (1H, br s), 11.76 (1H, s), 8.19 (1H, s), 7.63-7.58 (2H, br m), 7.42 (1H, s), 7.36 (1H, d, J = 7.9 Hz), 7.29 (1H, dd, J = 8.5, 1.8 Hz), 7.17 (1H, t, J = 7.9 Hz), 6.97 (2H, br s), 6.95 (1H, d, J = 7.9 Hz), 2.54 (3H, s), 1.51 (9H, s). |

TABLE 8-continued

| Example | Structure | Compound name | m/z | 1H-NMR |
|---|---|---|---|---|
| 180 | 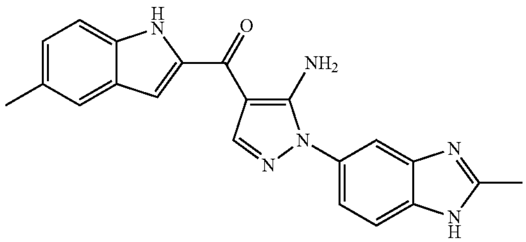 | [5-amino-1-(2-methyl-1H-benzimidazol-5-yl)-1H-pyrazol-4-yl]-(5-methyl-1H-indol-2-yl)-methanone | 371 | 1H-NMR (DMSO-D6) δ: 12.46 (1H, br s), 11.55 (1H, s), 8.27 (1H, s), 7.60-7.58 (2H, m), 7.45 (1H, s), 7.36 (1H, d, J = 8.4 Hz), 7.33 (1H, s), 7.27 (1H, dd, J = 8.4, 2.0 Hz), 7.07 (1H, dd, J = 8.3, 1.5 Hz), 6.96 (2H, br s), 2.52 (3H, s), 2.38 (3H, s). |
| 181 | 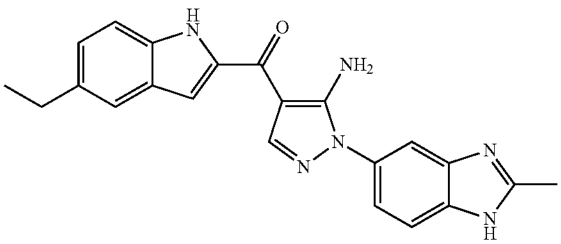 [SMILES: CCc1ccc2[nH]c(C(=O)c3cnn(-c4ccc5[nH]c(C)nc5c4)c3N)cc2c1] | [5-amino-1-(2-methyl-1H-benzimidazol-5-yl)-1H-pyrazol-4-yl]-(5-ethyl-1H-indol-2-yl)-methanone | 385 | 1H-NMR (DMSO-D6) δ: 12.46 (1H, s), 11.56 (1H, s), 8.27 (1H, s), 7.60-7.58 (2H, m), 7.47 (1H, s), 7.38 (1H, d, J = 8.5 Hz), 7.35-7.35 (1H, m), 7.28 (1H, dd, J = 8.5, 2.1 Hz), 7.11 (1H, dd, J = 8.5, 1.7 Hz), 6.96 (2H, s), 2.69-2.66 (2H, m), 2.52 (3H, s), 1.22 (3H, t, J = 7.5 Hz). |
| 182 | 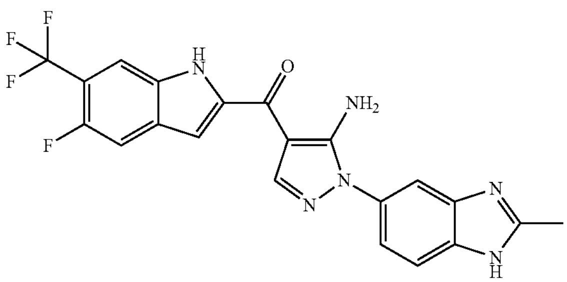 [SMILES: Cc1nc2cc(-n3ncc(C(=O)c4cc5cc(F)c(C(F)(F)F)cc5[nH]4)c3N)ccc2[nH]1] | [5-amino-1-(2-methyl-1H-benzimidazol-5-yl)-1H-pyrazol-4-yl]-(5-fluoro-6-trifluoromethyl-1H-indol-2-yl)-methanone | 443 | 1H-NMR (DMSO-D6) δ: 12.48 (1.0H, br s), 12.24 (1.0H, br s), 8.31 (1.0H, s), 7.82 (1.0H, d, J = 5.9 Hz), 7.73 (1.0H, d, J = 11.2 Hz), 7.65-7.54 (3.0H, m), 7.29 (1.0H, d, J = 8.3 Hz), 7.13-7.09 (2.0H, br m), 2.54 (3.0H, s). |
| 183 | 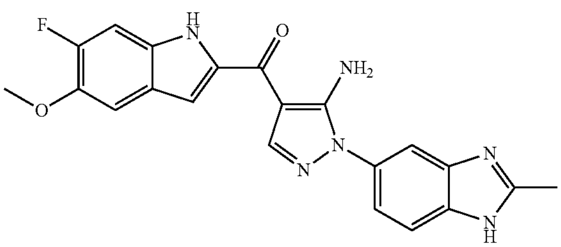 | [5-amino-1-(2-methyl-1H-benzimidazol-5-yl)-1H-pyrazol-4-yl]-(6-fluoro-5-methoxy-1H-indol-2-yl)-methanone | 405 | 1H-NMR (DMSO-D6) δ: 12.46 (1H, s), 11.64 (1H, s), 8.26 (1H, s), 7.64-7.57 (2H, br m), 7.38 (1H, s), 7.32 (1H, d, J = 9.1 Hz), 7.28 (1H, dd, J = 8.5, 2.4 Hz), 7.23 (1H, d, J = 11.6 Hz), 6.98 (2H, br s), 3.86 (3H, s), 2.53 (3H, s). |
| 184 | 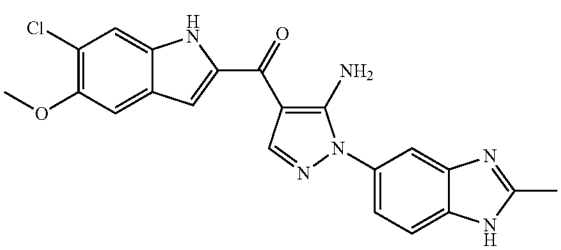 | [5-amino-1-(2-methyl-1H-benzimidazol-5-yl)-1H-pyrazol-4-yl]-(6-chloro-5-methoxy-1H-indol-2-yl)-methanone | 421, 423 | 1H-NMR (DMSO-D6) δ: 12.46 (1H, s), 11.65 (1H, s), 8.26 (1H, s), 7.85-7.55 (2H, br m), 7.51 (1H, s), 7.38 (1H, s), 7.31 (1H, s), 7.28 (1H, dd, J = 8.5, 2.4 Hz), 7.01 (2H, br s), 3.87 (3H, s), 2.53 (3H, s). |
| 185 | 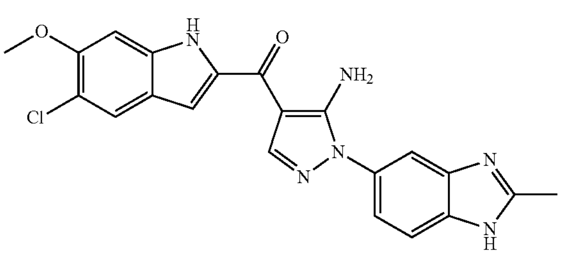 | [5-amino-1-(2-methyl-1H-benzimidazol-5-yl)-1H-pyrazol-4-yl]-(5-chloro-6-methoxy-1H-indol-2-yl)-methanone | 421, 423 | 1H-NMR (DMSO-D6) δ: 12.45 (1H, s), 11.70 (1H, s), 8.25 (1H, s), 7.73 (1H, s), 7.64-7.55 (2H, br m), 7.38 (1H, s), 7.28 (1H, dd, J = 8.5, 2.4 Hz), 7.06 (1H, s), 6.97 (2H, br s), 3.89 (3H, s), 2.53 (3H, s). |

TABLE 8-continued

| Example | Structure | Compound name | m/z | 1H-NMR |
|---|---|---|---|---|
| 186 | 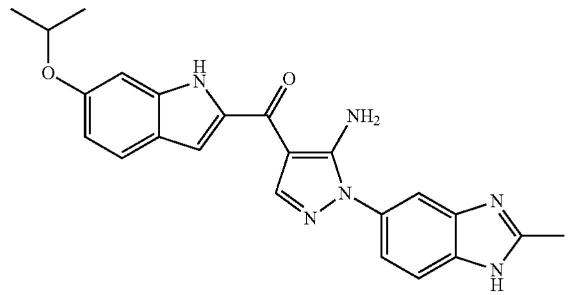 [SMILES: Cc1nc2cc(-n3ncc(C(=O)c4cc5ccc(OC(C)C)cc5[nH]4)c3N)ccc2[nH]1] | [5-amino-1-(2-methyl-1H-benzimidazol-5-yl)-1H-pyrazol-4-yl]-(6-isopropoxy-1H-indol-2-yl)-methanone | 415 | 1H-NMR (DMSO-D6) δ: 12.43 (1.0H, s), 13.41 (2.0H, s), 8.27 (1.0H, s), 7.7-7.50 (3.0H, m), 7.38 (1.0H, s), 7.29 (1.0H, dd, J = 8.5, 1.7 Hz), 6.95-6.90 (2.0H, m), 6.72 (1.0H, dd, J = 8.7, 2.2 Hz), 4.62-4.66 (1.0H, m), 2.53 (3.0H, s), 1.31 (6.0H, d, J = 6.1 Hz). |
| 187 | 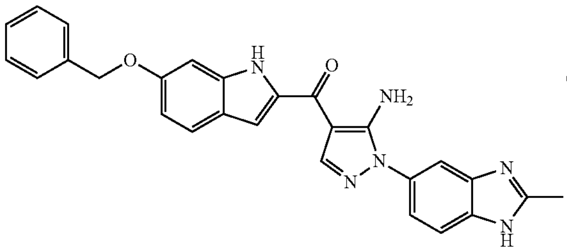 [SMILES: Cc1nc2cc(-n3ncc(C(=O)c4cc5ccc(OCc6ccccc6)cc5[nH]4)c3N)ccc2[nH]1] | [5-amino-1-(2-methyl-1H-benzimidazol-5-yl)-1H-pyrazol-4-yl]-(6-benzyloxy-1H-indol-2-yl)-methanone | 463 | 1H-NMR (DMSO-D6) δ: 12.45 (1H, s), 11.52 (1H, s), 8.27 (1H, d, J = 4.9 Hz), 7.64 (1H, dd, J = 4.9, 3.3 Hz), 7.57 (2H, dd, J = 8.5, 4.3 Hz), 7.50-7.49 (2H, m), 7.42-7.39 (3H, m), 7.35-7.26 (2H, m), 7.00-6.94 (3H, m), 6.82 (1H, dd, J = 8.8, 2.2 Hz), 5.14 (2H, s), 2.53 (3H, s). |
| 188 | 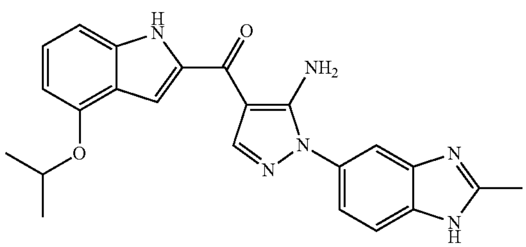 [SMILES: Cc1nc2cc(-n3ncc(C(=O)c4cc5c(OC(C)C)cccc5[nH]4)c3N)ccc2[nH]1] | [5-amino-1-(2-methyl-1H-benzimidazol-5-yl)-1H-pyrazol-4-yl]-(4-isopropoxy-1H-indol-2-yl)-methanone | 415 | 1H-NMR (DMSO-D6) δ: 12.47 (1.0H, br s), 11.69 (1.0H, br s), 8.23 (1.0H, s), 7.64-7.59 (2.0H, m), 7.29 (1.0H, dd, J = 8.3, 1.5 Hz), 7.25-7.25 (1.0H, br m), 7.15 (1.0H, dd, J = 8.0, 8.0 Hz), 7.04-6.97 (3.0H, m), 6.55 (1.0H, d, J = 8.0 Hz), 4.79-4.73 (1.0H, m), 2.53 (3.0H, s), 1.38 (6.0H, d, J = 5.9 Hz). |
| 189 | 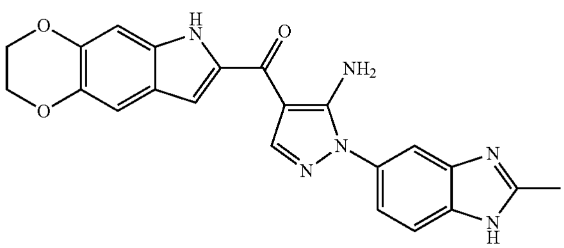 [SMILES: Cc1nc2cc(-n3ncc(C(=O)c4cc5cc6c(cc5[nH]4)OCCO6)c3N)ccc2[nH]1] | [5-amino-1-(2-methyl-1H-benzimidazol-5-yl)-1H-pyrazol-4-yl]-(2,3-dihydro-6H-[1,4]dioxino[2,3-f]indol-7-yl)-methanone | 415 | 1H-NMR (DMSO-D6) δ: 12.44 (1H, s), 11.27 (1H, d, J = 1.6 Hz), 8.24 (1H, s), 7.64-7.62 (1H, br m), 7.58-7.54 (1H, br m), 7.30-7.26 (1H, br m), 7.28 (1H, d, J = 1.6 Hz), 7.08 (1H, s) 6.97 (1H, br s), 6.91 (1H, br s), 6.87 (1H, br s), 4.27-4.22 (4H, m), 2.53 (3H, s). |
| 190 | 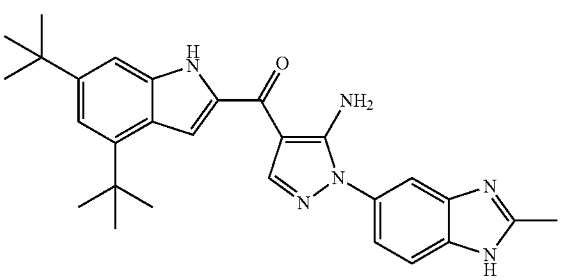 [SMILES: Cc1nc2cc(-n3ncc(C(=O)c4cc5c(C(C)(C)C)cc(C(C)(C)C)cc5[nH]4)c3N)ccc2[nH]1] | [5-amino-1-(2-methyl-1H-benzimidazol-5-yl)-1H-pyrazol-4-yl]-(4,6-di-tert-butyl-1H-indol-2-yl)-methanone | 469 | 1H-NMR (DMSO-D6) δ: 12.47 (1.0H, br s), 11.61 (1.0H, br s), 8.19 (1.0H, s), 7.62 (2.0H, br s), 7.37 (1.0H, s), 7.32-7.28 (2.0H, m), 7.05 (1.0H, s), 6.96 (2.0H, br s), 2.53 (3.0H, s), 1.51 (9.0H, s), 1.34 (9.0H, s). |

TABLE 8-continued

| Example | Structure | Compound name | m/z | 1H-NMR |
|---|---|---|---|---|
| 191 | 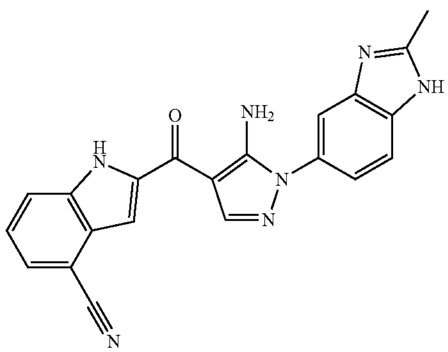 [SMILES: Cc1nc2cc(-n3ncc(C(=O)c4cc5c(C#N)cccc5[nH]4)c3N)ccc2[nH]1] | 2-[5-amino-1-(2-methyl-1H-benzimidazol-5-yl)-1H-pyrazole-4-carbonyl]-1H-indole-4-carbonitrile | 382 | 1H-NMR (DMSO-D6) δ: 12.44 (1.0H, s). 12.33 (1.0H, s), 8.36 (1.0H, s), 7.84 (1.0H, d, J = 8.2 Hz), 7.70-7.60 (3.0H, m), 7.45-7.35 (2.0H, m), 7.29 (1.0H, dd, J = 8.5, 1.9 Hz), 7.06 (1.0H, m), 2.53 (3.0H, s). |
| 192 | 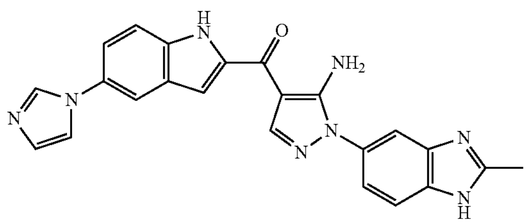 [SMILES: Cc1nc2cc(-n3ncc(C(=O)c4cc5cc(-n6ccnc6)ccc5[nH]4)c3N)ccc2[nH]1] | [5-amino-1-(2-methyl-1H-benzimidazol-5-yl)-1H-pyrazol-4-yl]-(5-imidazol-1-yl-1H-indol-2-yl)-methanone | 423 | 1H-NMR (DMSO-D6) δ: 8.31 (1H, s), 8.17 (1H, s), 7.86 (1H, d, J = 2.0 Hz), 7.70 (1H, s), 7.60-7.59 (3H, m), 7.50-7.47 (2H, m), 7.27 (1H, dd, J = 8.6, 2.0 Hz), 7.11 (1H, d, J = 0.8 Hz), 7.09 (2H, br s), 2.53 (3H, s). |
| 193 | 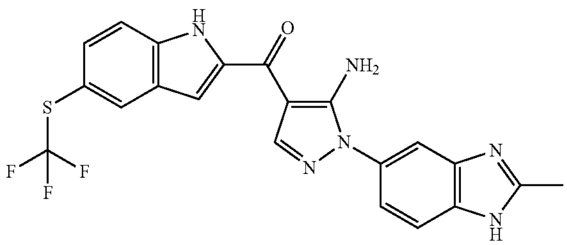 [SMILES: Cc1nc2cc(-n3ncc(C(=O)c4cc5cc(SC(F)(F)F)ccc5[nH]4)c3N)ccc2[nH]1] | [5-amino-1-(2-methyl-1H-benzimidazol-5-yl)-1H-pyrazol-4-yl]-(5-trifluoromethylsulfanyl-1H-indol-2-yl)-methanone | 457 | 1H-NMR (DMSO-D6) δ: 12.31 (1H, br s), 8.32 (1H, s), 8.09 (1H, s), 7.62 (1H, d, J = 2.0 Hz), 7.61-7.59 (2H, m), 7.54 (1H, s), 7.48 (1H, d, J = 8.4 Hz), 7.28 (1H, dd, J = 8.6, 2.0 Hz), 7.14 (2H, br s), 2.53 (3H, s). |
| 194 | 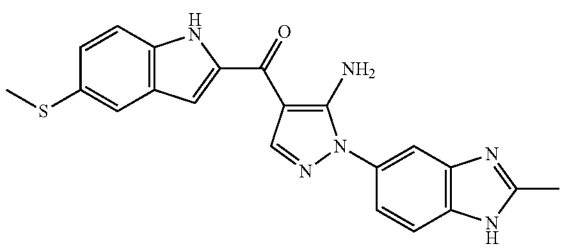 | [5-amino-1-(2-methyl-1H-benzimidazol-5-yl)-1H-pyrazol-4-yl]-(5-methylsulfanyl-1H-indol-2-yl)-methanone | 403 | 1H-NMR (DMSO-D6) δ: 12.48 (1H, s), 11.76 (1H, s), 8.29 (1H, s), 7.62-7.62 (3H, m), 7.44 (1H, d, J = 8.6 Hz), 7.39 (1H, s), 7.29 (1H, dd, J = 8.6, 2.0 Hz), 7.23 (1H, dd, J = 8.6, 1.8 Hz), 7.02 (2H, br s), 3.34 (3H, s), 2.54 (3H, s). |
| 195 | 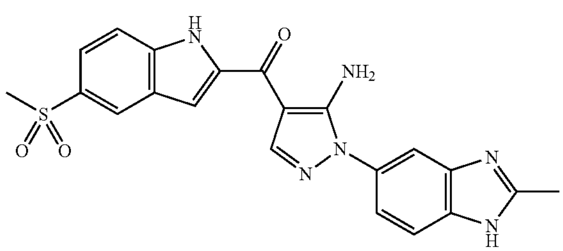 | [5-amino-1-(2-methyl-1H-benzimidazol-5-yl)-1H-pyrazol-4-yl]-(5-methanesulfonyl-1H-indol-2-yl)-methanone | 435 | 1H-NMR (DMSO-D6) δ: 12.46 (1H, br s), 12.30 (1H, br s), 8.34-8.30 (1H, m), 8.33 (1H, s), 7.76 (1H, dd, J = 8.6, 1.8 Hz), 7.72-7.68 (2H, m), 7.68-7.65 (1H, m), 7.62-7.60 (1H, m), 7.29 (1H, dd, J = 8.6, 2.0 Hz), 7.08 (2H, br s), 3.34 (3H, s), 2.54 (3H, s). |
| 247 | 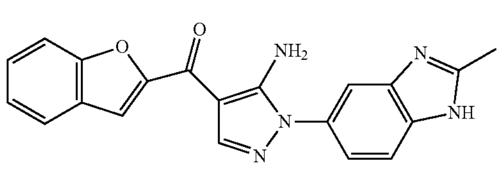 [SMILES: Cc1nc2cc(-n3ncc(C(=O)c4cc5ccccc5o4)c3N)ccc2[nH]1] | [5-amino-1-(2-methyl-1H-benzimidazol-5-yl)-1H-pyrazol-4-yl]-benzofuran-2-yl-methanone | 358 | 9.21 (m, 1H), 8.52 (s, 1H), 7.73 (d, J = 7.8 Hz, 1H), 7.64 (d, J = 8.4 Hz, 1H), 7.61 (s, 1H), 7.47 (t, J = 8 Hz, 1H), 7.40 (m, 1H), 7.32 (t, J = 7.6 Hz, 1H), 6.17 (m, 2H), 2.66 (s, 3H). |

TABLE 8-continued

| Example | Structure | Compound name | m/z | 1H-NMR |
|---|---|---|---|---|
| 248 | 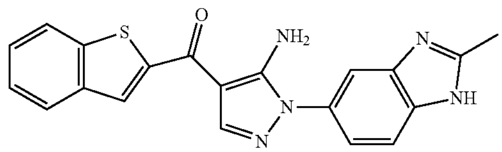 [SMILES: Cc1nc2cc(-n3ncc(C(=O)c4cc5ccccc5s4)c3N)ccc2[nH]1] | [5-amino-1-(2-methyl-1H-benzimidazol-5-yl)-1H-pyrazol-4-yl]-benzo[b]thiophen-2-yl-methanone | 374 | 12.46 (s, 1H), 8.42 (s, 1H), 8.35 (m, 1H), 8.05 (m, 2H), 7.65 (m, 1H), 7.56 (m, 1H), 7.51 (m, 2H), 7.28 (m, 1H), 7.09 (s, 1H), 7.03 (s, 1H), 2.54 (s, 3H). |
| 249 | 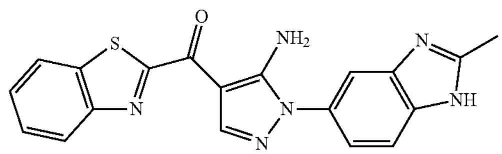 [SMILES: Cc1nc2cc(-n3ncc(C(=O)c4nc5ccccc5s4)c3N)ccc2[nH]1] | [5-amino-1-(2-methyl-1H-benzimidazol-5-yl)-1H-pyrazol-4-yl]-benzothiazol-2-yl-methanone | 375 | 8.83 (s, 1H), 8.27 (m, 2H), 7.86 (m, 2H), 7.64 (m, 2H), 7.57 (m, 1H), 7.44 (s, 2H), 2.73 (s, 3H). |
| 250 | 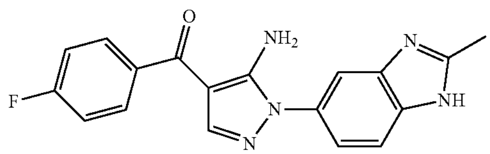 [SMILES: Cc1nc2cc(-n3ncc(C(=O)c4ccc(F)cc4)c3N)ccc2[nH]1] | [5-amino-1-(2-methyl-1H-benzimidazol-5-yl)-1H-pyrazol-4-yl]-(4-fluoro-phenyl)-methanone | 336 | 7.85 (m, 4H), 7.55 (d, J = 8.4 Hz, 1H), 7.36 (t, J = 8.7 Hz, 2H), 7.28 (s, 1H), 7.21 (s, 2H), 7.15 (s, 1H), 7.03 (s, 1H), 2.73 (s, 3H). |
| 251 | 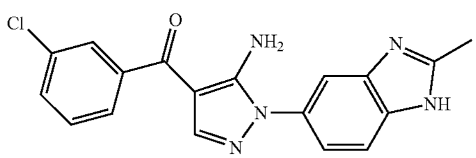 [SMILES: Cc1nc2cc(-n3ncc(C(=O)c4cccc(Cl)c4)c3N)ccc2[nH]1] | [5-amino-1-(2-methyl-1H-benzimidazol-5-yl)-1H-pyrazol-4-yl]-(3-chloro-phenyl)-methanone | 352 | 7.77 (m, 1H), 7.74 (m, 1H), 7.65 (m, 1H), 7.57 (m, 3H), 7.24 (d, J = 8.6 Hz, 2H), 7.03 (br s, 2H), 2.51 (m, 3H). |
| 252 | 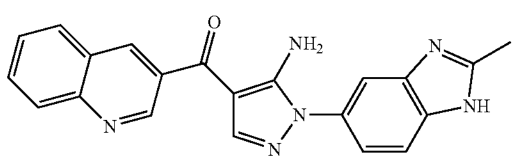 [SMILES: Cc1nc2cc(-n3ncc(C(=O)c4cnc5ccccc5c4)c3N)ccc2[nH]1] | [5-amino-1-(2-methyl-1H-benzimidazol-5-yl)-1H-pyrazol-4-yl]-quinolin-3-yl-methanone | 369 | 9.21 (s, 1H), 8.85 (s, 1H), 8.23 (d, J = 8.1 Hz, 1H), 8.12 (d, J = 8.4 Hz, 1H), 8.06 (s, 1H), 7.91 (m, 3H), 7.73 (t, J = 6.2 Hz, 1H), 7.64 (d, J = 8.4 Hz, 1H), 7.33 (s, 2H), 2.74 (s, 3H). |
| 253 | 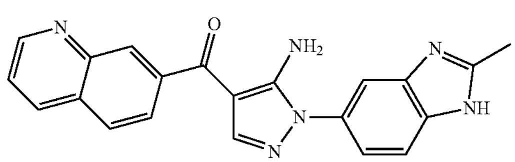 [SMILES: Cc1nc2cc(-n3ncc(C(=O)c4ccc5cccnc5c4)c3N)ccc2[nH]1] | [5-amino-1-(2-methyl-1H-benzimidazol-5-yl)-1H-pyrazol-4-yl]-quinolin-7-yl-methanone | 369 | 9.05 (m, 1H), 8.52 (d, J = 8.2 Hz, 1H), 8.38 (s, 1H), 8.17 (d, J = 8.4 Hz, 1H), 7.93 (m, 4H), 7.69 (m, 2H), 7.32 (s, 2H), 2.79 (s, 3H). |
| 254 | 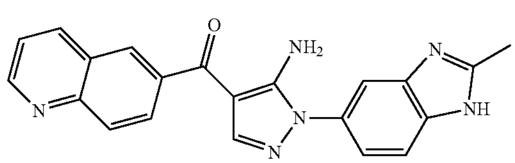 [SMILES: Cc1nc2cc(-n3ncc(C(=O)c4ccc5ncccc5c4)c3N)ccc2[nH]1] | [5-amino-1-(2-methyl-1H-benzimidazol-5-yl)-1H-pyrazol-4-yl]-quinolin-6-yl-methanone | 369 | 9.02 (d, J = 5.1 Hz, 1H), 8.51 (d, J = 8.4 Hz, 1H), 8.37 (s, 1H), 8.16 (d, J = 8.3 Hz, 1H), 7.92 (m, 4H), 7.66 (m, 2H), 7.32 (m, 2H), 2.74 (s, 3H). |

Step 2: Synthesis of 2-(1-benzenesulfonyl-1H-indole-2-carbonyl)-3-dimethylamino-acrylonitrile (1083)

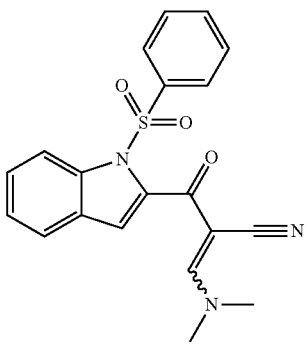 [SMILES: CN(C)C=C(C#N)C(=O)c1cc2ccccc2n1S(=O)(=O)c1ccccc1]

N,N-Dimethylformamide dimethylacetal (620 µl) was added at room temperature to a tetrahydrofuran (THF) solution (8.5 ml) of 3-(1-benzenesulfonyl-1H-indol-2-yl)-3-oxo-propionitrile (1.0 g, 3.08 mmol), and stirred for ten minutes. The reaction mixture was then concentrated under reduced pressure to give crude 2-(1-benzenesulfonyl-1H-indole-2-carbonyl)-3-dimethylamino-acrylonitrile as yellow amorphous material. The obtained crude product was used in subsequent reactions without purification.

ESI (LC-MS positive mode) m/z 380 [(M+H)$^+$]

The compounds of numbers 1084 to 1184, and 1528 to 1549 listed in Table 9 were synthesized by the same method as in Step 2.

TABLE 9

| Compound No. | Structure | Compound name | m/z |
|---|---|---|---|
| 1084 | 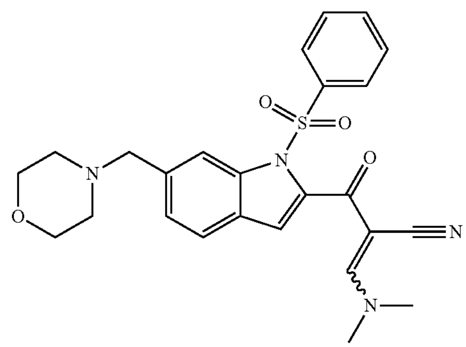 [SMILES: CN(C)C=C(C#N)C(=O)c1cc2ccc(CN3CCOCC3)cc2n1S(=O)(=O)c1ccccc1] | 2-(1-benzenesulfonyl-6-morpholin-4-ylmethyl-1H-indole-2-carbony)-3-dimethylamino-acrylonitrile | 479 |
| 1085 | 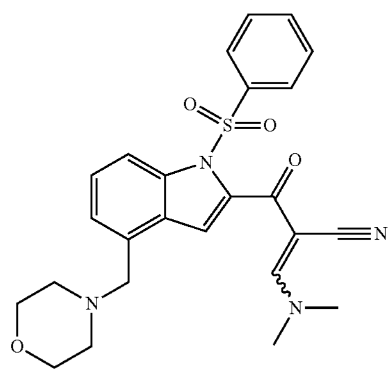 [SMILES: CN(C)C=C(C#N)C(=O)c1cc2c(CN3CCOCC3)cccc2n1S(=O)(=O)c1ccccc1] | 2-(1-benzenesulfonyl-5-morpholin-4-ylmethyl-1H-indole-2-carbonyl)-3-dimethylamino-acrylonitrile | 479 |
| 1086 | 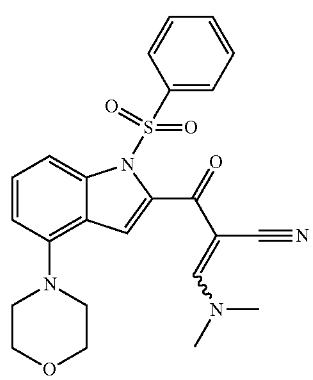 [SMILES: CN(C)C=C(C#N)C(=O)c1cc2c(N3CCOCC3)cccc2n1S(=O)(=O)c1ccccc1] | 2-(l-benzenesulfonyl-4-morpholin-4-yl-1H-indole-2-carbonyl)-3-dimethylamino-acrylonitrile | 465 |

TABLE 9-continued

| Compound No. | Structure | Compound name | m/z |
|---|---|---|---|
| 1087 | 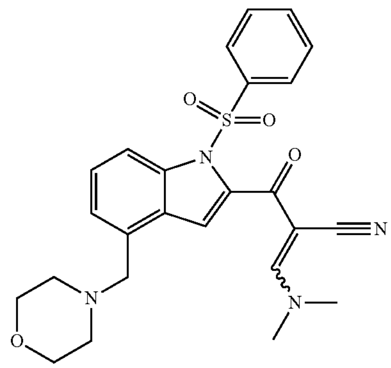 [SMILES: CN(C)C=C(C#N)C(=O)c1cc2c(CN3CCOCC3)cccc2n1S(=O)(=O)c1ccccc1] | 2-(1-benzenesulfonyl-4-morpholin-4-ylmethyl-1H-indole-2-carbonyl)-3-dimethylamino-acrylonitrile | 479 |
| 1088 | 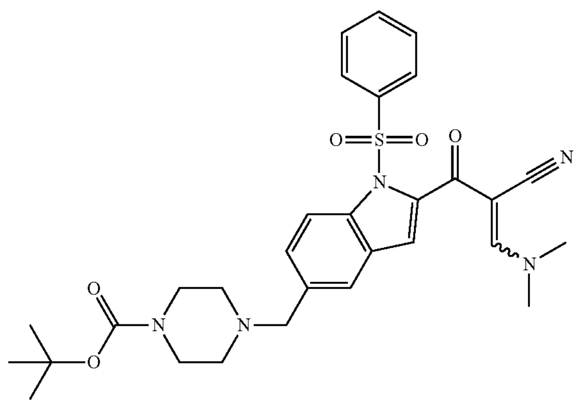 [SMILES: CN(C)C=C(C#N)C(=O)c1cc2cc(CN3CCN(C(=O)OC(C)(C)C)CC3)ccc2n1S(=O)(=O)c1ccccc1] | 4-[1-benzenesulfonyl-2-(2-cyano-3-dimethylamino-acryloyl)-1H-indol-5-ylmethyl]-piperazine-1-carboxylic acid tert-butyl ester | 578 |
| 1089 | 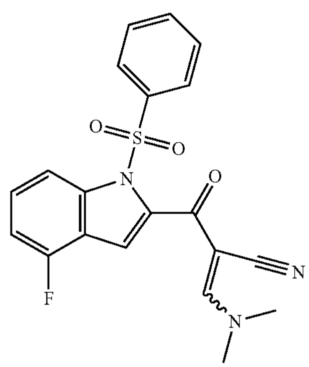 [SMILES: CN(C)C=C(C#N)C(=O)c1cc2c(F)cccc2n1S(=O)(=O)c1ccccc1] | 2-(1-benzenesulfonyl-4-fluoro-1H-indole-2-carbonyl)-3-dimethylamino-acrylonitrile | 398 |
| 1090 | 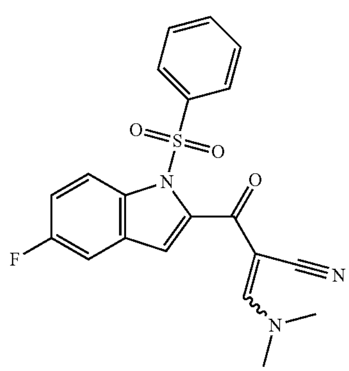 [SMILES: CN(C)C=C(C#N)C(=O)c1cc2cc(F)ccc2n1S(=O)(=O)c1ccccc1] | 2-(1-benzenesulfonyl-5-fluoro-1H-indole-2-carbonyl)-3-dimethylamino-acrylonitrile | 398 |

TABLE 9-continued

| Compound No. | Structure | Compound name | m/z |
|---|---|---|---|
| 1091 | 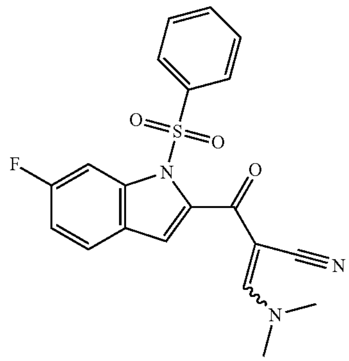 [SMILES: CN(C)C=C(C#N)C(=O)c1cc2ccc(F)cc2n1S(=O)(=O)c1ccccc1] | 2-(1-benzenesulfonyl-6-fluoro-1H-indole-2-carbonyl)-3-dimethylamino-acrylonitrile | 398 |
| 1092 | 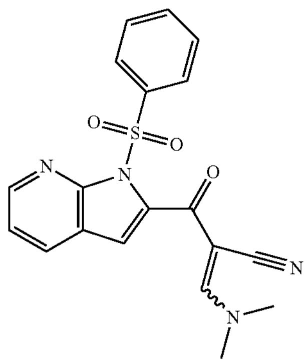 [SMILES: CN(C)C=C(C#N)C(=O)c1cc2cccnc2n1S(=O)(=O)c1ccccc1] | 2-(1-benzenesulfonyl-1H-pyrrolo[2,3-b]pyridine-2-carbonyl)-3-dimethylamino-acrylonitrile | 381 |
| 1093 | 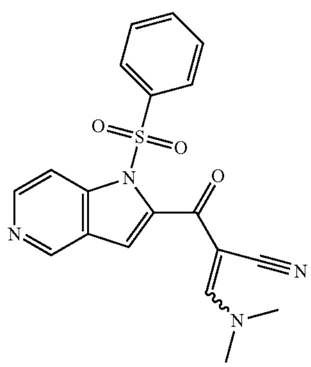 [SMILES: CN(C)C=C(C#N)C(=O)c1cc2cnccc2n1S(=O)(=O)c1ccccc1] | 2-(1-benzenesulfonyl-1H-pyrrolo[3,2-c]pyridine-2-carbonyl)-3-dimethylamino-acrylonitrile | 381 |
| 1094 | 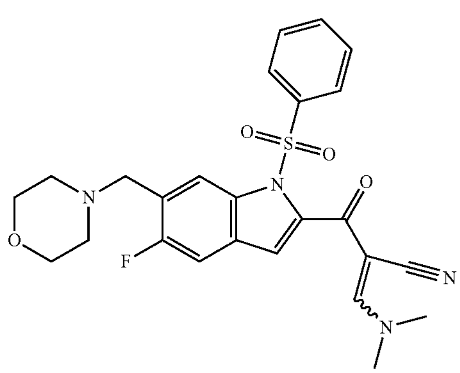 [SMILES: CN(C)C=C(C#N)C(=O)c1cc2cc(F)c(CN3CCOCC3)cc2n1S(=O)(=O)c1ccccc1] | 2-(1-benzenesulfonyl-5-fluoro-6-morpholin-4-ylmethyl-1H-indole-2-carbonyl)-3-dimethylamino-acrylonitrile | 497 |

TABLE 9-continued

| Compound No. | Structure | Compound name | m/z |
|---|---|---|---|
| 1095 | 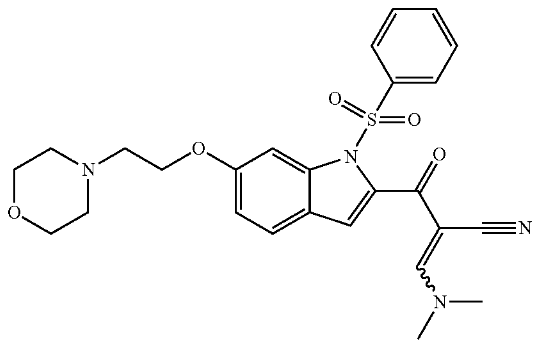 [SMILES: CN(C)C=C(C#N)C(=O)c1cc2ccc(OCCN3CCOCC3)cc2n1S(=O)(=O)c1ccccc1] | 2-[1-benzenesulfonyl-6-(2-morpholin-4-yl-ethoxy)-1H-indole-2-carbonyl]-3-dimethylamino-acrylonitrile | 509 |
| 1096 | 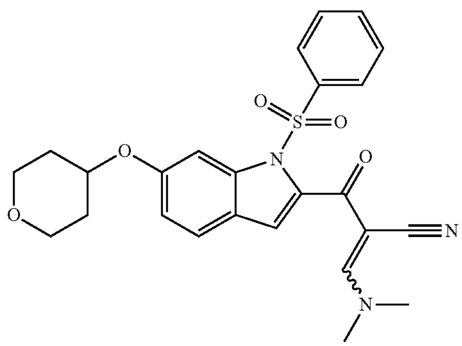 | 2-[1-benzenesnlfonyl-6-(tetrahydro-pyran-4-yloxy)-1H-indole-2-carbonyl]-3-dimethylamino-acrylonitrile | 480 |
| 1097 | 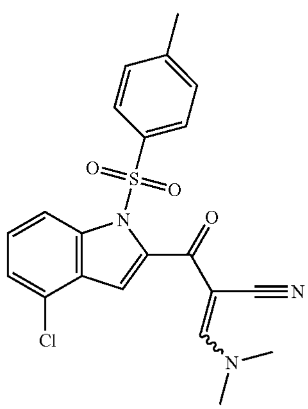 [SMILES: Cc1ccc(S(=O)(=O)n2c(C(=O)C(C#N)=CN(C)C)cc3c(Cl)cccc32)cc1] | 2-[4-chloro-1-(toluene-4-sulfonyl)-1H-indole-2-carbonyl]-3-dimethylamino-acrylonitrile | 428, 430 |
| 1098 | 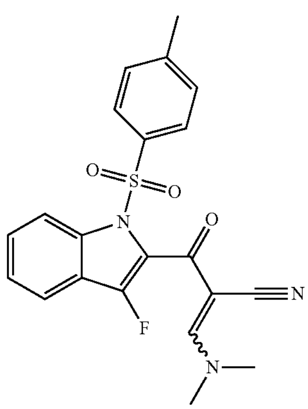 [SMILES: Cc1ccc(S(=O)(=O)n2c(C(=O)C(C#N)=CN(C)C)c(F)c3ccccc32)cc1] | 3-dimethylamino-2-[3-fluoro-1-(toluene-4-sulfonyl)-1H-indole-2-carbonyl]-acrylonitrile | 412 |

TABLE 9-continued

| Compound No. | Structure | Compound name | m/z |
|---|---|---|---|
| 1099 | 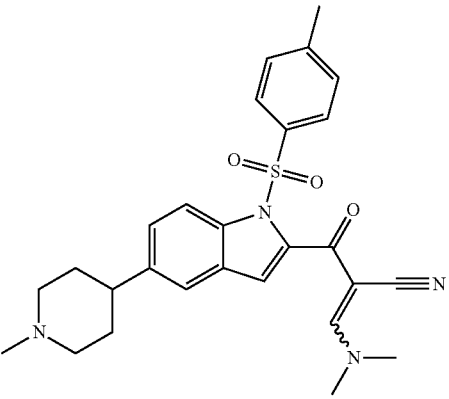 [SMILES: Cc1ccc(S(=O)(=O)n2c(C(=O)C(C#N)=CN(C)C)cc3cc(C4CCN(C)CC4)ccc32)cc1] | 3-dimethylamino-2-[5-(1-methyl-piperidin-4-yl)-1-(toluene-4-sulfonyl)-1H-indole-2-carbonyl]-acrylonitrile | 491 |
| 1100 | 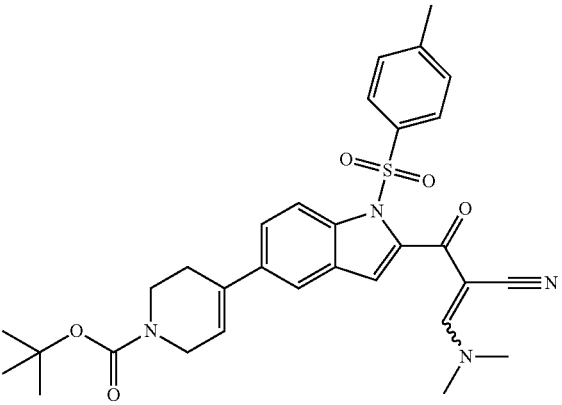 [SMILES: Cc1ccc(S(=O)(=O)n2c(C(=O)C(C#N)=CN(C)C)cc3cc(C4=CCN(C(=O)OC(C)(C)C)CC4)ccc32)cc1] | 4-[2-(2-cyano-3-dimethylamino-acryloyl)-1-(toluene-4-sulfonyl)-1H-indol-5-yl]-3,6-dihydro-2H-pyridine-1-carboxylic acid tert-butyl ester | 575 |
| 1101 | 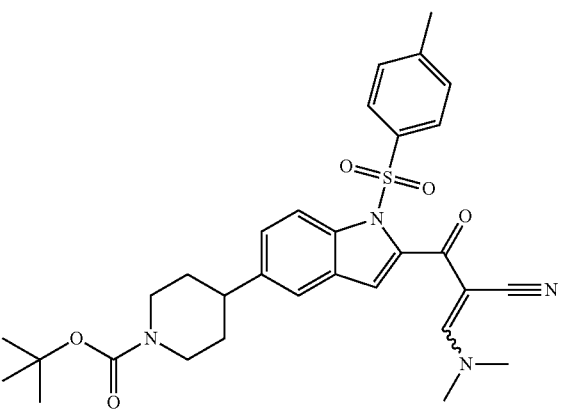 [SMILES: Cc1ccc(S(=O)(=O)n2c(C(=O)C(C#N)=CN(C)C)cc3cc(C4CCN(C(=O)OC(C)(C)C)CC4)ccc32)cc1] | 4-[2-(2-cyano-3-dimethylamino-acryloyl)-1-(toluene-4-sulfonyl)-1H-indol-5-yl]-piperidine-1-carboxylic acid tert-butyl ester | 577 |

TABLE 9-continued

| Compound No. | Structure | Compound name | m/z |
|---|---|---|---|
| 1102 | 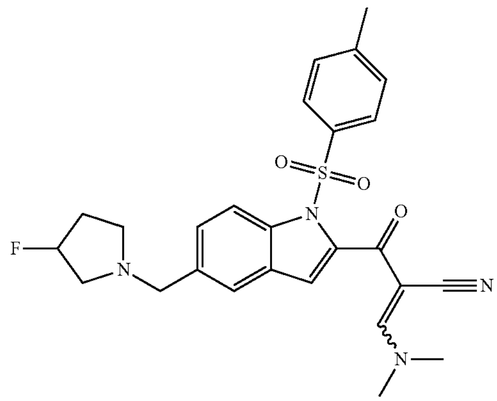 [SMILES: Cc1ccc(S(=O)(=O)n2c(C(=O)C(C#N)=CN(C)C)cc3cc(CN4CCC(F)C4)ccc32)cc1] | 3-dimethylamino-2-[5-((R)-3-fluoro-pyrrolidin-1-ylmethyl)-1-(toluene-4-sulfonyl)-1H-indole-2-carbonyl]-acrylonitrile | 495 |
| 1103 | 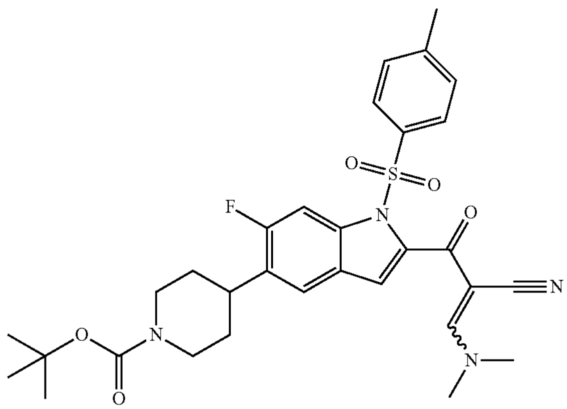 [SMILES: Cc1ccc(S(=O)(=O)n2c(C(=O)C(C#N)=CN(C)C)cc3cc(C4CCN(C(=O)OC(C)(C)C)CC4)c(F)cc32)cc1] | 4-[2-(2-cyano-3-dimethylamino-acryloyl)-6-fluoro-1-(toluene-4-sulfonyl)-1H-indol-5-yl]-piperidine-1-carboxylic acid tert-butyl ester | 595 |
| 1104 | 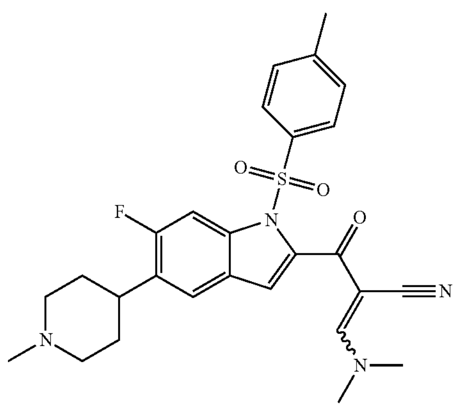 [SMILES: Cc1ccc(S(=O)(=O)n2c(C(=O)C(C#N)=CN(C)C)cc3cc(C4CCN(C)CC4)c(F)cc32)cc1] | 3-dimethylamino-2-[6-fluoro-5-(1-methyl-piperidin-4-yl)-1-(toluene-4-sulfonyl)-1H-indole-2-carbonyl]-acrylonitrile | 509 |
| 1105 | 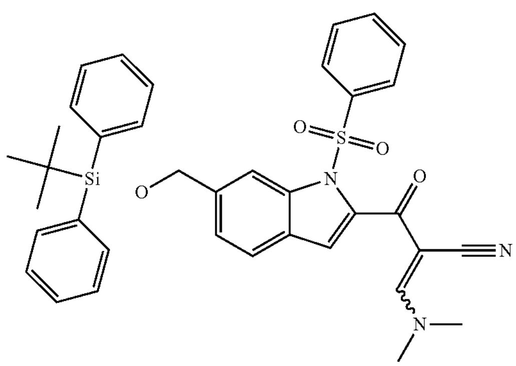 | 2-[1-benzenesulfonyl-6-(tert-butyldiphenyl-silanyloxymethyl)-1H-indole-2-carbonyl]-3-dimethylamino-acrylonitrile | 648 |

TABLE 9-continued

| Compound No. | Structure | Compound name | m/z |
|---|---|---|---|
| 1106 | 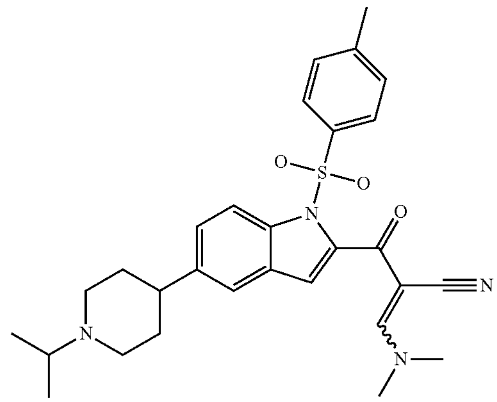 [SMILES: Cc1ccc(S(O)(O)n2c(C(=O)C(C#N)=CN(C)C)cc3cc(C4CCN(C(C)C)CC4)ccc32)cc1] | 3-dimethylamino-2-[5-(1-isopropyl-piperidin-4-yl)-1-(toluene-4-sulfonyl)-1H-indole-2-carbonyl]-acrylonitrile | 519 |
| 1107 | 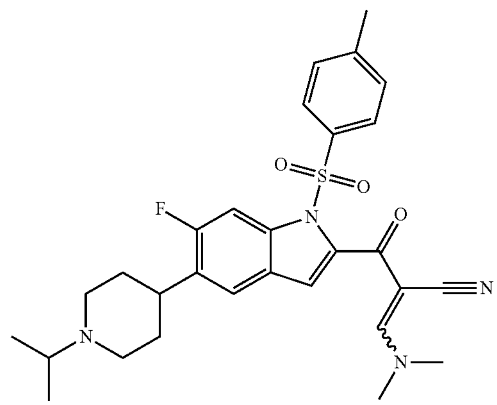 [SMILES: Cc1ccc(S(=O)(=O)n2c(C(=O)C(C#N)=CN(C)C)cc3cc(C4CCN(C(C)C)CC4)c(F)cc32)cc1] | 3-dimethylamino-2-[6-fluoro-5-(1-isopropyl-piperidin-4-yl)-1-(toluene-4-sulfonyl)-1H-indole-2-carbonyl]-acrylonitrile | 537 |
| 1108 | 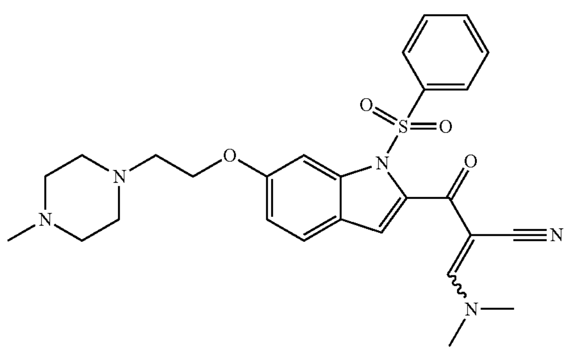 [SMILES: CN(C)C=C(C#N)C(=O)c1cc2ccc(OCCN3CCN(C)CC3)cc2n1S(=O)(=O)c1ccccc1] | 2-(1-benzenesulfonyl-6-[2-(4-methylpiperidin-1-yl)-ethoxy]-1H-indole-2-carbonyl)-3-dimethylamino-acrylonitrile | 522 |
| 1109 | 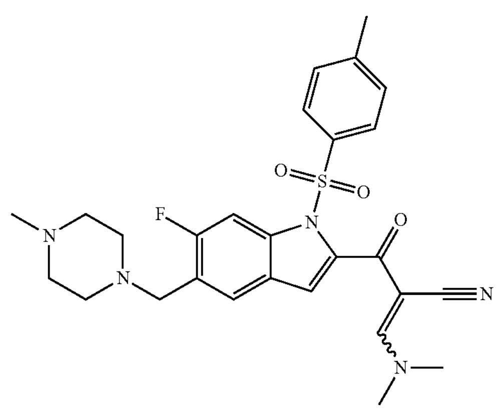 [SMILES: Cc1ccc(S(=O)(=O)n2c(C(=O)C(C#N)=CN(C)C)cc3cc(CN4CCN(C)CC4)c(F)cc32)cc1] | 3-dimethylamino-2-[6-fluoro-5-(4-methyl-piperazin-1-ylmethyl)-1-(toluene-4-sulfonyl)-1H-indole-2-carbonyl]-acrylonitrile | 524 |

TABLE 9-continued

| Compound No. | Structure | Compound name | m/z |
|---|---|---|---|
| 1110 | 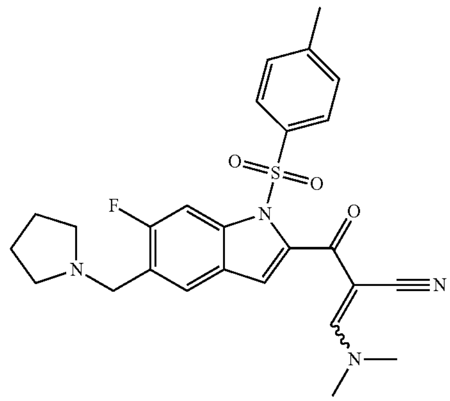 [SMILES: Cc1ccc(S(=O)(=O)n2c(C(=O)C(C#N)=CN(C)C)cc3cc(CN4CCCC4)c(F)cc32)cc1] | 3-dimethylamino-2-[6-fluoro-5-pyrrolidin-1-ylmethyl-1-(toluene-4-sulfonyl)-1H-indole-2-carbonyl]-acrylonitrile | 495 |
| 1111 | 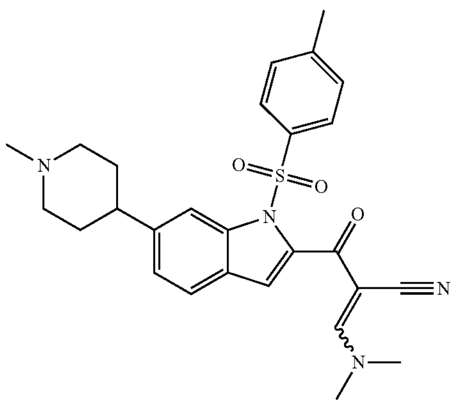 [SMILES: Cc1ccc(S(=O)(=O)n2c(C(=O)C(C#N)=CN(C)C)cc3ccc(C4CCN(C)CC4)cc32)cc1] | 3-dimethylamino-2-[6-(1-methyl-piperidin-4-yl)-1-(toluene-4-sulfonyl)-1H-indole-2-carbonyl]-acrylonitrile | 491 |
| 1112 | 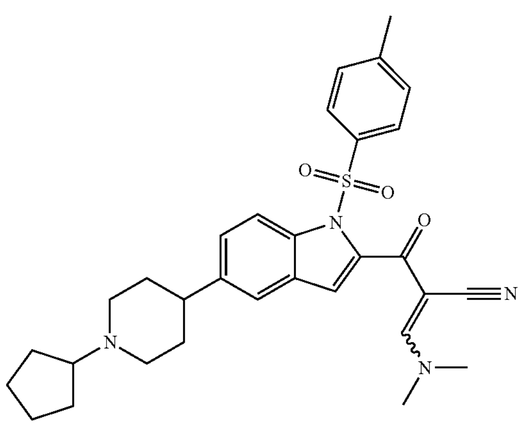 [SMILES: Cc1ccc(S(=O)(=O)n2c(C(=O)C(C#N)=CN(C)C)cc3cc(C4CCN(C5CCCC5)CC4)ccc32)cc1] | 2-[5-(1-cyclopentyl-piperidin-4-yl)-1-(toluene-4-sulfonyl)-1H-indole-2-carbonyl]-3-dimethylamino-acrylonitrile | 545 |

TABLE 9-continued

| Compound No. | Structure | Compound name | m/z |
|---|---|---|---|
| 1113 | 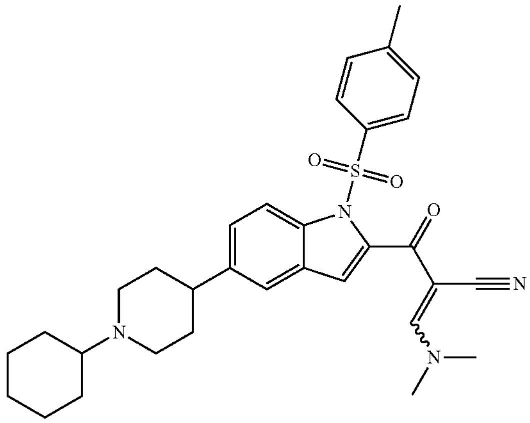 [SMILES: Cc1ccc(S(=O)(=O)n2c(C(=O)C(C#N)=CN(C)C)cc3cc(C4CCN(C5CCCCC5)CC4)ccc32)cc1] | 2-[5-(1-cyclohexyl-piperidin-4-yl)-1-(toluene-4-sulfonyl)-1H-indole-2-carbonyl]-3-dimethylamino-acrylonitrile | 559 |
| 1114 | 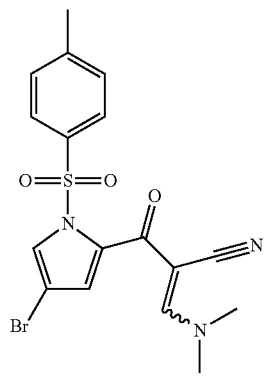 [SMILES: Cc1ccc(S(=O)(=O)n2cc(Br)cc2C(=O)C(C#N)=CN(C)C)cc1] | 2-[4-bromo-1-(toluene-4-sulfonyl)-1H-pyrrol-2-carbonyl]-3-dimethylamino-acrylonitrile | 422, 424 |
| 1115 | 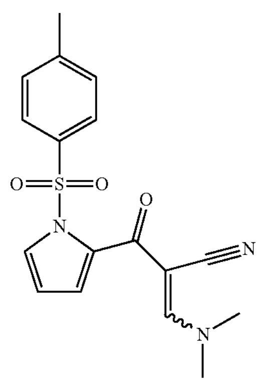 [SMILES: Cc1ccc(S(=O)(=O)n2cccc2C(=O)C(C#N)=CN(C)C)cc1] | 3-dimethylamino-2-[1-(toluene-4-sulfonyl)-1H-pyrrol-2-carbonyl]-acrylonitrile | 344 |
| 1116 | 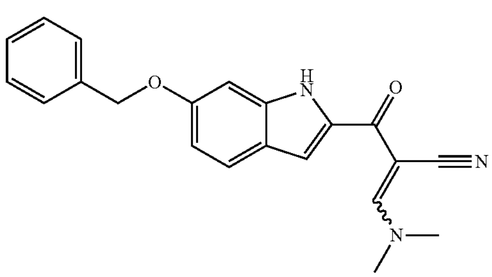 [SMILES: CN(C)C=C(C#N)C(=O)c1cc2ccc(OCc3ccccc3)cc2[nH]1] | 2-(6-benzyloxy-1H-indole-2-carbonyl)-3-dimethylamino-acrylonitrile | 346 |

TABLE 9-continued

| Compound No. | Structure | Compound name | m/z |
|---|---|---|---|
| 1117 | 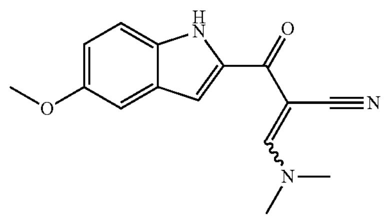 [SMILES: COc1ccc2[nH]c(C(=O)C(C#N)=CN(C)C)cc2c1] | 3-dimethylamino-2-(5-methoxy-1H-indole-2-carbonyl)-acrylonitrile | 270 |
| 1118 | 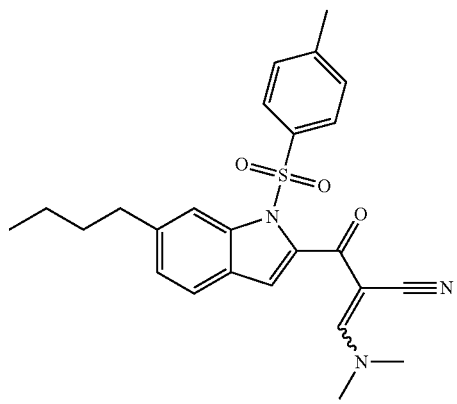 [SMILES: CCCCc1ccc2cc(C(=O)C(C#N)=CN(C)C)n(S(=O)(=O)c3ccc(C)cc3)c2c1] | 2-[6-butyl-1-(toluene-4-sulfonyl)-1H-indole-2-carbonyl]-3-dimethylamino-acrylonitrile | 450 |
| 1119 | 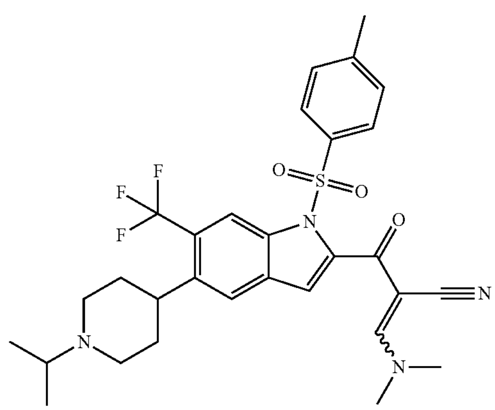 [SMILES: Cc1ccc(S(=O)(=O)n2c(C(=O)C(C#N)=CN(C)C)cc3cc(C4CCN(C(C)C)CC4)c(C(F)(F)F)cc32)cc1] | 3-dimethylamino-2-[5-(1-isopropryl-piperidin-4-yl)-1-(toluene-4-sulfonyl)-6-trifluoromethyl-1H-indole-2-carbonyl]-acrylonitrile | 587 |
| 1120 | 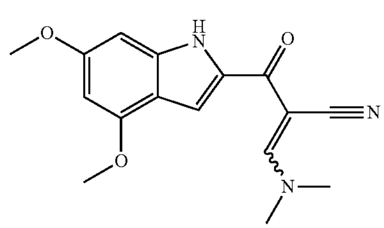 [SMILES: COc1cc(OC)c2cc(C(=O)C(C#N)=CN(C)C)[nH]c2c1] | 2-(4,6-dimethoxy-1H-indole-2-carbonyl)-3-dimethylamino-acrylonitrile | 300 |
| 1121 | 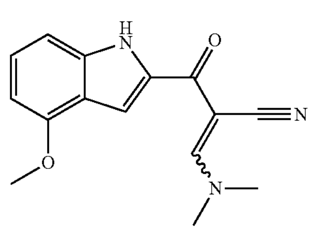 [SMILES: COc1cccc2[nH]c(C(=O)C(C#N)=CN(C)C)cc12] | 3-dimethylamino-2-(4-methoxy-1H-indole-2-carbonyl)-acrylonitrile | 270 |

TABLE 9-continued

| Compound No. | Structure | Compound name | m/z |
|---|---|---|---|
| 1122 | 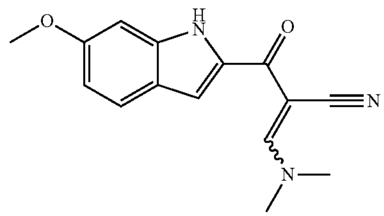 [SMILES: COc1ccc2cc(C(=O)C(C#N)=CN(C)C)[nH]c2c1] | 3-dimethylamino-2-(6-methoxy-1H-indole-2-carbonyl)-acrylonitrile | 270 |
| 1123 | 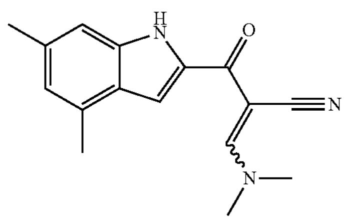 [SMILES: Cc1cc(C)c2cc(C(=O)C(C#N)=CN(C)C)[nH]c2c1] | 3-dimethylamino-2-(4,6-dimethyl-1H-indole-2-carbonyl)-acrylonitrile | 268 |
| 1124 | 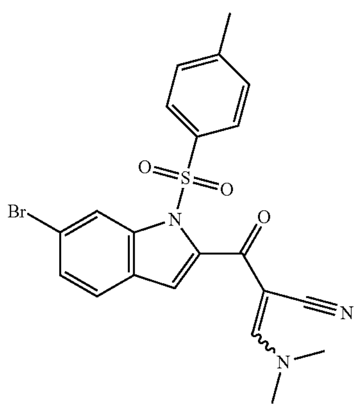 [SMILES: Cc1ccc(S(=O)(=O)n2c(C(=O)C(C#N)=CN(C)C)cc3ccc(Br)cc32)cc1] | 2-[6-bromo-1-(toluene-4-sulfonyl)-1H-indole-2-carbonyl]-3-dimethylamino-acrylonitrile | 472, 474 |
| 1125 | 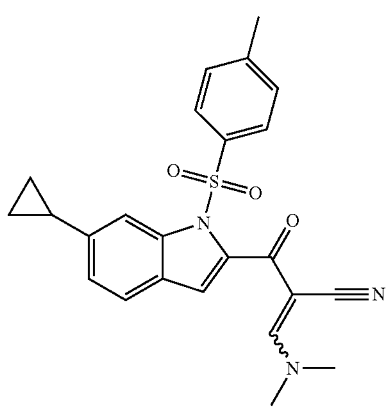 [SMILES: Cc1ccc(S(=O)(=O)n2c(C(=O)C(C#N)=CN(C)C)cc3ccc(C4CC4)cc32)cc1] | 2-[6-cyclopropyl-1-(toluene-4-sulfonyl)-1H-indole-2-carbonyl]-3-dimethylamino-acrylonitrile | 434 |
| 1126 | 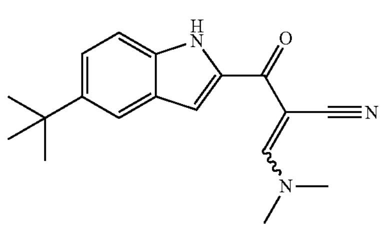 [SMILES: CN(C)C=C(C#N)C(=O)c1cc2cc(C(C)(C)C)ccc2[nH]1] | 2-(5-tert-buty-1H-indole-2-carbonyl)-3-dimethylamino-acrylonitrile | 296 |

TABLE 9-continued

| Compound No. | Structure | Compound name | m/z |
|---|---|---|---|
| 1127 | 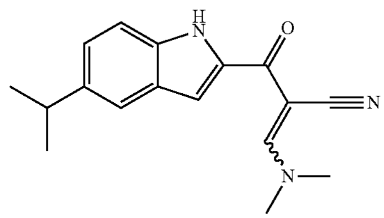 [SMILES: CC(C)c1ccc2[nH]c(C(=O)C(C#N)=CN(C)C)cc2c1] | 3-dimethylamino-2-(5-isopropryl-1H-indole-2-carbonyl)-acrylonitrile | 282 |
| 1128 | 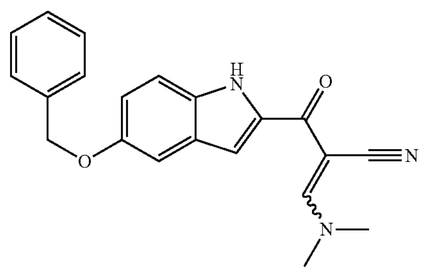 [SMILES: CN(C)C=C(C#N)C(=O)c1cc2cc(OCc3ccccc3)ccc2[nH]1] | 2-(5-benzyloxy-1H-indole-2-carbonyl)-3-dimethylamino-acrylonitrile | 346 |
| 1129 | 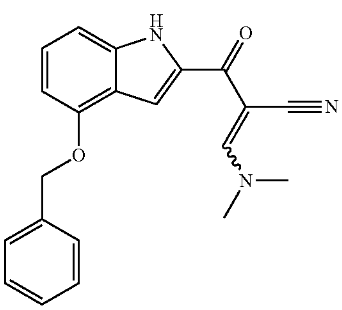 [SMILES: CN(C)C=C(C#N)C(=O)c1cc2c(OCc3ccccc3)cccc2[nH]1] | 2-(4-benzyloxy-1H-indole-2-carbonyl)-3-dimethylamino-acrylonitrile | 346 |
| 1130 | 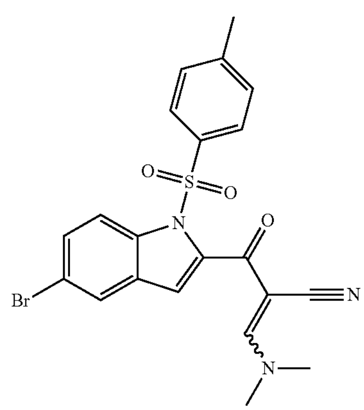 [SMILES: Cc1ccc(S(=O)(=O)n2c(C(=O)C(C#N)=CN(C)C)cc3cc(Br)ccc32)cc1] | 2-[5-bromo-1-(toluene-4-sulfonyl)-1H-indole-2-carbonyl]-3-dimethylamino-acrylonitrile | 472, 474 |
| 1131 | 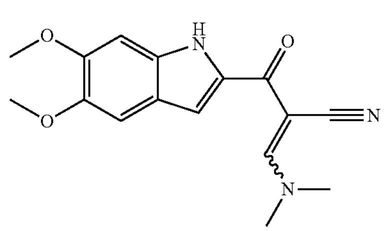 | 2-(5,6-dimethoxy-1H-indole-2-carbonyl)-3-dimethylamino-acrylonitrile | 300 |

TABLE 9-continued

| Compound No. | Structure | Compound name | m/z |
|---|---|---|---|
| 1132 | 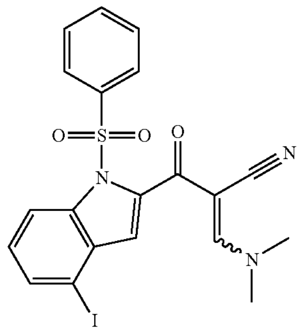 [SMILES: CN(C)C=C(C#N)C(=O)c1cc2c(I)cccc2n1S(=O)(=O)c1ccccc1] | 2-(1-benzenesulfonyl-4-iodo-1H-indole-2-carbonyl)-3-dimethylamino-acrylonitrile | 506 |
| 1133 | 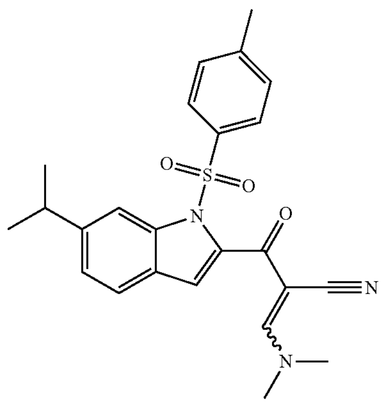 [SMILES: Cc1ccc(S(=O)(=O)n2c(C(=O)C(C#N)=CN(C)C)cc3ccc(C(C)C)cc32)cc1] | 3-dimethylamino-2-[6-isopropyl-1-(toluene-4-sulfonyl)-1H-indole-2-carbonyl]-acrylonitrile | 436 |
| 1134 | 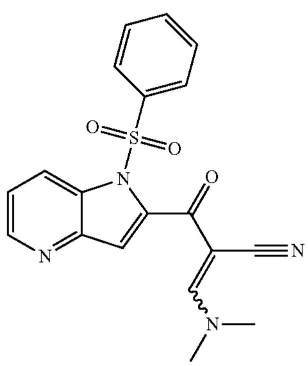 [SMILES: CN(C)C=C(C#N)C(=O)c1cc2ncccc2n1S(=O)(=O)c1ccccc1] | 2-(1-benzenesulfonyl-1H-pyrrolo[3,2-b]pyridine-2-carbonyl)-3-dimethylamino-acrylonitrile | 381 |
| 1135 | 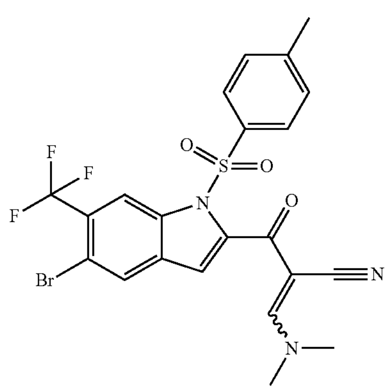 [SMILES: Cc1ccc(S(=O)(=O)n2c(C(=O)C(C#N)=CN(C)C)cc3cc(Br)c(C(F)(F)F)cc32)cc1] | 2-[5-bromo-1-(toluene-4-sulfonyl)-6-trifluoromethyl-1H-indole-2-carbonyl]-3-dimethylamino-acrylonitrile | 542, 542 |

TABLE 9-continued

| Compound No. | Structure | Compound name | m/z |
|---|---|---|---|
| 1136 | 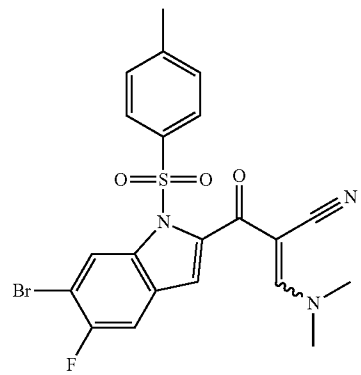 [SMILES: Cc1ccc(S(=O)(=O)n2c(C(=O)C(C#N)=CN(C)C)cc3cc(F)c(Br)cc32)cc1] | 2-[6-bromo-5-fluoro-1-(toluene-4-sulfonyl)-1H-indole-2-carbonyl]-3-dimethylamino-acrylonitrile | 490, 492 |
| 1137 | 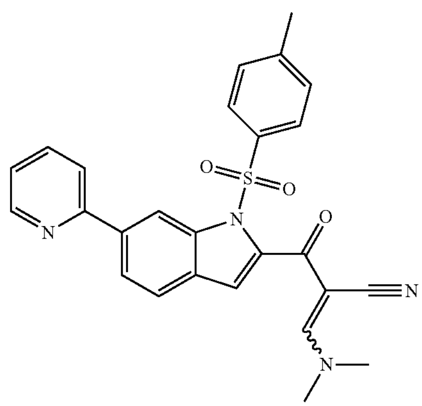 [SMILES: Cc1ccc(S(=O)(=O)n2c(C(=O)C(C#N)=CN(C)C)cc3ccc(-c4ccccn4)cc32)cc1] | 3-dimethylamino-2-[6-pyridin-2-yl-1-(toluene-4-sulfonyl)-1H-indole-2-carbonyl]-acrylonitrile | 471 |
| 1138 | 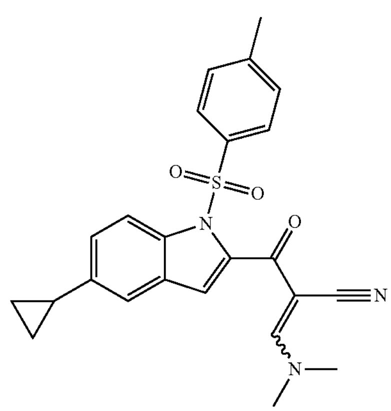 [SMILES: Cc1ccc(S(=O)(=O)n2c(C(=O)C(C#N)=CN(C)C)cc3cc(C4CC4)ccc32)cc1] | 2-[5-cyclopropyl-1-(toluene-4-sulfonyl)-1H-indole-2-carbonyl]-3-dimethylamino-acrylonitrile | 434 |
| 1139 | 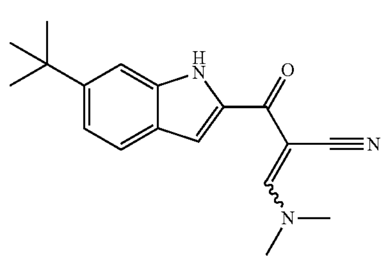 [SMILES: CN(C)C=C(C#N)C(=O)c1cc2ccc(C(C)(C)C)cc2[nH]1] | 2-(6-tert-butyl-1H-indole-2-carbonyl)-3-dimethylamino-acrylonitrile | 296 |

TABLE 9-continued

| Compound No. | Structure | Compound name | m/z |
|---|---|---|---|
| 1140 | 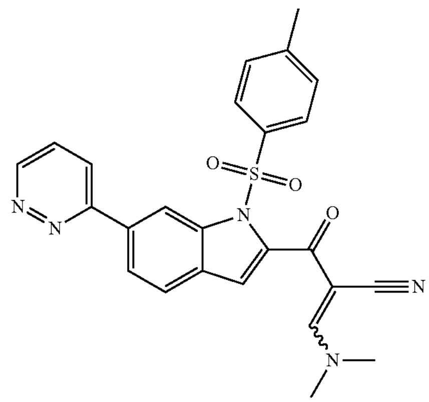 [SMILES: Cc1ccc(S(=O)(=O)n2c(C(=O)C(C#N)=CN(C)C)cc3ccc(-c4cccnn4)cc32)cc1] | 3-dimethylamino-2-[6-pyridazin-3-yl-1-(toluene-4-sulfonyl)-1H-indole-2-carbonyl]-acrylonitrile | 472 |
| 1141 | 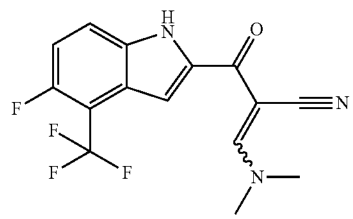 [SMILES: CN(C)C=C(C#N)C(=O)c1cc2c(C(F)(F)F)c(F)ccc2[nH]1] | 3-dimethylamino-2-(5-fluoro-4-trifluoromethyl-1H-indole-2-carbonyl]-acrylonitrile | 324 [M − H] |
| 1142 | 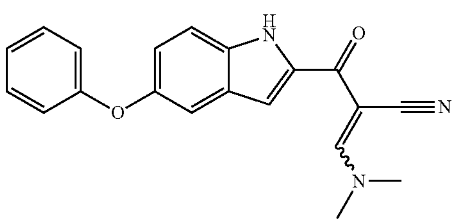 [SMILES: CN(C)C=C(C#N)C(=O)c1cc2cc(Oc3ccccc3)ccc2[nH]1] | 3-dimethylamino-2-(5-phenoxy-1H-indole-2-carbonyl)-acrylonitrile | 332 |
| 1143 | 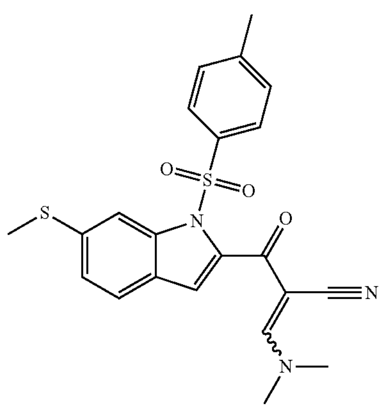 [SMILES: CSc1ccc2cc(C(=O)C(C#N)=CN(C)C)n(S(=O)(=O)c3ccc(C)cc3)c2c1] | 3-dimethylamino-2-[6-methylsulfanyl-1-(toluene-4-sulfonyl)-1H-indole-2-carbonyl]-acrylonitrile | 440 |
| 1144 | 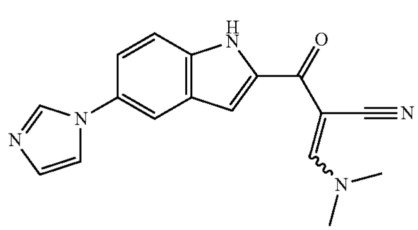 [SMILES: CN(C)C=C(C#N)C(=O)c1cc2cc(-n3ccnc3)ccc2[nH]1] | 3-dimethylamino-2-(5-imidazol-1-yl-1H-indole-2-carbonyl)-acrylonitrile | 306 |

TABLE 9-continued

| Compound No. | Structure | Compound name | m/z |
|---|---|---|---|
| 1145 | 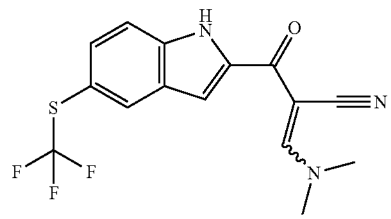 [SMILES: CN(C)C=C(C#N)C(=O)c1cc2cc(SC(F)(F)F)ccc2[nH]1] | 3-dimethylamino-2-(5-trifluoromethylsulfanyl-1H-indole-2-carbonyl)-acrylonitrile | 340 |
| 1146 | 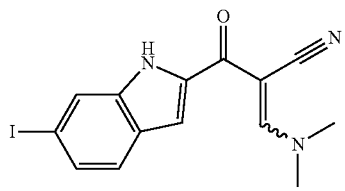 [SMILES: CN(C)C=C(C#N)C(=O)c1cc2ccc(I)cc2[nH]1] | 3-dimethylamino-2-(6-iodo-1H-indole-2-carbonyl)-acrylonitrile | M not detected |
| 1147 | 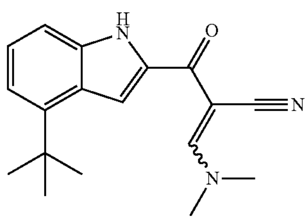 [SMILES: CN(C)C=C(C#N)C(=O)c1cc2c(C(C)(C)C)cccc2[nH]1] | (2-(4-tert-butyl-1H-indole-2-carbonyl)-3-dimethylamino-acrylonitrile | 296 |
| 1148 | 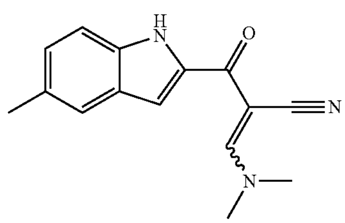 [SMILES: Cc1ccc2[nH]c(C(=O)C(C#N)=CN(C)C)cc2c1] | 3-dimethylamino-2-(5-methyl-1H-indole-2-carbonyl)-acrylonitrile | 254 |
| 1149 | 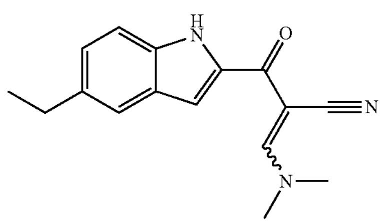 [SMILES: CCc1ccc2[nH]c(C(=O)C(C#N)=CN(C)C)cc2c1] | 3-dimethylamino-2-(5-ethyl-1H-indole-2-carbonyl)-acrylonitrile | 268 |
| 1150 | 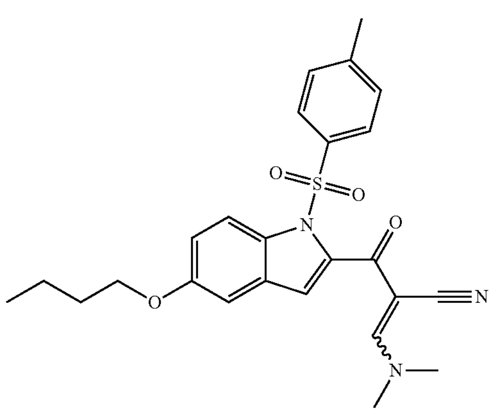 [SMILES: CCCCOc1ccc2c(c1)cc(C(=O)C(C#N)=CN(C)C)n2S(=O)(=O)c1ccc(C)cc1] | 2-[5-butoxy-1-(toluene-4-sulfonyl)-1H-indole-2-carbonyl]-3-dimethylamino-acrylonitrile | 466 |

TABLE 9-continued

| Compound No. | Structure | Compound name | m/z |
|---|---|---|---|
| 1151 | 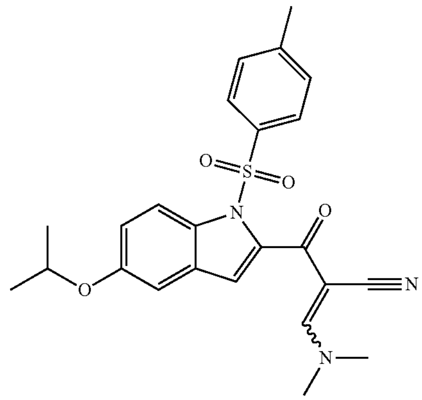 [SMILES: Cc1ccc(S(=O)(=O)n2c(C(=O)C(C#N)=CN(C)C)cc3cc(OC(C)C)ccc32)cc1] | 3-dimethylamino-2-[5-isopropoxy-1-(toluene-4-sulfonyl)-1H-indole-2-carbonyl]-acrylonitrile | 452 |
| 1152 | 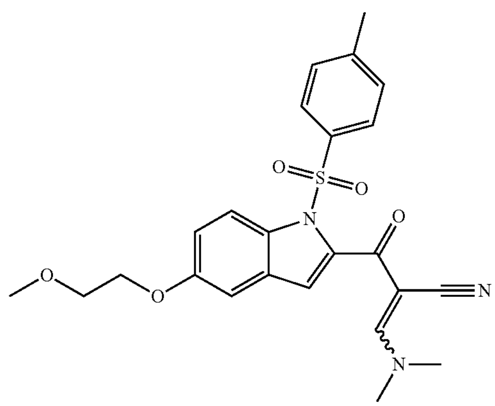 | 3-dimethylamino-2-[5-(2-methoxy-ethoxy)-1-(toluene-4-sulfonyl)-1H-indole-2-carbonyl]-acrylonitrile | 467.99 |
| 1153 | 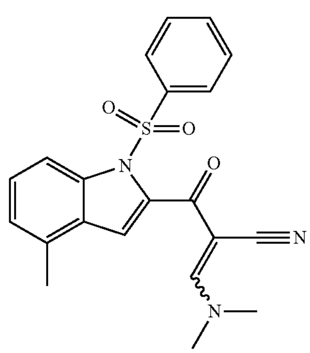 [SMILES: Cc1cccc2c1cc(C(=O)C(C#N)=CN(C)C)n2S(=O)(=O)c1ccccc1] | 2-(1-benzenesulfonyl-4-methyl-1H-indole-2-carbonyl)-3-dimethylamino-acrylonitrile | 394 |
| 1154 | 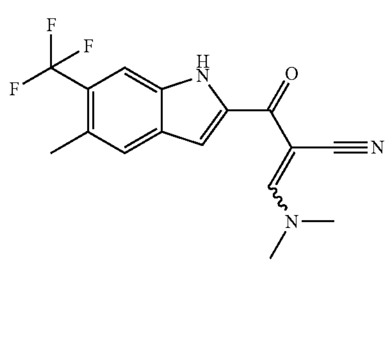 [SMILES: Cc1cc2cc(C(=O)C(C#N)=CN(C)C)[nH]c2cc1C(F)(F)F] | 3-dimethylamino-2-(5-fluoro-6-trifluoromethyl-1H-indole-2-carbonyl)-acrylonitrile | 324 [M − H] |

TABLE 9-continued

| Compound No. | Structure | Compound name | m/z |
|---|---|---|---|
| 1155 | 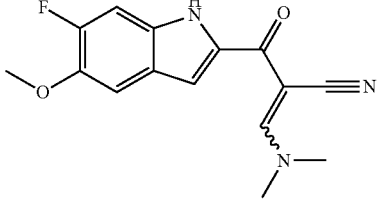 | 3-dimethylamino-2-(6-fluoro-5-methoxy-1H-indole-2-carbonyl)-acrylonitrile | 288 |
| 1156 | 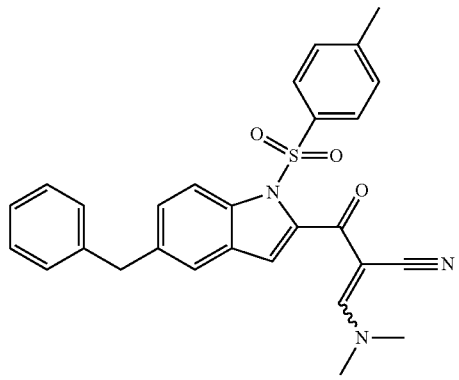 [SMILES: Cc1ccc(S(=O)(=O)n2c(C(=O)C(C#N)=CN(C)C)cc3cc(Cc4ccccc4)ccc32)cc1] | 2-[5-benzyl-1-(toluene-4-sulfonyl)-1H-indole-2-carbonyl]-3-dimethylamino-acrylonitrile | 484 |
| 1157 | 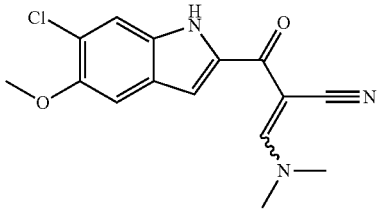 [SMILES: COc1cc2cc(C(=O)C(C#N)=CN(C)C)[nH]c2cc1Cl] | 2-(6-chloro-5-methoxy-1H-indole-2-carbonyl)-3-dimethylamino-acrylonitrile | 304, 306 |
| 1158 | 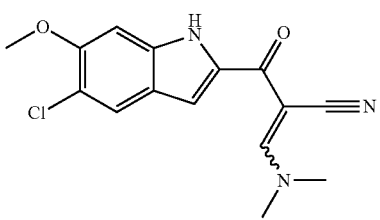 [SMILES: COc1cc2[nH]c(C(=O)C(C#N)=CN(C)C)cc2cc1Cl] | 2-(5-chloro-6-methoxy-1H-indole-2-carbonyl)-3-dimethylamino-acrylonitrile | 304, 306 |
| 1159 | 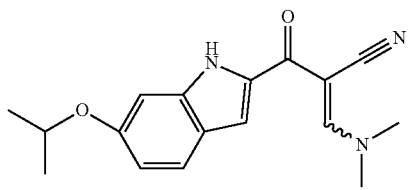 [SMILES: CC(C)Oc1ccc2cc(C(=O)C(C#N)=CN(C)C)[nH]c2c1] | 3-dimethylamino-2-(6-isopropoxy-1#H-indole-2-carbonyl]-acrylonitrile | 298 |

TABLE 9-continued

| Compound No. | Structure | Compound name | m/z |
|---|---|---|---|
| 1160 | 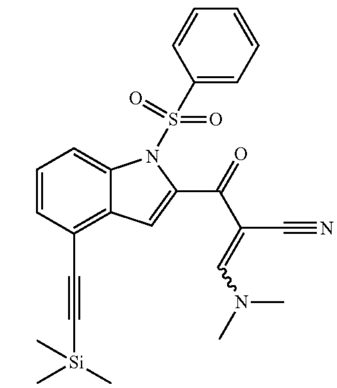 [SMILES: CN(C)C=C(C#N)C(=O)c1cc2c(C#C[Si](C)(C)C)cccc2n1S(=O)(=O)c1ccccc1] | 2-(1-benzenesulfonyl-4-trimethylsilanylethynyl-1H-indole-2-carbonyl)-3-dimethylamino-acrylonitrile | 476 |
| 1161 | 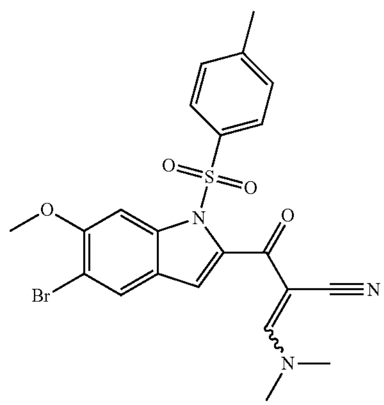 [SMILES: COc1cc2c(cc1Br)cc(C(=O)C(C#N)=CN(C)C)n2S(=O)(=O)c1ccc(C)cc1] | 2-[5-bromo-6-methoxy-1-(toluene-4-sulfonyl)-1H-indole-2-carbonyl]-3-dimethylamino-acrylonitrile | 502, 504 |
| 1162 | 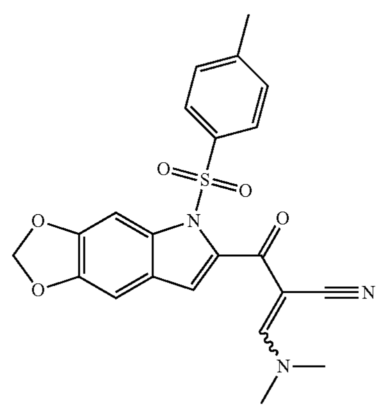 [SMILES: Cc1ccc(S(=O)(=O)n2c(C(=O)C(C#N)=CN(C)C)cc3cc4c(cc32)OCO4)cc1] | 3-dimethylamino-2-[5-(toluene-4-sulfonyl)-5H-[1,3]dioxolo[4,5-f]indole-6-carbonyl]-acrylonitrile | 438 |
| 1163 | 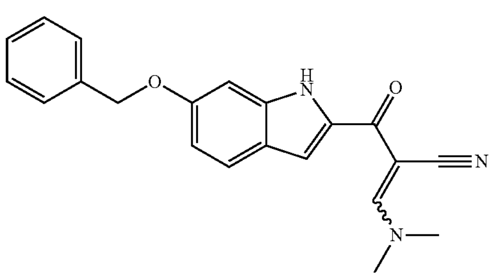 [SMILES: CN(C)C=C(C#N)C(=O)c1cc2ccc(OCc3ccccc3)cc2[nH]1] | 2-(6-benzyloxy-1H-indole-2-carbonyl)-3-dimethylamino-acrylonitrile | 346 |

TABLE 9-continued

| Compound No. | Structure | Compound name | m/z |
|---|---|---|---|
| 1164 | 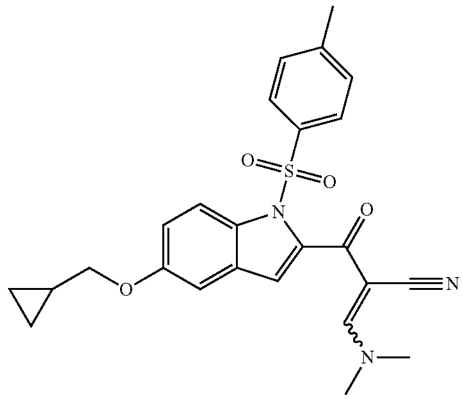 [SMILES: Cc1ccc(S(=O)(=O)n2c(C(=O)C(C#N)=CN(C)C)cc3cc(OCC4CC4)ccc32)cc1] | 2-[5-cyclopropylmethoxy-1-(toluene-4-sulfonyl)-1H-indole-2-carbonyl]-3-dimethylamino-acrylonitrile | 464 |
| 1165 | 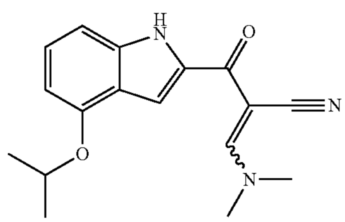 [SMILES: CC(C)Oc1cccc2[nH]c(C(=O)C(C#N)=CN(C)C)cc12] | 3-dimethylamino-2-(4-isopropoxy-1H-indole-2-carbonyl)-acrylonitrile | 298 |
| 1166 | 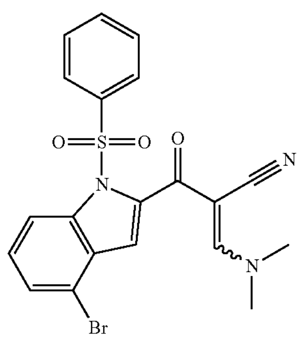 [SMILES: CN(C)C=C(C#N)C(=O)c1cc2c(Br)cccc2n1S(=O)(=O)c1ccccc1] | 2-(1-benzenesulfonyl-4-bromo-1H-indole-2-carbonyl)-3-dimethylamino-acrylonitrile | 458, 460 |
| 1167 | 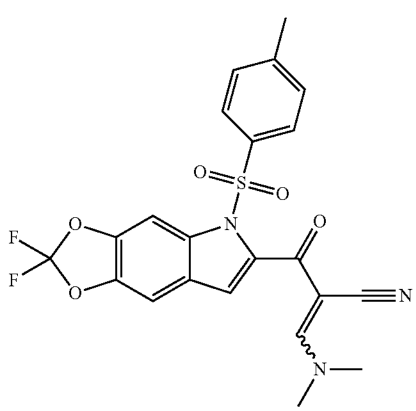 [SMILES: Cc1ccc(S(=O)(=O)n2c(C(=O)C(C#N)=CN(C)C)cc3cc4c(cc32)OC(F)(F)O4)cc1] | 2-[2,2-difluoro-5-(toluene-4-sulfonyl)-5H-[1,3]dioxolo[4,5-f]indole-6-carbonyl]-3-dimethylamino-acrylonitrile | 474 |

TABLE 9-continued
| Compound No. | Structure | Compound name | m/z |
|---|---|---|---|
| 1168 | 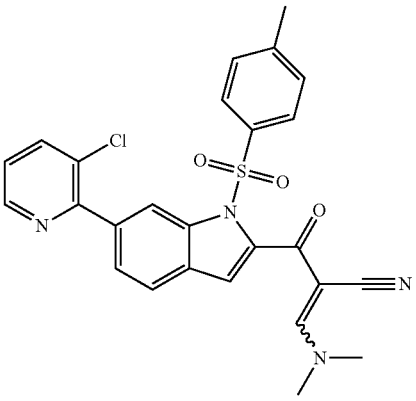 [SMILES: Cc1ccc(S(=O)(=O)n2c(C(=O)C(C#N)=CN(C)C)cc3ccc(-c4ncccc4Cl)cc32)cc1] | 2-[6-(3-chloro-pyridin-2-yl)-1-(toluene-4-sulfonyl)-1H-indole-2-carbonyl]-3-dimethylamino-acrylonitrile | 505, 507 |
| 1169 | 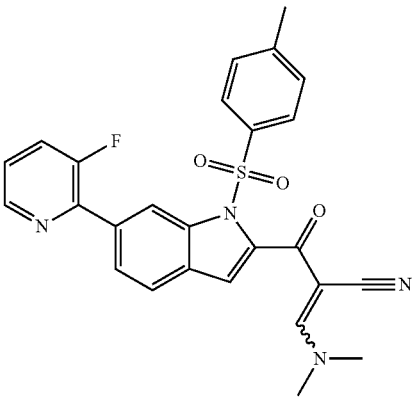 [SMILES: Cc1ccc(S(=O)(=O)n2c(C(=O)C(C#N)=CN(C)C)cc3ccc(-c4ncccc4F)cc32)cc1] | 3-dimethylamino-2-[6-(3-fluoropyridin-2-yl)-1-(toluene-4-sulfonyl)-1H-indole-2-carbonyl]-acrylonitrile | 489 |
| 1170 | 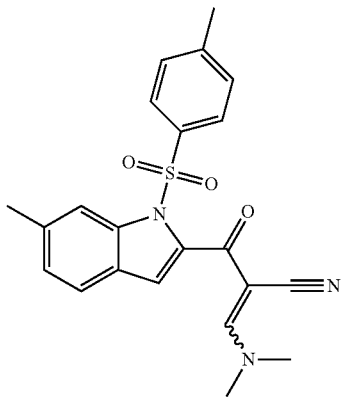 [SMILES: Cc1ccc(S(=O)(=O)n2c(C(=O)C(C#N)=CN(C)C)cc3ccc(C)cc32)cc1] | 3-dimethylamino-2-[6-methyl-1-(toluene-4-sulfonyl)-1H-indole-2-carbonyl]-acrylonitrile | 408 |

TABLE 9-continued

| Compound No. | Structure | Compound name | m/z |
| --- | --- | --- | --- |
| 1171 | 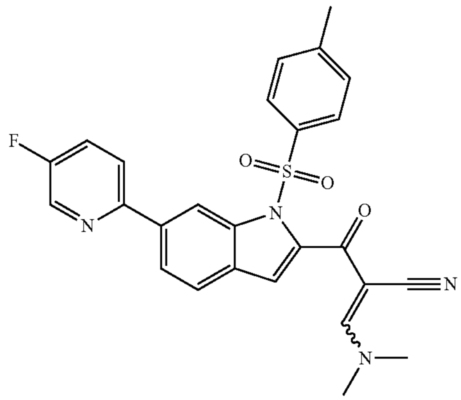 [SMILES: Cc1ccc(S(=O)(=O)n2c(C(=O)C(C#N)=CN(C)C)cc3ccc(-c4ccc(F)cn4)cc32)cc1] | 3-dimethylamino-2-[6-(5-fluoro-pyridin-2-yl)-1-(toluene-4-sulfonyl)-1H-indole-2-carbonyl]-acrylonitrile | 489 |
| 1172 | 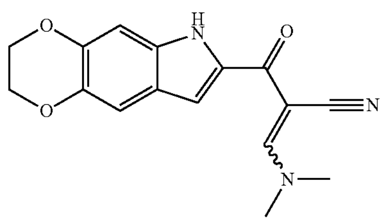 [SMILES: CN(C)C=C(C#N)C(=O)c1cc2cc3c(cc2[nH]1)OCCO3] | 2-(2,3-dihydro-6H-[1,4]dioxino[2,3-f]indole-7-carbonyl)-3-dimethylamino-acrylonitrile | 298 |
| 1173 | 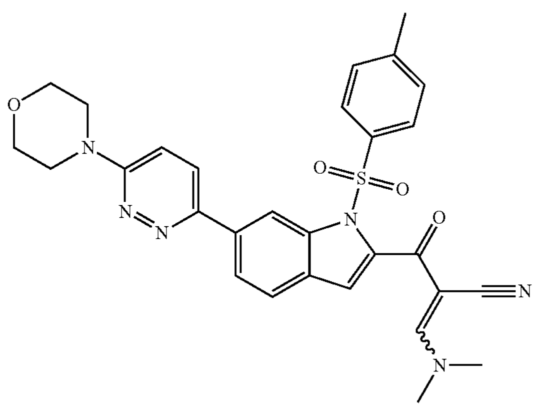 [SMILES: Cc1ccc(S(=O)(=O)n2c(C(=O)C(C#N)=CN(C)C)cc3ccc(-c4ccc(N5CCOCC5)nn4)cc32)cc1] | 3-dimethylamino-2-[6-(6-morpholin-4-yl-pyridazin-3-yl)-1-(toluene-4-sulfonyl)-1H-indole-2-carbonyl]-acrylonitrile | 557 |
| 1174 | 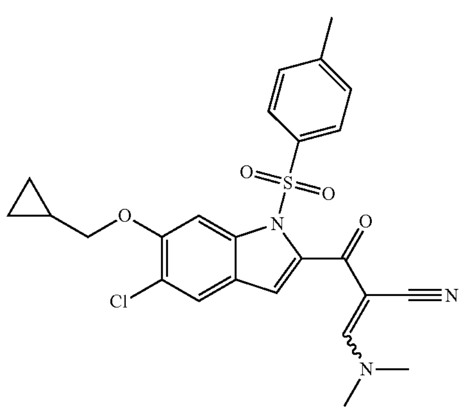 [SMILES: Cc1ccc(S(=O)(=O)n2c(C(=O)C(C#N)=CN(C)C)cc3cc(Cl)c(OCC4CC4)cc32)cc1] | 2-[5-chloro-6-cyclopropylmethoxy-1-(toluene-4-sulfonyl)-1H-indole-2-carbonyl]-3-dimethylamino-acrylonitrile | 498, 500 |

TABLE 9-continued

| Compound No. | Structure | Compound name | m/z |
|---|---|---|---|
| 1175 | 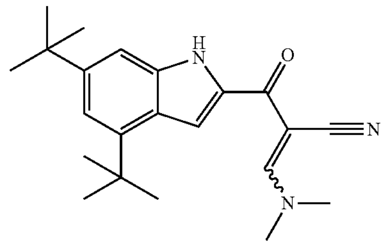 [SMILES: CN(C)C=C(C#N)C(=O)c1cc2c(C(C)(C)C)cc(C(C)(C)C)cc2[nH]1] | 2-(4,6-di-tert-butyl-1H-indole-2-carbonyl)-3-dimethylamino-acrylonitrile | 352 |
| 1176 | 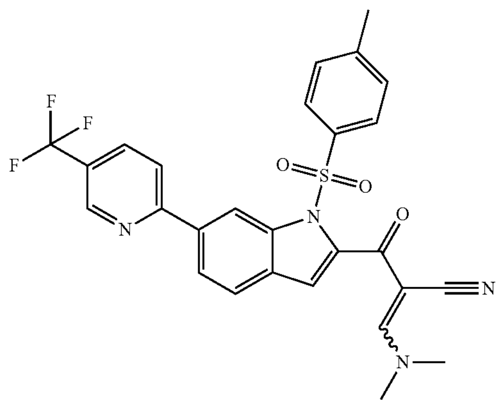 [SMILES: Cc1ccc(S(=O)(=O)n2c(C(=O)C(C#N)=CN(C)C)cc3ccc(-c4ccc(C(F)(F)F)cn4)cc32)cc1] | 3-dimethlamino-2-[1-(toluene-4-sulfonyl)-6-(5-trifluoromethylpyridin-2-yl)-1H-indole-2-carbonyl]-acrylonitrile | 539 |
| 1177 | 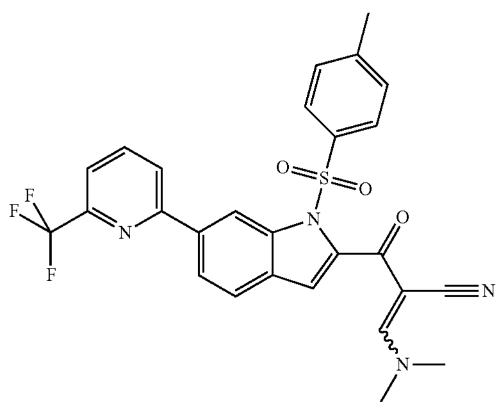 [SMILES: Cc1ccc(S(=O)(=O)n2c(C(=O)C(C#N)=CN(C)C)cc3ccc(-c4cccc(C(F)(F)F)n4)cc32)cc1] | 3-dimethlamino-2-[1-(toluene-4-sulfonyl)-6-(6-trifluoromethyl-pyridin-2-yl)-1H-indole-2-carbonyl]-acrylonitrile | 539 |
| 1178 | 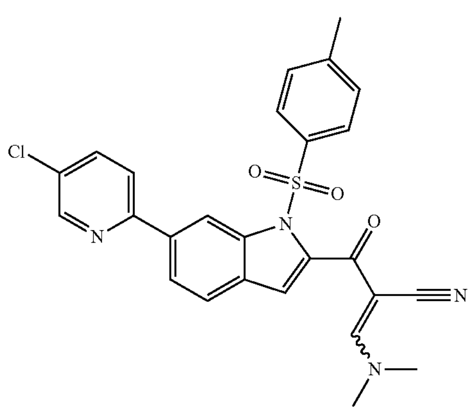 [SMILES: Cc1ccc(S(=O)(=O)n2c(C(=O)C(C#N)=CN(C)C)cc3ccc(-c4ccc(Cl)cn4)cc32)cc1] | 2-[6-(5-chloropyridin-2-yl)-1-(toluene-4-sulfonyl)-1H-indole-2-carbonyl]-3-dimethylamino-acrylonitrile | 505, 507 |

TABLE 9-continued

| Compound No. | Structure | Compound name | m/z |
|---|---|---|---|
| 1179 | 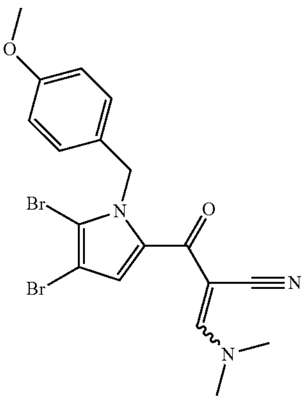 [SMILES: COc1ccc(Cn2c(C(=O)C(C#N)=CN(C)C)cc(Br)c2Br)cc1] | 2-[4,5-dibromo-1-(4-methoxy-benxyl)-1H-pyrrole-2-carbonyl)-3-dimethylamino-acrylonitrile | 466, 468, 470 |
| 1180 | 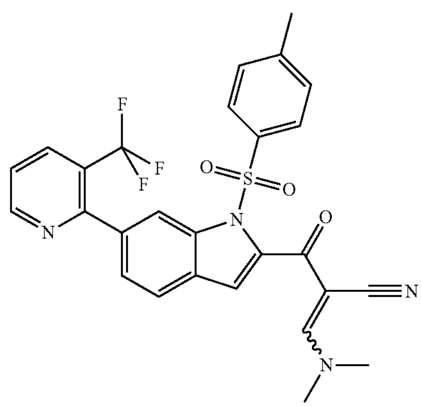 [SMILES: Cc1ccc(S(=O)(=O)n2c(C(=O)C(C#N)=CN(C)C)cc3ccc(-c4ncccc4C(F)(F)F)cc32)cc1] | 3-dimethylamino-2-[1-(toluene-4-sulfonyl)-6-(3-trifluoromethyl-pyridin-2-yl)-1H-indole-2-carbonyl]-acrylonitrile | 539 |
| 1181 | 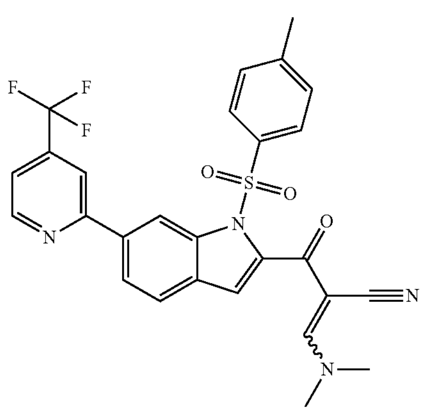 [SMILES: Cc1ccc(S(=O)(=O)n2c(C(=O)C(C#N)=CN(C)C)cc3ccc(-c4cc(C(F)(F)F)ccn4)cc32)cc1] | 3-dimethylamino-2-[1-(toluene-4-sulfonyl)-6-(4-trifluoromethyl-pyridin-2-yl)-1H-indole-2-carbonyl]-acrylonitrile | 539 |
| 1182 | 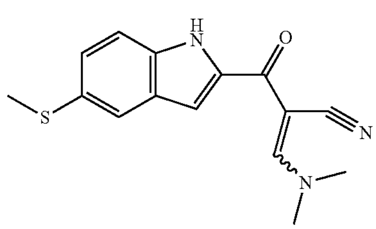 [SMILES: CSc1ccc2[nH]c(C(=O)C(C#N)=CN(C)C)cc2c1] | 3-dimethylamino-2-(5-methylsulfanyl-1H-indole-2-carbonyl)-acrylonitrile | 286 |

TABLE 9-continued

| Compound No. | Structure | Compound name | m/z |
| --- | --- | --- | --- |
| 1183 | 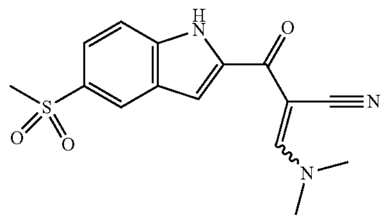 [SMILES: CN(C)C=C(C#N)C(=O)c1cc2cc(S(C)(=O)=O)ccc2[nH]1] | 3-dimethylamino-2-(5-methanesulfonyl-1H-indole-2-carbonyl)-acrylonitrile | 318 |
| 1184 | 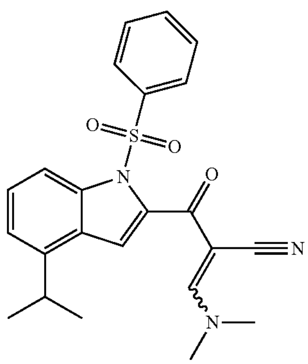 [SMILES: CC(C)c1cccc2c1cc(C(=O)C(C#N)=CN(C)C)n2S(=O)(=O)c1ccccc1] | 2-(1-benzenesulfonyl-4-isopropyl-1H-indole-2-carbonyl)-3-dimethylamino-acrylonitrile | 422 |
| 1528 | 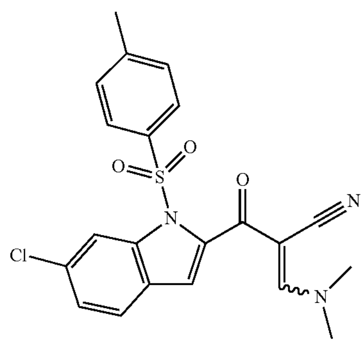 [SMILES: Cc1ccc(S(=O)(=O)n2c(C(=O)C(C#N)=CN(C)C)cc3ccc(Cl)cc32)cc1] | 2-[6-chloro-1-(toluene-4-sulfonyl)-1H-indole-2-carbonyl]-3-dimethylamino-acrylonitrile | 428 |
| 1529 | 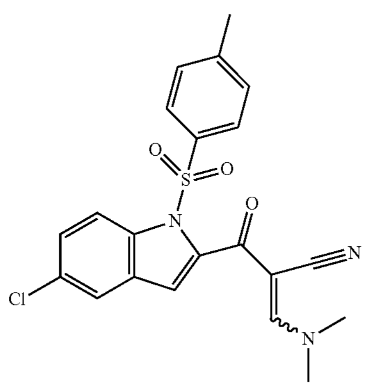 [SMILES: Cc1ccc(S(=O)(=O)n2c(C(=O)C(C#N)=CN(C)C)cc3cc(Cl)ccc32)cc1] | 2-[5-chloro-1-(toluene-4-sulfonyl)-1H-indole-2-carbonyl]-3-dimethylamino-acrylonitrile | 428 |
| 1530 | 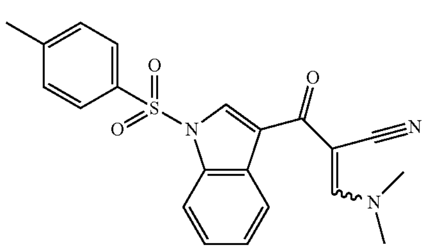 [SMILES: Cc1ccc(S(=O)(=O)n2cc(C(=O)C(C#N)=CN(C)C)c3ccccc32)cc1] | 3-dimethylamino-2-[1-(toluene-4-sulfonyl)-1H-indole-3-carbonyl]-acrylonitrile | 394 |

TABLE 9-continued

| Compound No. | Structure | Compound name | m/z |
|---|---|---|---|
| 1531 | 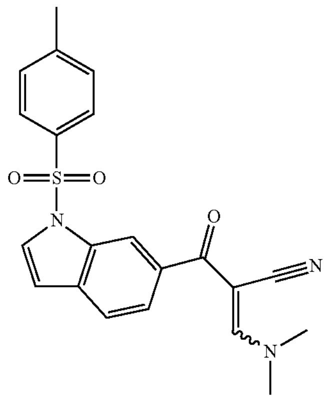 [SMILES: Cc1ccc(S(=O)(=O)n2ccc3ccc(C(=O)C(C#N)=CN(C)C)cc32)cc1] | 3-dimethylamino-2-[1-(toluene-4-sulfonyl)-1H-indole-6-carbonyl]-acrylonitrile | 394 |
| 1532 | 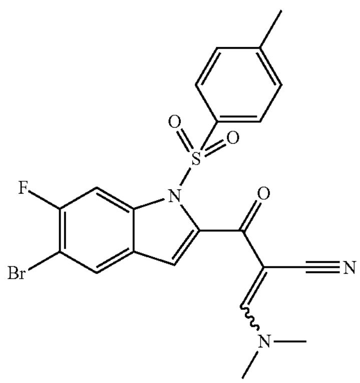 [SMILES: Cc1ccc(S(=O)(=O)n2c(C(=O)C(C#N)=CN(C)C)cc3cc(Br)c(F)cc32)cc1] | 2-[5-bromo-6-fluoro-1-(toluene-4-sulfonyl)-1H-indole-2-carbonyl]-3-dimethylamino-acrylonitrile | 490, 492 |
| 1533 | 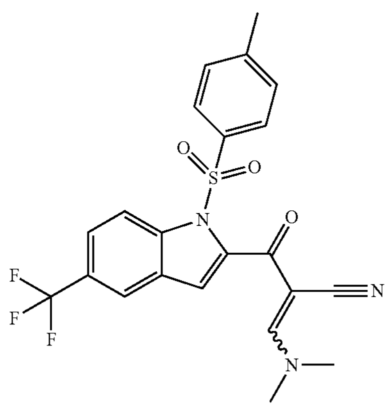 [SMILES: Cc1ccc(S(=O)(=O)n2c(C(=O)C(C#N)=CN(C)C)cc3cc(C(F)(F)F)ccc32)cc1] | 3-dimethylamino-2-[1-(toluene-4-sulfonyl)-5-trifluoromethyl-1H-indole-2-carbonyl]-acrylonitrile | 462 |
| 1534 | 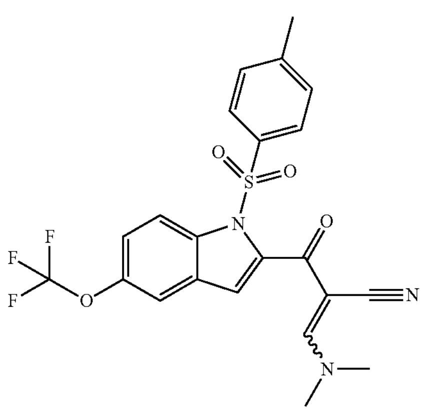 [SMILES: Cc1ccc(S(=O)(=O)n2c(C(=O)C(C#N)=CN(C)C)cc3cc(OC(F)(F)F)ccc32)cc1] | 3-dimethylamino-2-[1-(toluene-4-sulfonyl)-5-trifluoromethoxy-1H-indole-2-carbonyl]-acrylonitrile | 478 |

TABLE 9-continued

| Compound No. | Structure | Compound name | m/z |
|---|---|---|---|
| 1535 | 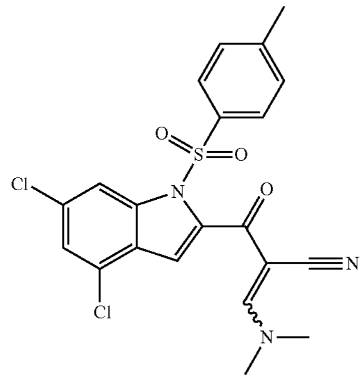 [SMILES: Cc1ccc(S(=O)(=O)n2c(C(=O)C(C#N)=CN(C)C)cc3c(Cl)cc(Cl)cc32)cc1] | 2-[4,6-dichloro-1-(toluene-4-sulfonyl)-1H-indole-2-carbonyl]-3-dimethylamino-acrylonitrile | 462 |
| 1536 | 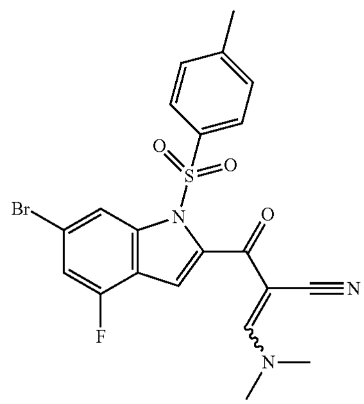 [SMILES: Cc1ccc(S(=O)(=O)n2c(C(=O)C(C#N)=CN(C)C)cc3c(F)cc(Br)cc32)cc1] | 2-[6-bromo-4-fluoro-1-(toluene-4-sulfonyl)-1H-indole-2-carbonyl]-3-dimethylamino-acrylonitrile | 490 |
| 1537 | 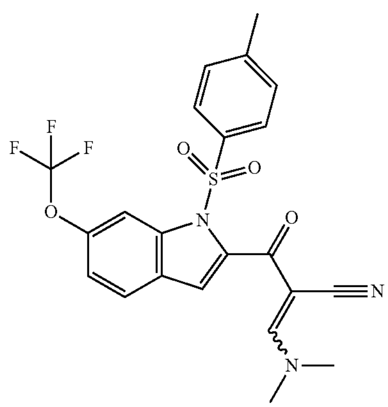 [SMILES: Cc1ccc(S(=O)(=O)n2c(C(=O)C(C#N)=CN(C)C)cc3ccc(OC(F)(F)F)cc32)cc1] | 3-dimethylamino-2-[1-(toluene-4-sulfonyl)-6-trifluoromethoxy-1H-indole-2-carbonyl]-acrylonitrile | 478 |
| 1538 | 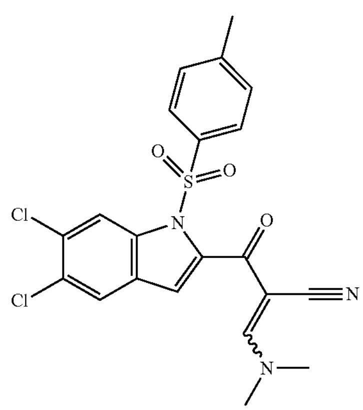 [SMILES: Cc1ccc(S(=O)(=O)n2c(C(=O)C(C#N)=CN(C)C)cc3cc(Cl)c(Cl)cc32)cc1] | 2-[5,6-dichloro-1-(toluene-4-sulfonyl)-1H-indole-2-carbonyl]-3-dimethylamino-acrylonitrile | 462 |

TABLE 9-continued

| Compound No. | Structure | Compound name | m/z |
|---|---|---|---|
| 1539 | 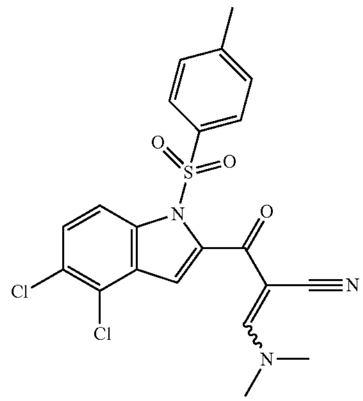 [SMILES: Cc1ccc(S(=O)(=O)n2c(C(=O)C(C#N)=CN(C)C)cc3c(Cl)c(Cl)ccc32)cc1] | 2-[4,5-dichloro-1-(toluene-4-sulfonyl)-1H-indole-2-carbonyl]-3-dimethylamino-acrylonitrile | 462 |
| 1540 | 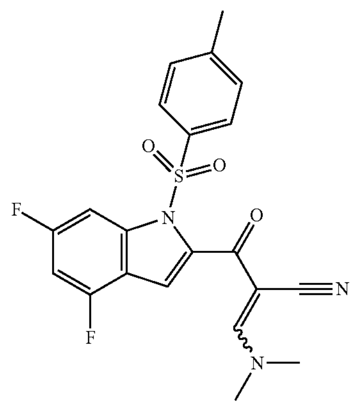 [SMILES: Cc1ccc(S(=O)(=O)n2c(C(=O)C(C#N)=CN(C)C)cc3c(F)cc(F)cc32)cc1] | 2-[4,6-difluoro-1-(toluene-4-sulfonyl)-1H-indole-2-carbonyl]-3-dimethylamino-acrylonitrile | 430 |
| 1541 | 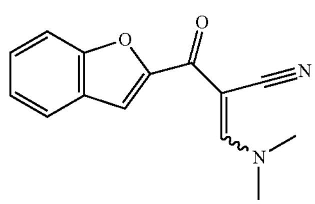 [SMILES: CN(C)C=C(C#N)C(=O)c1cc2ccccc2o1] | 2-(benzofuran-2-carbonyl)-3-dimethylamino-acrylonitrile | 241 |
| 1542 | 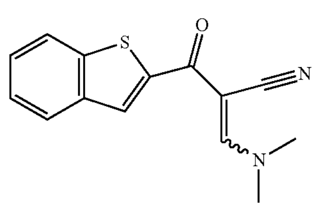 [SMILES: CN(C)C=C(C#N)C(=O)c1cc2ccccc2s1] | 2-(benzo[b]thiophene-2-carbonyl)-3-dimethylamino-acrylonitrile | 257 |
| 1543 | 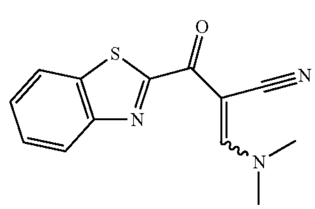 [SMILES: CN(C)C=C(C#N)C(=O)c1nc2ccccc2s1] | 2-(benzothiazole-2-carbonyl)-3-dimethylamino-acrylonitrile | 258 |

TABLE 9-continued

| Compound No. | Structure | Compound name | m/z |
|---|---|---|---|
| 1544 | 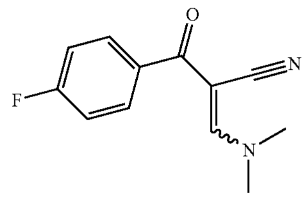 [SMILES: CN(C)C=C(C#N)C(=O)c1ccc(F)cc1] | 3-dimethylamino-2-(4-fluoro-benzoyl)-acrylonitrile | 219 |
| 1545 | 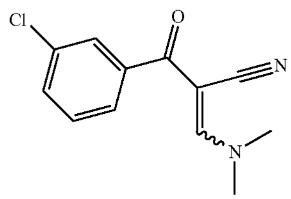 [SMILES: CN(C)C=C(C#N)C(=O)c1cccc(Cl)c1] | 2-(3-chloro-benzolyl)-3-dimethylamino-acrylonitrile | 235 |
| 1546 | 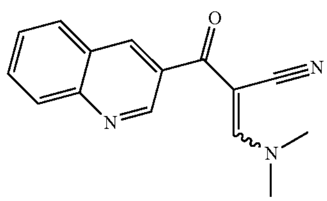 [SMILES: CN(C)C=C(C#N)C(=O)c1cnc2ccccc2c1] | 3-dimethylamino-2-(quinoline-3-carbonyl)-acrylonitrile | 252 |
| 1547 | 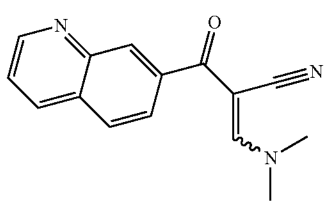 [SMILES: CN(C)C=C(C#N)C(=O)c1ccc2cccnc2c1] | 3-dimethylamino-2-(quinoline-7-carbonyl)-acrylonitrile | 252 |
| 1548 | 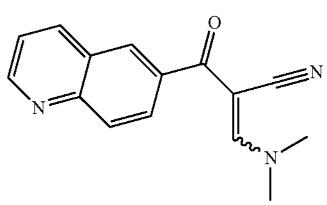 [SMILES: CN(C)C=C(C#N)C(=O)c1ccc2ncccc2c1] | 3-dimethylamino-2-(quinoline-6-carbonyl)-acrylonitrile | 252 |
| 1549 | 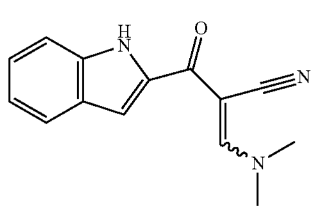 [SMILES: CN(C)C=C(C#N)C(=O)c1cc2ccccc2[nH]1] | 3-dimethylamino-2-(1H-indole-2-carbonyl)-acrylonitrile | 240 |

Step 3: Synthesis of 3-(1-benzenesulfonyl-1H-indol-2-yl)-3-oxo-propionitrile (1185)

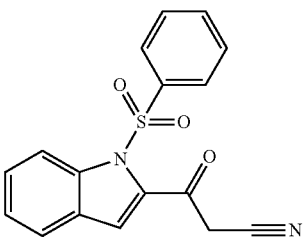 [SMILES: N#CCC(=O)c1cc2ccccc2n1S(=O)(=O)c1ccccc1]

Acetonitrile (10.6 g, 0.202 mol) was added to a tetrahydrofuran (THF) solution (135 ml) of 1-benzenesulfonyl-1H-indole-2-carboxylic acid ethyl ester (33.4 g, 0.101 mol), and cooled to −78° C. A tetrahydrofuran (THF) solution of 1 M lithium bis(trimethylsilyl) amide (213 ml, 0.213 mol) was added dropwise thereto, and stirred for 30 minutes. A saturated aqueous solution (83 ml) of ammonium chloride was added to the reaction mixture, and stirred for 10 minutes. Water (50 ml) was added to the mixture and warmed to room temperature. The solvent was distilled off under reduced pressure, and the resulting residue was extracted with ethyl acetate. The extract was washed with a saturated aqueous solution of sodium chloride and dried over anhydrous sodium sulfate. The desiccant was removed by filtration. The filtrate was concentrated under reduced pressure. The resulting crude product was washed with ethanol to give 3-(1-benzenesulfonyl-1H-indol-2-yl)-3-oxo-propionitrile (47.3 g, 70%).

$^1$H-NMR (CDCl$_3$) δ: 8.12 (1.0H, dq, J=8.5, 0.8 Hz), 7.79-7.76 (2.0H, m), 7.56-7.48 (3.0H, m), 7.42-7.38 (2.0H, m), 7.32-7.28 (1.0H, m), 7.20 (1.0H, d, J=0.8 Hz), 4.16 (2.0H, s)

ESI (LC-MS positive mode) m/z 325 [(M+H)$^+$]

The compounds of numbers 1186 to 1284, and 1550 to 1571 listed in Table 10 were synthesized by the same method as in Step 3.

TABLE 10

| Compound No. | Structure | Compound name | m/z |
|---|---|---|---|
| 1186 | 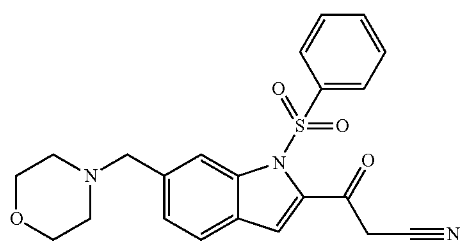 [SMILES: N#CCC(=O)c1cc2ccc(CN3CCOCC3)cc2n1S(=O)(=O)c1ccccc1] | 3-(1-benzenesulfonyl-6-morpholin-4-ylmethyl-1H-indol-2-yl)-3-oxo-propionitrile | 424 |
| 1187 | 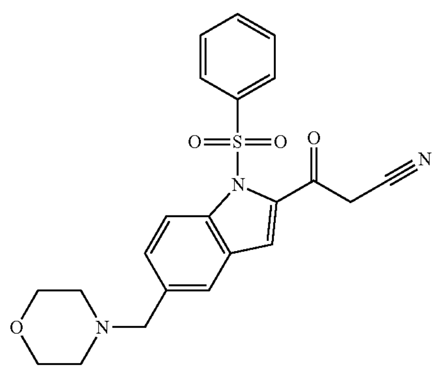 [SMILES: N#CCC(=O)c1cc2cc(CN3CCOCC3)ccc2n1S(=O)(=O)c1ccccc1] | 3-(1-benzenesulfonyl-5-morpholin-4-ylmethyl-1H-indol-2-yl)-3-oxo-propionitrile | 424 |
| 1188 | 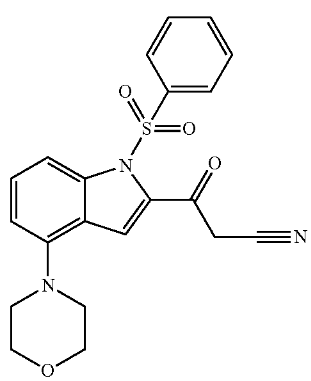 [SMILES: N#CCC(=O)c1cc2c(N3CCOCC3)cccc2n1S(=O)(=O)c1ccccc1] | 3-(1-benzenesulfonyl-4-morpholin-4-yl-1H-indol-2-yl)-3-oxo-propionitrile | 410 |

TABLE 10-continued

| Compound No. | Structure | Compound name | m/z |
|---|---|---|---|
| 1189 | 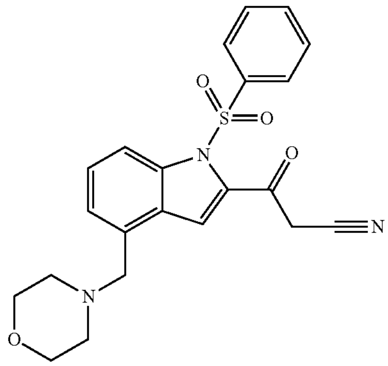 [SMILES: N#CCC(=O)c1cc2c(CN3CCOCC3)cccc2n1S(=O)(=O)c1ccccc1] | 3-(1-benzenesulfonyl-4-morpholin-4-ylmethyl-1H-indol-2-yl)-3-oxo-propionitrile | 424 |
| 1190 | 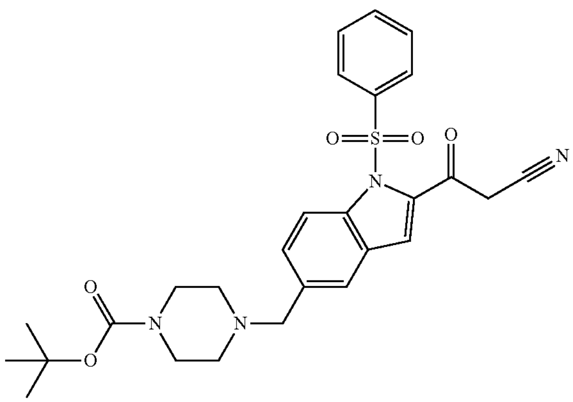 [SMILES: CC(C)(C)OC(=O)N1CCN(Cc2ccc3c(c2)cc(C(=O)CC#N)n3S(=O)(=O)c2ccccc2)CC1] | 4-[1-benzenesulfonyl-2-(2-cyanoacetyl)-1H-indol-5-ylmethyl]-piperazine-1-carboxylic acid tert-butyl ester | 523 |
| 1191 | 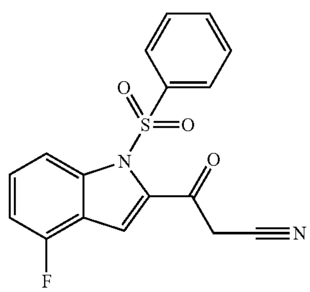 [SMILES: N#CCC(=O)c1cc2c(F)cccc2n1S(=O)(=O)c1ccccc1] | 3-(1-benzenesulfonyl-4-fluoro-1H-indol-2-yl)-3-oxo-propionitrile | 343 |
| 1192 | 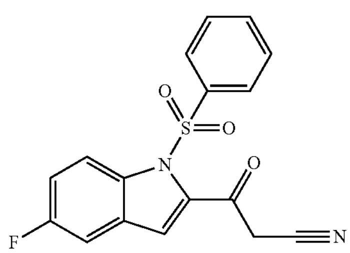 [SMILES: N#CCC(=O)c1cc2cc(F)ccc2n1S(=O)(=O)c1ccccc1] | 3-(1-benzenesulfonyl-5-fluoro-1H-indol-2-yl)-3-oxo-propionitrile | 343 |
| 1193 | 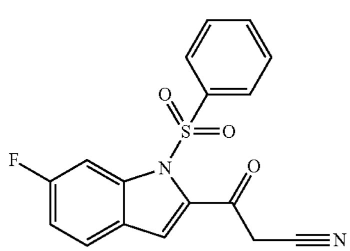 [SMILES: N#CCC(=O)c1cc2ccc(F)cc2n1S(=O)(=O)c1ccccc1] | 3-(1-benzenesulfonyl-6-fluoro-1H-indol-2-yl)-3-oxo-propionitrile | 343 |

TABLE 10-continued

| Compound No. | Structure | Compound name | m/z |
|---|---|---|---|
| 1194 | 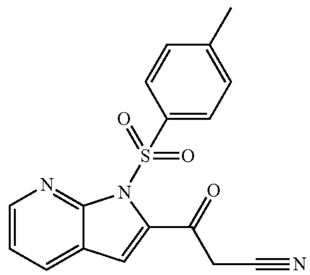 [SMILES: Cc1ccc(S(=O)(=O)n2c(C(=O)CC#N)cc3cccnc32)cc1] | 3-(1-benzenesulfonyl-1H-pyrrolo[2,3-b]pyridin-2-yl)-3-oxo-propionitrile | 340 |
| 1195 | 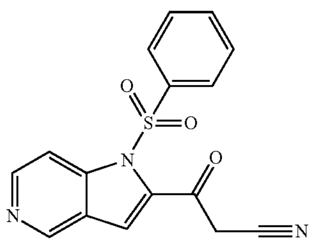 [SMILES: N#CCC(=O)c1cc2cnccc2n1S(=O)(=O)c1ccccc1] | 3-(1-benzenesulfonyl-1H-pyrrolo[3,2-c]pyridin-2-yl)-3-oxo-propionitrile | 326 |
| 1196 | 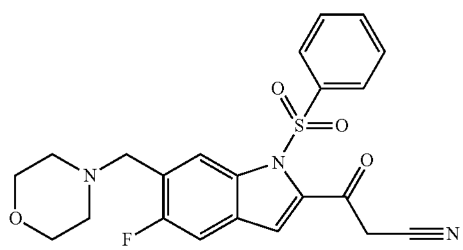 [SMILES: N#CCC(=O)c1cc2cc(F)c(CN3CCOCC3)cc2n1S(=O)(=O)c1ccccc1] | 3-(1-benzenesulfonyl-5-fluoro-6-morpholin-4-ylmethyl-1H-indol-2-yl)-3-oxo-propionitrile | 442 |
| 1197 | 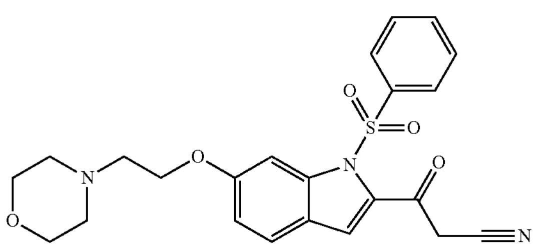 [SMILES: N#CCC(=O)c1cc2ccc(OCCN3CCOCC3)cc2n1S(=O)(=O)c1ccccc1] | 3-[1-benzenesulfonyl-6-(2-morpholin-4-yl-ethoxy)-1H-indol-2-yl]-3-oxo-propionitrile | 454 |
| 1198 | 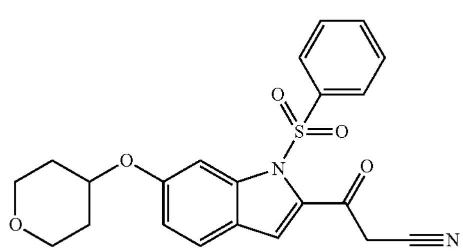 [SMILES: N#CCC(=O)c1cc2ccc(OC3CCOCC3)cc2n1S(=O)(=O)c1ccccc1] | 3-[1-benzenesulfonyl-6-(tetrahydro-pyran-4-yloxy)-1H-indol-2-yl]-3-oxo-propionitrile | 425 |

TABLE 10-continued

| Compound No. | Structure | Compound name | m/z |
|---|---|---|---|
| 1199 | 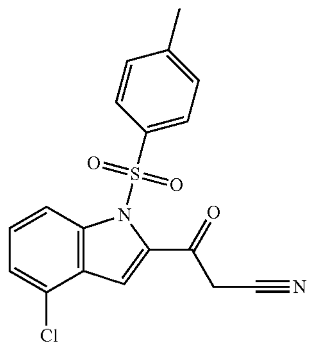 [SMILES: Cc1ccc(S(=O)(=O)n2c(C(=O)CC#N)cc3c(Cl)cccc32)cc1] | 3-[4-chloro-1-(toluene-4-sulfonyl)-1H-indol-2-yl]-3-oxo-propionitrile | 373, 375 |
| 1200 | 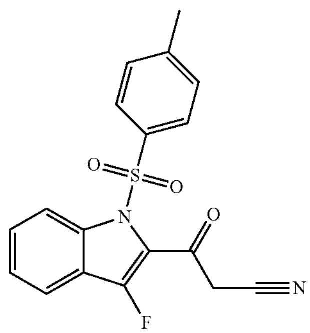 [SMILES: Cc1ccc(S(=O)(=O)n2c(C(=O)CC#N)c(F)c3ccccc32)cc1] | 3-[3-fluoro-1-(toluene-4-sulfonyl)-1H-indol-2-yl]-3-oxo-propionitrile | 357 |
| 1201 | 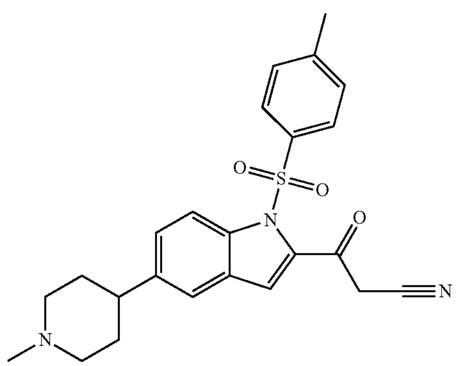 [SMILES: Cc1ccc(S(=O)(=O)n2c(C(=O)CC#N)cc3cc(C4CCN(C)CC4)ccc32)cc1] | 3-[5-(1-methyl-piperidin-4-yl)-1-(toluene-4-sulfonyl)-1H-indol-2-yl]-3-oxo-propionitrile | 436 |
| 1202 | 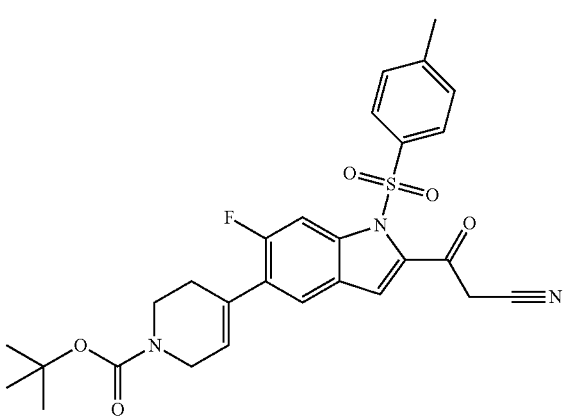 [SMILES: Cc1ccc(S(=O)(=O)n2c(C(=O)CC#N)cc3cc(C4=CCN(C(=O)OC(C)(C)C)CC4)c(F)cc32)cc1] | 4-[2-(2-cyano-acetyl)-6-fluoro-1-(toluene-4-sulfonyl)-1H-indol-5-yl]-3,6-dihydro-2H-pyridine-1-carboxylic acid tert-butyl ester | 538 |

TABLE 10-continued

| Compound No. | Structure | Compound name | m/z |
|---|---|---|---|
| 1203 | 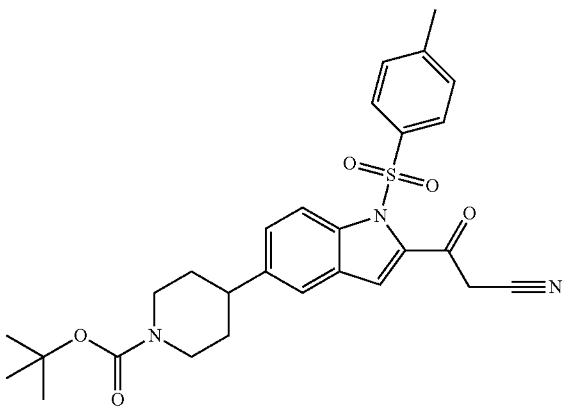 [SMILES: Cc1ccc(S(=O)(=O)n2c(C(=O)CC#N)cc3cc(C4CCN(C(=O)OC(C)(C)C)CC4)ccc32)cc1] | 4-[2-(2-cyano-acetyl)-1-(toluene-4-sulfonyl)-1H-indol-5-yl]-piperidine-1-carboxylic acid tert-butyl ester | 466 [M − tBu] |
| 1204 | 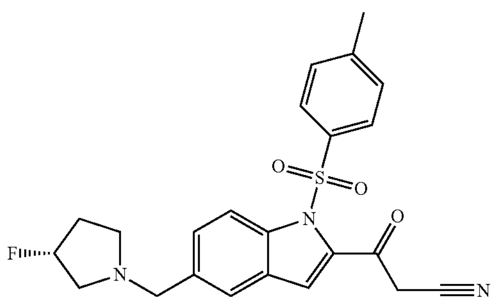 [SMILES: Cc1ccc(S(=O)(=O)n2c(C(=O)CC#N)cc3cc(CN4CC[C@@H](F)C4)ccc32)cc1] | 3-[5-((R)-3-fluoro-pyrrolidin-1-ylmethyl)-1-(toluene-4-sulfonyl)-1H-indol-2-yl]-3-oxo-propionitrile | 440 |
| 1205 | 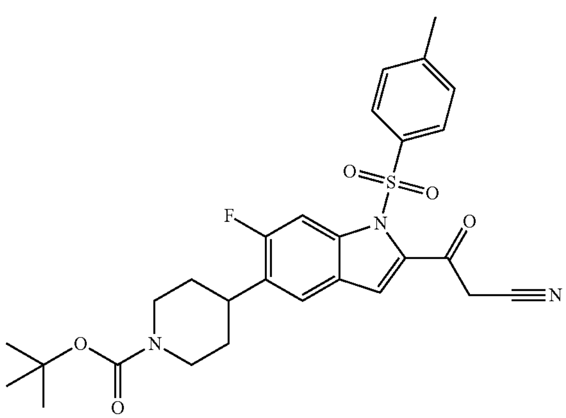 [SMILES: Cc1ccc(S(=O)(=O)n2c(C(=O)CC#N)cc3cc(C4CCN(C(=O)OC(C)(C)C)CC4)c(F)cc32)cc1] | 4-[2-(2-cyano-acetyl)-6-fluoro-1-(toluene-4-sulfonyl)-1H-indol-5-yl]-piperidine-1-carboxylic acid tert-butyl ester | 540 |
| 1206 | 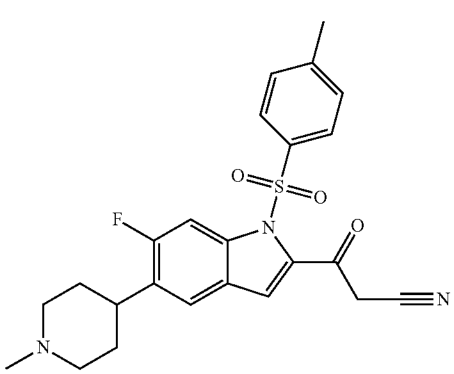 [SMILES: Cc1ccc(S(=O)(=O)n2c(C(=O)CC#N)cc3cc(C4CCN(C)CC4)c(F)cc32)cc1] | 3-[6-fluoro-5-(1-methyl-piperidin-4-yl)-1-(toluene-4-sulfonyl)-1H-indol-2-yl]-3-oxo-propionitrile | 454 |

TABLE 10-continued

| Compound No. | Structure | Compound name | m/z |
|---|---|---|---|
| 1207 | 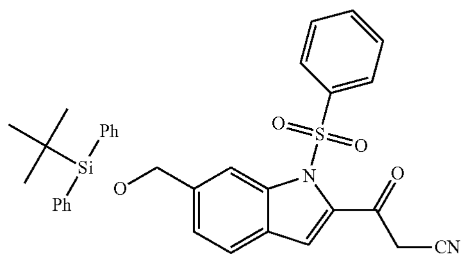 | 3-[1-benzenesulfonyl-6-(tert-butyl-diphenyl-silanyloxymethyl)-1H-indol-2-yl]-3-oxo-propionitrile | 593 |
| 1208 | 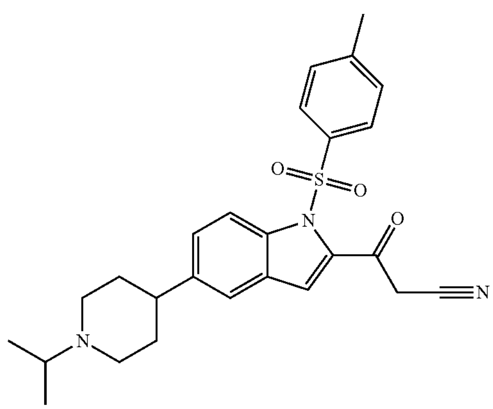 [SMILES: Cc1ccc(S(=O)(=O)n2c(C(=O)CC#N)cc3cc(C4CCN(C(C)C)CC4)ccc32)cc1] | 3-[5-(1-isopropyl-piperidin-4-yl)-1-(toluene-4-sulfonyl)-1H-indol-2-yl]-3-oxo-propionitrile | 464 |
| 1209 | 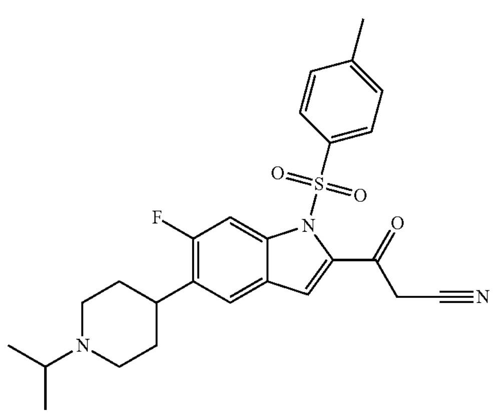 [SMILES: Cc1ccc(S(=O)(=O)n2c(C(=O)CC#N)cc3cc(C4CCN(C(C)C)CC4)c(F)cc32)cc1] | 3-[6-fluoro-5-(1-isopropyl-piperidin-4-yl)-1-(toluene-4-sulfonyl)-1H-indol-2-yl]-3-oxo-propionitrile | 482 |
| 1210 | 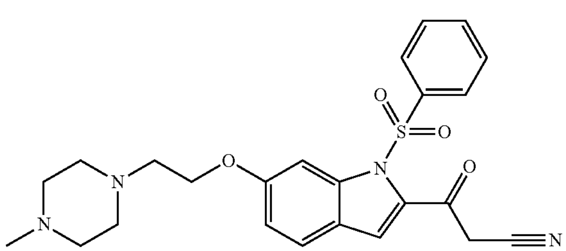 [SMILES: CN1CCN(CCOc2ccc3cc(C(=O)CC#N)n(S(=O)(=O)c4ccccc4)c3c2)CC1] | 3-{1-benzenesulfonyl-6-[2-(4-methyl-piperadin-1-yl)-ethoxy]-1H-indol-2-yl}-3-oxo-pr | 467 |

TABLE 10-continued

| Compound No. | Structure | Compound name | m/z |
|---|---|---|---|
| 1211 | 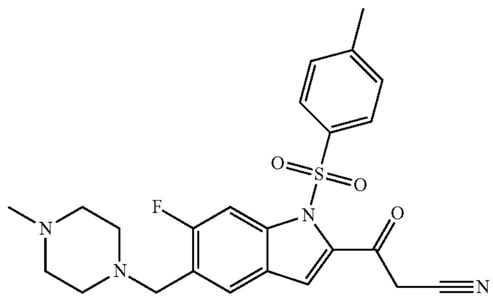 [SMILES: Cc1ccc(S(=O)(=O)n2c(C(=O)CC#N)cc3cc(CN4CCN(C)CC4)c(F)cc32)cc1] | 3-[6-fluoro-5-(4-methyl-piperadin-1-ylmethyl)-1-(toluene-4-sulfonyl)-1H-indol-2-yl]-3-oxo-propionitrile | 469 |
| 1212 | 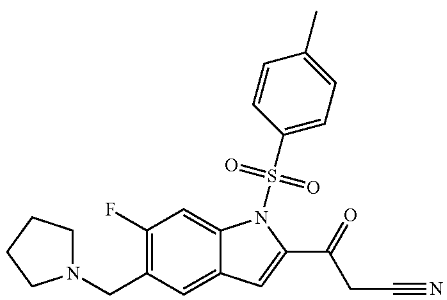 [SMILES: Cc1ccc(S(=O)(=O)n2c(C(=O)CC#N)cc3cc(CN4CCCC4)c(F)cc32)cc1] | 3-[6-fluoro-5-pyrrolidin-1-ylmethyl)-1-(toluene-4-sulfonyl)-1H-indol-2-yl]-3-oxo-propionitrile | 440 |
| 1213 | 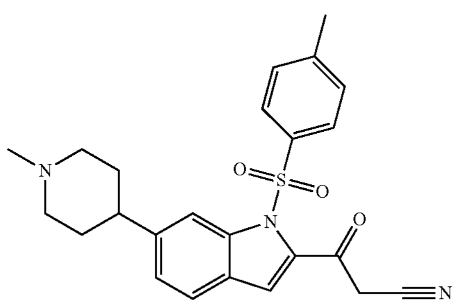 [SMILES: Cc1ccc(S(=O)(=O)n2c(C(=O)CC#N)cc3ccc(C4CCN(C)CC4)cc32)cc1] | 3-[6-(1-methyl-piperidin-4-yl)-1-(toluene-4-sulfonyl)-1H-indol-2-yl]-3-oxo-propionitrile | 436 |
| 1214 | 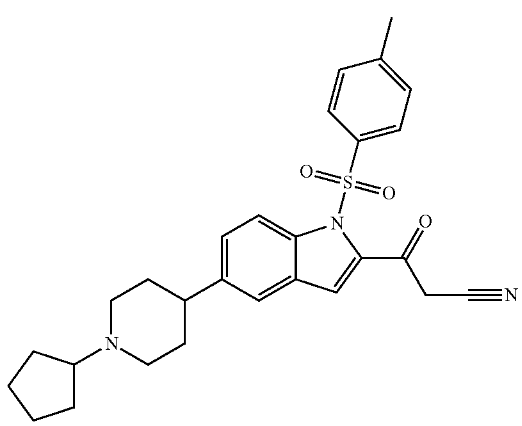 [SMILES: Cc1ccc(S(=O)(=O)n2c(C(=O)CC#N)cc3cc(C4CCN(C5CCCC5)CC4)ccc32)cc1] | 3-[5-(1-cyclopentyl-piperidin-4-yl)-1-(toluene-4-sulfonyl)-1H-indol-2-yl]-3-oxo-propionitrile | 490 |

TABLE 10-continued

| Compound No. | Structure | Compound name | m/z |
|---|---|---|---|
| 1215 | 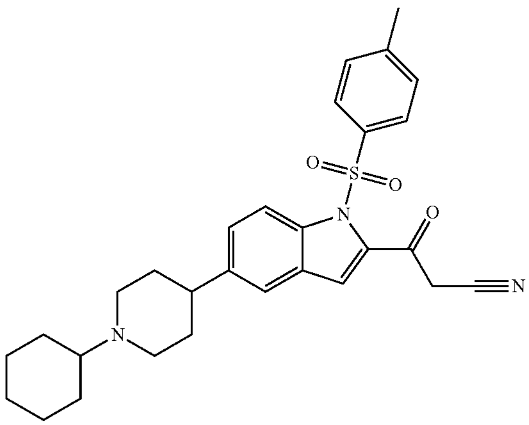 [SMILES: Cc1ccc(S(=O)(=O)n2c(C(=O)CC#N)cc3cc(C4CCN(C5CCCCC5)CC4)ccc32)cc1] | 3-[5-(1-cyclohexyl-piperidin-4-yl)-1-(toluene-4-sulfonyl)-1H-indol-2-yl]-3-oxo-propionitrile | 504 |
| 1216 | 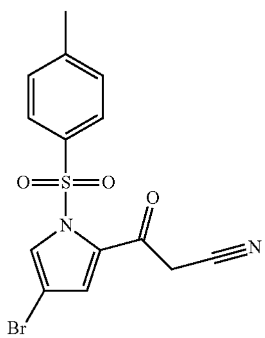 [SMILES: Cc1ccc(S(=O)(=O)n2cc(Br)cc2C(=O)CC#N)cc1] | 3-[4-bromo-1-(toluene-4-sulfonyl)-1H-pyrrol-2-yl]-3-oxo-propionitrile | 367, 369 |
| 1217 | 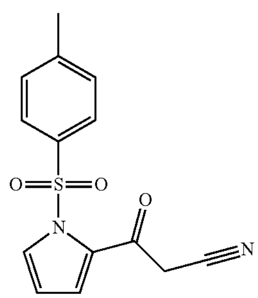 [SMILES: Cc1ccc(S(=O)(=O)n2cccc2C(=O)CC#N)cc1] | 3-oxo-3-[1-(toluene-4-sulfonyl)-1H-pyrrol-2-yl]-propionitrile | 289 |
| 1218 | 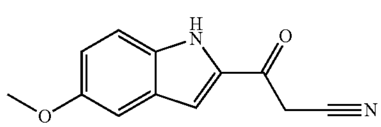 [SMILES: COc1ccc2[nH]c(C(=O)CC#N)cc2c1] | 3-(5-methoxy-1H-indol-2-yl)-3-oxo-propionitrile | 215 |
| 1219 | 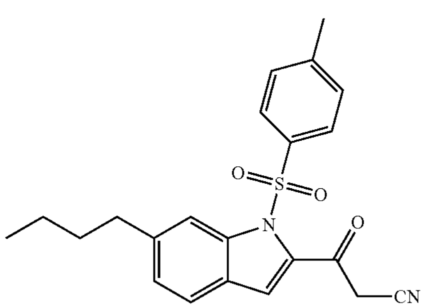 [SMILES: CCCCc1ccc2cc(C(=O)CC#N)n(S(=O)(=O)c3ccc(C)cc3)c2c1] | 3-[6-butyl-1-(toluene-4-sulfonyl)-1H-indol-2-yl]-3-oxo-propionitrile | 395 |

TABLE 10-continued

| Compound No. | Structure | Compound name | m/z |
|---|---|---|---|
| 1220 | 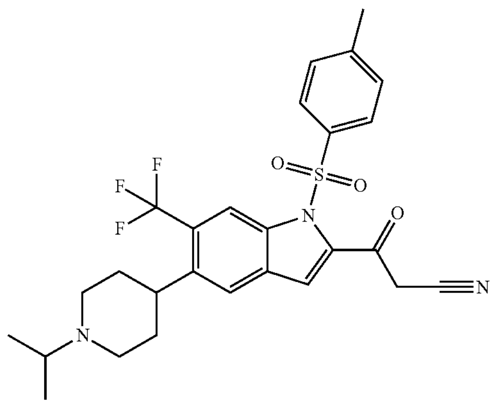 [SMILES: Cc1ccc(S(=O)(=O)n2c(C(=O)CC#N)cc3cc(C4CCN(C(C)C)CC4)c(C(F)(F)F)cc32)cc1] | 3-[5-(1-isopropyl-piperidin-4-yl)-1-(toluene-4-sulfonyl)-6-trifluoromethyl-1H-indol-2-yl]-3-oxo-propionitrile | 532 |
| 1221 | 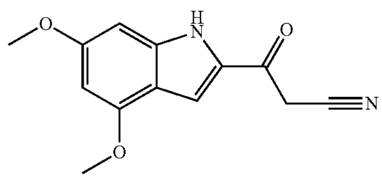 [SMILES: COc1cc(OC)c2cc(C(=O)CC#N)[nH]c2c1] | 3-(4,6-dimethoxy-1H-indol-2-yl)-3-propionitrile | 245 |
| 1222 | 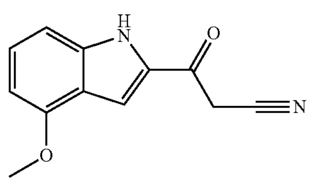 [SMILES: COc1cccc2[nH]c(C(=O)CC#N)cc12] | 3-(4-methoxy-1H-indol-2-yl)-3-oxo-propionitrile | 215 |
| 1223 | 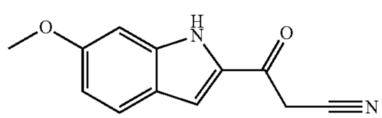 | 3-(6-methoxy-1H-indol-2-yl)-3-oxo-propionitrile | 215 |
| 1224 | 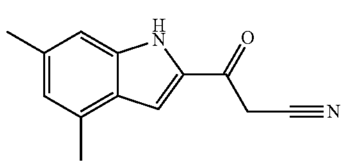 [SMILES: Cc1cc(C)c2cc(C(=O)CC#N)[nH]c2c1] | 3-(4,6-dimethyl-1H-indol-2-yl)-3-oxo-propionitrile | 213 |
| 1225 | 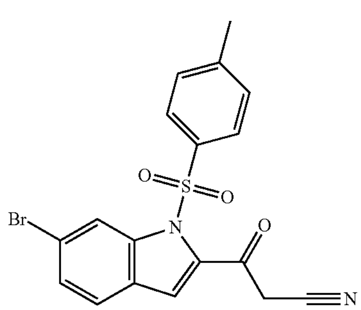 [SMILES: Cc1ccc(S(=O)(=O)n2c(C(=O)CC#N)cc3ccc(Br)cc32)cc1] | 3-[6-bromo-1-(toluene-4-sulfonyl)-1H-indol-2-yl]-3-oxo-propionitrile | 417, 419 |

TABLE 10-continued

| Compound No. | Structure | Compound name | m/z |
|---|---|---|---|
| 1226 | 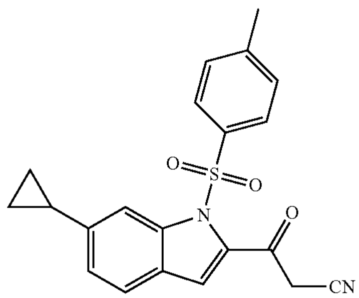 [SMILES: Cc1ccc(S(=O)(=O)n2c(C(=O)CC#N)cc3ccc(C4CC4)cc32)cc1] | 3-[6-cyclopropyl-1-(toluene-4-sulfonyl)-1H-indol-2-yl]-3-oxo-propionitrile | 379 |
| 1227 | 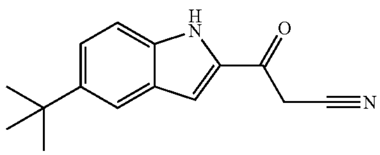 [SMILES: CC(C)(C)c1ccc2[nH]c(C(=O)CC#N)cc2c1] | 3-(5-tert-butyl-1H-indol-2-yl)-3-oxo-propionitrile | 241 |
| 1228 | 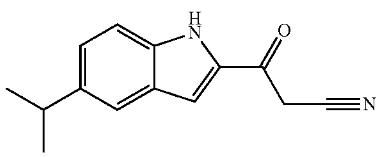 [SMILES: CC(C)c1ccc2[nH]c(C(=O)CC#N)cc2c1] | 3-(5-isopropyl-1H-indol-2-yl)-3-oxo-propionitrile | 227 |
| 1229 | 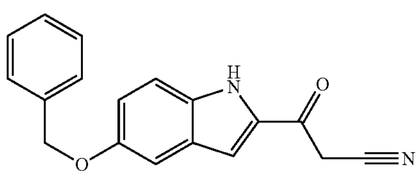 [SMILES: N#CCC(=O)c1cc2cc(OCc3ccccc3)ccc2[nH]1] | 3-(5-benzyloxy-1H-indol-2-yl)-3-oxo-propionitrile | 291 |
| 1230 | 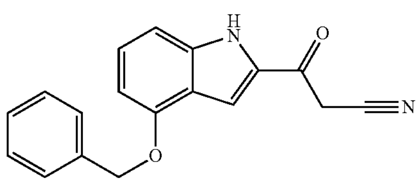 [SMILES: N#CCC(=O)c1cc2c(OCc3ccccc3)cccc2[nH]1] | 3-(4-benzyloxy-1H-indol-2-yl)-3-oxo-propionitrile | 291 |
| 1231 | 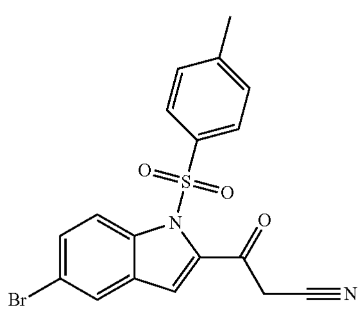 [SMILES: Cc1ccc(S(=O)(=O)n2c(C(=O)CC#N)cc3cc(Br)ccc32)cc1] | 3-[5-bromo-1-(toluene-4-sulfonyl)-1H-indol-2-yl]-3-oxo-propionitrile | 417, 419 |
| 1232 | 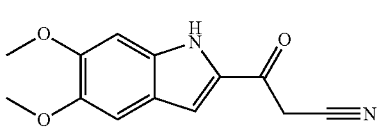 [SMILES: COc1cc2cc(C(=O)CC#N)[nH]c2cc1OC] | 3-(5,6-dimethoxy-1H-indol-2-yl)-3-oxo-propionitrile | 245 |

TABLE 10-continued

| Compound No. | Structure | Compound name | m/z |
|---|---|---|---|
| 1233 | 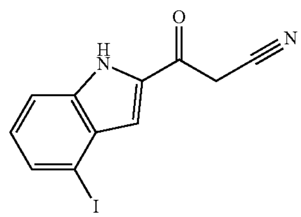 [SMILES: N#CCC(=O)c1cc2c(I)cccc2[nH]1] | 3-(4-iodo-1H-indol-2-yl)-3-oxo-propionitrile | 309 [M − H] |
| 1234 | 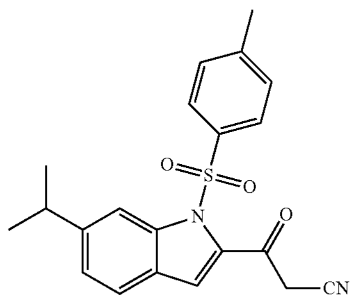 [SMILES: Cc1ccc(S(=O)(=O)n2c(C(=O)CC#N)cc3ccc(C(C)C)cc32)cc1] | 3-[6-isopropyl-1-(toluene-4-sulfonyl)-1H-indol-2-yl]-3-oxo-propionitrile | 381 |
| 1235 | 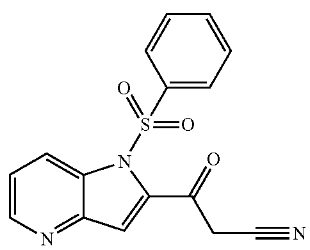 [SMILES: N#CCC(=O)c1cc2ncccc2n1S(=O)(=O)c1ccccc1] | 3-(1-benzenesulfonyl-1H-pyrrolo[3,2-b]pyridin-2-yl)-3-oxo-propionitrile | 326 |
| 1236 | 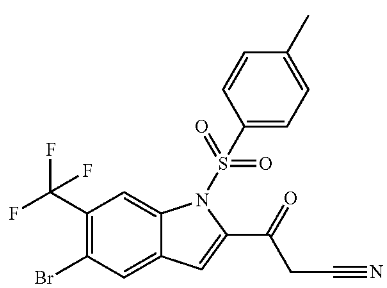 [SMILES: Cc1ccc(S(=O)(=O)n2c(C(=O)CC#N)cc3cc(Br)c(C(F)(F)F)cc32)cc1] | 3-[5-bromo-1-(toluene-4-sulfonyl)-6-trifluoromethyl-1H-indol-2-yl]-3-oxo-propionitrile | 483, 485 [M − H] |
| 1237 | 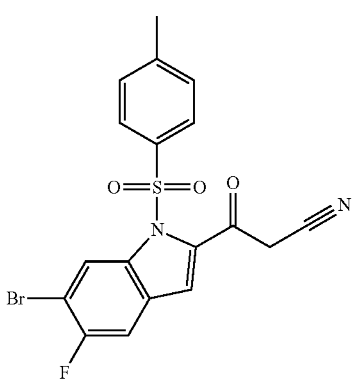 [SMILES: Cc1ccc(S(=O)(=O)n2c(C(=O)CC#N)cc3cc(F)c(Br)cc32)cc1] | 3-[6-bromo-5-fluoro-1-(toluene-4-sulfonyl)-1H-indol-2-yl]-3-oxo-propionitrile | 435, 437 |

TABLE 10-continued

| Compound No. | Structure | Compound name | m/z |
|---|---|---|---|
| 1238 | 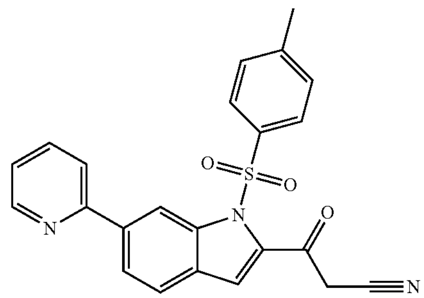 [SMILES: Cc1ccc(S(=O)(=O)n2c(C(=O)CC#N)cc3ccc(-c4ccccn4)cc32)cc1] | 3-oxo-3-[6-pyridin-2-yl-1-(toluene-4-sulfonyl)-1H-indol-2-yl]-propionitrile | 416 |
| 1239 | 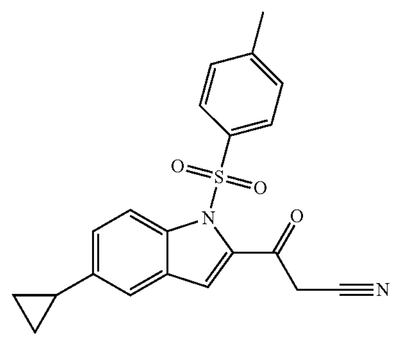 [SMILES: Cc1ccc(S(=O)(=O)n2c(C(=O)CC#N)cc3cc(C4CC4)ccc32)cc1] | 3-[5-cyclopropyl-1-(toluene-4-sulfonyl)-1H-indol-2-yl]-3-oxo-propionitrile | 379 |
| 1240 | 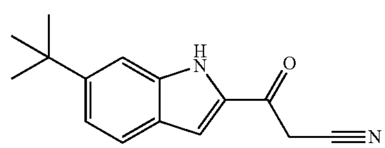 [SMILES: CC(C)(C)c1ccc2cc(C(=O)CC#N)[nH]c2c1] | 3-(6-tert-butyl-1H-indol-2-yl)-3-oxo-propionitrile | 241 |
| 1241 | 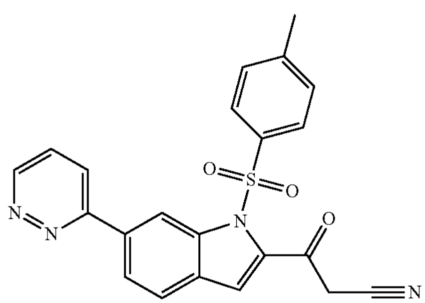 [SMILES: Cc1ccc(S(=O)(=O)n2c(C(=O)CC#N)cc3ccc(-c4cccnn4)cc32)cc1] | 3-oxo-3-[6-pyridazin-3-yl-1-(toluene-4-sulfonyl)-1H-indol-2-yl]-propionitrile | 417 |
| 1242 | 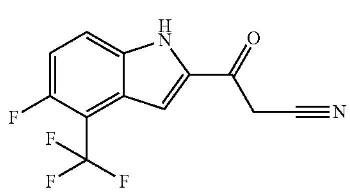 [SMILES: N#CCC(=O)c1cc2c(C(F)(F)F)c(F)ccc2[nH]1] | 3-(5-fluoro-4-trifluoromethyl-1H-indol-2-yl)-3-oxo-propionitrile | 269 [M − H] |
| 1243 | 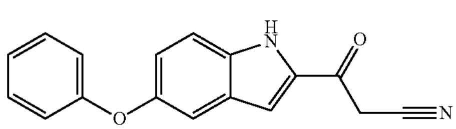 [SMILES: N#CCC(=O)c1cc2cc(Oc3ccccc3)ccc2[nH]1] | 3-oxo-3-(5-phenoxy-1H-indol-2-yl)-propionitrile | 277 |

TABLE 10-continued

| Compound No. | Structure | Compound name | m/z |
|---|---|---|---|
| 1244 | 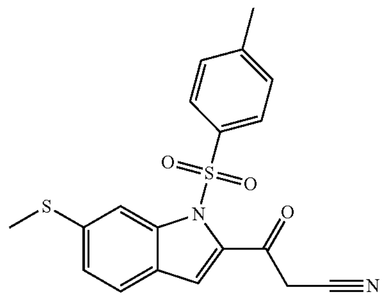 [SMILES: CSc1ccc2cc(C(=O)CC#N)n(S(=O)(=O)c3ccc(C)cc3)c2c1] | 3-[6-methylsulfanyl-1-(toluene-4-sulfonyl)-1H-indol-2-yl]-3-oxo-propionitrile | 385 |
| 1245 | 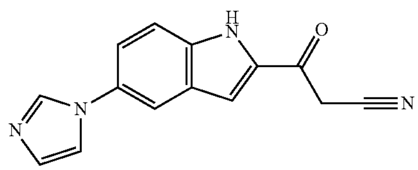 [SMILES: N#CCC(=O)c1cc2cc(-n3ccnc3)ccc2[nH]1] | 3-(5-imidazol-1-yl-1H-indol-2-yl)-3-oxo-propionitrile | 251 |
| 1246 | 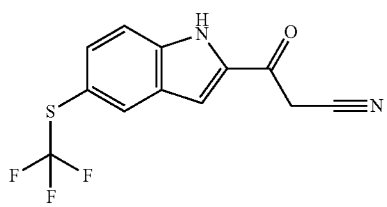 [SMILES: N#CCC(=O)c1cc2cc(SC(F)(F)F)ccc2[nH]1] | 3-oxo-3-(5-trifluoromethylsulfanyl-1H-indol-2-yl)-propionitrile | 285 |
| 1247 | 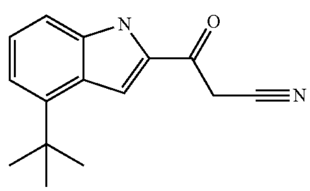 [SMILES: CC(C)(C)c1cccc2[nH]c(C(=O)CC#N)cc12] | 3-(4-tert-butyl-1H-indol-2-yl)-3-oxo-propionitrile | 241 |
| 1248 | 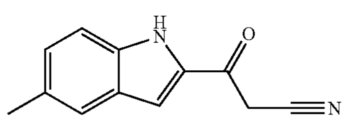 | 3-(5-methyl-1H-indol-2-yl)-3-oxo-propionitrile | 199 |
| 1249 | 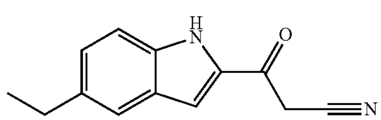 [SMILES: CCc1ccc2[nH]c(C(=O)CC#N)cc2c1] | 3-(5-ethyl-1H-indol-2-yl)-3-oxo-propionitrile | 213 |
| 1250 | 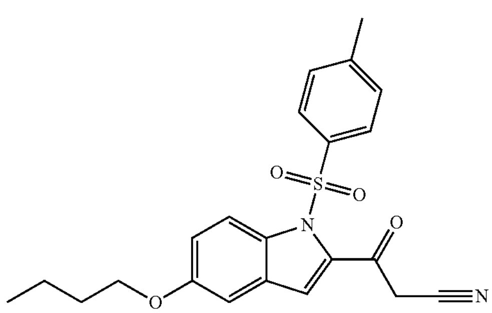 [SMILES: CCCCOc1ccc2c(c1)cc(C(=O)CC#N)n2S(=O)(=O)c1ccc(C)cc1] | 3-[5-butoxy-1-(toluene-4-sulfonyl)-1H-indol-2-yl]-3-oxo-propionitrile | 411 |

TABLE 10-continued

| Compound No. | Structure | Compound name | m/z |
|---|---|---|---|
| 1251 | 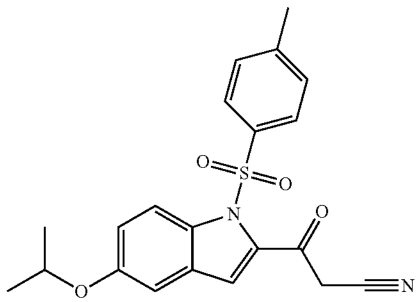 [SMILES: Cc1ccc(S(=O)(=O)n2c(C(=O)CC#N)cc3cc(OC(C)C)ccc32)cc1] | 3-[5-isopropoxy-1-(toluene-4-sulfonyl)-1H-indol-2-yl]-3-oxo-propionitrile | 397 |
| 1252 | 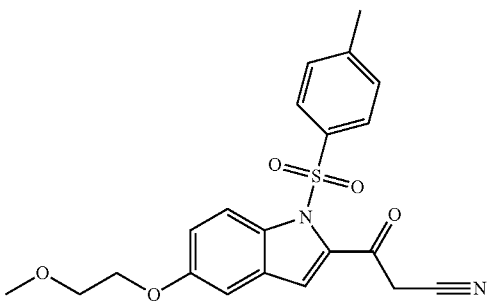 [SMILES: COCCOc1ccc2c(c1)cc(C(=O)CC#N)n2S(=O)(=O)c1ccc(C)cc1] | 3-[5-(2-methoxy-ethoxy)-1-(toluene-4-sulfonyl)-1H-indol-2-yl]-3-oxo-propionitrile | 413 |
| 1253 | 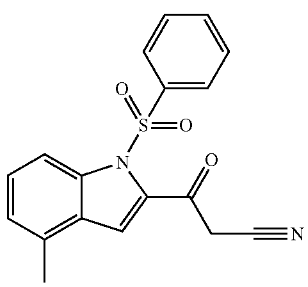 [SMILES: Cc1cccc2c1cc(C(=O)CC#N)n2S(=O)(=O)c1ccccc1] | 3-(1-benzenesulfonyl-4-methyl-1H-indol-2-yl)-3-oxo-propionitrile | 337 [M − H] |
| 1254 | 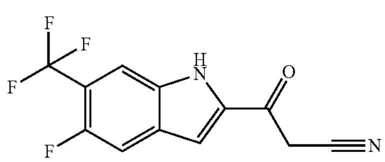 [SMILES: N#CCC(=O)c1cc2cc(F)c(C(F)(F)F)cc2[nH]1] | 3-(5-fluoro-6-trifluoromethyl-1H-indol-2-yl)-3-oxo-propionitrile | 269 [M − H] |
| 1255 | 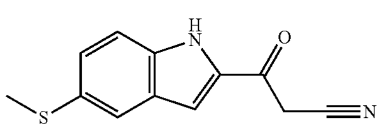 [SMILES: CSc1ccc2[nH]c(C(=O)CC#N)cc2c1] | 3-(5-methylsulfanyl-1H-indol-2-yl)-3-oxo-propionitrile | 231 |
| 1256 | 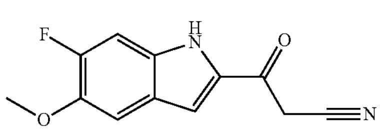 [SMILES: COc1cc2cc(C(=O)CC#N)[nH]c2cc1F] | 3-(6-fluoro-5-methoxy-1H-indol-2-yl)-3-oxo-propionitrile | 233 |

TABLE 10-continued

| Compound No. | Structure | Compound name | m/z |
|---|---|---|---|
| 1257 | 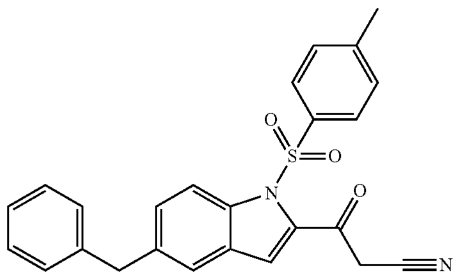 [SMILES: Cc1ccc(S(=O)(=O)n2c(C(=O)CC#N)cc3cc(Cc4ccccc4)ccc32)cc1] | 3-[5-benzyl-1-(toluene-4-sulfonyl)-1H-indol-2-yl]-3-oxo-propionitrile | 429 |
| 1258 | 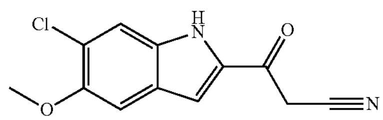 | 3-(6-chloro-5-methoxy-1H-indol-2-yl)-3-oxo-propionitrile | 249, 251 |
| 1259 | 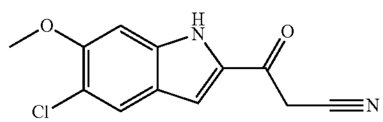 [SMILES: COc1cc2[nH]c(C(=O)CC#N)cc2cc1Cl] | 3-(5-chloro-6-methoxy-1H-indol-2-yl)-3-oxo-propionitrile | 249, 251 |
| 1260 | 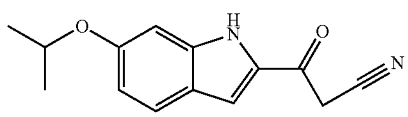 [SMILES: CC(C)Oc1ccc2cc(C(=O)CC#N)[nH]c2c1] | 3-(6-isopropoxy-1H-indol-2-yl)-3-propionitrile | 243 |
| 1261 | 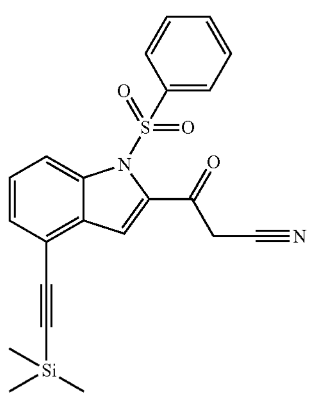 [SMILES: C[Si](C)(C)C#Cc1cccc2c1cc(C(=O)CC#N)n2S(=O)(=O)c1ccccc1] | 3-(1-benzenesulfonyl-4-trimethylsilanylethynyl-1H-indol-2-yl)-3-oxo-propionitrile | 421 |
| 1262 | 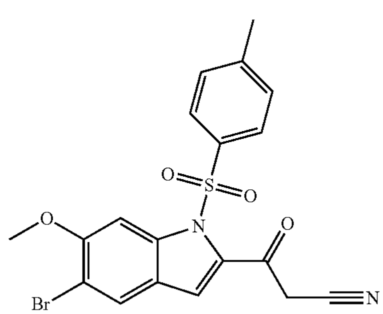 [SMILES: COc1cc2c(cc1Br)cc(C(=O)CC#N)n2S(=O)(=O)c1ccc(C)cc1] | 3-[5-bromo-6-methoxy-1-(toluene-4-sulfonyl)-1H-indol-2-yl]-3-oxo-propionitrile | 447, 449 |

| Compound No. | Structure | Compound name | m/z |
|---|---|---|---|
| 1263 | 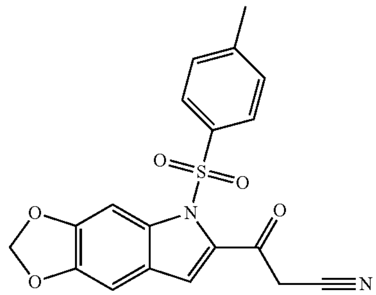 [SMILES: Cc1ccc(S(=O)(=O)n2c(C(=O)CC#N)cc3cc4c(cc32)OCO4)cc1] | 3-oxo-3-[5-(toluene-4-sulfonyl)-5H-[1,3]dioxolo[4,5-f]indol-6-yl]-propionitrile | 383 |
| 1264 | 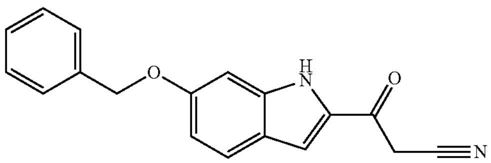 [SMILES: N#CCC(=O)c1cc2ccc(OCc3ccccc3)cc2[nH]1] | 3-(6-benzyloxy-1H-indol-2-yl)-3-oxo-propionitrile | 291 |
| 1265 | 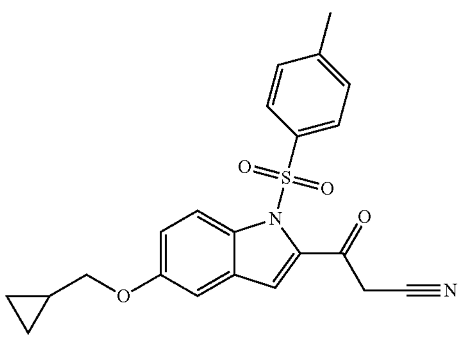 [SMILES: Cc1ccc(S(=O)(=O)n2c(C(=O)CC#N)cc3cc(OCC4CC4)ccc32)cc1] | 3-[5-cyclopropylmethoxy-1-(toluene-4-sulfonyl)-1H-indol-2-yl]-3-oxo-propionitrile | 409 |
| 1266 | 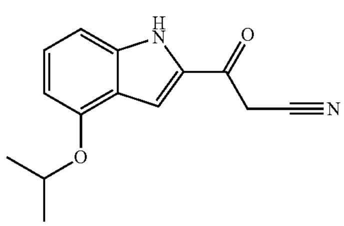 [SMILES: CC(C)Oc1cccc2[nH]c(C(=O)CC#N)cc12] | 3-(4-isopropoxy-1H-indol-2-yl)-3-propionitrile | 243 |
| 1267 | 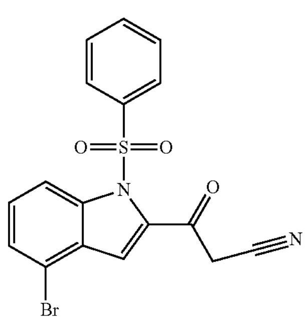 [SMILES: N#CCC(=O)c1cc2c(Br)cccc2n1S(=O)(=O)c1ccccc1] | 3-(1-benzenesulfonyl-4-bromo-1H-indol-2-yl)-3-oxo-propionitrile | 403, 405 |

TABLE 10-continued

| Compound No. | Structure | Compound name | m/z |
|---|---|---|---|
| 1268 | 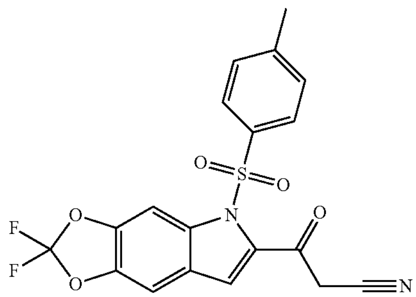 [SMILES: Cc1ccc(S(=O)(=O)n2c(C(=O)CC#N)cc3cc4c(cc32)OC(F)(F)O4)cc1] | 3-[2,2-difluoro-5-(toluene-4-sulfonyl)-5H-[1,3]dioxolo[4,5-f]indol-6-yl]-3-oxo-propionitrile | 419 |
| 1269 | 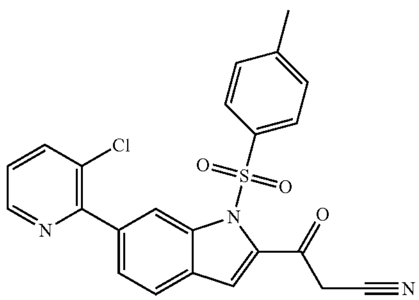 [SMILES: Cc1ccc(S(=O)(=O)n2c(C(=O)CC#N)cc3ccc(-c4ncccc4Cl)cc32)cc1] | 3-[6-(3-chloro-pyridin-2-yl)-1-(toluene-4-sulfonyl)-1H-indol-2-yl]-3-oxo-propionitrile | 450, 452 |
| 1270 | 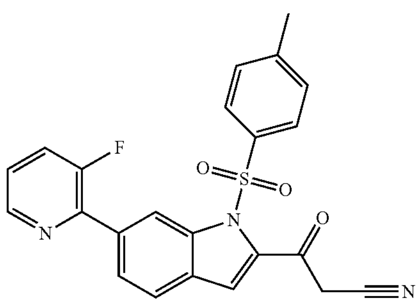 | 3-[6-(3-fluoro-pyridin-2-yl)-1-(toluene-4-sulfonyl)-1H-indol-2-yl]-3-oxo-propionitrile | 434 |
| 1271 | 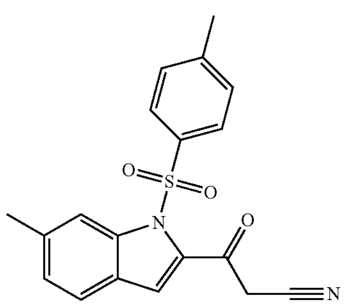 [SMILES: Cc1ccc(S(=O)(=O)n2c(C(=O)CC#N)cc3ccc(C)cc32)cc1] | 3-[6-methyl-1-(toluene-4-sulfonyl)-1H-indol-2-yl]-3-oxo-propionitrile | 353 |
| 1272 | 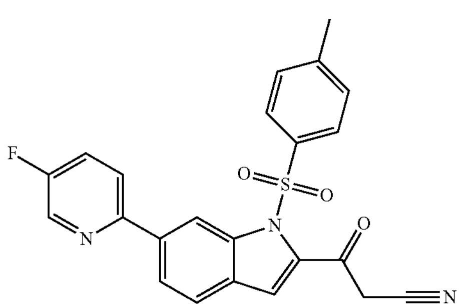 [SMILES: Cc1ccc(S(=O)(=O)n2c(C(=O)CC#N)cc3ccc(-c4ccc(F)cn4)cc32)cc1] | 3-[6-(5-fluoro-pyridin-2-yl)-1-(toluene-4-sulfonyl)-1H-indol-2-yl]-3-oxo-propionitrile | 434 |

TABLE 10-continued

| Compound No. | Structure | Compound name | m/z |
|---|---|---|---|
| 1273 | 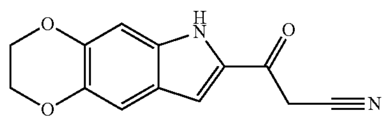 [SMILES: N#CCC(=O)c1cc2cc3c(cc2[nH]1)OCCO3] | 3-{2,3-dihydro-6H-[1,4]dioxino[2,3-f]indol-7-yl)-3-oxo-propionitrile | 243 |
| 1274 | 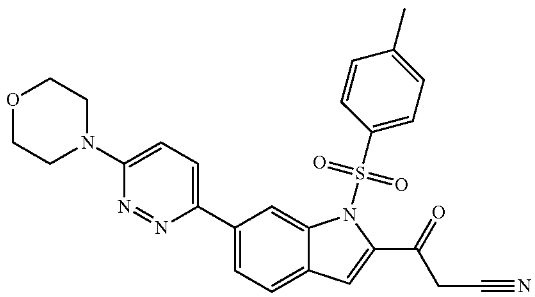 [SMILES: Cc1ccc(S(=O)(=O)n2c(C(=O)CC#N)cc3ccc(-c4ccc(N5CCOCC5)nn4)cc32)cc1] | 3-[6-(6-morpholin-4-yl-pyridazin-3-yl)-1-(toluene-4-sulfonyl)-1H-indol-2-yl]-3-oxo-propionitrile | 502 |
| 1275 | 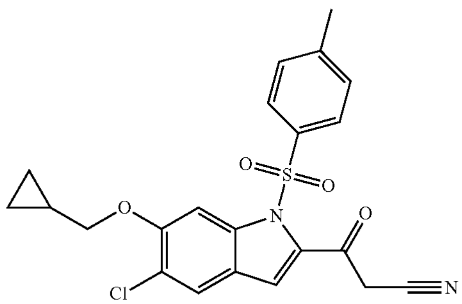 [SMILES: Cc1ccc(S(=O)(=O)n2c(C(=O)CC#N)cc3cc(Cl)c(OCC4CC4)cc32)cc1] | 3-[5-chloro-6-cyclopropylmethoxy-1-(toluene-4-sulfonyl)-1H-indol-2-yl]-3-oxo-propionitrile | 443, 445 |
| 1276 | 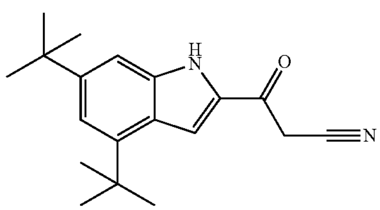 [SMILES: CC(C)(C)c1cc(C(C)(C)C)c2cc(C(=O)CC#N)[nH]c2c1] | 3-(4,6-di-tert-butyl-1H-indole-2-yl)-3-oxopropionitrile | 352 |
| 1277 | 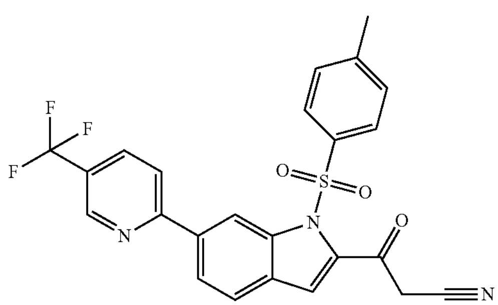 [SMILES: Cc1ccc(S(=O)(=O)n2c(C(=O)CC#N)cc3ccc(-c4ccc(C(F)(F)F)cn4)cc32)cc1] | 3-oxo-3-[1-(toluene-4-sulfonyl)-6-(5-trifluoromethyl-pyridin-2-yl)-1H-indol-2-yl]-propionitrile | 484 |
| 1278 | 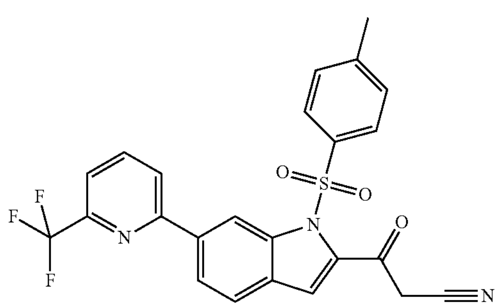 [SMILES: Cc1ccc(S(=O)(=O)n2c(C(=O)CC#N)cc3ccc(-c4cccc(C(F)(F)F)n4)cc32)cc1] | 3-oxo-3-[1-(toluene-4-sulfonyl)-6-(6-trifluoromethyl-pyridin-2-yl)-1H-indol-2-yl]-propionitrile | 484 |

TABLE 10-continued

| Compound No. | Structure | Compound name | m/z |
|---|---|---|---|
| 1279 | 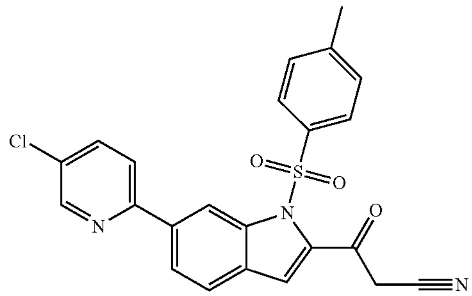 [SMILES: Cc1ccc(S(=O)(=O)n2c(C(=O)CC#N)cc3ccc(-c4ccc(Cl)cn4)cc32)cc1] | 3-[6-(5-chloro-pyridin-2-yl)-1-(toluene-4-sulfonyl)-1H-indol-2-yl]-3-oxo-propionitrile | 450, 452 |
| 1280 | 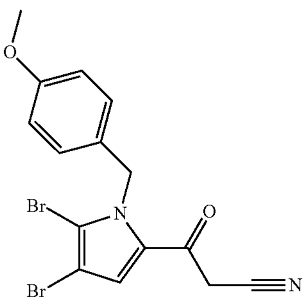 [SMILES: COc1ccc(Cn2c(C(=O)CC#N)cc(Br)c2Br)cc1] | 3-[4,5-dibromo-1-(4-methoxy-benzyl)-1H-pyrrol-2-yl]-3-oxo-propionitrile | 411, 413, 415 |
| 1281 | 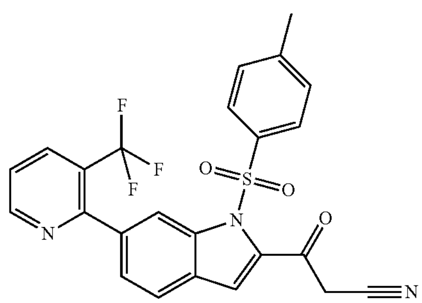 [SMILES: Cc1ccc(S(=O)(=O)n2c(C(=O)CC#N)cc3ccc(-c4ncccc4C(F)(F)F)cc32)cc1] | 3-oxo-3-[1-(toluene-4-sulfonyl)-6-(3-trifluoromethyl-pyridin-2-yl)-1H-indol-2-yl]-propionitrile | 484 |
| 1282 | 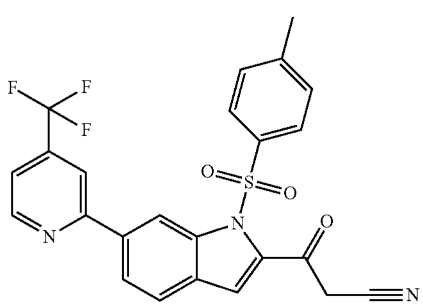 [SMILES: Cc1ccc(S(=O)(=O)n2c(C(=O)CC#N)cc3ccc(-c4cc(C(F)(F)F)ccn4)cc32)cc1] | 3-oxo-3-[1-(toluene-4-sulfonyl)-6-(4-trifluoromethyl-pyridin-2-yl)-1H-indol-2-yl]-propionitrile | 484 |
| 1283 | 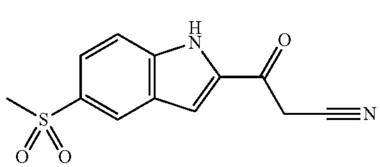 [SMILES: CS(=O)(=O)c1ccc2[nH]c(C(=O)CC#N)cc2c1] | 3-(5-methanesulfonyl-1H-indol-2-yl)-3-oxo-propionitrile | 263 |

TABLE 10-continued

| Compound No. | Structure | Compound name | m/z |
|---|---|---|---|
| 1284 | 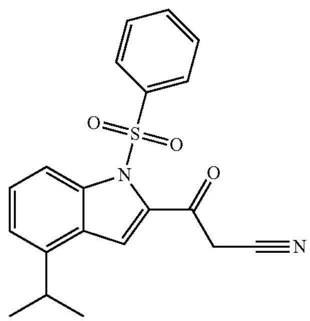 [SMILES: CC(C)c1cccc2c1cc(C(=O)CC#N)n2S(=O)(=O)c1ccccc1] | 3-(1-benzenesulfonyl-4-isopropyl-1H-indol-2-yl)-3-oxo-propionitrile | 367 |
| 1550 | 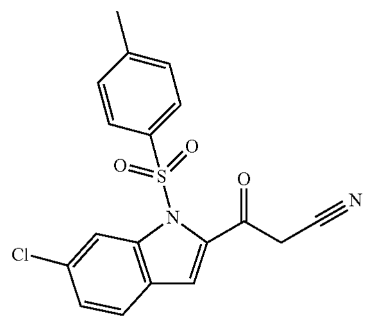 [SMILES: Cc1ccc(S(=O)(=O)n2c(C(=O)CC#N)cc3ccc(Cl)cc32)cc1] | 3-[6-chloro-1-(toluene-4-sulfonyl)-1H-indol-2-yl]-3-oxo-propionitrile | 373 |
| 1551 | 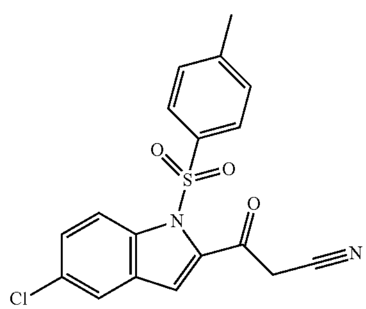 [SMILES: Cc1ccc(S(=O)(=O)n2c(C(=O)CC#N)cc3cc(Cl)ccc32)cc1] | 3-[5-chloro-1-(toluene-4-sulfonyl)-1H-indol-2-yl]-3-oxo-propionitrile | 373 |
| 1552 | 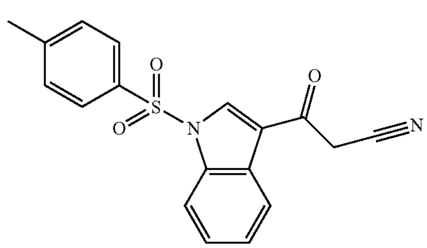 [SMILES: Cc1ccc(S(=O)(=O)n2cc(C(=O)CC#N)c3ccccc32)cc1] | 3-oxo-3-[1-(toluene-4-sulfonyl)-1H-indol-3-yl]-propionitrile | 339 |
| 1553 | 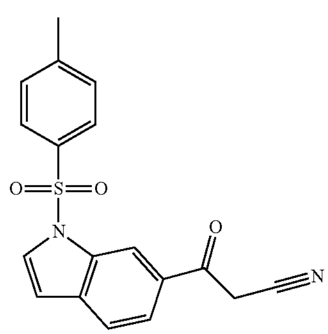 [SMILES: Cc1ccc(S(=O)(=O)n2ccc3ccc(C(=O)CC#N)cc32)cc1] | 3-oxo-3-[1-(toluene-4-sulfonyl)-1H-indol-6-yl]-propionitrile | 339 |

TABLE 10-continued

| Compound No. | Structure | Compound name | m/z |
|---|---|---|---|
| 1554 | 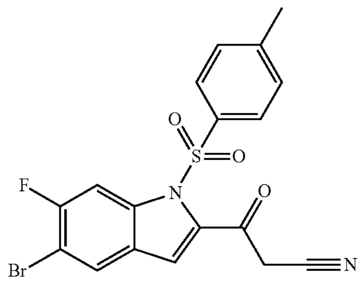 [SMILES: Cc1ccc(S(=O)(=O)n2c(C(=O)CC#N)cc3cc(Br)c(F)cc32)cc1] | 3-[5-bromo-6-fluoro-1-(toluene-4-sulfonyl)-1H-indol-2-yl]-3-oxo-propionitrile | 435 |
| 1555 | 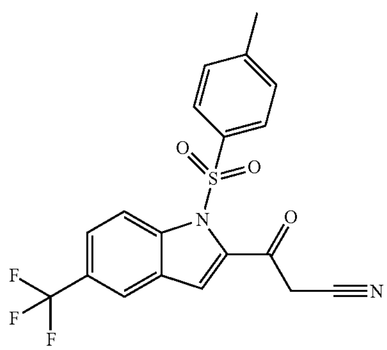 [SMILES: Cc1ccc(S(=O)(=O)n2c(C(=O)CC#N)cc3cc(C(F)(F)F)ccc32)cc1] | 3-oxo-3-[1-(toluene-4-sulfonyl)-5-trifluoromethyl-1H-indol-2-yl]-propionitrile | 407 |
| 1556 | 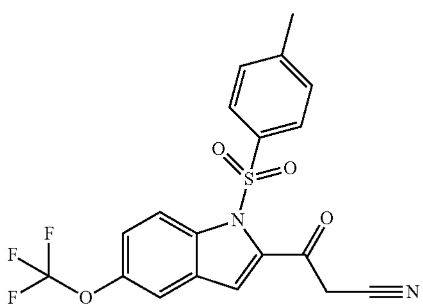 [SMILES: Cc1ccc(S(=O)(=O)n2c(C(=O)CC#N)cc3cc(OC(F)(F)F)ccc32)cc1] | 3-oxo-3-[1-(toluene-4-sulfonyl)-5-trifluoromethoxy-1H-indol-2-yl]-propionitrile | 423 |
| 1557 | 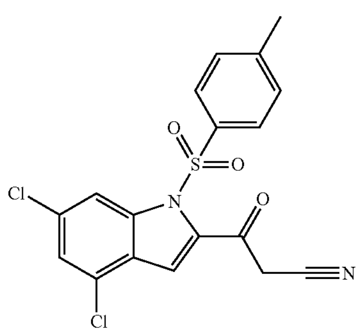 [SMILES: Cc1ccc(S(=O)(=O)n2c(C(=O)CC#N)cc3c(Cl)cc(Cl)cc32)cc1] | 3-[4,6-dichloro-1-(toluene-4-sulfonyl)-1H-indol-2-yl]-3-oxo-propionitrile | 407 |

TABLE 10-continued

| Compound No. | Structure | Compound name | m/z |
|---|---|---|---|
| 1558 | 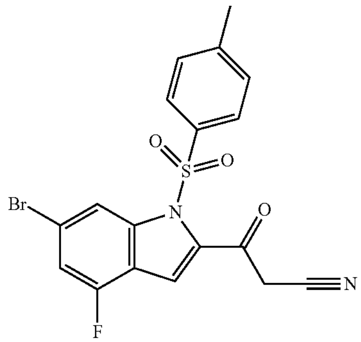 [SMILES: Cc1ccc(S(=O)(=O)n2c(C(=O)CC#N)cc3c(F)cc(Br)cc32)cc1] | 3-[6-bromo-4-fluoro-1-(toluene-4-sulfonyl)-1H-indol-2-yl]-3-oxo-propionitrile | 435 |
| 1559 | 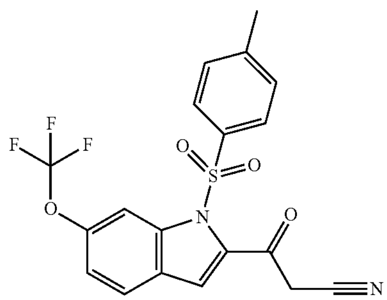 [SMILES: Cc1ccc(S(=O)(=O)n2c(C(=O)CC#N)cc3ccc(OC(F)(F)F)cc32)cc1] | 3-oxo-3-[1-(toluene-4-sulfonyl)-6-trifluoromethoxy-1H-indol-2-yl]-propionitrile | 423 |
| 1560 | 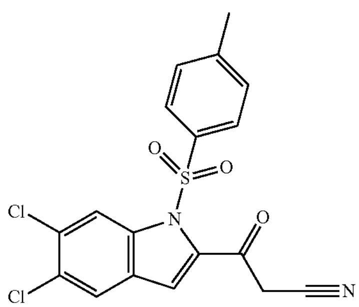 [SMILES: Cc1ccc(S(=O)(=O)n2c(C(=O)CC#N)cc3cc(Cl)c(Cl)cc32)cc1] | 3-[5,6-dichloro-1-(toluene-4-sulfonyl)-1H-indol-2-yl]-3-oxo-propionitrile | 407 |
| 1561 | 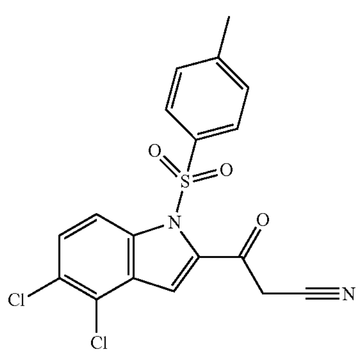 [SMILES: Cc1ccc(S(=O)(=O)n2c(C(=O)CC#N)cc3c(Cl)c(Cl)ccc32)cc1] | 3-[4,5-dichloro-1-(toluene-4-sulfonyl)-1H-indol-2-y]-3-oxo-propionitrile | 407 |

TABLE 10-continued
| Compound No. | Structure | Compound name | m/z |
|---|---|---|---|
| 1562 | 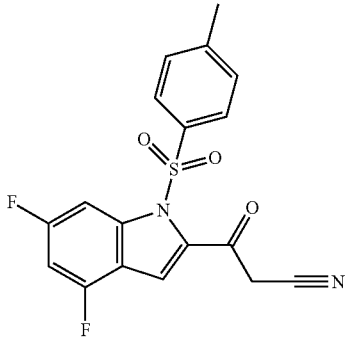 [SMILES: Cc1ccc(S(=O)(=O)n2c(C(=O)CC#N)cc3c(F)cc(F)cc32)cc1] | 3-[4,6-difluoro-1-(toluene-4-sulfonyl)-1H-indol-2-yl]-3-oxo-propionitrile | 375 |
| 1563 | 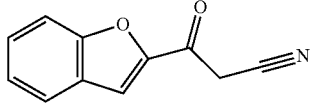 | 3-benzofuran-2-yl-3-oxo-propionitrile | 186 |
| 1564 | 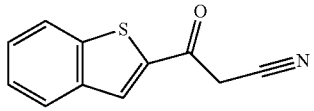 [SMILES: N#CCC(=O)c1cc2ccccc2o1] | 3-benzo[b]thiophen-2-yl-3-oxo-propionitrile | 202 |
| 1565 | 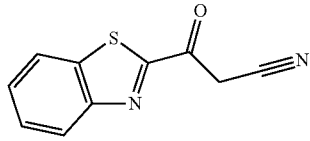 [SMILES: N#CCC(=O)c1nc2ccccc2s1] | 3-benzothiazol-2-yl-3-oxo-propionitrile | 203 |
| 1566 | 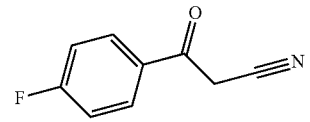 [SMILES: N#CCC(=O)c1ccc(F)cc1] | 3-(4-fluoro-phenyl)-3-oxo-propionitrile | 164 |
| 1567 | 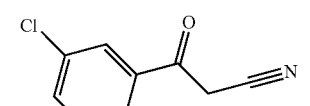 | 3-(3-chloro-phenyl)-3-oxo-propionitrile | 180 |
| 1568 | 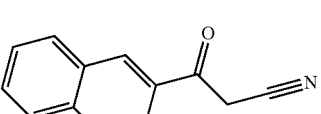 | 3-oxo-3-quinolin-3-yl-propionitrile | 197 |
| 1569 | 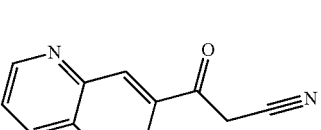 | 3-oxo-3-quinolin-7-yl-propionitrile | 197 |

TABLE 10-continued

| Compound No. | Structure | Compound name | m/z |
|---|---|---|---|
| 1570 | 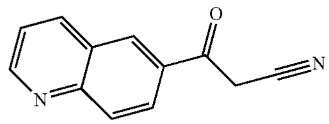 [SMILES: N#CCC(=O)c1ccc2ncccc2c1] | 3-oxo-3-quinolin-6-yl-propionitrile | 197 |
| 1571 | 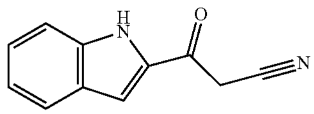 [SMILES: N#CCC(=O)c1cc2ccccc2[nH]1] | 3-(1H-indol-2-yl)-3-oxo-propionitrile | 185 |

Step 4: Synthesis of 1-benzenesulfonyl-1H-indole-2-carboxylic acid ethyl ester (1285)

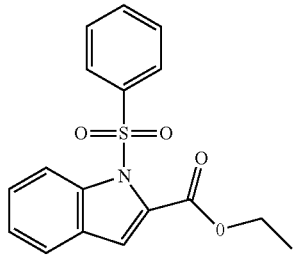

With cooling on ice, an anhydrous N,N-dimethylformamide (DMF) solution (70 ml) of 1H-indole-2-carboxylic acid ethyl ester (45 g, 0.238 mol) was added dropwise to a solution of 50% sodium hydride (13.7 g, 0.286 mol) in anhydrous N,N-dimethylformamide (DMF) (90 ml). After one and half hour of stirring with cooling on ice, the reaction mixture was warmed to room temperature, and then stirred for one hour. After cooling on ice, an anhydrous N,N-dimethylformamide (DMF) solution of benzenesulfonyl chloride (50.4 g) was added dropwise, and the resulting mixture was stirred for one hour. An aqueous solution of 0.5 N hydrochloric acid was added dropwise to the reaction mixture, and then water was added thereto. The mixture was stirred for 30 minutes. The resulting solid was collected by filtration, and washed with water and then with n-hexane. The solid was dissolved in ethyl acetate, and washed with a saturated aqueous solution of sodium bicarbonate and then with a saturated aqueous solution of sodium chloride. The organic layer was dried over anhydrous sodium sulfate. The desiccant was removed by filtration. The filtrate was concentrated under reduced pressure to give crude 1-benzenesulfonyl-1H-indole-2-carboxylic acid ethyl ester. The obtained crude product was recrystallized (ethyl acetate/hexane) to give 1-benzenesulfonyl-1H-indole-2-carboxylic acid ethyl ester (68.9 g, 79%).

$^1$H-NMR (CDCl$_3$) δ: 8.12 (1H, d, J=8.3 Hz), 8.04 (2H, d, J=7.8 Hz), 7.60-7.52 (2H, m), 7.51-7.40 (3H, m), 7.31-7.21 (1H, m), 7.17 (1H, s), 4.40 (2H, q, J=7.0 Hz), 1.39 (3H, t, J=7.0 Hz)

ESI (LC-MS positive mode) m/z 330 [(M+H)$^+$]

The compounds of numbers 1286 to 1312 listed in Table 11 were synthesized by the same method as in Step 4.

TABLE 11

| Compound No. | Structure | Compound name | m/z |
|---|---|---|---|
| 1286 | 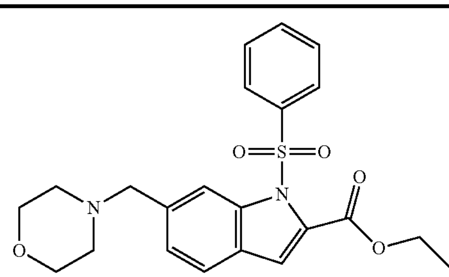 | 6-morpholin-4-ylmethyl-1-(benzenesulfonyl)-1H-indole-2-carboxylic acid ethyl ester | 429 |
| 1287 | 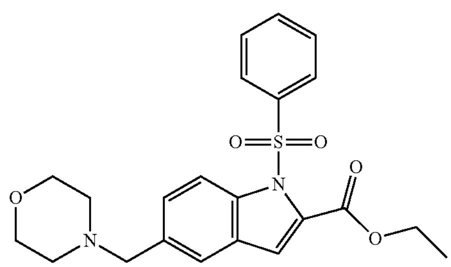 [SMILES: CCOC(=O)c1cc2cc(CN3CCOCC3)ccc2n1S(=O)(=O)c1ccccc1] | 5-morpholin-4-ylmethyl-1-(benzenesulfonyl)-1H-indole-2-carboxylic acid ethyl ester | 429 |

TABLE 11-continued

| Compound No. | Structure | Compound name | m/z |
|---|---|---|---|
| 1288 | 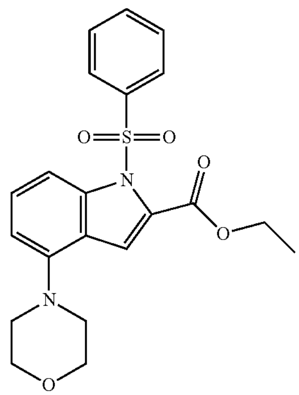 [SMILES: CCOC(=O)c1cc2c(N3CCOCC3)cccc2n1S(=O)(=O)c1ccccc1] | 1-benzenesulfonyl-4-morpholin-4-yl-1H-indole-2-carboxylic acid ethyl ester | 415 |
| 1289 | 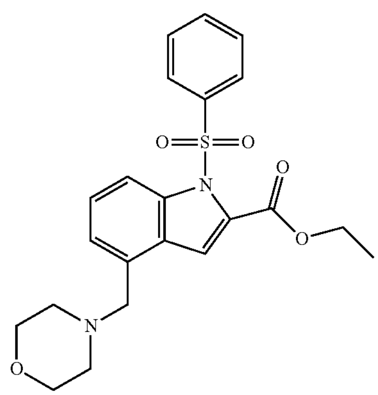 [SMILES: CCOC(=O)c1cc2c(CN3CCOCC3)cccc2n1S(=O)(=O)c1ccccc1] | 1-benzenesulfonyl-4-morpholin-4-ylmethyl-1H-indole-2-carboxylic acid ethyl ester | 429 |
| 1290 | 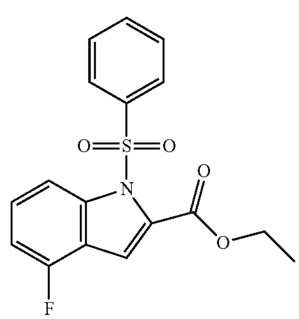 | 1-benzenesulfonyl-4-fluoro-1H-indole-2-carboxylic acid ethyl ester | 348 |
| 1291 | 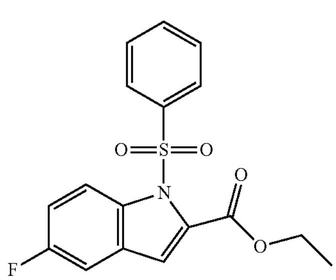 [SMILES: CCOC(=O)c1cc2cc(F)ccc2n1S(=O)(=O)c1ccccc1] | 1-benzenesulfonyl-5-fluoro-1H-indole-2-carboxylic acid ethyl ester | 348 |

TABLE 11-continued

| Compound No. | Structure | Compound name | m/z |
|---|---|---|---|
| 1292 | 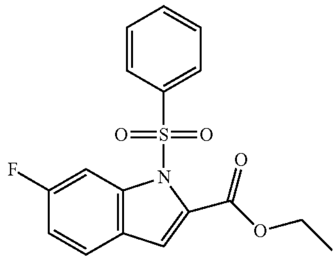 [SMILES: CCOC(=O)c1cc2ccc(F)cc2n1S(=O)(=O)c1ccccc1] | 1-benzenesulfonyl-6-fluoro-1H-indole-2-carboxylic acid ethyl ester | 348 |
| 1293 | 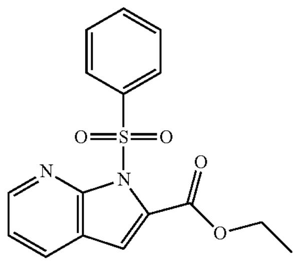 [SMILES: CCOC(=O)c1cc2cccnc2n1S(=O)(=O)c1ccccc1] | 1-benzenesulfonyl-1H-pyrrolo[2,3-b]pyridine-2-carboxylic acid ethyl ester | 331 |
| 1294 | 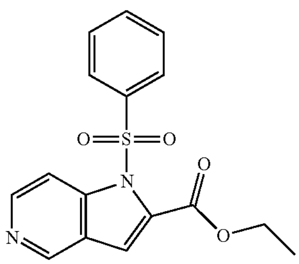 [SMILES: CCOC(=O)c1cc2cnccc2n1S(=O)(=O)c1ccccc1] | 1-benzenesulfonyl-1H-pyrrolo[3,2-c]pyridine-2-carboxylic acid ethyl ester | 331 |
| 1295 | 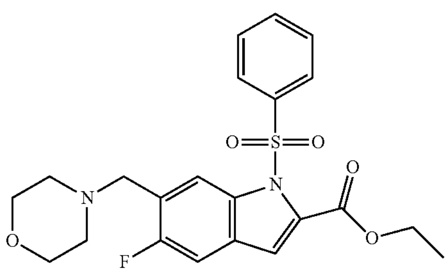 [SMILES: CCOC(=O)c1cc2cc(F)c(CN3CCOCC3)cc2n1S(=O)(=O)c1ccccc1] | 1-benzenesulfonyl-5-fluoro-6-morpholin-4-ylmethyl-1H-indole-2-carboxylic acid ethyl ester | 447 |
| 1296 | 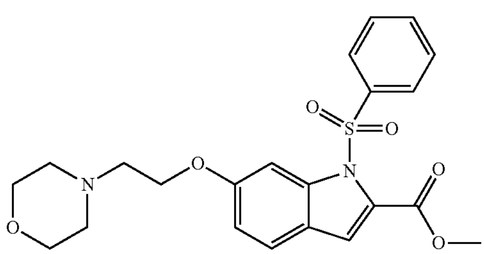 [SMILES: COC(=O)c1cc2ccc(OCCN3CCOCC3)cc2n1S(=O)(=O)c1ccccc1] | 1-benzenesulfonyl-6-(2-morpholin-4-yl-ethoxy)-1H-indole-2-carboxylic acid methyl ester | 445 |
| 1297 | 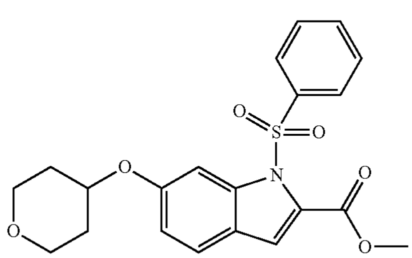 [SMILES: COC(=O)c1cc2ccc(OC3CCOCC3)cc2n1S(=O)(=O)c1ccccc1] | 1-benzenesulfonyl-6-(tetrahydro-pyran-4-yloxy)-1H-indole-2-carboxylic acid methyl ester | 416 |

TABLE 11-continued

| Compound No. | Structure | Compound name | m/z |
|---|---|---|---|
| 1298 | 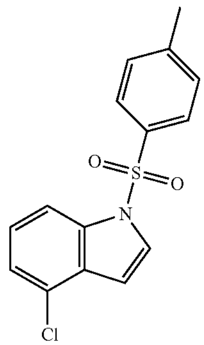 [SMILES: Cc1ccc(S(=O)(=O)n2ccc3c(Cl)cccc32)cc1] | 4-chloro-1-(toluene-4-sulfonyl)-1H-indole | 306, 308 |
| 1299 | 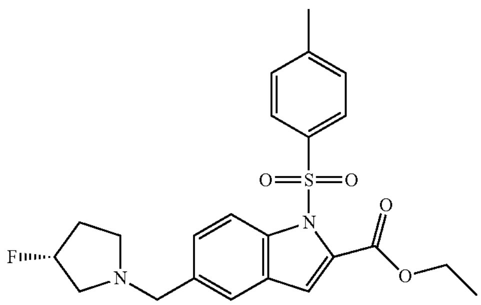 [SMILES: CCOC(=O)c1cc2cc(CN3CC[C@@H](F)C3)ccc2n1S(=O)(=O)c1ccc(C)cc1] | 5-((R)-3-fluoro-pyrrolidin-1-ylmethyl)-1-(toluene-4-sulfonyl)-1H-indole-2-carboxylic acid ethyl ester | 445 |
| 1300 | 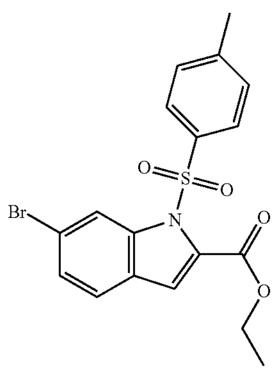 [SMILES: CCOC(=O)c1cc2ccc(Br)cc2n1S(=O)(=O)c1ccc(C)cc1] | 6-bromo-1-(toluene-4-sulfonyl)-1H-indole-2-carboxylic acid ethyl ester | 422, 424 |
| 1301 | 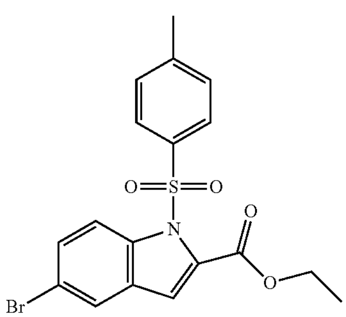 [SMILES: CCOC(=O)c1cc2cc(Br)ccc2n1S(=O)(=O)c1ccc(C)cc1] | 5-bromo-1-(toluene-4-sulfonyl)-1H-indole-2-carboxylic acid ethyl ester | 422, 424 |

TABLE 11-continued

| Compound No. | Structure | Compound name | m/z |
|---|---|---|---|
| 1302 | 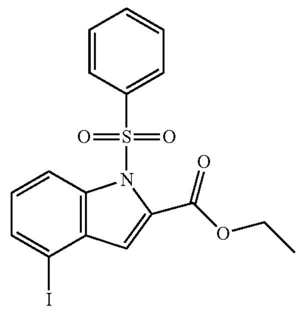 [SMILES: CCOC(=O)c1cc2c(I)cccc2n1S(=O)(=O)c1ccccc1] | 1-benzenesulfonyl-4-iodo-1H-indole-2-carboxylic acid ethyl ester | 456 |
| 1303 | 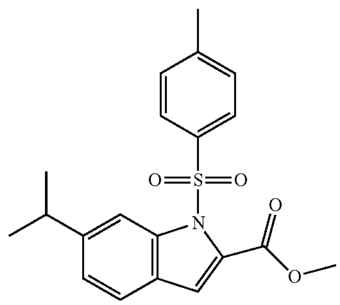 [SMILES: COC(=O)c1cc2ccc(C(C)C)cc2n1S(=O)(=O)c1ccc(C)cc1] | 6-isopropyl-1-(toluene-4-sulfonyl)-1H-indole-2-carboxylic acid methyl ester | 372 |
| 1304 | 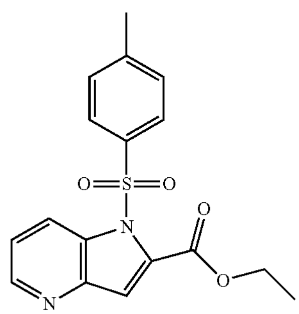 [SMILES: CCOC(=O)c1cc2ncccc2n1S(=O)(=O)c1ccc(C)cc1] | 1-(toluene-4-sulfonyl)-1H-pyrrolo[3,2-b]pyridine-2-carboxylic acid ethyl ester | 345 |
| 1305 | 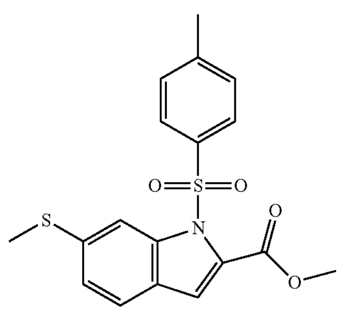 | 6-methylsulfanyl-1-(toluene-4-sulfonyl)-1H-indole-2-carboxylic acid methyl ester | 376 |
| 1306 | 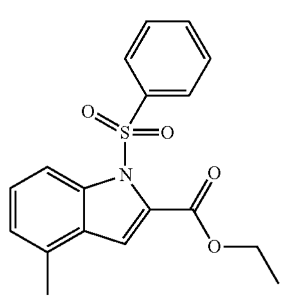 [SMILES: CCOC(=O)c1cc2c(C)cccc2n1S(=O)(=O)c1ccccc1] | 4-methyl-1-(toluene-4-sulfonyl)-1H-indole-2-carboxylic acid methyl ester | 344 |

TABLE 11-continued

| Compound No. | Structure | Compound name | m/z |
|---|---|---|---|
| 1307 | 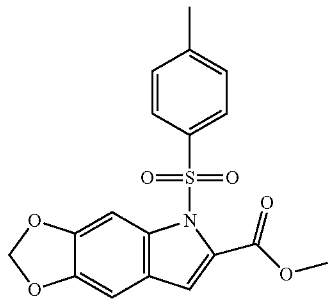 [SMILES: COC(=O)c1cc2cc3c(cc2n1S(=O)(=O)c1ccc(C)cc1)OCO3] | 5-(toluene-4-sulfonyl)-5H-[1,3]dioxolo[4,5-f]indol-6-carboxylic acid methyl ester | 374 |
| 1308 | 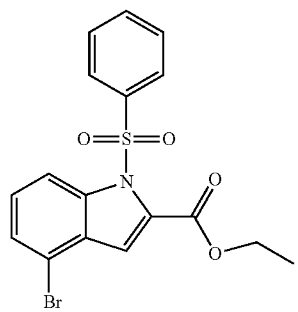 [SMILES: CCOC(=O)c1cc2c(Br)cccc2n1S(=O)(=O)c1ccccc1] | 1-benzenesulfonyl-4-bromo-1H-indole-2-carboxylic acid ethyl ester | 408, 410 |
| 1309 | 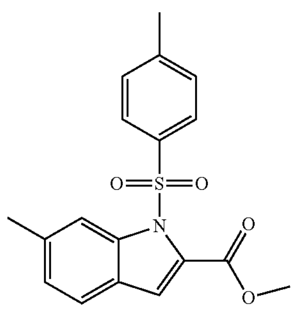 | 6-methyl-1-(toluene-4-sulfonyl)-1H-indole-2-carboxylic acid methyl ester | 344 |
| 1310 | 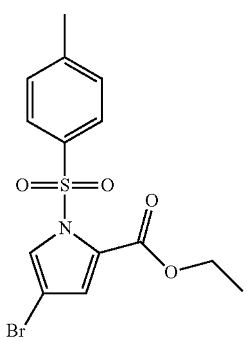 [SMILES: CCOC(=O)c1cc(Br)cn1S(=O)(=O)c1ccc(C)cc1] | 4-bromo-1-(toluene-4-sulfonyl)-1H-pyrrole-2-carboxylic acid ethyl ester | 372, 374 |
| 1311 | 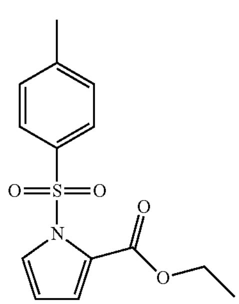 [SMILES: CCOC(=O)c1cccn1S(=O)(=O)c1ccc(C)cc1] | 1-(toluene-4-sulfonyl)-1H-pyrrole-2-carboxylic acid ethyl ester | 294 |

TABLE 11-continued

| Compound No. | Structure | Compound name | m/z |
|---|---|---|---|
| 1312 | 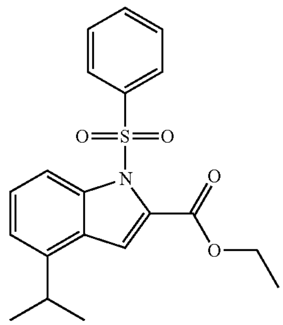 [SMILES: CCOC(=O)c1cc2c(C(C)C)cccc2n1S(=O)(=O)c1ccccc1] | 1-benzenesulfonyl-4-isopropyl-1H-indole-2-carboxylic acid ethyl ester | 372 |

Step 5: Synthesis of [5-amino-1-(2-methyl-1H-benzimidazol-5-yl)-1H-pyrazol-4-yl]-[4-(2-methoxy-ethylamino)-1-(toluene-4-sulfonyl)-1H-indol-2-yl]-methanone (1313)

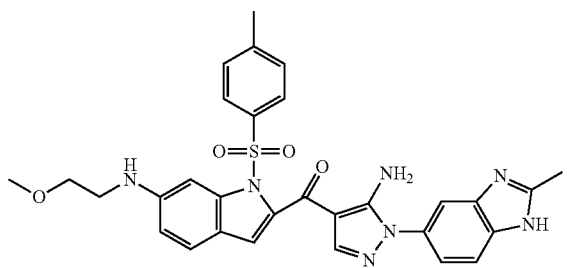

Copper (I) iodide (16 mg, 0.086 mmol), L-proline (37 mg, 0.32 mmol), and [5-amino-1-(2-methyl-1H-benzimidazol-5-yl)-1H-pyrazol-4-yl]-[6-iodo-1-(toluene-4-sulfonyl)-1H-indol-2-yl]-methanone (104 mg) were dissolved in anhydrous dimethylsulfoxide (DMSO), and then 1,8-diazabicyclo[5.4.0]undec-7-ene (49 µl) and 2-methoxyethylamine (43 µl) were added thereto. The mixture was heated at 80° C. with stirring under a nitrogen atmosphere for 18 hours. After the reaction mixture was cooled to room temperature, 25% ammonia water was added thereto. The resulting mixture was extracted with ethyl acetate. The organic layer was isolated, washed with an aqueous solution of 1 M hydrochloric acid and then with a saturated aqueous solution of sodium chloride, and dried over anhydrous magnesium sulfate. After the desiccant was removed by filtration, the solvent was distilled off under reduced pressure. The resulting residue was purified by chromatography (dichloromethane/methanol=100/5) using a small amount of silica gel to give crude product of [5-amino-1-(2-methyl-1H-benzimidazol-5-yl)-1H-pyrazol-4-yl]-[4-(2-methoxy-ethylamino)-1-(toluene-4-sulfonyl)-1H-indol-2-yl]-methanone. The obtained crude product was used in subsequent reactions without purification.

ESI (LC-MS positive mode) m/z 584 [(M+H)$^+$]

The compounds of numbers 1314 to 1320 listed in Table 12 were synthesized by the same method as in Step 5.

TABLE 12

| Compound No. | Structure | Compound name | m/z |
|---|---|---|---|
| 1314 | 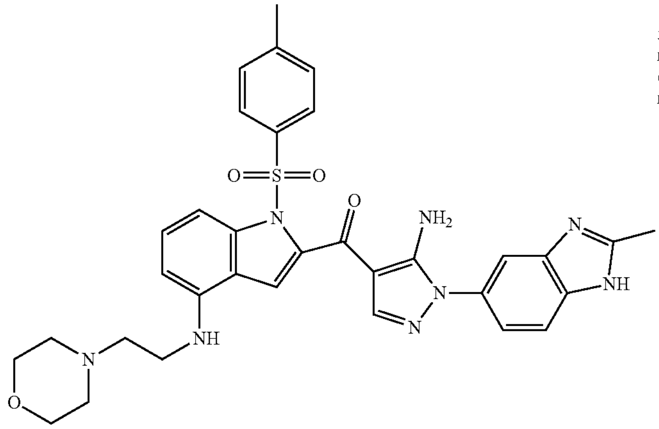 [SMILES: Cc1ccc(S(=O)(=O)n2c(C(=O)c3cnn(-c4ccc5[nH]c(C)nc5c4)c3N)cc3c(NCCN4CCOCC4)cccc32)cc1] | [5-amino-1-(2-methyl-1H-benzimidazol-5-yl)-1H-pyrazol-4-yl]-[4-(2-morpholin-4-yl-ethylamino)-1-(toluene-4-sulfonyl)-1H-indol-2-yl]-methanone | 639 |

TABLE 12-continued

| Compound No. | Structure | Compound name | m/z |
|---|---|---|---|
| 1315 | 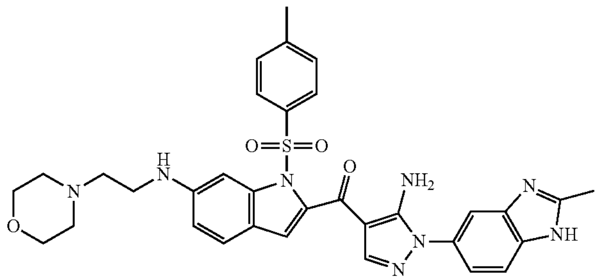 [SMILES: Cc1ccc(S(=O)(=O)n2c(C(=O)c3cnn(-c4ccc5[nH]c(C)nc5c4)c3N)cc3ccc(NCCN4CCOCC4)cc32)cc1] | [5-amino-1-(2-methyl-1H-benzimidazol-5-yl)-1H-pyrazol-4-yl]-[6-(2-morpholin-4-yl-ethylamino)-1-(toluene-4-sulfonyl)-1H-indol-2-yl]-methanone | 639 |
| 1316 | 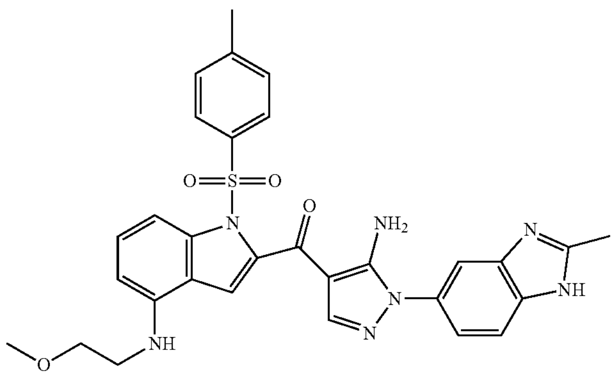 | [5-amino-1-(2-methyl-1H-benzimidazol-5-yl)-1H-pyrazol-4-yl]-[4-(2-methoxy-ethylamino)-1-(toluene-4-sulfonyl)-1H-indol-2-yl]-methanone | 584 |
| 1317 | 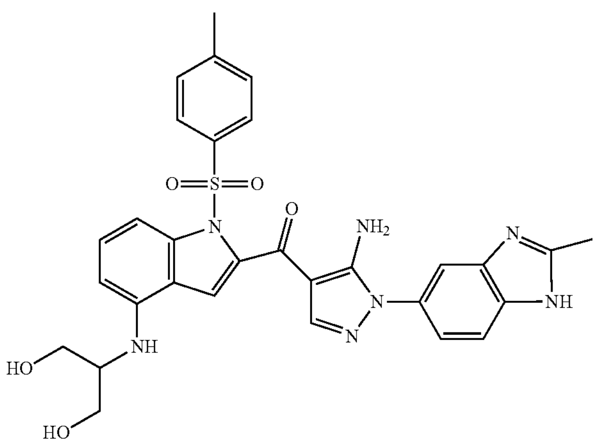 [SMILES: Cc1ccc(S(=O)(=O)n2c(C(=O)c3cnn(-c4ccc5[nH]c(C)nc5c4)c3N)cc3c(NC(CO)CO)cccc32)cc1] | [5-amino-1-(2-methyl-1H-benzimidazol-5-yl)-1H-pyrazol-4-yl]-[4-(2-hydroxy-1-hydroxymethyl-ethylamino)-1-(toluene-4-sulfonyl)-1H-indol-2-yl]-methanone | 600 |
| 1318 | 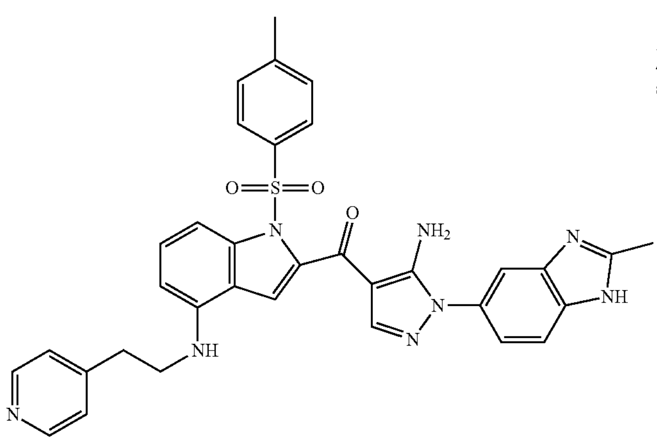 [SMILES: Cc1ccc(S(=O)(=O)n2c(C(=O)c3cnn(-c4ccc5[nH]c(C)nc5c4)c3N)cc3c(NCCc4ccncc4)cccc32)cc1] | [5-amino-1-(2-methyl-1H-benzimidazol-5-yl)-1H-pyrazol-4-yl]-[4-(2-pyridin-4-yl-ethylamino)-1-(toluene-4-sulfonyl)-1H-indol-2-yl]-methanone | 631 |

TABLE 12-continued

| Compound No. | Structure | Compound name | m/z |
|---|---|---|---|
| 1319 | 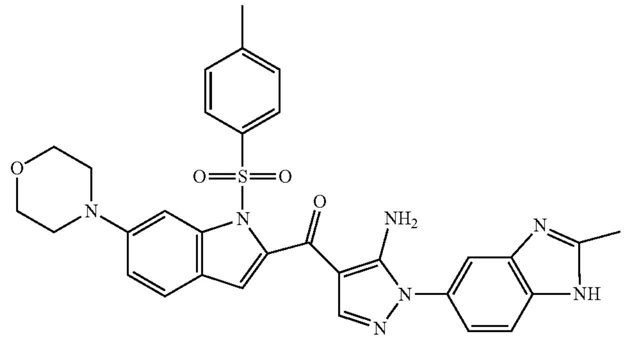 [SMILES: Cc1ccc(S(=O)(=O)n2c(C(=O)c3cnn(-c4ccc5[nH]c(C)nc5c4)c3N)cc3ccc(N4CCOCC4)cc32)cc1] | [5-amino-1-(2-methyl-1H-benzimidazol-5-yl)-1H-pyrazol-4-yl]-[6-morpholin-4-yl-1-(toluene-4-sulfonyl)-1H-indol-2-yl]-methanone | 596 |
| 1320 | 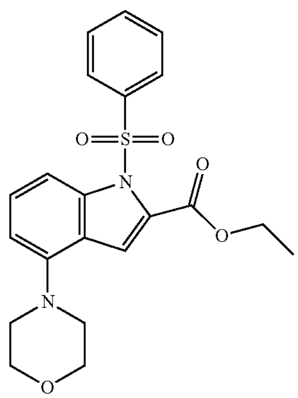 [SMILES: CCOC(=O)c1cc2c(N3CCOCC3)cccc2n1S(=O)(=O)c1ccccc1] | 1-benzenesulfonyl-4-morpholin-4-yl-1H-indole-2-carboxylic acid ethyl ester | 415 |

Step 6: Synthesis of [5-amino-1-(2-methyl-1H-benzimidazol-5-yl)-1H-pyrazol-4-yl]-[5-(morpholine-4-carbonyl)-1-(toluene-4-sulfonyl)-1H-indol-2-yl]methanone (1321)

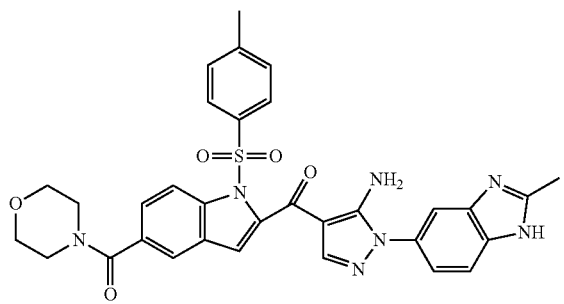 [SMILES: Cc1ccc(S(=O)(=O)n2c(C(=O)c3cnn(-c4ccc5[nH]c(C)nc5c4)c3N)cc3cc(C(=O)N4CCOCC4)ccc32)cc1]

2-[5-Amino-1-(2-methyl-1H-benzimidazol-5-yl)-1H-pyrazole-4-carbonyl]-1-(toluene-4-sulfonyl)-1H-indole-5-carboxylic acid (113 mg) was dissolved in water (5 ml) and tetrahydrofuran (THF) (10 ml), and then morpholine (53.5 µl) and N-(3-dimethylaminopropyl)-N'-ethylcarbodiimide hydrochloride (WSC-HCl) (43 mg) were added thereto. The mixture was stirred at room temperature for 24 hours. The reaction mixture was then concentrated under reduced pressure. The resulting residue was purified by silica gel column chromatography (methanol/dichloromethane=0/100 to 17/100) to give [5-amino-1-(2-methyl-1H-benzimidazol-5-yl)-1H-pyrazol-4-yl]-[5-(morpholine-4-carbonyl)-1-(toluene-4-sulfonyl)-1H-indol-2-yl]-methanone (59 mg).

$^1$H-NMR (DMSO-D$_6$) δ: 12.49 (1.0H, d, J=9.3 Hz), 8.08 (3.0H, m), 7.82-7.74 (2.0H, m), 7.70-7.64 (1.0H, m), 7.58 (1.0H, d, J=8.3 Hz), 7.53-7.42 (3.0H, m), 7.35-7.25 (2.0H, m), 7.13-6.89 (2.0H, m), 3.69-3.51 (4.0H, m), 3.40-3.28 (4.0H, m), 2.54 (3.0H, s), 2.38 (3.0H, s)

ESI (LC-MS positive mode) m/z 624 [(M+H)$^+$]

The compounds of numbers 1322 to 1326, 1572 to 1579 listed in Table 13 were synthesized by the same method as in Step 6.

TABLE 13

| Compound No. | Structure | Compound name | m/z |
|---|---|---|---|
| 1322 | 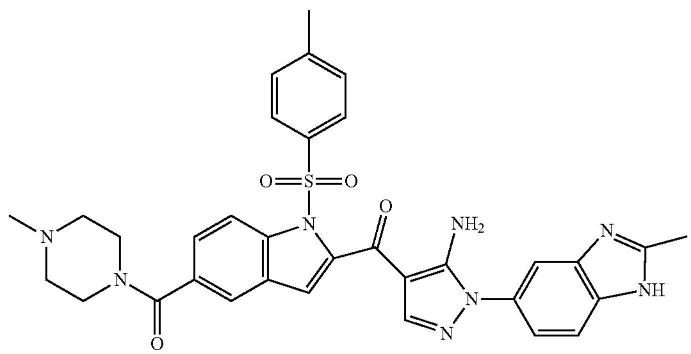 | [5-amino-1-(2-methyl-1H-benzimidazol-5-yl)-1H-pyrazol-4-yl]-[5-(4-methylpiperadine-1-carbonyl)-1-(toluene-4-sulfonyl)-1H-indol-2-yl]-methanone | 637 |
| 1323 | 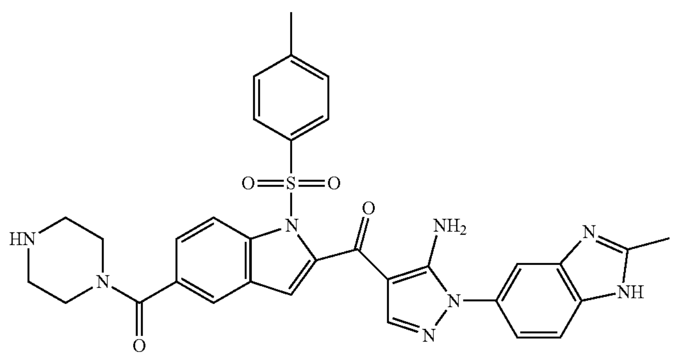 [SMILES: Cc1ccc(S(=O)(=O)n2c(C(=O)c3cnn(-c4ccc5[nH]c(C)nc5c4)c3N)cc3cc(C(=O)N4CCNCC4)ccc32)cc1] | [5-amino-1-(2-methyl-1H-benzimidazol-5-yl)-1H-pyrazol-4-yl]-[5-(piperadine-1-carbonyl)-1-(toluene-4-sulfonyl)-1H-indol-2-yl]-methanone | 623 |
| 1324 | 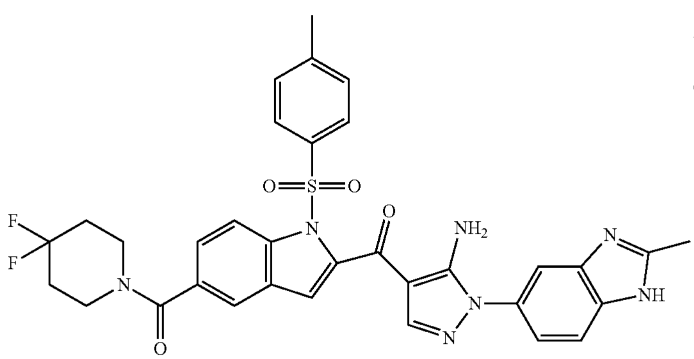 | [5-amino-1-(2-methyl-1H-benzimidazol-5-yl)-1H-pyrazol-4-yl]-[5-(4,4-difluoro-piperidine-1-carbonyl)-1-(toluene-4-sulfonyl)-1H-indol-2-yl]-methanone | 658 |
| 1325 | 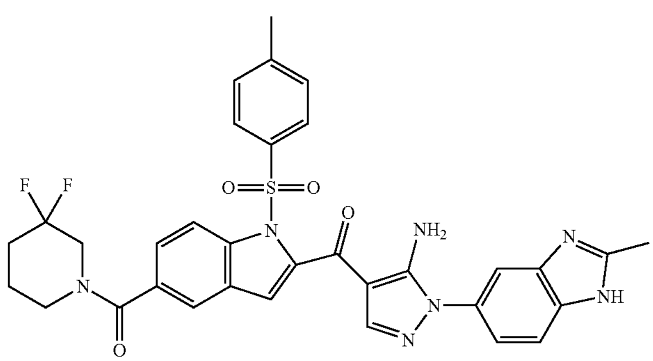 [SMILES: Cc1ccc(S(=O)(=O)n2c(C(=O)c3cnn(-c4ccc5[nH]c(C)nc5c4)c3N)cc3cc(C(=O)N4CCCC(F)(F)C4)ccc32)cc1] | [5-amino-1-(2-methyl-1H-benzimidazol-5-yl)-1H-pyrazol-4-yl]-[5-(3,3-difluoro-piperidine-1-carbonyl)-1-(toluene-4-sulfonyl)-1H-indol-2-yl]-methanone | 658 |

TABLE 13-continued

| Compound No. | Structure | Compound name | m/z |
|---|---|---|---|
| 1326 | 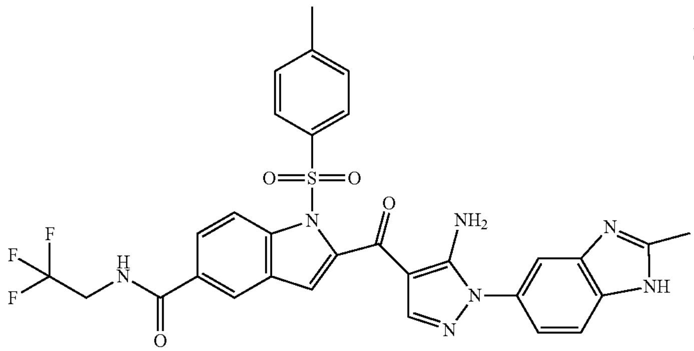 [SMILES: Cc1ccc(S(=O)(=O)n2c(C(=O)c3cnn(-c4ccc5[nH]c(C)nc5c4)c3N)cc3cc(C(=O)NCC(F)(F)F)ccc32)cc1] | [5-amino-1-(2-methyl-1H-benzimidazol-5-yl)-1H-pyrazol-4-carbonyl]-1-(toluene-4-sulfonyl)-1H-indol-5-carboxylic acid (2,2,2-trifluoro-ethyl)-amide | 636 |
| 1572 | 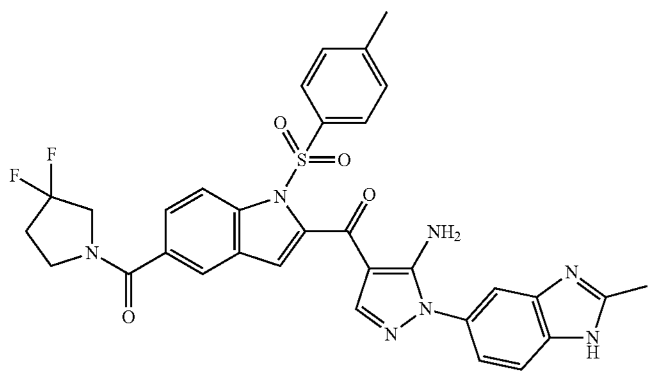 [SMILES: Cc1ccc(S(=O)(=O)n2c(C(=O)c3cnn(-c4ccc5[nH]c(C)nc5c4)c3N)cc3cc(C(=O)N4CCC(F)(F)C4)ccc32)cc1] | [5-amino-1-(2-methyl-1H-benzimidazol-5-yl)-1H-pyrazol-4-yl]-[5-(3,3-difluoro-pyrrolidine-1-carbonyl)-1-(toluene-4-sulfonyl)-1H-indol-2-yl]-methanone | 644 |
| 1573 | 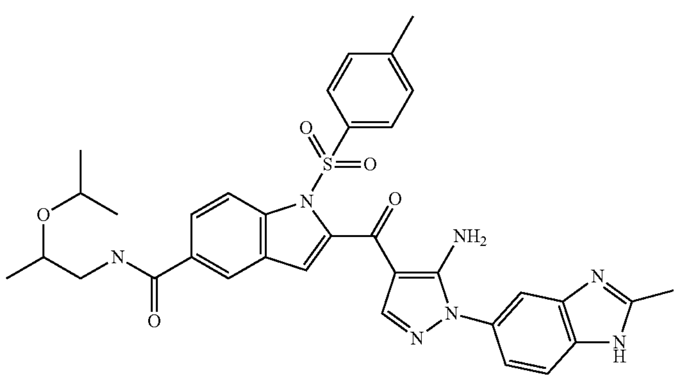 [SMILES: Cc1ccc(S(=O)(=O)n2c(C(=O)c3cnn(-c4ccc5[nH]c(C)nc5c4)c3N)cc3cc(C(=O)NCC(C)OC(C)C)ccc32)cc1] | [5-amino-1-(2-methyl-1H-benzimidazol-5-yl)-1H-pyrazol-4-yl]-[5-(2,6-dimethyl-morpholine-4-carbonyl)-1-(toluene-4-sulfonyl)-1H-indol-2-yl]-methanone | 652 |
| 1574 | 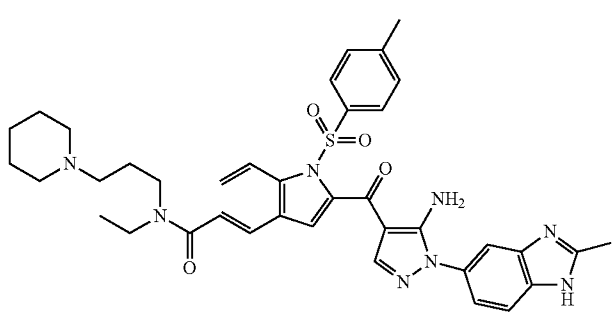 [SMILES: C=Cc1c(/C=C/C(=O)N(CC)CCCN2CCCCC2)cc(C(=O)c2cnn(-c3ccc4[nH]c(C)nc4c3)c2N)n1S(=O)(=O)c1ccc(C)cc1] | [5-amino-1-(2-methyl-1H-benzimidazol-5-yl)-1H-pyrazol-4-yl]-[5-([1,4']bipiperidinyl-1'-carbonyl)-1-(toluene-4-sulfonyl)-1H-indol-2-yl]-methanone | 705 |

TABLE 13-continued

| Compound No. | Structure | Compound name | m/z |
|---|---|---|---|
| 1575 | 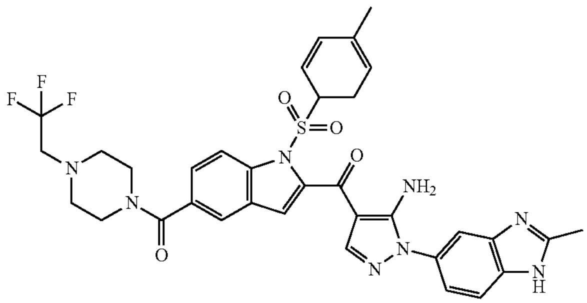 [SMILES: CC1=CCC(S(=O)(=O)n2c(C(=O)c3cnn(-c4ccc5[nH]c(C)nc5c4)c3N)cc3cc(C(=O)N4CCN(CC(F)(F)F)CC4)ccc32)C=C1] | [5-amino-1-(2-methyl-1H-benzimidazol-5-yl)-1H-pyrazol-4-yl]-{1-(toluene-4-sulfonyl)-5-[4-(2,2,2-trifluoro-ethyl)-piperazine-1-carbonyl]-1H-indol-2-yl}-methanone | 705 |
| 1576 | 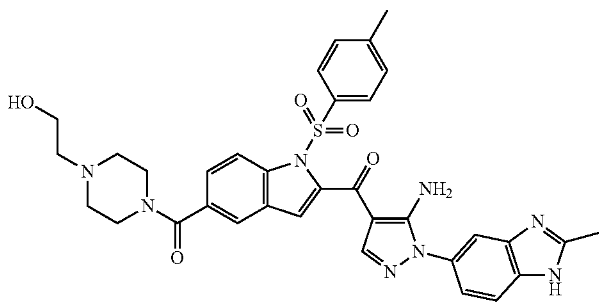 [SMILES: Cc1ccc(S(=O)(=O)n2c(C(=O)c3cnn(-c4ccc5[nH]c(C)nc5c4)c3N)cc3cc(C(=O)N4CCN(CCO)CC4)ccc32)cc1] | [5-amino-1-(2-methyl-1H-benzimidazol-5-yl)-1H-pyrazol-4-yl]-[5-[4-(2-hydroxy-ethyl)-piperazine-1-carbonyl]-1-(toluene-4-sulfonyl)-1H-indol-2-yl]-methanone | 667 |
| 1577 | 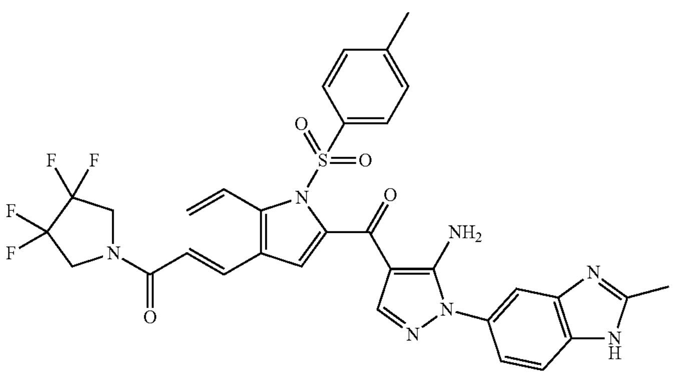 [SMILES: C=Cc1c(/C=C/C(=O)N2CC(F)(F)C(F)(F)C2)cc(C(=O)c2cnn(-c3ccc4[nH]c(C)nc4c3)c2N)n1S(=O)(=O)c1ccc(C)cc1] | [5-amino-1-(2-methyl-1H-benzimidazol-5-yl)-1H-pyrazol-4-yl]-[5-(3,3,4,4-tetrafluoro-pyrrolidine-1-carbonyl)-1-(toluene-4-sulfonyl)-1H-indol-2-yl]-methanone | 680 |
| 1578 | 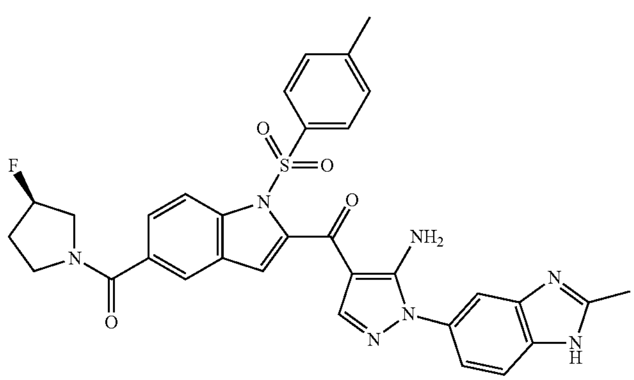 [SMILES: Cc1ccc(S(=O)(=O)n2c(C(=O)c3cnn(-c4ccc5[nH]c(C)nc5c4)c3N)cc3cc(C(=O)N4CC[C@@H](F)C4)ccc32)cc1] | [5-amino-1-(2-methyl-1H-benzimidazol-5-yl)-1H-pyrazol-4-yl]-[5-((R)-3-fluoro-pyrrolidine-1-carbonyl)-1-(toluene-4-sulfonyl)-1H-indol-2-yl]-methanone | 626 |

TABLE 13-continued

| Compound No. | Structure | Compound name | m/z |
|---|---|---|---|
| 1579 | 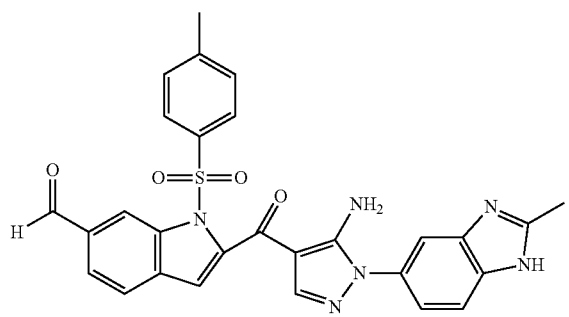 [SMILES: Cc1ccc(S(=O)(=O)n2c(C(=O)c3cnn(-c4ccc5[nH]c(C)nc5c4)c3N)cc3ccc(C=O)cc32)cc1] | [5-amino-1-(2-methyl-1H-benzimidazol-5-yl)-1H-pyrazol-4-yl]-[5-((S)-3-fluoro-pyrrolidine-1-carbonyl)-1-(toluene-4-sulfonyl)-1H-indol-2-yl]-methanone | 626 |

Step 7: Synthesis of 2-[5-amino-1-(2-methyl-1H-benzimidazol-5-yl)-1H-pyrazole-4-carbonyl]-1-(toluene-4-sulfonyl)-1H-indole-6-carbaldehyde (1327)

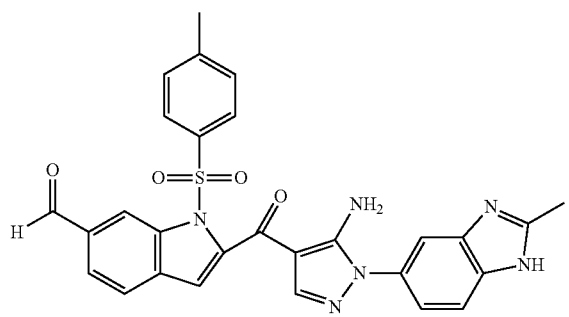 [SMILES: Cc1ccc(S(=O)(=O)n2c(C(=O)c3cnn(-c4ccc5[nH]c(C)nc5c4)c3N)cc3ccc(C=O)cc32)cc1]

In a pressure-proof container, palladium acetate (1.0 mg, 0.0044 mmol), 1,3-bis(diphenylphosphino) propane (1.8 mg, 0.0044 mmol), [5-amino-1-(2-methyl-1H-benzimidazol-5-yl)-1H-pyrazol-4-yl]-[6-iodo-1-(toluene-4-sulfonyl)-1H-indol-2-yl]-methanone (100 mg, 0.16 mmol), and sodium carbonate (18 mg, 0.17 mmol) were dissolved in anhydrous N,N-dimethylformamide (DMF) (0.22 ml). After triethylsilane (52 µl, 0.33 mmol) was added, the air inside the container was replaced with carbon monoxide. Then, the reaction mixture was heated at 60° C. with stirring under pressure with carbon monoxide (3 atm) for 24 hours. After the reaction mixture was cooled to room temperature, the pressure was released to ambient pressure. The reaction mixture was diluted with ethyl acetate. The sodium carbonate was removed by filtration. The filtrate was concentrated under reduced pressure. The resulting residue was purified by silica gel column chromatography (dichloromethane/methanol=100/5) to give 2-[5-amino-1-(2-methyl-1H-benzimidazol-5-yl)-1H-pyrazole-4-carbonyl]-1-(toluene-4-sulfonyl)-1H-indole-6-carbaldehyde as a yellow solid (80 mg, 85%).

$^1$H-NMR (CDCl$_3$) δ: 10.14 (1.0H, s), 9.81-9.40 (1.0H, brm), 8.61 (1.0H, d, J=3.9 Hz), 8.09 (2.0H, d, J=7.3 Hz), 7.86-7.72 (4.0H, m), 7.52-7.30 (4.0H, m), 7.02 (1.0H, s), 6.07 (1.0H, brs), 6.04 (1.0H, brs), 2.67 (3.0H, s), 2.40 (3.0H, s)

ESI (LC-MS positive mode) m/z 539 [(M+H)$^+$]

Synthesis of 2-[5-amino-1-(2-methyl-1H-benzimidazol-5-yl)-1H-pyrazole-4-carbonyl]-1-(toluene-4-sulfonyl)-1H-indole-5-carbaldehyde (1328)

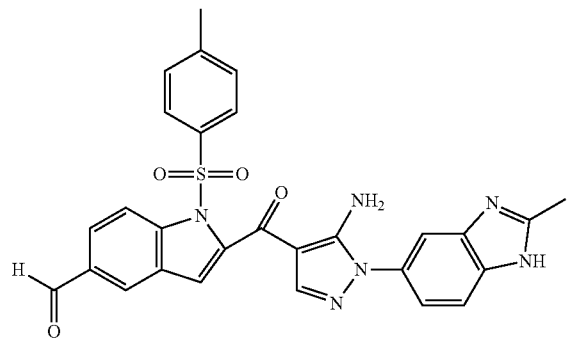 [SMILES: Cc1ccc(S(=O)(=O)n2c(C(=O)c3cnn(-c4ccc5[nH]c(C)nc5c4)c3N)cc3cc(C=O)ccc32)cc1]

2-[5-Amino-1-(2-methyl-1H-benzimidazol-5-yl)-1H-pyrazole-4-carbonyl]-1-(toluene-4-sulfonyl)-1H-indole-5-carbaldehyde was synthesized by the same method as in Step 7.

ESI (LC-MS positive mode) m/z 539 [(M+H)$^+$]

Step 8: Synthesis of 2-[5-amino-1-(2-methyl-1H-benzimidazol-5-yl)-1H-pyrazole-4-carbonyl]-1H-indole-6-carbaldehyde (1329)

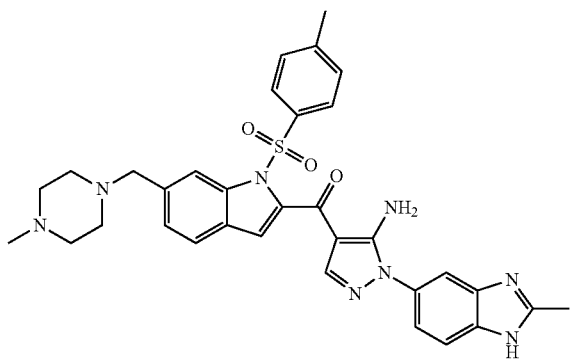

2-[5-Amino-1-(2-methyl-1H-benzimidazol-5-yl)-1H-pyrazole-4-carbonyl]-1-(toluene-4-sulfonyl)-1H-indole-6-carbaldehyde (29 mg, 0.054 mmol), 1-methylpiperazine (7 μl, 0.066 mmol), and sodium triacetoxyborohydride (17 mg, 0.083 mmol) were dissolved in anhydrous dichloromethane (0.5 ml) and stirred at room temperature under a nitrogen atmosphere for 14 hours. A saturated aqueous solution of sodium bicarbonate was added to the reaction mixture. Then, the mixture was extracted with ethyl acetate. The organic layer was isolated, washed with a saturated aqueous solution of sodium chloride, and dried over anhydrous magnesium sulfate. The desiccant was removed by filtration. The filtrate was concentrated under reduced pressure. The resulting residue was purified by silica gel column chromatography (dichloromethane/methanol=100/15) to give [5-amino-1-(2-methyl-1H-benzimidazol-5-yl)-1H-pyrazol-4-yl]-[6-(4-methyl-piperazin-1-ylmethyl)-1-(toluene-4-sulfonyl)-1H-indol-2-yl]-methanone as a yellow solid (29 mg, 86%).

ESI (LC-MS positive mode) m/z 623 [(M+H)$^+$]

The compounds of numbers 1330 to 1358 listed in Table 14 were synthesized by the same method as in Step 8.

TABLE 14

| Compound No. | Structure | Compound name | m/z |
|---|---|---|---|
| 1330 | 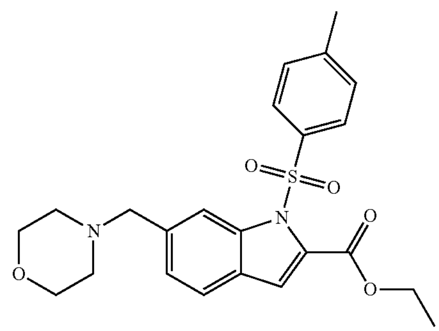 [SMILES: CCOC(=O)c1cc2ccc(CN3CCOCC3)cc2n1S(=O)(=O)c1ccc(C)cc1] | 6-morpholin-4-ylmethyl-1-(toluene-4-sulfonyl)-1H-indole-2-carboxylic acid ethyl ester | 443 |
| 1331 | 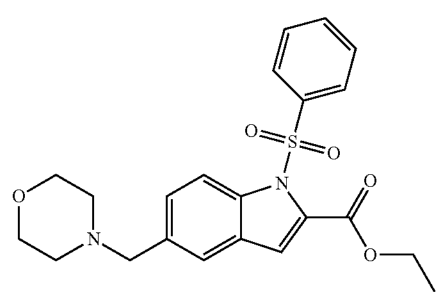 [SMILES: CCOC(=O)c1cc2cc(CN3CCOCC3)ccc2n1S(=O)(=O)c1ccccc1] | 5-morpholin-4-ylmethyl-1-benzenesulfonyl-1H-indole-2-carboxylic acid ethyl ester | 429 |
| 1332 | 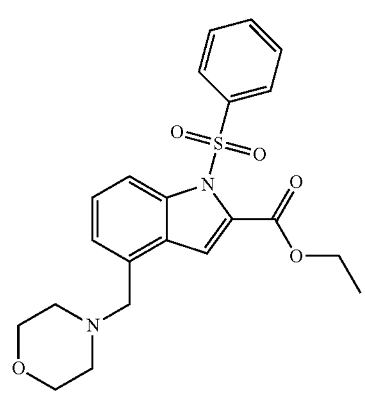 [SMILES: CCOC(=O)c1cc2c(CN3CCOCC3)cccc2n1S(=O)(=O)c1ccccc1] | 1-benzenesulfonyl-4-molpholin-4-ylmethyl-1H-indole-2-carboxylic acid ethyl ester | 429 |

TABLE 14-continued

| Compound No. | Structure | Compound name | m/z |
| --- | --- | --- | --- |
| 1333 | 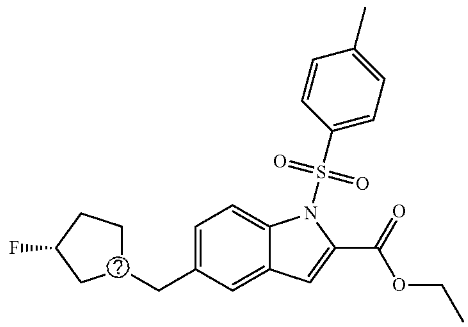 [SMILES: CCOC(=O)c1cc2cc(CN3CC[C@@H](F)C3)ccc2n1S(=O)(=O)c1ccc(C)cc1] | 5-((R)-3-fluoro-pyrrolidin-1-ylmethyl)-1-(toluene-4-sulfonyl)-1H-indole-2-carboxylic acid ethyl ester | 445 |
| 1334 | 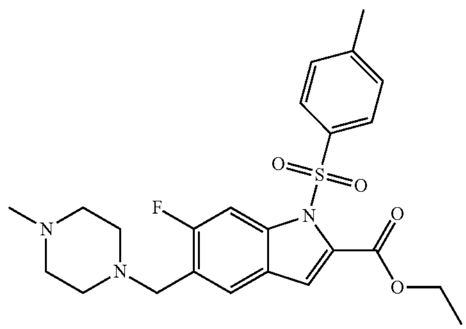 [SMILES: CCOC(=O)c1cc2cc(CN3CCN(C)CC3)c(F)cc2n1S(=O)(=O)c1ccc(C)cc1] | 6-fluoro-5-(4-methyl-piperazin-1-ylmethyl)-1-(toluene-4-sulfonyl)-1H-indole-2-carboxylic acid ethyl ester | 474 |
| 1335 | 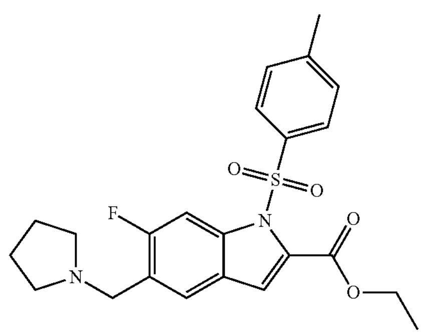 [SMILES: CCOC(=O)c1cc2cc(CN3CCCC3)c(F)cc2n1S(=O)(=O)c1ccc(C)cc1] | 6-fluoro-5-pyrrolidin-1-ylmethyl-1-(toluene-4-sulfonyl)-1H-indole-2-carboxylic acid ethyl ester | 445 |
| 1336 | 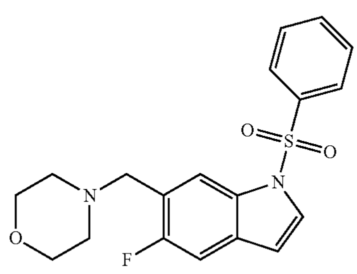 [SMILES: O=S(=O)(c1ccccc1)n1ccc2cc(F)c(CN3CCOCC3)cc21] | 1-benzenesulfonyl-5-fluoro-6-morpholin-4-ylmethly-1H-indole | 375 |
| 1337 | 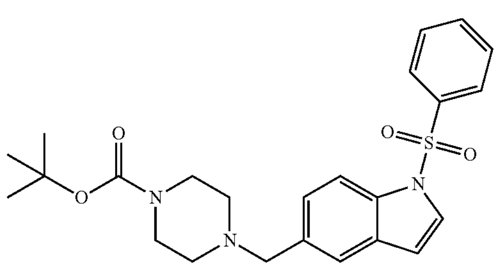 [SMILES: CC(C)(C)OC(=O)N1CCN(Cc2ccc3c(ccn3S(=O)(=O)c3ccccc3)c2)CC1] | 4-(1-benzenesulfonyl-1H-indol-5-ylmethyl)-piperadin-1-carboxylic acid tert-butyl ester | 456 |

TABLE 14-continued

| Compound No. | Structure | Compound name | m/z |
|---|---|---|---|
| 1338 | 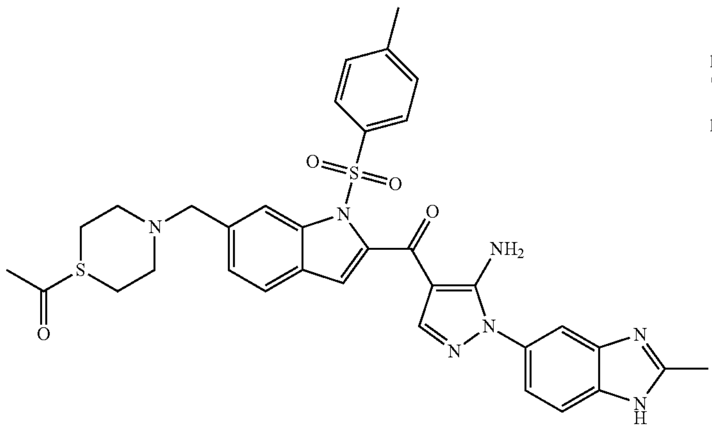 | 1-{4-[2-[5-amino-1-(2-methyl-1H-benzimidazol-5-yl)-1H-pyrazol-4-carbonyl]-1-(toluene-4-sulfonyl)-1H-indol-6-ylmethyl]-piperazin-1-yl}-ethanone | 651 |
| 1339 | 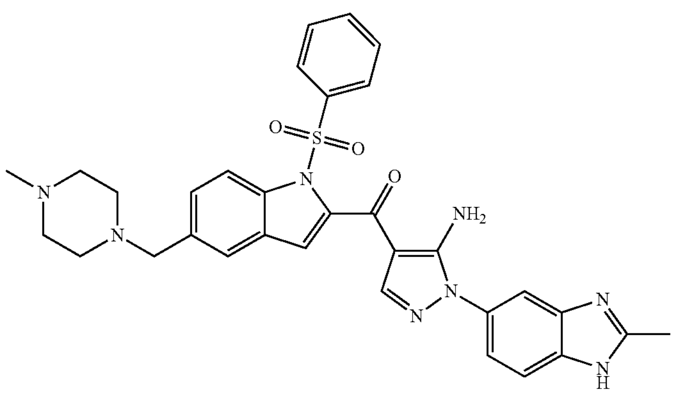 | [5-amino-1-(2-methyl-1H-benzimidazol-5-yl)-1H-pyrazol-4-yl]-[1-benzene-sulfonyl-5-(4-methyl-piperazin-1-ylmethy)-1H-indol-2-yl]-methanone | 609 |
| 1340 | 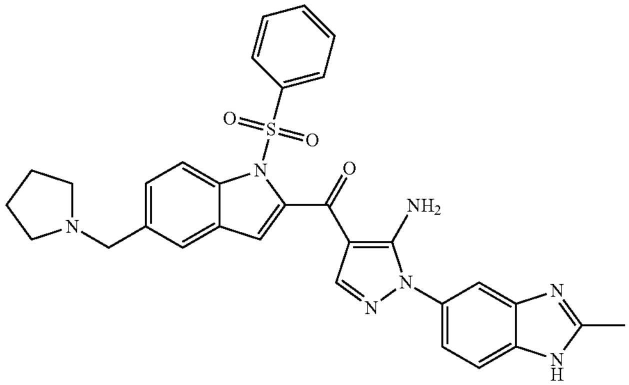 [SMILES: Cc1nc2cc(-n3ncc(C(=O)c4cc5cc(CN6CCCC6)ccc5n4S(=O)(=O)c4ccccc4)c3N)ccc2[nH]1] | [5-amino-1-(2-methyl-1H-benzimidazol-5-yl)-1H-pyrazol-4-yl]-(1-benzene-sulfonyl-5-pyrrolidin-1-ylmethyl-1H-indol-2-yl)-methanone | 580 |

TABLE 14-continued

| Compound No. | Structure | Compound name | m/z |
|---|---|---|---|
| 1341 | 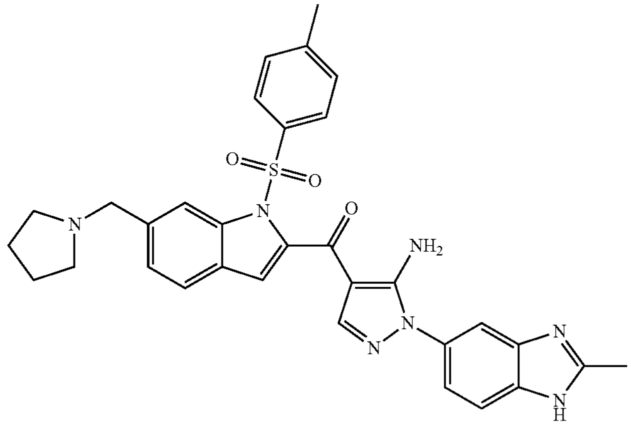 [SMILES: Cc1ccc(S(=O)(=O)n2c(C(=O)c3cnn(-c4ccc5[nH]c(C)nc5c4)c3N)cc3ccc(CN4CCCC4)cc32)cc1] | [5-amino-1-(2-methyl-1H-benzimidazol-5-yl)-1H-pyrazol-4-yl]-[6-pyrrolidin-1-ylmethyl-1-(toluene-4-sulfonyl)-1H-indol-2-yl]-methanone | 594 |
| 1342 | 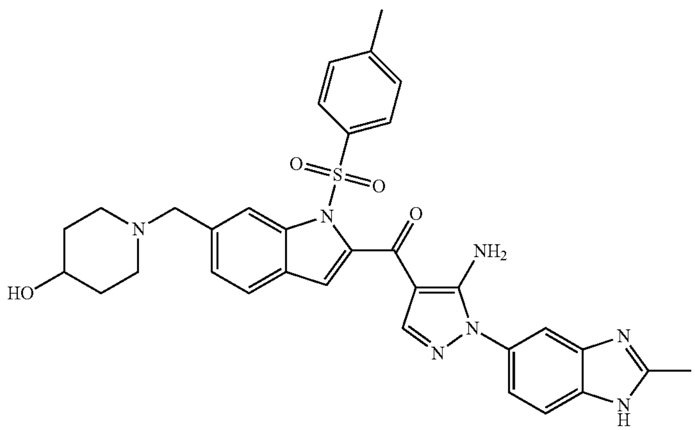 [SMILES: Cc1ccc(S(=O)(=O)n2c(C(=O)c3cnn(-c4ccc5[nH]c(C)nc5c4)c3N)cc3ccc(CN4CCC(O)CC4)cc32)cc1] | [5-amino-1-(2-methyl-1H-benzimidazol-5-yl)-1H-pyrazol-4-yl]-[6-(4-hydroxy-piperidin-1-ylmethyl)-1-(toluene-4-sulfonyl)-1H-indol-2-yl]-methanone | 624 |
| 1343 | 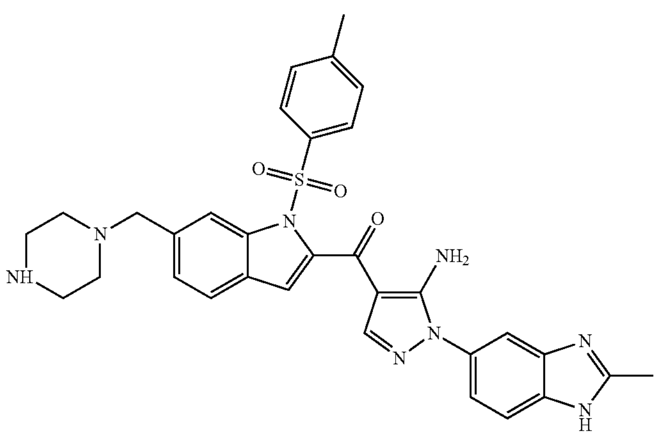 [SMILES: Cc1ccc(S(=O)(=O)n2c(C(=O)c3cnn(-c4ccc5[nH]c(C)nc5c4)c3N)cc3ccc(CN4CCNCC4)cc32)cc1] | [5-amino-1-(2-methyl-1H-benzimidazol-5-yl)-1H-pyrazol-4-yl]-[6-piperadin-1-ylmethyl)-1-(toluene-4-sulfonyl)-1H-indol-2-yl]-methanone | 609 |

| Compound No. | Structure | Compound name | m/z |
|---|---|---|---|
| 1344 | 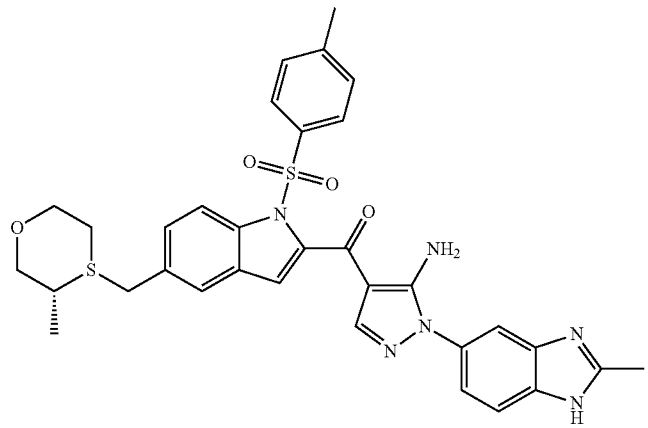 | [5-amino-1-(2-methyl-1H-benzimidazol-5-yl)-1H-pyrazol-4-yl]-[5-((R)-3-methyl-morpholin-4-ylmethyl)-1-(toluene-4-sulfonyl)-1H-indol-2-yl]-methanone | 624 |
| 1345 | 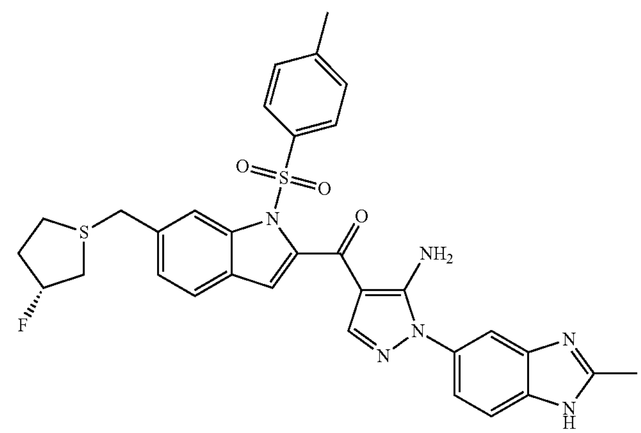 | [5-amino-1-(2-methyl-1H-benzimidazol-5-yl)-1H-pyrazol-4-yl]-[6-((R)-3-fluoro-pyrrolidin-1-ylmethyl)-1-(toluene-4-sulfonyl)-1H-indol-2-yl]-methanone | 612 |
| 1346 | 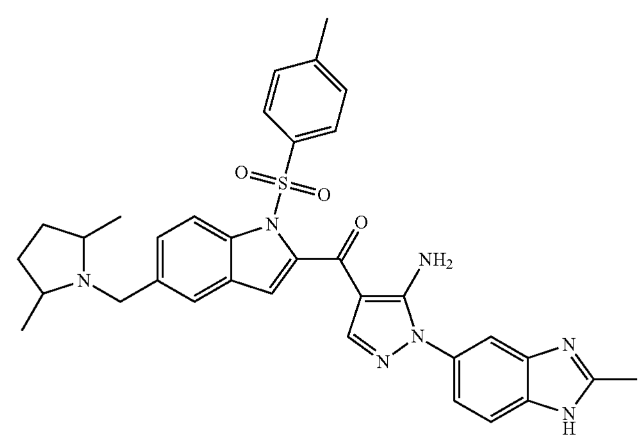 [SMILES: Cc1ccc(S(=O)(=O)n2c(C(=O)c3cnn(-c4ccc5[nH]c(C)nc5c4)c3N)cc3cc(CN4C(C)CCC4C)ccc32)cc1] | [5-amino-1-(2-methyl-1H-benzimidazol-5-yl)-1H-pyrazol-4-yl]-[5-(2,5-dimethyl-pyrrolidin-1-ylmethyl)-1-(toluene-4-sulfonyl)-1H-indol-2-yl]-methanone | 622 |

TABLE 14-continued

| Compound No. | Structure | Compound name | m/z |
|---|---|---|---|
| 1347 | 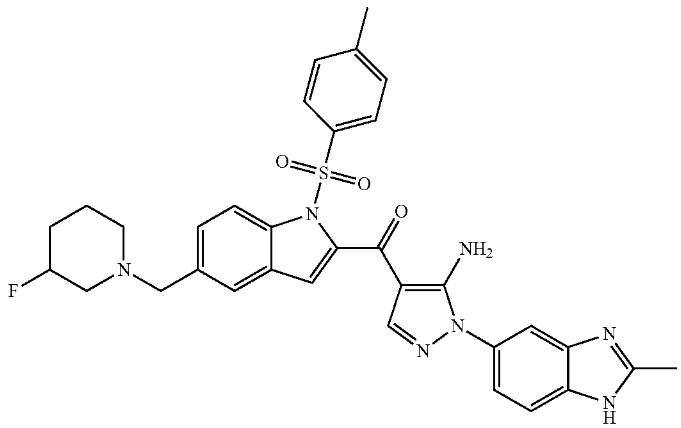 [SMILES: Cc1ccc(S(=O)(=O)n2c(C(=O)c3cnn(-c4ccc5[nH]c(C)nc5c4)c3N)cc3cc(CN4CCCC(F)C4)ccc32)cc1] | [5-amino-1-(2-methyl-1H-benzimidazol-5-yl)-1H-pyrazol-4-yl]-[5-(3-fluoro-piperidin-1-ylmethyl)-1-(toluene-4-sulfonyl)-1H-indol-2-yl]-methanone | 626 |
| 1348 | 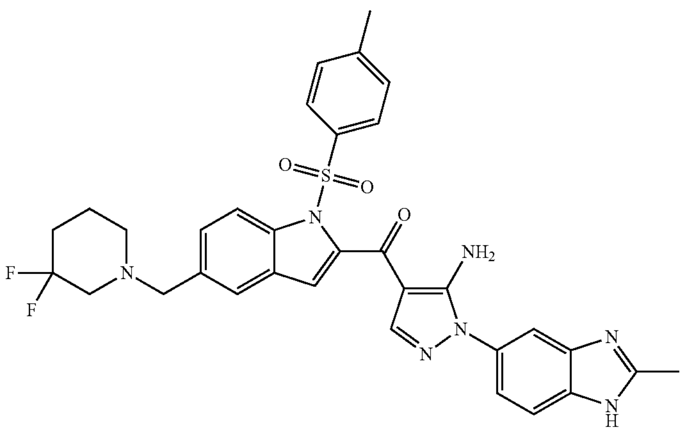 [SMILES: Cc1ccc(S(=O)(=O)n2c(C(=O)c3cnn(-c4ccc5[nH]c(C)nc5c4)c3N)cc3cc(CN4CCCC(F)(F)C4)ccc32)cc1] | [5-amino-1-(2-methyl-1H-benzimidazol-5-yl)-1H-pyrazol-4-yl]-[5-(3,3-difluoro-piperidin-1-ylmethyl)-1-(toluene-4-sulfonyl)-1H-indol-2-yl]-methanone | 644 |
| 1349 | 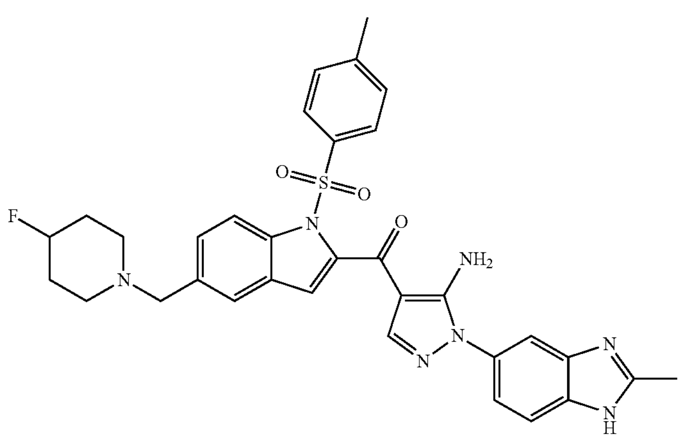 [SMILES: Cc1ccc(S(=O)(=O)n2c(C(=O)c3cnn(-c4ccc5[nH]c(C)nc5c4)c3N)cc3cc(CN4CCC(F)CC4)ccc32)cc1] | [5-amino-1-(2-methyl-1H-benzimidazol-5-yl)-1H-pyrazol-4-yl]-[5-(4-fluoro-piperidin-1-ylmethyl)-1-(toluene-4-sulfonyl)-1H-indol-2-yl]-methanone | 626 |

TABLE 14-continued

| Compound No. | Structure | Compound name | m/z |
|---|---|---|---|
| 1350 | 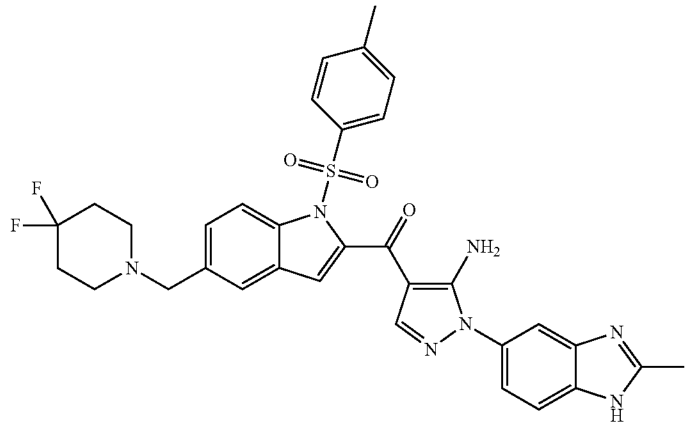 [SMILES: Cc1ccc(S(=O)(=O)n2c(C(=O)c3cnn(-c4ccc5[nH]c(C)nc5c4)c3N)cc3cc(CN4CCC(F)(F)CC4)ccc32)cc1] | [5-amino-1-(2-methyl-1H-benzimidazol-5-yl)-1H-pyrazol-4-yl]-[5-(4,4-difluoro-piperidin-1-ylmethyl)-1-(toluene-4-sulfonyl)-1H-indol-2-yl]-methanone | 644 |
| 1351 | 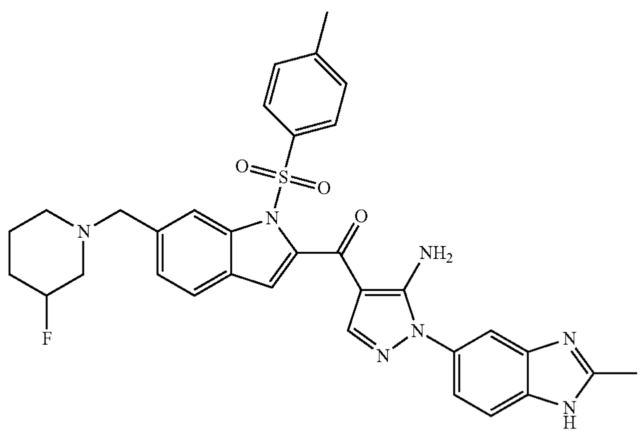 [SMILES: Cc1ccc(S(=O)(=O)n2c(C(=O)c3cnn(-c4ccc5[nH]c(C)nc5c4)c3N)cc3ccc(CN4CCCC(F)C4)cc32)cc1] | [5-amino-1-(2-methyl-1H-benzimidazol-5-yl)-1H-pyrazol-4-yl]-[6-(3-fluoro-piperidin-1-ylmethyl)-1-(toluene-4-sulfonyl)-1H-indol-2-yl]-methanone | 626 |
| 1352 | 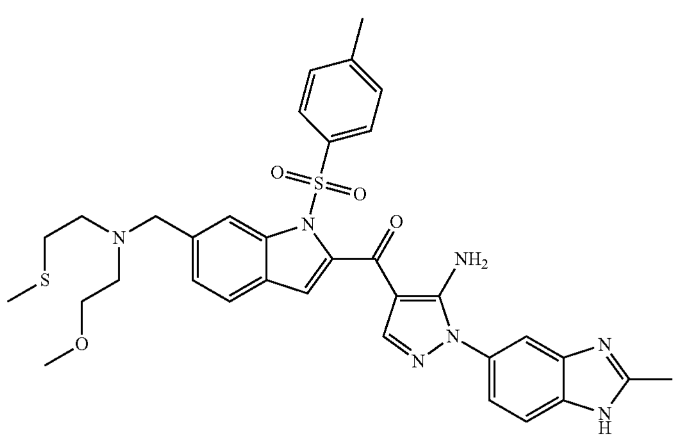 | [5-amino-1-(2-methyl-1H-benzimidazol-5-yl)-1H-pyrazol-4-yl]-[6-{[bis-(2-methoxy-ethyl)-amino]-methyl-1-(toluene-4-sulfonyl)-1H-indol-2-yl]-methanone | 656 |

TABLE 14-continued

| Compound No. | Structure | Compound name | m/z |
|---|---|---|---|
| 1353 | 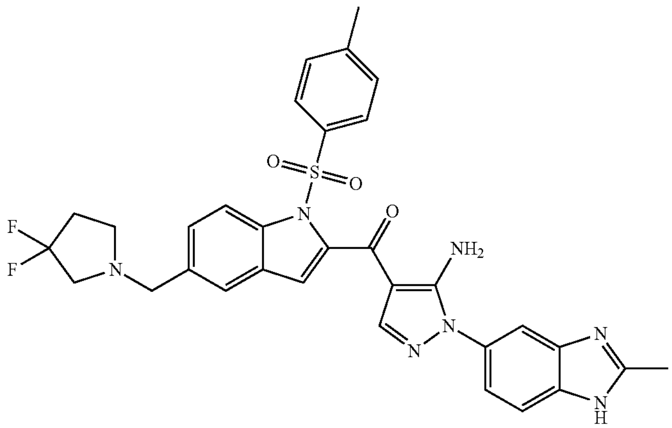 [SMILES: Cc1ccc(S(=O)(=O)n2c(C(=O)c3cnn(-c4ccc5[nH]c(C)nc5c4)c3N)cc3cc(CN4CCC(F)(F)C4)ccc32)cc1] | [5-amino-1-(2-methyl-1H-benzimidazol-5-yl)-1H-pyrazol-4-yl]-[5-(3,3-difluoro-pyrrolidin-1-ylmethyl)-1-(toluene-4-sulfonyl)-1H-indol-2-yl]-methanone | 630 |
| 1354 | 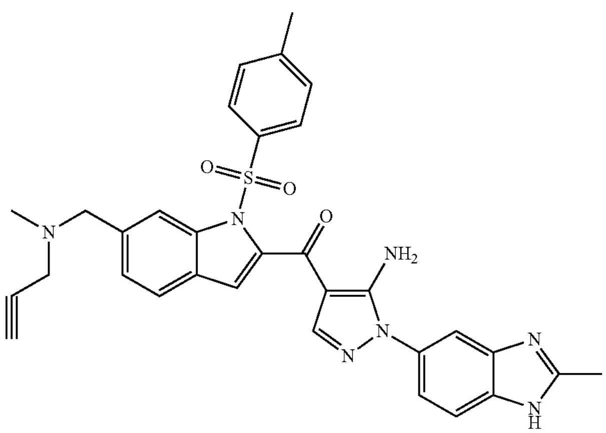 [SMILES: C#CCN(C)Cc1ccc2cc(C(=O)c3cnn(-c4ccc5[nH]c(C)nc5c4)c3N)n(S(=O)(=O)c3ccc(C)cc3)c2c1] | [5-amino-1-(2-methyl-1H-benzimidazol-5-yl)-1H-pyrazol-4-yl]-{6-[(methyl-prop-2-ynyl-amino)-methyl]-1-(toluene-4-sulfonyl)-1H-indol-2-yl}-methanone | 592 |
| 1355 | 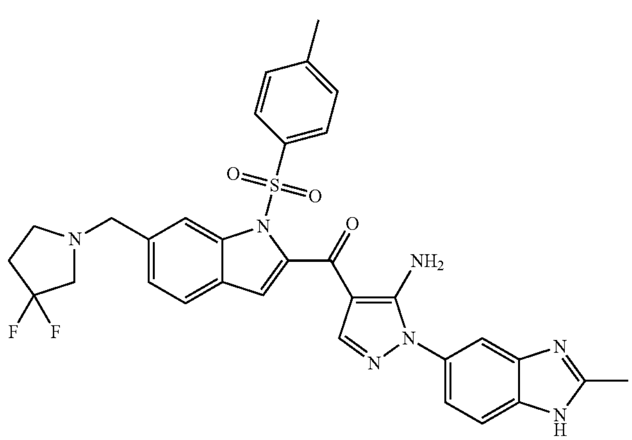 [SMILES: Cc1ccc(S(=O)(=O)n2c(C(=O)c3cnn(-c4ccc5[nH]c(C)nc5c4)c3N)cc3ccc(CN4CCC(F)(F)C4)cc32)cc1] | [5-amino-1-(2-methyl-1H-benzimidazol-5-yl)-1H-pyrazol-4-yl]-[6-(3,3-difluoro-pyrrolidin-1-ylmethyl)-1-(toluene-4-sulfonyl)-1H-indol-2-yl]-methanone | 630 |

TABLE 14-continued

| Compound No. | Structure | Compound name | m/z |
|---|---|---|---|
| 1356 | 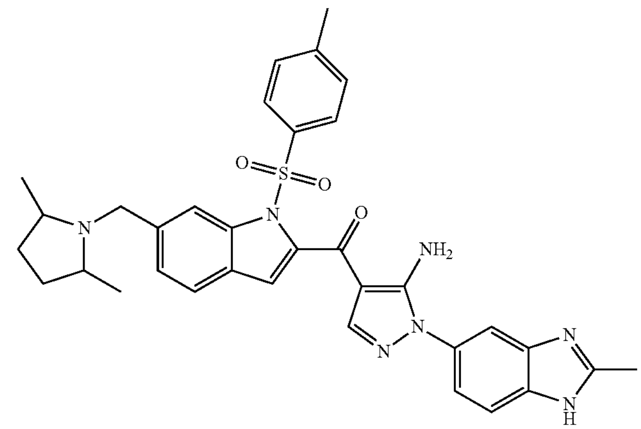 [SMILES: Cc1ccc(S(=O)(=O)n2c(C(=O)c3cnn(-c4ccc5[nH]c(C)nc5c4)c3N)cc3ccc(CN4C(C)CCC4C)cc32)cc1] | [5-amino-1-(2-methyl-1H-benzimidazol-5-yl)-1H-pyrazol-4-yl]-[6-(2,5-dimethyl-pyrrolidin-1-ylmethyl)-1-(toluene-4-sulfonyl)-1H-indol-2-yl]-methanone | 622 |
| 1357 | 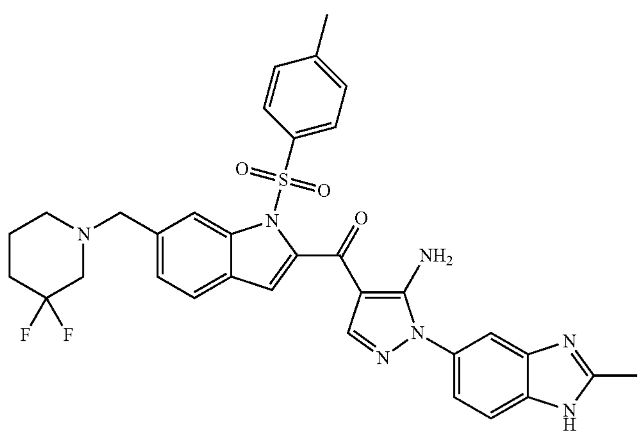 [SMILES: Cc1ccc(S(=O)(=O)n2c(C(=O)c3cnn(-c4ccc5[nH]c(C)nc5c4)c3N)cc3ccc(CN4CCCC(F)(F)C4)cc32)cc1] | [5-amino-1-(2-methyl-1H-benzimidazol-5-yl)-1H-pyrazol-4-yl]-[6-(3,3-difluoro-piperidin-1-ylmethyl)-1-(toluene-4-sulfonyl)-1H-indol-2-yl]-methanone | 644 |
| 1358 | 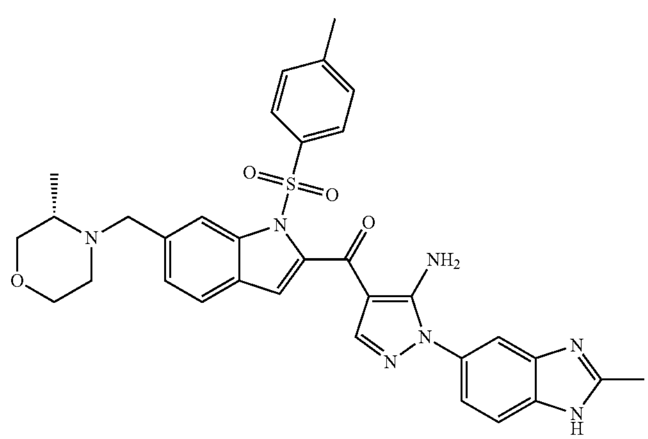 [SMILES: Cc1ccc(S(=O)(=O)n2c(C(=O)c3cnn(-c4ccc5[nH]c(C)nc5c4)c3N)cc3ccc(CN4CCOC[C@@H]4C)cc32)cc1] | [5-amino-1-(2-methyl-1H-benzimidazol-5-yl)-1H-pyrazol-4-yl]-[6-((S)-3-methyl-morpholin-4-ylmethyl)-1-(toluene-4-sulfonyl)-1H-indol-2-yl]-methanone | 624 |

Examples 196 and 197

The compounds of Examples 196 and 197 listed in Table 15 were synthesized by the same method as in Step 8.

TABLE 15

| Example | Structure | Compound name |
|---|---|---|
| 196 | 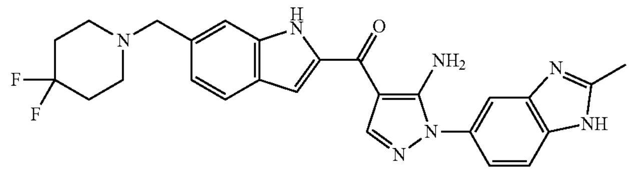 [SMILES: Cc1nc2cc(-n3ncc(C(=O)c4cc5ccc(CN6CCC(F)(F)CC6)cc5[nH]4)c3N)ccc2[nH]1] | [5-amino-1-(2-methyl-1H-benzimidazol-5-yl)-1H-pyrazol-4-yl]-[6-(4,4-difluoro-piperidin-1-ylmethyl)-1H-indol-2-yl]-methanone |
| 197 | 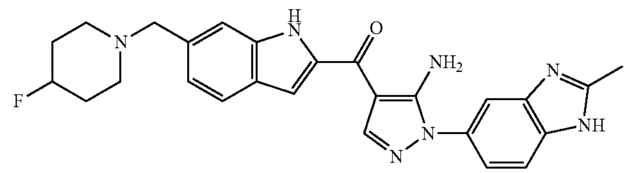 [SMILES: Cc1nc2cc(-n3ncc(C(=O)c4cc5ccc(CN6CCC(F)CC6)cc5[nH]4)c3N)ccc2[nH]1] | [5-amino-1-(2-methyl-1H-benzimidazol-5-yl)-1H-pyrazol-4-yl]-[6-(4-fluoro-piperidin-1-ylmethyl)-1H-indol-2-yl]-methanone |

| Example | m/z | NMR |
|---|---|---|
| 196 | 490 | 1H-NMR (DMSO-D6) δ: 12.46 (1.0H, s), 11.65 (1.0H, s), 8.30 (1.0H, s), 7.64 (3.0H, m), 7.42 (2.0H, t, J = 2.4 Hz), 7.30 (1.0H, dd, J = 8.3, 2.0 Hz), 7.07 (1.0H, dd, J = 8.3, 1.0 Hz), 7.00 (2.0H, m), 3.64 (3.0H, s), 2.55-2.48 (4.2H, m), 2.54 (2.5H, s), 2.01-1.91 (4.2H, m). |
| 197 | 472 | 1H-NMR (DMSO-D6) δ: 12.46 (1.0H, s), 11.63 (1.0H, s), 8.30 (1.0H, s), 7.62 (3.0H, m), 7.41 (2.0H, d, J = 5.9 Hz), 7.30 (1.0H, dd, J = 8.5, 2.2 Hz), 7.05 (1.0H, dd, J = 8.3, 1.0 Hz), 7.00 (2H, m), 4.69 (1.0H, m), 3.56 (2.0H, s), 2.60-2.50 (2.0H, m), 2.54 (3H, s), 2.37-2.26 (2.0H, m), 1.94-1.78 (2.0H, m), 1.78-1.65 (2.0H, m). |

Step 9: Synthesis of 1-(4-{2-[5-amino-1-(2-methyl-1H-benzimidazol-5-yl)-1H-pyrazole-4-carbonyl]-1-benzenesulfonyl-1-indol-5-ylmethyl}-piperazin-1-yl)-ethanone (1359)

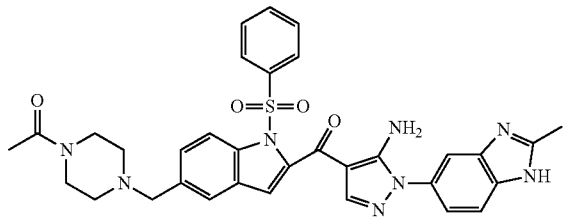 [SMILES: CC(=O)N1CCN(Cc2ccc3c(c2)cc(C(=O)c2cnn(-c4ccc5[nH]c(C)nc5c4)c2N)n3S(=O)(=O)c2ccccc2)CC1]

[5-Amino-1-(2-methyl-1H-benzimidazol-5-yl)-1H-pyrazol-4-yl]-(5-piperazin-1-ylmethyl-1H-indol-2-yl)-methanone (103 mg) was dissolved in a saturated aqueous solution of sodium bicarbonate (25 ml) containing dichloromethane (20 ml) and methanol (3 ml), and cooled to 0° C. Then, acetyl chloride (326 μl) was added thereto in three parts, and stirred for 1.5 hour. The reaction mixture was extracted with dichloromethane. The extract was dried over anhydrous sodium sulfate. The desiccant was removed by filtration, and the filtrate was concentrated under reduced pressure. The resulting residue was purified by silica gel column chromatography (methanol/dichloromethane=0/100 to 10/100) to give 1-(4-{2-[5-amino-1-(2-methyl-1H-benzimidazol-5-yl)-1H-pyrazole-4-carbonyl]-1-benzenesulfonyl-1-indol-5-ylmethyl}-piperazin-1-yl)-ethanone (32 mg).

1H-NMR (CDCl3) δ: 8.18-8.14 (2.0H, m), 8.05 (1.0H, d, J=8.8 Hz), 7.78 (1.1H, s), 7.60-7.56 (1.0H, m), 7.50 (3.0H, m), 7.40 (1.0H, dd, J=8.8, 1.5 Hz), 7.35 (1.0H, m), 6.98 (1.0H, s), 6.03 (2.0H, m), 3.62 (2.0H, t, J=5.0 Hz), 3.58 (2.0H, s), 3.45 (2.0H, t, J=5.0 Hz), 2.64 (3.0H, s), 2.42 (4.0H, m), 2.07 (3.0H, s)

ESI (LC-MS positive mode) m/z 637 [(M+H)⁺]

Step 10: Synthesis of 5-amino-1-(2-methyl-1H-benzimidazol-5-yl)-1H-pyrazol-4-yl]-[1-benzenesulfonyl-5-(4-methanesulfonylpiperazin-1-ylmethyl)-1H-indol-2-yl]-methanone (1360)

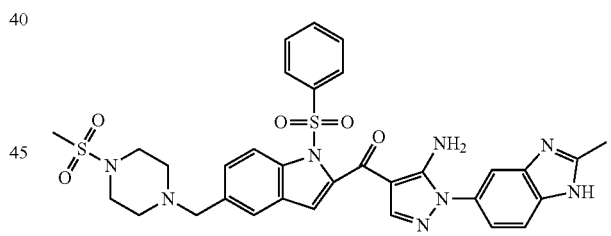

[5-Amino-1-(2-methyl-1H-benzimidazol-5-yl)-1H-pyrazol-4-yl]-(5-piperazin-1-ylmethyl-1H-indol-2-yl)-methanone (94 mg) was dissolved in tetrahydrofuran (THF) (5 ml) and a saturated aqueous solution of sodium bicarbonate (5 ml), and cooled to 0° C. Then methanesulfonyl chloride (94 μl) was added thereto and stirred at 0° C. for 1.5 hour. Then ammonia water (5 ml) was added thereto, and stirred at 0° C. for two hours. The reaction mixture was extracted with ethyl acetate, and the extract was washed with a saturated sodium chloride solution and dried over anhydrous sodium sulfate. The desiccant was removed by filtration. The filtrate was concentrated under reduced pressure. The resulting residue was purified by silica gel column chromatography (methanol/dichloromethane=0/100 to 15/100) to give 5-amino-1-(2-methyl-1H-benzimidazol-5-yl)-1H-pyrazol-4-yl]-[1-benzenesulfonyl-5-(4-methanesulfonylpiperazin-1-ylmethyl)-1H-indol-2-yl]-methanone (39 mg).

¹H-NMR (CD₃OD) δ: 8.09 (2.0H, m), 7.98 (2.0H, m), 7.84 (1.0H, m), 7.75 (1.0H, m), 7.65-7.57 (3.0H, m), 7.53-7.40 (3.0H, m), 7.12 (1.0H, d, J=3.9 Hz), 3.64 (2.0H, m), 3.25-3.15 (4.0H, m), 2.86 (3.0H, s), 2.82 (3.0H, s), 2.54 (4.0H, m)

ESI (LC-MS positive mode) m/z 673 [(M+H)⁺]

Step 11: Synthesis of 5-isopropoxy-1-(toluene-4-sulfonyl)-1H-indole-2-carboxylic acid ethyl ester (1361)

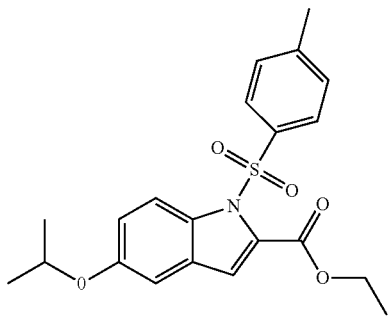

Diisopropyl azodicarboxylate (0.15 ml, 0.75 mmol) was added to an anhydrous tetrahydrofuran (THF) solution (2.5 ml) of 5-hydroxy-1-(toluene-4-sulfonyl)-1H-indole-2-carboxylic acid ethyl ester (175 mg, 0.48 mmol), triphenylphosphine (197 mg, 0.75 mmol), and 2-propanol (0.2 ml, 4.0 mmol), and stirred at room temperature for one hour. The reaction mixture was concentrated under reduced pressure. The resulting residue was purified by silica gel column chromatography to give 5-isopropoxy-1-(toluene-4-sulfonyl)-1H-indole-2-carboxylic acid ethyl ester as a colorless gum-like material (166.7 mg, 87%).

¹H-NMR (DMSO-D₆) δ: 7.86 (1H, d, J=9.1 Hz), 7.79 (2H, d, J=8.5 Hz), 7.39 (2H, d, J=8.5 Hz), 7.25 (1H, s), 7.15 (1H, d, J=2.4 Hz), 7.04 (1H, dd, J=9.1, 2.4 Hz), 4.62-4.53 (1H, m), 4.34 (2H, q, J=7.1 Hz), 2.34 (3H, s), 1.31 (3H, t, J=7.1 Hz), 1.25 (6H, d, J=6.1 Hz)

ESI (LC-MS positive mode) m/z 402 [(M+H)⁺]

The compounds of numbers 1362 to 1367 listed in Table 16 were synthesized by the same method as in Step 11.

TABLE 16

| Compound No. | Structure | Compound name | m/z |
|---|---|---|---|
| 1362 | 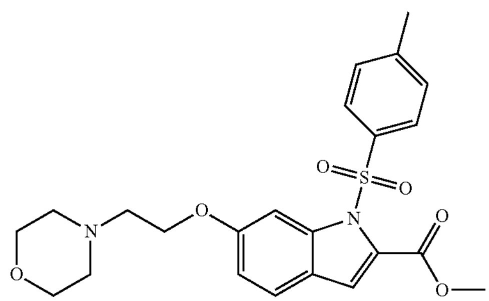 [SMILES: COC(=O)c1cc2ccc(OCCN3CCOCC3)cc2n1S(=O)(=O)c1ccc(C)cc1] | 6-(2-morpholin-4-yl-ethoxy)-1-(toluene-4-sulfonyl)-1H-indole-2-carboxylic acid methyl ester | 459 |
| 1363 | 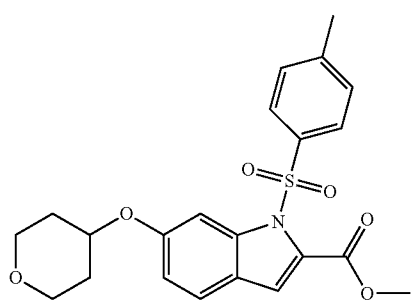 [SMILES: COC(=O)c1cc2ccc(OC3CCOCC3)cc2n1S(=O)(=O)c1ccc(C)cc1] | 6-(tetrahydro-pyran-4-yloxy)-1-(toluene-4-sulfonyl)-1H-indole-2-carboxylic acid methyl ester | 430 |
| 1364 | 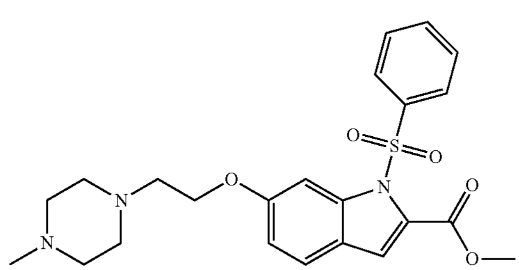 | 1-benzenesulfonyl-6-[2-(4-methyl-piperadin-1-yl)-ethoxy]-1H-indole-2-carboxylic acid methyl ester | 458 |

TABLE 16-continued

| Compound No. | Structure | Compound name | m/z |
|---|---|---|---|
| 1365 | 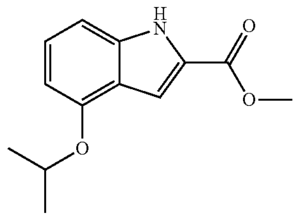 [SMILES: COC(=O)c1cc2c(OC(C)C)cccc2[nH]1] | 4-isopropoxy-1H-indole-2-carboxylic acid methyl ester | 234 |
| 1366 | 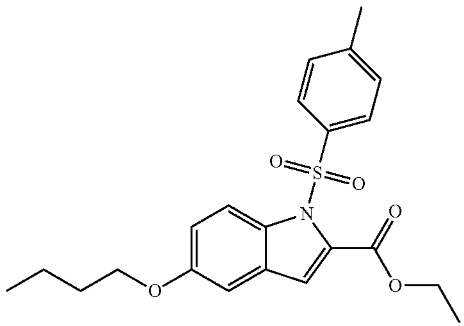 [SMILES: CCCCOc1ccc2c(c1)cc(C(=O)OCC)n2S(=O)(=O)c1ccc(C)cc1] | 5-(2-methoxy-ethoxy)-1-(toluene-4-sulfonyl)-1H-indole-2-carboxylic acid ethyl ester | 416 |
| 1367 | 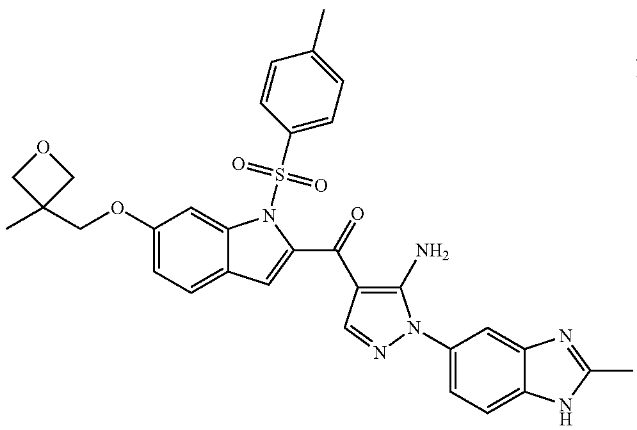 | [5-amino-1-(2-methyl-1H-benzimidazol-5-yl)-1H-pyrazol-4-yl]-[6-(3-methyl-oxetan-3-ylmethoxy)-1-(toluene-4-sulfonyl)-1H-indol-2-yl]-methanone | 611 |

Step 12: Synthesis of 5-cyclopropylmethoxy-1-(toluene-4-sulfonyl)-1H-indole-2-carboxylic acid ethyl ester (1368)

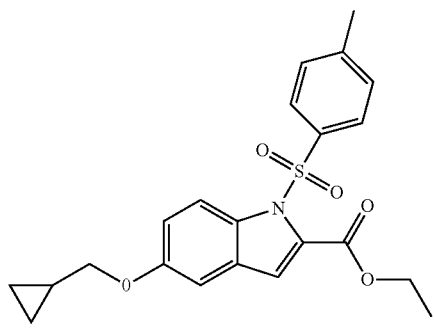

Cyclopropylmethyl bromide (0.072 ml, 0.75 mmol) was added to a suspension (5.0 ml) of 5-hydroxy-1-(toluene-4-sulfonyl)-1H-indole-2-carboxylic acid ethyl ester (173 mg, 0.48 mmol) and potassium carbonate (276 mg, 1.0 mmol) in acetonitrile, and stirred at 80° C. for five hours. After cooling to room temperature, the reaction mixture was combined with ethyl acetate and water and extracted with ethyl acetate. The extract was washed with water and a saturated aqueous solution of sodium chloride, and dried over anhydrous sodium sulfate. The desiccant was removed by filtration. The filtrate was concentrated under reduced pressure. The resulting residue was purified by silica gel column chromatography to give 5-cyclopropylmethoxy-1-(toluene-4-sulfonyl)-1H-indole-2-carboxylic acid ethyl ester as a colorless gum-like material (112.5 mg, 56%).

$^1$H-NMR (DMSO-D$_6$) δ: 7.87 (1H, d, J=9.2 Hz), 7.76 (2H, d, J=8.2 Hz), 7.38 (2H, d, J=8.2 Hz), 7.25 (1H, s), 7.11 (1H, d, J=2.6 Hz), 7.07 (1H, dd, J=9.2, 2.6 Hz), 4.33 (2H, q, J=8.1 Hz), 3.80 (2H, d, J=6.6 Hz), 2.33 (3H, s), 1.32 (3H, t, J=8.1 Hz), 1.25-1.19 (1H, m), 0.58-0.52 (2H, m), 0.33-0.28 (2H, m)

ESI (LC-MS positive mode) m/z 414 [(M+H)$^+$]

Example 198

Synthesis of [5-amino-1-(2-methyl-1H-benzimidazol-5-yl)-1H-pyrazol-4-yl]-[6-(oxetan-3-yloxy)-1H-indol-2-yl]-methanone

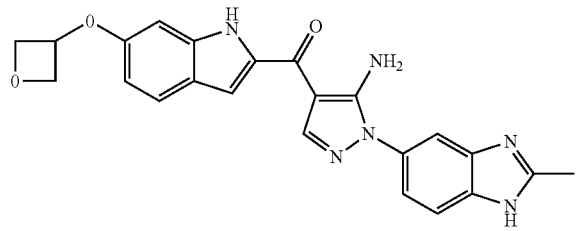

[5-Amino-1-(2-methyl-1H-benzimidazol-5-yl)-1H-pyrazol-4-yl]-(6-hydroxy-1H-indol-2-yl)-methanone (21 mg, 0.056 mmol), toluene-4-sulfonic acid oxetan-3-yl ester (19 mg, 0.084 mmol), and potassium carbonate (13 mg, 0.095 mmol) were dissolved in anhydrous N,N-dimethylformamide (DMF), and heated at 80° C. with stirring under a nitrogen atmosphere for six days. After cooling to room temperature, the reaction mixture was combined with water, and extracted with an ethyl acetate/methanol (10/1) solution. The organic layer was isolated, washed with water, and dried over anhydrous magnesium sulfate. The desiccant was removed by filtration. The filtrate was concentrated under reduced pressure. The resulting residue was purified by silica gel column chromatography (dichloromethane/methanol=100/3) to give [5-amino-1-(2-methyl-1H-benzimidazol-5-yl)-1H-pyrazol-4-yl]-[6-(oxetan-3-yloxy)-1H-indol-2-yl]-methanone as a yellow solid (6.9 mg, 29%).

$^1$H-NMR (DMSO-D$_6$) δ: 12.48 (1.0H, brs), 11.48 (1.0H, brs), 8.28 (1.0H, s), 7.62-7.60 (3.0H, m), 7.41 (1.0H, brs), 7.28 (1.0H, dd, J=8.3, 2.0 Hz), 6.96 (1.0H, brs), 6.94 (1.0H, brs), 6.71 (1.0H, dd, J=8.5, 2.2 Hz), 6.67 (1.0H, brs), 5.34-5.29 (1.0H, m), 4.94 (2.0H, dd, J=6.8, 6.8 Hz), 4.60 (2.0H, dd, J=6.8, 5.1 Hz), 2.53 (3.0H, s)

ESI (LC-MS positive mode) m/z 429 [(M+H)$^+$]

Example 199

Synthesis of [5-amino-1-(2-methyl-1H-benzimidazol-5-yl)-1H-pyrazol-4-yl]-(6-hydroxy-1H-indol-2-yl)-methanone

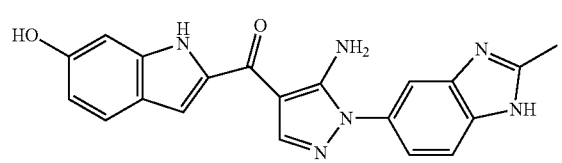 [SMILES: Cc1nc2cc(-n3ncc(C(=O)c4cc5ccc(O)cc5[nH]4)c3N)ccc2[nH]1]

2-[5-Amino-1-(2-methyl-1H-benzimidazol-5-yl)-1H-pyrazole-4-carbonyl]-1-(toluene-4-sulfonyl)-1H-indole-6-carbaldehyde (650 mg, 1.0 mmol), 1,1'-bis(diphenylphosphino)ferrocene palladium(II) dichloride (42 mg, 0.051 mmol), bis(pinacolato) diboron (312 mg, 1.23 mmol), and potassium acetate (323 mg, 3.3 mmol) were dissolved in anhydrous N,N-dimethylformamide (DMF) (4.1 ml). After deaeration, the mixture was heated at 100° C. with stirring under a nitrogen atmosphere for eight hours. The reaction mixture was cooled to room temperature, and then water was added thereto. The precipitated solid was collected by filtration, washed with water, and then dried to give a brown solid (538 mg). The obtained crude product was used in subsequent reactions without purification.

The obtained brown solid crude product of 4-methyl-morpholine N-oxide (256 mg, 2.2 mmol) was dissolved in tetrahydrofuran (THF) (7.0 ml), and heated at 70° C. with stirring under a nitrogen atmosphere for three and half hours. After the reaction mixture was cooled to room temperature, water and ethyl acetate were added thereto. The mixture was filtered through Celite®, and the filtrate was divided into organic and aqueous layers. The organic layer was concentrated under reduced pressure, and the resulting residue was purified by silica gel column chromatography (amino silica; dichloromethane/methanol=100/5 to 100/10) to give [5-amino-1-(2-methyl-1H-benzimidazol-5-yl)-1H-pyrazol-4-yl]-(6-hydroxy-1H-indol-2-yl)-methanone as a yellow amorphous material (123 mg, with a two-step yield of 23%).

$^1$H-NMR (DMSO-D$_6$) δ: 12.51 (1.0H, brs), 11.30 (1.0H, brs), 9.40 (1.0H, brs), 8.26 (1.0H, s), 7.61-7.59 (2.0H, m), 7.47 (1.0H, d, J=8.8 Hz), 7.34 (1.0H, s), 7.28 (1.0H, d, J=8.8 Hz), 6.91 (2.0H, brs), 6.82 (1.0H, s), 6.62 (1.0H, d, J=8.8 Hz), 2.53 (3.0H, s)

ESI (LC-MS positive mode) m/z 373 [(M+H)$^+$]

Step 13: Synthesis of [5-amino-1-(2-methyl-1H-benzimidazol-5-yl)-1H-pyrazol-4-yl]-[6-iodo-1-(toluene-4-sulfonyl)-1H-indol-2-yl]-methanone (1369)

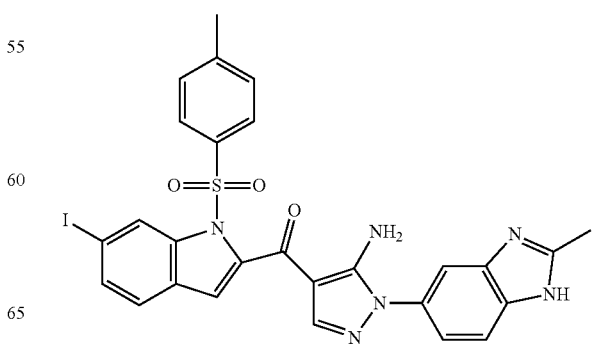

A mixture consisting of [5-amino-1-(2-methyl-3H-benzimidazol-5-yl)-1H-pyrazol-4-yl]-[6-bromo-1-(toluene-4-sulfonyl)-1H-indol-2-yl]-methanone (1 g), copper (I) iodide (161 mg), sodium iodide (508 mg), trans-N,N'-dimethylcyclohexane-1,2-diamine (267 μl), and anhydrous dioxane (5 ml) was stirred in a pressure-proof container at 105 to 112° C. under a nitrogen atmosphere for 20 hours. The reaction mixture was poured into an aqueous solution of 2 M ammonia, and the mixture was extracted with ethyl acetate. The organic layer was washed with a saturated aqueous solution of sodium chloride, and dried over anhydrous sodium sulfate. The desiccant was removed by filtration. The filtrate was concentrated under reduced pressure. The resulting residue was purified by silica gel column chromatography (methanol/dichloromethane=0/100 to 20/100) to give [5-amino-1-(2-methyl-1H-benzimidazol-5-yl)-1H-pyrazol-4-yl]-[6-iodo-1-(toluene-4-sulfonyl)-1H-indol-2-yl]-methanone (0.67 g, 62%).

$^1$H-NMR (DMSO-$D_6$) δ: 12.44 (1.0H, s), 8.30 (1.0H, d, J=0.6 Hz), 7.98 (2.0H, d, J=8.5 Hz), 7.75 (1.0H, s), 7.66 (1.0H, dd, J=8.2, 1.4 Hz), 7.51 (1.0H, d, J=8.0 Hz), 7.46 (2.0H, d, J=8.5 Hz), 7.28 (1.0H, d, J=7.6 Hz), 7.23 (1.0H, d, J=0.4 Hz), 7.10-6.92 (2.0H, m), 2.53 (3.0H, s), 2.37 (3.0H, s)

ESI (LC-MS positive mode) m/z 637 [(M+H)$^+$]

The compounds of numbers 1370 and 1371 listed in Table 17 were synthesized by the same method as in Step 13.

Step 14: Synthesis of 2-[5-amino-1-(2-methyl-1H-benzimidazol-5-yl)-1H-pyrazole-4-carbonyl]-1-(benzenesulfonyl)-1H-indole-5-carbonitrile (1372)

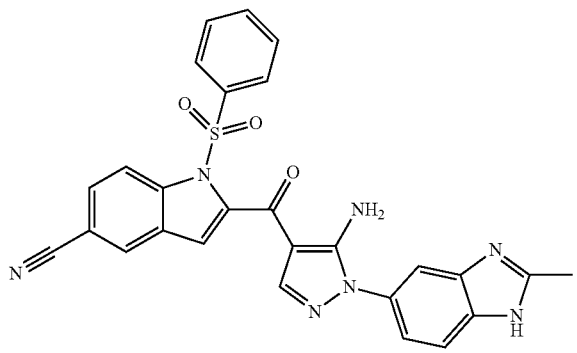 [SMILES: Cc1nc2cc(-n3ncc(C(=O)c4cc5cc(C#N)ccc5n4S(=O)(=O)c4ccccc4)c3N)ccc2[nH]1]

A mixture of 2-[5-amino-1-(2-methyl-1H-benzimidazol-5-yl)-1H-pyrazole-4-carbonyl]-1-(benzenesulfonyl)-5-iodo-1H-indole (117 mg), copper (I) cyanide (84 mg), and 1-methyl-2-pyrrolidinone was reacted in a microwave reactor (190° C., 20 minutes). The reaction mixture was poured into a mixed solution of 2 M ammonia water (40 ml), ethyl acetate (60 ml), and methanol (7 ml), and sonicated for five minutes. After ethyl acetate extraction, the extract was washed with water and then dried over anhydrous sodium sulfate. The desiccant was removed by filtration. The filtrate was concentrated under reduced pressure. The resulting residue was purified by silica gel column chromatography (methanol/dichlo-

TABLE 17

| Compound No. | Structure | Compound name | m/z |
|---|---|---|---|
| 1370 | 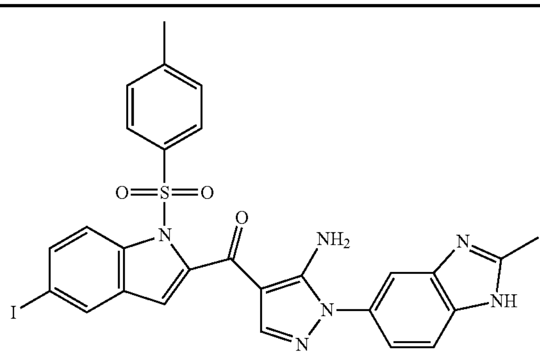 | [5-amino-1-(2-methyl-1H-benzimidazol-5-yl)-1H-pyrazol-4-yl]-[5-iodo-1-(toluene-4-sulfonyl)-1H-indol-2-yl]-methanone | 637 |
| 1371 | | 1-benzenesulfonyl-4-iodo-1H-indole-2-carboxylic acid ethyl ester | 456 | romethane=0/100 to 20/100) to give 2-[5-amino-1-(2-methyl-1H-benzimidazol-5-yl)-1H-pyrazole-4-carbonyl]-1-(benzenesulfonyl)-1H-indole-5-carbonitrile (87 mg, 89%).

$^1$H-NMR (DMSO-D$_6$) δ: 12.47 (1.0H, d, J=8.4 Hz), 8.27-8.21 (4.0H, m), 7.86 (1.0H, dd, J=8.8, 1.8 Hz), 7.80-7.76 (2.0H, m), 7.72-7.64 (3.0H, m), 7.60-7.55 (1.0H, m), 7.35-7.25 (2.0H, m), 7.12-7.02 (2.0H, m), 2.54 (3.0H, s)

ESI (LC-MS positive mode) m/z 522 [(M+H)$^+$]

The compounds of numbers 1373 and 1374 listed in Table 18 were synthesized by the same method as in Step 14.

deaeration and argon replacement was performed again. The reaction container was placed in a reaction device preheated at 80° C. and the reaction mixture was stirred for 20 hours. After cooling to room temperature, the reaction mixture was diluted with ethyl acetate and an aqueous solution of 1 M hydrochloric acid, and filtered through Celite. The resulting filtrate was washed with 1 M hydrochloric acid, water, and a saturated aqueous solution of sodium chloride, and then dried over anhydrous sodium sulfate. The desiccant was removed by filtration. The filtrate was concentrated under reduced pressure, and the resulting residue was purified by silica gel

TABLE 18

| Compound No. | Structure | Compound name | m/z |
| --- | --- | --- | --- |
| 1373 | 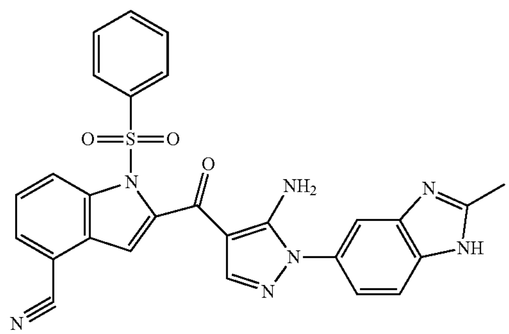 [SMILES: Cc1nc2cc(-n3ncc(C(=O)c4cc5c(C#N)cccc5n4S(=O)(=O)c4ccccc4)c3N)ccc2[nH]1] | 2-[5-amino-1-(2-methyl-1H-benzimidazol-5-yl)-1H-pyrazol-4-carbonyl]-1-benzenesulfonyl-1H-indole-4-carbonitrile | 522 |
| 1374 | 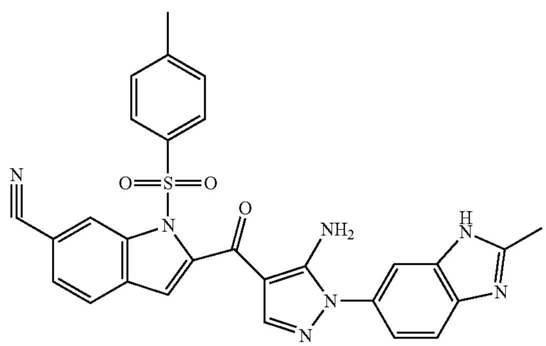 [SMILES: Cc1ccc(S(=O)(=O)n2c(C(=O)c3cnn(-c4ccc5nc(C)[nH]c5c4)c3N)cc3ccc(C#N)cc32)cc1] | 2-[5-amino-1-(2-methyl-1H-benzimidazol-5-yl)-1H-pyrazol-4-carbonyl]-1-(toluene-4-sulfonyl)-1H-indole-6-carbonitrile | 536 |

Step 15: Synthesis of 1-(toluene-4-sulfonyl)-1H-indole-2,5-dicarboxylic acid 2-ethyl ester (1375)

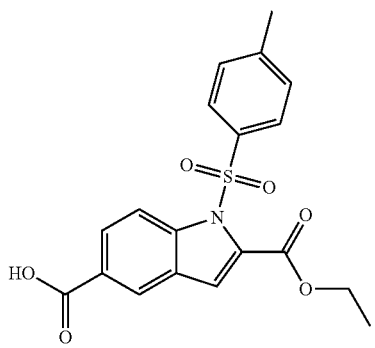 [SMILES: CCOC(=O)c1cc2cc(C(=O)O)ccc2n1S(=O)(=O)c1ccc(C)cc1]

A mixture of 5-bromo-1-(toluene-4-sulfonyl)-1H-indole-2-carboxylic acid ethyl ester (948.4 mg, 2.24 mmol), Tris(dibenzylideneacetone) dipalladium (0) (0.112 mmol, 103 mg), 4,5-bis(diphenylphosphino)-9,9-dimethylxanthene (Xantphos) (0.225 mmol, 130 mg), lithium formate monohydrate (5.6 mmol, 394 mg), lithium chloride (286 mg, 6.75 mmol), and anhydrous N,N-dimethylformamide (DMF) (5.9 ml) was evacuated, and backfilled with argon. Then, N,N-diisopropylethyl amine (4.5 mmol, 0.78 ml) and acetic anhydride (4.5 mmol, 0.43 ml) were added to the mixture, and column chromatography (hexane/ethyl acetate=5/1 to 1/3, and finally ethyl acetate/methanol=15/1) to give 1-(toluene-4-sulfonyl)-1H-indole-2,5-dicarboxylic acid 2-ethyl ester as a yellow amorphous material (930 mg).

$^1$H-NMR (DMSO-D$_6$) δ: 8.32 (1H, d, J=1.5 Hz), 8.13 (1H, d, J=8.8 Hz), 8.05 (1H, dd, J=8.8, 1.5 Hz), 7.93 (2H, d, J=8.2 Hz), 7.50 (1H, s), 7.46 (2H, d, J=8.2 Hz), 4.38 (2H, q, J=7.1 Hz), 2.37 (3H, s), 1.34 (3H, t, J=7.1 Hz)

ESI (LC-MS positive mode) m/z 388 [(M+H)$^+$]

Synthesis of 2-[5-amino-1-(2-methyl-1H-benzimidazol-5-yl)-1H-pyrazole-4-carbonyl]-1-(toluene-4-sulfonyl)-1H-indole-6-carboxylic acid (1376)

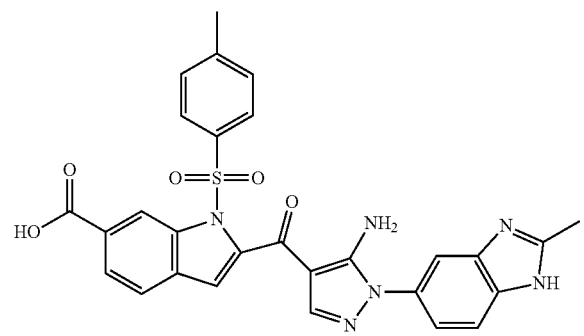 [SMILES: Cc1ccc(S(=O)(=O)n2c(C(=O)c3cnn(-c4ccc5[nH]c(C)nc5c4)c3N)cc3ccc(C(=O)O)cc32)cc1]

2-[5-Amino-1-(2-methyl-1H-benzimidazol-5-yl)-1H-pyrazole-4-carbonyl]-1H-indole-6-carboxylic acid was synthesized by the same method as in Step 15.
ESI (LC-MS positive mode) m/z 555 [(M+H)⁺]

Step 16: Synthesis of 1-(toluene-4-sulfonyl)-1H-indole-2,5-dicarboxylic acid 5-tert-butyl ester 2-ethyl ester (1377)

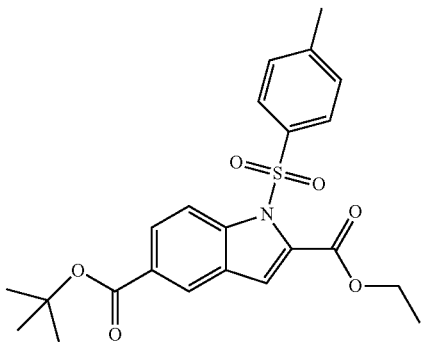 [SMILES: CCOC(=O)c1cc2cc(C(=O)OC(C)(C)C)ccc2n1S(=O)(=O)c1ccc(C)cc1]

1-(Toluene-4-sulfonyl)-1H-indole-2,5-dicarboxylic acid 2-ethyl ester (690 mg, 1.85 mmol) was dissolved in N,N-dimethylformamide di-tert-butyl acetal (3.0 ml), and stirred at 80° C. for two and half hours. N,N-dimethylformamide di-tert-butyl acetal (2.0 ml) was further added thereto and stirred at 80° C. for three hours. After cooling to room temperature, the reaction mixture was diluted with ethyl acetate (150 ml) and water (75 ml). The organic layer was isolated, washed with water and a saturated aqueous solution of sodium chloride, and then dried over anhydrous sodium sulfate. The desiccant was removed by filtration. The filtrate was concentrated under reduced pressure. The resulting residue was purified by silica gel column chromatography (hexane/ethyl acetate=25/1 to 5/1) to give 1-(toluene-4-sulfonyl)-1H-indole-2,5-dicarboxylic acid 5-tert-butyl ester 2-ethyl ester (551 mg, 69%).
¹H-NMR (DMSO-D₆) δ: 8.25 (1H, d, J=1.4 Hz), 8.12 (1H, d, J=8.8 Hz), 8.00 (1H, dd, J=8.8, 1.4 Hz), 7.88 (2H, d, J=8.0 Hz), 7.48 (1H, s), 7.43 (2H, d, J=8.0 Hz), 4.37 (2H, q, J=7.2 Hz), 2.37 (3H, s), 1.56 (9H, s), 1.34 (3H, t, J=7.2 Hz)
ESI (LC-MS positive mode) m/z 444 [(M+H)⁺]

Step 17: Synthesis of [5-amino-1-(2-methyl-1H-benzimidazol-5-yl)-1H-pyrazol-4-yl]-[1-(toluene-4-sulfonyl)-5-trimethyl-silanylethynyl-1H-indol-2-yl]methanone (1378)

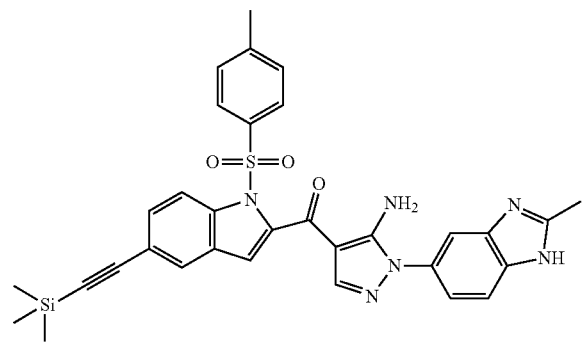

[5-Amino-1-(2-methyl-1H-benzimidazol-5-yl)-1H-pyrazol-4-yl]-[5-bromo-1-(toluene-4-sulfonyl)-1H-indol-2-yl]-methanone (150 mg), dichloro-bis(triphenylphosphine)palladium (II)(54 mg), copper (I) iodide (10 mg), triethylamine (0.7 ml), and anhydrous N,N-dimethylformamide (DMF) (0.7 ml) were combined together in a pressure-proof container, and trimethylsilyl acetylene (150 mg) was added thereto. The mixture was stirred at 80 to 85° C. under nitrogen for 15 hours. After cooling to room temperature, the reaction mixture was diluted with ethyl acetate, washed with a saturated aqueous solution of sodium chloride, and dried over anhydrous sodium sulfate. The desiccant was removed by filtration. The filtrate was concentrated under reduced pressure. The resulting residue was purified by silica gel column chromatography (methanol/dichloromethane=0/100 to 20/100) to give [5-amino-1-(2-methyl-1H-benzimidazol-5-yl)-1H-pyrazol-4-yl]-[1-(toluene-4-sulfonyl)-5-trimethyl-silanylethynyl-1H-indol-2-yl]-methanone (65 mg, 42%).
¹H-NMR (DMSO-D₆) δ: 12.48 (1H, d, J=8.4 Hz), 8.04-7.95 (3H, m), 7.80 (1H, s), 7.75 (1H, d, J=3.7 Hz), 7.69-7.62 (1H, m), 7.62-7.54 (1H, m), 7.50 (1H, dd, J=8.7, 1.7 Hz), 7.44 (2H, d, J=8.6 Hz), 7.29 (1H, t, J=7.9 Hz), 7.20 (1H, s), 7.09-6.97 (2H, m), 2.54 (3H, s), 2.36 (3.0H, s), 0.23 (9.0H, s)
ESI (LC-MS positive mode) m/z 607 [(M+H)⁺]

Synthesis of 1-benzenesulfonyl-4-trimethyl-silanyl-ethynyl-1H-indole-2-carboxylic acid ethyl ester (1379)

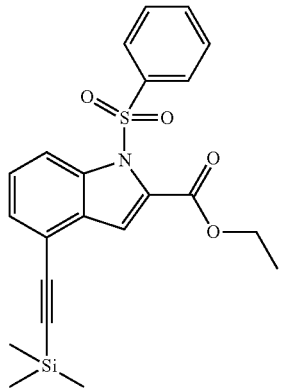 [SMILES: CCOC(=O)c1cc2c(C#C[Si](C)(C)C)cccc2n1S(=O)(=O)c1ccccc1]

1-Benzenesulfonyl-4-trimethyl-silanylethynyl-1H-indole-2-carboxylic acid ethyl ester was synthesized by the same method as in Step 17.
ESI (LC-MS positive mode) m/z 426 [(M+H)⁺]

Step 18: Synthesis of N-[2-[5-amino-1-(2-methyl-1H-benzimidazol-5-yl)-1H-pyrazole-4-carbonyl]-1-(toluene-4-sulfonyl)-1H-indol-6-yl]-methanesulfonamide (1380)

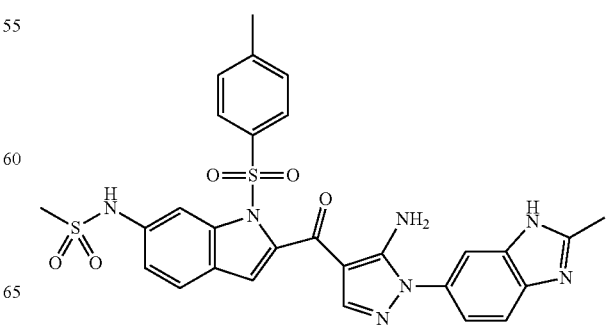

[5-Amino-1-(2-methyl-1H-benzimidazol-5-yl)-1H-pyrazol-4-yl]-[6-iodo-1-(toluene-4-sulfonyl)-1H-indol-2-yl]-methanone (80.3 mg, 0.126 mmol), copper (I) iodide (37.5 mg, 0.197 mmol), methanesulfonamide (37.5 mg, 0.394 mmol), sarcosine (36.2 mg, 0.406 mmol), and tripotassium phosphate (86.0 mg, 9.405 mmol) were dissolved in anhydrous 1-methyl-2-pyrrolidinone (0.36 ml), and heated at 140° C. with stirring under an argon atmosphere for 30 minutes. The reaction mixture was added dropwise to an aqueous solution (20 ml) of 20% ammonium chloride, and extracted with ethyl acetate, the organic layer was washed with an aqueous solution of 20% sodium chloride and dried over anhydrous sodium sulfate. The desiccant was removed by filtration. The filtrate was concentrated under reduced pressure, and the resulting residue was purified by amino gel column chromatography (dichloromethane/methanol=15/1) to give N-[2-[5-amino-1-(2-methyl-1H-benzimidazol-5-yl)-1H-pyrazole-4-carbonyl]-1-(toluene-4-sulfonyl)-1H-indol-6-yl]methanesulfonamide as a yellow amorphous material (17.9 mg with a yield of 24%).

$^1$H-NMR (DMSO-D$_6$) δ: 12.47 (1H, s), 9.93 (1H, brs), 7.97 (1H, s), 7.94 (2H, d, J=7.9 Hz), 7.77 (1H, s), 7.64-7.59 (3H, m), 7.43 (2H, d, J=6.7 Hz), 7.29 (1H, d, J=7.9 Hz), 7.22-7.15 (2H, t, J=5.2 Hz), 7.01 (2H, brs), 2.97 (3H, s), 2.53 (3H, s), 2.35 (3H, s)

ESI (LC-MS positive mode) m/z 604 [(M+H)$^+$]

Example 200

Synthesis of [5-amino-1-(2-methyl-1H-benzimidazol-5-yl)-1H-pyrazol-4-yl]-(6-methanesulfonyl-1H-indol-2-yl)-methanone

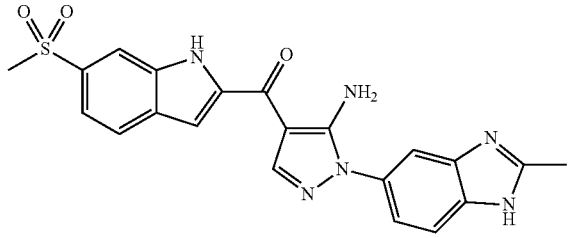

[5-Amino-1-(2-methyl-1H-benzimidazol-5-yl)-1H-pyrazol-4-yl]-(6-methyl-sulfanyl-1H-indol-2-yl)-methanone (23 mg, 0.057 mmol) was dissolved in trifluoroethanol (5 ml), and an aqueous solution (0.5 ml) of oxone (105 mg, 0.171 mmol) was added thereto. The mixture was stirred at room temperature under a nitrogen atmosphere for 1.75 hours. The reaction mixture was filtered, and the filtrate was concentrated. The resulting residue was purified by amino gel column chromatography (dichloromethane/methanol=99/1 to 92/8). Thus, [5-amino-1-(2-methyl-1H-benzimidazol-5-yl)-1H-pyrazol-4-yl]-(6-methanesulfonyl-1H-indol-2-yl)-methanone was obtained as a pale yellow solid (8 mg, 32%).

$^1$H-NMR (DMSO-D$_6$) δ: 12.48 (1H, d, J=4.9 Hz), 12.33 (1H, s), 8.35 (1H, d, J=4.9 Hz), 8.05 (1H, s), 7.94 (1H, d, J=8.5 Hz), 7.65-7.59 (4H, m), 7.31-7.27 (1H, m), 7.11 (2H, d, J=21.4 Hz), 3.22 (3H, s), 2.54 (3H, s)

ESI (LC-MS positive mode) m/z 435 [(M+H)$^+$]

Step 19: Synthesis of 6-cyclopropyl-1-(toluene-4-sulfonyl)-1H-indole-2-carboxylic acid methyl ester (1381)

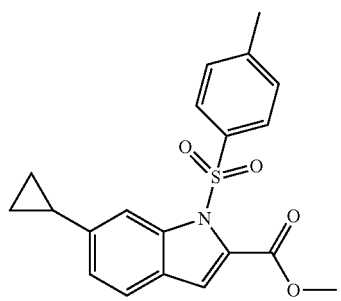 [SMILES: COC(=O)c1cc2ccc(C3CC3)cc2n1S(=O)(=O)c1ccc(C)cc1]

Predetermined amounts of 6-bromo-1-(toluene-4-sulfonyl)-1H-indole-2-carboxylic acid methyl ester (300 mg, 0.73 mmol), palladium acetate (16.5 mg, 0.07 mmol), bis(1,1-dimethylethyl)phenylphosphine (0.028 ml, 0.12 mmol), potassium cyclopropyl trifluoroborate (163 mg, 1.1 mmol), and cesium carbonate (718 mg, 2.2 mmol) were placed in a reaction container, and toluene (5 ml) and water (0.5 ml) were added thereto. The resulting mixture was then stirred at 100° C. for 14 hours. After cooling it to room temperature, the mixture was diluted with ethyl acetate, and washed twice with water, and then dried over anhydrous sodium sulfate. The desiccant was removed by filtration, and concentration was performed. Then, the residue obtained by concentration under reduced pressure was purified by silica gel column chromatography (hexane/ethyl acetate=97/3 to 7/3). Thus, a yellow solid was obtained (208 mg, 77%).

$^1$H-NMR (DMSO-D$_6$) δ: 7.82-7.80 (2H, m), 7.68 (1H, brs), 7.52 (1H, d, J=8.2 Hz), 7.42-7.39 (2H, m), 7.32 (1H, d, J=0.8 Hz), 7.00 (1H, dd, J=8.3, 1.5 Hz), 3.83 (3H, s), 2.33 (3H, s), 2.11-2.09 (1H, m), 1.03 (2H, ddd, J=9.6, 5.2, 3.1 Hz), 0.73-0.70 (2H, m)

ESI (LC-MS positive mode) m/z 370 [(M+H)$^+$]

The compounds of numbers 1382 to 1384 listed in Table 19 were synthesized as described in Step 19.

TABLE 19

| Compound No. | Structure | Compound name | m/z |
|---|---|---|---|
| 1382 | (structure shown) | 6-butyl-1-(toluene-4-sulfonyl)-1H-indole-2-carboxylic acid methyl ester | 386 |

TABLE 19-continued

| Compound No. | Structure | Compound name | m/z |
|---|---|---|---|
| 1383 | 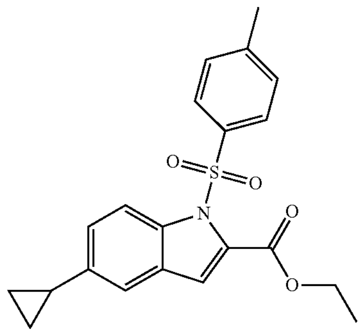 [SMILES: CCOC(=O)c1cc2cc(C3CC3)ccc2n1S(=O)(=O)c1ccc(C)cc1] | 5-cyclopropyl-1-(toluene-4-sulfonyl)-1H-indole-2-carboxylic acid ethyl ester | 384 |
| 1384 | 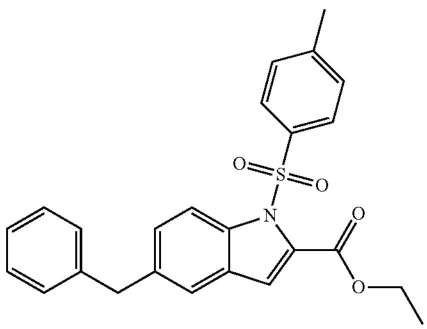 [SMILES: CCOC(=O)c1cc2cc(Cc3ccccc3)ccc2n1S(=O)(=O)c1ccc(C)cc1] | 5-benzyl-1-(toluene-4-sulfonyl)-1H-indole-2-carboxylic acid ethyl ester | 434 |

Step 20: Synthesis of 5-imidazol-1-yl-1H-indole-2-carboxylic acid ethyl ester (1385)

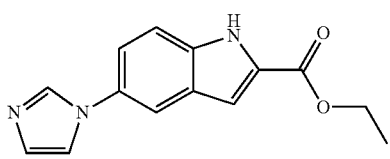 [SMILES: CCOC(=O)c1cc2cc(-n3ccnc3)ccc2[nH]1]

Hydrazone-Based Synthesis Method

Synthesis of 2-[(E)-4-imidazol-1-yl-phenylimino]-propionic acid ethyl ester 4-imidazol-1-yl-phenyl amine (637 mg) was dissolved in 2 M hydrochloric acid/MeOH (3 ml), and this was concentrated under reduced pressure. The residue was suspended in concentrated hydrochloric acid (1 ml), and an aqueous solution of sodium nitrite (304 mg, 2.5 ml) was added dropwise thereto over 30 minutes at 0° C. on ice. The reaction mixture was slowly added dropwise to an aqueous solution prepared in advance from aqueous solutions of sodium hydrosulfite (2.3 g, 13 ml) and 5 M sodium hydroxide (400 μl), while keeping the temperature of the reaction mixture at 5° C. or lower. Then, the mixture was stirred at 25° C. for one hour. An ethanol solution (5 ml) of ethyl pyruvate (465 μl) was added dropwise to the reaction mixture. After stirring at 50° C. for 30 minutes, the mixture was further stirred at 25° C. for 10 hours. The pH of the mixture was adjusted to 11 using an aqueous solution (about 10 ml) of 20% potassium phosphate. The resulting precipitate was collected by filtration, and dried. Thus, 2-[(E)-4-imidazol-1-yl-phenylimino]-propionic acid ethyl ester was obtained as a pale yellow powder (1.1 g, 99%).

Indole-Based Synthesis Method

Synthesis of 5-imidazol-1-yl-1H-indole-2-carboxylic acid ethyl ester

2-[(E)-4-Imidazol-1-yl-phenylimino]-propionic acid ethyl ester (842 mg) was added to an Eaton's reagent (4 ml), and this was stirred at 100° C. for one hour. After adjusting the pH of the reaction mixture to 11 using an aqueous solution (about 10 ml) of 20% potassium phosphate, the mixture was extracted with ethyl acetate (30 ml). The organic layer was washed with an aqueous solution saturated with sodium chloride (20 ml), and the organic layer was concentrated under reduced pressure. The resulting residue was purified by silica gel column chromatography (dichloromethane/methanol). Thus, 5-imidazol-1-yl-1H-indole-2-carboxylic acid ethyl ester was obtained as a yellow amorphous material (370 mg, 47%).

ESI (LC-MS positive mode) m/z 256 [(M+H)$^+$]

The compounds of numbers 1386 to 1394 listed in Table 20 were synthesized as described in Step 20.

TABLE 20

| Compound No. | Structure | Compound name | m/z |
| --- | --- | --- | --- |
| 1386 | 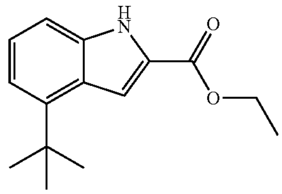 [SMILES: CCOC(=O)c1cc2c(C(C)(C)C)cccc2[nH]1] | 4-tert-butyl-1H-indole-2-carboxylic acid ethyl ester | 246 |
| 1387 | 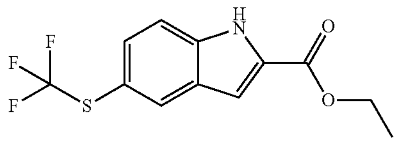 [SMILES: CCOC(=O)c1cc2cc(SC(F)(F)F)ccc2[nH]1] | 5-trifluoromethylsulfanyl-1H-indole-2-carboxylic acid ethyl ester | 290 |
| 1388 | 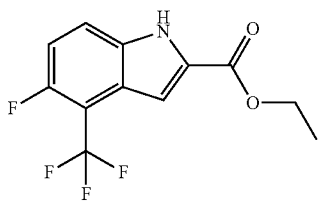 [SMILES: CCOC(=O)c1cc2c(C(F)(F)F)c(F)ccc2[nH]1] | 5-trifluoromethylsulfanyl-1H-indole-2-carboxylic acid ethyl ester | 274 [M − H] |
| 1389 | 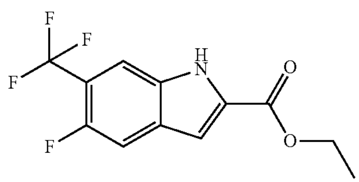 [SMILES: CCOC(=O)c1cc2cc(F)c(C(F)(F)F)cc2[nH]1] | 5-fluoro-4-trifluoromethyl-1H-indole-2-carboxylic acid ethyl ester | 274 [M − H] |
| 1390 | 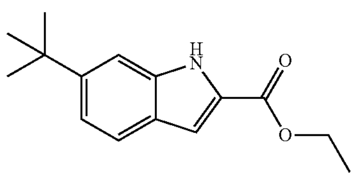 [SMILES: CCOC(=O)c1cc2ccc(C(C)(C)C)cc2[nH]1] | 6-tert-butyl-1H-indole-2-carboxylic acid ethyl ester | 246 |
| 1391 | 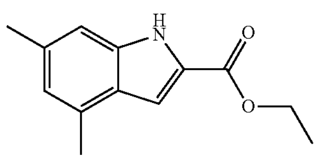 [SMILES: CCOC(=O)c1cc2c(C)cc(C)cc2[nH]1] | 4,6-dimethyl-1H-indole-2-carboxylic acid ethyl ester | 218 |
| 1392 | 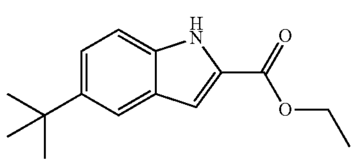 [SMILES: CCOC(=O)c1cc2cc(C(C)(C)C)ccc2[nH]1] | 5-tert-butyl-1H-indole-2-carboxylic acid ethyl ester | 246 |
| 1393 | 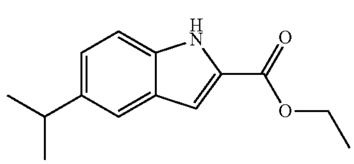 [SMILES: CCOC(=O)c1cc2cc(C(C)C)ccc2[nH]1] | 5-isopropyl-1H-indole-2-carboxylic acid ethyl ester | 232 |
| 1394 | 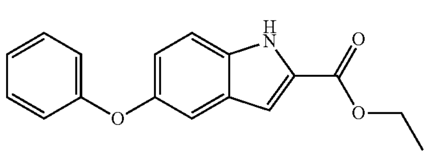 [SMILES: CCOC(=O)c1cc2cc(Oc3ccccc3)ccc2[nH]1] | 5-phenoxy-1H-indole-2-carboxylic acid ethyl ester | 282 |

Step 21: Synthesis of 1-chloro-2-cyclopropylmethoxy-4-nitro-benzene (1395)

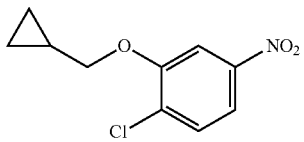 [SMILES: O=[N+]([O-])c1ccc(Cl)c(OCC2CC2)c1]

Cyclopropylmethyl bromide (2.0 ml, 20 mmol, 2.0 eq.) was added to a mixture solution of 2-chloro-5-nitro-phenol (1.7 g, 10 mmol), potassium carbonate (2.7 g, 20 mmol), and anhydrous acetonitrile (20 ml). This was stirred at 80° C. for eight hours. After cooling it to room temperature, the reaction mixture was filtered through Celite, and washed with ethyl acetate. The filtrate was concentrated under reduced pressure. This yielded crude 1-chloro-2-cyclopropyl-methoxy-4-nitro-benzene as a pale red solid. The crude product was used in subsequent reactions without being purified.

$^1$H-NMR (DMSO-D$_6$) δ: 7.84 (1H, dd, J=8.4, 2.5 Hz), 7.81 (1H, d, J=2.5 Hz), 7.74 (1H, d, J=8.4 Hz), 4.08 (2H, d, J=7.1 Hz), 1.33-1.23 (1H, m), 0.63-0.59 (2H, m), 0.41-0.37 (2H, m)

Step 22: Synthesis of 4-chloro-3-cyclopropylmethoxy-phenylamine (1396)

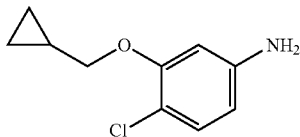 [SMILES: Nc1ccc(Cl)c(OCC2CC2)c1]

1-chloro-2-cyclopropylmethoxy-4-nitro-benzene (2.3 g, 10 mmol) was dissolved in ethanol (30 ml) and water (30 ml), and then sodium dithionite was gradually added thereto. This was stirred at 80° C. for four and half hours. After cooling it to room temperature, an aqueous solution of 5 M hydrochloride (40 ml) was added to the reaction mixture. This was stirred at room temperature for one hour. Then, an aqueous solution (42 ml) of 5 M sodium hydroxide was added, and the solution was alkalinized and extracted with ethyl acetate. The extract was washed with water and an aqueous solution saturated with sodium chloride, and dried over anhydrous sodium sulfate. The desiccant was removed by filtration, and concentration was performed. Then, the residue obtained by concentration under reduced pressure was purified by silica gel column chromatography. Thus, 4-chloro-3-cyclopropylmethoxy-phenylamine was obtained as a pale yellow gum-like material (1.4 g).

$^1$H-NMR (DMSO-D$_6$) δ: 6.95 (1H, d, J=8.3 Hz), 6.28 (1H, d, J=2.4 Hz), 6.11 (1H, dd, J=8.3, 2.4 Hz), 5.19 (2H, s), 3.76 (2H, d, J=7.1 Hz), 1.24-1.18 (1H, m), 0.59-0.54 (2H, m), 0.35-0.30 (2H, m)

ESI (LC-MS positive mode) m/z 198, 200 [(M+H)$^+$]

Step 23: Synthesis of 4-bromo-2-iodo-5-trifluoromethyl-phenylamine (1397)

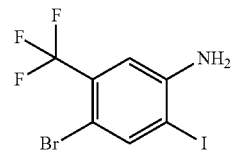 [SMILES: Nc1cc(C(F)(F)F)c(Br)cc1I]

Iodine (1.4 g, 5.5 mmol, 1.1 eq.) was gradually added to a mixture solution of 4-bromo-3-trifluoromethyl aniline (1.2 g, 1.0 mmol), silver sulfate (1.72 g, 5.5 mmol, 1.1 eq.), and anhydrous ethanol (35 ml). This was stirred at room temperature for two and half hours. The reaction mixture was filtered through Celite, and washed with ethyl acetate. The wash solution was washed with aqueous solutions of 10% sodium thiosulfate, saturated sodium bicarbonate, and saturated sodium chloride, and then dried over anhydrous sodium sulfate. The desiccant was removed by filtration, and concentration was performed. Crude solid 4-bromo-2-iodo-5-trifluoromethyl-phenylamine was obtained by concentration under reduced pressure. The resulting crude product was used in subsequent reactions without being purified.

$^1$H-NMR (DMSO-D$_6$) δ: 7.94 (1H, s), 7.15 (1H, s), 5.86 (2H, s)

ESI (LC-MS positive mode) m/z 366, 368 [(M+H)$^+$]

The compounds of numbers 1398 to 1402 listed in Table 21 were synthesized as described in Step 23.

TABLE 21

| Compound No. | Structure | Compound name | m/z |
|---|---|---|---|
| 1398 | ![structure] | 5-bromo-4-fluoro-2-iodo-phenylamine | 316, 318 |
| 1399 | ![structure] | 4-bromo-5-fluoro-2-iodo-phenylamine | 316, 318 |
| 1400 | ![structure] | 2,2-difluoro-6-iodo-benzo[1,3]dioxol-5-ylamine | 300 |

TABLE 21-continued

| Compound No. | Structure | Compound name | m/z |
|---|---|---|---|
| 1401 | 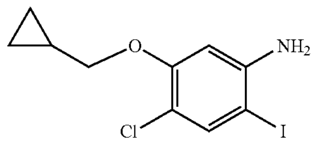 [SMILES: Nc1cc(OCC2CC2)c(Cl)cc1I] | 4-chloro-5-cyclopropyl-methoxy-2-iodo-phenylamine | 324, 326 |
| 1402 | 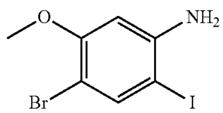 | 4-bromo-2-iodo-5-methoxy-phenylamine | 3281, 330 |

Step 24: Synthesis of N-(4-bromo-2-iodo-5-trifluoromethyl-phenyl)-4-methyl benzenesulfonamide (1403)

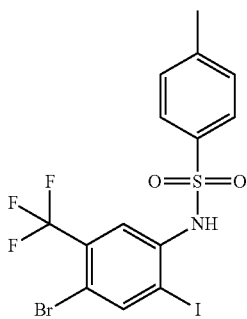 [SMILES: Cc1ccc(S(=O)(=O)Nc2cc(C(F)(F)F)c(Br)cc2I)cc1]

4-Bromo-2-iodo-5-trifluoromethyl-phenylamine (366 mg, 1.0 mmol) and p-toluene sulfonyl chloride (286 mg, 1.5 mmol, 1.5 eq.) were dissolved in anhydrous pyridine (2.5 ml). This was stirred at room temperature for 16 hours. An aqueous solution of 1 M sodium hydroxide was added to the reaction mixture, and this was stirred for five minutes. The reaction mixture was diluted with ethyl acetate. The organic layer was isolated, and washed with an aqueous solution of 1 M hydrochloric acid and an aqueous solution saturated with sodium chloride, and dried over anhydrous sodium sulfate. The desiccant was removed by filtration, and concentration was performed. Then, the residue obtained by concentration under reduced pressure was dissolved in tetrahydrofuran (THF) (2.5 ml), and then a tetrahydrofuran (THF) solution of 1 M tetrabutylammonium fluoride was added thereto. This was stirred at room temperature for 17 hours. The reaction mixture was diluted with ethyl acetate. The organic layer was isolated, and washed with water and an aqueous solution saturated with sodium chloride, and then dried over anhydrous sodium sulfate. The desiccant was removed by filtration and concentration was performed. Then, the residue obtained by concentration under reduced pressure was purified by silica gel column chromatography. Thus, N-(4-bromo-2-iodo-5-trifluoromethyl-phenyl)-4-methyl benzynesulfonamide was obtained as a pale brown solid (494 mg, three-step yield of 95%).

$^1$H-NMR (DMSO-$D_6$) δ: 10.10 (1H, s), 8.34 (1H, s), 7.58 (2H, d, J=8.2 Hz), 7.39 (2H, d, J=8.2 Hz), 7.27 (1H, s), 2.38 (3H, s)

ESI (LC-MS positive mode) m/z 520, 522 [(M+H)$^+$]

The compounds of numbers 1404 to 1408 listed in Table 22 were synthesized as described in Step 24.

TABLE 22

| Compound No. | Structure | Compound name | m/z |
|---|---|---|---|
| 1404 | 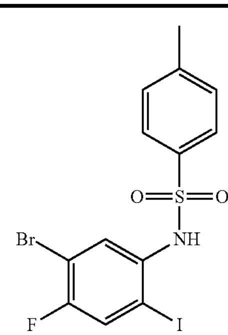 | N-(5-bromo-4-fluoro-2-iodo-phenyl)-4-methyl-benzenesulfonamide | 470, 472 |

TABLE 22-continued
| Compound No. | Structure | Compound name | m/z |
|---|---|---|---|
| 1405 | 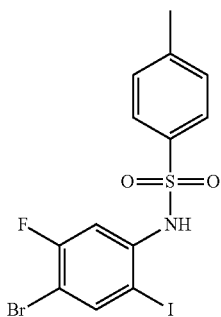 [SMILES: Cc1ccc(S(=O)(=O)Nc2cc(F)c(Br)cc2I)cc1] | N-(4-bromo-5-fluoro-2-iodo-phenyl)-4-methyl-benzenesulfonamide | Not observed |
| 1406 | 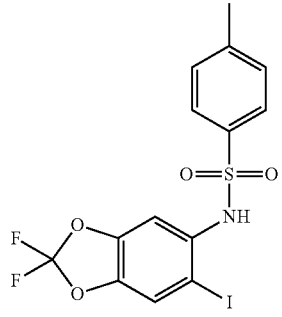 [SMILES: Cc1ccc(S(=O)(=O)Nc2cc3c(cc2I)OC(F)(F)O3)cc1] | N-(2,2-difluoro-6-iodo-benzo[1,3]dioxol-5-yl)-4-methyl-benzenesulfonamide | 454 |
| 1407 | 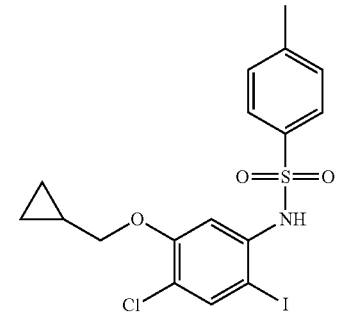 [SMILES: Cc1ccc(S(=O)(=O)Nc2cc(OCC3CC3)c(Cl)cc2I)cc1] | N-(4-chloro-5-cyclopropyl-methoxy-2-iodo-phenyl)-4-methyl-benzenesulfonamide | 478, 480 |
| 1408 | 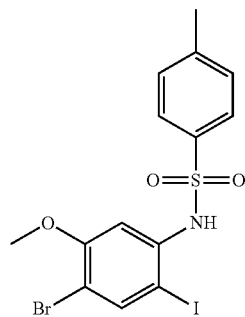 [SMILES: COc1cc(NS(=O)(=O)c2ccc(C)cc2)c(I)cc1Br] | N-(4-bromo-2-iodo-5-methoxy-phenyl)-4-methyl-benzenesulfonamide | 482, 484 |

Step 25: Synthesis of 5-bromo-1-(toluene-4-sulfonyl)-6-trifluoromethyl-1H-indole-2-carboxylic acid ethyl ester (1409)

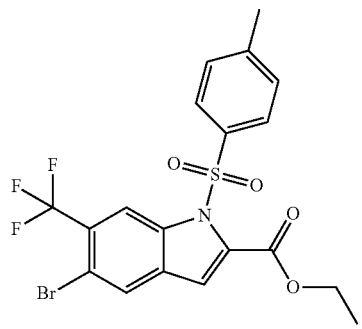 [SMILES: CCOC(=O)c1cc2cc(Br)c(C(F)(F)F)cc2n1S(=O)(=O)c1ccc(C)cc1]

N,N-diisopropylethyl amine (0.42 ml, 2.4 mmol), ethyl propionate (0.12 ml, 1.2 mmol), and tetrakis(triphenylphosphine)palladium (46 mg, 0.04 mmol) were added to an anhydrous tetrahydrofuran (THF) solution (3.2 ml) containing N-(4-bromo-2-iodo-5-trifluoromethyl-phenyl)-4-methyl-benzenesulfonamide (208 mg, 0.4 mmol) and zinc bromide (270 mg, 1.2 mmol). Then, the mixture was evacuated, and backfilled with argon. This was stirred at 80° C. for 13 hours. After cooling it to room temperature, the reaction mixture was filtered through Celite, and washed with ethyl acetate. The wash solution was washed with an aqueous solution saturated with sodium bicarbonate and an aqueous solution saturated with sodium chloride, and dried over anhydrous sodium sulfate. The desiccant was removed by filtration, and concentration was performed. Then, the residue obtained by concentration under reduced pressure was purified by silica gel column chromatography. Thus, 5-bromo-1-(toluene-4-sulfonyl)-6-trifluoromethyl-1H-indole-2-carboxylic acid ethyl ester was obtained as a pale brown solid (195 mg, 50%).

$^1$H-NMR (DMSO-D$_6$) δ: 8.37 (1H, s), 8.29 (1H, s), 7.89 (2H, d, J=8.2 Hz), 7.47 (2H, d, J=8.2 Hz), 7.43 (1H, s), 4.36 (2H, q, J=7.1 Hz), 2.38 (3H, s), 1.30 (3H, t, J=7.1 Hz)

ESI (LC-MS positive mode) m/z 490, 492 [(M+H)$^+$]

The compounds of numbers 1410 to 1414 listed in Table 23 were synthesized as described in Step 25.

TABLE 23

| Compound No. | Structure | Compound name | m/z |
| --- | --- | --- | --- |
| 1410 | 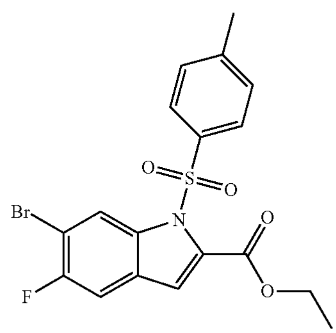 [SMILES: CCOC(=O)c1cc2cc(F)c(Br)cc2n1S(=O)(=O)c1ccc(C)cc1] | 6-bromo-5-fluoro-1-(toluene-4-sulfonyl)-1H-indole-2-carboxylic acid ethyl ester | 440, 442 |
| 1411 | 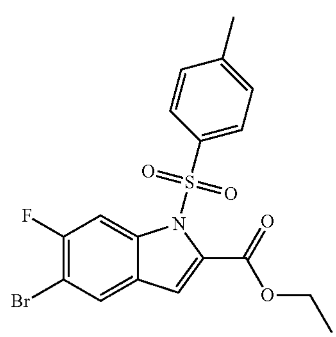 [SMILES: CCOC(=O)c1cc2cc(Br)c(F)cc2n1S(=O)(=O)c1ccc(C)cc1] | 5-bromo-6-fluoro-1-(toluene-4-sulfonyl)-1H-indole-2-carboxylic acid ethyl ester | Not observed |
| 1412 | 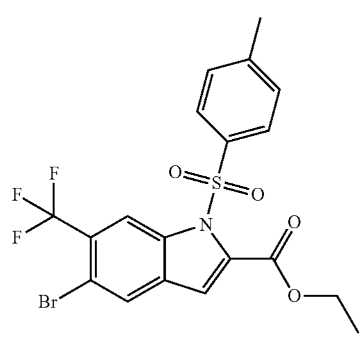 [SMILES: CCOC(=O)c1cc2cc(Br)c(C(F)(F)F)cc2n1S(=O)(=O)c1ccc(C)cc1] | 5-bromo-1-(toluene-4-sulfonyl)-6-trifluoromethyl-1H-indole-2-carboxylic acid ethyl ester | 490, 492 |

TABLE 23-continued

| Compound No. | Structure | Compound name | m/z |
| --- | --- | --- | --- |
| 1413 | 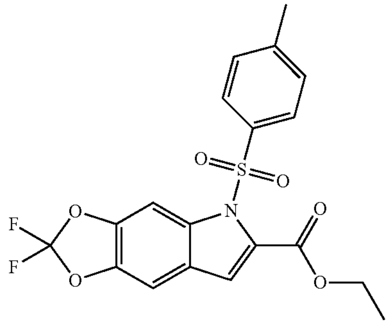 [SMILES: CCOC(=O)c1cc2cc3c(cc2n1S(=O)(=O)c1ccc(C)cc1)OC(F)(F)O3] | 2,2-difluoro-5-(toluene-4-sulfonyl)-5H-[1,3]dioxolo[4,5-f]indole-6-carboxylic acid ethyl ester | 424 |
| 1414 | 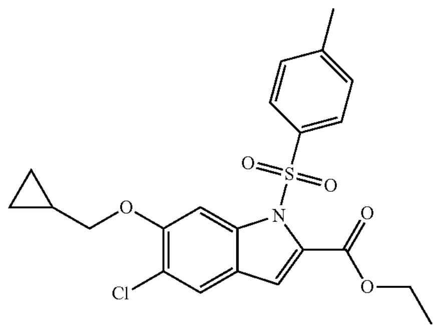 [SMILES: CCOC(=O)c1cc2cc(Cl)c(OCC3CC3)cc2n1S(=O)(=O)c1ccc(C)cc1] | 5-chloro-6-cyclopropylmethoxy-1-(toluene-4-sulfonyl)-1H-indole-2-carboxylic acid ethyl ester | 448, 450 |

Step 26: Synthesis of N-benzhydrylidene-N'-(3,5-di-tert-butyl-phenyl)-hydrazine (1415)

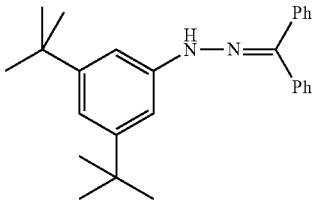 [SMILES: CC(C)(C)c1cc(NN=C(c2ccccc2)c2ccccc2)cc(C(C)(C)C)c1]

Palladium acetate (8.4 mg, 0.037 mmol) and 2-dicyclohexylphosphino-2',4',6'-tri-i-propyl-1,1'-biphenyl (X-PHOS) (35.6 mg, 0.074 mmol) were dissolved in tert-amyl alcohol (10 μl, 0.093 mmol) and anhydrous ethylene glycol dimethyl ether (0.25 ml). The mixture was heated and stirred at 60° C. for five minutes under a nitrogen atmosphere to prepare a catalyst. In a separate reaction container under a nitrogen atmosphere, 1-bromo-3,5-di-t-butyl benzene (501 mg, 1.9 mmol), lithium bis(trimethylsilyl) amide (475 mg, 2.8 mmol), and benzophenone hydrazone (401 mg, 2.0 mmol) were dissolved in anhydrous ethylene glycol dimethyl ether (2.5 ml). Then, a solution containing the prepared catalyst was added thereto. After deaeration, this was heated and stirred at 90° C. for two hours under a nitrogen atmosphere. The reaction mixture was cooled to room temperature, and then concentrated under reduced pressure. The resulting residue was purified by silica gel column chromatography (hexane/ethyl acetate=100/5). Thus, N-benzhydrylidene-N'-(3,5-di-tert-butyl-phenyl)-hydrazine was obtained as a yellow amorphous material (699 mg, 97.7%).

$^1$H-NMR (DMSO-$D_6$) δ: 8.72 (1.0H, s), 7.63-7.53 (3.0H, m), 7.42-7.25 (7.0H, m), 7.11 (2.0H, s), 6.83 (1.0H, s), 1.26 (18.0H, s)

ESI (LC-MS positive mode) m/z 385 [(M+H)$^+$]

Step 27: Synthesis of 4,6-di-tert-butyl-1H-indole-2-carbonic acid ethyl ester (1416)

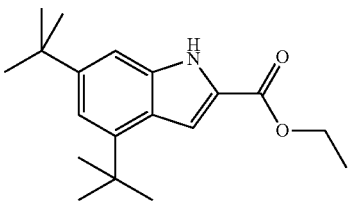 [SMILES: CCOC(=O)c1cc2c(C(C)(C)C)cc(C(C)(C)C)cc2[nH]1]

N-Benzhydrylidene-N'-(3,5-di-tert-butyl-phenyl)-hydrazine (617 mg, 1.6 mmol) was dissolved in ethanol (12 ml). Then, ethyl pyruvate (212 μl, 1.9 mmol) and p-toluene sulfonic acid monohydrate (914 mg, 4.8 mmol) were added thereto. This was heated and stirred at 150° C. by microwave under a nitrogen atmosphere for one hour. After cooling it to room temperature, the reaction mixture was combined with water and an aqueous solution saturated with sodium bicarbonate. The product was extracted into ethyl acetate. The organic layer was isolated, and washed with an aqueous solution saturated with sodium chloride, and dried over magnesium sulfate. The desiccant was removed by filtration, and concentration was performed. Then, the residue obtained by concentration under reduced pressure was purified by silica gel column chromatography (hexane/ethyl acetate=100/5). Thus, 4,6-di-tert-butyl-1H-indole-2-carboxylic acid ethyl ester was obtained as a brown solid (268 mg, 56%).

$^1$H-NMR (DMSO-$D_6$) δ: 11.76 (1.0H, brs), 7.27 (1.0H, s), 7.22-7.22 (1.0H, brm), 7.04-7.03 (1.0H, brm), 4.33 (2.0H, q, J=7.2 Hz), 1.44 (9.0H, s), 1.36-1.32 (12.0H, m)

ESI (LC-MS positive mode) m/z 302 [(M+H)$^+$]

Step 28: Synthesis of 6-(5-fluoro-pyridin-2-yl)-1-(toluene-4-sulfonyl)-1H-indole-2-carboxylic acid methyl ester (1417)

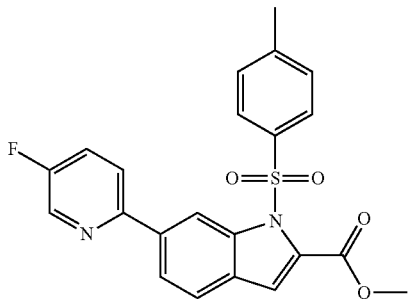 [SMILES: COC(=O)c1cc2ccc(-c3ccc(F)cn3)cc2n1S(=O)(=O)c1ccc(C)cc1]

6-Bromo-1-(toluene-4-sulfonyl)-1H-indole-2-carboxylic acid methyl ester (202.0 mg, 0.495 mmol), dichlorobis(triphenylphosphine)palladium (II) (35.6 mg, 0.051 mmol), bis(pinacol)diborane (189.3 mg, 0.745 mmol), potassium acetate (147.3 mg, 1.51 mmol), and dioxane (1.6 ml) were mixed. The air was replaced three times with argon under reduced pressure. The mixture was microwaved at 120° C. for 30 minutes. Dichlorobis(triphenylphosphine)palladium (II) (35.6 mg, 0.051 mmol) and 2-bromo-5-fluoro-pyridine (206.9 mg, 1.48 mmol) were added to the reaction mixture. After deaeration, the air was replaced three times with argon. This was heated and stirred at 100° C. for three hours. The reaction mixture was extracted with ethyl acetate, and the extract was dried over anhydrous sodium sulfate. The desiccant was removed by filtration, and concentration was performed. Then, the residue obtained by concentration under reduced pressure was purified by amino gel column chromatography (n-hexane/ethyl acetate=7/100 to 63/100). Thus, 6-(5-fluoro-pyridin-2-yl)-1-(toluene-4-sulfonyl)-1H-indole-2-carboxylic acid methyl ester was obtained as a pale yellow amorphous material (150.5 mg, yield of 72%).

$^1$H-NMR (CDCl$_3$) δ: 8.70 (1H, s), 8.59 (1H, d, J=2.7 Hz), 7.93 (3H, d, J=8.2 Hz), 7.83 (1H, dd, J=8.8, 3.8 Hz), 7.65 (1H, d, J=8.2 Hz), 7.53 (1H, td, J=8.4, 2.9 Hz), 7.29-7.25 (2H, m), 7.19 (1H, s), 3.95 (3H, s), 2.37 (3H, s)

ESI (LC-MS positive mode) m/z 425 [(M+H)$^+$]

The compounds of numbers 1418 to 1427 listed in Table 24 were synthesized as described in Step 28.

TABLE 24

| Compound No. | Structure | Compound name | m/z |
|---|---|---|---|
| 1418 | 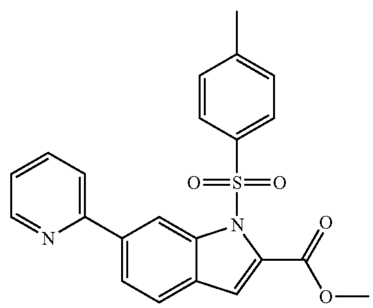 [SMILES: COC(=O)c1cc2ccc(-c3ccccn3)cc2n1S(=O)(=O)c1ccc(C)cc1] | 6-pyridin-2-yl-1-(toluene-4-sulfonyl)-1H-indole-2-carboxylic acid methyl ester | 407 |
| 1419 | 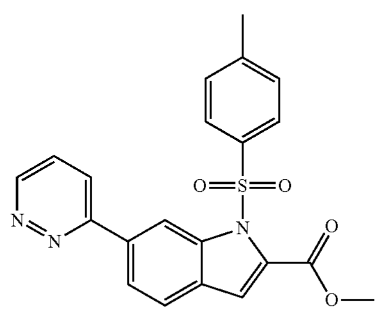 [SMILES: COC(=O)c1cc2ccc(-c3cccnn3)cc2n1S(=O)(=O)c1ccc(C)cc1] | 6-pyridazin-3-yl-1-(toluene-4-sulfonyl)-1H-indole-2-carboxylic acid methyl ester | 408 |
| 1420 | 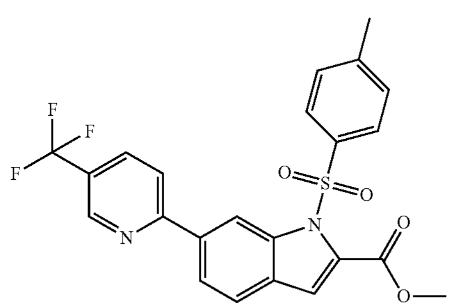 [SMILES: COC(=O)c1cc2ccc(-c3ccc(C(F)(F)F)cn3)cc2n1S(=O)(=O)c1ccc(C)cc1] | 1-(toluene-4-sulfonyl)-6-(5-trifluoromethyl-pyridin-2-yl)-1H-indole-2-carboxylic acid methyl ester | 475 |

TABLE 24-continued

| Compound No. | Structure | Compound name | m/z |
|---|---|---|---|
| 1421 | 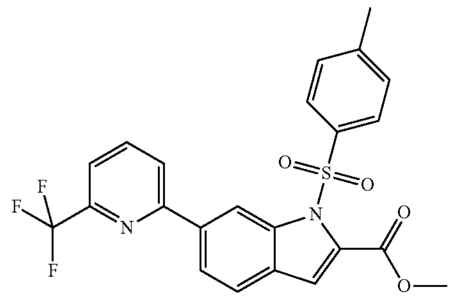 [SMILES: COC(=O)c1cc2ccc(-c3cccc(C(F)(F)F)n3)cc2n1S(=O)(=O)c1ccc(C)cc1] | 1-(toluene-4-sulfonyl)-6-(6-trifluoromethyl-pyridin-2-yl)-1H-indole-2-carboxylic acid methyl ester | 475 |
| 1422 | 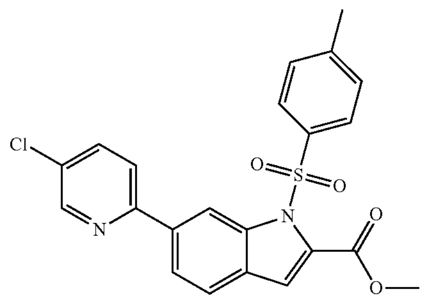 [SMILES: COC(=O)c1cc2ccc(-c3ccc(Cl)cn3)cc2n1S(=O)(=O)c1ccc(C)cc1] | 6-(5-chloro-pyridin-2-yl)-1-(toluene-4-sulfonyl)-1H-indole-2-carboxylic acid methyl ester | 441 |
| 1423 | 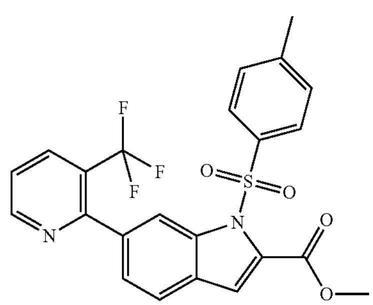 [SMILES: COC(=O)c1cc2ccc(-c3ncccc3C(F)(F)F)cc2n1S(=O)(=O)c1ccc(C)cc1] | 1-(toluene-4-sulfonyl)-6-(3-trifluoromethyl-pyridin-2-yl)-1H-indole-2-carboxylic acid methyl ester | 475 |
| 1424 | 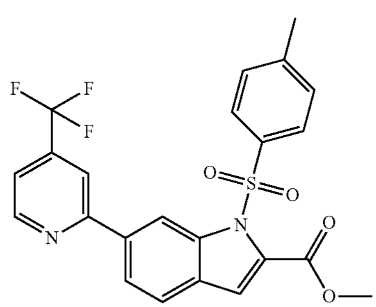 [SMILES: COC(=O)c1cc2ccc(-c3cc(C(F)(F)F)ccn3)cc2n1S(=O)(=O)c1ccc(C)cc1] | 1-(toluene-4-sulfonyl)-6-(4-trifluoromethyl-pyridin-2-yl)-1H-indole-2-carboxylic acid methyl ester | 475 |

TABLE 24-continued

| Compound No. | Structure | Compound name | m/z |
|---|---|---|---|
| 1425 | 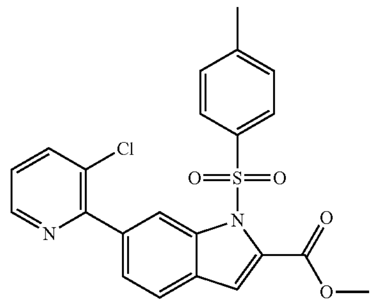 [SMILES: COC(=O)c1cc2ccc(-c3ncccc3Cl)cc2n1S(=O)(=O)c1ccc(C)cc1] | 6-(3-chloro-pyridin-2-yl)-1-(toluene-4-sulfonyl)-1H-indole-2-carboxylic acid methyl ester | 441, 443 |
| 1426 | 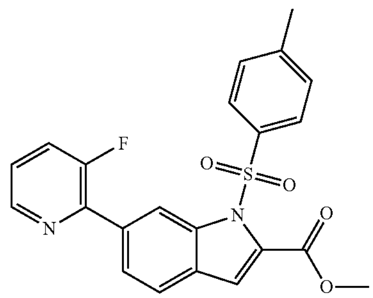 [SMILES: COC(=O)c1cc2ccc(-c3ncccc3F)cc2n1S(=O)(=O)c1ccc(C)cc1] | 6-(3-fluoro-pyridin-2-yl)-1-(toluene-4-sulfonyl)-1H-indole-2-carboxylic acid methyl ester | 425 |
| 1427 | 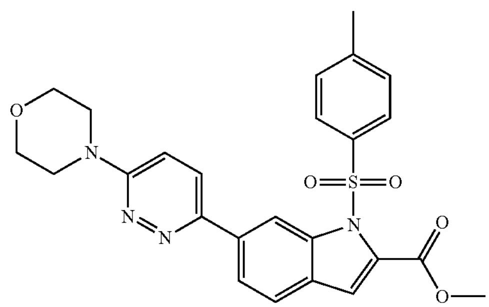 [SMILES: COC(=O)c1cc2ccc(-c3ccc(N4CCOCC4)nn3)cc2n1S(=O)(=O)c1ccc(C)cc1] | 6-(6-morpholin-4-yl-pyridazin-3-yl)-1-(toluene-4-sulfonyl)-1H-indole-2-carboxylic acid methyl ester | 493 |

Step 29: Synthesis of [5-amino-1-(2-methyl-1H-benzimidazol-5-yl)-1H-pyrazol-4-yl]-[5-(6-methoxy-pyridin-3-yl)-1-(toluene-4-sulfonyl)-1H-indol-2-yl] methanone (1428)

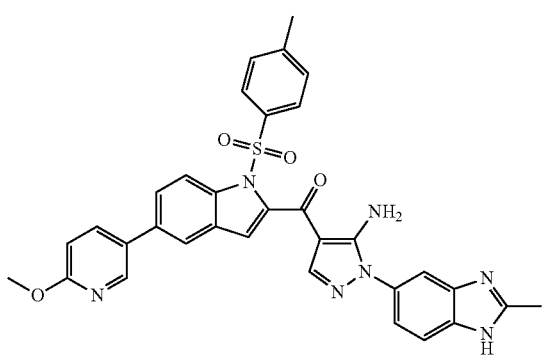

A mixture of dioxane (0.6 ml), [5-amino-1-(2-methyl-1H-benzimidazol-5-yl)-1H-pyrazol-4-yl]-[5-bromo-1-(toluene-4-sulfonyl)-1H-indol-2-yl]-methanone (60 mg, 0.102 mmol), dichlorobis(triphenylphosphine)palladium (II) (14 mg, 0.020 mmol), 2-methoxy-5-pyridine boronic acid (39 mg, 0.255 mmol), and an aqueous solution of 2 M sodium bicarbonate (0.255 mL, 0.51 mmol) was stirred at 140° C. for six minutes in a microwave reactor. The reaction mixture was filtered through Celite, and washed with ethyl acetate and then with methanol. The filtrate was dried over anhydrous sodium sulfate. The desiccant was removed by filtration and concentration was performed. The residue obtained was purified by amino gel chromatography (dichloromethane/methanol=99/1 to 92/8). Thus, [5-amino-1-(2-methyl-1H-benzimidazol-5-yl)-1H-pyrazol-4-yl]-[5-(6-methoxy-pyridin-3-yl)-1-(toluene-4-sulfonyl)-1H-indol-2-yl]-methanone was obtained as a pale yellow solid (54 mg, 85%).

$^1$H-NMR (DMSO-D$_6$) δ: 12.50 (1H, s), 8.50 (1H, d, J=2.4 Hz), 8.08-8.04 (4H, m), 7.94 (1H, d, J=1.8 Hz), 7.77 (1H, s), 7.74 (1H, dd, J=9.1, 1.8 Hz), 7.63-7.61 (2H, m), 7.46-7.40 (2H, m), 7.30 (1H, dd, J=8.5, 1.8 Hz), 7.25 (1H, s), 7.06 (2H, s), 6.93 (1H, d, J=8.5 Hz), 3.90 (3H, s), 2.54 (3H, s), 2.37 (3H, s)

ESI (LC-MS positive mode) m/z 618 [(M+H)$^+$]

The compounds of numbers 1429 to 1462, and 1580 to 1590 listed in Table 25 were synthesized as described in Step 29.

TABLE 25

| Compound No. | Structure | Compound name | m/z |
|---|---|---|---|
| 1429 | 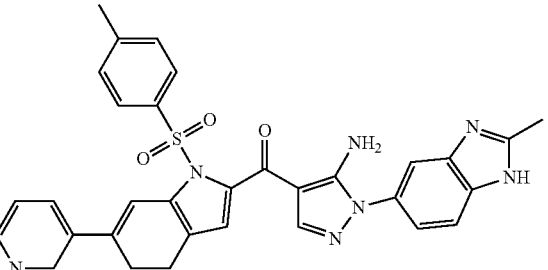 | [5-amino-1-(2-methyl-1H-benzimidazol-5-yl)-1H-pyrazol-4-yl]-[6-(6-morpholin-4-yl-pyridin-3-yl)-1-(toluene-4-sulfonyl)-1H-indol-2-yl]-methanone | 673 |
| 1430 | 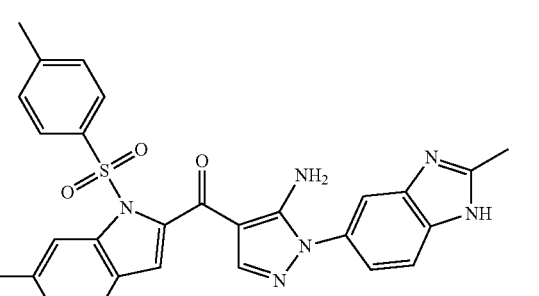 | [5-amino-1-(2-methyl-1H-benzimidazol-5-yl)-1H-pyrazol-4-yl]-[6-pyridin-3-yl)-1-(toluene-4-sulfonyl)-1H-indol-2-yl]-methanone | 588 |
| 1431 | 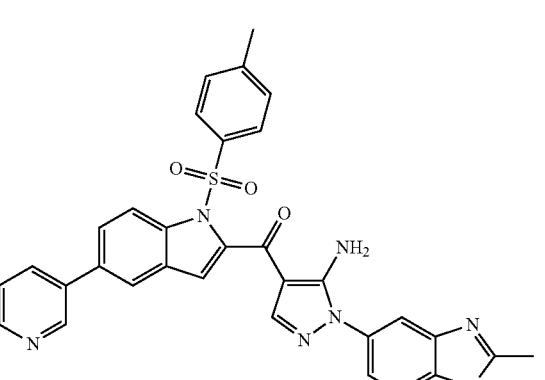 | [5-amino-1-(2-methyl-1H-benzimidazol-5-yl)-1H-pyrazol-4-yl]-[5-(6-morpholin-4-yl-pyridin-3-yl)-1-(toluene-4-sulfonyl)-1H-indol-2-yl]-methanone | 673 |
| 1432 | 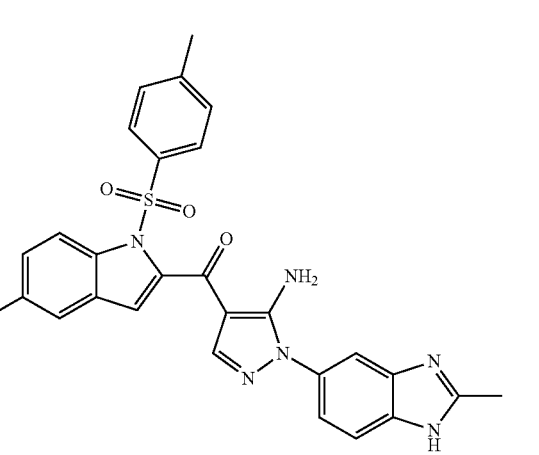 | [5-amino-1-(2-methyl-1H-benzimidazol-5-yl)-1H-pyrazol-4-yl]-[5-pyridin-3-yl-1-(toluene-4-sulfonyl)-1H-indol-2-yl]-methanone | 588 |

TABLE 25-continued

| Compound No. | Structure | Compound name | m/z |
|---|---|---|---|
| 1433 | 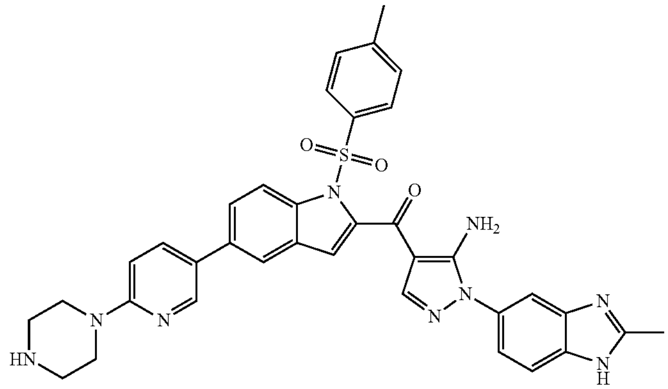 [SMILES: Cc1ccc(S(=O)(=O)n2c(C(=O)c3cnn(-c4ccc5[nH]c(C)nc5c4)c3N)cc3cc(-c4ccc(N5CCNCC5)nc4)ccc32)cc1] | [5-amino-1-(2-methyl-1H-benzimidazol-5-yl)-1H-pyrazol-4-yl]-[5-(6-piperadin-1-yl-pyridin-3-yl)-1-(toluene-4-sulfonyl)-1H-indol-2-yl]-methanone | 672 |
| 1434 | 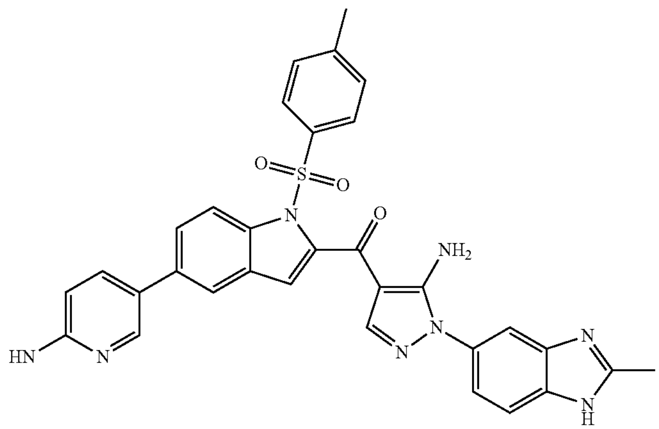 [SMILES: Cc1ccc(S(=O)(=O)n2c(C(=O)c3cnn(-c4ccc5[nH]c(C)nc5c4)c3N)cc3cc(-c4ccc(N)nc4)ccc32)cc1] | [5-amino-1-(2-methyl-1H-benzimidazol-5-yl)-1H-pyrazol-4-yl]-(5-(6-hydroxy-pyridin-3-yl)-1-(toluene-4-sulfonyl)-1H-indol-2-yl]-methanone | 604 |
| 1435 | 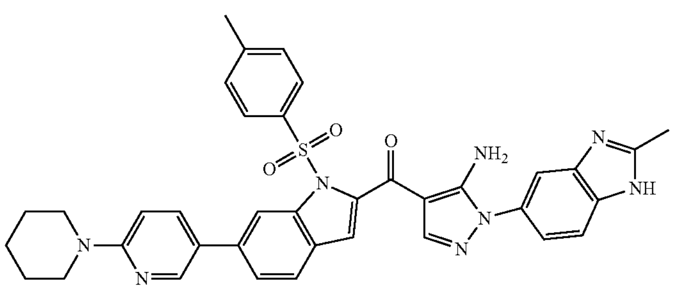 [SMILES: Cc1ccc(S(=O)(=O)n2c(C(=O)c3cnn(-c4ccc5[nH]c(C)nc5c4)c3N)cc3ccc(-c4ccc(N5CCCCC5)nc4)cc32)cc1] | [5-amino-1-(2-methyl-1H-benzimidazol-5-yl)-1H-pyrazol-4-yl]-[6-(3,4,5,6-tetrahydro-2H[1,2']bipyridin-5'-yl)-1-(toluene-4-sulfonyl)-1H-indol-2-yl]-methanone | 671 |
| 1436 | 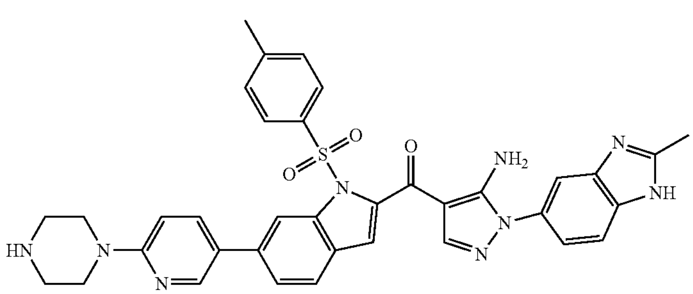 [SMILES: Cc1ccc(S(=O)(=O)n2c(C(=O)c3cnn(-c4ccc5[nH]c(C)nc5c4)c3N)cc3ccc(-c4ccc(N5CCNCC5)nc4)cc32)cc1] | [5-amino-1-(2-methyl-1H-benzimidazol-5-yl)-1H-pyrazol-4-yl]-[6-(6-piperadin-1-yl-pyridin-3-yl)-1-(toluene-4-sulfonyl)-1H-indol-2-yl]-methanone | 672 |

TABLE 25-continued

| Compound No. | Structure | Compound name | m/z |
|---|---|---|---|
| 1437 | 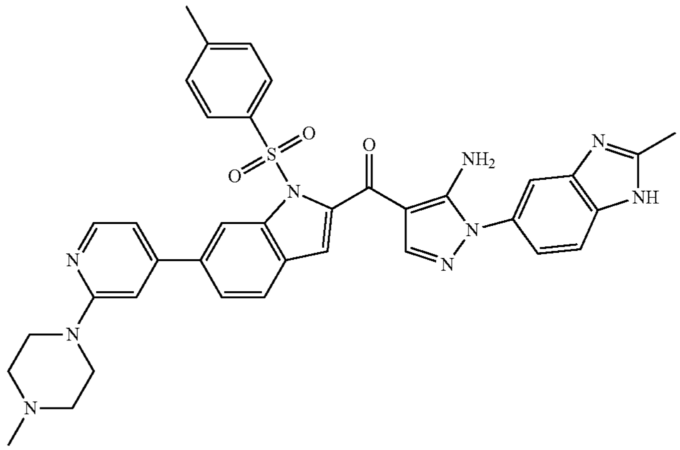 [SMILES: Cc1ccc(S(=O)(=O)n2c(C(=O)c3cnn(-c4ccc5[nH]c(C)nc5c4)c3N)cc3ccc(-c4ccnc(N5CCN(C)CC5)c4)cc32)cc1] | [5-amino-1-(2-methyl-1H-benzimidazol-5-yl)-1H-pyrazol-4-yl]-[6-[2-(4-methyl-piperadin-1-yl)-pyridin-4-yl]-1-(toluene-4-sulfonyl)-1H-indol-2-yl]-methanone | 686 |
| 1438 | 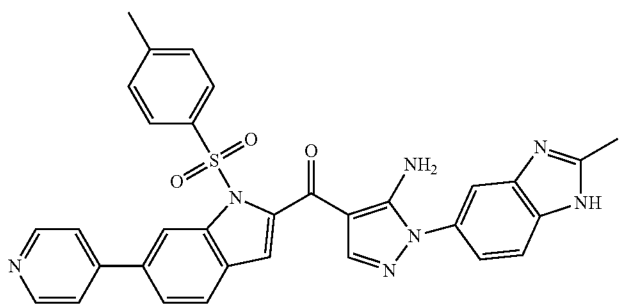 [SMILES: Cc1ccc(S(=O)(=O)n2c(C(=O)c3cnn(-c4ccc5[nH]c(C)nc5c4)c3N)cc3ccc(-c4ccncc4)cc32)cc1] | [5-amino-1-(2-methyl-1H-benzimidazol-5-yl)-1H-pyrazol-4-yl]-[6-pyridin-4-yl-1-(toluene-4-sulfonyl)-1H-indol-2-yl]-methanone | 588 |
| 1439 | 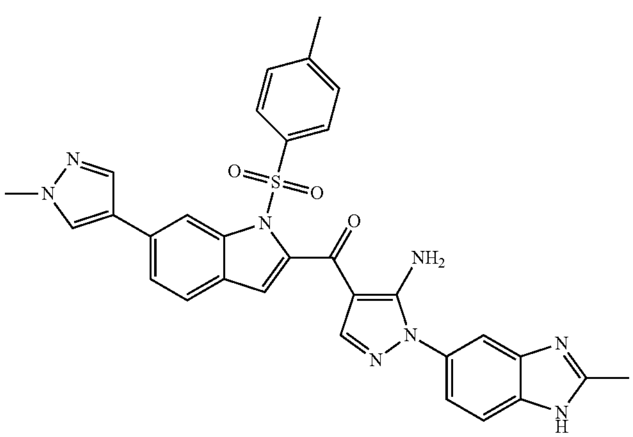 | [5-amino-1-(2-methyl-1H-benzimidazol-5-yl)-1H-pyrazol-4-yl]-[6-(1-methyl-1H-pyrazol-4-yl)-1-(toluene-4-sulfonyl)-1H-indol-2-yl]-methanone | 591 |

TABLE 25-continued

| Compound No. | Structure | Compound name | m/z |
|---|---|---|---|
| 1440 | 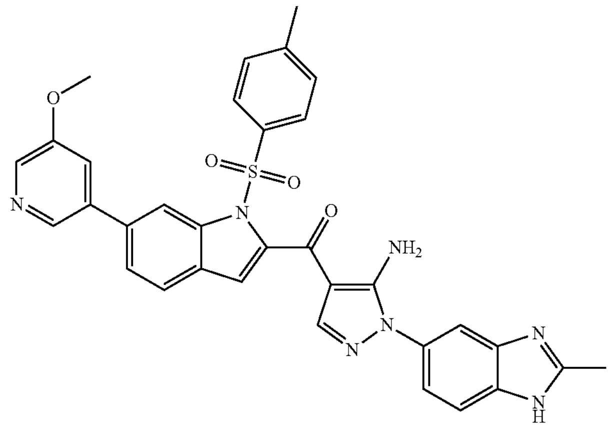 [SMILES: COc1cncc(-c2ccc3cc(C(=O)c4cnn(-c5ccc6[nH]c(C)nc6c5)c4N)n(S(=O)(=O)c4ccc(C)cc4)c3c2)c1] | [5-amino-1-(2-methyl-1H-benzimidazol-5-yl)-1H-pyrazol-4-yl]-[6-(5-methoxy-pyridin-3-yl)-1-(toluene-4-sulfonyl)-1H-indol-2-yl]-methanone | 618 |
| 1441 | 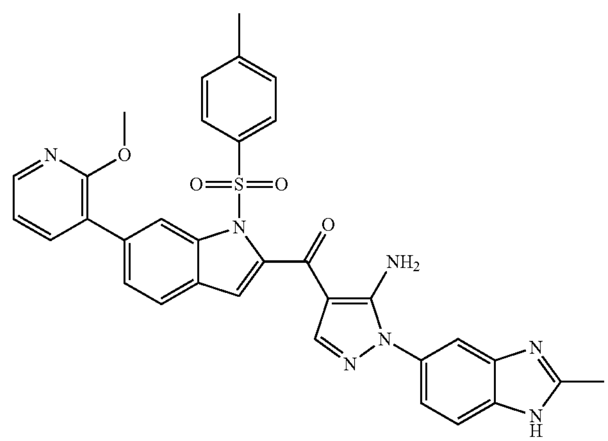 [SMILES: COc1ncccc1-c1ccc2cc(C(=O)c3cnn(-c4ccc5[nH]c(C)nc5c4)c3N)n(S(=O)(=O)c3ccc(C)cc3)c2c1] | [5-amino-1-(2-methyl-1H-benzimidazol-5-yl)-1H-pyrazol-4-yl]-[6-(2-methoxy-pyridin-3-yl)-1-(toluene-4-sulfonyl)-1H-indol-2-yl]-methanone | 618 |
| 1442 | 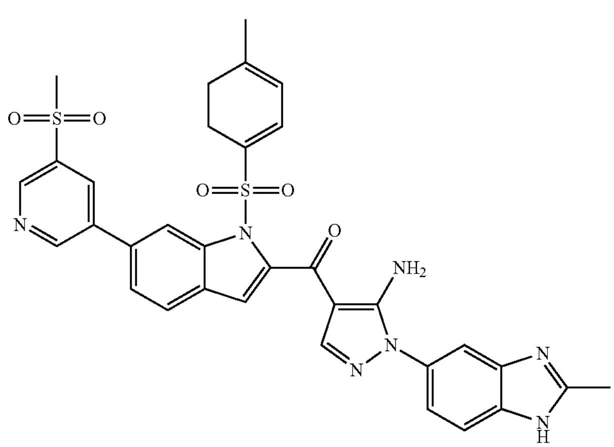 [SMILES: CC1=CC=C(S(=O)(=O)n2c(C(=O)c3cnn(-c4ccc5[nH]c(C)nc5c4)c3N)cc3ccc(-c4cncc(S(C)(=O)=O)c4)cc32)CC1] | [5-amino-1-(2-methyl-1H-benzimidazol-5-yl)-1H-pyrazol-4-yl]-[6-(5-methanesulfonyl-pyridin-3-yl)-1-(toluene-4-sulfonyl)-1H-indol-2-yl]-methanone | 666 |

| Compound No. | Structure | Compound name | m/z |
|---|---|---|---|
| 1443 | 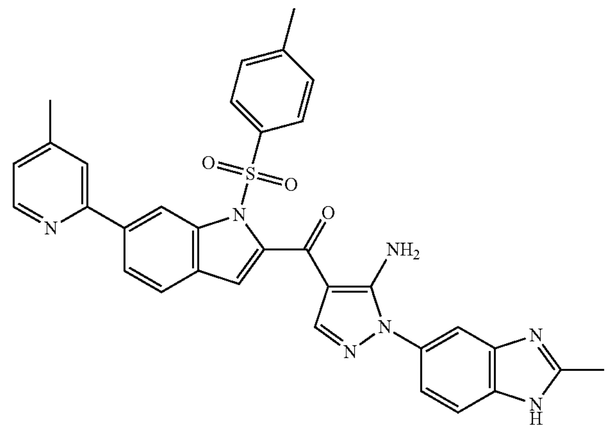 [SMILES: Cc1ccc(S(=O)(=O)n2c(C(=O)c3cnn(-c4ccc5[nH]c(C)nc5c4)c3N)cc3ccc(-c4cc(C)ccn4)cc32)cc1] | [5-amino-1-(2-methyl-1H-benzimidazol-5-yl)-1H-pyrazol-4-yl]-[6-(4-methyl-pyridin-2-yl)-1-(toluene-4-sulfonyl)-1H-indol-2-yl]-methanone | 602 |
| 1444 | 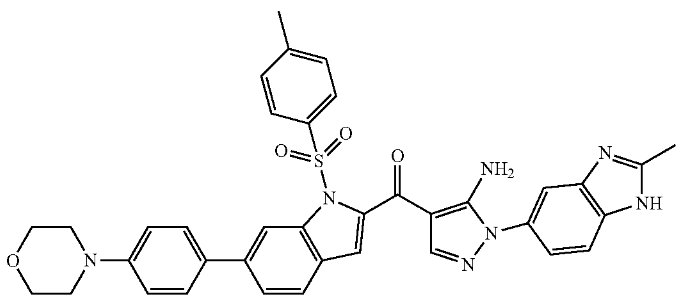 [SMILES: Cc1ccc(S(=O)(=O)n2c(C(=O)c3cnn(-c4ccc5[nH]c(C)nc5c4)c3N)cc3ccc(-c4ccc(N5CCOCC5)cc4)cc32)cc1] | [5-amino-1-(2-methyl-1H-benzimidazol-5-yl)-1H-pyrazol-4-yl]-[6-(4-morpholin-4-yl-phenyl)-1-(toluene-4-sulfonyl)-1H-indol-2-yl]-methanone | 672 |
| 1445 | 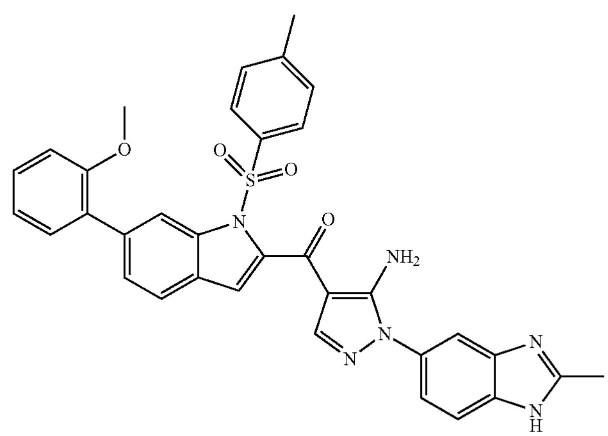 [SMILES: COc1ccccc1-c1ccc2cc(C(=O)c3cnn(-c4ccc5[nH]c(C)nc5c4)c3N)n(S(=O)(=O)c3ccc(C)cc3)c2c1] | [5-amino-1-(2-methyl-1H-benzimidazol-5-yl)-1H-pyrazol-4-yl]-[6-(2-methoxy-phenyl)-1-(toluene-4-sulfonyl)-1H-indol-2-yl]-methanone | 617 |
| 1446 | 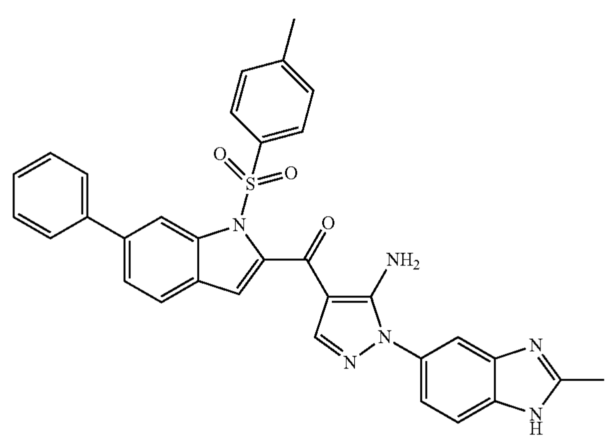 [SMILES: Cc1ccc(S(=O)(=O)n2c(C(=O)c3cnn(-c4ccc5[nH]c(C)nc5c4)c3N)cc3ccc(-c4ccccc4)cc32)cc1] | [5-amino-1-(2-methyl-1H-benzimidazol-5-yl)-1H-pyrazol-4-yl]-[6-phenyl-1-(toluene-4-sulfonyl)-1H-indol-2-yl]-methanone | 587 |

| Compound No. | Structure | Compound name | m/z |
|---|---|---|---|
| 1447 | 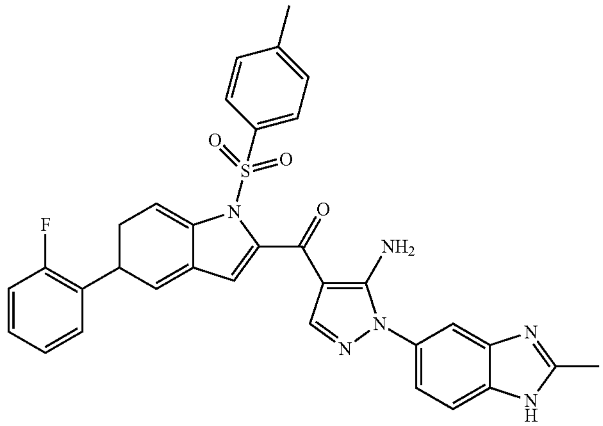 [SMILES: Cc1ccc(S(=O)(=O)n2c(C(=O)c3cnn(-c4ccc5[nH]c(C)nc5c4)c3N)cc3c2=CCC(c2ccccc2F)C=3)cc1] | [5-amino-1-(2-methyl-1H-benzimidazol-5-yl)-1H-pyrazol-4-yl]-[5-(2-fluoro-phenyl)-1-(toluene-4-sulfonyl)-1H-indol-2-yl]-methanone | 605 |
| 1448 | 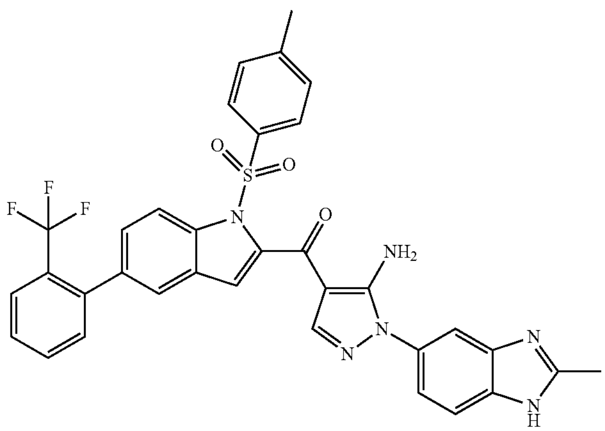 [SMILES: Cc1ccc(S(=O)(=O)n2c(C(=O)c3cnn(-c4ccc5[nH]c(C)nc5c4)c3N)cc3cc(-c4ccccc4C(F)(F)F)ccc32)cc1] | [5-amino-1-(2-methyl-1H-benzimidazol-5-yl)-1H-pyrazol-4-yl]-[1-(toluene-4-sulfonyl)-5-(2-trifluoromethyl-phenyl)-1H-indol-2-yl]methanone | 655 |
| 1449 | 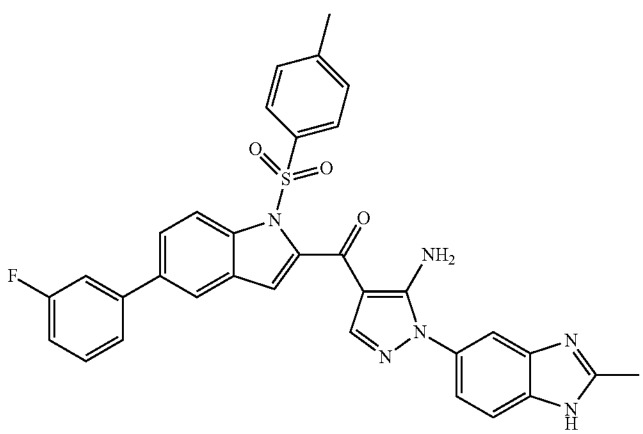 [SMILES: Cc1ccc(S(=O)(=O)n2c(C(=O)c3cnn(-c4ccc5[nH]c(C)nc5c4)c3N)cc3cc(-c4cccc(F)c4)ccc32)cc1] | [5-amino-1-(2-methyl-1H-benzimidazol-5-yl)-1H-pyrazol-4-yl]-[5-(3-fluoro-phenyl)-1-(toluene-4-sulfonyl)-1H-indol-2-yl]-methanone | 605 |

TABLE 25-continued

| Compound No. | Structure | Compound name | m/z |
|---|---|---|---|
| 1450 | 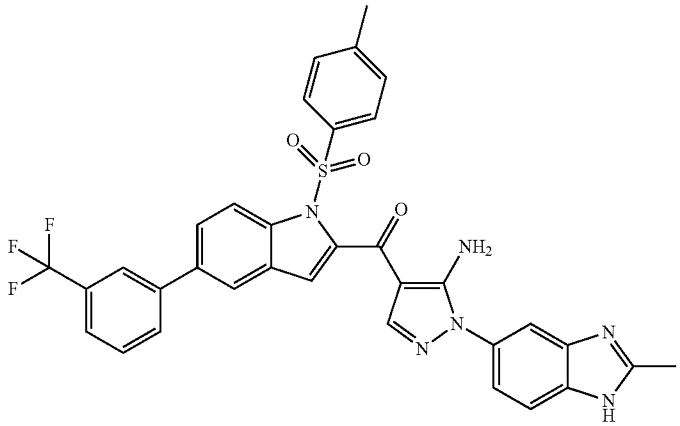 [SMILES: Cc1ccc(S(=O)(=O)n2c(C(=O)c3cnn(-c4ccc5[nH]c(C)nc5c4)c3N)cc3cc(-c4cccc(C(F)(F)F)c4)ccc32)cc1] | [5-amino-1-(2-methyl-1H-benzimidazol-5-yl)-1H-pyrazol-4-yl]-[1-(toluene-4-sulfonyl)-5-(3-trifluoromethyl-phenyl)-1H-indol-2-yl]-methanone | 655 |
| 1451 | 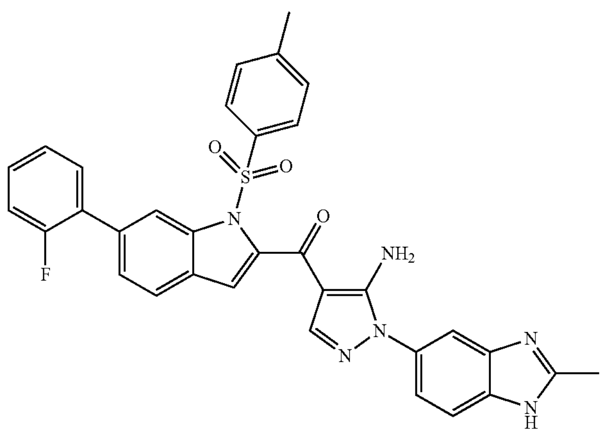 [SMILES: Cc1ccc(S(=O)(=O)n2c(C(=O)c3cnn(-c4ccc5[nH]c(C)nc5c4)c3N)cc3ccc(-c4ccccc4F)cc32)cc1] | [5-amino-1-(2-methyl-1H-benzimidazol-5-yl)-1H-pyrazol-4-yl]-[6-(2-fluoro-phenyl)-1-(toluene-4-sulfonyl)-1H-indol-2-yl]-methanone | 605 |
| 1452 | 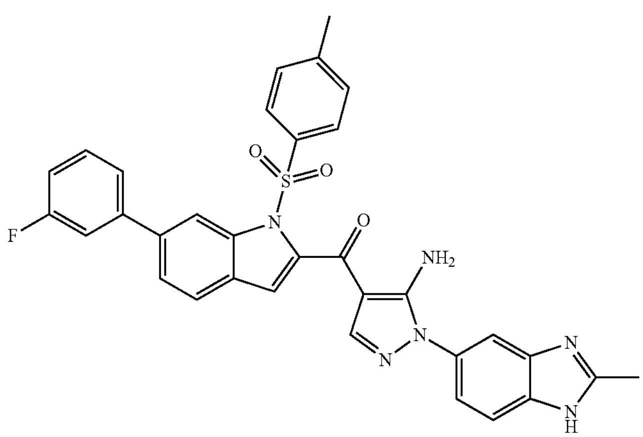 [SMILES: Cc1ccc(S(=O)(=O)n2c(C(=O)c3cnn(-c4ccc5[nH]c(C)nc5c4)c3N)cc3ccc(-c4cccc(F)c4)cc32)cc1] | [5-amino-1-(2-methyl-1H-benzimidazol-5-yl)-1H-pyrazol-4-yl]-[6-(3-fluoro-phenyl)-1-(toluene-4-sulfonyl)-1H-indol-2-yl]-methanone | 605 |

| Compound No. | Structure | Compound name | m/z |
|---|---|---|---|
| 1453 | 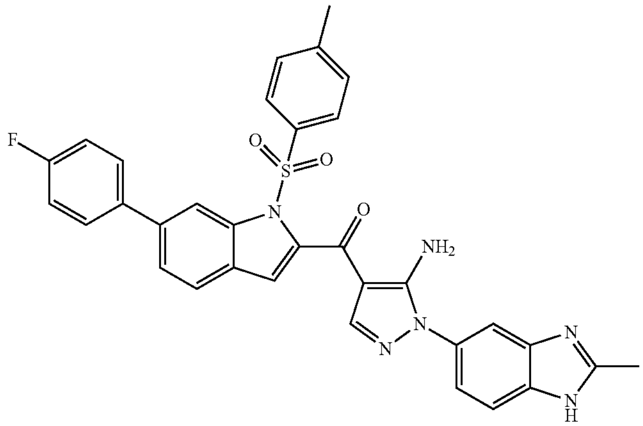 [SMILES: Cc1ccc(S(=O)(=O)n2c(C(=O)c3cnn(-c4ccc5[nH]c(C)nc5c4)c3N)cc3ccc(-c4ccc(F)cc4)cc32)cc1] | [5-amino-1-(2-methyl-1H-benzimidazol-5-yl)-1H-pyrazol-4-yl]-[6-(4-fluoro-phenyl)-1-(toluene-4-sulfonyl)-1H-indol-2-yl]-methanone | 605 |
| 1454 | 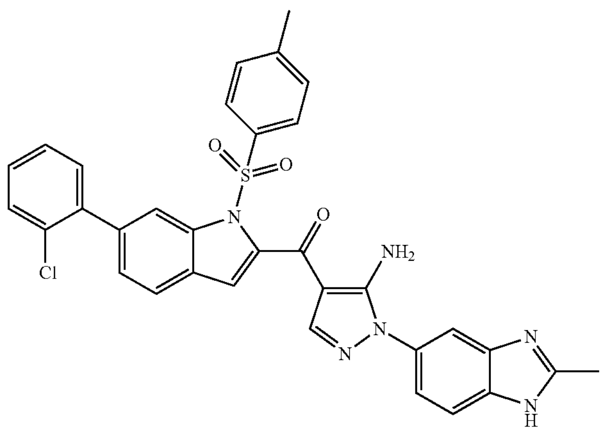 [SMILES: Cc1ccc(S(=O)(=O)n2c(C(=O)c3cnn(-c4ccc5[nH]c(C)nc5c4)c3N)cc3ccc(-c4ccccc4Cl)cc32)cc1] | [5-amino-1-(2-methyl-1H-benzimidazol-5-yl)-1H-pyrazol-4-yl]-[6-(2-chloro-phenyl)-1-(toluene-4-sulfonyl)-1H-indol-2-yl]-methanone | 621, 623 |
| 1455 | 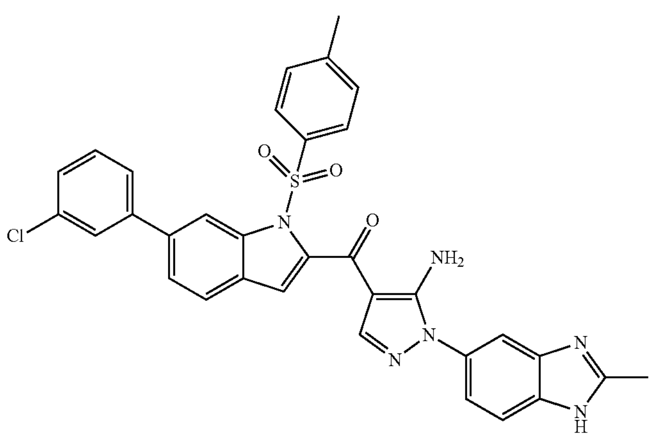 [SMILES: Cc1ccc(S(=O)(=O)n2c(C(=O)c3cnn(-c4ccc5[nH]c(C)nc5c4)c3N)cc3ccc(-c4cccc(Cl)c4)cc32)cc1] | [5-amino-1-(2-methyl-1H-benzimidazol-5-yl)-1H-pyrazol-4-yl]-[6-(3-chlorophenyl)-1-(toluene-4-sulfonyl)-1H-indol-2-yl]-methanone | 621, 623 |

TABLE 25-continued

| Compound No. | Structure | Compound name | m/z |
|---|---|---|---|
| 1456 | 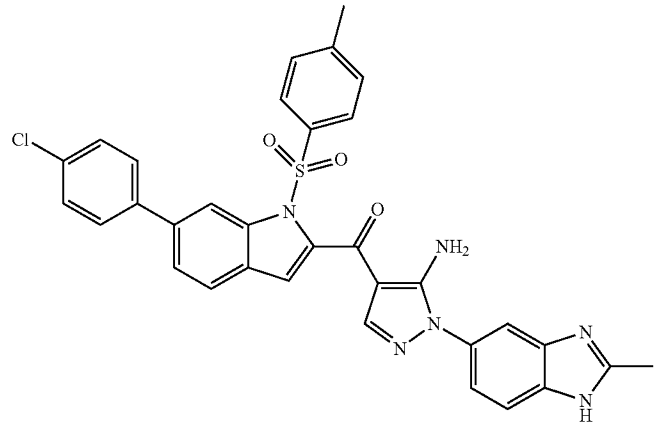 [SMILES: Cc1ccc(S(=O)(=O)n2c(C(=O)c3cnn(-c4ccc5[nH]c(C)nc5c4)c3N)cc3ccc(-c4ccc(Cl)cc4)cc32)cc1] | [5-amino-1-(2-methyl-1H-benzimidazol-5-yl)-1H-pyrazol-4-yl]-[6-(4-chloro-phenyl)-1-(toluene-4-sulfonyl)-1H-indol-2-yl]-methanone | 621, 623 |
| 1457 | 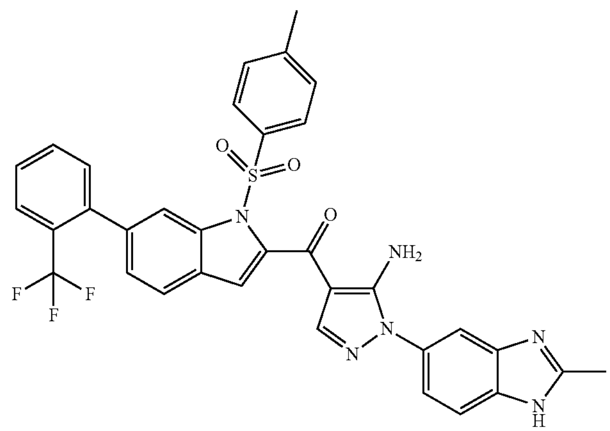 [SMILES: Cc1ccc(S(=O)(=O)n2c(C(=O)c3cnn(-c4ccc5[nH]c(C)nc5c4)c3N)cc3ccc(-c4ccccc4C(F)(F)F)cc32)cc1] | [5-amino-1-(2-methyl-1H-benzimidazol-5-yl)-1H-pyrazol-4-yl]-[1-(toluene-4-sulfonyl)-6-(2-trifluoromethyl-phenyl)-1H-indol-2-yl]-methanone | 655 |
| 1458 | 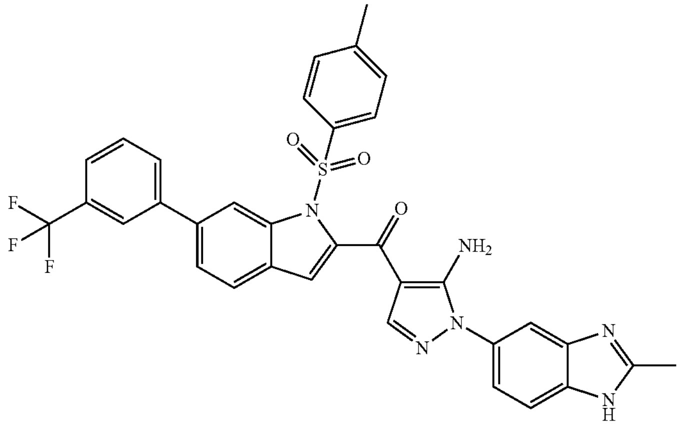 [SMILES: Cc1ccc(S(=O)(=O)n2c(C(=O)c3cnn(-c4ccc5[nH]c(C)nc5c4)c3N)cc3ccc(-c4cccc(C(F)(F)F)c4)cc32)cc1] | [5-amino-1-(2-methyl-1H-benzimidazol-5-yl)-1H-pyrazol-4-yl]-[1-(toluene-4-sulfonyl)-6-(3-trifluoromethylphenyl)-1H-indol-2-yl]-methanone | 655 |

TABLE 25-continued

| Compound No. | Structure | Compound name | m/z |
|---|---|---|---|
| 1459 | 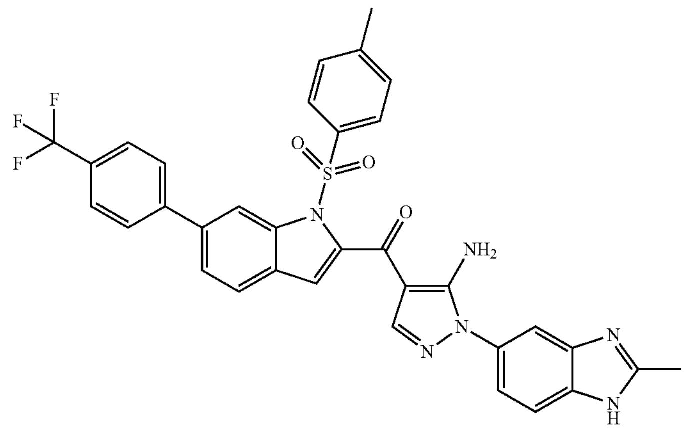 [SMILES: Cc1ccc(S(=O)(=O)n2c(C(=O)c3cnn(-c4ccc5[nH]c(C)nc5c4)c3N)cc3ccc(-c4ccc(C(F)(F)F)cc4)cc32)cc1] | [5-amino-1-(2-methyl-1H-benzimidazol-5-yl)-1H-pyrazol-4-yl]-[1-(toluene-4-sulfonyl)-6-(4-trifluoromethyl-phenyl)-1H-indol-2-yl]-methanone | 655 |
| 1460 | 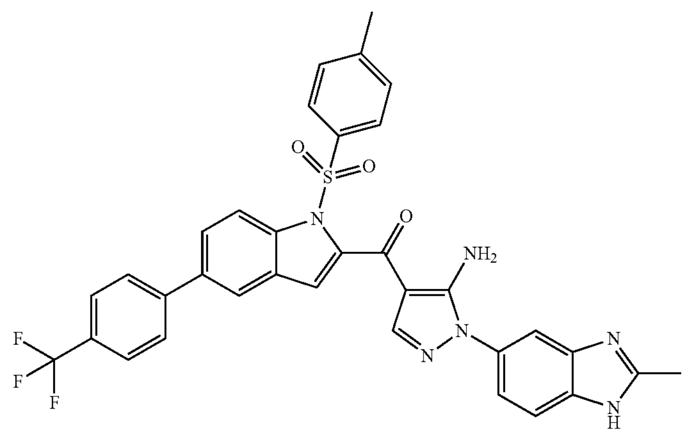 [SMILES: Cc1ccc(S(=O)(=O)n2c(C(=O)c3cnn(-c4ccc5[nH]c(C)nc5c4)c3N)cc3cc(-c4ccc(C(F)(F)F)cc4)ccc32)cc1] | [5-amino-1-(2-methyl-1H-benzimidazol-5-yl)-1H-pyrazol-4-yl]-[1-(toluene-4-sulfonyl)-5-(4-trifluoromethyl-phenyl)-1H-indol-2-yl]-methanone | 655 |
| 1461 | 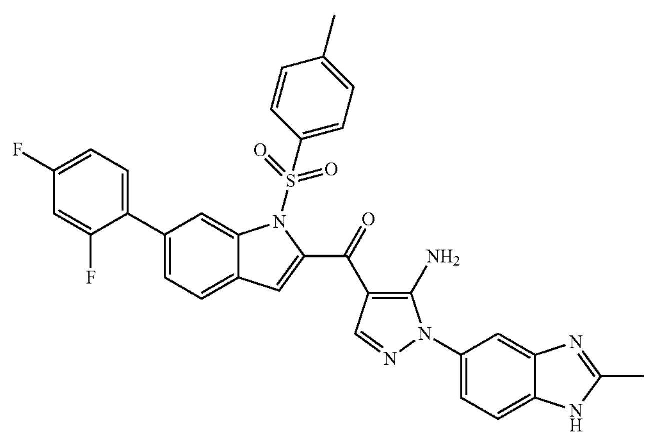 [SMILES: Cc1ccc(S(=O)(=O)n2c(C(=O)c3cnn(-c4ccc5[nH]c(C)nc5c4)c3N)cc3ccc(-c4ccc(F)cc4F)cc32)cc1] | [5-amino-1-(2-methyl-1H-benzimidazol-5-yl)-1H-pyrazol-4-yl]-[6-(2,4-difluoro-phenyl)-1-(toluene-4-sulfonyl)-1H-indol-2-yl]-methanone | 623 |

TABLE 25-continued

| Compound No. | Structure | Compound name | m/z |
|---|---|---|---|
| 1462 | 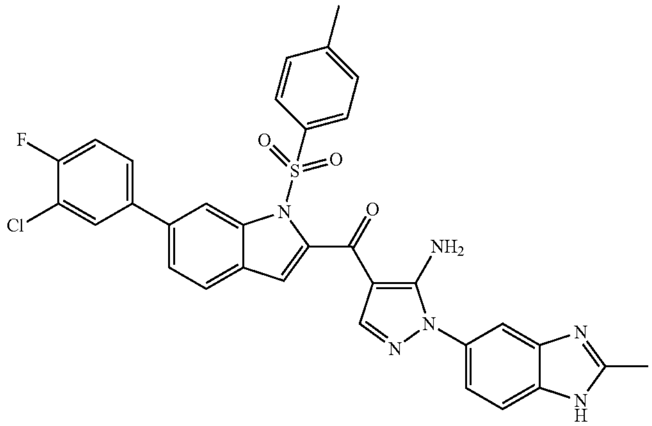 [SMILES: Cc1ccc(S(=O)(=O)n2c(C(=O)c3cnn(-c4ccc5[nH]c(C)nc5c4)c3N)cc3ccc(-c4ccc(F)c(Cl)c4)cc32)cc1] | [5-amino-1-(2-methyl-1H-benzimidazol-5-yl)-1H-pyrazol-4-yl]-[6-(3-chloro-4-fluoro-phenyl)-1-(toluene-4-sulfonyl)-1H-indol-2-yl]-methanone | 640, 642 |
| 1580 | 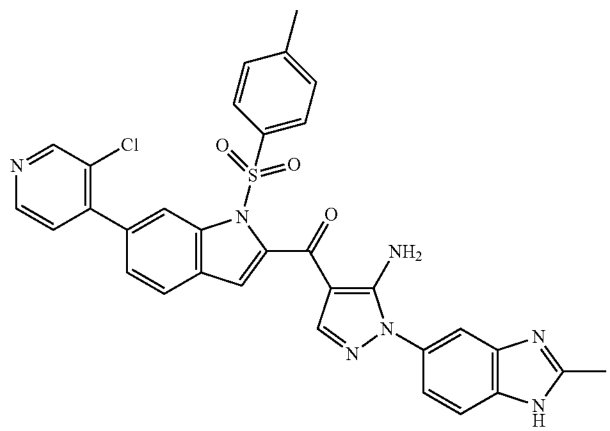 [SMILES: Cc1ccc(S(=O)(=O)n2c(C(=O)c3cnn(-c4ccc5[nH]c(C)nc5c4)c3N)cc3ccc(-c4ccncc4Cl)cc32)cc1] | [5-amino-1-(2-methyl-1H-benzimidazol-5-yl)-1H-pyrazol-4-yl]-[6-(3-chloro-pyridin-4-yl)-1-(toluene-4-sulfonyl)-1H-indol-2-yl]-methanone | 622 |
| 1581 | 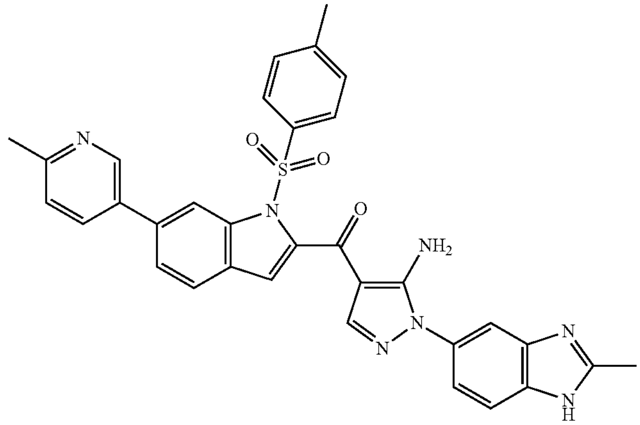 | [5-amino-1-(2-methyl-1H-benzimidazol-5-yl)-1H-pyrazol-4-yl]-[6-(6-methylpyridin-3-yl)-1-(toluene-4-sulfonyl)-1H-indol-2-yl]-methanone | 602 |

TABLE 25-continued

| Compound No. | Structure | Compound name | m/z |
|---|---|---|---|
| 1582 | 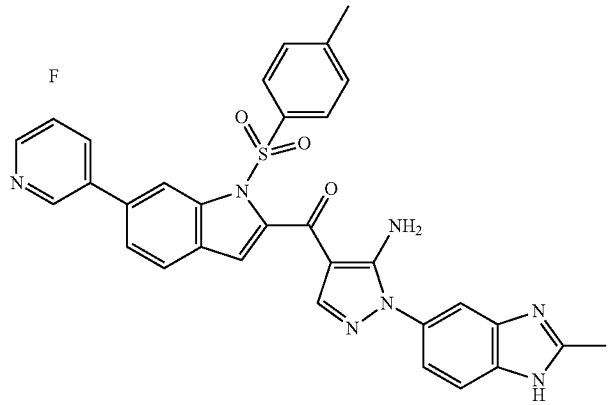 | [5-amino-1-(2-methyl-1H-benzimidazol-5-yl)-1H-pyrazol-4-yl]-[6-(5-fluoro-pyridin-3-yl)-1-(toluene-4-sulfonyl)-1H-indol-2-yl]-methanone | 606 |
| 1583 | 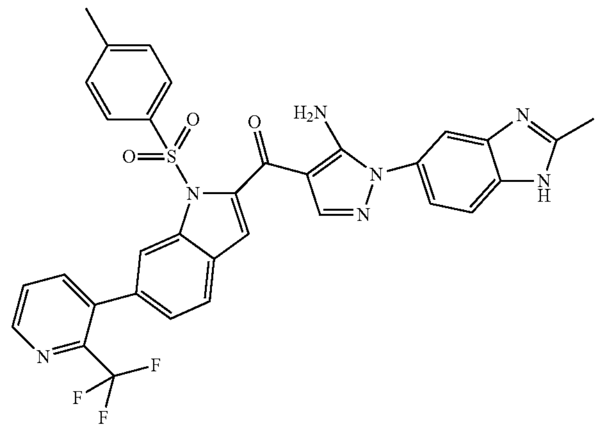 [SMILES: Cc1ccc(S(=O)(=O)n2c(C(=O)c3cnn(-c4ccc5[nH]c(C)nc5c4)c3N)cc3ccc(-c4cccnc4C(F)(F)F)cc32)cc1] | [5-amino-1-(2-methyl-1H-benzimidazol-5-yl)-1H-pyrazol-4-yl]-[1-(toluene-4-sulfonyl)-6-(2-trifluoromethyl-pyridin-3-yl)-1H-indol-2-yl]-methanone | 656 |
| 1584 | 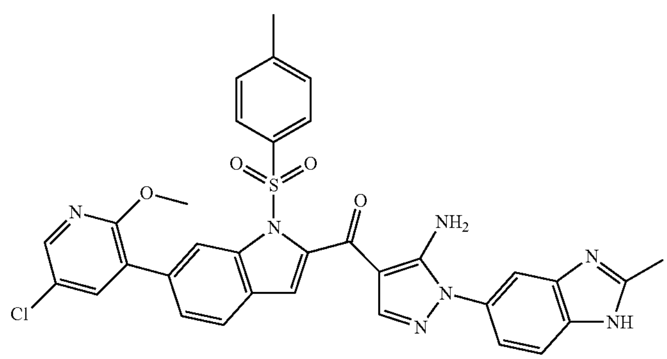 [SMILES: COc1ncc(Cl)cc1-c1ccc2cc(C(=O)c3cnn(-c4ccc5[nH]c(C)nc5c4)c3N)n(S(=O)(=O)c3ccc(C)cc3)c2c1] | [5-amino-1-(2-methyl-1H-benzimidazol-5-yl)-1H-pyrazol-4-yl]-[6-(5-chloro-2-methoxy-pyridin-3-yl)-1-(toluene-4-sulfonyl)-1H-indol-2-yl]-methanone | 652 |
| 1585 | 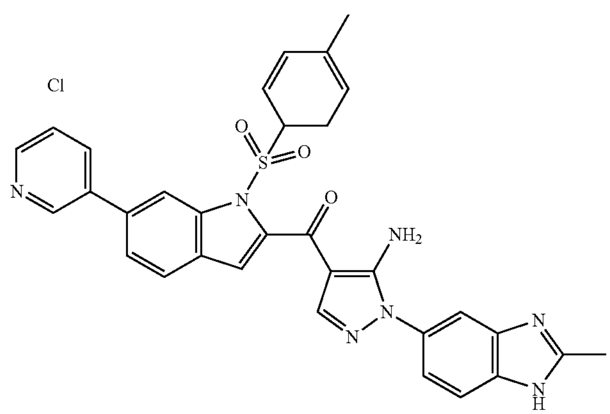 [SMILES: CC1=CCC(S(=O)(=O)n2c(C(=O)c3cnn(-c4ccc5[nH]c(C)nc5c4)c3N)cc3ccc(-c4cccnc4)cc32)C=C1 ; Cl] | [5-amino-1-(2-methyl-1H-benzimidazol-5-yl)-1H-pyrazol-4-yl]-[6-(5-chloro-pyridin-3-yl)-1-(toluene-4-sulfonyl)-1H-indol-2-yl]-methanone | 622 |

TABLE 25-continued

| Compound No. | Structure | Compound name | m/z |
|---|---|---|---|
| 1586 | 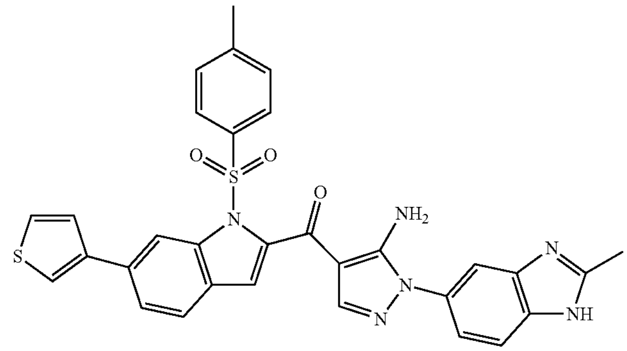 [SMILES: Cc1ccc(S(=O)(=O)n2c(C(=O)c3cnn(-c4ccc5[nH]c(C)nc5c4)c3N)cc3ccc(-c4ccsc4)cc32)cc1] | [5-amino-1-(2-methyl-1H-benzimidazol-5-yl)-1H-pyrazol-4-yl]-[6-thiophen-3-yl-1-(toluene-4-sulfonyl)-1H-indol-2-yl]-methanone | 593 |
| 1587 | 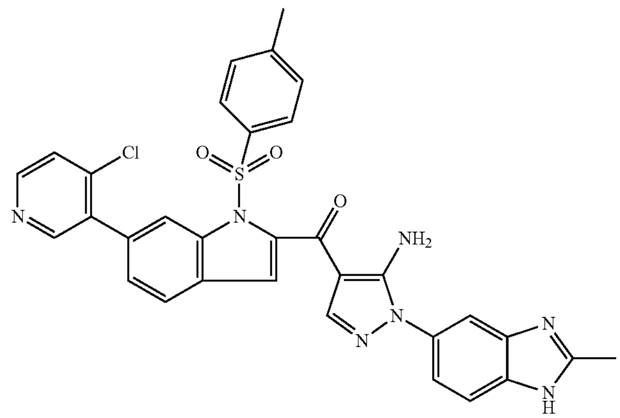 [SMILES: Cc1ccc(S(=O)(=O)n2c(C(=O)c3cnn(-c4ccc5[nH]c(C)nc5c4)c3N)cc3ccc(-c4cnccc4Cl)cc32)cc1] | [5-amino-1-(2-methyl-1H-benzimidazol-5-yl)-1H-pyrazol-4-yl]-[6-(4-chloropyridin-3-yl)-1-(toluene-4-sulfonyl)-1H-indol-2-yl]-methanone | 622 |
| 1588 | 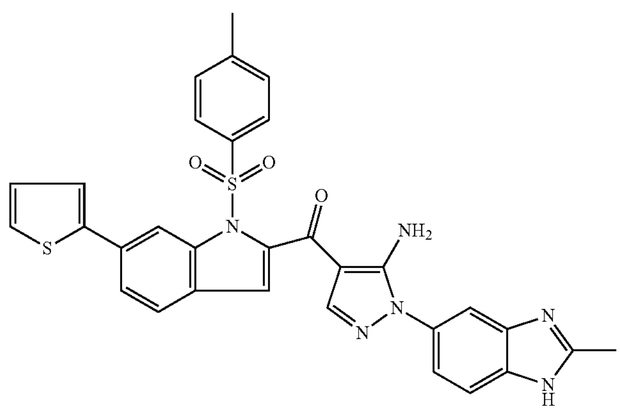 [SMILES: Cc1ccc(S(=O)(=O)n2c(C(=O)c3cnn(-c4ccc5[nH]c(C)nc5c4)c3N)cc3ccc(-c4cccs4)cc32)cc1] | [5-amino-1-(2-methyl-1H-benzimidazol-5-yl)-1H-pyrazol-4-yl]-[6-thiphen-2-yl-1-(toluene-4-sulfonyl)-1H-indol-2-yl]-methanone | 593 |
| 1589 | 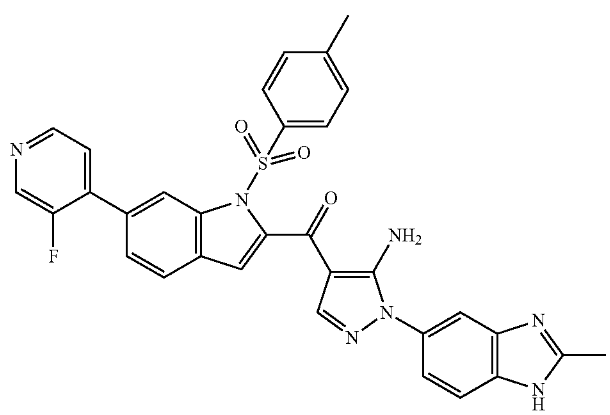 [SMILES: Cc1ccc(S(=O)(=O)n2c(C(=O)c3cnn(-c4ccc5[nH]c(C)nc5c4)c3N)cc3ccc(-c4ccncc4F)cc32)cc1] | [5-amino-1-(2-methyl-1H-benzimidazol-5-yl)-1H-pyrazol-4-yl]-[6-(3-fluoro-pyridin-4-yl)-1-(toluene-4-sulfonyl)-1H-indol-2-yl]-methanone | 606 |

| Compound No. | Structure | Compound name | m/z |
|---|---|---|---|
| 1590 | 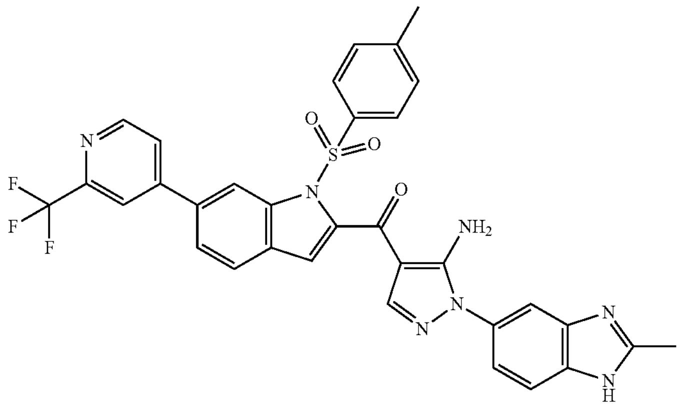 [SMILES: Cc1ccc(S(=O)(=O)n2c(C(=O)c3cnn(-c4ccc5[nH]c(C)nc5c4)c3N)cc3ccc(-c4ccnc(C(F)(F)F)c4)cc32)cc1] | [5-amino-1-(2-methyl-1H-benzimidazol-5-yl)-1H-pyrazol-4-yl]-[1-(toluene-4-sulfonyl)-6-(2-trifluoromethyl-pyridin-4-yl)-1H-indol-2-yl]-methanone | 656 |

Step 30: Synthesis of [5-amino-1-(2-methyl-1H-benzimidazol-5-yl)-1H-pyrazol-4-yl]-[6-pyridazin-4-yl-1-(toluene-4-sulfonyl)-1H-indol-2-yl]-methanone (1463)

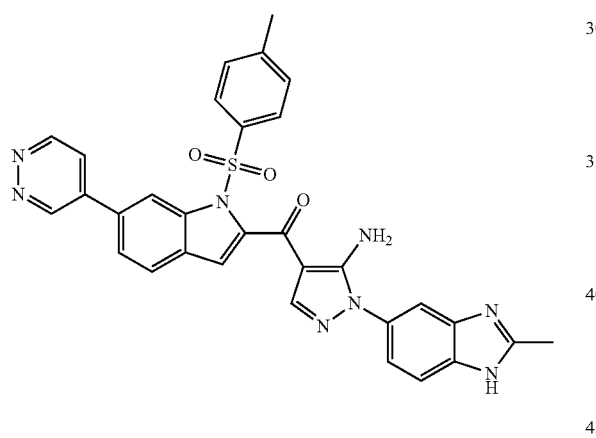

A mixture of [5-amino-1-(2-methyl-1H-benzimidazol-5-yl)-1H-pyrazol-4-yl]-[6-iodo-1-(toluene-4-sulfonyl)-1H-indol-2-yl]-methanone (194.9 mg, 0.306 mmol), [1,1'-bis(diphenylphosphino)ferrocene]dichloro-palladium (II)/dichloromethane adduct (14.4 mg, 0.015 mmol) bis(pinacol) diborane (100.9 mg, 0.397 mmol), potassium acetate (132.3 mg, 1.35 mmol), and anhydrous dimethylsulfoxide (DMSO) (1.5 ml) was deaerated. Then, the air was replaced three times with argon, and was heated and stirred at 110° C. for six hours. Then, the reaction mixture was extracted with ethyl acetate. The extract was dried over anhydrous sodium sulfate. The desiccant was removed by filtration, and concentration was performed. Then, the residue obtained by concentration under reduced pressure was subjected to silica gel column chromatography (dichloromethane/methanol=15/1). The resulting crude product was mixed with 4-bromo-pyridazine (78.0 mg, 0.491 mol), dichlorobis(triphenylphosphine)palladium (II) (17.2 mg, 0.025 mmol), an aqueous solution of 2 M sodium bicarbonate (0.325 mmol), and dioxane (0.4 ml). After deaeration, the air was replaced three times with argon, and this was microwaved at 150° C. for five minutes. Then, the reaction mixture was extracted with ethyl acetate. The extract was dried over anhydrous sodium sulfate. The desiccant was removed by filtration, and concentration was performed. Then, the residue obtained by concentration under reduced pressure was purified by silica gel column chromatography (dichloromethane/methanol=1% to 12%). Thus, [5-amino-1-(2-methyl-1H-benzimidazol-5-yl)-1H-pyrazol-4-yl]-[6-pyridazin-4-yl-1-(toluene-4-sulfonyl)-1H-indol-2-yl]-methanone was obtained as a pale yellow amorphous material (20.0 mg, yield of 11%).

ESI (LC-MS positive mode) m/z 589 [(M+H)$^+$]

Step 31: Synthesis of (1-benzenesulfonyl-1H-indol-6-yl)methanol (1464)

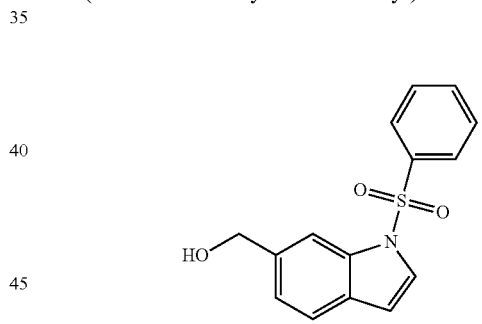

A predetermined amount of lithium aluminum hydride (167 mg, 4.42 mmol) was placed into a reaction container, and anhydrous tetrahydrofuran (THF) (15 ml) was added thereto, and this was cooled to 0° C. An anhydrous tetrahydrofuran (THF) solution (5 ml) of 1-benzenesulfonyl-1H-indole-6-carboxylic acid methyl ester (930 mg, 2.95 mmol) was added to the mixture. This was stirred at 0° C. for 30 minutes. An aqueous solution saturated with ammonium chloride (1 ml) was added to the mixture. After Celite filtration, the Celite was washed with dichloromethane. The filtrate was dried over anhydrous sodium sulfate. The desiccant was removed by filtration, and concentration was performed. Then, by concentration under reduced pressure, (1-benzenesulfonyl-1H-indol-6-yl)-methanol was obtained as an oily brown material (859 mg, 100%).

$^1$H-NMR (DMSO-D$_6$) δ: 7.96-7.92 (3H, m), 7.74 (1H, d, J=3.7 Hz), 7.68-7.67 (1H, m), 7.60-7.55 (2H, m), 7.52 (1H, d, J=8.0 Hz), 7.19-7.17 (1H, m), 6.80 (1H, dd, J=3.7, 0.8 Hz), 5.30 (1H, t, J=5.7 Hz), 4.59 (2H, d, J=5.7 Hz)

ESI (LC-MS positive mode) m/z 288 [(M+H)$^+$]

Step 32: Synthesis of 1-benzenesulfonyl-6-(tert-butyl-diphenyl-silanyloxymethyl)-1H-indole (1465)

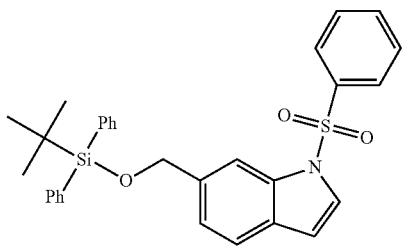 [SMILES: CC(C)(C)[Si](OCc1ccc2ccn(S(=O)(=O)c3ccccc3)c2c1)(c1ccccc1)c1ccccc1]

Predetermined amounts of 1-benzenesulfonyl-1H-indol-6-yl)-methanol (859 mg, 2.99 mmol), tert-butyl diphenyl chlorosilane (2.3 ml, 8.97 mmol), and imidazole (1.2 g, 17.9 mmol) were placed into a reaction container, and dimethylformamide (30 ml) was added thereto. This was stirred at room temperature for 20 hours. The reaction mixture was diluted with ethyl acetate (60 ml). This was washed twice with water, and dried over anhydrous sodium sulfate. The desiccant was removed by filtration, and concentration was performed. The resulting crude product was used in subsequent reactions.

ESI (LC-MS positive mode) m/z 526 [(M+H)$^+$]

Step 33: Synthesis of 1-benzenesulfonyl-6-(tert-butyl-diphenyl-silanyloxymethyl)-1H-indole-2-carboxylic acid methyl ester (1466)

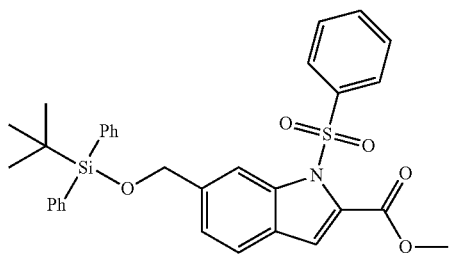 [SMILES: COC(=O)c1cc2ccc(CO[Si](c3ccccc3)(c3ccccc3)C(C)(C)C)cc2n1S(=O)(=O)c1ccccc1]

A tetrahydrofuran (THF) solution of lithium diisopropyl amide (LDA) was prepared by adding a hexane solution of 1.0 M n-butyl lithium (2.8 ml, 4.49 mmol) dropwise to a precooled (0° C.) anhydrous tetrahydrofuran (THF) solution (5 ml) of N,N-diisopropyl amine (0.64 ml, 4.49 mmol).

An anhydrous tetrahydrofuran (THF) solution (20 ml) of crude 1-benzenesulfonyl-6-(tert-butyl-diphenyl-silanyloxymethyl)-1H-indole was cooled to −78° C., and a prepared tetrahydrofuran (THF) solution of lithium diisopropyl amide (LDA) was added thereto. This was stirred at −78° C. for 30 minutes. Methyl chloroformate (0.43 ml, 5.98 mmol) was added thereto, and this was stirred at −78° C. for 30 minutes. An aqueous solution saturated with ammonium chloride was added to the reaction mixture, and this was warmed to room temperature. After ethyl acetate extraction, the organic layer was dried over anhydrous sodium sulfate. The desiccant was removed by filtration and concentration was performed. Then, the residue obtained by concentration under reduced pressure was purified by silica gel column chromatography (hexane/ethyl acetate=98/2 to 4/1). Thus, 1-benzenesulfonyl-6-(tert-butyl-diphenyl-silanyloxymethyl)-1H-indole-2-carboxylic acid methyl ester was obtained as a brown amorphous material (882 mg, 51%).

ESI (LC-MS positive mode) m/z 584 [(M+H)$^+$]

Step 34: Synthesis of 5-(1-tert-butoxycarbonyl-1,2,3,6-tetrahydro-pyridin-4-yl)-1-(toluene-4-sulfonyl)-1H-indole-2-carboxylic acid ethyl ester (1467)

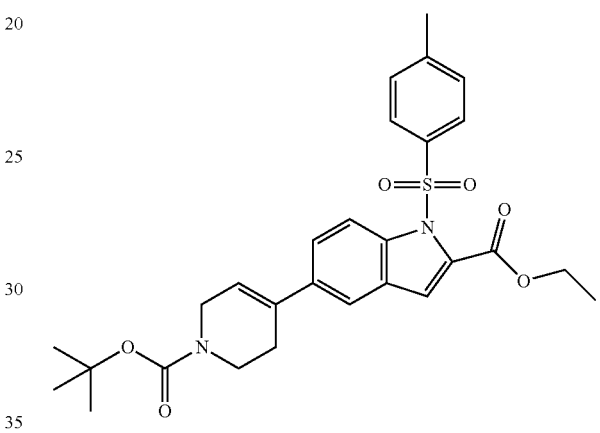

5-Bromo-1-(toluene-4-sulfonyl)-1H-indole-2-carboxylic acid ethyl ester (844 mg, 2.0 mmol), 4-(4,4,5,5-tetramethyl-[1,3,2]dioxaborolan-2-yl)-3,6-dihydro-2H-pyridine-1-carboxylic acid tert-butyl ester (742 mg, 2.4 mmol), potassium phosphate (848 mg, 4.0 mmol), and tetrakis(triphenylphosphine) palladium (116 mg, 0.1 mmol) were placed into a flask. After deaeration, the air was replaced with nitrogen. Anhydrous dioxane (16 ml) and water (4 ml) were added to the flask, and this was stirred at 80° C. for 15 hours. After cooling it to room temperature, the reaction mixture was filtered through Celite, and then washed with ethyl acetate. The filtrate was concentrated, and the residue obtained by concentration under reduced pressure was purified by silica gel column chromatography. Thus, 5-(1-tert-butoxycarbonyl-1,2,3,6-tetrahydro-pyridin-4-yl)-1-(toluene-4-sulfonyl)-1H-indole-2-carboxylic acid ethyl ester was obtained as a colorless amorphous material (1.0 g, 97.2%).

$^1$H-NMR (DMSO-D$_6$) δ: 7.96 (1H, d, J=9.1 Hz), 7.84 (2H, d, J=8.2 Hz), 7.68 (1H, d, J=1.8 Hz), 7.60 (1H, dd, J=9.1, 1.8 Hz), 7.41 (2H, d, J=8.2 Hz), 7.34 (1H, s), 6.17 (1H, s), 4.34 (2H, q, J=7.0 Hz), 4.02-3.98 (2H, m), 3.57-3.51 (2H, m), 2.51-2.45 (1H, m), 2.34 (3H, s), 1.42 (9H, s), 1.32 (3H, t, J=7.0 Hz)

ESI (LC-MS positive mode) m/z 525 [(M+H)$^+$]

The compounds of numbers 1468 and 1469 listed in Table 26 were synthesized as described in Step 34.

TABLE 26

| Compound No. | Structure | Compound name | m/z |
|---|---|---|---|
| 1468 | 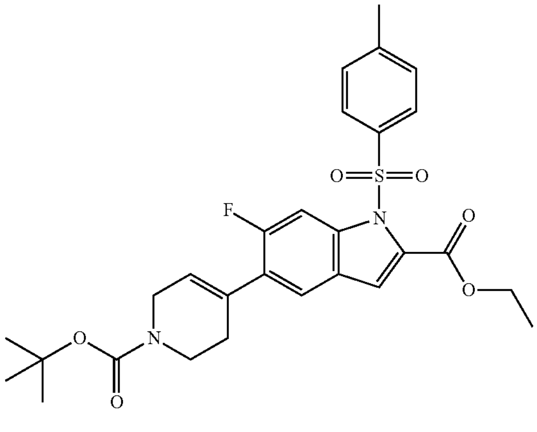 [SMILES: CCOC(=O)c1cc2cc(C3=CCN(C(=O)OC(C)(C)C)CC3)c(F)cc2n1S(=O)(=O)c1ccc(C)cc1] | 5-(1-tert-butoxycarbonyl-1,2,3,6-tetrahydro-pyridin-4-yl)-6-fluoro-1-(toluene-4-sulfonyl)-1H-indole-2-carboxylic acid ethyl ester | 543 |
| 1469 | 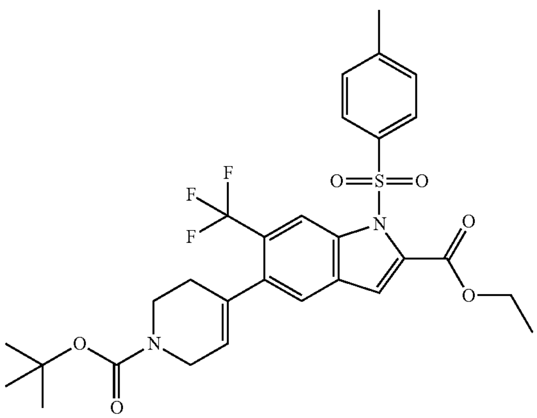 [SMILES: CCOC(=O)c1cc2cc(C3=CCN(C(=O)OC(C)(C)C)CC3)c(C(F)(F)F)cc2n1S(=O)(=O)c1ccc(C)cc1] | 5-(1-tert-butoxycarbonyl-1,2,3,6-tetrahydro-pyridin-4-yl)-1-(toluene-4-sulfonyl)-6-trifluoromethyl-1H-indole-2-carboxylic acid ethyl ester | 593 |

Step 35: Synthesis of 5-(1-tert-butoxycarbonyl-piperidin-4-yl)-1-(toluene-4-sulfonyl)-1H-indole-2-carboxylic acid ethyl ester (1470)

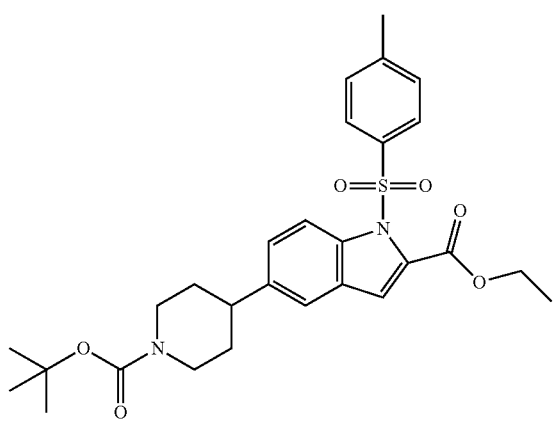 [SMILES: CCOC(=O)c1cc2cc(C3CCN(C(=O)OC(C)(C)C)CC3)ccc2n1S(=O)(=O)c1ccc(C)cc1]

A mixture of 5-(1-tert-butoxycarbonyl-1,2,3,6-tetrahydro-pyridin-4-yl)-1-(toluene-4-sulfonyl)-1H-indole-2-carboxylic acid ethyl ester (495 mg, 0.9 mmol), 5% palladium carbon (100 mg), and methanol (20 ml) was stirred under a hydrogen atmosphere for 13 hours. The reaction mixture was filtered through Celite, and washed with ethyl acetate, and the filtrate was concentrated. The residue obtained by concentration under reduced pressure was purified by silica gel column chromatography. Thus, 5-(1-tert-butoxycarbonyl-piperidin-4-yl)-1-(toluene-4-sulfonyl)-1H-indole-2-carboxylic acid ethyl ester was obtained as a colorless amorphous material (315.9 mg, 64%).

$^1$H-NMR (DMSO-D$_6$) δ: 7.92 (1H, d, J=8.8 Hz), 7.87 (2H, d, J=7.9 Hz), 7.53 (1H, d, J=1.5 Hz), 7.42 (2H, d, J=7.9 Hz), 7.39 (1H, dd, J=8.8, 1.5 Hz), 7.30 (1H, s), 4.33 (2H, q, J=7.0 Hz), 4.12-4.00 (2H, m), 2.85-2.70 (3H, m), 2.35 (3H, s), 1.78-1.70 (2H, m), 1.54-1.44 (2H, m), 1.41 (9H, s), 1.31 (3H, t, J=7.0 Hz)

ESI (LC-MS positive mode) m/z 527 [(M+H)$^+$]

The compounds of numbers 1471 and 1472 listed in Table 27 were synthesized as described in Step 35.

TABLE 27

| Compound No. | Structure | Compound name | m/z |
|---|---|---|---|
| 1471 | 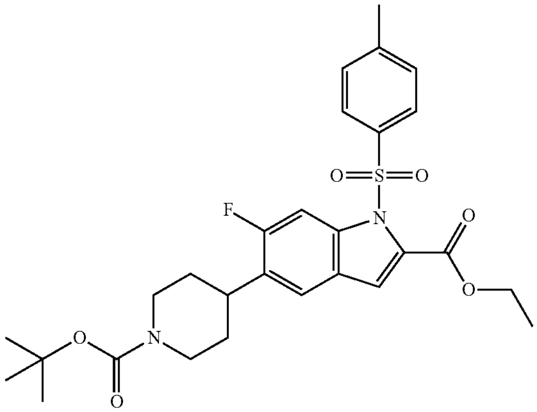 [SMILES: CCOC(=O)c1cc2cc(C3CCN(C(=O)OC(C)(C)C)CC3)c(F)cc2n1S(=O)(=O)c1ccc(C)cc1] | 5-(1-tert-butoxycarbonyl-piperidin-4-yl)-6-fluoro-1-(toluene-4-sulfonyl)-1H-indole-2-carboxylic acid ethyl ester | 489 [M − tert-Bu] |
| 1472 | 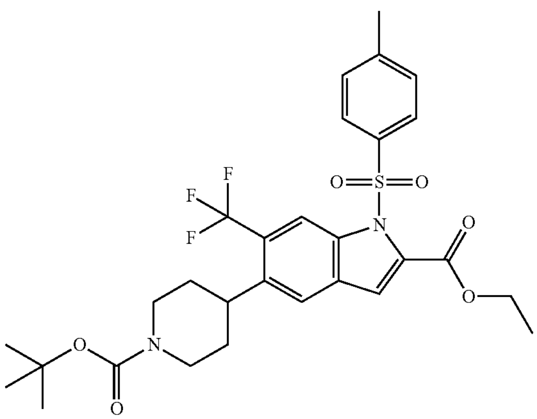 [SMILES: CCOC(=O)c1cc2cc(C3CCN(C(=O)OC(C)(C)C)CC3)c(C(F)(F)F)cc2n1S(=O)(=O)c1ccc(C)cc1] | 5-(1-tert-butoxycarbonyl-piperidin-4-yl)-1-(toluene-4-sulfonyl)-6-trifluoromethyl-1H-indole-2-carboxylic acid ethyl ester | 595 |

Step 36: Synthesis of 5-piperidin-4-yl-1-(toluene-4-sulfonyl)-1H-indole-2-carboxylic acid ethyl ester (1473)

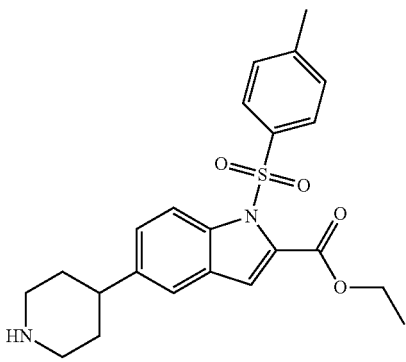 [SMILES: CCOC(=O)c1cc2cc(C3CCNCC3)ccc2n1S(=O)(=O)c1ccc(C)cc1]

5-(1-tert-Butoxycarbonyl-piperidin-4-yl)-1-(toluene-4-sulfonyl)-1H-indole-2-carboxylic acid ethyl ester (362 mg, 0.687 mmol) was dissolved in a mixture solution of ethyl acetate (4 ml) and 4 M hydrochloric acid/ethyl acetate (8 ml). This was stirred at room temperature under a nitrogen atmosphere for 1.5 hours. The reaction mixture was concentrated under reduced pressure. Thus, 5-piperidin-4-yl-1-(toluene-4-sulfonyl)-1H-indole-2-carboxylic acid ethyl ester hydrochloride was obtained as a colorless amorphous material (332 mg).

$^1$H-NMR (DMSO-D$_6$) δ: 8.78 (1H, brs), 7.98 (1H, d, J=8.5 Hz), 7.90 (2H, d, J=8.5 Hz), 7.51 (1H, s), 7.44 (2H, d, J=8.5 Hz), 7.38-7.36 (2H, m), 4.34 (2H, q, J=7.1 Hz), 3.02-2.90 (4H, m), 2.36 (3H, s), 1.95-1.78 (5H, m), 1.31 (3H, t, J=7.1 Hz)

ESI (LC-MS positive mode) m/z 427 [(M+H)$^+$]

The compounds of numbers 1474 and 1475 listed in Table 28 were synthesized as described in Step 36.

TABLE 28

| Compound No. | Structure | Compound name | m/z |
|---|---|---|---|
| 1474 | 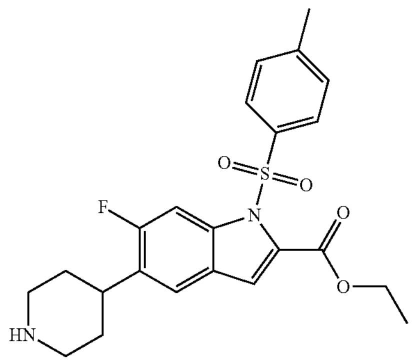 [SMILES: CCOC(=O)c1cc2cc(C3CCNCC3)c(F)cc2n1S(=O)(=O)c1ccc(C)cc1] | 6-fluoro-5-piperidin-4-yl-1-(toluene-4-sulfonyl)-1H-indole-2-carboxylic acid ethyl ester | 445 |
| 1475 | 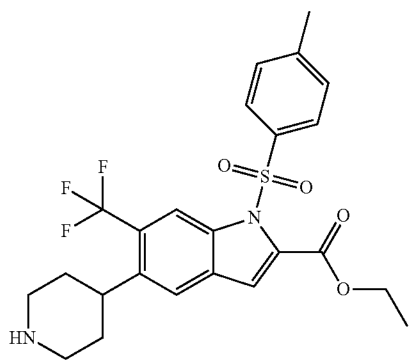 [SMILES: CCOC(=O)c1cc2cc(C3CCNCC3)c(C(F)(F)F)cc2n1S(=O)(=O)c1ccc(C)cc1] | 5-piperidin-4-yl-1-(toluene-4-sulfonyl)-6-trifluoromethyl-1H-indole-2-carboxylic acid ethyl ester | 495 |

Step 37: Synthesis of 5-(1-isopropyl-piperidin-4-yl)-1-(toluene-4-sulfonyl)-1H-indole-2-carboxylic acid ethyl ester (1476)

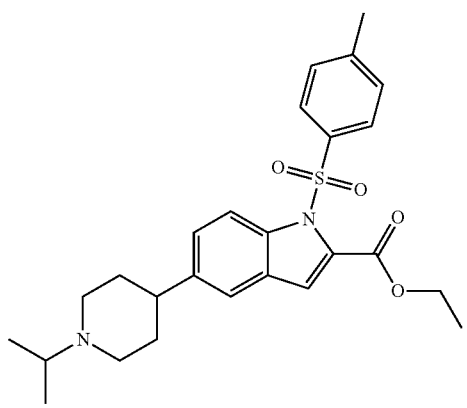 [SMILES: CCOC(=O)c1cc2cc(C3CCN(C(C)C)CC3)ccc2n1S(=O)(=O)c1ccc(C)cc1]

A mixture of 5-piperidin-4-yl-1-(toluene-4-sulfonyl)-1H-indole-2-carboxylic acid ethyl ester hydrochloride (253 mg, 0.592 mmol) in dichloroethane (4 ml), triethylamine (0.17 ml, 1.18 mmol), acetone (1.44 ml, 19.6 mmol), acetic acid (0.28 ml, 4.89 mmol), and sodium triacetoxyborohydride (318 mg, 1.50 mmol) was stirred at room temperature for 14.5 hours. The pH of the reaction mixture was adjusted to 9 (basic) using an aqueous solution saturated with sodium bicarbonate. The mixture was extracted with ethyl acetate. The extract was washed with an aqueous solution saturated with sodium chloride, and then dried over anhydrous sodium sulfate. The desiccant was removed by filtration, and concentration was performed. The resulting residue was purified by amino gel column chromatography (hexane/ethyl acetate=92/8 to 35/65). Thus, 5-(1-isopropyl-piperidin-4-yl)-1-(toluene-4-sulfonyl)-1H-indole-2-carboxylic acid ethyl ester was obtained as a colorless gum-like material (191 mg, 69%).

$^1$H-NMR (DMSO-D$_6$) δ: 7.91 (1H, d, J=8.5 Hz), 7.87 (2H, d, J=8.5 Hz), 7.52 (1H, d, J=1.8 Hz), 7.42 (2H, d, J=8.5 Hz), 7.39 (1H, dd, J=9.2, 1.8 Hz), 7.31 (1H, s), 4.34 (2H, q, J=7.1 Hz), 2.87 (2H, d, J=11.6 Hz), 2.74-2.67 (1H, m), 2.56-2.53 (1H, m), 2.35 (3H, s), 2.21 (2H, dd, J=11.6, 5.8 Hz), 1.77-1.74 (2H, m), 1.63-1.57 (2H, m), 1.31 (3H, t, J=7.1 Hz), 0.98 (6H, d, J=6.7 Hz)

ESI (LC-MS positive mode) m/z 469 [(M+H)$^+$]

The compounds of numbers 1477 to 1480 listed in Table 29 were synthesized as described in Step 37.

TABLE 29

| Compound No. | Structure | Compound name | m/z |
|---|---|---|---|
| 1477 | 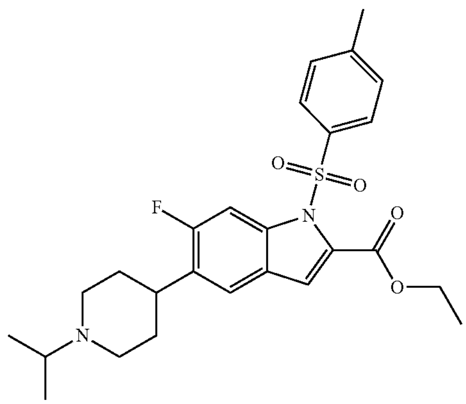 [SMILES: CCOC(=O)c1cc2cc(C3CCN(C(C)C)CC3)c(F)cc2n1S(=O)(=O)c1ccc(C)cc1] | 6-fluoro-5-(1-isopropyl-piperidin-4-yl)-1-(toluene-4-sulfonyl)-1H-indole-2-carboxylic acid ethyl ester | 487 |
| 1478 | 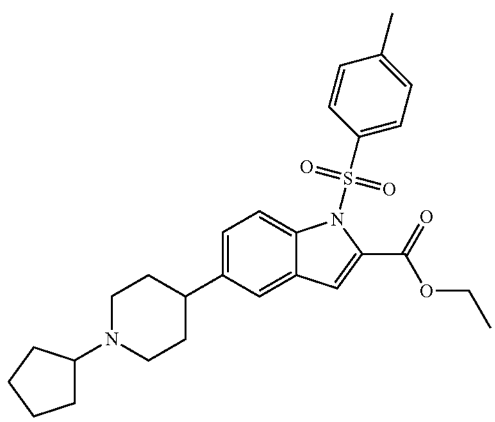 [SMILES: CCOC(=O)c1cc2cc(C3CCN(C4CCCC4)CC3)ccc2n1S(=O)(=O)c1ccc(C)cc1] | 5-(1-cyclopentyl-piperidin-4-yl)-1-(toluene-4-sulfonyl)-1H-indole-2-carboxylic acid ethyl ester | 495 |
| 1479 | 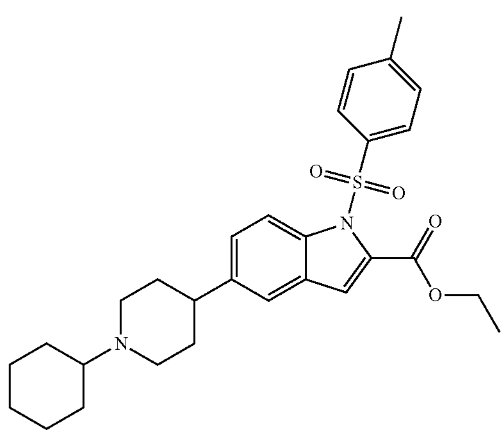 [SMILES: CCOC(=O)c1cc2cc(C3CCN(C4CCCCC4)CC3)ccc2n1S(=O)(=O)c1ccc(C)cc1] | 5-(1-cyclohexyl-piperidin-4-yl)-1-(toluene-4-sulfonyl)-1H-indole-2-carboxylic acid ethyl ester | 509 |

TABLE 29-continued

| Compound No. | Structure | Compound name | m/z |
|---|---|---|---|
| 1480 | 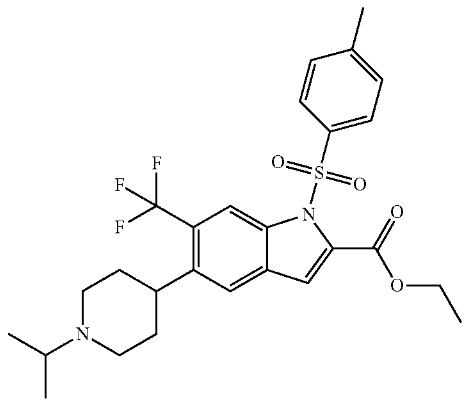 [SMILES: CCOC(=O)c1cc2cc(C3CCN(C(C)C)CC3)c(C(F)(F)F)cc2n1S(=O)(=O)c1ccc(C)cc1] | 5-(1-isopropyl-piperidin-4-yl)-1-(toluene-4-sulfonyl)-6-trifluoromethyl-1H-indole-2-carboxylic acid ethyl ester | 537 |

Step 38: Synthesis of 6-(1-methyl-piperidin-4-yl)-1-(toluene-4-sulfonyl)-1H-indole (1481)

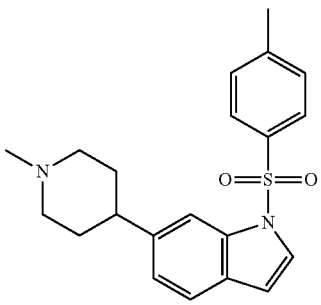 [SMILES: Cc1ccc(S(=O)(=O)n2ccc3ccc(C4CCN(C)CC4)cc32)cc1]

Preparation of Zinc Reagent:

An anhydrous tetrahydrofuran (THF) solution (3.5 ml) of 4-chloro-1-methyl-piperidine (8.56 mmol, 1.1 ml) was added at 80° C. to a suspension (0.5 ml) of magnesium (234 mg, 9.6 mmol) in anhydrous tetrahydrofuran (THF). This was stirred for one hour. After cooling it to room temperature, the reaction mixture was added dropwise to a mixed solution of zinc bromide (1.1 g, 4.8 mmol) in anhydrous tetrahydrofuran (THF) (2.0 ml) and anhydrous 1-methyl-2-pyrrolidinone (0.6 ml). This was stirred for 30 minutes.

Coupling Reaction:

6-Bromo-1-(toluene-4-sulfonyl)-1H-indole (340 mg, 0.97 mmol), Tris(dibenzylideneacetone)dipalladium (0) (23 mg, 0.025 mmol), and (3-diethoxyphosphinothioylsulfanyl-1,4-dioxan-2-yl)sulfanyl-diethoxy-sulfanylidene-phosphorane (Ruphos) (47 mg, 0.1 mmol) were placed into a reaction container. After deaeration, the air was replaced with nitrogen. Anhydrous tetrahydrofuran (THF) (5.0 ml) and a prepared zinc reagent suspension were added thereto, and this was stirred at 70° C. for 17 hours. After cooling it to room temperature, the reaction mixture was alkalinized with an aqueous solution saturated with sodium bicarbonate. The precipitated solid was removed by filtration. The filtrate was extracted with ethyl acetate. The extract was washed with water and an aqueous solution saturated with sodium chloride, and dried over anhydrous sodium sulfate. The desiccant was removed by filtration and concentration was performed. The residue obtained by concentration under reduced pressure was purified by silica gel column chromatography. Thus, 6-(1-methyl-piperidin-4-yl)-1-(toluene-4-sulfonyl)-1H-indole was obtained as a wax-like solid (293.7 mg, 82%).

$^1$H-NMR (DMSO-D$_6$) δ: 7.83 (2H, d, J=8.2 Hz), 7.75 (1H, d, J=1.5 Hz), 7.71 (1H, d, J=3.7 Hz), 7.48 (1H, d, J=8.1 Hz), 7.38 (2H, d, J=8.2 Hz), 7.14 (1H, dd, J=8.1, 1.5 Hz), 6.76 (1H, d, J=3.7 Hz), 2.89-2.87 (2H, m), 2.61-2.52 (1H, m), 2.31 (3H, s), 2.21 (3H, s), 1.99 (2H, td, J=11.4, 5.7 Hz), 1.76-1.62 (4H, m)

ESI (LC-MS positive mode) m/z 369 [(M+H)$^+$]

The compounds of numbers 1482 and 1483 listed in Table 30 were synthesized as described in Step 38.

TABLE 30

| Compound No. | Structure | Compound name | m/z |
|---|---|---|---|
| 1482 | 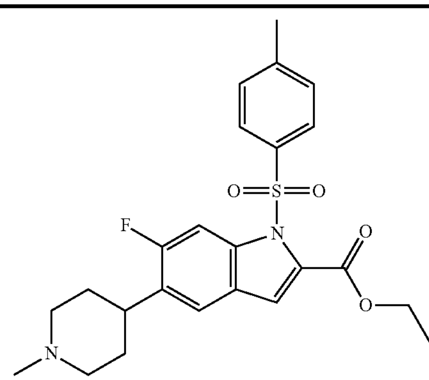 | 6-fluoro-5-(1-methyl-piperidin-4-yl)-1-(toluene-4-sulfonyl)-1H-indole-2-carboxylic acid ethyl ester | 459 |

TABLE 30-continued

| Compound No. | Structure | Compound name | m/z |
|---|---|---|---|
| 1483 | 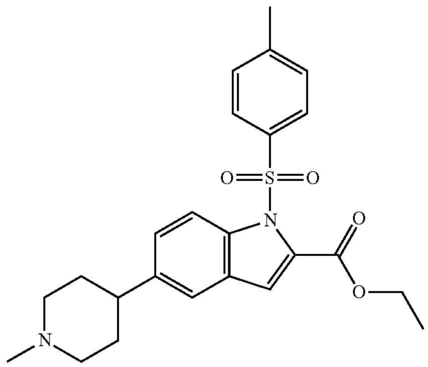 [SMILES: CCOC(=O)c1cc2cc(C3CCN(C)CC3)ccc2n1S(=O)(=O)c1ccc(C)cc1] | 5-(1-methyl-piperidin-4-yl)-1-(toluene-4-sulfonyl)-1H-indole-2-carboxylic acid ethyl ester | 441 |

Step 40: Synthesis of 4-chloro-1-(toluene-4-sulfonyl)-1H-indole-2-carboxylic acid methyl ester (1484)

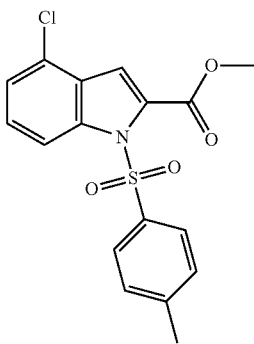 [SMILES: COC(=O)c1cc2c(Cl)cccc2n1S(=O)(=O)c1ccc(C)cc1]

A lithium diisopropyl amide solution was prepared by adding, at −78° C., a hexane solution of 1.0 M n-butyl lithium to an anhydrous tetrahydrofuran (THF) solution (1.5 ml) of diisopropyl amine (370 μl). The prepared solution was added at −78° C. to a tetrahydrofuran (THF) solution (6 ml) of 4-chloro-1-(toluene-4-sulfonyl)-1H-indole. This was stirred for 15 minutes. After adding methyl chloroformate (169 μl) thereto, the reaction mixture was stirred at −78° C. for 15 minutes, and then an aqueous solution (4 ml) of 1 M hydrochloric acid was added thereto at −78° C. After warming it to room temperature, the reaction mixture was extracted with ethyl acetate (10 ml). The organic layer was washed with an aqueous solution saturated with sodium chloride, and the organic layer was concentrated under reduced pressure. The resulting residue was purified by silica gel column chromatography (hexane/ethyl acetate). Thus, 4-chloro-1-(toluene-4-sulfonyl)-1H-indole-2-carboxylic acid methyl ester was obtained as a colorless solid (591 mg, 82%).

ESI (LC-MS positive mode) m/z 364, 366 [(M+H)$^+$]

The compounds of numbers 1485 to 1490 listed in Table 31 were synthesized as described in Step 39.

TABLE 31

| Compound No. | Structure | Compound name | m/z |
|---|---|---|---|
| 1485 | 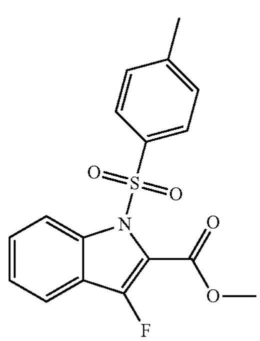 [SMILES: COC(=O)c1c(F)c2ccccc2n1S(=O)(=O)c1ccc(C)cc1] | 3-fluoro-1-(toluene-4-sulfonyl)-1H-indole-2-carboxylic acid methyl ester | 348 |

TABLE 31-continued

| Compound No. | Structure | Compound name | m/z |
|---|---|---|---|
| 1486 | 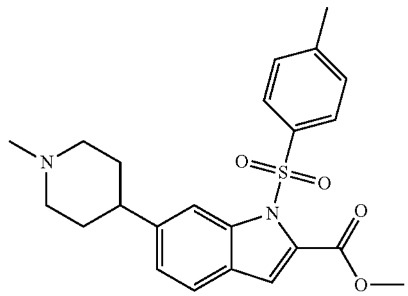 | 6-(1-methyl-piperidin-4-yl)-1-(toluene-4-sulfonyl)-1H-indole-2-carboxylic acid methyl ester | 427 |
| 1487 | 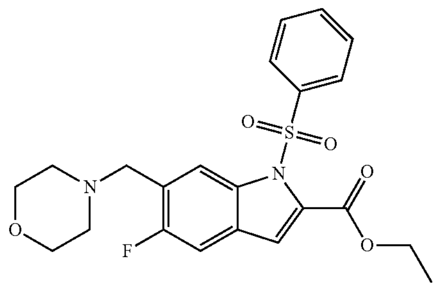 [SMILES: CCOC(=O)c1cc2cc(F)c(CN3CCOCC3)cc2n1S(=O)(=O)c1ccccc1] | 1-benzenesulfonyl-5-fluoro-6-morpholin-4-ylmethyl-1H-indole-2-carboxylic acid ethyl ester | 447 |
| 1488 | 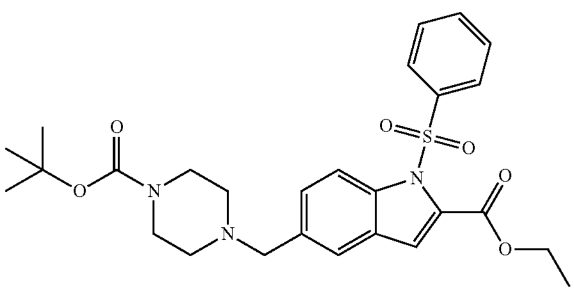 [SMILES: CCOC(=O)c1cc2cc(CN3CCN(C(=O)OC(C)(C)C)CC3)ccc2n1S(=O)(=O)c1ccccc1] | 1-benzenesulfonyl-5-(4-tert-butoxycarbonyl-piperadin-1-ylmethyl)-1H-indole-2-carboxylic acid ethyl ester | 528 |
| 1489 | 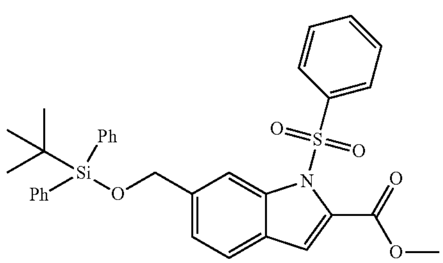 [SMILES: COC(=O)c1cc2ccc(CO[Si](c3ccccc3)(c3ccccc3)C(C)(C)C)cc2n1S(=O)(=O)c1ccccc1] | 1-benzenesulfonyl-6-(tert-butyl-diphenyl-silanyloxymethyl)-1H-indole-2-carboxylic acid methyl ester | 584 |
| 1490 | 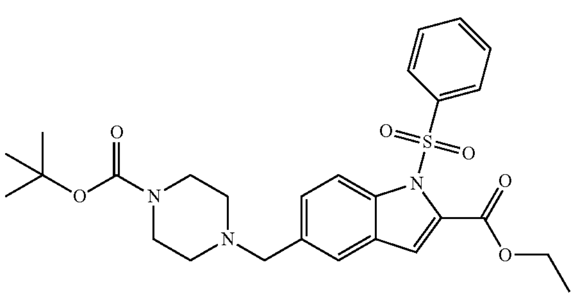 [SMILES: CCOC(=O)c1cc2cc(CN3CCN(C(=O)OC(C)(C)C)CC3)ccc2n1S(=O)(=O)c1ccccc1] | 1-benzenesulfonyl-5-(4-tert-butoxycarbonyl-piperadin-1-ylmethyl)-1H-indole-2-carboxylic acid ethyl ester | 528 |

Step 40: Synthesis of (2-methyl-1H-benzimidazol-5-yl)-hydrazine dihydrochloride (1491)

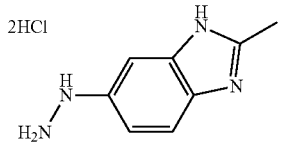

5-Amino-2-methyl-1H-benzimidazol hydrochloride (16.51 g) was dissolved in concentrated hydrochloric acid (200 ml), and this was cooled to 0° C. An aqueous solution (15 ml) of sodium nitrite (7.59 g) was added dropwise thereto at 0° C. over 20 minutes. This was stirred for 20 minutes. Then, a concentrated hydrochloric acid solution (20 ml) of tin (II) chloride dihydrate (55.7 g) was added dropwise thereto at 0° C. over one hour, and then this was stirred for 30 minutes. The precipitated solid was collected by filtration, and washed with water, and dried. Thus, crude (2-methyl-1H-benzimidazol-5-yl)-hydrazine dihydrochlide was obtained.

ESI (LC-MS positive mode) m/z 163 [(M+H)$^+$]

The compounds of numbers 1492 to 1496 listed in Table 32 were synthesized as described in Step 40.

Step 41: Synthesis of (7-fluoro-2-methyl-1H-benzimidazol-5-yl)-hydrazine dihydrochloride (1497)

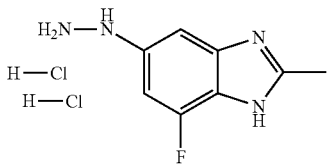

A catalyst was prepared as follows. Palladium acetate (1.2 mg, 0.0052 mmol) and 2-dicyclohexyl phosphino-2',4',6'-tri-i-propyl-1,1'-biphenyl (X-PHOS) (4.2 mg, 0.0088 mmol) were dissolved in tert-amyl alcohol (2.4 μl, 0.022 mmol) and N-methyl-morpholine (0.05 ml). The resulting solution was heated and stirred at 60° C. under a nitrogen atmosphere for five minutes.

In a separate reaction container, 7-fluoro-2-methyl-3H-benzimidazol-5-yl amine (100 mg, 0.44 mmol), lithium bis (trimethylsilyl) amide (190 mg, 1.1 mmol), and benzophenone hydrazone (94.3 mg, 0.48 mmol) were dissolved in N-methyl-morpholine (0.5 ml) under a nitrogen atmosphere. Then, the prepared solution containing the catalyst was added thereto. After deaeration, this was heated and stirred at 100°

TABLE 32

| Compound No. | Structure | Compound name | m/z |
|---|---|---|---|
| 1492 | 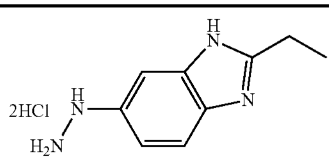 | (2-ethyl-1H-benzimidazol-5-yl)-hydrazine dihydrochloride | 177 |
| 1493 | 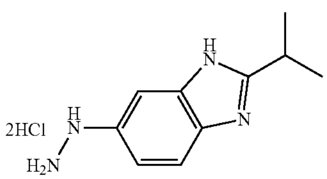 | (2-isopropyl-1H-benzimidazol-5-yl)-hydrazine dihydrochloride | 191 |
| 1494 | 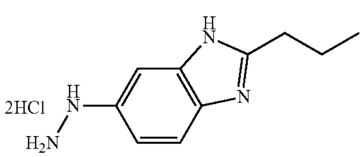 | (2-propyl-1H-benzimidazol-5-yl)-hydrazine dihydrochloride | 191 |
| 1495 | 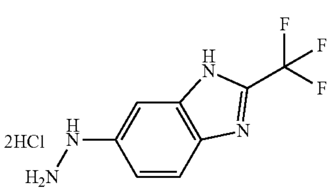 [SMILES: NNc1ccc2nc(C(F)(F)F)[nH]c2c1] | (2-trifluoromethyl-1H-benzimidazol-5-yl)-hydrazine dihydrochloride | 217 |
| 1496 | 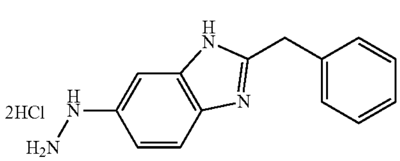 [SMILES: NNc1ccc2nc(Cc3ccccc3)[nH]c2c1] | (2-benzyl-1H-benzimidazol-5-yl)-hydrazine dihydrochloride | 239 |

C. under a nitrogen atmosphere for two hours. The reaction mixture was cooled to room temperature, and then an aqueous solution of 6 M hydrochloric acid (0.5 ml) was added thereto. The organic layer was isolated, and concentrated under reduced pressure. Thus, crude N-benzhydrylidene-N'-(7-fluoro-2-methyl-1H-benzimidazol-5-yl)-hydrazine was obtained. The obtained crude product was used in subsequent reactions without being purified.

Concentrated hydrochloric acid (0.7 ml) was added to a mixture of the crude N-benzhydrylidene-N'-(7-fluoro-2-methyl-1H-benzimidazol-5-yl)-hydrazine (325 mg) and ethanol (0.7 ml). This was stirred at 59 to 64° C. for one hour, and the reaction mixture was cooled to room temperature. Then, the precipitated solid was collected by filtration and dried. Thus, 7-fluoro-2-methyl-1H-benzimidazol-5-yl-hydrazine dihydrochloride (90 mg, 80%) was obtained.

$^1$H-NMR (DMSO-D$_6$) δ: 7.11 (1.0H, d, J=1.8 Hz), 6.99 (1.0H, dd, J=12.4, 1.8 Hz), 2.69 (3.1H, s)

ESI (LC-MS positive mode) m/z 181 [(M+H)$^+$]

6-Fluoro-2-methyl-1H-benzimidazol-5-yl-hydrazine dihydrochloride (1498) was synthesized as described in Step 41.

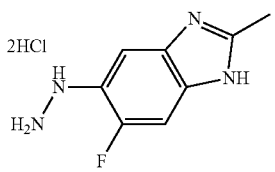

ESI (LC-MS positive mode) m/z 181 [(M+H)$^+$]

Step 42: Synthesis of 6-bromo-2-difluoromethyl-1H-benzimidazole (1499)

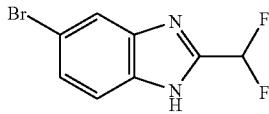 [SMILES: FC(F)c1nc2cc(Br)ccc2[nH]1]

4-Bromophenylene diamine (935 mg, 5.0 mmol) and difluoroacetic acid (0.47 ml, 7.5 mmol, 1.5 eq.) were dissolved in an aqueous solution (10 ml) of 5 M hydrochloric acid. This was stirred at 100° C. for 24 hours. After cooling it to room temperature, the reaction mixture was alkalinized by adding an aqueous solution (10 ml) of 5 M sodium hydroxide thereto. After ethyl acetate extraction, the extract was dried over anhydrous sodium sulfate. The desiccant was removed by filtration and concentration was performed. The residue obtained by concentration under reduced pressure was purified by silica gel column chromatography. Thus, 6-bromo-2-difluoro-methyl-1H-benzimidazole was obtained as a pale yellow solid (1.0 g, 85.4%).

$^1$H-NMR (DMSO-D$_6$) δ: 13.51 (1H, brs), 7.86 (1H, d, J=1.8 Hz), 7.62 (1H, d, J=8.5 Hz), 7.44 (1H, dd, J=8.5, 1.8 Hz), 7.41-7.14 (1H, m)

ESI (LC-MS positive mode) m/z 247, 249 [(M+H)$^+$]

Step 43: Synthesis of 6-bromo-2-difluoromethyl-1-(2-trimethylsilanyl-ethoxymethyl)-1H-benzimidazole (1500)

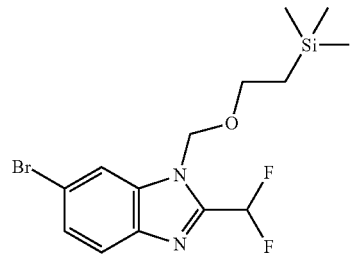 [SMILES: C[Si](C)(C)CCOCn1c(C(F)F)nc2ccc(Br)cc21]

(2-Chloro-methoxy-ethyl)-trimethyl-silane (1.1 ml, 6.4 mmol, 1.5 eq.) was added to an anhydrous dichloromethane solution (22 ml) of 6-bromo-2-difluoromethyl-1H-benzimidazol (1.0 g, 4.27 mmol) and N,N-diisopropyl ethyl amine (1.9 ml, 10.6 mmol, 2.5 eq.). This was stirred at room temperature for 18 hours. The reaction mixture was concentrated. The residue obtained by concentration under reduced pressure was purified by silica gel column chromatography. Thus, 6-bromo-2-difluoromethyl-1-(2-trimethylsilanyl-ethoxymethyl)-1H-benzimidazole was obtained as a yellow solid (1.37 g, 85%).

$^1$H-NMR (DMSO-D$_6$) δ: 8.07-8.02 (1H, m), 7.78-7.74 (1H, m), 7.60-7.28 (2H, m), 5.76 (2H, s), 3.52 (2H, td, J=8.4, 2.6 Hz), 0.83 (2H, td, J=8.4, 2.6 Hz), −0.10 (9H, s)

ESI (LC-MS positive mode) m/z 377, 379 [(M+H)$^+$]

Step 44: Synthesis of 2-difluoromethyl-3-(2-trimethylsilanyl-ethoxymethyl)-3H-benzimidazol-5-yl]-hydrazine hydrochloride (1501)

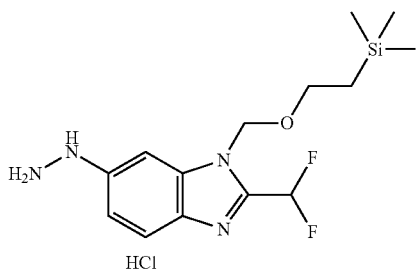 [SMILES: C[Si](C)(C)CCOCn1c(C(F)F)nc2ccc(NN)cc21 ; Cl]

6-Bromo-2-difluoromethyl-1-(2-trimethylsilanyl-ethoxymethyl)-1H-benzimidazole (754 mg, 2.0 mmol), Tris (dibenzylideneacetone)dipalladium (0) (92 mg, 0.1 mmol), 2-dicyclohexylphosphino-2',4',6'-tri-i-propyl-1,1'-biphenyl (X-PHOS) (143 mg, 0.3 mmol), cesium carbonate (1.3 g, 4.0 mmol), and tert-butyl carbazate (794 mg, 6.0 mmol) were placed into a flask. After deaeration, the air was replaced with argon. Anhydrous toluene (8.0 ml) was added thereto, and this was stirred at 100° C. for 20 hours. After cooling it to room temperature, the reaction mixture was filtered through Celite, and washed with ethyl acetate. The filtrate was concentrated. The residue obtained by concentration under reduced pressure was purified by silica gel column chromatography. Thus, tert-butoxycarbonylated hydrazine was obtained as a pale yellow gum-like material (220 mg, 26%). A 4 M hydrochloric acid/ethyl acetate solution (6.0 ml) was added to an ethyl acetate solution (3.0 ml) of the prepared tert-butoxycarbonylated hydrazine. This was stirred at room temperature for one and a half hours. The precipitated solid was collected by filtration, washed with ethyl acetate, and dried. Thus, crude [2-difluoromethyl-3-(2-trimethylsilanyl-ethoxymethyl)-3H-benzimidazol-5-yl]-hydrazine hydrochloride was obtained as a yellow solid. The crude product was used in subsequent reactions without being purified.

ESI (LC-MS positive mode) m/z 329 [(M+H)+]

Synthesis of 1-(2-methyl-1H-benzo[d]imidazol-5-yl)hydrazine-1,2-dicarboxylic acid di-tert-butyl mesilate

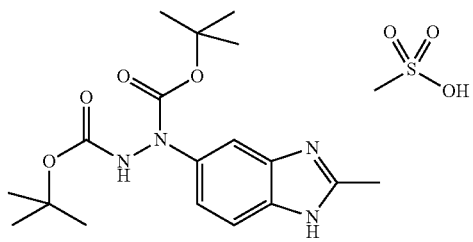

Step A

A mixture solution of 5-iodo-2-methyl-1H-benzimidazole (10 g, 39 mmol), trimethoxy-methane (200 ml), and chlorotrimethylsilane (0.075 ml, 0.59 mmol) was heated and stirred at 100° C. for five hours under a nitrogen atmosphere while distilling off the solvent (a reaction conversion rate of 97%). The reaction mixture was cooled to 40° C., and then a tetrahydrofuran solution (0.87 ml, 0.87 mmol) of potassium tert-butoxide was added thereto. This was concentrated under reduced pressure to provide crude 1-dimethoxymethyl-5-iodo-2-methyl-1H-benzimidazole.

Step B

A tetrahydrofuran solution (44 ml, 47 mmol) of 1.06 M cyclohexyl magnesium chloride was added to a mixed solution of crude 1-dimethoxymethyl-5-iodo-2-methyl-1H-benzimidazole and tetrahydrofuran (79 ml). This was stirred at −20° C. under a nitrogen atmosphere for two hours. A toluene solution (40 ml) of di-tert-butyl azodicarboxylate (10.7 g, 46 mmol) was added to the reaction mixture, and this was stirred under a nitrogen atmosphere at −20° C. for one hour and at 0° C. for another one hour (a reaction conversion rate of 96%). An aqueous solution (60 ml) of 15% ammonium chloride was added to the reaction mixture. After extraction with a solution of isopropyl acetate/heptane (1/1; 50 ml), the organic layer was washed with an aqueous solution (50 ml) of 2% sodium bicarbonate. Then, 1-methyl-pyrrolidin-2-one (15 ml) was added thereto, and this was concentrated under reduced pressure to provide a 1-methyl-pyrrolidin-2-one solution (48 ml) of crude 1-(1-(dimethoxymethyl)-2-methyl-1H-benzo[d]imidazol-5-yl)hydrazine-1,2-dicarboxylic acid di-tert-butyl.

Isopropyl acetate (61 ml), water (0.2 ml), and mesylic acid (0.87 ml) were added to the 1-methyl-pyrrolidin-2-one solution (16 ml) of crude 1-(1-(dimethoxymethyl)-2-methyl-1H-benzo[d]imidazol-5-yl)hydrazine-1,2-dicarboxylic acid di-tert-butyl. This was stirred at 40° C. for two hours. After cooling it to 5° C., the precipitated solid was collected by filtration, and dried to provide 1-(2-methyl-1H-benzo[d]imidazol-5-yl)hydrazine-1,2-dicarboxylic acid di-tert-butyl mesilate (4.3 g, 73%).

¹H-NMR (CD₃OD) δ: 7.87 (1.0H, m), 7.69-7.53 (2.0H, m), 2.84 (3.0H, s), 2.70 (3.0H, s), 1.52-1.47 (18H, m)

Crude 1-dimethoxymethyl-5-iodo-2-methyl-1H-benzimidazole was prepared using magnesium chloride instead of chlorotrimethylsilane in step A (a reaction conversion rate of 98%).

Crude 1-dimethoxymethyl-5-iodo-2-methyl-1H-benzimidazole was prepared using lithium chloride instead of chlorotrimethylsilane in step A (a reaction conversion rate of 98%).

Crude 1-dimethoxymethyl-5-iodo-2-methyl-1H-benzimidazole was prepared using benzoic acid instead of chlorotrimethylsilane in step A (a reaction conversion rate of 97%).

Crude 1-(1-(dimethoxymethyl)-2-methyl-1H-benzo[d]imidazol-5-yl)hydrazine-1,2-dicarboxylic acid di-tert-butyl was prepared using a tetrahydrofuran solution of isopropyl magnesium chloride instead of a tetrahydrofuran solution of cyclohexyl magnesium chloride in step B (a reaction conversion rate of 96%).

Synthesis of 1-(2-methyl-1H-benzo[d]imidazol-5-yl)hydrazine-1,2-dicarboxylic acid di-tert-butyl malate tetrahydrofuran solvate

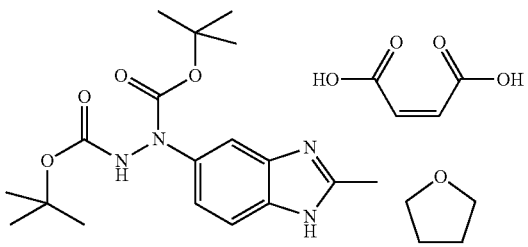

1-(2-Methyl-1H-benzo[d]imidazol-5-yl)hydrazine-1,2-dicarboxylic acid di-tert-butyl malate tetrahydrofuran solvate was prepared using tetrahydrofuran, maleic acid, and heptane instead of mesylic acid and isopropyl acetate in step B (a yield of 62%).

¹H-NMR (CD₃OD) δ: 7.77 (1.0H, m), 7.64-7.53 (2.0H, m), 6.26 (2.0H, s), 3.74-3.71 (4.0H, m), 2.80 (3.0H, s), 1.90-1.85 (4.0H, m), 1.51-1.48 (18H, m)

481

Step 45: Synthesis of 1-(4-methoxy-benzyl)-1H-pyrrole-2-carboxylic acid ethyl ester (1502)

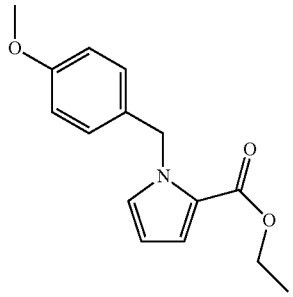 [SMILES: CCOC(=O)c1cccn1Cc1ccc(OC)cc1]

60% Oily sodium hydride (362 mg) was washed with hexane, and this was suspended in anhydrous N,N-dimethylformamide (DMF) (5 ml). An N,N-dimethylformamide (DMF) solution (15 ml) of 1H-pyrrole-2-carboxylic acid ethyl ester (1.05 g) was added dropwise to the suspension at 0° C. with argon flow. The reaction mixture was stirred at 25° C. for one hour, and then 4-methoxybenzyl chloride (1.5 ml) was added thereto at 0° C. The reaction mixture was stirred at 25° C. for 10 hours. Then, ice (about 10 g) was added to the reaction mixture, and this was extracted with ethyl acetate (20 ml). The organic layer was washed with an aqueous solution (60 ml) saturated with sodium chloride, and then concentrated. The residue obtained by concentration under reduced pressure was purified by silica gel column chromatography (hexane/ethyl acetate). Thus, a yellow oily material was obtained (1.64 g, 83%).

ESI (LC-MS positive mode) m/z 260 [(M+H)+]

Step 46: Synthesis of 4-bromo-1H-pyrrole-2-carboxylic acid ethyl ester (1503)

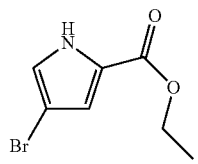

1H-Pyrrole-2-carboxylic acid ethyl ester (10 g) was dissolved in carbon tetrachloride (50 ml). A carbon tetrachloride solution (50 ml) of bromine was added dropwise thereto on ice over 30 minutes. The reaction mixture was stirred at 25° C. for one hour. The suspension of reaction mixture was added dropwise to an ethanol solution (100 ml) of 10% sodium ethoxide on ice over 20 minutes. The solvent was concentrated under reduced pressure. The resulting residue was diluted with ethyl acetate (40 ml) and water (20 ml). The organic layer was washed with an aqueous solution saturated with sodium chloride (10 ml), and then concentrated. The residue obtained by concentration under reduced pressure was purified by silica gel column chromatography (hexane/ethyl acetate). Thus, a brown solid was obtained (10 g, 99%).

ESI (LC-MS positive mode) m/z 218, 220 [(M+H)+]

482

Step 47: Synthesis of 4,5-dibromo-1-(4-methoxy-benzyl)-1H-pyrrole-2-carboxylic acid ethyl ester (1504)

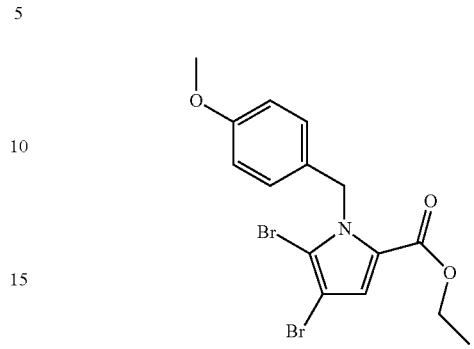

An anhydrous N,N-dimethylformamide (DMF) solution (9 ml) of N-bromosuccinimide (2.7 g) was added dropwise to an anhydrous N,N-dimethylformamide (DMF) solution (8 ml) of 1-(4-methoxy-benzyl)-1H-pyrrole-2-carboxylic acid ethyl ester (2 g) at 0° C. with argon flow. The reaction mixture was stirred at 0° C., and then water (20 ml) was added thereto. After extraction with ethyl acetate (30 ml), the organic layer was washed with an aqueous solution saturated with sodium chloride (70 ml), and the organic layer was concentrated under reduced pressure. The resulting residue was purified by silica gel column chromatography (hexane/ethyl acetate). Thus, 4,5-dibromo-1-(4-methoxy-benzyl)-1H-pyrrole-2-carboxylic acid ethyl ester was obtained as an oily pale brown material (2.99 g, 92%).

ESI (LC-MS positive mode) m/z 416, 418, 420 [(M+H)+]

Step 48: Synthesis of [5-amino-1-(2-methyl-1H-benzimidazol-5-yl)-1H-pyrazol-4-yl]-[4-phenyl-1-(toluene-4-sulfonyl)-1H-pyrrol-2-yl]-methanone (1505)

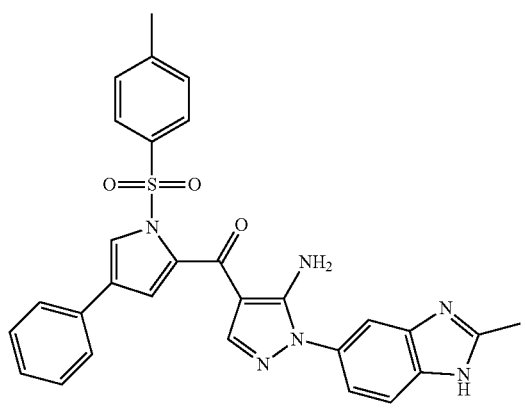 [SMILES: Cc1ccc(S(=O)(=O)n2cc(-c3ccccc3)cc2C(=O)c2cnn(-c3ccc4[nH]c(C)nc4c3)c2N)cc1]

Dioxane (1.5 ml) and an aqueous solution (1.5 ml) of 1 M sodium bicarbonate were added to [5-amino-1-(2-methyl-1H-benzimidazol-5-yl)-1H-pyrazol-4-yl]-[4-bromo-1-(toluene-4-sulfonyl)-1H-pyrrol-2-yl]-methanone (57 mg), palladium chloride bis-triphenylphosphine complex (10 mg), and phenylboronic acid (37 mg). The mixture was reacted at 140° C. in a microwave reactor for ten minutes. The reaction mixture was diluted with water (5 ml), and then extracted with ethyl acetate. The organic layers were combined, and concentrated under reduced pressure. After HPLC purification, the eluate was desalted using PLHCO3 cartridge (PolymerLabs), and then concentrated under reduced pressure. Thus, [5-amino-1-(2-methyl-1H-benzimidazol-5-yl)-1H-pyrazol-4-yl]-[4-phenyl-1-(toluene-4-sulfonyl)-1H-pyrrol-2-yl]-methanone was obtained as a yellow powder (15 mg, 26%).

ESI (LC-MS positive mode) m/z 537 [(M+H)$^+$]

The compounds of numbers 1506 to 1510, and 1591 to 1598 listed in Table 33 were synthesized as described in Step 48.

TABLE 33

| Compound No. | Structure | Compound name | m/z |
|---|---|---|---|
| 1506 | 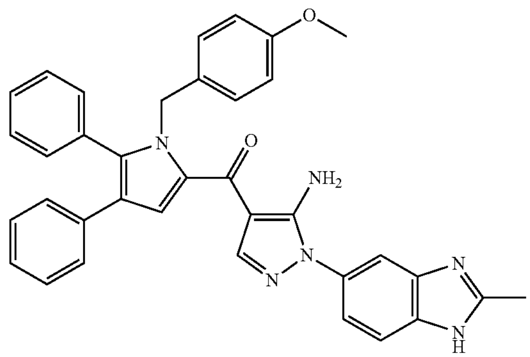 [SMILES: COc1ccc(Cn2c(C(=O)c3cnn(-c4ccc5[nH]c(C)nc5c4)c3N)cc(-c3ccccc3)c2-c2ccccc2)cc1] | [5-amino-1-(2-methyl-1H-benzimidazol-5-yl)-1H-pyrazol-4-yl]-[1-(4-methoxy-benzyl)-4,5-diphenyl-1H-pyrrol-2-yl]-methanone | 579 |
| 1507 | 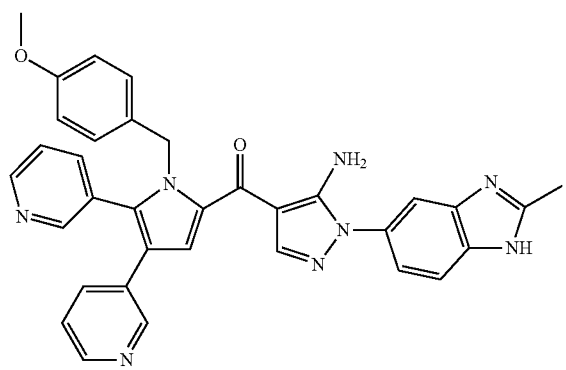 [SMILES: COc1ccc(Cn2c(C(=O)c3cnn(-c4ccc5[nH]c(C)nc5c4)c3N)cc(-c3cccnc3)c2-c2cccnc2)cc1] | [5-amino-1-(2-methyl-1H-benzimidazol-5-yl)-1H-pyrazol-4-yl]-[1-(4-methoxy-benzyl)-4,5-dipyridin-3-yl-1H-pyrrol-2-yl]-methanone | 581 |
| 1508 | 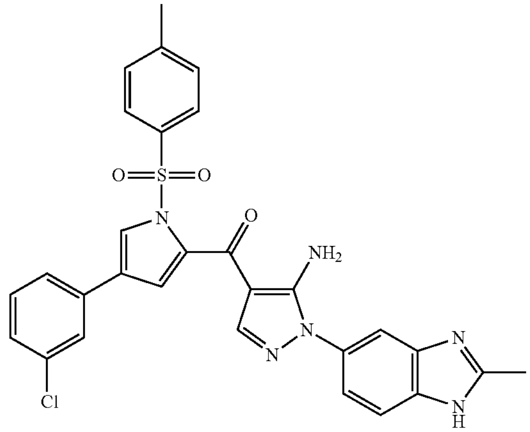 [SMILES: Cc1ccc(S(=O)(=O)n2cc(-c3cccc(Cl)c3)cc2C(=O)c2cnn(-c3ccc4[nH]c(C)nc4c3)c2N)cc1] | [5-amino-1-(2-methyl-1H-benzimidazol-5-yl)-1H-pyrazol-4-yl]-[4-(3-chloro-phenyl)-1-(toluene-4-sulfonyl)-1H-pyrrol-2-yl]-methanone | 571, 573 |

TABLE 33-continued

| Compound No. | Structure | Compound name | m/z |
|---|---|---|---|
| 1509 | 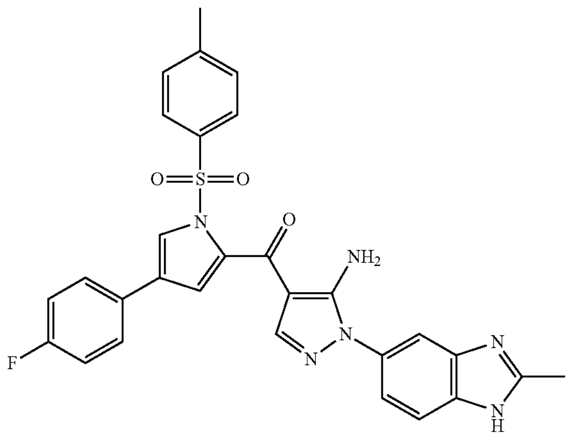 [SMILES: Cc1ccc(S(=O)(=O)n2cc(-c3ccc(F)cc3)cc2C(=O)c2cnn(-c3ccc4[nH]c(C)nc4c3)c2N)cc1] | [5-amino-1-(2-methyl-1H-benzimidazol-5-yl)-1H-pyrazol-4-yl]-[4-(4-fluoro-phenyl)-1-(toluene-4-sulfonyl)-1H-pyrrol-2-yl]-methanone | 555 |
| 1510 | 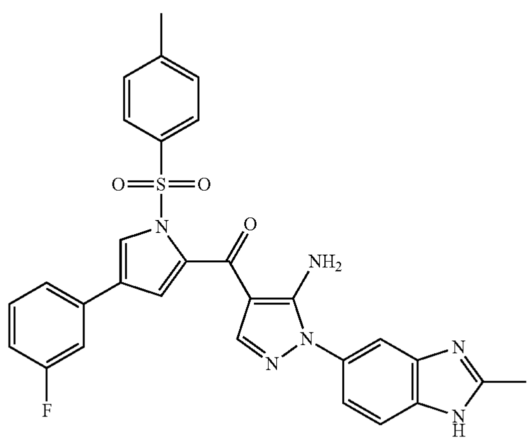 [SMILES: Cc1ccc(S(=O)(=O)n2cc(-c3cccc(F)c3)cc2C(=O)c2cnn(-c3ccc4[nH]c(C)nc4c3)c2N)cc1] | [5-amino-1-(2-methyl-1H-benzimidazol-5-yl)-1H-pyrazol-4-yl]-[4-(3-fluoro-phenyl)-1-(toluene-4-sulfonyl)-1H-pyrrol-2-yl]-methanone | 555 |
| 1591 | 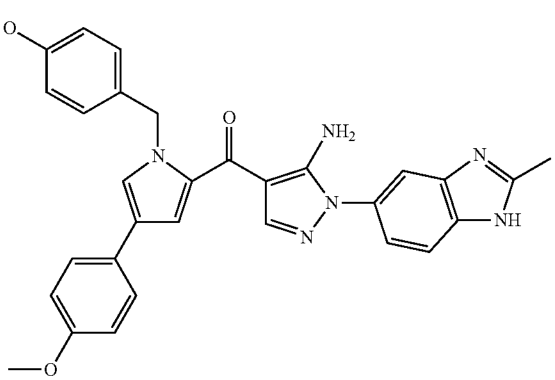 | [5-amino-1-(2-methyl-1H-benzimidazol-5-yl)-1H-pyrazol-4-yl]-[1-(4-methoxy-benzyl)-4-(4-methoxy-phenyl)-1H-pyrrol-2-yl]-methanone | 533 |

TABLE 33-continued

| Compound No. | Structure | Compound name | m/z |
|---|---|---|---|
| 1592 | 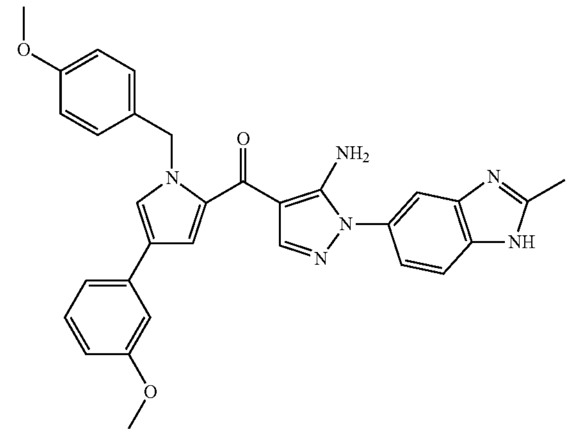 [SMILES: COc1ccc(Cn2cc(-c3cccc(OC)c3)cc2C(=O)c2cnn(-c3ccc4[nH]c(C)nc4c3)c2N)cc1] | [5-amino-1-(2-methyl-1H-benzimidazol-5-yl)-1H-pyrazol-4-yl]-[1-(4-methoxy-benzyl)-4-(3-methoxy-phenyl)-1H-pyrrol-2-yl]-methanone | 533 |
| 1593 | 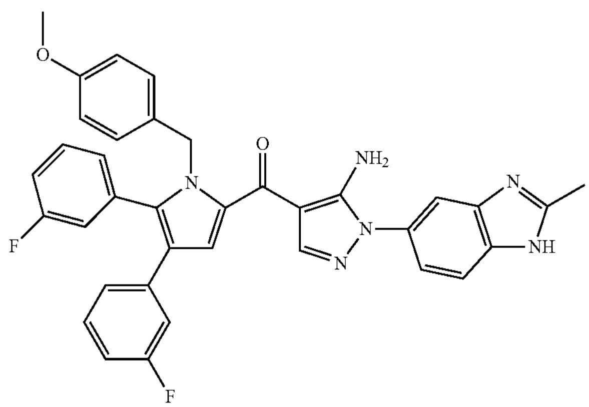 [SMILES: COc1ccc(Cn2c(C(=O)c3cnn(-c4ccc5[nH]c(C)nc5c4)c3N)cc(-c3cccc(F)c3)c2-c2cccc(F)c2)cc1] | [5-amino-1-(2-methyl-1H-benzimidazol-5-yl)-1H-pyrazol-4-yl]-[4,5-bis-(3-fluoro-phenyl)-1-(4-methoxy-benzyl)-1H-pyrrol-2-yl]-methanone | 615 |
| 1594 | 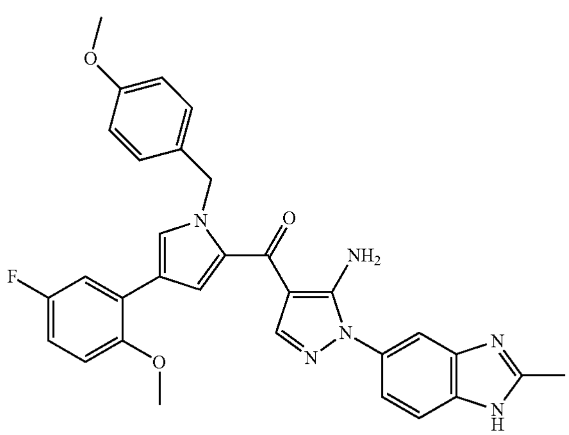 [SMILES: COc1ccc(Cn2cc(-c3cc(F)ccc3OC)cc2C(=O)c2cnn(-c3ccc4[nH]c(C)nc4c3)c2N)cc1] | [5-amino-1-(2-methyl-1H-benzimidazol-5-yl)-1H-pyrazol-4-yl]-[4-(5-fluoro-2-methoxy-phenyl)-1-(4-methoxy-benzyl)-1H-pyrrol-2-yl]-methanone | 551 |

TABLE 33-continued

| Compound No. | Structure | Compound name | m/z |
|---|---|---|---|
| 1595 | 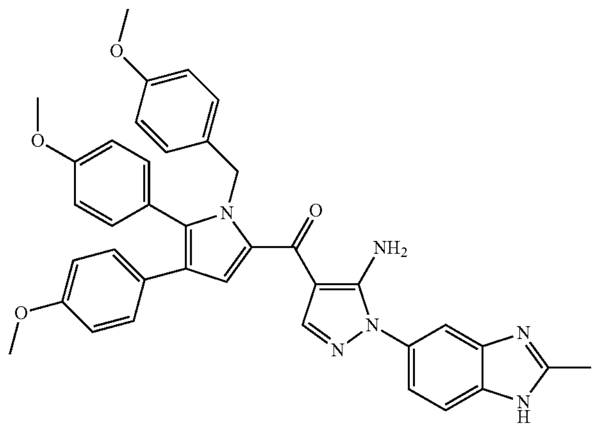 | [5-amino-1-(2-methyl-1H-benzimidazol-5-yl)-1H-pyrazol-4-yl]-[1-(4-methoxy-benzyl)-4,5-bis-(4-methoxy-phenyl)-1H-pyrrol-2-yl]-methanone | 639 |
| 1596 | 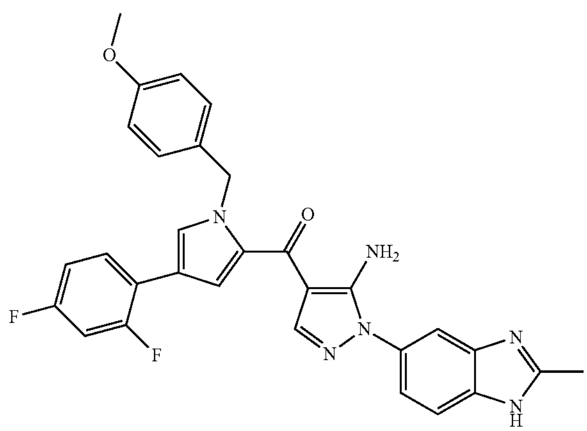 [SMILES: COc1ccc(Cn2cc(-c3ccc(F)cc3F)cc2C(=O)c2cnn(-c3ccc4[nH]c(C)nc4c3)c2N)cc1] | [5-amino-1-(2-methyl-1H-benzimidazol-5-yl)-1H-pyrazol-4-yl]-[4-(2,4-difluoro-phenyl)-1-(4-methoxy-benzyl)-1H-pyrrol-2-yl]-methanone | 539 |
| 1597 | 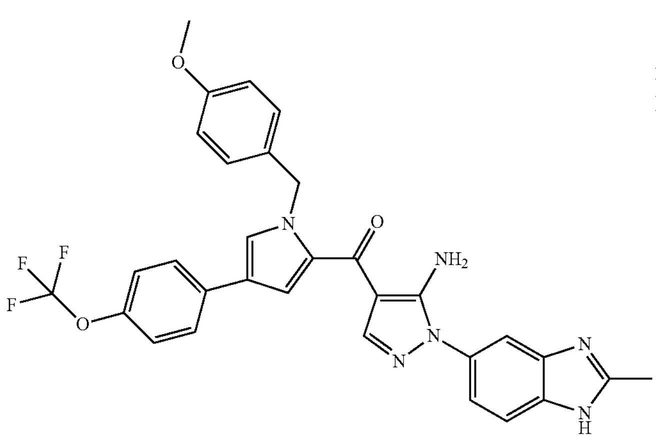 [SMILES: COc1ccc(Cn2cc(-c3ccc(OC(F)(F)F)cc3)cc2C(=O)c2cnn(-c3ccc4[nH]c(C)nc4c3)c2N)cc1] | [5-amino-1-(2-methyl-1H-benzimidazol-5-yl)-1H-pyrazol-4-yl]-[1-(4-methoxy-benzyl)-4-(4-trifluoromethoxy-phenyl)-1H-pyrrol-2-yl]-methanone | 589 |

TABLE 33-continued

| Compound No. | Structure | Compound name | m/z |
|---|---|---|---|
| 1598 | 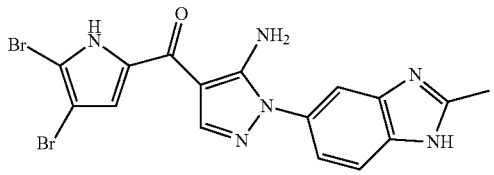 [SMILES: Cc1nc2cc(-n3ncc(C(=O)c4cc(Br)c(Br)[nH]4)c3N)ccc2[nH]1] | [5-amino-1-(2-methyl-1H-benzimidazol-5-yl)-1H-pyrazol-4-yl]-[1-(4-methoxy-benzyl)-4,5-bis-(3-methoxy-phenyl)-1H-pyrrol-2-yl]-methanone | 439 |

Examples 201

Synthesis of [5-amino-1-(2-methyl-1H-benzimidazol-5-yl)-1H-pyrazol-4-yl]-(4,5-dibromo-1H-pyrrol-2-yl)-methanone

[5-Amino-1-(2-methyl-1H-benzimidazol-5-yl)-1H-pyrazol-4-yl]-[4,5-dibromo-1-(4-methoxy-benzyl)-1H-pyrrol-2-yl]-methanone (317 mg) was dissolved in ethyl acetate/sulfuric acid (4/1; 5 ml). This was stirred at 80° C. for four hours. The pH of the reaction mixture was adjusted to 11 (basic) using an aqueous solution of 5 M sodium hydroxide while cooling it on ice. The reaction mixture was extracted with ethyl acetate/tetrahydrofuran (THF) (10 ml). The organic layer was washed with an aqueous solution saturated with sodium chloride (5 ml), and the organic layer was concentrated under reduced pressure. The resulting residue was purified by silica gel column chromatography (dichloromethane/methanol). Thus, a brown solid was obtained (135 mg, 54%).

$^1$H-NMR (DMSO-D$_6$) δ: 12.88 (1H, s), 12.46 (1H, s), 8.19 (1H, s), 7.63 (1H, d, J=8.7 Hz), 7.56-7.54 (1H, m), 7.27-7.26 (3H, m), 6.90 (1H, t, J=14.2 Hz), 2.53 (3H, s)

ESI (LC-MS positive mode) m/z 463, 465, 467 [(M+H)$^+$]

Examples 202 and 203

The compounds of Examples 202, 203, and 240-246 listed in Table 34 were synthesized as described in Example 201.

TABLE 34

| Example | Structure | Compound name | m/z | 1H-NMR |
|---|---|---|---|---|
| 202 | 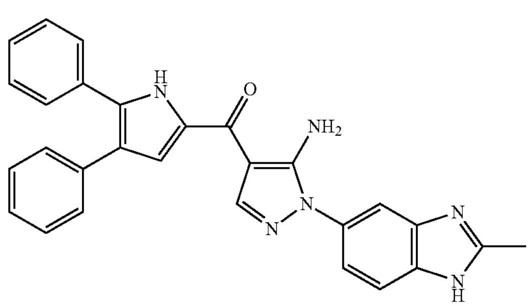 [SMILES: Cc1nc2cc(-n3ncc(C(=O)c4cc(-c5ccccc5)c(-c5ccccc5)[nH]4)c3N)ccc2[nH]1] | [5-amino-1-(2-methyl-1H-benzimidazol-5-yl)-1H-pyrazol-4-yl]-(4,5-diphenyl-1H-pyrrol-2-yl)-methanone | 459 | 1H-NMR (CD3OD) δ: 8.22 (1H, s), 7.34-7.64 (3H, m), 7.60-7.51 (2H, m), 7.45-7.38 (3H, m), 7.37-7.18 (9H, m), 2.61 (3H, m). |

TABLE 34-continued

| Example | Structure | Compound name | m/z | 1H-NMR |
|---|---|---|---|---|
| 203 | 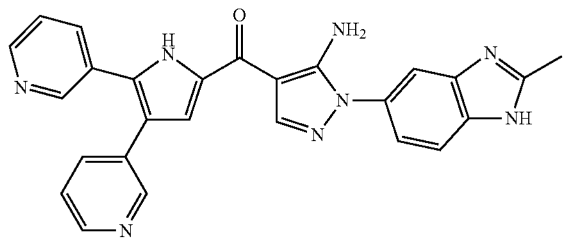 [SMILES: Cc1nc2cc(-n3ncc(C(=O)c4cc(-c5cccnc5)c(-c5cccnc5)[nH]4)c3N)ccc2[nH]1] | [5-amino-1-(2-methyl-1H-benzimidazol-5-yl)-1H-pyrazol-4-yl]-(4,5-dipyridin-3-yl-1H-pyrrol-2-yl)-methanone | 461 | 1H-NMR (DMSO-D6) δ: 12.39 (1H, s), 8.56 (1H, dd, J = 7.9, 2.1 Hz), 8.52 (1H, dd, J = 4.7, 1.1 Hz), 8.43 (1H, dd, J = 4.7, 1.6 Hz), 8.38 (1H, s), 7.81 (1H, dt, J = 7.9, 1.9 Hz), 7.72 (1H, dt, J = 8.0, 2.0 Hz), 7.63-7.59 (2H, m), 7.42 (1H, t, J = 3.7 Hz), 7.36 (1H, dd, J = 8.5, 3.7 Hz), 7.30 (1H, dd, J = 8.6, 2.0 Hz), 6.98 (2H, br s), 2.54 (3H, s). |
| 240 | 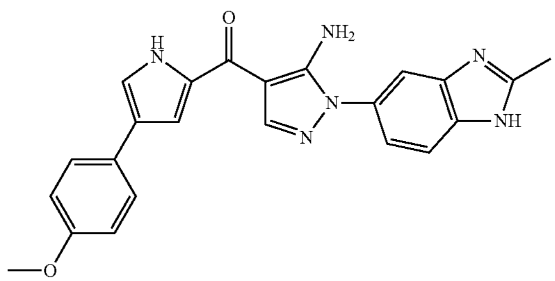 | [5-amino-1-(2-methyl-1H-benzimidazol-5-yl)-1H-pyrazol-4-yl]-[4-(4-methoxyphenyl)-1H-pyrrol-2-yl]-methanone | 413 | 11.9 (1H, br s), 7.64-7.62 (2H, m), 7.56 (1H, m), 7.51 (1H, m), 7.33-7.31 (3H, m), 7.27-7.23 (1H, m), 6.96 (1H, m), 6.90 (2H, m), 6.75-6.73 (1H, m), 3.82 (3H, s), 2.60 (3H, s) |
| 241 | 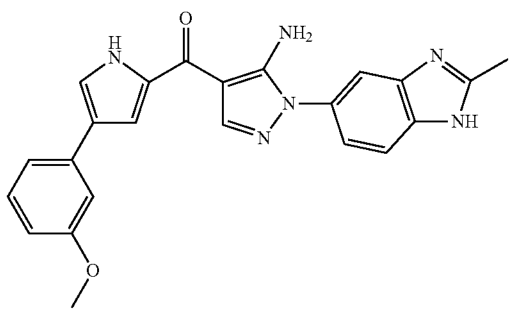 [SMILES: COc1cccc(-c2c[nH]c(C(=O)c3cnn(-c4ccc5[nH]c(C)nc5c4)c3N)c2)c1] | [5-amino-1-(2-methyl-1H-benzimidazol-5-yl)-1H-pyrazol-4-yl]-[4-(3-methoxyphenyl)-1H-pyrrol-2-yl]-methanone | 413 | 11.9 (1H, br s), 7.69-7.62 (2H, m), 7.56 (1H, m), 7.51 (1H, m), 7.33-7.31 (3H, m), 7.27-7.23 (1H, m), 6.96 (1H, m), 6.90 (2H, m), 6.75-6.73 (1H, m), 3.82 (3H, s), 2.60 (3H, s) |
| 242 | 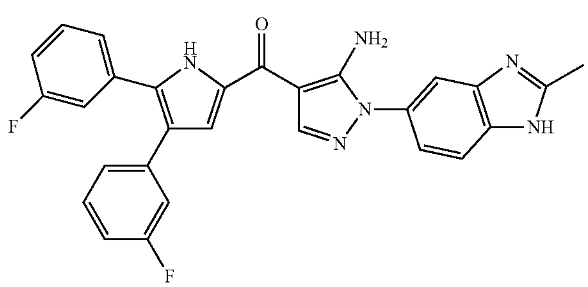 [SMILES: Cc1nc2cc(-n3ncc(C(=O)c4cc(-c5cccc(F)c5)c(-c5cccc(F)c5)[nH]4)c3N)ccc2[nH]1] | [5-amino-1-(2-methyl-1H-benzimidazol-5-yl)-1H-pyrazol-4-yl]-[4,5-bis-(3-fluorophenyl)-1H-pyrrol-2-yl]-methanone | 495 | 7.67 (1H, m), 7.41-7.28 (3H, m), 7.25-7.23 (2H, m), 7.16-7.14 (2H, m), 7.10-7.05 (2H, m), 6.99-6.95 (1H, m), 2.65 (3H, s) |
| 243 | 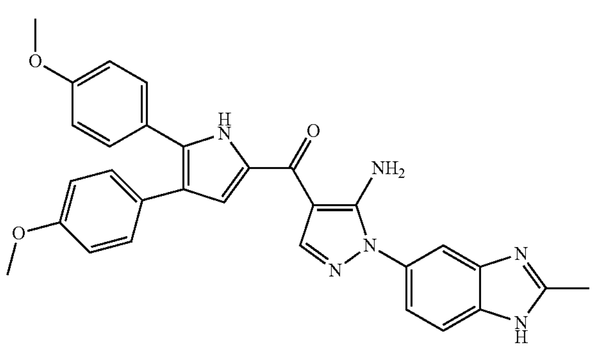 | [5-amino-1-(2-methyl-1H-benzimidazol-5-yl)-1H-pyrazol-4-yl]-[4,5-bis-(4-methoxyphenyl)-1H-pyrrol-2-yl]-methanone | 519 | 8.19 (1H, m), 7.66-7.64 (2H, m), 7.38-7.34 (3H, m), 7.25-7.23 (2H, m), 7.14 (1H, m), 6.91-6.84 (4H, s), 3.80 (3H, s), 3.76 (3H, s), 2.61 (3H, s) |

TABLE 34-continued

| Example | Structure | Compound name | m/z | 1H-NMR |
|---|---|---|---|---|
| 244 | 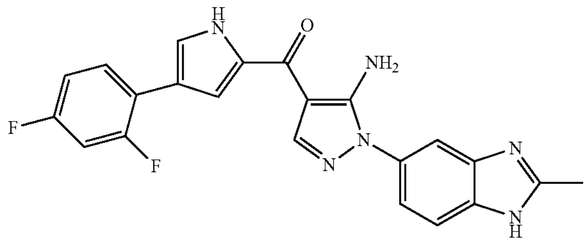 [SMILES: Cc1nc2cc(-n3ncc(C(=O)c4cc(-c5ccc(F)cc5F)c[nH]4)c3N)ccc2[nH]1] | [5-amino-1-(2-methyl-1H-benzimidazol-5-yl)-1H-pyrazol-4-yl]-[4-(2,4-difluoro-phenyl)-1H-pyrrol-2-yl]-methanone | 419 | 8.30 (1H, m), 7.96-7.89 (1H, m), 7.69 (2H, m), 7.47-7.45 (2H, m), 7.42-7.39 (1H, m), 7.26-7.21 (1H, m), 7.12-7.08 (1H, m), 2.60 (3H, s) |
| 245 | 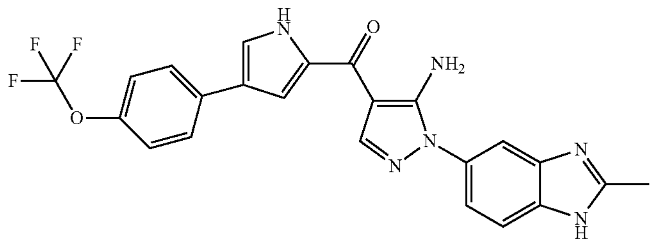 [SMILES: Cc1nc2cc(-n3ncc(C(=O)c4cc(-c5ccc(OC(F)(F)F)cc5)c[nH]4)c3N)ccc2[nH]1] | [5-amino-1-(2-methyl-1H-benzimidazol-5-yl)-1H-pyrazol-4-yl]-[4-(4-trifluoro-methoxy-phenyl)-1H-pyrrol-2-yl]-methanone | 467 | 12.5 (1H, br s), 11.9 (1H, br s), 8.39 (1H, m), 7.89-7.87 (2H, m), 7.64-7.55 (4H, m), 7.33-7.31 (3H, m), 6.91-6.85 (2H, m), 2.54 (3H, s) |
| 246 | 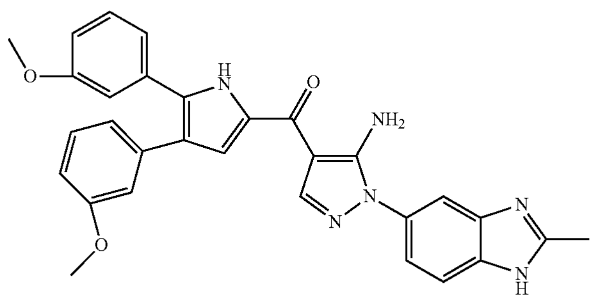 | [5-amino-1-(2-methyl-1H-benzimidazol-5-yl)-1H-pyrazol-4-yl]-[4,5-bis-(3-methoxy-phenyl)-1H-pyrrol-2-yl]-methanone | 519 | 12.5 (1H, br s), 11.9 (1H, br s), 7.65-7.63 (1H, m), 7.58-7.55 (1H, m), 7.31-7.28 (1H, m), 7.25-7.18 (3H, m), 7.07 (1H, m), 6.96-6.86 (6H, m), 6.80-6.78 (1H, m), 3.73 (3H, s), 3.69 (3H, s), 2.53 (3H, s) |

Pharmacological Test Methods

1. Inhibitory Activity Against the FGFR1 Enzyme

The FGFR1-inhibiting activity was measured based on the activity to inhibit phosphorylation of the biotinylated peptide EGPWLEEEEEAYGWMDF (SEQ ID NO:1) by the human FGFR1 enzyme (Carna Biosciences, cat. 08-133). Phosphorylated biotinylated peptides were detected by the time-resolved fluorescent measurement using a europium cryptate-linked anti-phophotyrosine antibody and a streptavidin to which XL665, a derivative of allophycocyanine, is linked. The 50% inhibitory concentration ($IC_{50}$) was calculated based on the inhibitory rate against the control group without test substances.

2. Inhibitory Activity Against the FGFR2 Enzyme

The FGFR2-inhibiting activity was measured based on the activity to inhibit phosphorylation of the biotinylated peptide EGPWLEEEEEAYGWMDF (SEQ ID NO:1) by the human FGFR2 enzyme prepared using a baculovirus expression system. Phosphorylated biotinylated peptides were detected by the time-resolved fluorescent measurement using a europium cryptate-linked anti-phophotyrosine antibody and a streptavidin to which XL665, a derivative of allophycocyanine, is linked. The 50% inhibitory concentration ($IC_{50}$) was calculated based on the inhibitory rate against the control group without test substances.

3. Inhibitory Activity Against the FGFR3 Enzyme

The FGFR3-inhibiting activity was measured based on the activity to inhibit phosphorylation of the biotinylated peptide EGPWLEEEEEAYGWMDF (SEQ ID NO:1) by the human FGFR3 enzyme (Calm Biosciences, cat. 08-135). Phosphorylated biotinylated peptides were detected by the time-resolved fluorescent measurement using a europium cryptate-linked anti-phophotyrosine antibody and a streptavidin to which XL665, a derivative of allophycocyanine, is linked. The 50% inhibitory concentration ($IC_{50}$) was calculated based on the inhibitory rate against the control group without test substances.

Test Results

Compounds that have an activity of inhibiting FGFR1 ($IC_{50}$ of 0.3 μM or less):

Examples 1-14, 16-18, 23-25, 27-32, 35-62, 64-87, 89-108, 110, 112-125, 130-161, 163-175, 177-191, and 192-201

Compounds that have an activity of inhibiting FGFR2 ($IC_{50}$ of 0.3 μM or less):

Examples 1-14, 16-62, 64-108, 110, 112-126, 128-150, 152-161, 163-191, and 192-201

Compounds that have an activity of inhibiting FGFR3 ($IC_{50}$ of 0.3 μM or less):

Examples 1-3, 5-9, 12-13, 25, 27-29, 32, 36, 38-50, 52-54, 56, 61, 64-67, 69-72, 74-81, 85-87, 89, 91-100, 102-108, 110, 112-121, 123-125, 132-150, 152-161, 163-169, 174-176, 178, 180-187, 189-191, 192, and 194-200

TABLE 35

| Example | FGFR1 | FGFR2 | FGFR3 |
|---|---|---|---|
| 1 | 0.0050 | 0.023 | 0.018 |
| 3 | 0.0053 | 0.0055 | 0.013 |
| 5 | 0.028 | 0.0056 | 0.038 |

TABLE 35-continued

| Example | FGFR1 | FGFR2 | FGFR3 |
|---|---|---|---|
| 6 | 0.0027 | 0.0032 | 0.0054 |
| 7 | 0.0030 | 0.0043 | 0.0067 |
| 12 | 0.031 | 0.0085 | 0.50 |
| 16 | 0.042 | 0.031 | 0.36 |
| 21 | 0.46 | 0.064 | 50 |
| 27 | 0.030 | 0.0054 | 0.0031 |
| 28 | 0.099 | 0.021 | 0.21 |
| 29 | 0.093 | 0.019 | 0.35 |
| 38 | 0.015 | 0.023 | 0.077 |
| 39 | 0.010 | 0.015 | 0.046 |
| 40 | 0.00081 | 0.012 | 0.0037 |
| 42 | 0.0096 | 0.023 | 0.034 |
| 43 | 0.017 | 0.017 | 0.070 |
| 47 | 0.0027 | 0.0043 | 0.0054 |
| 48 | 0.030 | 0.0089 | 0.11 |
| 50 | 0.042 | 0.026 | 0.15 |
| 52 | 0.016 | 0.0086 | 0.21 |
| 53 | 0.043 | 0.021 | 0.15 |
| 54 | 0.089 | 0.042 | 0.19 |
| 56 | 0.051 | 0.034 | 0.18 |
| 57 | 0.26 | 0.086 | 0.58 |
| 60 | 0.077 | 0.022 | 0.32 |
| 62 | 0.035 | 0.016 | 0.36 |
| 64 | 0.022 | 0.012 | 0.16 |
| 66 | 0.025 | 0.048 | 0.043 |
| 67 | 0.029 | 0.025 | 0.082 |
| 68 | 0.23 | 0.20 | 0.40 |
| 69 | 0.023 | 0.016 | 0.060 |
| 71 | 0.060 | 0.027 | 0.13 |
| 72 | 0.045 | 0.021 | 0.082 |
| 73 | 0.076 | 0.036 | 0.80 |
| 74 | 0.050 | 0.026 | 0.23 |
| 75 | 0.043 | 0.022 | 0.086 |
| 79 | 0.018 | 0.010 | 0.027 |
| 81 | 0.018 | 0.012 | 0.045 |
| 82 | 0.024 | 0.0083 | 0.37 |
| 83 | 0.057 | 0.014 | 0.67 |
| 85 | 0.022 | 0.0055 | 0.094 |
| 87 | 0.062 | 0.014 | 0.090 |
| 90 | 0.075 | 0.040 | 0.38 |
| 91 | 0.039 | 0.018 | 0.077 |
| 92 | 0.009 | 0.0062 | 0.032 |
| 93 | 0.043 | 0.039 | 0.015 |
| 96 | 0.033 | 0.038 | 0.068 |
| 98 | 0.011 | 0.017 | 0.065 |
| 102 | 0.048 | 0.039 | 0.16 |
| 104 | 0.036 | 0.031 | 0.14 |
| 107 | 0.0069 | 0.0084 | 0.018 |
| 114 | 0.00032 | 0.012 | 0.012 |
| 115 | 0.00067 | 0.0085 | 0.030 |
| 121 | 0.087 | 0.11 | 0.13 |
| 124 | 0.011 | 0.012 | 0.041 |
| 126 | 0.39 | 0.26 | 2.1 |
| 127 | 0.98 | 0.51 | 5.5 |
| 131 | 0.21 | 0.067 | 9.8 |
| 132 | 0.0014 | 0.0034 | 0.0035 |
| 133 | 0.0051 | 0.026 | 0.19 |
| 134 | 0.0020 | 0.012 | 0.035 |
| 137 | 0.0064 | 0.019 | 0.026 |
| 138 | 0.0042 | 0.006 | 0.0056 |
| 139 | 0.0085 | 0.029 | 0.018 |
| 141 | 0.0025 | 0.0040 | 0.0016 |
| 145 | 0.0038 | 0.0091 | 0.010 |
| 149 | 0.024 | 0.20 | 0.28 |
| 150 | 0.0029 | 0.065 | 0.079 |
| 151 | 0.082 | 0.32 | 0.92 |
| 153 | 0.0079 | 0.011 | 0.036 |
| 154 | 0.066 | 0.038 | 0.13 |
| 155 | 0.0018 | 0.0063 | 0.0012 |
| 157 | 0.0016 | 0.0048 | 0.012 |
| 158 | 0.0014 | 0.0046 | 0.010 |
| 159 | 0.070 | 0.028 | 0.19 |
| 163 | 0.018 | 0.0036 | 0.019 |
| 164 | 0.0030 | 0.010 | 0.0084 |
| 166 | 0.040 | 0.015 | 0.080 |
| 168 | 0.048 | 0.021 | 0.079 |
| 169 | 0.03 | 0.015 | 0.14 |
| 170 | 0.15 | 0.056 | 0.95 |
| 177 | 0.12 | 0.11 | 0.38 |
| 178 | 0.033 | 0.020 | 0.077 |
| 182 | 0.060 | 0.029 | 0.18 |
| 185 | 0.0055 | 0.0040 | 0.029 |
| 187 | 0.046 | 0.016 | 0.25 |
| 188 | 0.091 | 0.026 | 1.3 |
| 189 | 0.038 | 0.0076 | 0.10 |
| 190 | 0.034 | 0.0055 | 0.094 |
| 192 | 0.031 | 0.020 | 0.11 |
| 193 | 0.14 | 0.078 | 0.37 |
| 196 | 0.0029 | 0.0094 | 0.13 |
| 198 | 0.021 | 0.020 | 0.090 |
| 199 | 0.027 | 0.018 | 0.12 |
| 200 | 0.056 | 0.021 | 0.068 |
| 201 | 0.26 | 0.066 | 1.4 |
| 203 | 1.7 | 0.393 | 1.8 |
| 204 | 0.091 | 0.057 | 0.37 |
| 207 | 3.6 | 1.9 | 7.9 |
| 210 | 0.092 | 0.037 | 0.33 |
| 213 | 0.045 | 0.026 | 0.15 |
| 222 | 0.053 | 0.017 | 0.21 |
| 225 | 0.053 | 0.028 | 0.26 |
| 229 | 0.036 | 0.010 | 0.35 |
| 232 | 0.056 | 0.22 | 0.26 |
| 233 | 0.210 | 0.35 | 0.88 |
| 239 | 2.8 | 0.538 | 4.0 |
| 240 | 0.85 | 0.18 | 3.18 |
| 249 | 0.038 | 0.022 | 0.082 |
| 250 | 0.095 | 0.040 | 0.32 |
| 251 | 0.077 | 0.032 | 0.23 |

INDUSTRIAL APPLICABILITY

The present invention provides compounds having an activity of inhibiting FGFR family kinases. Furthermore, the present invention provides pharmaceutical agents for preventing and/or treating cancers (for example, breast cancer, acute myelocytic leukemia, pancreatic cancer, bladder cancer, prostatic cancer, esophageal cancer, angiogenesis, stomach cancer, uterine body cancer, ovarian cancer, brain tumor including glioblastoma, colon cancer, multiple myeloma, hepatocellular carcinoma, pulmonary cancer including small cell and non-small cell lung cancers, and thyroid cancer).

The invention claimed is:

1. A compound represented by formula (I), or a pharmaceutically acceptable salt thereof:

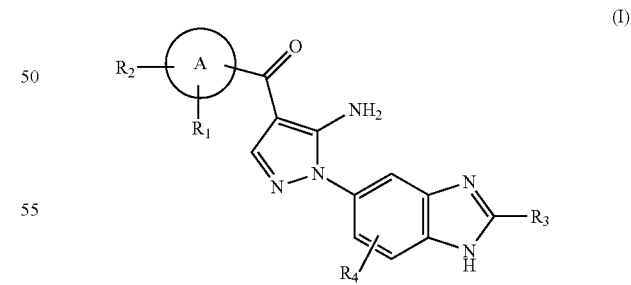

(I)

wherein $R_1$, $R_2$, $R_3$, and $R_4$ each independently represents the group listed below:

$R_1$ represents hydrogen, hydroxy, halogen, cyano, nitro, $C_{1-4}$ haloalkyl, $C_{1-6}$ alkyl, $C_{2-6}$ alkenyl, $C_{2-6}$ alkynyl, $C_{3-7}$ cycloalkyl, $C_{6-10}$ aryl $C_{1-4}$ alkyl, —$OR_5$, —$NR_6R_7$, —$(CR_8R_9)_nZ_1$, —$C(O)NR_{12}R_{13}$, —$SR_{14}$, —$SOR_{15}$, —$SO_2R_{16}$, —$NR_{17}SO_2R_{18}$, COOH, $C_{6-10}$ aryl which is optionally substituted by one or more groups independently selected from group P, 5- to 10-membered heteroaryl or 3- to 10-membered heterocyclyl which is optionally substituted by one or more groups independently selected from group Q, $-COR_{19}$, $-COOR_{20}$, $-OC(O)R_{21}$, $-NR_{22}C(O)R_{23}$, $-NR_{24}C(S)R_{25}$, $-C(S)NR_{26}R_{27}$, $-SO_2NR_{28}R_{29}$, $-OSO_2R_{30}$, $-SO_3R_{31}$, or $-Si(R_{32})_3$;

$R_2$ represents hydrogen, hydroxy, halogen, cyano, nitro, $C_{1-4}$ haloalkyl, $C_{1-6}$ alkyl, $C_{2-6}$ alkenyl, $C_{2-6}$ alkynyl, $C_{3-7}$ cycloalkyl, $C_{6-10}$ aryl $C_{1-4}$ alkyl, $-OR_5$, $-NR_6R_7$, $-(CR_8R_9)_nZ_1$, $-C(O)NR_{12}R_{13}$, $-SR_{14}$, $-SOR_{15}$, $-SO_2R_{16}$, $-NR_{17}SO_2R_{18}$, COOH, $C_{6-10}$ aryl which is optionally substituted by one or more groups independently selected from group P, 5- to 10-membered heteroaryl or 3- to 10-membered heterocyclyl which is optionally substituted by one or more groups independently selected from group Q, $-COR_{19}$, $-COOR_{20}$, $-OC(O)R_{21}$, $-NR_{22}C(O)R_{23}$, $-NR_{24}C(S)R_{25}$, $-C(S)NR_{26}R_{27}$, $-SO_2NR_{28}R_{29}$, $-OSO_2R_{30}$, $-SO_3R_{31}$, or $-Si(R_{32})_3$; or $R_1$ and $R_2$, together with an atom linked thereto, form 3- to 10-membered heterocyclyl or 5- to 10-membered heteroaryl, wherein the heterocyclyl or heteroaryl is optionally substituted by halogen;

$R_3$ represents hydrogen, $C_{1-5}$ alkyl, $C_{6-10}$ aryl $C_{1-6}$ alkyl, or $C_{1-4}$ haloalkyl;

$R_4$ represents hydrogen, halogen, $C_{1-3}$ alkyl, $C_{1-4}$ haloalkyl, hydroxy, cyano, nitro, $C_{1-4}$ alkoxy, $-(CH_2)_nZ_1$, $-NR_6R_7$, $-OR_5$, $-C(O)NR_{12}R_{13}$, $-SR_{14}$, $-SOR_{15}$, $-SO_2R_{16}$, $NR_{17}SO_2R_{18}$, COOH, $-COR_{19}$, $-COOR_{20}$, $-OC(O)R_{21}$, $-NR_{22}C(O)R_{23}$, $-NR_{24}C(S)R_{25}$, $-C(S)NR_{26}R_{27}$, $-SO_2NR_{28}R_{29}$, $-OSO_2R_{30}$, $-SO_3R_{31}$, or $-Si(R_{32})_3$;

A represents a 5- to 10-membered heteroaryl ring or $C_{6-10}$ aryl ring;

$R_5$ represents $C_{1-5}$ alkyl, $C_{3-7}$ cycloalkyl, $C_{3-7}$ cycloalkyl $C_{1-3}$ alkyl, $C_{2-6}$ alkenyl, $C_{2-6}$ alkynyl, $C_{1-4}$ haloalkyl, $C_{1-3}$ alkoxy $C_{1-4}$ alkyl, $C_{1-3}$ alkoxy $C_{1-4}$ alkoxy $C_{1-4}$ alkyl, $C_{1-4}$ aminoalkyl, $C_{1-4}$ alkylamino $C_{1-4}$ alkyl, di($C_{1-4}$ alkyl)amino $C_{1-4}$ alkyl, $C_{6-10}$ aryl, $C_{6-10}$ aryl $C_{1-3}$ alkyl, or 3- to 10-membered heterocyclyl $C_{1-3}$ alkyl, 3- to 10-membered heterocyclyl, 5- to 10-membered heteroaryl, 5- to 10-membered heteroaryl $C_{1-3}$ alkyl, $C_{1-6}$ monohydroxy alkyl, $C_{1-6}$ dihydroxy alkyl, or $C_{1-6}$ trihydroxy alkyl which is optionally substituted by one or more groups independently selected from group Q;

$R_6$ and $R_7$, which are the same or different, each represents hydrogen, $C_{1-4}$ alkyl, $C_{2-6}$ alkenyl, $C_{2-6}$ alkynyl, $C_{1-4}$ haloalkyl, $C_{1-3}$ alkoxy $C_{1-4}$ alkyl, $C_{6-10}$ aryl $C_{1-3}$ alkyl, 3- to 10-membered heterocyclyl $C_{1-3}$ alkyl, 5- to 10-membered heteroaryl $C_{1-3}$ alkyl, $C_{1-6}$ monohydroxy alkyl, $C_{1-6}$ dihydroxy alkyl, $C_{1-6}$ trihydroxy alkyl, 3- to 10-membered heterocyclyl, $C_{1-4}$ aminoalkyl, $C_{1-4}$ alkylamino $C_{1-4}$ alkyl, di($C_{1-4}$ alkyl)amino $C_{1-4}$ alkyl, or cyano($C_{1-3}$ alkyl); or $R_6$ and $R_7$, together with a nitrogen atom linked thereto, form 3- to 10-membered heterocyclyl or 5- to 10-membered heteroaryl;

n represents 1 to 3;

$R_8$ and $R_9$, which are the same or different, each represents hydrogen, $C_{1-4}$ alkyl, or halogen; or alternatively, $R_8$ and $R_9$, together with a carbon atom linked thereto, form a cycloaliphatic ring;

$Z_1$ represents hydrogen, $NR_{10}R_{11}$, $-OH$, or 3- to 10-membered heterocyclyl or 5- to 10-membered heteroaryl which is optionally substituted by one or more groups independently selected from group Q;

$R_{10}$ and $R_{11}$, which are the same or different, each represents $C_{1-4}$ alkyl, $C_{2-6}$ alkenyl, $C_{2-6}$ alkynyl, $C_{1-4}$ haloalkyl, $C_{1-3}$ alkoxy $C_{1-4}$ alkyl, cyano($C_{1-3}$ alkyl), or $C_{1-3}$ alkylsulfonyl $C_{1-4}$ alkyl; or alternatively, $R_{10}$ and $R_{11}$, together with a nitrogen atom linked thereto, form 3- to 10-membered heterocyclyl or 5- to 10-membered heteroaryl;

$R_{12}$ and $R_{13}$, which are the same or different, each represents hydrogen, $C_{1-4}$ alkyl, $C_{2-6}$ alkenyl, $C_{2-6}$ alkynyl, $C_{1-4}$ haloalkyl, $C_{1-3}$ alkoxy $C_{1-4}$ alkyl, $C_{6-10}$ aryl, 5- to 10-membered heteroaryl, 3- to 10-membered heterocyclyl, $C_{6-10}$ aryl $C_{1-4}$ alkyl, 3- to 10-membered heterocyclyl $C_{1-3}$ alkyl, 5- to 10-membered heteroaryl $C_{1-3}$ alkyl, cyano($C_{1-3}$ alkyl), $C_{1-3}$ alkylsulfonyl $C_{1-4}$ alkyl, 3- to 10-membered cycloaliphatic ring, 5- to 10-membered heteroaryl, or 3- to 10-membered heterocyclyl; or alternatively, $R_{12}$ and $R_{13}$, together with a nitrogen atom linked thereto, form 3- to 10-membered heterocyclyl or 5- to 10-membered heteroaryl which is optionally substituted by one or more groups independently selected from group Q;

$R_{14}$ represents $C_{1-4}$ alkyl, $C_{2-6}$ alkenyl, $C_{2-6}$ alkynyl, $C_{1-4}$ haloalkyl, $C_{6-10}$ aryl which is optionally substituted by one or more groups independently selected from group P, or 5- to 10-membered heteroaryl or 3- to 10-membered heterocyclyl which is optionally substituted by one or more groups independently selected from group Q;

$R_{15}$ represents $C_{1-4}$ alkyl, $C_{2-6}$ alkenyl, $C_{2-6}$ alkynyl, $C_{1-4}$ haloalkyl, $C_{6-10}$ aryl which is optionally substituted by one or more groups independently selected from group P, or 5- to 10-membered heteroaryl or 3- to 10-membered heterocyclyl which is optionally substituted by one or more groups independently selected from group Q;

$R_{16}$ represents $C_{1-4}$ alkyl, $C_{2-6}$ alkenyl, $C_{2-6}$ alkynyl, $C_{1-4}$ haloalkyl, $C_{6-10}$ aryl which is optionally substituted by one or more groups independently selected from group P, or 5- to 10-membered heteroaryl or 3- to 10-membered heterocyclyl which is optionally substituted by one or more groups independently selected from group Q;

$R_{17}$ represents hydrogen or $C_{1-4}$ alkyl;

$R_{18}$ represents $C_{1-4}$ alkyl, $C_{2-6}$ alkenyl, $C_{2-6}$ alkynyl, $C_{1-4}$ haloalkyl, $C_{6-10}$ aryl which is optionally substituted by one or more groups independently selected from group P, or 5- to 10-membered heteroaryl or 3- to 10-membered heterocyclyl which is optionally substituted by one or more groups independently selected from group Q;

$R_{19}$ represents hydrogen, $C_{1-4}$ alkyl, $C_{3-7}$ cycloalkyl, $C_{1-4}$ haloalkyl, $C_{6-10}$ aryl, or 5- to 10-membered heteroaryl or 3- to 10-membered heterocyclyl which is optionally substituted by one or more groups independently selected from group Q;

$R_{20}$ represents $C_{1-4}$ alkyl, $C_{3-7}$ cycloalkyl, $C_{1-4}$ haloalkyl, $C_{6-10}$ aryl, 5- to 10-membered heteroaryl, or 3- to 10-membered heterocyclyl;

$R_{21}$ represents $C_{1-4}$ alkyl, $C_{3-7}$ cycloalkyl, $C_{1-4}$ haloalkyl, $C_{6-10}$ aryl, 5- to 10-membered heteroaryl, or 3- to 10-membered heterocyclyl;

$R_{22}$ represents hydrogen, $C_{1-4}$ alkyl, or $C_{1-4}$ haloalkyl;

$R_{23}$ represents hydrogen, $C_{1-4}$ alkyl, $C_{3-7}$ cycloalkyl, $C_{1-4}$ haloalkyl, $C_{6-10}$ aryl, 5- to 10-membered heteroaryl, or 3- to 10-membered heterocyclyl;

$R_{24}$ represents hydrogen, $C_{1-4}$ alkyl, or $C_{1-4}$ haloalkyl;

$R_{25}$ represents $C_{1-4}$ alkyl, $C_{3-7}$ cycloalkyl, $C_{1-4}$ haloalkyl, $C_{6-10}$ aryl, 5- to 10-membered heteroaryl, or 3- to 10-membered heterocyclyl;

$R_{26}$ and $R_{27}$, which are the same or different, each represents hydrogen, $C_{1-4}$ alkyl, $C_{2-6}$ alkenyl, $C_{2-6}$ alkynyl, $C_{1-4}$ haloalkyl, $C_{1-3}$ alkoxyl $C_{1-4}$ alkyl, $C_{6-10}$ aryl, 5- to 10-membered heteroaryl, 3- to 10-membered heterocyclyl, $C_{6-10}$ aryl $C_{1-4}$ alkyl, 3- to 10-membered heterocyclyl $C_{1-3}$ alkyl, 5- to 10-membered heteroaryl $C_{1-3}$ alkyl, cyano($C_{1-3}$ alkyl), $C_{1-3}$ alkylsulfonyl $C_{1-4}$ alkyl, or 3- to 10-membered cycloaliphatic ring; or alternatively, $R_{26}$ and $R_{27}$, together with a nitrogen atom linked thereto, form 3- to 10-membered heterocyclyl or 5- to 10-membered heteroaryl;

$R_{28}$ and $R_{29}$, which are the same or different, each represents hydrogen, $C_{1-4}$ alkyl, $C_{2-6}$ alkenyl, $C_{2-6}$ alkynyl, $C_{1-4}$ haloalkyl, $C_{1-3}$ alkoxyl $C_{1-4}$ alkyl, $C_{6-10}$ aryl, 5- to 10-membered heteroaryl, 3- to 10-membered heterocyclyl, $C_{6-10}$ aryl $C_{1-4}$ alkyl, 3- to 10-membered heterocyclyl $C_{1-3}$ alkyl, 5- to 10-membered heteroaryl $C_{1-3}$ alkyl, cyano($C_{1-3}$ alkyl), $C_{1-3}$ alkylsulfonyl $C_{1-4}$ alkyl, or 3- to 10-membered cycloaliphatic ring; or alternatively, $R_{28}$ and $R_{29}$, together with a nitrogen atom linked thereto, form 3- to 10-membered heterocyclyl or 5- to 10-membered heteroaryl;

$R_{30}$ represents $C_{1-4}$ alkyl, $C_{3-7}$ cycloalkyl, $C_{1-4}$ haloalkyl, $C_{6-10}$ aryl, 5- to 10-membered heteroaryl, or 3- to 10-membered heterocyclyl;

$R_{31}$ represents $C_{1-4}$ alkyl, $C_{3-7}$ cycloalkyl, $C_{1-4}$ haloalkyl, $C_{6-10}$ aryl, 5- to 10-membered heteroaryl, or 3- to 10-membered heterocyclyl;

$R_{32}$ represents $C_{1-4}$ alkyl or $C_{6-10}$ aryl;

group P is a halogen, $C_{1-4}$ alkyl, —OH, $C_{1-3}$ alkoxy, $C_{1-3}$ haloalkoxy, 3- to 10-membered heterocyclylamino, —SO$_2$R$_{16}$, —CN, —NO$_2$, or 3- to 10-membered heterocyclyl; and group Q is a halogen, $C_{1-4}$ alkyl, $C_{1-4}$ haloalkyl, —OH, $C_{1-3}$ alkoxy, $C_{1-6}$ monohydroxy alkyl, $C_{1-6}$ dihydroxy alkyl, $C_{1-6}$ trihydroxy alkyl, 3- to 10-membered heterocyclyl amine, —SO$_2$R$_{16}$, —CN, —NO$_2$, $C_{3-7}$ cycloalkyl, —COR$_{19}$, or 3- to 10-membered heterocyclyl which is optionally substituted by $C_{1-4}$ alkyl.

2. The compound of claim 1 or a pharmaceutically acceptable salt thereof, wherein A represents benzene, indole, azaindole, benzofuran, benzothiophene, benzothiazole, quinoline, or pyrrole.

3. The compound of claim 1 or a pharmaceutically acceptable salt thereof, wherein $R_3$ represents hydrogen, $C_{1-4}$ alkyl, $C_{6-10}$ aryl $C_{1-4}$ alkyl, or $C_{1-3}$ perfluoroalkyl.

4. The compound of claim 1 or a pharmaceutically acceptable salt thereof, wherein $R_4$ represents hydrogen, halogen, $C_{1-3}$ alkyl, $C_{1-3}$ perfluoroalkyl, cyano, methanesulfonyl, hydroxyl, alkoxy, or amino.

5. A compound selected from the group consisting of:
(1) [5-amino-1-(2-methyl-1H-benzimidazol-5-yl)-1H-pyrazol-4-yl]-(1H-indol-2-yl)-methanone;
(2) [5-amino-1-(2-methyl-1H-benzimidazol-5-yl)-1H-pyrazol-4-yl]-(6-pyrrolidin-1-ylmethyl-1H-indol-2-yl)-methanone;
(3) [5-amino-1-(2-methyl-1H-benzimidazol-5-yl)-1H-pyrazol-4-yl]-[6-(4-hydroxy-piperidin-1-ylmethyl)-1H-indol-2-yl]-methanone;
(4) [5-amino-1-(2-methyl-1H-benzimidazol-5-yl)-1H-pyrazol-4-yl]-(1H-pyrrolo[3,2-c]pyridin-2-yl)-methanone;
(5) [5-amino-1-(2-methyl-1H-benzimidazol-5-yl)-1H-pyrazol-4-yl]-(6-piperazin-1-ylmethyl-1H-indol-2-yl)-methanone;
(6) [5-amino-1-(2-methyl-1H-benzimidazol-5-yl)-1H-pyrazol-4-yl]-[6-(2-morpholin-4-yl-ethoxy)-1H-indol-2-yl]-methanone;
(7) [5-amino-1-(2-methyl-1H-benzimidazol-5-yl)-1H-pyrazol-4-yl]-[6-(tetrahydro-pyran-4-yloxy)-1H-indol-2-yl]-methanone;
(8) [5-amino-1-(2-methyl-1H-benzimidazol-5-yl)-1H-pyrazol-4-yl]-(4-chloro-1H-indol-2-yl)-methanone;
(9) [5-amino-1-(2-methyl-1H-benzimidazol-5-yl)-1H-pyrazol-4-yl]-(5-bromo-1H-indol-2-yl)-methanone;
(10) [5-amino-1-(2-methyl-1H-benzimidazol-5-yl)-1H-pyrazol-4-yl]-(4-iodo-1H-indol-2-yl)-methanone;
(11) 2-[5-amino-1-(2-methyl-1H-benzimidazol-5-yl)-1H-pyrazole-4-carbonyl]-1H-indole-5-carbonitrile;
(12) [5-amino-1-(2-methyl-1H-benzimidazol-5-yl)-1H-pyrazol-4-yl]-(6-bromo-5-fluoro-1H-indol-2-yl)-methanone;
(13) [5-amino-1-(2-methyl-1H-benzimidazol-5-yl)-1H-pyrazol-4-yl]-(5-ethynyl-1H-indol-2-yl)-methanone;
(14) [5-amino-1-(2-methyl-1H-benzimidazol-5-yl)-1H-pyrazol-4-yl]-[6-(2-fluoro-phenyl)-1H-indol-2-yl]-methanone;
(15) [5-amino-1-(2-methyl-1H-benzimidazol-5-yl)-1H-pyrazol-4-yl]-[6-(3-fluoro-phenyl)-1H-indol-2-yl]-methanone;
(16) [5-amino-1-(2-methyl-1H-benzimidazol-5-yl)-1H-pyrazol-4-yl]-[6-(4-fluoro-phenyl)-1H-indol-2-yl]-methanone;
(17) [5-amino-1-(2-methyl-1H-benzimidazol-5-yl)-1H-pyrazol-4-yl]-[6-(2-chloro-phenyl)-1H-indol-2-yl]-methanone;
(18) [5-amino-1-(2-methyl-1H-benzimidazol-5-yl)-1H-pyrazol-4-yl]-[6-(3-chloro-phenyl)-1H-indol-2-yl]-methanone;
(19) [5-amino-1-(2-methyl-1H-benzimidazol-5-yl)-1H-pyrazol-4-yl]-[6-(4-chloro-phenyl)-1H-indol-2-yl]-methanone;
(20) [5-amino-1-(2-methyl-1H-benzimidazol-5-yl)-1H-pyrazol-4-yl]-[6-(2-trifluoromethyl-phenyl)-1H-indol-2-yl]-methanone;
(21) [5-amino-1-(2-methyl-1H-benzimidazol-5-yl)-1H-pyrazol-4-yl]-[6-(3-trifluoromethyl-phenyl)-1H-indol-2-yl]-methanone;
(22) [5-amino-1-(2-methyl-1H-benzimidazol-5-yl)-1H-pyrazol-4-yl]-[6-(4-trifluoromethyl-phenyl)-1H-indol-2-yl]-methanone;
(23) [5-amino-1-(2-methyl-1H-benzimidazol-5-yl)-1H-pyrazol-4-yl]-(4-bromo-1H-indol-2-yl)-methanone;
(24) [5-amino-1-(2-methyl-1H-benzimidazol-5-yl)-1H-pyrazol-4-yl]-[6-(3-fluoro-pyridin-2-yl)-1H-indol-2-yl]-methanone;
(25) [5-amino-1-(2-methyl-1H-benzimidazol-5-yl)-1H-pyrazol-4-yl]-(6-methyl-1H-indol-2-yl)-methanone;
(26) [5-amino-1-(2-methyl-1H-benzimidazol-5-yl)-1H-pyrazol-4-yl]-[5-(4,4-difluoro-piperidine-1-carbonyl)-1H-indol-2-yl]-methanone;
(27) [5-amino-1-(2-methyl-1H-benzimidazol-5-yl)-1H-pyrazol-4-yl]-[5-(3,3-difluoro-piperidine-1-carbonyl)-1H-indol-2-yl]-methanone;
(28) 2-[5-amino-1-(2-methyl-1H-benzimidazol-5-yl)-1H-pyrazole-4-carbonyl]-1H-indole-5-carboxylic acid (2,2,2-trifluoro-ethyl)-amide;

(29) [5-amino-1-(2-methyl-1H-benzimidazol-5-yl)-1H-pyrazol-4-yl]-[6-(5-trifluoromethyl-pyridin-2-yl)-1H-indol-2-yl]-methanone;
(30) [5-amino-1-(2-methyl-1H-benzimidazol-5-yl)-1H-pyrazol-4-yl]-[6-(6-trifluoromethyl-pyridin-2-yl)-1H-indol-2-yl]-methanone;
(31) [5-amino-1-(2-methyl-1H-benzimidazol-5-yl)-1H-pyrazol-4-yl]-[6-(5-chloro-pyridin-2-yl)-1H-indol-2-yl]-methanone;
(32) [5-amino-1-(2-methyl-1H-benzimidazol-5-yl)-1H-pyrazol-4-yl]-[6-(4-methyl-pyridin-2-yl)-1H-indol-2-yl]-methanone;
(33) [5-amino-1-(2-methyl-1H-benzimidazol-5-yl)-1H-pyrazol-4-yl]-[6-(3-chloro-4-fluoro-phenyl)-1H-indol-2-yl]-methanone;
(34) [5-amino-1-(2-methyl-1H-benzimidazol-5-yl)-1H-pyrazol-4-yl]-[6-(3-trifluoromethyl-pyridin-2-yl)-1H-indol-2-yl]-methanone;
(35) [5-amino-1-(2-methyl-1H-benzimidazol-5-yl)-1H-pyrazol-4-yl]-[6-(4-trifluoromethyl-pyridin-2-yl)-1H-indol-2-yl]-methanone;
(36) [5-amino-1-(6-fluoro-2-methyl-1H-benzimidazol-5-yl)-1H-pyrazol-4-yl]-(1H-indol-2-yl)-methanone;
(37) 2-[5-amino-1-(2-methyl-1H-benzimidazol-5-yl)-1H-pyrazole-4-carbonyl]-1H-indole-6-carboxylic acid;
(38) [5-amino-1-(2-methyl-1H-benzimidazol-5-yl)-1H-pyrazol-4-yl]-(6-hydroxymethyl-1H-indol-2-yl)-methanone;
(39) [5-amino-1-(2-methyl-1H-benzimidazol-5-yl)-1H-pyrazol-4-yl]-{6-[2-(4-methyl-piperazin-1-yl)-ethoxy]-1H-indol-2-yl}-methanone;
(40) [5-amino-1-(2-methyl-1H-benzimidazol-5-yl)-1H-pyrazol-4-yl]-[6-(3-methyl-oxetan-3-ylmethoxy)-1H-indol-2-yl]-methanone;
(41) [5-amino-1-(2-methyl-1H-benzimidazol-5-yl)-1H-pyrazol-4-yl]-[6-(3-fluoro-piperidin-1-ylmethyl)-1H-indol-2-yl]-methanone;
(42) [5-amino-1-(2-methyl-1H-benzimidazol-5-yl)-1H-pyrazol-4-yl]-(6-{[bis(2-methoxy-ethyl)amino]-methyl}-1H-indol-2-yl)-methanone;
(43) [5-amino-1-(2-methyl-1H-benzimidazol-5-yl)-1H-pyrazol-4-yl]-{6-[(methyl-prop-2-ynyl-amino)methyl]-1H-indol-2-yl}-methanone;
(44) [5-amino-1-(2-methyl-1H-benzimidazol-5-yl)-1H-pyrazol-4-yl]-[6-(3,3-difluoro-pyrrolidin-1-ylmethyl)-1H-indol-2-yl]-methanone;
(45) [5-amino-1-(2-methyl-1H-benzimidazol-5-yl)-1H-pyrazol-4-yl]-[6-(2,5-dimethyl-pyrrolidin-1-ylmethyl)-1H-indol-2-yl]-methanone;
(46) [5-amino-1-(2-methyl-1H-benzimidazol-5-yl)-1H-pyrazol-4-yl]-[6-(3,3-difluoro-piperidin-1-ylmethyl)-1H-indol-2-yl]-methanone;
(47) [5-amino-1-(2-methyl-1H-benzimidazol-5-yl)-1H-pyrazol-4-yl]-[6-((S)-3-methyl-morpholin-4-ylmethyl)-1H-indol-2-yl]-methanone;
(48) [5-amino-1-(2-methyl-1H-benzimidazol-5-yl)-1H-pyrazol-4-yl]-(6-bromo-1H-indol-2-yl)-methanone;
(49) [5-amino-1-(2-methyl-1H-benzimidazol-5-yl)-1H-pyrazol-4-yl]-(5-iodo-1H-indol-2-yl)-methanone;
(50) [5-amino-1-(2-methyl-1H-benzimidazol-5-yl)-1H-pyrazol-4-yl]-(1H-pyrrolo[3,2-b]pyridin-2-yl)-methanone;
(51) [5-amino-1-(2-methyl-1H-benzimidazol-5-yl)-1H-pyrazol-4-yl]-(5-bromo-6-trifluoromethyl-1H-indol-2-yl)-methanone;
(52) [5-amino-1-(2-methyl-1H-benzimidazol-5-yl)-1H-pyrazol-4-yl]-(6-iodo-1H-indol-2-yl)-methanone;
(53) [5-amino-1-(2-methyl-1H-benzimidazol-5-yl)-1H-pyrazol-4-yl]-(4-methyl-1H-indol-2-yl)-methanone;
(54) [5-amino-1-(2-methyl-1H-benzimidazol-5-yl)-1H-pyrazol-4-yl]-(4-isopropyl-1H-indol-2-yl)-methanone;
(55) [5-amino-1-(2-methyl-1H-benzimidazol-5-yl)-1H-pyrazol-4-yl]-[5-(2-fluoro-phenyl)-1H-indol-2-yl]-methanone;
(56) [5-amino-1-(2-methyl-1H-benzimidazol-5-yl)-1H-pyrazol-4-yl]-(5-benzyl-1H-indol-2-yl)-methanone;
(57) [5-amino-1-(2-methyl-1H-benzimidazol-5-yl)-1H-pyrazol-4-yl]-[5-(2-trifluoromethyl-phenyl)-1H-indol-2-yl]-methanone;
(58) [5-amino-1-(2-methyl-1H-benzimidazol-5-yl)-1H-pyrazol-4-yl]-[5-(3-fluorophenyl)-1H-indol-2-yl]-methanone;
(59) [5-amino-1-(2-methyl-1H-benzimidazol-5-yl)-1H-pyrazol-4-yl]-[5-(3-trifluoromethyl-phenyl)-1H-indol-2-yl]-methanone;
(60) [5-amino-1-(2-methyl-1H-benzimidazol-5-yl)-1H-pyrazol-4-yl]-(4-ethynyl-1H-indol-2-yl)-methanone;
(61) [5-amino-1-(2-methyl-1H-benzimidazol-5-yl)-1H-pyrazol-4-yl]-(5H-[1,3]dioxolo[4,5-f]indol-6-yl)-methanone;
(62) [5-amino-1-(7-fluoro-2-methyl-1H-benzimidazol-5-yl)-1H-pyrazol-4-yl]-(1H-indol-2-yl)-methanone;
(64) [5-amino-1-(2-methyl-1H-benzimidazol-5-yl)-1H-pyrazol-4-yl]-(5-butoxy-1H-indol-2-yl)-methanone;
(65) [5-amino-1-(2-methyl-1H-benzimidazol-5-yl)-1H-pyrazol-4-yl]-[5-(1-methyl-piperidin-4-yl)-1H-indol-2-yl]-methanone;
(66) N-{2-[5-amino-1-(2-methyl-1H-benzimidazol-5-yl)-1H-pyrazole-4-carbonyl]-1H-indol-6-yl}-methanesulfonamide;
(67) [5-amino-1-(2-methyl-1H-benzimidazol-5-yl)-1H-pyrazol-4-yl]-[6-(6-morpholin-4-yl-pyridin-3-yl)-1H-indol-2-yl]-methanone;
(68) [5-amino-1-(2-methyl-1H-benzimidazol-5-yl)-1H-pyrazol-4-yl]-(6-butyl-1H-indol-2-yl)-methanone;
(69) [5-amino-1-(2-methyl-1H-benzimidazol-5-yl)-1H-pyrazol-4-yl]-[6-(1-methyl-1H-pyrazol-4-yl)-1H-indol-2-yl]-methanone;
(70) [5-amino-1-(2-methyl-1H-benzimidazol-5-yl)-1H-pyrazol-4-yl]-[6-(5-methoxy-pyridin-3-yl)-1H-indol-2-yl]-methanone;
(71) [5-amino-1-(2-methyl-1H-benzimidazol-5-yl)-1H-pyrazol-4-yl]-[6-(2-methoxy-pyridin-3-yl)-1H-indol-2-yl]-methanone;
(72) [5-amino-1-(2-methyl-1H-benzimidazol-5-yl)-1H-pyrazol-4-yl]-(6-cyclopropyl-1H-indol-2-yl)-methanone;
(73) [5-amino-1-(2-methyl-1H-benzimidazol-5-yl)-1H-pyrazol-4-yl]-[6-(2-methoxy-phenyl)-1H-indol-2-yl]-methanone;
(74) [5-amino-1-(2-methyl-1H-benzimidazol-5-yl)-1H-pyrazol-4-yl]-(6-phenyl-1H-indol-2-yl)-methanone;
(75) [5-amino-1-(2-methyl-1H-benzimidazol-5-yl)-1H-pyrazol-4-yl]-[6-(5-methanesulfonyl-pyridin-3-yl)-1H-indol-2-yl]-methanone;
(76) [5-amino-1-(2-methyl-1H-benzimidazol-5-yl)-1H-pyrazol-4-yl]-(6-isopropyl-1H-indol-2-yl)-methanone;
(77) [5-amino-1-(2-methyl-1H-benzimidazol-5-yl)-1H-pyrazol-4-yl]-(6-pyridin-2-yl-1H-indol-2-yl)-methanone;
(78) [5-amino-1-(2-methyl-1H-benzimidazol-5-yl)-1H-pyrazol-4-yl]-(5-cyclopropyl-1H-indol-2-yl)-methanone;

(79) [5-amino-1-(2-methyl-1H-benzimidazol-5-yl)-1H-pyrazol-4-yl]-(6-pyridazin-3-yl-1H-indol-2-yl)-methanone;
(80) [5-amino-1-(2-methyl-1H-benzimidazol-5-yl)-1H-pyrazol-4-yl]-(5-isopropoxy-1H-indol-2-yl)-methanone;
(81) [5-amino-1-(2-methyl-1H-benzimidazol-5-yl)-1H-pyrazol-4-yl]-[5-(2-methoxy-ethoxy)-1H-indol-2-yl]-methanone;
(82) [5-amino-1-(2-methyl-1H-benzimidazol-5-yl)-1H-pyrazol-4-yl]-(5-cyclopropylmethoxy-1H-indol-2-yl)-methanone;
(83) [5-amino-1-(2-methyl-1H-benzimidazol-5-yl)-1H-pyrazol-4-yl]-(2,2-difluoro-5H-[1,3]dioxolo[4,5-f]indol-6-yl)-methanone;
(84) [5-amino-1-(2-methyl-1H-benzimidazol-5-yl)-1H-pyrazol-4-yl]-[6-(3-chloro-pyridin-2-yl)-1H-indol-2-yl]-methanone;
(85) [5-amino-1-(2-methyl-1H-benzimidazol-5-yl)-1H-pyrazol-4-yl]-[6-(5-fluoro-pyridin-2-yl)-1H-indol-2-yl]-methanone;
(86) [5-amino-1-(2-methyl-1H-benzimidazol-5-yl)-1H-pyrazol-4-yl]-[6-(6-morpholin-4-yl-pyridazin-3-yl)-1H-indol-2-yl]-methanone;
(87) [5-amino-1-(2-methyl-1H-benzimidazol-5-yl)-1H-pyrazol-4-yl]-(5-chloro-6-cyclopropylmethoxy-1H-indol-2-yl)-methanone;
(88) [5-amino-1-(2-methyl-1H-benzimidazol-5-yl)-1H-pyrazol-4-yl]-[6-(2,4-difluoro-phenyl)-1H-indol-2-yl]-methanone;
(89) [5-amino-1-(2-methyl-1H-benzimidazol-5-yl)-1H-pyrazol-4-yl]-(6-pyridazin-4-yl-1H-indol-2-yl)-methanone;
(90) [5-amino-1-(2-methyl-1H-benzimidazol-5-yl)-1H-pyrazol-4-yl]-(3-fluoro-1H-indol-2-yl)-methanone;
(91) [5-amino-1-(2-methyl-1H-benzimidazol-5-yl)-1H-pyrazol-4-yl]-[5-(1-isopropyl-piperidin-4-yl)-6-trifluoromethyl-1H-indol-2-yl]-methanone;
(92) 2-[5-amino-1-(2-methyl-1H-benzimidazol-5-yl)-1H-pyrazole-4-carbonyl]-1H-indole-6-carbonitrile;
(93) [5-amino-1-(2-methyl-1H-benzimidazol-5-yl)-1H-pyrazol-4-yl]-[5-(1,2,3,6-tetrahydro-pyridin-4-yl)-1H-indol-2-yl]-methanone;
(94) [5-amino-1-(2-methyl-1H-benzimidazol-5-yl)-1H-pyrazol-4-yl]-(5-piperidin-4-yl-1H-indol-2-yl)-methanone;
(95) [5-amino-1-(2-methyl-1H-benzimidazol-5-yl)-1H-pyrazol-4-yl]-[5-((R)-3-fluoro-pyrrolidin-1-ylmethyl)-1H-indol-2-yl]-methanone;
(96) [5-amino-1-(2-methyl-1H-benzimidazol-5-yl)-1H-pyrazol-4-yl]-(6-fluoro-5-piperidin-4-yl-1H-indol-2-yl)-methanone;
(97) [5-amino-1-(2-methyl-1H-benzimidazol-5-yl)-1H-pyrazol-4-yl]-[6-fluoro-5-(1-methyl-piperidin-4-yl)-1H-indol-2-yl]-methanone;
(98) [5-amino-1-(2-methyl-1H-benzimidazol-5-yl)-1H-pyrazol-4-yl]-[5-(1-isopropyl-piperidin-4-yl)-1H-indol-2-yl]-methanone;
(99) [5-amino-1-(2-methyl-1H-benzimidazol-5-yl)-1H-pyrazol-4-yl]-[6-fluoro-5-(1-isopropyl-piperidin-4-yl)-1H-indol-2-yl]-methanone;
(100) [5-amino-1-(2-methyl-1H-benzimidazol-5-yl)-1H-pyrazol-4-yl]-(6-pyridin-3-yl-1H-indol-2-yl)-methanone;
(101) [5-amino-1-(2-methyl-1H-benzimidazol-5-yl)-1H-pyrazol-4-yl]-[5-(6-morpholin-4-ylpyridin-3-yl)-1H-indol-2-yl]-methanone;
(102) [5-amino-1-(2-methyl-1H-benzimidazol-5-yl)-1H-pyrazol-4-yl]-(5-pyridin-3-yl-1H-indol-2-yl)-methanone;
(103) [5-amino-1-(2-methyl-1H-benzimidazol-5-yl)-1H-pyrazol-4-yl]-[5-(6-piperazin-1-yl-pyridin-3-yl)-1H-indol-2-yl]-methanone;
(104) [5-amino-1-(2-methyl-1H-benzimidazol-5-yl)-1H-pyrazol-4-yl]-[5-(6-hydroxy-pyridin-3-yl)-1H-indol-2-yl]-methanone;
(105) [5-amino-1-(2-methyl-1H-benzimidazol-5-yl)-1H-pyrazol-4-yl]-[6-fluoro-5-(4-methyl-piperazin-1-ylmethyl)-1H-indol-2-yl]-methanone;
(106) [5-amino-1-(2-methyl-1H-benzimidazol-5-yl)-1H-pyrazol-4-yl]-(6-fluoro-5-pyrrolidin-1-ylmethyl-1H-indol-2-yl)-methanone;
(107) [5-amino-1-(2-methyl-1H-benzimidazol-5-yl)-1H-pyrazol-4-yl]-[6-(1-methyl-piperidin-4-yl)-1H-indol-2-yl]-methanone;
(108) [5-amino-1-(2-methyl-1H-benzimidazol-5-yl)-1H-pyrazol-4-yl]-[6-(4-morpholin-4-yl-phenyl)-1H-indol-2-yl]-methanone;
(109) [5-amino-1-(2-methyl-1H-benzimidazol-5-yl)-1H-pyrazol-4-yl]-[6-(3,4,5,6-tetrahydro-2H-[1,2']bipyridin-5'-yl)-1H-indol-2-yl]-methanone;
(110) [5-amino-1-(2-methyl-1H-benzimidazol-5-yl)-1H-pyrazol-4-yl]-[6-(6-piperazin-1-yl-pyridin-3-yl)-1H-indol-2-yl]-methanone;
(111) [5-amino-1-(2-methyl-1H-benzimidazol-5-yl)-1H-pyrazol-4-yl]-[5-(6-methoxy-pyridin-3-yl)-1H-indol-2-yl]-methanone;
(112) [5-amino-1-(2-methyl-1H-benzimidazol-5-yl)-1H-pyrazol-4-yl]-[5-((S)-3-methyl-morpholin-4-ylmethyl)-1H-indol-2-yl]-methanone;
(113) [5-amino-1-(2-methyl-1H-benzimidazol-5-yl)-1H-pyrazol-4-yl]-[6-((R)-3-fluoro-pyrrolidin-1-ylmethyl)-1H-indol-2-yl]-methanone;
(114) [5-amino-1-(2-methyl-1H-benzimidazol-5-yl)-1H-pyrazol-4-yl]-[5-(2,5-dimethyl-pyrrolidin-1-ylmethyl)-1H-indol-2-yl]-methanone;
(115) [5-amino-1-(2-methyl-1H-benzimidazol-5-yl)-1H-pyrazol-4-yl]-[5-(3-fluoro-piperidin-1-ylmethyl)-1H-indol-2-yl]-methanone;
(116) [5-amino-1-(2-methyl-1H-benzimidazol-5-yl)-1H-pyrazol-4-yl]-[5-(3,3-difluoro-piperidin-1-ylmethyl)-1H-indol-2-yl]-methanone;
(117) [5-amino-1-(2-methyl-1H-benzimidazol-5-yl)-1H-pyrazol-4-yl]-{6-[2-(4-methyl-piperazin-1-yl)pyridin-4-yl]-1H-indol-2-yl}-methanone;
(118) [5-amino-1-(2-methyl-1H-benzimidazol-5-yl)-1H-pyrazol-4-yl]-(6-pyridin-4-yl-1H-indol-2-yl)-methanone;
(119) [5-amino-1-(2-methyl-1H-benzimidazol-5-yl)-1H-pyrazol-4-yl]-[5-(4-fluoropiperidin-1-ylmethyl)-1H-indol-2-yl]-methanone;
(120) [5-amino-1-(2-methyl-1H-benzimidazol-5-yl)-1H-pyrazol-4-yl]-[5-(4,4-difluoro-piperidin-1-ylmethyl)-1H-indol-2-yl]-methanone;
(121) [5-amino-1-(2-difluoromethyl-1H-benzimidazol-5-yl)-1H-pyrazol-4-yl]-[5-(1-methyl-piperidin-4-yl)-1H-indol-2-yl]-methanone;
(122) [5-amino-1-(2-difluoromethyl-1H-benzimidazol-5-yl)-1H-pyrazol-4-yl]-(1H-indol-2-yl)-methanone;
(123) [5-amino-1-(2-methyl-1H-benzimidazol-5-yl)-1H-pyrazol-4-yl]-[5-(3,3-difluoro-pyrrolidin-1-ylmethyl)-1H-indol-2-yl]-methanone;

(124) [5-amino-1-(2-methyl-1H-benzimidazol-5-yl)-1H-pyrazol-4-yl]-[5-(1-cyclopentyl-piperidin-4-yl)-1H-indol-2-yl]-methanone;
(125) [5-amino-1-(2-methyl-1H-benzimidazol-5-yl)-1H-pyrazol-4-yl]-[5-(1-cyclohexyl-piperidin-4-yl)-1H-indol-2-yl]-methanone;
(126) [5-amino-1-(2-methyl-1H-benzimidazol-5-yl)-1H-pyrazol-4-yl]-(4-bromo-1H-pyrrol-2-yl)-methanone;
(127) [5-amino-1-(2-methyl-1H-benzimidazol-5-yl)-1H-pyrazol-4-yl]-(1H-pyrrol-2-yl)-methanone;
(128) [5-amino-1-(2-methyl-1H-benzimidazol-5-yl)-1H-pyrazol-4-yl]-(4-phenyl-1H-pyrrol-2-yl)-methanone;
(129) [5-amino-1-(2-methyl-1H-benzimidazol-5-yl)-1H-pyrazol-4-yl]-[4-(3-chloro-phenyl)-1H-pyrrol-2-yl]-methanone;
(130) [5-amino-1-(2-methyl-1H-benzimidazol-5-yl)-1H-pyrazol-4-yl]-[4-(4-fluoro-phenyl)-1H-pyrrol-2-yl]-methanone;
(131) [5-amino-1-(2-methyl-1H-benzimidazol-5-yl)-1H-pyrazol-4-yl]-[4-(3-fluoro-phenyl)-1H-pyrrol-2-yl]-methanone;
(132) [5-amino-1-(2-methyl-1H-benzimidazol-5-yl)-1H-pyrazol-4-yl]-(6-morpholin-4-ylmethyl-1H-indol-2-yl)-methanone;
(133) [5-amino-1-(2-methyl-1H-benzimidazol-5-yl)-1H-pyrazol-4-yl]-[4-(2-morpholin-4-yl-ethylamino)-1H-indol-2-yl]-methanone;
(134) [5-amino-1-(2-methyl-1H-benzimidazol-5-yl)-1H-pyrazol-4-yl]-[5-(4-methyl-piperazine-1-carbonyl)-1H-indol-2-yl]-methanone;
(135) [5-amino-1-(2-methyl-1H-benzimidazol-5-yl)-1H-pyrazol-4-yl]-[6-(2-morpholin-4-yl-ethylamino)-1H-indol-2-yl]-methanone;
(136) [5-amino-1-(2-methyl-1H-benzimidazol-5-yl)-1H-pyrazol-4-yl]-[5-(piperazine-1-carbonyl)-1H-indol-2-yl]-methanone;
(137) [5-amino-1-(2-methyl-1H-benzimidazol-5-yl)-1H-pyrazol-4-yl]-[4-(2-methoxy-ethylamino)-1H-indol-2-yl]-methanone;
(138) [5-amino-1-(2-methyl-1H-benzimidazol-5-yl)-1H-pyrazol-4-yl]-[4-(2-hydroxy-1-hydroxymethyl-ethylamino)-1H-indol-2-yl]-methanone;
(139) [5-amino-1-(2-methyl-1H-benzimidazol-5-yl)-1H-pyrazol-4-yl]-[4-(2-pyridin-4-yl-ethylamino)-1H-indol-2-yl]-methanone;
(140) [5-amino-1-(2-methyl-1H-benzimidazol-5-yl)-1H-pyrazol-4-yl]-[6-(2-methoxy-ethylamino)-1H-indol-2-yl]-methanone;
(141) [5-amino-1-(2-methyl-1H-benzimidazol-5-yl)-1H-pyrazol-4-yl]-(6-morpholin-4-yl-1H-indol-2-yl)-methanone;
(142) [5-amino-1-(2-methyl-1H-benzimidazol-5-yl)-1H-pyrazol-4-yl]-(4-morpholin-4-yl-1H-indol-2-yl)-methanone;
(143) [5-amino-1-(2-methyl-1H-benzimidazol-5-yl)-1H-pyrazol-4-yl]-(4-morpholin-4-ylmethyl-1H-indol-2-yl)-methanone;
(144) [5-amino-1-(2-methyl-1H-benzimidazol-5-yl)-1H-pyrazol-4-yl]-(5-morpholin-4-ylmethyl-1H-indol-2-yl)-methanone;
(145) [5-amino-1-(2-methyl-1H-benzimidazol-5-yl)-1H-pyrazol-4-yl]-[5-(morpholine-4-carbonyl)-1H-indol-2-yl]-methanone;
(146) [5-amino-1-(2-isopropyl-1H-benzimidazol-5-yl)-1H-pyrazol-4-yl]-(1H-indol-2-yl)-methanone;
(147) [5-amino-1-(2-propyl-1H-benzimidazol-5-yl)-1H-pyrazol-4-yl]-(1H-indol-2-yl)-methanone;
(148) [5-amino-1-(1H-benzimidazol-5-yl)-1H-pyrazol-4-yl]-(1H-indol-2-yl)-methanone;
(149) [5-amino-1-(2-trifluoromethyl-1H-benzimidazol-5-yl)-1H-pyrazol-4-yl]-(1H-indol-2-yl)-methanone;
(150) [5-amino-1-(2-ethyl-1H-benzimidazol-5-yl)-1H-pyrazol-4-yl]-(1H-indol-2-yl)-methanone;
(151) [5-amino-1-(2-benzyl-1H-benzimidazol-5-yl)-1H-pyrazol-4-yl]-(1H-indol-2-yl)-methanone;
(152) 1-(4-{2-[5-amino-1-(2-methyl-1H-benzimidazol-5-yl)-1H-pyrazole-4-carbonyl]-1H-indol-5-ylmethyl}-piperazin-1-yl)-ethanone;
(153) [5-amino-1-(2-methyl-1H-benzimidazol-5-yl)-1H-pyrazol-4-yl]-[5-(4-methanesulfonyl-piperazin-1-ylmethyl)-1H-indol-2-yl]-methanone;
(154) [5-amino-1-(2-methyl-1H-benzimidazol-5-yl)-1H-pyrazol-4-yl]-(5-piperazin-1-ylmethyl-1H-indol-2-yl)-methanone;
(155) 1-(4-{2-[5-amino-1-(2-methyl-1H-benzimidazol-5-yl)-1H-pyrazole-4-carbonyl]-1H-indol-6-ylmethyl}-piperazin-1-yl)-ethanone;
(156) [5-amino-1-(2-methyl-1H-benzimidazol-5-yl)-1H-pyrazol-4-yl]-[6-(4-methyl-piperazin-1-ylmethyl)-1H-indol-2-yl]-methanone;
(157) [5-amino-1-(2-methyl-1H-benzimidazol-5-yl)-1H-pyrazol-4-yl]-[5-(4-methyl-piperazin-1-ylmethyl)-1H-indol-2-yl]-methanone;
(158) [5-amino-1-(2-methyl-1H-benzimidazol-5-yl)-1H-pyrazol-4-yl]-(5-pyrrolidin-1-ylmethyl-1H-indol-2-yl)-methanone;
(159) [5-amino-1-(2-methyl-1H-benzimidazol-5-yl)-1H-pyrazol-4-yl]-(4-fluoro-1H-indol-2-yl)-methanone;
(160) [5-amino-1-(2-methyl-1H-benzimidazol-5-yl)-1H-pyrazol-4-yl]-(5-fluoro-1H-indol-2-yl)-methanone;
(161) [5-amino-1-(2-methyl-1H-benzimidazol-5-yl)-1H-pyrazol-4-yl]-(6-fluoro-1H-indol-2-yl)-methanone;
(162) [5-amino-1-(2-methyl-1H-benzimidazol-5-yl)-1H-pyrazol-4-yl]-(1H-pyrrolo[2,3-b]pyridin-2-yl)-methanone;
(163) [5-amino-1-(2-methyl-1H-benzimidazol-5-yl)-1H-pyrazol-4-yl]-(5-fluoro-6-morpholin-4-ylmethyl-1H-indol-2-yl)-methanone;
(164) 2-[5-amino-1-(2-methyl-1H-benzimidazol-5-yl)-1H-pyrazole-4-carbonyl]-1H-indole-5-carboxylic acid;
(165) [5-amino-1-(2-methyl-1H-benzimidazol-5-yl)-1H-pyrazol-4-yl]-(5-methoxy-1H-indol-2-yl)-methanone;
(166) [5-amino-1-(2-methyl-1H-benzimidazol-5-yl)-1H-pyrazol-4-yl]-(4,6-dimethoxy-1H-indol-2-yl)-methanone;
(167) [5-amino-1-(2-methyl-1H-benzimidazol-5-yl)-1H-pyrazol-4-yl]-(4-methoxy-1H-indol-2-yl)-methanone;
(168) [5-amino-1-(2-methyl-1H-benzimidazol-5-yl)-1H-pyrazol-4-yl]-(6-methoxy-1H-indol-2-yl)-methanone;
(169) [5-amino-1-(2-methyl-1H-benzimidazol-5-yl)-1H-pyrazol-4-yl]-(4,6-dimethyl-1H-indol-2-yl)-methanone;
(170) [5-amino-1-(2-methyl-1H-benzimidazol-5-yl)-1H-pyrazol-4-yl]-(5-tert-butyl-1H-indol-2-yl)-methanone;
(171) [5-amino-1-(2-methyl-1H-benzimidazol-5-yl)-1H-pyrazol-4-yl]-(5-isopropyl-1H-indol-2-yl)-methanone;
(172) [5-amino-1-(2-methyl-1H-benzimidazol-5-yl)-1H-pyrazol-4-yl]-(5-benzyloxy-1H-indol-2-yl)-methanone;
(173) [5-amino-1-(2-methyl-1H-benzimidazol-5-yl)-1H-pyrazol-4-yl]-(4-benzyloxy-1H-indol-2-yl)-methanone;

(174) [5-amino-1-(2-methyl-1H-benzimidazol-5-yl)-1H-pyrazol-4-yl]-(5,6-dimethoxy-1H-indol-2-yl)-methanone;
(175) [5-amino-1-(2-methyl-1H-benzimidazol-5-yl)-1H-pyrazol-4-yl]-(6-tert-butyl-1H-indol-2-yl)-methanone;
(176) [5-amino-1-(2-methyl-1H-benzimidazol-5-yl)-1H-pyrazol-4-yl]-(5-fluoro-4-trifluoromethyl-1H-indol-2-yl)-methanone;
(177) [5-amino-1-(2-methyl-1H-benzimidazol-5-yl)-1H-pyrazol-4-yl]-(5-phenoxy-1H-indol-2-yl)-methanone;
(178) [5-amino-1-(2-methyl-1H-benzimidazol-5-yl)-1H-pyrazol-4-yl]-(6-methylsulfanyl-1H-indol-2-yl)-methanone;
(179) [5-amino-1-(2-methyl-1H-benzimidazol-5-yl)-1H-pyrazol-4-yl]-(4-tert-butyl-1H-indol-2-yl)-methanone;
(180) [5-amino-1-(2-methyl-1H-benzimidazol-5-yl)-1H-pyrazol-4-yl]-(5-methyl-1H-indol-2-yl)-methanone;
(181) [5-amino-1-(2-methyl-1H-benzimidazol-5-yl)-1H-pyrazol-4-yl]-(5-ethyl-1H-indol-2-yl)-methanone;
(182) [5-amino-1-(2-methyl-1H-benzimidazol-5-yl)-1H-pyrazol-4-yl]-(5-fluoro-6-trifluoromethyl-1H-indol-2-yl)-methanone;
(183) [5-amino-1-(2-methyl-1H-benzimidazol-5-yl)-1H-pyrazol-4-yl]-(6-fluoro-5-methoxy-1H-indol-2-yl)-methanone;
(184) [5-amino-1-(2-methyl-1H-benzimidazol-5-yl)-1H-pyrazol-4-yl]-(6-chloro-5-methoxy-1H-indol-2-yl)-methanone;
(185) [5-amino-1-(2-methyl-1H-benzimidazol-5-yl)-1H-pyrazol-4-yl]-(5-chloro-6-methoxy-1H-indol-2-yl)-methanone;
(186) [5-amino-1-(2-methyl-1H-benzimidazol-5-yl)-1H-pyrazol-4-yl]-(6-isopropoxy-1H-indol-2-yl)-methanone;
(187) [5-amino-1-(2-methyl-1H-benzimidazol-5-yl)-1H-pyrazol-4-yl]-(6-benzyloxy-1H-indol-2-yl)-methanone;
(188) [5-amino-1-(2-methyl-1H-benzimidazol-5-yl)-1H-pyrazol-4-yl]-(4-isopropoxy-1H-indol-2-yl)-methanone;
(189) [5-amino-1-(2-methyl-1H-benzimidazol-5-yl)-1H-pyrazol-4-yl]-(2,3-dihydro-6H-[1,4]dioxino[2,3-f]indol-7-yl)-methanone;
(190) [5-amino-1-(2-methyl-1H-benzimidazol-5-yl)-1H-pyrazol-4-yl]-(4,6-di-tert-butyl-1H-indol-2-yl)-methanone;
(191) 2-[5-amino-1-(2-methyl-1H-benzimidazol-5-yl)-1H-pyrazole-4-carbonyl]-1H-indole-4-carbonitrile;
(192) [5-amino-1-(2-methyl-1H-benzimidazol-5-yl)-1H-pyrazol-4-yl]-(5-imidazol-1-yl-1H-indol-2-yl)-methanone;
(193) [5-amino-1-(2-methyl-1H-benzimidazol-5-yl)-1H-pyrazol-4-yl]-(5-trifluoromethylsulfanyl-1H-indol-2-yl)-methanone;
(194) [5-amino-1-(2-methyl-1H-benzimidazol-5-yl)-1H-pyrazol-4-yl]-(5-methylsulfanyl-1H-indol-2-yl)-methanone;
(195) [5-amino-1-(2-methyl-1H-benzimidazol-5-yl)-1H-pyrazol-4-yl]-(5-methanesulfonyl-1H-indol-2-yl)-methanone;
(196) [5-amino-1-(2-methyl-1H-benzimidazol-5-yl)-1H-pyrazol-4-yl]-[6-(4,4-difluoro-piperidin-1-ylmethyl)-1H-indol-2-yl]-methanone;
(197) [5-amino-1-(2-methyl-1H-benzimidazol-5-yl)-1H-pyrazol-4-yl]-[6-(4-fluoro-piperidin-1-ylmethyl)-1H-indol-2-yl]-methanone;
(198) [5-amino-1-(2-methyl-1H-benzimidazol-5-yl)-1H-pyrazol-4-yl]-[6-(oxetan-3-yloxy)-1H-indol-2-yl]-methanone;
(199) [5-amino-1-(2-methyl-1H-benzimidazol-5-yl)-1H-pyrazol-4-yl]-(6-hydroxy-1H-indol-2-yl)-methanone;
(200) [5-amino-1-(2-methyl-1H-benzimidazol-5-yl)-1H-pyrazol-4-yl]-(6-methanesulfonyl-1H-indol-2-yl)-methanone;
(201) [5-amino-1-(2-methyl-1H-benzimidazol-5-yl)-1H-pyrazol-4-yl]-(4,5-dibromo-1H-pyrrol-2-yl)-methanone;
(202) [5-amino-1-(2-methyl-1H-benzimidazol-5-yl)-1H-pyrazol-4-yl]-(4,5-diphenyl-1H-pyrrol-2-yl)-methanone;
(203) [5-amino-1-(2-methyl-1H-benzimidazol-5-yl)-1H-pyrazol-4-yl]-(4,5-dipyridin-3-yl-1H-pyrrol-2-yl)-methanone;
(204) [5-amino-1-(2-methyl-3H-benzimidazol-5-yl)-1H-pyrazol-4-yl]-(6-chloro-1H-indol-2-yl)-methanone;
(205) [5-amino-1-(2-methyl-1H-benzimidazol-5-yl)-1H-pyrazol-4-yl]-(5-chloro-1H-indol-2-yl)-methanone;
(206) [5-amino-1-(2-methyl-1H-benzimidazol-5-yl)-1H-pyrazol-4-yl]-(1H-indol-3-yl)-methanone;
(207) [5-amino-1-(2-methyl-1H-benzimidazol-5-yl)-1H-pyrazol-4-yl]-(1H-indol-6-yl)-methanone;
(208) [5-amino-1-(2-methyl-1H-benzimidazol-5-yl)-1H-pyrazol-4-yl]-(5-bromo-6-fluoro-1H-indol-2-yl)-methanone;
(209) [5-amino-1-(2-ethyl-1H-benzimidazol-5-yl)-1H-pyrazol-4-yl]-(5-bromo-6-fluoro-1H-indol-2-yl)-methanone;
(210) [5-amino-1-(2-methyl-1H-benzimidazol-5-yl)-1H-pyrazol-4-yl]-(5-trifluoromethyl-1H-indol-2-yl)-methanone;
(211) [5-amino-1-(2-methyl-1H-benzimidazol-5-yl)-1H-pyrazol-4-yl]-(5-trifluoromethoxy-1H-indol-2-yl)-methanone;
(212) [5-amino-1-(2-methyl-1H-benzimidazol-5-yl)-1H-pyrazol-4-yl]-(4,6-dichloro-1H-indol-2-yl)-methanone;
(213) [5-amino-1-(2-methyl-1H-benzimidazol-5-yl)-1H-pyrazol-4-yl]-(6-bromo-4-fluoro-1H-indol-2-yl)-methanone;
(214) [5-amino-1-(2-methyl-1H-benzimidazol-5-yl)-1H-pyrazol-4-yl]-(6-trifluoromethoxy-1H-indol-2-yl)-methanone;
(215) [5-amino-1-(2-ethyl-1H-benzimidazol-5-yl)-1H-pyrazol-4-yl]-(5-trifluoromethoxy-1H-indol-2-yl)-methanone;
(216) [5-amino-1-(2-ethyl-1H-benzimidazol-5-yl)-1H-pyrazol-4-yl]-(5-trifluoromethyl-1H-indol-2-yl)-methanone;
(217) [5-amino-1-(2-methyl-1H-benzimidazol-5-yl)-1H-pyrazol-4-yl]-(5,6-dichloro-1H-indol-2-yl)-methanone;
(218) [5-amino-1-(2-ethyl-1H-benzimidazol-5-yl)-1H-pyrazol-4-yl]-(6-bromo-5-fluoro-1H-indol-2-yl)-methanone;
(219) [5-amino-1-(2-methyl-1H-benzimidazol-5-yl)-1H-pyrazol-4-yl]-(4,5-dichloro-1H-indol-2-yl)-methanone;
(220) [5-amino-1-(2-methyl-1H-benzimidazol-5-yl)-1H-pyrazol-4-yl]-(4,6-difluoro-1H-indol-2-yl)-methanone;
(221) [5-amino-1-(2-methyl-1H-benzimidazol-5-yl)-1H-pyrazol-4-yl]-[6-(3-chloro-pyridin-4-yl)-1H-indol-2-yl]-methanone;

(222) [5-amino-1-(2-methyl-1H-benzimidazol-5-yl)-1H-pyrazol-4-yl]-[6-(6-methyl-pyridine-3-yl)-1H-indol-2-yl]-methanone;
(223) [5-amino-1-(2-methyl-1H-benzimidazol-5-yl)-1H-pyrazol-4-yl]-[6-(5-fluoro-pyridin-3-yl)-1H-indol-2-yl]-methanone;
(224) [5-amino-1-(2-methyl-1H-benzimidazol-5-yl)-1H-pyrazol-4-yl]-[6-(2-trifluoromethyl-pyridin-3-yl)-1H-indol-2-yl]-methanone;
(225) [5-amino-1-(2-methyl-1H-benzimidazol-5-yl)-1H-pyrazol-4-yl]-[6-(5-chloro-2-methoxy-pyridin-3-yl)-1H-indol-2-yl]-methanone;
(226) [5-amino-1-(2-methyl-1H-benzimidazol-5-yl)-1H-pyrazol-4-yl]-[6-(5-chloro-pyridin-3-yl)-1H-indol-2-yl]-methanone;
(227) [5-amino-1-(2-methyl-1H-benzimidazol-5-yl)-1H-pyrazol-4-yl]-(6-thiophen-3-yl-1H-indol-2-yl)-methanone;
(228) [5-amino-1-(2-methyl-1H-benzimidazol-5-yl)-1H-pyrazol-4-yl]-[6-(4-chloropyridin-3-yl)-1H-indol-2-yl]-methanone;
(229) [5-amino-1-(2-methyl-1H-benzimidazol-5-yl)-1H-pyrazol-4-yl]-(6-thiophen-2-yl-1H-indol-2-yl)-methanone;
(230) [5-amino-1-(2-methyl-1H-benzimidazol-5-yl)-1H-pyrazol-4-yl]-[6-(3-fluoro-pyridin-4-yl)-1H-indol-2-yl]-methanone;
(231) [5-amino-1-(2-methyl-1H-benzimidazol-5-yl)-1H-pyrazol-4-yl]-[6-(2-trifluoromethyl-pyridin-4-yl)-1H-indol-2-yl]-methanone;
(232) [5-amino-1-(2-methyl-1H-benzimidazol-5-yl)-1H-pyrazol-4-yl]-[5-(3,3-difluoro-pyrrolidine-1-carbonyl)-1H-indol-2-yl]-methanone;
(233) [5-amino-1-(2-methyl-1H-benzimidazol-5-yl)-1H-pyrazol-4-yl]-[5-(2,6-dimethyl-morpholine-4-carbonyl)-1H-indol-2-yl]-methanone;
(234) [5-amino-1-(2-methyl-1H-benzimidazol-5-yl)-1H-pyrazol-4-yl]-[5-([1,4']bipiperidinyl-1'-carbonyl)-1H-indol-2-yl]-methanone;
(235) [5-amino-1-(2-methyl-1H-benzimidazol-5-yl)-1H-pyrazol-4-yl]-{5-[4-(2,2,2-trifluoro-ethyl)-piperazine-1-carbonyl]-1H-indol-2-yl}-methanone;
(236) [5-amino-1-(2-methyl-1H-benzimidazol-5-yl)-1H-pyrazol-4-yl]-{5-[4-(2-hydroxy-ethyl)-piperazine-1-carbonyl]-1H-indol-2-yl}-methanone;
(237) [5-amino-1-(2-methyl-1H-benzimidazol-5-yl)-1H-pyrazol-4-yl]-[5-(3,3,4,4-tetrafluoro-pyrrolidine-1-carbonyl)-1H-indol-2-yl]-methanone;
(238) [5-amino-1-(2-methyl-1H-benzimidazol-5-yl)-1H-pyrazol-4-yl]-[5-((R)-3-fluoro-pyrrolidine-1-carbonyl)-1H-indol-2-yl]-methanone;
(239) [5-amino-1-(2-methyl-1H-benzimidazol-5-yl)-1H-pyrazol-4-yl]-[5-((S)-3-fluororo-pyrrolidine-1-carbonyl)-1H-indol-2-yl]-methanone;
(240) [5-amino-1-(2-methyl-1H-benzimidazol-5-yl)-1H-pyrazol-4-yl]-[4-(4-methoxy-phenyl)-1H-pyrrol-2-yl]-methanone;
(241) [5-amino-1-(2-methyl-1H-benzimidazol-5-yl)-1H-pyrazol-4-yl]-[4-(3-methoxy-phenyl)-1H-pyrrol-2-yl]-methanone;
(242) [5-amino-1-(2-methyl-1H-benzimidazol-5-yl)-1H-pyrazol-4-yl]-[4,5-bis-(3-fluoro-phenyl)-1H-pyrrol-2-yl]-methanone;
(243) [5-amino-1-(2-methyl-1H-benzimidazol-5-yl)-1H-pyrazol-4-yl]-[4,5-bis-(4-methoxy-phenyl)-1H-pyrrol-2-yl]-methanone;
(244) [5-amino-1-(2-methyl-1H-benzimidazol-5-yl)-1H-pyrazol-4-yl]-[4-(2,4-difluoro-phenyl)-1H-pyrrol-2-yl]-methanone;
(245) [5-amino-1-(2-methyl-1H-benzimidazol-5-yl)-1H-pyrazol-4-yl]-[4-(4-trifluoromethoxy-phenyl)-1H-pyrrol-2-yl]-methanone;
(246) [5-amino-1-(2-methyl-1H-benzimidazol-5-yl)-1H-pyrazol-4-yl]-[4,5-bis-(3-methoxy-phenyl)-1H-pyrrol-2-yl]-methanone;
(247) [5-amino-1-(2-methyl-1H-benzimidazol-5-yl)-1H-pyrazol-4-yl]-benzofuran-2-yl-methanone;
(248) [5-amino-1-(2-methyl-1H-benzimidazol-5-yl)-1H-pyrazol-4-yl]-benzo[b]thiophen-2-yl-methanone;
(249) [5-amino-1-(2-methyl-1H-benzimidazol-5-yl)-1H-pyrazol-4-yl]-benzothiazol-2-yl-methanone;
(250) [5-amino-1-(2-methyl-1H-benzimidazol-5-yl)-1H-pyrazol-4-yl]-(4-fluoro-phenyl)-methanone;
(251) [5-amino-1-(2-methyl-1H-benzimidazol-5-yl)-1H-pyrazol-4-yl]-(3-chloro-phenyl)-methanone;
(252) [5-amino-1-(2-methyl-1H-benzimidazol-5-yl)-1H-pyrazol-4-yl]-quinolin-3-yl-methanone;
(253) [5-amino-1-(2-methyl-1H-benzimidazol-5-yl)-1H-pyrazol-4-yl]-quinolin-7-yl-methanone; and
(254) [5-amino-1-(2-methyl-1H-benzimidazol-5-yl)-1H-pyrazol-4-yl]-quinolin-6-yl-methanone or
a pharmaceutically acceptable salt thereof.

6. A pharmaceutical composition comprising the compound of claim 1 or a pharmaceutically acceptable salt thereof, and a carrier.

7. An agent for inhibiting FGFR activity, which comprises as an active ingredient the compound of claim 1 or a pharmaceutically acceptable salt thereof, wherein the compound or pharmaceutically acceptable salt thereof is present in an amount sufficient to inhibit FGFR activity in a subject.

8. The compound of claim 5, wherein the compound is [5-amino-1-(2-methyl-1H-benzimidazol-5-yl)-1H-pyrazol-4-yl]-(1H-indol-2-yl)-methanone or a pharmaceutically acceptable salt thereof.

9. A compound represented by formula (I), or a pharmaceutically acceptable salt thereof:

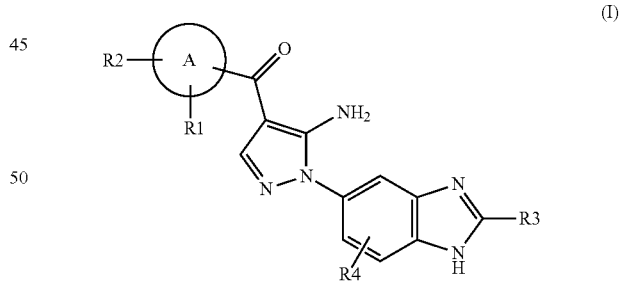

wherein $R_1$, $R_2$, $R_3$, and $R_4$ each independently represents the group listed below:

$R_1$ represents hydrogen, hydroxy, halogen, cyano, nitro, $C_{1-4}$ haloalkyl, $C_{1-6}$ alkyl, $C_{2-6}$ alkenyl, $C_{2-6}$ alkynyl, $C_{3-7}$ cycloalkyl, $C_{6-10}$ aryl $C_{1-4}$ alkyl, —$OR_5$, —$NR_6R_7$, —$(CR_8R_9)_nZ_1$, —$C(O)NR_{12}R_{13}$, —$SR_{14}$, —$SOR_{15}$, —$SO_2R_{16}$, —$NR_{17}SO_2R_{18}$, COOH, $C_{6-10}$ aryl which is optionally substituted by one or more groups independently selected from group P, 5- to 10-membered heteroaryl or 3- to 10-membered heterocyclyl which is optionally substituted by one or more groups independently selected from group Q, —$COR_{19}$, —$COOR_{20}$, —OC(O)R$_{21}$, —NR$_{22}$C(O)R$_{23}$, —NR$_{24}$C(S)R$_{25}$, —C(S)NR$_{26}$R$_{27}$, —SO$_2$NR$_{28}$R$_{29}$, —OSO$_2$R$_{30}$, —SO$_3$R$_{31}$, or —Si(R$_{32}$)$_3$;

R$_2$ represents hydrogen, hydroxy, halogen, cyano, nitro, C$_{1-4}$ haloalkyl, C$_{1-6}$ alkyl, C$_{2-6}$ alkenyl, C$_{2-6}$ alkynyl, C$_{3-7}$ cycloalkyl, C$_{6-10}$ aryl C$_{1-4}$ alkyl, —OR$_5$, —NR$_6$R$_7$, —(CR$_8$R$_9$)$_n$Z$_1$, —C(O)NR$_{12}$R$_{13}$, —SR$_{14}$, —SOR$_{15}$, —SO$_2$R$_{16}$, —NR$_{17}$SO$_2$R$_{18}$, COOH, C$_{6-10}$ aryl which is optionally substituted by one or more groups independently selected from group P, 5- to 10-membered heteroaryl or 3- to 10-membered heterocyclyl which is optionally substituted by one or more groups independently selected from group Q, —COR$_{19}$, —COOR$_{20}$, —OC(O)R$_{21}$, —NR$_{22}$C(O)R$_{23}$, —NR$_{24}$C(S)R$_{25}$, —C(S)NR$_{26}$R$_{27}$, —SO$_2$NR$_{28}$R$_{29}$, —OSO$_2$R$_{30}$, —SO$_3$R$_{31}$, or —Si(R$_{32}$)$_3$; or R$_1$ and R$_2$, together with an atom linked thereto, form 3- to 10-membered heterocyclyl or 5- to 10-membered heteroaryl, wherein the heterocyclyl or heteroaryl is optionally substituted by halogen;

R$_3$ represents hydrogen, C$_{1-5}$ alkyl, C$_{6-10}$ aryl C$_{1-6}$ alkyl, or C$_{1-4}$ haloalkyl;

R$_4$ represents hydrogen, halogen, C$_{1-3}$ alkyl, C$_{1-4}$ haloalkyl, hydroxy, cyano, nitro, C$_{1-4}$ alkoxy, —(CH$_2$)$_n$Z$_1$, —NR$_6$R$_7$, —OR$_5$, —C(O)NR$_{12}$R$_{13}$, —SR$_{14}$, —SOR$_{15}$, —SO$_2$R$_{16}$, NR$_{17}$SO$_2$R$_{18}$, COOH, —COR$_{19}$, —COOR$_{20}$, —OC(O)R$_{21}$, —NR$_{22}$C(O)R$_{23}$, —NR$_{24}$C(S)R$_{25}$, —C(S)NR$_{26}$R$_{27}$, —SO$_2$NR$_{28}$R$_{29}$, —OSO$_2$R$_{30}$, —SO$_3$R$_{31}$, or —Si(R$_{32}$)$_3$;

A represents a 5- to 10-membered heteroaryl ring or C$_{6-10}$ aryl ring;

R$_5$ represents C$_{1-5}$ alkyl, C$_{3-7}$ cycloalkyl, C$_{3-7}$ cycloalkyl C$_{1-3}$ alkyl, C$_{2-6}$ alkenyl, C$_{2-6}$ alkynyl, C$_{1-4}$ haloalkyl, C$_{1-3}$ alkoxy C$_{1-4}$ alkyl, C$_{1-3}$ alkoxy C$_{1-4}$ alkoxy C$_{1-4}$ alkyl, C$_{1-4}$ aminoalkyl, C$_{1-4}$ alkylamino C$_{1-4}$ alkyl, di(C$_{1-4}$ alkyl)amino C$_{1-4}$ alkyl, C$_{6-10}$ aryl, C$_{6-10}$ aryl C$_{1-3}$ alkyl, or 3- to 10-membered heterocyclyl C$_{1-3}$ alkyl, 3- to 10-membered heterocyclyl, 5- to 10-membered heteroaryl, 5- to 10-membered heteroaryl C$_{1-3}$ alkyl, C$_{1-6}$ monohydroxy alkyl, C$_{1-6}$ dihydroxy alkyl, or C$_{1-6}$ trihydroxy alkyl which is optionally substituted by one or more groups independently selected from group Q;

R$_6$ and R$_7$, which are the same or different, each represents hydrogen, C$_{1-4}$ alkyl, C$_{2-6}$ alkenyl, C$_{2-6}$ alkynyl, C$_{1-4}$ haloalkyl, C$_{1-3}$ alkoxy C$_{1-4}$ alkyl, C$_{6-10}$ aryl C$_{1-3}$ alkyl, 3- to 10-membered heterocyclyl C$_{1-3}$ alkyl, 5- to 10-membered heteroaryl C$_{1-3}$ alkyl, C$_{1-6}$ monohydroxy alkyl, C$_{1-6}$ dihydroxy alkyl, C$_{1-6}$ trihydroxy alkyl, 3- to 10-membered heterocyclyl, C$_{1-4}$ aminoalkyl, C$_{1-4}$ alkylamino C$_{1-4}$ alkyl, di(C$_{1-4}$ alkyl)amino C$_{1-4}$ alkyl, or cyano(C$_{1-3}$ alkyl); or R$_6$ and R$_7$, together with a nitrogen atom linked thereto, form 3- to 10-membered heterocyclyl or 5- to 10-membered heteroaryl;

n represents 1 to 3;

R$_8$ and R$_9$, which are the same or different, each represents hydrogen, C$_{1-4}$ alkyl, or halogen; or alternatively, R$_8$ and R$_9$, together with a carbon atom linked thereto, form a cycloaliphatic ring;

Z$_1$ represents hydrogen, NR$_{10}$R$_{11}$, —OH, or 3- to 10-membered heterocyclyl or 5- to 10-membered heteroaryl which is optionally substituted by one or more groups independently selected from group Q;

R$_{10}$ and R$_{11}$, which are the same or different, each represents C$_{1-4}$ alkyl, C$_{2-6}$ alkenyl, C$_{2-6}$ alkynyl, C$_{1-4}$ haloalkyl, C$_{1-3}$ alkoxy C$_{1-4}$ alkyl, cyano(C$_{1-3}$ alkyl), or C$_{1-3}$ alkylsulfonyl C$_{1-4}$ alkyl; or alternatively, R$_{10}$ and R$_{11}$, together with a nitrogen atom linked thereto, form 3- to 10-membered heterocyclyl or 5- to 10-membered heteroaryl;

R$_{12}$ and R$_{13}$, which are the same or different, each represents hydrogen, C$_{1-4}$ alkyl, C$_{2-6}$ alkenyl, C$_{2-6}$ alkynyl, C$_{1-4}$ haloalkyl, C$_{1-3}$ alkoxy C$_{1-4}$ alkyl, C$_{6-10}$ aryl, 5- to 10-membered heteroaryl, 3- to 10-membered heterocyclyl, C$_{6-10}$ aryl C$_{1-4}$ alkyl, 3- to 10-membered heterocyclyl C$_{1-3}$ alkyl, 5- to 10-membered heteroaryl C$_{1-3}$ alkyl, cyano(C$_{1-3}$ alkyl), C$_{1-3}$ alkylsulfonyl C$_{1-4}$ alkyl, 3- to 10-membered cycloaliphatic ring, 5- to 10-membered heteroaryl, or 3- to 10-membered heterocyclyl; or alternatively, R$_{12}$ and R$_{13}$, together with a nitrogen atom linked thereto, form 3- to 10-membered heterocyclyl or 5- to 10-membered heteroaryl which is optionally substituted by one or more groups independently selected from group Q;

R$_{14}$ represents C$_{1-4}$ alkyl, C$_{2-6}$ alkenyl, C$_{2-6}$ alkynyl, C$_{1-4}$ haloalkyl, C$_{6-10}$ aryl which is optionally substituted by one or more groups independently selected from group P, or 5- to 10-membered heteroaryl or 3- to 10-membered heterocyclyl which is optionally substituted by one or more groups independently selected from group Q;

R$_{15}$ represents C$_{1-4}$ alkyl, C$_{2-6}$ alkenyl, C$_{2-6}$ alkynyl, C$_{1-4}$ haloalkyl, C$_{6-10}$ aryl which is optionally substituted by one or more groups independently selected from group P, or 5- to 10-membered heteroaryl or 3- to 10-membered heterocyclyl which is optionally substituted by one or more groups independently selected from group Q;

R$_{16}$ represents C$_{1-4}$ alkyl, C$_{2-6}$ alkenyl, C$_{2-6}$ alkynyl, C$_{1-4}$ haloalkyl, C$_{6-10}$ aryl which is optionally substituted by one or more groups independently selected from group P, or 5- to 10-membered heteroaryl or 3- to 10-membered heterocyclyl which is optionally substituted by one or more groups independently selected from group Q;

R$_{17}$ represents hydrogen or C$_{1-4}$ alkyl;

R$_{18}$ represents C$_{1-4}$ alkyl, C$_{2-6}$ alkenyl, C$_{2-6}$ alkynyl, C$_{1-4}$ haloalkyl, C$_{6-10}$ aryl which is optionally substituted by one or more groups independently selected from group P, or 5- to 10-membered heteroaryl or 3- to 10-membered heterocyclyl which is optionally substituted by one or more groups independently selected from group Q;

R$_{19}$ represents hydrogen, C$_{1-4}$ alkyl, C$_{3-7}$ cycloalkyl, C$_{1-4}$ haloalkyl, C$_{6-10}$ aryl, or 5- to 10-membered heteroaryl or 3- to 10-membered heterocyclyl which is optionally substituted by one or more groups independently selected from group Q;

R$_{20}$ represents C$_{1-4}$ alkyl, C$_{3-7}$ cycloalkyl, C$_{1-4}$ haloalkyl, C$_{6-10}$ aryl, 5- to 10-membered heteroaryl, or 3- to 10-membered heterocyclyl;

R$_{21}$ represents C$_{1-4}$ alkyl, C$_{3-7}$ cycloalkyl, C$_{1-4}$ haloalkyl, C$_{6-10}$ aryl, 5- to 10-membered heteroaryl, or 3- to 10-membered heterocyclyl;

R$_{22}$ represents hydrogen, C$_{1-4}$ alkyl, or C$_{1-4}$ haloalkyl;

R$_{23}$ represents hydrogen, C$_{1-4}$ alkyl, C$_{3-7}$ cycloalkyl, C$_{1-4}$ haloalkyl, C$_{6-10}$ aryl, 5- to 10-membered heteroaryl, or 3- to 10-membered heterocyclyl;

R$_{24}$ represents hydrogen, C$_{1-4}$ alkyl, or C$_{1-4}$ haloalkyl;

R$_{25}$ represents C$_{1-4}$ alkyl, C$_{3-7}$ cycloalkyl, C$_{1-4}$ haloalkyl, C$_{6-10}$ aryl, 5- to 10-membered heteroaryl, or 3- to 10-membered heterocyclyl;

$R_{26}$ and $R_{27}$, which are the same or different, each represents hydrogen, $C_{1-4}$ alkyl, $C_{2-6}$ alkenyl, $C_{2-6}$ alkynyl, $C_{1-4}$ haloalkyl, $C_{1-3}$ alkoxyl $C_{1-4}$ alkyl, $C_{6-10}$ aryl, 5- to 10-membered heteroaryl, 3- to 10-membered heterocyclyl, $C_{6-10}$ aryl $C_{1-4}$ alkyl, 3- to 10-membered heterocyclyl $C_{1-3}$ alkyl, 5- to 10-membered heteroaryl $C_{1-3}$ alkyl, cyano($C_{1-3}$ alkyl), $C_{1-3}$ alkylsulfonyl $C_{1-4}$ alkyl, or 3- to 10-membered cycloaliphatic ring; or alternatively, $R_{26}$ and $R_{27}$, together with a nitrogen atom linked thereto, form 3- to 10-membered heterocyclyl or 5- to 10-membered heteroaryl;

$R_{28}$ and $R_{29}$, which are the same or different, each represents hydrogen, $C_{1-4}$ alkyl, $C_{2-6}$ alkenyl, $C_{2-6}$ alkynyl, $C_{1-4}$ haloalkyl, $C_{1-3}$ alkoxyl $C_{1-4}$ alkyl, $C_{6-10}$ aryl, 5- to 10-membered heteroaryl, 3- to 10-membered heterocyclyl, $C_{6-10}$ aryl $C_{1-4}$ alkyl, 3- to 10-membered heterocyclyl $C_{1-3}$ alkyl, 5- to 10-membered heteroaryl $C_{1-3}$ alkyl, cyano($C_{1-3}$ alkyl), $C_{1-3}$ alkylsulfonyl $C_{1-4}$ alkyl, or 3- to 10-membered cycloaliphatic ring; or alternatively, $R_{28}$ and $R_{29}$, together with a nitrogen atom linked thereto, form 3- to 10-membered heterocyclyl or 5- to 10-membered heteroaryl;

$R_{30}$ represents $C_{1-4}$ alkyl, $C_{3-7}$ cycloalkyl, $C_{1-4}$ haloalkyl, $C_{6-10}$ aryl, 5- to 10-membered heteroaryl, or 3- to 10-membered heterocyclyl;

$R_{31}$ represents $C_{1-4}$ alkyl, $C_{3-7}$ cycloalkyl, $C_{1-4}$ haloalkyl, $C_{6-10}$ aryl, 5- to 10-membered heteroaryl, or 3- to 10-membered heterocyclyl;

$R_{32}$ represents $C_{1-4}$ alkyl or $C_{6-10}$ aryl;

group P is a halogen, $C_{1-4}$ alkyl, $C_{1-4}$ haloalkyl, —OH, $C_{1-3}$ alkoxy, $C_{1-3}$ haloalkoxy, 3- to 10-membered heterocyclylamino, —SO$_2$R$_{16}$, —CN, —NO$_2$, or 3- to 10-membered heterocyclyl; and group Q is a halogen, $C_{1-4}$ alkyl, $C_{1-4}$ haloalkyl, —OH, $C_{1-3}$ alkoxy, $C_{1-6}$ monohydroxy alkyl, $C_{1-6}$ dihydroxy alkyl, $C_{1-6}$ trihydroxy alkyl, 3- to 10-membered heterocyclyl amine, —SO$_2$R$_{16}$, —CN, —NO$_2$, $C_{3-7}$ cycloalkyl, —COR$_{19}$, or 3- to 10-membered heterocyclyl which is optionally substituted by $C_{1-4}$ alkyl;

provided that a compound represented by the formula (I) does not include [5-amino-1-(2-methyl-1H-benzimidazol-5-yl)-1H-pyrazol-4-yl]-[5-(4-trifluoromethyl-phenyl)-1H-indol-2-yl]-methanone.

* * * * *

UNITED STATES PATENT AND TRADEMARK OFFICE
CERTIFICATE OF CORRECTION

Page 1 of 3

PATENT NO. : 8,829,199 B2
APPLICATION NO. : 13/389146
DATED : September 9, 2014
INVENTOR(S) : Naoki Taka et al.

It is certified that error appears in the above-identified patent and that said Letters Patent is hereby corrected as shown below:

In The Specification

Column 34, Line 34: Delete "$C_{3-7}$ cycloalkyl$C_{1-3}$ alkyl," and insert -- $C_{3-7}$ cycloalkyl $C_{1-3}$ alkyl, --, therefor.

Column 38, Line 38: Delete "to to" and insert -- to --, therefor.

Column 57, Line 53 (approx.): Delete "candissolve" and insert -- can dissolve --, therefor.

Column 61, Line 3: Delete "substitutent" and insert -- substituent --, therefor.

Column 83-84, Line 43 (approx.): Delete " 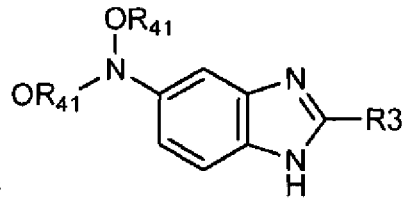 " and insert -- 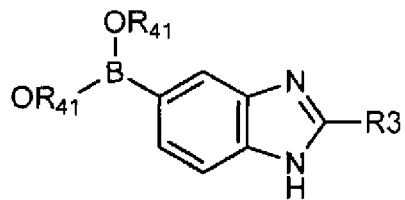 --, therefor.

Column 88, Line 56 (approx.): Delete "10-1" and insert -- 10-l --, therefor.

Column 88, Line 61 (approx.): Delete "10-1" and insert -- 10-l --, therefor.

Column 90, Lines 2-3: Delete "methanone1-methanesulfonate" and insert
-- methanone-1-methanesulfonate --, therefor.

Column 90, Lines 41-42 (approx.): Delete "methanone1-methanesulfonate" and insert
-- methanone-1-methanesulfonate --, therefor.

Signed and Sealed this
Twenty-fourth Day of March, 2015

Michelle K. Lee
*Director of the United States Patent and Trademark Office*

CERTIFICATE OF CORRECTION (continued)
U.S. Pat. No. 8,829,199 B2

Column 351, Lines 24-34 (approx.): Delete " 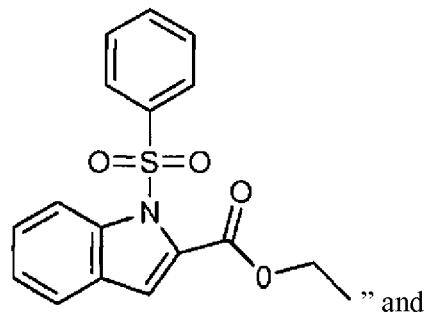 " and insert -- 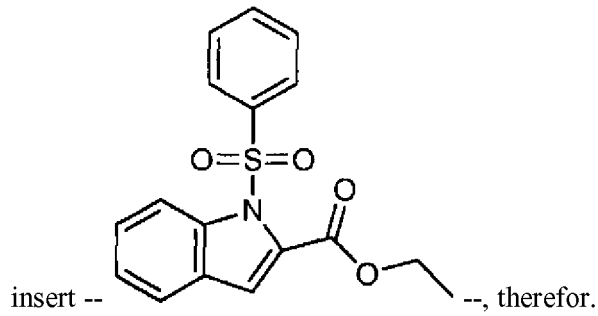 --, therefor.

Column 397, Lines 11-22 (approx.): Delete " 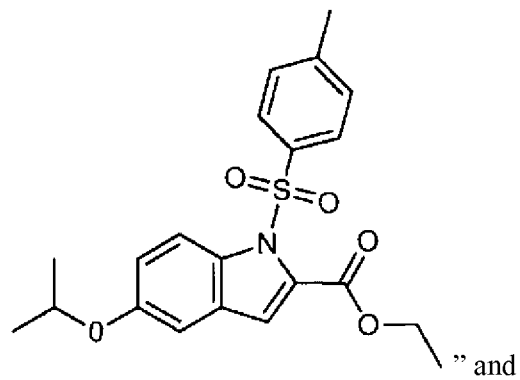 " and insert -- 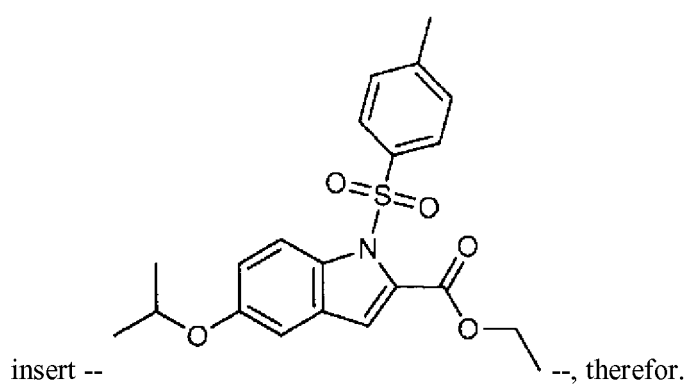 --, therefor.

CERTIFICATE OF CORRECTION (continued)

Column 401, Lines 11-18 (approx.): Delete " 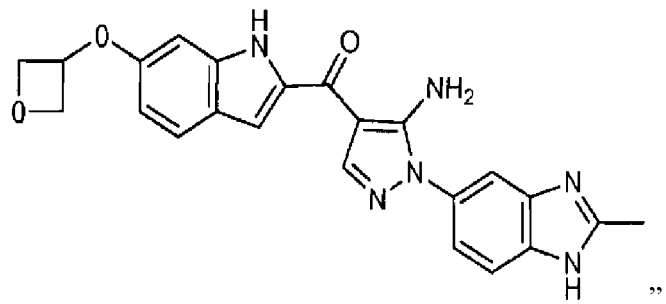 "

and insert -- 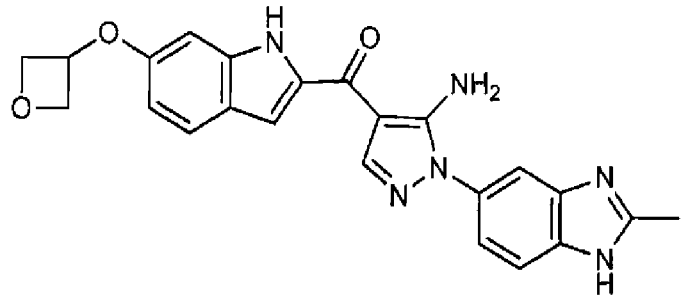 --, therefor.

Column 418, Lines 39-40 (approx.): Delete "benzynesulfonamide" and insert -- benzenesulfonamide --, therefor.

Column 475, Line 24 (approx.): Delete "dihydrochlide" and insert -- dihydrochloride --, therefor.

Column 495, Line 47: Delete "anti-phophotyrosine" and insert -- anti-phosphotyrosine --, therefor.

Column 495, Line 58 (approx.): Delete "anti-phophotyrosine" and insert -- anti-phosphotyrosine --, therefor.

Column 495, Line 67: Delete "(Calm" and insert -- (Carna --, therefor.

Column 496, Line 41 (approx.): Delete "anti-phophotyrosine" and insert -- anti-phosphotyrosine --, therefor.

In The Claims

Column 512, Line 26: Delete "methanone" and insert -- methanone, --, therefor.